US010526610B2

(12) United States Patent
Cogan et al.

(10) Patent No.: US 10,526,610 B2
(45) **Date of Patent: *Jan. 7, 2020**

(54) FAD3 PERFORMANCE LOCI AND CORRESPONDING TARGET SITE SPECIFIC BINDING PROTEINS CAPABLE OF INDUCING TARGETED BREAKS

(71) Applicants: Dow AgroSciences LLC, Indianapolis, IN (US); Sangamo Therapeutics, Inc., Richmond, CA (US)

(72) Inventors: Noel Cogan, Macleod (AU); John Forster, Diamond Creek (AU); Matthew Hayden, Templestowe (AU); Tim Sawbridge, Coburg (AU); German Spangenberg, Bundoora (AU); Steven R. Webb, Westfield, IN (US); Manju Gupta, Carmel, IN (US); W. Michael Ainley, Carmel, IN (US); Matthew J. Henry, Indianapolis, IN (US); Jeffrey C. Miller, Richmond, CA (US); Dmitry Y. Guschin, Richmond, CA (US)

(73) Assignees: Dow AgroSciences LLC, Indianapolis, IN (US); Sangamo Therapeutics, Inc., Richmond, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 15/882,609

(22) Filed: Jan. 29, 2018

(65) Prior Publication Data

US 2018/0163217 A1 Jun. 14, 2018

Related U.S. Application Data

(63) Continuation of application No. 14/019,211, filed on Sep. 5, 2013, now Pat. No. 9,914,930.

(60) Provisional application No. 61/820,260, filed on May 7, 2013, provisional application No. 61/697,854, filed on Sep. 7, 2012.

(51) Int. Cl.

| | |
|---|---|
| ***C12N 15/79*** | (2006.01) |
| ***C12N 15/82*** | (2006.01) |
| ***C12N 9/22*** | (2006.01) |
| ***C12N 15/63*** | (2006.01) |

(52) U.S. Cl.

CPC ............... *C12N 15/79* (2013.01); *C12N 9/22* (2013.01); *C12N 15/63* (2013.01); *C12N 15/8241* (2013.01); *C12N 15/8247* (2013.01)

(58) Field of Classification Search

None

See application file for complete search history.

(56) References Cited

U.S. PATENT DOCUMENTS

| | | | |
|---|---|---|---|
| 4,769,061 | A | 9/1988 | Comai |
| 4,810,648 | A | 3/1989 | Stalker |
| 4,940,835 | A | 7/1990 | Fraley et al. |
| 4,940,840 | A | 7/1990 | Suslow et al. |
| 4,975,374 | A | 12/1990 | DasSarma et al. |
| 5,266,317 | A | 11/1993 | Miller et al. |
| 5,494,813 | A | 2/1996 | Hepher et al. |
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,081 | A | 10/2000 | Barbas |
| 6,140,466 | A | 10/2000 | Barbas et al. |
| 6,200,759 | B1 | 3/2001 | Dove et al. |
| 6,242,568 | B1 | 6/2001 | Barbas et al. |
| 6,248,876 | B1 | 6/2001 | Barry et al. |
| 6,271,341 | B1 | 8/2001 | Baron et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox et al. |
| 6,599,692 | B1 | 6/2003 | Case et al. |
| 6,689,558 | B2 | 2/2004 | Case |
| 6,794,136 | B1 | 9/2004 | Eisenberg et al. |
| 6,903,185 | B2 | 6/2005 | Kim et al. |
| 6,933,113 | B2 | 8/2005 | Case et al. |
| 7,030,215 | B2 | 4/2006 | Liu et al. |
| 7,067,317 | B2 | 6/2006 | Rebar et al. |
| 7,070,934 | B2 | 7/2006 | Cox, III et al. |
| 7,081,564 | B2 | 7/2006 | Somers et al. |
| 7,153,949 | B2 | 12/2006 | Kim et al. |

(Continued)

FOREIGN PATENT DOCUMENTS

| | | |
|---|---|---|
| GB | 2338237 | 8/1998 |
| WO | WO 1993/02197 | 2/1993 |

(Continued)

OTHER PUBLICATIONS

Abe et al., "Molecular Cloning of Cysteine Proteinase Inhibitor of Rice (*Oryzacystatin*)," *J. Biol. Chem.* 262:16793(1987).

(Continued)

*Primary Examiner* — Matthew R Keogh

(74) *Attorney, Agent, or Firm* — Dahna S. Pasternak; Pasternak Patent Law

(57) ABSTRACT

A method of gene editing or gene stacking within a FAD3 loci by cleaving, in a site directed manner, a location in a FAD3 gene in a cell, to generate a break in the FAD3 gene and then ligating into the break a nucleic acid molecule associated with one or more traits of interest is disclosed.

10 Claims, 55 Drawing Sheets

Specification includes a Sequence Listing.

(56) References Cited

U.S. PATENT DOCUMENTS

| | | | | |
|---|---|---|---|---|
| 7,253,273 | B2 | 8/2007 | Collingwood | |
| 7,262,054 | B2 | 8/2007 | Jamieson et al. | |
| 7,361,635 | B2 | 4/2008 | Miller et al. | |
| 8,420,782 | B2 | 4/2013 | Bonas et al. | |
| 8,440,431 | B2 | 5/2013 | Voytas et al. | |
| 9,914,930 | B2 * | 3/2018 | Cogan | C12N 15/8247 |
| 2003/0150020 | A1 | 8/2003 | Somers et al. | |
| 2003/0232410 | A1 | 12/2003 | Liljedahl et al. | |
| 2005/0026157 | A1 | 2/2005 | Baltimore et al. | |
| 2005/0064474 | A1 | 3/2005 | Holmes et al. | |
| 2005/0208489 | A1 | 9/2005 | Carroll et al. | |
| 2006/0188987 | A1 | 8/2006 | Guschin et al. | |
| 2006/0248611 | A1 | 11/2006 | Hu et al. | |
| 2007/0218528 | A1 | 9/2007 | Miller | |
| 2008/0131962 | A1 | 6/2008 | Miller | |
| 2008/0182332 | A1 | 7/2008 | Cai | |
| 2009/0055973 | A1 | 2/2009 | Vrinten et al. | |
| 2009/0068164 | A1 | 3/2009 | Barbas et al. | |
| 2009/0111119 | A1 | 4/2009 | Doyon et al. | |
| 2009/0117617 | A1 | 5/2009 | Holmes et al. | |
| 2009/0205083 | A1 | 8/2009 | Gupta et al. | |
| 2009/0263900 | A1 | 10/2009 | DeKelver et al. | |
| 2010/0047805 | A1 | 2/2010 | Wang | |
| 2010/0199389 | A1 | 8/2010 | Butler et al. | |
| 2011/0145940 | A1 | 6/2011 | Voytas et al. | |
| 2011/0167521 | A1 | 6/2011 | DeKelver et al. | |
| 2011/0189775 | A1 | 8/2011 | Ainley et al. | |
| 2011/0201055 | A1 | 8/2011 | Doyon et al. | |
| 2011/0207221 | A1 | 8/2011 | Cost et al. | |
| 2011/0239315 | A1 | 9/2011 | Bonas et al. | |
| 2011/0281361 | A1 | 11/2011 | DeKelver et al. | |
| 2011/0301073 | A1 | 12/2011 | Gregory et al. | |

FOREIGN PATENT DOCUMENTS

| | | |
|---|---|---|
| WO | WO 1993/19181 | 9/1993 |
| WO | WO 1995/19431 | 7/1995 |
| WO | WO 1996/06166 | 7/1995 |
| WO | WO 1996/30517 | 2/1996 |
| WO | WO 1998/37186 | 2/1996 |
| WO | WO 1998/53057 | 8/1998 |
| WO | WO 1998/53058 | 11/1998 |
| WO | WO 1998/53059 | 11/1998 |
| WO | WO 1998/53060 | 11/1998 |
| WO | WO 1998/54311 | 11/1998 |
| WO | WO 2000/27878 | 12/1998 |
| WO | WO 2001/25453 | 4/2001 |
| WO | WO 2001/60970 | 8/2001 |
| WO | WO 2001/88197 | 11/2001 |
| WO | WO 2002/016536 | 2/2002 |
| WO | WO 2002/077227 | 10/2002 |
| WO | WO 2002/099084 | 12/2002 |
| WO | WO 2003/016496 | 2/2003 |
| WO | WO 2005/100393 | 10/2005 |
| WO | WO 2007/014275 | 2/2007 |
| WO | WO 2010/053541 | 5/2010 |
| WO | WO 2010/079430 | 7/2010 |
| WO | WO 2011/049627 | 4/2011 |
| WO | WO 2011/060946 | 5/2011 |
| WO | WO 2014/039692 | 3/2013 |
| WO | WO 2014/039702 | 3/2013 |
| WO | WO 2014/039872 | 3/2013 |
| WO | WO 2014/039970 | 3/2013 |

OTHER PUBLICATIONS

Ainley et al., "Trait Stacking via Targeted Genome Editing," *Plant Biotechnol. J.* 11(9):1126-1134 (2013).
Alonso et al., "Genome-Wide Insertional Mutagenesis of *Arabidopsis thaliana,*" *Science* 301:653-657 (2003).
ATCC Accession No. 39256 printed on Jan. 12, 2015.
ATCC Accession No. 31995 printed on Feb. 24, 2015.
ATCC Accession No. 31998 printed on Feb. 24, 2015.
ATCC Accession No. 40098 printed on Feb. 24, 2015.
ATCC Accession No. 53435 printed on Jan. 12, 2015.
ATCC Accession No. 67136 printed on Feb. 4, 2015.
ATCC Accession No. 67441 printed on Jan. 12, 2015.
ATCC Accession No. 67442 printed on Jan. 12, 2015.
Baim et al., "A Chimeric Mammalian Transactivator Based on the LAC Repressor That Is Regulated by Temperature and Isopropyl B-D-Thiogalactopyranoside," *PNAS USA* 88(12):5072-5076 (1991).
Barrett et al., "Low Linolenic Acid Level in Rapeseed Can Be Easily Assessed Through the Detection of Two Single Base Substitution in FAD3 Genes," *Proc 10th International Rapeseed Congress,* vol. 26, No. 29.09, p. 1999 (1999).
Beachy, et al., "Coat Protein-Mediated Resistance Against Virus Infection," *Annu. Rev. Phytopathol.* 28:451-474.(1990).
Beerli et al., "Engineering Polydactyl Zinc-Finger Transcription Factors," *Nature Biotechnol.* 20:135-141(2002).
Beerli et al., "Toward Controlling Gene Expression at Will: Specific Regulation of the ERBB-2/HER-2 Promoter by Using Polydactyl Zinc Finger Proteins Constructed From Modular Building Blocks," *PNAS USA* 95(25):14628-14633 (1998).
Bibikova et al., "Stimulation of Gomologous Recombination Through Targeted Cleavage by Chimeric Nucleases," *Mol. Cell. Biol.* 21(1):289-297 (2001).
Bibikova el al., "Enhancing Gene Targeting With Designed Zinc Finger Nucleases," *Science* 300(5620):764 (2003).
Bilyeu et al., "Mutations in Soybean Microsomal Omega-3 Fatty Acid Desaturase Genes Reduce Linolenic Acid Concentration in Soybean Seeds," *Crop Science* 45(5): 1830-1836 (2005).
Bilyeu et al., "Three Microsomal Omega-3 Fatty-Acid Desaturase Genes Contribute to Soybean Linolenic Acid Levels," *Crop Science* 43(5): 1833-1838 (2003).
Bitinate et al., "Foki Dimerization Is Required for DNA Cleavage," *PNAS USA* 95:10570-10575 (1998).
Bocianowski et al., "Determination of Fatty Acid Composition in Seed Oil of Rapeseed (*Brassica napus* L.) by Mutated Alleles of the FAD3 Desaturase Genes," *Journal of Applied Genetics* 53(1): 27-30 (2012).
Bogdanove et al., "Tal Effectors: Customizable Proteins for DNA Targeting," *Science* 333(6051):1843-1846 (2010).
Bonas et al., "Genetic and Structural Characterization of the Avirulence Gene AVRBS3 From *Xanthomonas campestris* pv. *vesicatori," Mol. Gen. Genet.* 218:127-136 (1989).
Botella et al., "Differential Expression of Two Calmodulin Genes in Response to Physical and Chemical Stimuli," *Plant Molec. Biol.* 24(5):757-766 (1994).
Brent and Ptashne, "A Eukaryotic Transcriptional Activator Bearing the DNA Specificity of a Prokaryotic Repressor," *Cell* 43:729-736 (1985).
Browse et al., "Mutants of *Arabidopsis* Deficient in the Synthesis of Alpha-Linolenate," *Biological Chemistry* 268(22):16345-16351 (1993).
Cai et al., "Targeted Transgene Integration in Plant Cells Using Designed Zinc Finger Nucleases," *Plant Mol. Biol.* 69(6):699-709 (2009).
Choo et al., "Advances in Zinc Finger Engineering," *Curr. Opin. Struct. Biol.* 10:411-416 (2000).
Curtin et al., Targeted Mutagenesis of Duplicated Gene in Soybean With Zinc-Finger Nucleases, *Plant Physiology* 156(2):466-473 (2011).
D'Halluin et al., "Homologous Recombination: A Basis for Targeted Genome Optimization in Crop Species Such as Maize," *Plant Biotechnology Journal* 6(1):93-102 (2008).
DeGreef et al., "Evaluation of Herbicide Resistance in Transgenic Crops Under Field Conditions," *Nat Biotechnology* 7:61-64 (1989).
Doyon et al., "Heritable Targeted Gene Disruption in Zebrafish Using Designed Zinc-Finger Nucleases," *Nat. Biotechnol.* 26:702-708 (2008).
Elliott et al.,"Isolation and Characterization of Fruit Vacuolar Invertase Genes From Two Tomato Species and Temporal Differences in MRNA Levels During Fruit Ripening," *Plant Molec. Biol.* 21:515-524 (1993).
Elliston et al., "Superactive Estrogen Receptors," *J. Biol. Chem.* 265:11517-11521(1990).
Fisher et al., "Starch Branching Enzyme II From Maize Endosperm," *Plant Physiol.* 102:1045-1046 (1993).

(56) References Cited

OTHER PUBLICATIONS

Geiser et al., "The Hypervariable Region in the Genes Coding for Entomopathogenic Crystal Proteins of Bacillus Thuringiensis: Nucleotide Sequence of the KURHD1 Gene of Subsp. *kurstaki* HD1," *Gene* 41:109 (1986).
Genbank Accession No. At2g29980 (Sep. 18, 2002).
Genbank Accession No. AAS02365 2 pages (Jan. 31, 2014).
Genbank Accession No. HM138371 2 pages (Mar. 18, 2011).
Genbank Accession No. JN992610 2 pages (May 12, 2012).
Genbank Accession No. JN992611 3 pages (May 12, 2012).
Genbank Accession No. JN992612 2 pages (May 12, 2012).
Genbank Accession No. JN992613 2 pages (May 12, 2012).
Genbank Accession No. JN992614 2 pages (May 12, 2012).
Genbank Accession No. JN992615 2 pages (May 12, 2012).
Genbank Accession No. JN992616 2 pages (May 12, 2012).
Genbank Accession No. JN992617 2 pages (May 12, 2012).
Guerts et al., "Knockout Rats via Embryo Microinjection of Zinc-Finger Nucleases," *Science* 325(5939):433 (2009).
Griess et al., "Isolation and Sequence Comparison of a Maize Calmodulin CDNA," *Plant Physiol.* 104:1467-1468 (1994).
Haft et al., "A Guild of 45 CRISPR-Associated (CAS) Protein Families and Multiple CRISPR/CAS Subtypes Exist in Prokaryotic Genomes," *PLoS Comput. Biol.* 1:e60 (2005) <http://www.jcvi.org/cms/nc/publications/listing/browse/3/article//Haft/#sthash.bXXP6pOi.dpuf>.
Hammock et al., "Expression and Effects of the Juvenile Hormone Esterase in a Baculovirus Vector," *Nature* 344:458-461 (1990).
Hayes et al., "Molecular Cloning and Heterologous Expression of a CDNA Encoding a Mouse Glutathione S-Transferase YC Subunit Possessing High Catalytic Activity for Aflatoxin B1-8,9-Epoxide," *Biochem. J.* 285:173-180 (1992).
Heuer et al., "Repeat Domain Diversity of AVRBS3-Like Genes in Ralstonia Solanacearum Strains and Association With Host Preferences in the Field," *Appl. and Envir. Micro.* 73(13):4379-4384 (2007).
Hu et al., "Mapping of the Loci Controlling Oleic and Linolenic Acid Contents and Development of FAD2 and FAD3 Allele-Specific Markers in Canola (*Brassica napus* L)," *Theoretical and Applied Genetics* 113(3):497-507 (2006).
Huub et al., "Tobacco Proteinase Inhibitor I Genes Are Locally, but Not Systemically Induced by Stressm" *Plant Mol. Biol.* 21:985-992 (1993).
Isalan et al., "A Rapid, Generally Applicable Method to Engineer Zinc Fingers Illustrated by Targeting the HIV-1 Promoter," *Nature Biotechnol.* 19:656-660 (2001).
Jagannath, et al., "Eliminating Expression of Erucic Acid-Encoding Loci Allows the Identification of "Hidden" QTL Contributing to Oil Quality Fractions and Oil Content in *Brassica juncea* (Indian Mustard)" *Theoretical and Applied Genetics* 122(6):1091-1103 (2011).
Jansen et al., "Identification of Genes That Are Associated With DNA Repeats in Prokaryotes," *Mol. Microbiol.* 43:1565-1575 (2002).
Jaynes et al., "Expression of a Cecropin B Lytic Peptide Analog in Transgenic Tobacco Confers Enhanced Resistance to Bacterial Wilt Caused by Pseudomonas Solanacearum," *Plant Sci.* 89:43-53 (1993).
Jones et al., "Isolation of the Tomato CF-9 Gene for Resistance to Cladosporiu Fulvum by Transposon Tagging," *Science* 266:789-793 (1994).
Kawelleck et al., "Polyubiquitin Gene Expression and Structural Properties of the UBI4-2 Gene in Petroselinum Crispum," *Plant Molec. Biol.* 21:673-684 (1993).
Kay et al., "A Bacterial Effector Acts as a Plant Transcription Factor and Induces a Cell Size Regulator," *Science* 318:648-651 (2007).
Kim and Pabo, "Getting a Handhold on DNA: Design of Poly-Zinc Finger Proteins With Femtomolar Dissociation Constants," *PNAS USA* 95:2812-2817 (1998).
Knutzon, et al., "Modification of *Brassica* Seed Oil by Antisense Expression of a Stearoyl-Acyl Carrier Protein Desaturase Gene," *Proc. Natl. Acad. Sci. U.S.A.*, 89:2624-2628 (1992).
Kramer et al., "Sequence of a CDNA and Expression of the Gene Encoding Epidermal and Gut Chitinases of Manduca Sexta," *Insect Biochem. Molec. Biol.* 23:691(1993).
Kumar and Fladung, "Controlling Transgene Integration in Plants," *Trends Plant Sci.* 6:155-159 (2001).
Labow et al., "Conversion of the LAC Repressor Into an Allosterically Regulated Transcriptional Activator for Mammalian Cells," *Mol. Cell Biol.* 10(7):3343-3356 (1990).
Lamb et al., "Emerging Strategies for Enhancing Crop Resistance to Microbial Pathogens," *Bio/Technology* 10(11):1436-1445 (1992).
Le et al., "Simultaneous Generation and Germline Transmission of Multiple Gene Mutations in Rat Using CRISPR-CAS Systems," *Nature Biotechnology* 31:684-686 (2013).
Lee et al., "The Molecular Basis of Sulfonylurea Herbicide Resistance in Tobacco," *EMBO J.* 7(5):1241 (1988).
Li et al., "Stacking Multiple Transgenes at a Selected Genomix Site via Repeated Recombinase-Mediate DNA Cassette Exchanges," *Plant Physiology* 154(2):622-631 (2010).
Liu et al., "Design of Polydactyl Zinc-Finger Proteins for Unique Addressing Within Complex Genomes," *PNAS USA* 94:5525-5530 (1997).
Logemann et al., "Expression of a Barley Ribosome-Inactivating Protein Leads to Increased Fungal Protection in Transgenic Tobacco Plants," *Bio/Technology* 10:305-308 (1992).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct.* 1:7 (2006).
Makarova et al., "A DNA Repair System Specific for the Thermophilic Archaea and Bacteria Predicted by Genomic Context Analysis," *Nucleic Acids Res.* 30:482-496 (2002).
Mani et al., "Binding of Two Zinc Finger Nuclease Monomers to Two Specific Sites Is Required for Effective Double-Strand DNA Cleavage," *Biochem. Biophys. Res. Commun.* 334:1191-1197 (2005).
Marshall et al., "Allelic Mutations in Acetyl-Coenzyme A Carboxylase Confer Herbicide Tolerance in Maize," *Theor. Appl. Genet.* 83:435-442 (1992).
Martin et al., "Map-Based Cloning of a Protein Kinase Gene Conferring Disease Resistance to Tomato," *Science* 262:1432-1436 (1993).
Miki et al., "Transformation of *Brassica napus* Canola Cultivars With *Arabidopsis thaliana* Acetohydroxy Acid Synthase Genes and Analysis of Herbicide Resistance," *Theor. Appl. Genet.* 80:449 (1990).
Mikolajczyk et al., "Allele-Specific SNP Markers for the New Low Linolenic Mutant Genotype of Winter Oilseed Rape," *Plant Breeding* 129(5): 502-507 (2010).
Mindrinos et al., "The *A. thaliana* Disease Resistance Gene RPS2 Encodes a Protein Containing a Nucleotide-Binding Site and Leucine-Rich Repeats," *Cell* 78:1089 (1994).
Moehle et al., "Targeted Gene Addition Into a Specified Location in the Human Genome Using Designed Zinc Finger Nucleases," *Proc. Natl. Acad. Sci. USA* 104(9):3055-3060 (2007).
Nekrasov et al., "Targeted Mutagenesis in the Model Plant *Nicotiana benthamiana* Using CAS9 RNA-Guided Endonuclease," *Nature Biotechnology* 31:691-693 (2013).
Pabo et al., "Design and Selection of Novel CYS2HIS2 Zincfinger Proteins," *Ann. Rev. Biochem.* 70:313-340(2001).
Pang et al., "Expression of a Gene Encoding Scorpion Insectotoxin Peptide in Yeast, Bacteria, and Plants," *Gene* 116:165-172 (1992).
Paszkowski et al., "Gene Targeting in Plants," *EMBO J.* 7:4021-4026(1988).
Pen et al., "Production of Active Bacillus Licheniformis Alpha-Amylase in Tobacco and Its Application in Starch Liquefaction," *Bio/Technology* 10:292 (1992).
Prakash and Hinata, "Taxnomy, Cytogenetics and Origin of Crop *Brassicas*—A Review," *Opera Botanica* 55:1-57 (1980).
Przibila et al., "Site-Specific Mutagenesis of the D1 Subunit of Photosystem II in Wild-Type Chlamydomonas," *Plant Cell* 3:169-174 (1991).

(56) References Cited

OTHER PUBLICATIONS

Puchta et al., "Homologous Recombination in Plant Cells Is Enhanced by In Vivo Induction of Double Strand Breaks Into DNA by a Site-Specific Endonuclease," *Nucleic Acid Research* 21:5034-5040 (1993).
Raboy et al., "A Survey of Maize Kernel Mutants for Variation in Phytic Acid," *Maydica* 35:383-390 (1990).
Regan, "Expression Cloning of an Insect Diuretic Hormone Receptor. A Member of the Calcitonin/Secretin Receptor Family," *J. Biol. Chem.* 269:9-12 (1994).
Rucker et al, "Impact of Low Linolenic Acid Content on Seed Yield of Winter Oilseed Rape (*Brassica napus* L.)," *Plant Breeding* 115(4): 226-230 (2012).
Scheffler et al., "Desaturase Multigene Families of *Brassica napus* Arose Through Genome Duplication," *TAG* 94(5):583-591 (1997).
Schierholt et al., "Inheritance of High Oleic Acid Mutations in Winter Oilseed Rape (*Brassica napus* L.)," *Crop Sci.* 41:1444-1449(2001).
Schierholt et al., "Mapping a High Oleic Acid Mutation in Winter Oilseed Rape (*Brassica napus* L.)" *Theoretical and Applied Genetics* 101(5-6):897-903 (2000).
Schornack et al., "Gene-for-Gene-Mediated Recognition of Nuclear-Targeted AVRBS3-Like Bacterial Effector Proteins," *J. Plant Physiol.* 163(3):256-272 (2006).
Schranz et al., "The ABC's of Comparative Genomics in the *Brassicaceae*: Building Blocks of Crucifer Genomes," *Trends in Plant Sciences* 11(11):535-542 (2006).
Segal, "Custom DNA-Binding Proteins Come of Age:Polydactyl Zinc-Finger Proteins," *Curr. Opin. Biotechnol.* 12:632-637 (2001).
Shan et al., "Targeted Genome Modification of Crop Plants Using a CRISPR-CAS System," *Nature Biotechnology* 31:686-680 (2013).
Shiroza et al., "Sequence Analysis of the *Streptococcus mutans* Fructosyltransferase Gene and Flanking Regions," *J. Bacteriol.* 170(2):810-816 (1988).
Shukla et al., "Precise Genome Modification in the Crop Species *Zea mays* Using Zinc-Finger Nucleases," *Nature* 459:437-441 (2009).
Siebert and Puchta, "Efficient Repair of Genomic Double-Strand Breaks by Homologous Recombination Between Directly Repeated Sequences in the Plant Genome," *Plant Cell* 14:1121-1131 (2002).
Smith et al., "Requirements for Double-Strand Cleavage by Chimeric Restriction Enzymes With Zinc Finger DNA-Recognition Domains," *Nucleic Acids Res.* 28:3361-3369 (2000).
Sogaard et al., "Site-Directed Mutagenesis of Histidine 93, Aspartic Acid 180, Glutamic Acid 205, Hisitidine 290, and Aspartic Acid 291 at the Active Site and Tryptophan 279 at the Raw Starch Binding Site in Barley A-Amylase 1," *J. Biol. Chem.* 268:22480 (1993).
Song et al., "Polyphyletic Origins of *Brassica napus*: New Evidence Based on Organelle and Nuclear RFLP Analyses," *Genome* 35:992-1001 (1992).
Song et al., "A Linkage Map of *Brassica rapa* (Syn. Campestris) Based on Restriction Fragment Length Polymorphism Loci," *Theor. Appl. Genet.* 82:296-304 (1991).
Steinmetz et al., "The DNA Sequence of the Gene for the Secreted *Bacillus subtilis* Enzyme Levansucrase and Its Genetic Control Sites," *Mol. Gen. Genet.* 20:220 (1985).
Sumitani et al., "Molecular Cloning and Expression of Proteinaceous Alpha-Amylase Inhibitor Gene From Streptomyces Nitrosporeus in *Escherichia coli," Biosci. Biotech. Biochem.* 57(8):1243-1248 (1993).
Tanhuanpaa et al., "Mapping and Cloning of FAD2 Gene to Develop Allele-Specific PCR for Oleic Acid in Spring Turnip Rape (*Brassica rapa* ssp. *oleifera*)," *Mol. Breed.* 4:543-550 (1998).
Tavladoraki et al., "Transgenic Plants Expressing a Functional Single-Chain FV Antibody Are Specifically Protected From Virus Attack," *Nature* 366:469 (1993).
Taylor et al., "An Unusual Repetitive Element From Highly Virulent Isolates of Leptosphaeria Maculans and Evidence of Its Transfer to a Weakly Virulent Isolate," *Mol Plant Microbe Interact* 7(2):181-188 (1994).
Terada et al., "Efficient Gene Targeting by Homologous Recombination in Rice," *Nat. Biotechnol.* 20(10):1030 (2002).
Terada et al., "Gene Targeting by Homologous Recombination as a Biotechnological Tool for Rice Functional Genomics," *Plant Physiol.* 144(2):846 (2007).
Toubart et al., "Cloning and Characterization of the Gene Encoding the Endopolygalacturonase-Inhibiting Protein (PGIP) of *Phaseolus vulgaris* L," *Plant J.* 2:367 (1992).
Townsend et al., "High Frequency Modification of Plant Genes Using Engineered Zinc-Finger Nucleaes," *Nature* 459(7245):442-445 (2009).
Urnov et al., "Genome Editing With Engineered Zinc Finger Nucleases," *Nature* 435(7042):646-651(2010).
Urnov et al., "Highly Efficient Endogenous Human Gene Correction Using Designed Zinc-Finger Nucleases," *Nature* 435:646-651 (2005).
Van Damme et al., "Molecular Cloning of Mannose-Binding Lectins From Clivia Minata," *Plant Molecular Biology* 24:825-830 (1994).
Van Hartingsveldt et al., "Cloning, Characterization and Overexpression of the Phytase-Encoding Gene (PHYA) of Aspergillus Niger," *Gene* 127:87-94 (1993).
Vrinten et al., "Two FAD3 Desaturase Genes Control the Level of Linolenic Acid in Flax Seed," *Plant Physiology* 139(1): 79-87 (2005).
Wah et al., "Structure of Foki Has Implications for DNA Cleavage," *PNAS* 95:10564-10569 (1998).
Wang et al. "A Regulatory System for Use in Gene Transfer," *PNAS* 91(17):8180-8184 (1994).
Wilcox et al., "Relationships Between the Fan Allele and Agronomic Traits in Soybean," *Crop Science* 33(1): 87-89 (1993).
Yang et al., "Identification of FAD2 and FAD3 Genes in *Brassica napus* Genome and Development of Allele-Specific Markers for High Oleic and Low Linolenic Acid Contents," *Theoretical and Applied Genetics* 125(4):715-729 (2012).

* cited by examiner

```
                                 1                                      40
 FAD3A (SEQ ID NO:7)      (1)  CATCAGACCCTTTCTTCACCACATTTCACTCAGAGCCCAC
 FAD3A' (SEQ ID NO:8)     (1)  CATCGAACCCTTTCTTCACCACATTCCACTTCCCACACTC
 FAD3C' (SEQ ID NO:12)    (1)  CATCGAACCCTTTCTTCACCACATTCCAGTTCCCACACTT
 FAD3A'' (SEQ ID NO:9)    (1)  CATCAAAC-CTTTCTTCACCACATTTCACTGAAAGGCCAC
 FAD3C'' (SEQ ID NO:11)   (1)  CATCAAAC-CTTTATTCACCACATTTCACTGAAAGGCCAC
 FAD3C (SEQ ID NO:10)     (1)  CATCAAA--CTCTCTCCACCACATTTCACTCAGAGCCCAC
                                 41                                     80
 FAD3A (SEQ ID NO:7)     (41)  ACAGTTTTAG------AGAGAGAGAGAAACATCCCTCAAA
 FAD3A' (SEQ ID NO:8)    (41)  TCTTTTTTTTTGAATTATAGAGAGAGAATCCTCCTCCAAA
 FAD3C' (SEQ ID NO:12)   (41)  TCTTTTTTTT-GAATTATAGAGAGAGAATCTTCCTCCAAA
 FAD3A'' (SEQ ID NO:9)   (40)  ACATCT----------AGAGAGAGA--AACTTCGTCCAAA
 FAD3C'' (SEQ ID NO:11)  (40)  ACATCT----------AGAGAGAGA--AACTTCGTCCAAA
 FAD3C (SEQ ID NO:10)    (39)  ACAGTTTTAG------AGAGAGAGA--AACATCCCTCAAA
                                 81                                    120
 FAD3A (SEQ ID NO:7)     (75)  GCTCTCTCTCTTTCTCCGGCGATGGTTGTCGCTATGGACC
 FAD3A' (SEQ ID NO:8)    (81)  TCTCTCTCTCTC----CCAGGATGGTTGTTGCTATGGACC
 FAD3C' (SEQ ID NO:12)   (80)  TCTCTCTCTCTCTCTCCCAGGATGGTTGTTGCTATGGACC
 FAD3A'' (SEQ ID NO:9)   (68)  TCTCTCTC------TCCAGCAATGGTTGTTGCTATGGACC
 FAD3C'' (SEQ ID NO:11)  (68)  TCTCTCTC------TCCAGCGATGGTTGTTGCTATGGACC
 FAD3C (SEQ ID NO:10)    (71)  GCTCTCTC--TTTCTCCGGCGATGGTTGTCGCTATGGACC
                                 121                                   160
 FAD3A (SEQ ID NO:7)    (115)  AGCGTAGCAATGCGAACGGAGA------------------
 FAD3A' (SEQ ID NO:8)   (117)  AACGCACCAATGTGAACGGAGATGCCGGTGCCCGGAAGGA
 FAD3C' (SEQ ID NO:12)  (120)  AACGCACCAATGTGAACGAAGATGCCGGTGCCCGGAAGGA
 FAD3A'' (SEQ ID NO:9)  (102)  AGCGCAGCAATGTTAACGGAGATTCCGGTGCCCGGAAGGA
 FAD3C'' (SEQ ID NO:11) (102)  AGCGCAGCAATGTTAACGGAGATTCCGGTGCCCGGAAGGA
 FAD3C (SEQ ID NO:10)   (109)  AGCGTAGCAATGTGAACGGAGATTCC---------AAGGA
                                 161                                   200
 FAD3A (SEQ ID NO:7)    (137)  CGAAAGGTTTGATCCGAGCGCACAACCACCGTTCAAGATC
 FAD3A' (SEQ ID NO:8)   (157)  AGAAGGGTTTGATCCGAGCGCACAACCGCCGTTTAAGATC
 FAD3C' (SEQ ID NO:12)  (160)  AGAAGGGTTTGATCCGAGCGCACAACCGCCGTTTAAGATC
 FAD3A'' (SEQ ID NO:9)  (142)  AGAAGGGTTTGATCCAAGCGAACAACCACCGTTTAAGATC
 FAD3C'' (SEQ ID NO:11) (142)  AGAAGGGTTTGATCCAAGCGCACAACCACCGTTTAAGATC
 FAD3C (SEQ ID NO:10)   (140)  CGAAAGGTTTGATCCGAGCGCACAACCACCGTTTAAGATC
                                 201                                   240
 FAD3A (SEQ ID NO:7)    (177)  GGAGATATAAGGGCGGCCATTCCTAAGCATTGTTGGGTAA
 FAD3A' (SEQ ID NO:8)   (197)  GGGGACATAAGGGCTGCGATTCCTAAGCATTGTTGGGTGA
 FAD3C' (SEQ ID NO:12)  (200)  GGGGACATAAGGGCTGCGATTCCTAAGCATTGTTGGGTGA
```

FIG. 1A

```
FAD3A'' (SEQ ID NO:9)   (182) GGAGATATCAGGGCGGCGATTCCTAAGCATTGTTGGGTGA
FAD3C'' (SEQ ID NO:11)  (182) GGAGATATAAGGGCGGCGATTCCTAAGCATTGCTGGGTGA
  FAD3C (SEQ ID NO:10)  (180) GGAGATATAAGGGCTGCGATTCCTAAGCATTGTTGGGTCA
                              241                                   280
   FAD3A (SEQ ID NO:7)  (217) AGAGTCCTTTGAGATCCATGAGCTATGTCGCCAGAGACAT
  FAD3A' (SEQ ID NO:8)  (237) AAAGTCCTTTGAGATCTATGAGCTACGTAGCCAGAGACAT
 FAD3C' (SEQ ID NO:12)  (240) AAAGTCCTTTGAGATCTATGAGCTACGTAGCCAGAGACAT
 FAD3A'' (SEQ ID NO:9)  (222) AGAGTCCTTTGAGATCTATGAGCTACGTCGCCAGAGACAT
FAD3C'' (SEQ ID NO:11)  (222) AGAGTCCTTTGAGATCTATGAGCTACGTCGCCAGAGACAT
  FAD3C (SEQ ID NO:10)  (220) AGAGTCCTTTGAGATCCATGAGCTACGTCGCGAGAGACAT
                              281                                   320
   FAD3A (SEQ ID NO:7)  (257) TTTCGCCGTCGTGGCTCTTGCCGTCGCCGCCGTGTATTTT
  FAD3A' (SEQ ID NO:8)  (277) TTGTGCCGTCGCGGCTTTGGCCATTGCCGCCGTGTATTTT
 FAD3C' (SEQ ID NO:12)  (280) TTGTGCCGTCGCTGCTTTGGCCATTGCCGCCGTGTATTTT
 FAD3A'' (SEQ ID NO:9)  (262) TTTCGCCGTCGCGGCTCTGGCCATGGCCGCCGTGTATTTT
```

FIG. 1A (CONT.)

```
FAD3C'' (SEQ ID NO:11)  (262) TTTCGCCGTCGCGGCTCTGGCCATGGCCGCCGTGTATTTT
  FAD3C (SEQ ID NO:10)  (260) TTTCTCCGTCGTGGCTCTGGCCGTCGCCGCCGTGTATTTT
                              321                                   360
   FAD3A (SEQ ID NO:7)  (297) GATAGCTGGTTCTTTTGGCCTCTTTATTGGGCCGCCCAAG
  FAD3A' (SEQ ID NO:8)  (317) GATAGCTGGTTCCTCTGTCCTCTCTATTGGGTCGCCCAAG
 FAD3C' (SEQ ID NO:12)  (320) GATAGCTGGTTCCTCTGGCCTCTCTATTGGGTCGCCCAAG
 FAD3A'' (SEQ ID NO:9)  (302) GATAGCTGGTTCCTCTGGCCACTCTACTGGGTTGCCCAAG
FAD3C'' (SEQ ID NO:11)  (302) GATAGCTGGTTCCTCTGGCCACTCTACTGGGTTGCCCAAG
  FAD3C (SEQ ID NO:10)  (300) GATAGCTGGTTCTTCTGGCCTCTTTATTGGGCCGCCCAAG
                              361                                   400
   FAD3A (SEQ ID NO:7)  (337) GAACCCTGTTCTGGGCTATCTTCGTACTCGGCCACGACTG
  FAD3A' (SEQ ID NO:8)  (357) GAACCCTTTTCTGGGCCATCTTCGTCCTCGGCCACGACTG
 FAD3C' (SEQ ID NO:12)  (360) GAACCCTTTTCTGGGCCATCTTCGTCCTCGGCCACGACTG
 FAD3A'' (SEQ ID NO:9)  (342) GAACCCTTTTCTGGGCCATCTTCGTTCTTGGCCACGACTG
FAD3C'' (SEQ ID NO:11)  (342) GAACCCTTTTCTGGGCCATCTTCGTTCTTGGCCACGACTG
  FAD3C (SEQ ID NO:10)  (340) GAACCCTTTTCTGGGCCATCTTCGTACTCGGCCACGACTG
                              401                                   440
   FAD3A (SEQ ID NO:7)  (377) GTAATTTAATTTT-----------TCTTTCAACTTCTTAA
  FAD3A' (SEQ ID NO:8)  (397) GTAA----AGTTT---------------------------
 FAD3C' (SEQ ID NO:12)  (400) GTAA----AGTTT---------------------------
 FAD3A'' (SEQ ID NO:9)  (382) GTAAATTAAATTT-----------------------TCTG
FAD3C'' (SEQ ID NO:11)  (382) GTAAATTAAATTT-----------------------TCAG
  FAD3C (SEQ ID NO:10)  (380) GTAATTTAATTTTCAATTTATTTTTCTTCAACTTCTTAA
                              441                                   480
```

FIG. 1B

```
FAD3A (SEQ ID NO:7)    (406) TTTTGATATGTTTATATGTTTTTTTCGTTTTTTGCATTGT
  FAD3A' (SEQ ID NO:8)    (406) CTTCCAT-----------------------TTTGCATTGC
 FAD3C' (SEQ ID NO:12)    (409) CTTCCAT-----------------------TTTGCATTGC
 FAD3A'' (SEQ ID NO:9)    (399) TTTTAAT-------TATTTTGACT-CTTTTTGTTCAATTT
FAD3C'' (SEQ ID NO:11)    (399) TTTTAAT-------TATTTTGTCT-CTTTTTGTTCAATTT
  FAD3C (SEQ ID NO:10)    (420) TTTTGATATGTTTATATGTTTTTT-CGTTTTTTGCATCGT
                                481                                  520
   FAD3A (SEQ ID NO:7)    (446) CTTTGATTTCTTGACCGTACGTTCGATATGAGATTTTC--
  FAD3A' (SEQ ID NO:8)    (423) ATCG-ATTTATTGAATGCACGTTCTACGAGT-ATTGTTTG
 FAD3C' (SEQ ID NO:12)    (426) ATCG-ATTTATTGAATGCACGTTCTATGAGT-ATTGT---
 FAD3A'' (SEQ ID NO:9)    (431) ATTA-ATTTCTTGAATGCACGTTCGATGAGT-ATCGTCGT
FAD3C'' (SEQ ID NO:11)    (431) ATTA-ATTTCTTGAATGCACGTTCGATGAGT-ATCGTC--
  FAD3C (SEQ ID NO:10)    (459) CTTTGATTTCTTGAACGCACGTTCGATATGAGATTTTC--
                                521                                  560
   FAD3A (SEQ ID NO:7)    (484) --ACTGACTTCAAGATTTGATTCTCTTCAGGTTTACTTTT
  FAD3A' (SEQ ID NO:8)    (461) TCAGTTACTTCGTAAAATGATTCTTTTGATGTTCATTTTT
 FAD3C' (SEQ ID NO:12)    (461) -CAGT-ACTTTATGAATTGATTCTTTTGATGTTCATTTTT
 FAD3A'' (SEQ ID NO:9)    (469) -CACTGACTTCAAGATTTAATTCTTTTGAGGTT-ACCTTT
FAD3C'' (SEQ ID NO:11)    (467) --ACTGACTTCAAGATTTAATTCTTTTGAGGTT-ACTTTT
  FAD3C (SEQ ID NO:10)    (497) --ACTGACTTCAAGATTTGATTCTCTTCAGGTTTACTTTT
                                561                                  600
   FAD3A (SEQ ID NO:7)    (522) TTCAATTTTAATTATTATGTTCATCCAATTTGGCCTATTT
  FAD3A' (SEQ ID NO:8)    (501) TGAAGATCTAAG-ATTT--------------------TTT
 FAD3C' (SEQ ID NO:12)    (499) TGAAGATCTAAG-ATTT--------------------TTT
 FAD3A'' (SEQ ID NO:9)    (507) T-CATGTTCAATTATTA---------AA--------AAAT
FAD3C'' (SEQ ID NO:11)    (504) T-CATGTTTAATTATTA---------AA--------AAAT
  FAD3C (SEQ ID NO:10)    (535) AAAAAAAAAAATTATTATGTTCACCCAAATTGGCCTATTT
                                601                                  640
   FAD3A (SEQ ID NO:7)    (562) TAAAAGCAAAAGGGGATCTAAGATTTTTAATTCTTTTGTT
  FAD3A' (SEQ ID NO:8)    (520) T---------------TTT-AGATTTTCT-TTTTAAATCA
 FAD3C' (SEQ ID NO:12)    (518) T---------------TTTTAGATTTTCT-TTTTAAATCA
```

FIG. 1B (CONT.)

```
FAD3A'' (SEQ ID NO:9)   (529) AAAATAAAATATAGGATCTAAGATTTTT--TTCTTCATCA
FAD3C'' (SEQ ID NO:11)  (526) AAAAGAAAATATAGGATCTAAGATTTTT--TTCTTCATCA
FAD3C (SEQ ID NO:10)    (575) TAAAAGCAAAAGGGGATCTAAGATTTTTAATTCTTCTCTT
                              641                                   680
FAD3A (SEQ ID NO:7)     (602) TTTTTTTGGT---------------TCTTTTTCATCAG-T
FAD3A' (SEQ ID NO:8)    (543) TTGTTCCACCACCA-------------CCTTTCATCGG-T
FAD3C' (SEQ ID NO:12)   (542) TTGTTCCACCACC----------------TTTCATCGG-T
FAD3A'' (SEQ ID NO:9)   (567) --GTTCAAGCA-------------TCATCACTCATCAG-T
FAD3C'' (SEQ ID NO:11)  (564) ATGTTCAAGCA-------------TCGTCACTCATCAG-T
FAD3C (SEQ ID NO:10)    (615) TTTCAGTCGTAACACTGCTAACTTTTTTTTTTGATCAAAT
                              681                                   720
FAD3A (SEQ ID NO:7)     (626) CGTAACACTC-------CTAACTAAACATCTTTTTCTTTC
FAD3A' (SEQ ID NO:8)    (569) CGTACGACTC----GTTACAACACCACATCTT--TATTTT
FAD3C' (SEQ ID NO:12)   (565) CGTACGACTC----GTTACAAAACCACATCTT--TATTTT
FAD3A'' (SEQ ID NO:9)   (591) CGTAAGACTC-------GTAACAAAATATCTT---CTTTT
FAD3C'' (SEQ ID NO:11)  (590) CGTCAGACTC-------GTAACAAAATATCTT---CTTTT
FAD3C (SEQ ID NO:10)    (655) CGTAACACTCATAAGTCCTAACTAAACATCTTTTTCTTTC
                              721                                   760
FAD3A (SEQ ID NO:7)     (659) CTATAATTATTGTTGTTTCCGCGTTTTATGGATCTACGTT
FAD3A' (SEQ ID NO:8)    (603) CTATAATTACTACTGCTTCCGCATTTTATGGATCTCTCAA
FAD3C' (SEQ ID NO:12)   (599) CTATAATTACGACTGCTTCCGCATTTTATGGATCTCTCAA
FAD3A'' (SEQ ID NO:9)   (621) CTATAATTAATATTATTTCCGCATTTAATGGATCTACGTT
FAD3C'' (SEQ ID NO:11)  (620) CTATAATTAATATTATTTCCGCATTTTATGGATCTACGTT
FAD3C (SEQ ID NO:10)    (695) CTATAATTATTGTTGGTTCCGCATTTTATGGATCTACGTT
                              761                                   800
FAD3A (SEQ ID NO:7)     (699) T-GAAATTTTCAA------------------TAAAAC---
FAD3A' (SEQ ID NO:8)    (643) CTTATAATTAAAG------------------TATAATATC
FAD3C' (SEQ ID NO:12)   (639) CTTATAATTAAAG------------------TATAAAATC
FAD3A'' (SEQ ID NO:9)   (661) TTGATGTTCTCAAATTTTGTTTCTCTTTCTCTAGATCCCC
FAD3C'' (SEQ ID NO:11)  (660) TTGATGTTCTCAATTTTTGTTTCTCTTTCTCTAGATCCCC
FAD3C (SEQ ID NO:10)    (735) T-GAAAGTTTCAA------------------TAAAAC---
                              801                                   840
FAD3A (SEQ ID NO:7)     (717) ---ACATTTTATTGTT-TTCT-GTA----ACAATTT----
FAD3A' (SEQ ID NO:8)    (665) AAGAATATCTATTATTTTTCTTAAACAAGA-AAGAT----
FAD3C' (SEQ ID NO:12)   (661) AAGAATATCTATTGTTTTTCTAAAACAAGA-AAGAT----
FAD3A'' (SEQ ID NO:9)   (701) GGAACTTTTAATTATAATTATAGTATAGTATAATATCAAG
FAD3C'' (SEQ ID NO:11)  (700) GGAACTTTTAATTATAATTATAGTATAGTATAATATCAAG
FAD3C (SEQ ID NO:10)    (753) ---ACATTTTATTGTT-TGAAAGTA----ACAATAT----
                              841                                   880
```

FIG. 1C

```
  FAD3A (SEQ ID NO:7)    (744) --AAT-TACTGTTTATTGGTTC------------------
 FAD3A' (SEQ ID NO:8)    (700) --AAT--ATTGTTTCTTTGTTA------------------
FAD3C' (SEQ ID NO:12)    (696) --AAT--ATTGTTTCTTTGTTA------------------
FAD3A'' (SEQ ID NO:9)    (741) AAAATATACTGTTTATTTTTTTTGGCAACAAATATATTAC
FAD3C'' (SEQ ID NO:11)   (740) AAAATATACTGTTTATTTTTTT-GGCAACAAATATATT--
 FAD3C (SEQ ID NO:10)    (781) --AAT-TACTGTATATTGATTC------------------
                               881                                  920
  FAD3A (SEQ ID NO:7)    (763) ----TTTT----------------A-----------ATTA
 FAD3A' (SEQ ID NO:8)    (718) -------------------------------------TTT
FAD3C' (SEQ ID NO:12)    (714) -------------------------------------TTT
FAD3A'' (SEQ ID NO:9)    (781) TCTTGTTTCTTTGACAAGAAAAAAATATATTGTTTTTTTC
FAD3C'' (SEQ ID NO:11)   (777) ----GTTT-TTTGACAAGAAAAA--TATATTGTTTTTTTC
 FAD3C (SEQ ID NO:10)    (800) ----TTTT----------------A-----------ATTA
                               921                                  960
  FAD3A (SEQ ID NO:7)    (772) TTGTGTGT-TGTTCCAATCTATTTTCGAAATATAGTCATG
 FAD3A' (SEQ ID NO:8)    (721) TGGTGTAT---TTCCAATCTA-TTTCGAGATTTAGAAATG
```

FIG. 1C (CONT.)

```
FAD3C' (SEQ ID NO:12)    (717) TGGTGTAT---T-CCAATCTA-TTTCGAGATTTAGAAATG
 FAD3A'' (SEQ ID NO:9)   (821) TTCTTTTTGTGTTCCAATCTATTTTCGAGATTTAGACAAG
FAD3C'' (SEQ ID NO:11)   (810) TTCTTTTTGTGTTCCAATCTATTTT-GTGATTTAGACAAG
  FAD3C (SEQ ID NO:10)   (809) TTGTGTGT-TGTTCCAATCTACTTTCGAAATATAGTCATG
                               961                                 1000
   FAD3A (SEQ ID NO:7)   (811) TGACACGTCATATTCTATTTTTGTTACCTTGTTGAAACGT
  FAD3A' (SEQ ID NO:8)   (757) TGACACGTCAT-------------TACCTTGTTGAAGTGT
 FAD3C' (SEQ ID NO:12)   (752) TGTCACGTCAT-------------TACCTTGTTGAAGCTT
 FAD3A'' (SEQ ID NO:9)   (861) TGACACGTCATATACCGGATTTGTTACCTTGTTAAAGAGT
FAD3C'' (SEQ ID NO:11)   (849) TGACACGTCATATACCGGATTTGTTACCTTGTTAAAGAGT
  FAD3C (SEQ ID NO:10)   (848) TGACACGTCATATTCTATTTTTGTTACCTTGTTGGAACGT
                               1001                                1040
   FAD3A (SEQ ID NO:7)   (851) TTG----------AATTGAGGAAAGTTCAGTTAACATTGT
  FAD3A' (SEQ ID NO:8)   (784) TTA------AAACAAACATGGAAAGTTTAAATAA-ATAGT
 FAD3C' (SEQ ID NO:12)   (779) TTA------AAACAAACATGGAAAGTTTAAATAA-ATAGT
 FAD3A'' (SEQ ID NO:9)   (901) TTGGGTTAAAACAAATGTAGAAAAGTTAAAATAA-ATTGT
FAD3C'' (SEQ ID NO:11)   (889) TTGAGTTAAAACAAATGTAGAAAAGTTAAAATAA-ATTGT
  FAD3C (SEQ ID NO:10)   (888) TTG----------AATTGAGTAAAGTTTAATTAACATTGT
                               1041                                1080
   FAD3A (SEQ ID NO:7)   (881) GCAATAAATGATAAA-TGTGTTT------------ATGAT
  FAD3A' (SEQ ID NO:8)   (817) GCAATAAATGATATA-TATGTAT--ATGATGAATAATGAT
 FAD3C' (SEQ ID NO:12)   (812) GCAATAAATGATATACTATATTT--ACGATGAATAATGAT
 FAD3A'' (SEQ ID NO:9)   (940) GCAATAAATGATAAA-TACGTTTTTATGTTAAACAATGAT
FAD3C'' (SEQ ID NO:11)   (928) GCACTAAATGATAAA-TACGTTTTTATGTTAAATAATGAT
  FAD3C (SEQ ID NO:10)   (918) GCAATAAATGATAAA-CATGTTT------------ATGAT
                               1081                                1120
   FAD3A (SEQ ID NO:7)   (908) GTAAAATTTCATTTGAATAATA-CAGTGGACATGGGAGCT
  FAD3A' (SEQ ID NO:8)   (854) GTGAAA-TATAATTGAATAATGGCAGTGGACATGGGAGTT
 FAD3C' (SEQ ID NO:12)   (850) GTGAAA-TATAATTGAATAATGGCAGTGGACATGTGAGTT
 FAD3A'' (SEQ ID NO:9)   (979) GTGAAAATAAAATTGAATAATGGCAGTGGACATGGGAGTT
FAD3C'' (SEQ ID NO:11)   (967) GTGAAAATAAAATTGAATAATGGCAGTGGACATGGGAGTT
  FAD3C (SEQ ID NO:10)   (945) GTAAAATTCAATTTGAATAATA-CAGTGGACATGGGAGCT
                               1121                                1160
   FAD3A (SEQ ID NO:7)   (947) TCTCAGACATTCCTCTTCTGAATACTGCGGTTGGTCATAT
  FAD3A' (SEQ ID NO:8)   (893) TCTCAGACATTCCTCTGCTGAATAGTGTGGTTGGCCATAT
 FAD3C' (SEQ ID NO:12)   (889) TCTCAGACATTCCTCTGCTGAATAGCGTGGTTGGCCATAT
 FAD3A'' (SEQ ID NO:9)  (1019) TTTCAGACATTCCTCTGCTGAACAGTGTGGTTGGTCACAT
FAD3C'' (SEQ ID NO:11)  (1007) TCTCAGACATTCCTCTGCTGAACAGTGTGGTTGGTCACAT
  FAD3C (SEQ ID NO:10)   (984) TCTCAGACATTCCTCTTCTGAATACTGCGGTTGGTCATAT
```

FIG. 1D

```
                                   1161                                    1200
   FAD3A (SEQ ID NO:7)    (987)  TCTTCATTCCTTCATTCTCGTTCCATACCATGGTTGGTAA
  FAD3A' (SEQ ID NO:8)    (933)  TCTTCATTCCTTCATCCTCGTTCCTTACCATGGTTGGTAA
 FAD3C' (SEQ ID NO:12)    (929)  TCTTCATTCCTTCATCCTCGTTCCTTACCATGGTTGGTAA
 FAD3A'' (SEQ ID NO:9)   (1059)  TCTTCATTCATTCATCCTCGTTCCTTACCATGGTTGGTAA
FAD3C'' (SEQ ID NO:11)   (1047)  TCTTCATTCATTCATCCTCGTTCCTTACCATGGTTGGTAA
  FAD3C (SEQ ID NO:10)   (1024)  TCTTCATTCCTTCATTCTCGTTCCATACCATGGTTGGTAA
                                   1201                                    1240
   FAD3A (SEQ ID NO:7)   (1027)  GTCAT-TTATTTTAACTTCTTTTTTCATGCAAA---TTTA
  FAD3A' (SEQ ID NO:8)    (973)  GTCAGCTTATC--AACC-CTTTTT--ACTAT-ATTATTAA
 FAD3C' (SEQ ID NO:12)    (969)  GTCAACTTATT--AACC-CTTTTT--ATTATTATTATTAA
 FAD3A'' (SEQ ID NO:9)   (1099)  GTCAT-TTATT--AAC---TATTTCCATGTAAACTATTAG
FAD3C'' (SEQ ID NO:11)   (1087)  GTCAT-TTATT--AAC---TATTTCCATGTAAATTATTAG
  FAD3C (SEQ ID NO:10)   (1064)  GTCAT-TTATTTAAACATCTTTTT-CATGCAAA---TTTA
                                   1241                                    1280
   FAD3A (SEQ ID NO:7)   (1063)  TTCTTGTTTTCGTATTTCTTACATTTTCCTT-GTCATTCT
```

FIG. 1D (CONT.)

```
  FAD3A' (SEQ ID NO:8)   (1007)  TTATTAAACTTGCATTTGT-ATACTT-----GGTGCAAGT
 FAD3C' (SEQ ID NO:12)   (1004)  TTATTAAACTTTCATTTGTTATACTTTTTTTGGTTTAAAT
 FAD3A'' (SEQ ID NO:9)   (1133)  TACTTGTTTTCGTATTTCTTACATTTTCGTTTGTCATTCT
FAD3C'' (SEQ ID NO:11)   (1121)  TACTTGTTTTCGTATTTCTTACATTTTCGTTTGTTATTCT
  FAD3C (SEQ ID NO:10)   (1099)  TTCTTGTTTTCGTATTTCTTACATTTTCCTT-GTCATTCT
                                   1281                                    1320
   FAD3A (SEQ ID NO:7)   (1102)  T----GGTGCA-TGTTAGCAAACAGTAATCTGA--TAACT
  FAD3A' (SEQ ID NO:8)   (1041)  TGGTAAATGTAATCTGATAACTGAA-AATCTAT--TCATT
 FAD3C' (SEQ ID NO:12)   (1044)  -GTTAAATGAATTACTTGGTGCAAG-AATCTAT--TCATT
 FAD3A'' (SEQ ID NO:9)   (1173)  TCTTGGGTGCA-TGCTAGCAAACTGTAATCAGTATTAACT
FAD3C'' (SEQ ID NO:11)   (1161)  T---GGGTGCAATGCTAGGAAACTGTAATCAGTATTAACT
  FAD3C (SEQ ID NO:10)   (1138)  T----GGTGCA-TGTTAGCAAACTGTAATCTGA--TAACT
                                   1321                                    1360
   FAD3A (SEQ ID NO:7)   (1135)  GAAAA----------TATATTAATT-------------TT
  FAD3A' (SEQ ID NO:8)   (1078)  GCTCGTTCTA-----TTTTTTTTTTGGCT-AGAGACAATT
 FAD3C' (SEQ ID NO:12)   (1080)  GCTCGTTCT------TTTTTTTTTTGGCT-AGAGCCAATT
 FAD3A'' (SEQ ID NO:9)   (1212)  GGGAACTACCAACTGTTTTTTTTTTGCTAGAGTAGCAATT
FAD3C'' (SEQ ID NO:11)   (1198)  GGAAGCTACCAACT-TTTTTTTGTTGCTAGAGTAGCAATT
  FAD3C (SEQ ID NO:10)   (1171)  GAAAA----------TATATTAATT-------------TT
                                   1361                                    1400
   FAD3A (SEQ ID NO:7)   (1152)  TCATAGTAAAATAA------------------TGCATGTG
  FAD3A' (SEQ ID NO:8)   (1112)  TTATAATTAAATAATGCATGTGAGAATATGACTATTTATG
 FAD3C' (SEQ ID NO:12)   (1113)  TTATAATTAAATAATGCATGTGAAAGTATGACTATATATG
```

FIG. 1E

```
FAD3A'' (SEQ ID NO:9)  (1252) TTATAATTAAATAAGAATCCTATTA--AACAATGCATGTG
FAD3C'' (SEQ ID NO:11) (1237) TTATAATTAAATAAGAATCCTATTA--AACAATGCATGTG
 FAD3C (SEQ ID NO:10)  (1188) CCATAGTAAAATAA------------------TGCATGTG
                              1401                                1440
 FAD3A (SEQ ID NO:7)   (1174) ACTAAAAGCA--------------TCAAAA--------TC
 FAD3A' (SEQ ID NO:8)  (1152) TGAGGTAGCTTTTCTTATTCCTGTCGAAAAGCATCAAATC
FAD3C' (SEQ ID NO:12)  (1153) TGAGGTAGCTTTTCTTATTCTTGACGAAAAGCATCGAATC
FAD3A'' (SEQ ID NO:9)  (1290) ACAATATGAGGTTGCTTTT-CTGTTCAAAA----CAAATC
FAD3C'' (SEQ ID NO:11) (1275) ACTATATGAGGTTGCTTTTTCTGTTCAAAAGCATCAAATC
 FAD3C (SEQ ID NO:10)  (1210) ACTAAAAGCA--------------TCAAAA--------TC
                              1441                                1480
 FAD3A (SEQ ID NO:7)   (1192) TTTAGCATCGAAGAAAAAAGAA-CCAAACTTTTATTT--A
 FAD3A' (SEQ ID NO:8)  (1192) TTTAGCAACGAAGGAAAAAGGAATCAAATTTTTTATT-AA
FAD3C' (SEQ ID NO:12)  (1193) TTTAGCAACGAAGGAAAAAGGAATCAAAACTTTTATT-AA
FAD3A'' (SEQ ID NO:9)  (1325) TTTAGAAGCCAATGAAAAAGAATCCAAAACTTTTTTTTAA
FAD3C'' (SEQ ID NO:11) (1315) TTTAGCAGCCAATGAAAAAGAATCCAAACCTTTTCTT-AA
 FAD3C (SEQ ID NO:10)  (1228) TTTAGCATCGAAGAAAAAAGAA-CCAAACTTTTATTT--A
                              1481                                1520
 FAD3A (SEQ ID NO:7)   (1229) ATGCTATGGGCCTATTTATGG--------TCCA-------
 FAD3A' (SEQ ID NO:8)  (1231) ATGCAATGGGTCTATGTCTTGG-------TCATTAGTTTT
FAD3C' (SEQ ID NO:12)  (1232) ATGCAATGGGCCTATATCT-GG-------TCATTAGTATT
FAD3A'' (SEQ ID NO:9)  (1365) ATGATATGCGCCTATCTATTGGTCCTGACTCCTGAGTTTT
FAD3C'' (SEQ ID NO:11) (1354) ATGATATGCGCCTATCTATGG--------TCCTGAGTTTT
 FAD3C (SEQ ID NO:10)  (1265) ATGCTATGGGCCTATTTATGG--------TCCA-------
                              1521                                1560
 FAD3A (SEQ ID NO:7)   (1254) --------A--TTAGCTATTATCATATGAC-ATGTCCTTG
 FAD3A' (SEQ ID NO:8)  (1264) TTGCATATAATTTATTTATATTTTTTCTTAACAGCAGCT
FAD3C' (SEQ ID NO:12)  (1264) TTGAATATAATTTATTTATAATTTTTTTGAACAACAGCT
FAD3A'' (SEQ ID NO:9)  (1405) CTTACTTTC--TTAAGTATAATTAGATTTTGATTTTTTTT
FAD3C'' (SEQ ID NO:11) (1386) CTTAGTTCA--TTAAGTATAATTAGATTTTGATTTTTTTT
 FAD3C (SEQ ID NO:10)  (1290) --------A--TTAGCTATTATCATATGAC-ATGTCCTTG
                              1561                                1600
```

FIG. 1E (CONT.)

```
 FAD3A (SEQ ID NO:7)   (1283) AA--------TAAATTAATGT-A----------TAAGTTT
 FAD3A' (SEQ ID NO:8)  (1304) AATTTAATTATAATTAAATATTCATTTTATAAATAATATT
FAD3C' (SEQ ID NO:12)  (1304) AATTTATTTATAATTAAATATTCATTTTATAAATAATATT
FAD3A'' (SEQ ID NO:9)  (1443) TATAGGTTT-TCACT-ATTGTTATTTGTTTACATCAGCTT
FAD3C'' (SEQ ID NO:11) (1424) TA--GGTTT-TCACTTATTGTTATTTGTTTACATCAGCTT
 FAD3C (SEQ ID NO:10)  (1319) AA--------TAAATTAATGT-AGCTTCATATGTGAGTTT
                              1601                                1640
```

FIG. 1F

```
FAD3A (SEQ ID NO:7)  (1304) AATAT-----------------------AATATTTAT--A
  FAD3A' (SEQ ID NO:8)  (1344) AGACCAATTATTAAAGGTTAGATATTTTAAGAATTATTCA
 FAD3C' (SEQ ID NO:12)  (1344) AAACCAATTATTAAAGGTTAGATATTTGAAGAATTATTCA
 FAD3A'' (SEQ ID NO:9)  (1481) CAGATATCTTCGAAA-------------AAGATTTAC--A
FAD3C'' (SEQ ID NO:11)  (1461) CAAACATCTTCGAAA-------------AAGACTTAC--A
  FAD3C (SEQ ID NO:10)  (1350) AAT-------------------------AATATTTAT--A
                               1641                                1680
   FAD3A (SEQ ID NO:7)  (1319) TATATTTGTTT---------TAATGGCTTAT---TTTA-T
  FAD3A' (SEQ ID NO:8)  (1384) TGACTTTGTTTATTGGAA-----CTCCTTTTATCTTTTAA
 FAD3C' (SEQ ID NO:12)  (1384) TGACTTTGTTTATTGGGAAATTACTCCTTTTATCTTTTAT
 FAD3A'' (SEQ ID NO:9)  (1506) TGCATCAATTTCATGAGGATTTATAGTTTTTCT-TTTACT
FAD3C'' (SEQ ID NO:11)  (1486) TGCATCAATTTCCTGAGGATTTATAGTTTTT---TTTACT
  FAD3C (SEQ ID NO:10)  (1363) TATTTTTGTTT---------TAATGGCTTAT---TTTA-T
                               1681                                1720
   FAD3A (SEQ ID NO:7)  (1346) TGTTA-------AATGGATAC-----ATCAGCTTGAAATA
  FAD3A' (SEQ ID NO:8)  (1419) TCTTTT---CTATTTCTCCATTTTTAATAATGAGAAACTG
 FAD3C' (SEQ ID NO:12)  (1424) TCTTTT---CTATTTCTCTATTTTTAATATTGAGAAACTG
 FAD3A'' (SEQ ID NO:9)  (1545) TATTTCCGACACAATGTTTAGTAGTAAAAAGCATTAAATG
FAD3C'' (SEQ ID NO:11)  (1523) TATTTCTG-CACAATGTTTATTAGTAAAAAGCATCAAATG
  FAD3C (SEQ ID NO:10)  (1390) TGTTA-------AATGGATAC-----ATCAGCTTGAAATG
                               1721                                1760
   FAD3A (SEQ ID NO:7)  (1374) TCT-----------ACGAACAT-GCATCATTTTCCTAGAT
  FAD3A' (SEQ ID NO:8)  (1456) ACTTCAAATCTCCAATAAAGATGGTCTTATGTAGTAACAG
 FAD3C' (SEQ ID NO:12)  (1461) ACTTCAAACCTCCAATAAAAATGGTTTCCTGTAGTAACAT
 FAD3A'' (SEQ ID NO:9)  (1585) TTTTTTTG-CTCAAAAAAAAAA-GAATGGGATTGTTAGAG
FAD3C'' (SEQ ID NO:11)  (1562) TTTTTTTG-CTCAAAAAAAA---GAATGGGATTGTTAGAG
  FAD3C (SEQ ID NO:10)  (1418) TCT-----------ACGAACAT-GCATCATTTTCCTAGAT
                               1761                                1800
   FAD3A (SEQ ID NO:7)  (1402) A---CATTTGTTTGTTGCTCAAAAAATGAATAACGTAGTT
  FAD3A' (SEQ ID NO:8)  (1496) TA-TAATTTTTTGTTTGGTAAATGTAACATCATCTTCAAA
 FAD3C' (SEQ ID NO:12)  (1501) CA-TAATTTTTTGTTTGGTAAATGTAACATCATCTTCAAA
 FAD3A'' (SEQ ID NO:9)  (1623) CACTCTATTGTTAGTTGTTCAATAAATATACCAACTAAAA
FAD3C'' (SEQ ID NO:11)  (1598) CACTCTATTGTTAGTTGTTCAATAAATATATCAACTAAAA
  FAD3C (SEQ ID NO:10)  (1446) A---CACTTGTTTGTTGCTCAAAAA-TGAATAACTTAGTT
                               1801                                1840
   FAD3A (SEQ ID NO:7)  (1439) AAAC-------------------GAGTGAGA---------
  FAD3A' (SEQ ID NO:8)  (1535) TATCTTTGAAAATAGACTTACATGCATTATTTTGCTGCGA
 FAD3C' (SEQ ID NO:12)  (1540) TATCTTTGAAAATAGACTTACATGCATTATTTTGCTGCGA
 FAD3A'' (SEQ ID NO:9)  (1663) AAACAAAATAAATATA---AAATGAGTGAGATTGTTAAAT
FAD3C'' (SEQ ID NO:11)  (1638) AAACAAAATAAATATA---AAATGAGTGAGATTGTTAAAT
  FAD3C (SEQ ID NO:10)  (1482) AAAC-------------------GAGTGAGCATGTTCTAT
```

FIG. 1F (CONT.)

```
                                 1841                                    1880
   FAD3A (SEQ ID NO:7)   (1451)  ---------------------TTCTTAG------------
  FAD3A' (SEQ ID NO:8)   (1575)  CATTATTGTCACTTATTCCTGGCAATAAAT-TAGTTTATT
 FAD3C' (SEQ ID NO:12)   (1580)  CATTATTGTAACTTATTCCTGGCAATAAAAATAATTTATT
 FAD3A'' (SEQ ID NO:9)   (1700)  CATTATAGAGACAATTTCATTTTCACAAAAATAAATAAAT
FAD3C'' (SEQ ID NO:11)   (1675)  CATTATAGAGACAATTTCATTTTCACAAAAATAAATAAAT
  FAD3C (SEQ ID NO:10)   (1503)  GGGG----------------TTTCTTAGAGCATGATTATT
                                 1881                                    1920
```

FIG. 1F (CONT.)

```
FAD3A (SEQ ID NO:7)  (1458) ----------------------------------------
  FAD3A' (SEQ ID NO:8)   (1614)  ACTG-AACTTTTTTTTGGTCAATTTATTACTAGTAACTTT
 FAD3C' (SEQ ID NO:12)   (1620)  ACTGGAAACTATTTTTGGTCAATTTATTACTAGTAACTTA
 FAD3A'' (SEQ ID NO:9)   (1740)  ACAT--AACTTTTTATAATTGGGGTTTGCAGGAGAATAAG
FAD3C'' (SEQ ID NO:11)   (1715)  ACAT--AACTTTTG-TAATTGGGGTTTGCAGGAGAATAAG
  FAD3C (SEQ ID NO:10)   (1527)  GAGA--AGTTCCTA-GAGTGAGGTTCTTACCGGAATATAA
                                 1921                                    1960
   FAD3A (SEQ ID NO:7)   (1458)  ----------------------------------------
  FAD3A' (SEQ ID NO:8)   (1653)  AAACTTAAAAGAGTGAGATTGTTTGATCAAAAAAAAT---
 FAD3C' (SEQ ID NO:12)   (1660)  AAACTTAAAAGAGTGAGATTGTTTGATCAAAAAAAAAGAG
 FAD3A'' (SEQ ID NO:9)   (1778)  CCATCGGACACACCACCAGAACCATGGCCATGTTGAAAAC
FAD3C'' (SEQ ID NO:11)   (1752)  CCATCGGACACACCACCAGAACCATGGCCATGTTGAAAAC
  FAD3C (SEQ ID NO:10)   (1564)  GAATCTATCTCTTAACTTTTAACTAAAAAAATTAAGAACC
                                 1961                                    2000
   FAD3A (SEQ ID NO:7)   (1458)  ----------------------------------------
  FAD3A' (SEQ ID NO:8)   (1690)  ---AAAAATAGAGTGAGATAGTTAGAATCTGCCATGAAAG
 FAD3C' (SEQ ID NO:12)   (1700)  AAAAAAAATAGAGTGAGATTGTTAGAATCTGCCATGAAAG
 FAD3A'' (SEQ ID NO:9)   (1818)  GACGAGTCTTGGGTTCCGGTAATCTTTCCTACTCTCGTAG
FAD3C'' (SEQ ID NO:11)   (1792)  GACGAGTCTTGGGTTCCGGTAATCTTTCCTACTCTCATTG
  FAD3C (SEQ ID NO:10)   (1604)  GGCTTTTAAAACTCGTATTTAAGAACCGTTTTTTAGTTTT
                                 2001                                    2040
   FAD3A (SEQ ID NO:7)   (1458)  ----------------------------------------
  FAD3A' (SEQ ID NO:8)   (1727)  CAACACTATATAG---------------------------
 FAD3C' (SEQ ID NO:12)   (1740)  CAACACTATATAGGTGATGATTGGTTCGACTGTGGCCGTA
 FAD3A'' (SEQ ID NO:9)   (1858)  TTTCTCTTGTCTTTTATTTATTTGTTTGTTTTTCGGAATT
FAD3C'' (SEQ ID NO:11)   (1832)  TTTCTCTTGTCTTTTATTTATTTGTTCTTTTTTGGGAATT
  FAD3C (SEQ ID NO:10)   (1644)  TTTAGTTAAAAATCAAGAGACGAGTTCTTATATTCCGCTA
                                 2041                                    2080
   FAD3A (SEQ ID NO:7)   (1458)  ----------------------------------------
  FAD3A' (SEQ ID NO:8)   (1740)  ----------------------------------------
 FAD3C' (SEQ ID NO:12)   (1780)  GAATTTTAGCTGTAGATAAATTGGTTGTAGTTGTAAAGTT
 FAD3A'' (SEQ ID NO:9)   (1898)  TATTCTTA--TGTC--TATGTTCTTAGGATTCTATATGTT
FAD3C'' (SEQ ID NO:11)   (1872)  CATTCTTA--TGTC--TAAGTTCTTATGATTATTGAAGTT
```

FIG. 1G

```
FAD3C (SEQ ID NO:10)  (1684) AGAACTCC--ACCC--TGAGAACTTCTCAATAATCATGCT
                               2081                                 2120
    FAD3A (SEQ ID NO:7)  (1458) ----------------------------------------
   FAD3A' (SEQ ID NO:8)  (1740) ----------------------------------------
 FAD3C' (SEQ ID NO:12)  (1820) GTTACTGTT-GATTATTTTTGCAGAGACTTTTGCTGTAGT
  FAD3A'' (SEQ ID NO:9)  (1934) TATTTTATTAGTTTATGTTTTCAGTCTGAGGTCA-GACCG
FAD3C'' (SEQ ID NO:11)  (1908) CTTAAGGTGGGGTTCTTAACGGAATATGAGAACCTGTCTC
   FAD3C (SEQ ID NO:10)  (1720) CTTAGTGCTCTAAGAAGGGTCCTTAACAAAATAT------
                               2121                                 2160
    FAD3A (SEQ ID NO:7)  (1458) ----------------------------------------
   FAD3A' (SEQ ID NO:8)  (1740) ----------------------------------------
 FAD3C' (SEQ ID NO:12)  (1859) TAAATTTGTTGTAGCTGTAAGCTATAGGCTGCAGATATTT
  FAD3A'' (SEQ ID NO:9)  (1973) ACCACTTGTCAG-------ATCTGTTTTCTAGCTGT--AG
FAD3C'' (SEQ ID NO:11)  (1948) TTAACTTTTAACTAAAA-AAGCTAAGAACCAGCTTTTAAA
   FAD3C (SEQ ID NO:10)  (1754) --TAATAATAAG-------ATATAGTGTGGGCCCAA----
                               2161                                 2200
    FAD3A (SEQ ID NO:7)  (1458) ----------------------------------------
   FAD3A' (SEQ ID NO:8)  (1740) ----------------------------------------
 FAD3C' (SEQ ID NO:12)  (1899) TAAAATAAAATATGTAAAATATGTGATGCATGTATATATA
  FAD3A'' (SEQ ID NO:9)  (2004) TAAAA--------AACAA-TTTGCAAGTGTAATAGTTCAG
FAD3C'' (SEQ ID NO:11)  (1987) TAAGAGTTTTATGAACACGTTCTTAATTTTTTTAGTTAAA
   FAD3C (SEQ ID NO:10)  (1781) -AAAA--------AACAAAAAACCGGTTACAAAAGTCGCG
                               2201                                 2240
```

FIG. 1G (CONT.)

```
    FAD3A (SEQ ID NO:7)  (1458) ----------------------------------------
   FAD3A' (SEQ ID NO:8)  (1740) ----------------------------------------
 FAD3C' (SEQ ID NO:12)  (1939) AAATAATTATTATTTTTATCACTTAAAAT-AATTTATATT
  FAD3A'' (SEQ ID NO:9)  (2035) CATAATTGATCTTGTT--------------AGAGCAT-TT
FAD3C'' (SEQ ID NO:11)  (2027) AGTTAAGAAACGGGTTCTTATATTCCGCTAAGAACCTCTT
   FAD3C (SEQ ID NO:10)  (1812) AAAGAAGGATCGATTT--------------TGGTCTTTTA
                               2241                                 2280
    FAD3A (SEQ ID NO:7)  (1458) ----------------------------------------
   FAD3A' (SEQ ID NO:8)  (1740) ----------------------------------------
 FAD3C' (SEQ ID NO:12)  (1978) AATATTTTTTAAAATTATCAAAGTTTACTGTTATTTAAAA
  FAD3A'' (SEQ ID NO:9)  (2060) CCAAAA-----CAA--------------------------
FAD3C'' (SEQ ID NO:11)  (2067) CCTAAAAACCCCAATAATCATACTC--CTAGGATTCTATA
   FAD3C (SEQ ID NO:10)  (1838) CTTGTA----------------------------------
                               2281                                 2320
    FAD3A (SEQ ID NO:7)  (1458) ----------------------------------------
   FAD3A' (SEQ ID NO:8)  (1740) ----------------------------------------
```

FIG. 1H

```
 FAD3C' (SEQ ID NO:12)  (2018) TGTGATATGTAAATAATCTATATTATTTAAAATATTTCAA
FAD3A'' (SEQ ID NO:9)   (2069) ------ACTTTATAATTTTAAATATACAGT-TT-------
FAD3C'' (SEQ ID NO:11)  (2105) TGTT-TATTTTATTAGTTTATGTTTTCAGTCTGAGGTCAG
   FAD3C (SEQ ID NO:10) (1844) ------CTGTTTGTGGATCCCACTGGTGGT----------
                               2321                                 2360
   FAD3A (SEQ ID NO:7)  (1458) ----------------------------------------
  FAD3A' (SEQ ID NO:8)  (1740) ----------------------------------------
 FAD3C' (SEQ ID NO:12)  (2058) TAATTTAAAAGCACCCAAAATTAGAGTAAAATATTTATAG
FAD3A'' (SEQ ID NO:9)   (2095) ---------TT--------TGTTCTCT---------AAAA
FAD3C'' (SEQ ID NO:11)  (2144) ACCGGCCACTTGTCAGATCTGTTTTCTAGCTGTAGTAAAA
   FAD3C (SEQ ID NO:10) (1868) ------------------GGTCCGCG---------ATTG
                               2361                                 2400
   FAD3A (SEQ ID NO:7)  (1458) ----------------------------------------
  FAD3A' (SEQ ID NO:8)  (1740) ----------------------------------------
 FAD3C' (SEQ ID NO:12)  (2098) ATGTTTTTTTATTATGATTATCTTATT--TATTTAATATT
FAD3A'' (SEQ ID NO:9)   (2109) AAGAATTT--------AAAAATT---------TTAAAGTT
FAD3C'' (SEQ ID NO:11)  (2184) AACAATTTGCAAGTGTAATAGTTCAGCGGTAATTAATGTT
   FAD3C (SEQ ID NO:10) (1880) GTTTCTTT--------TTTAATT------TAATTTATTTT
                               2401                                 2440
   FAD3A (SEQ ID NO:7)  (1458) ----------------------------------------
  FAD3A' (SEQ ID NO:8)  (1740) ----------------------------------------
 FAD3C' (SEQ ID NO:12)  (2136) ATAGATATTTTTTGTTCTTACAGTTTCTACAGCTTATAAA
FAD3A'' (SEQ ID NO:9)   (2132) TGAGGGACGA-------------------AACTTCAAATT
FAD3C'' (SEQ ID NO:11)  (2224) CTCGGATCTATCTCAAAAAAAAATTTTATAACTTCAAATA
   FAD3C (SEQ ID NO:10) (1906) TTTAATCGGA-------------------GAAAAAAATTA
                               2441                                 2480
   FAD3A (SEQ ID NO:7)  (1458) ----------------------------------------
  FAD3A' (SEQ ID NO:8)  (1740) ----------------------------------------
 FAD3C' (SEQ ID NO:12)  (2176) TGAAAGATGTAAGTTGTTTAACTAAAATACATAAGAA---
FAD3A'' (SEQ ID NO:9)   (2153) TGAAC-----------TTTCACTACTCAACTTC-AAATTT
FAD3C'' (SEQ ID NO:11)  (2264) TAAAGATTTTTTTGTTTTTCAAAAATGAACTTCGAAACTT
   FAD3C (SEQ ID NO:10) (1927) AGAAA---------C----CAAAAAACAGTTTT-----AA
                               2481                                 2520
   FAD3A (SEQ ID NO:7)  (1458) ----------------------------------------
  FAD3A' (SEQ ID NO:8)  (1740) ----------------------------------------
 FAD3C' (SEQ ID NO:12)  (2213) -AAATGTTTGGTTTTTTTTTTGCTGTAGCTTTATTTTTAA
FAD3A'' (SEQ ID NO:9)   (2181) GAAATTTCATCTTTTTTATTTACATTTTGATCATTATAAT
FAD3C'' (SEQ ID NO:11)  (2304) CAAATTTGAAGTTTTTTTTTTGCATTTTGATCATTATAAT
   FAD3C (SEQ ID NO:10) (1949) TCATGGCCTCATGTTGGGGTTGAGTTTTATATTCTGATAA
                               2521                                 2560
```

FIG. 1H (CONT.)

```
   FAD3A (SEQ ID NO:7)  (1458) --------------------------------------CA
  FAD3A' (SEQ ID NO:8)  (1740) ----------------------------------------
 FAD3C' (SEQ ID NO:12)  (2252) -AGTTAAAGCATG-ATTGGTAAAAATTAATAGAAATTTGA
  FAD3A'' (SEQ ID NO:9) (2221) TAATTATACATTACATTTATGATTCTTAAGTATTTTCTCA
FAD3C'' (SEQ ID NO:11)  (2344) TAATTACACGTTACATTTATAATTCTTAAGTATTTTTTCA
  FAD3C (SEQ ID NO:10)  (1989) GAATCCCATCTTAAAAACCCCGTTAAACATGCTCTTACCA
                               2561                                2600
   FAD3A (SEQ ID NO:7)  (1460) TCTGCC--------TCGAAAACG----ATATGTTATTGAC
  FAD3A' (SEQ ID NO:8)  (1740) ----------------------------------------
 FAD3C' (SEQ ID NO:12)  (2290) TGTAGACTTTAATTTTGAAAAGT----AAACGTAAAGCAT
  FAD3A'' (SEQ ID NO:9) (2261) TTTATTGTTTTAATTCTTAAATTTTTTATACATCATAAAT
FAD3C'' (SEQ ID NO:11)  (2384) TTTATCGTTTTAATTCTTAAATTTTTTATATATTATAAAT
  FAD3C (SEQ ID NO:10)  (2029) TCTGCT--------TCGAAAATG----ATATGTTATTGAC
                               2601                                2640
   FAD3A (SEQ ID NO:7)  (1488) AATTCCAA---TTTCAT--TTT------------------
  FAD3A' (SEQ ID NO:8)  (1740) ----------------------------------------
 FAD3C' (SEQ ID NO:12)  (2326) GATTGGTAAAGTTTAATGATTTAGAAA--AAAATAAAGCT
  FAD3A'' (SEQ ID NO:9) (2301) ATTTCCAA---TTTGTT--TTTATAAATTCAAATTTTACA
FAD3C'' (SEQ ID NO:11)  (2424) ATTTCCAA---TTTGTT--TTTATAAATTCAAATTTTATA
  FAD3C (SEQ ID NO:10)  (2057) AATTCCAA---TTTCAT--TTT------------------
                               2641                                2680
   FAD3A (SEQ ID NO:7)  (1505) --------TATGAAAA---TAA--AAT-----------AA
  FAD3A' (SEQ ID NO:8)  (1740) --------------------------------------AC
 FAD3C' (SEQ ID NO:12)  (2364) AAAGTAGGTAGATAAAACCCAACCAATCACCTCCATGGAC
  FAD3A'' (SEQ ID NO:9) (2336) CAAAAAAGTAATAAAAATTTTA--AAT-----------AA
FAD3C'' (SEQ ID NO:11)  (2459) CATAAAAGTAATAAAAATGTTA--AAT-----------AA
  FAD3C (SEQ ID NO:10)  (2074) --------TATGAAAA---TAA--AAT-----------AA
                               2681                                2720
   FAD3A (SEQ ID NO:7)  (1521) TAGTT----TATTT-------TATAATTGGGGGTGG----
  FAD3A' (SEQ ID NO:8)  (1742) AATTTAATTTTTATGAAAACACAT--TTAATAATTTGAG-
 FAD3C' (SEQ ID NO:12)  (2404) AATTTAATTTTTATGTAAACACATATTTAATAATTTGAG-
  FAD3A'' (SEQ ID NO:9) (2363) GATTTATAATATTTTAAAAC-TATAATTAGGCAAAAAAAA
FAD3C'' (SEQ ID NO:11)  (2486) GATTTATAATATTT-AAGAC-TATAATTAGTCAACAAAA-
  FAD3C (SEQ ID NO:10)  (2090) TAGTT----TATTT-------TATAACTGAGGGTGG----
                               2721                                2760
   FAD3A (SEQ ID NO:7)  (1546) --TTGCAGGA------GAATAAG----------CCATCGG
  FAD3A' (SEQ ID NO:8)  (1779) -GCTGCAGGA------GAATAAG----------CCATCGG
 FAD3C' (SEQ ID NO:12)  (2443) -GCTGCAGGA------GAATAAG----------CCATCGG
  FAD3A'' (SEQ ID NO:9) (2402) TATTACAAAA-AAATGTAATAA---AAACTTTAAAATAAG
FAD3C'' (SEQ ID NO:11)  (2523) TATTACAAAAGAAATGTAATAATAAAAAATTTAAAATAAG
  FAD3C (SEQ ID NO:10)  (2115) --TTGCAGGA------GAATAAG----------CCATCGG
                               2761                                2800
```

FIG. 1I

```
FAD3A (SEQ ID NO:7)    (1568) ACACACCAC--CAGAACCATGGCCATGTTGAAA----ACG
  FAD3A' (SEQ ID NO:8)    (1802) ACACACCAC--CAGAACCATGGCCATGTTGAAA----ACG
 FAD3C' (SEQ ID NO:12)   (2466) ACACACCAC--CAGAACCATGGCCATGTTGAAA----ACG
 FAD3A'' (SEQ ID NO:9)    (2438) ATATATCAAGACATAATTATTAGAAATTTTAAATATTATA
FAD3C'' (SEQ ID NO:11)   (2563) ATACATGAAGACATAACTATTAGAAAATTTAAATATTATA
  FAD3C (SEQ ID NO:10)   (2137) ACACACCAC--CAGAACCATGGCCATGTTGAAA----ACG
                                2801                                2840
   FAD3A (SEQ ID NO:7)    (1602) ACGAGTCTTGGGTTCCGGTAA------TC-----CCCCTC
  FAD3A' (SEQ ID NO:8)    (1836) ACGAGTCTTGGGTTCCGGTAACATT--TC-----CCTCTT
 FAD3C' (SEQ ID NO:12)   (2500) ACGAGTCTTGGGTTCCGGTAACATT--TC-----CCTCTT
 FAD3A'' (SEQ ID NO:9)    (2478) ACAATATTAATAATCTGGTAAATTTGCTCCAAAACCTCAA
FAD3C'' (SEQ ID NO:11)   (2603) ACAATACTAATAATCTGGTAAATTTGCTCTGGAACCTCTA
  FAD3C (SEQ ID NO:10)   (2171) ACGAGTCTTGGGTTCCGGTAA------TCTTTC-CCTCTC
                                2841                                2880
```

FIG. 1I (CONT.)

```
   FAD3A (SEQ ID NO:7)    (1631) TCATT---------------------ATTTTTTTT-----
  FAD3A' (SEQ ID NO:8)    (1869) TAATA---------ATT------TCTATTTTTCT------
 FAD3C' (SEQ ID NO:12)   (2533) TAATA---------ATT------TCTATTTTTCTT--T--
 FAD3A'' (SEQ ID NO:9)    (2518) AAATTTCTAAATTATTGTCCAAACAAATTT-GTTTAACCG
FAD3C'' (SEQ ID NO:11)   (2643) AAATT--------ATTGTCTAAACAAATTTTGTGTAACCG
  FAD3C (SEQ ID NO:10)   (2204) TCAT----------------------ATTTTTTTT-----
                                2881                                2920
   FAD3A (SEQ ID NO:7)    (1645) --------------------TCTTTTTTTGAAAC------
  FAD3A' (SEQ ID NO:8)    (1888) ---------GTCAAAATAATTAGTTTTTCGAAATTTGAGG
 FAD3C' (SEQ ID NO:12)   (2554) ---------GTCAAAATAATTTGTTTTTCGAAATTTGAGG
 FAD3A'' (SEQ ID NO:9)    (2557) AATATGGAGCATTACAAAAATAATTTTATGGAATAGTGTG
FAD3C'' (SEQ ID NO:11)   (2675) AAGATGGAGCATTACGAAAATAATTTTATGAAATAATATG
  FAD3C (SEQ ID NO:10)   (2217) --------------------CTTTTTTTTGAAAT------
                                2921                                2960
   FAD3A (SEQ ID NO:7)    (1659) ------------------T--CTTTCATTTTAATTTTCT-
  FAD3A' (SEQ ID NO:8)    (1919) CCAGAACGACCACTTGTCAA-ATTTGATT-TTTAGCTGTA
 FAD3C' (SEQ ID NO:12)   (2585) CCAGAACGACCACTTGTCAG-ATTTGATT-TCTAGCTGTA
 FAD3A'' (SEQ ID NO:9)    (2597) GTATTTTGCTTGTAGTT-AATATTTAATTATGTATTTCTA
FAD3C'' (SEQ ID NO:11)   (2715) GTATTTTGCTTCTAGTTTAATATTTAATTATATATTTCTA
  FAD3C (SEQ ID NO:10)   (2231) ------------------T--CTTTCATTTTAATTTTCT-
                                2961                                3000
   FAD3A (SEQ ID NO:7)    (1678) --TAGAATTCTATGTATTTA-----------TTTTAATCA
  FAD3A' (SEQ ID NO:8)    (1957) GTAAAAACAGTTTGCTAGTGTCACAGTTAACCGGTAATTG
 FAD3C' (SEQ ID NO:12)   (2623) GTAAAAACAGTTTGCTAGTGTCACAGTTAACCGGTAATTG
 FAD3A'' (SEQ ID NO:9)    (2636) TTTATAATTTTATATATTTAATGTAAGATTTTTTTAATTA
```

FIG. 1J

```
FAD3C'' (SEQ ID NO:11)  (2755) TTTATAATTTTATATATTTAATGTAAATTTTTATTAATTA
  FAD3C (SEQ ID NO:10)  (2250) --TAGGATTCTATGTATTTA-----------TTTTAATCA
                               3001                                3040
  FAD3A (SEQ ID NO:7)   (1705) ATCCT-----------------------------------
 FAD3A' (SEQ ID NO:8)   (1997) ATTCTTTTTAACGATTTATAGAAGTAACATTTTTGTAAAA
 FAD3C' (SEQ ID NO:12)  (2663) ATTCTTTTTAGCGATTTATAGAAGTAACATTTTTGTAAAA
FAD3A'' (SEQ ID NO:9)   (2676) ATATTACTGTAATATTTTTATATATGTACTAGTTATTTAT
FAD3C'' (SEQ ID NO:11)  (2795) ATATTACTGTAATATTTTTATATATGTGCTAGTTATTTAT
  FAD3C (SEQ ID NO:10)  (2277) ATCCT-----------------------------------
                               3041                                3080
  FAD3A (SEQ ID NO:7)   (1710) -----TTTT-------------------------------
 FAD3A' (SEQ ID NO:8)   (2037) TAAAATATACATTATGGTATGTGACAACGGACCACGCTTA
 FAD3C' (SEQ ID NO:12)  (2703) TAAAATATACATAATAGTATGTGACAACGGACCACGCCTA
FAD3A'' (SEQ ID NO:9)   (2716) AAAAGTTTT-ATAGATTTGTATTAGTTATAACAAAAATAA
FAD3C'' (SEQ ID NO:11)  (2835) AATTTTTTTTATGGATTTATATTAG----ACCATGATTAA
  FAD3C (SEQ ID NO:10)  (2282) -----TTTT-------------------------------
                               3081                                3120
  FAD3A (SEQ ID NO:7)   (1714) ---------------------------C-------CAGTG
 FAD3A' (SEQ ID NO:8)   (2077) TTTGTATTGGTGAATCTTTTAATTAC-TC--CCT-CCAAT
 FAD3C' (SEQ ID NO:12)  (2743) TTTGTATCGGTGAATCTTCTAATTAC-TT--CCT-CCGAT
FAD3A'' (SEQ ID NO:9)   (2755) GGATCATTGTGTAAAATACAAATAATTTTGAAATTACGTT
FAD3C'' (SEQ ID NO:11)  (2871) CCCGGAGTTCTTAGAGTG-----------GAGTTTTAGTT
  FAD3C (SEQ ID NO:10)  (2286) ---------------------------C-------CAGTT
                               3121                                3160
  FAD3A (SEQ ID NO:7)   (1720) TGAGGCTTG-------------------------------
 FAD3A' (SEQ ID NO:8)   (2113) TTATTTTAGTTGCAGATTTAGATTTATGCACATAGATTAA
 FAD3C' (SEQ ID NO:12)  (2779) TTATTTTAGTTACAGTTTTAGATTTATACACATAGATTAC
FAD3A'' (SEQ ID NO:9)   (2795) TAAAGTTTTGGTTATGAAAAAAATACTTTGAAACTTTAAA
FAD3C'' (SEQ ID NO:11)  (2900) AAACGTT----------AAGAAACAGTTTCTTAACTTCCG
  FAD3C (SEQ ID NO:10)  (2292) TGAGGCTAG-------------------------------
```

FIG. 1J (CONT.)

```
                                   3161                                  3200
   FAD3A (SEQ ID NO:7)    (1729) -----------G---ACGACCACTTGTCAGATTTGTCG--
  FAD3A' (SEQ ID NO:8)    (2153) TAAAAATA-----TTTTGCACATTTTCAAAATAAAAACAC
 FAD3C' (SEQ ID NO:12)    (2819) AAAAAATAAAATATTTTGTCCATTTTTAAAATAAAAACAT
 FAD3A'' (SEQ ID NO:9)    (2835) TTTAGAGTTTTGCAAACTTTAAAATGTTAGATAGATAGTT
FAD3C'' (SEQ ID NO:11)    (2930) GTAAGAACC---CCATCCTAAGAATCCCAGGTTAATC---
   FAD3C (SEQ ID NO:10)   (2301) -----------G---ACGACCACTTGTCAGATTTGTCG--
                                 3201                                  3240
   FAD3A (SEQ ID NO:7)    (1753) -------T-------TTAGCTGTAG---------------
  FAD3A' (SEQ ID NO:8)    (2188) CATTAC-TTATACAACTAACCATATTTCAACCAATAAAAA
 FAD3C' (SEQ ID NO:12)    (2859) CACTAA-TTATACACCTAACAATATTTTAACCAATAAAAA
 FAD3A'' (SEQ ID NO:9)    (2875) TTTTTGGAGATGCATTTAGTGGTTATGGTAGTAACTCAGA
FAD3C'' (SEQ ID NO:11)    (2964) ---------ATGCTCTTAGTTATAA-----------CAAA
   FAD3C (SEQ ID NO:10)   (2325) -------T-------TTAGCTGTAG---------------
                                 3241                                  3280
   FAD3A (SEQ ID NO:7)    (1764) ----------------------------------------
  FAD3A' (SEQ ID NO:8)    (2227) --TAAATTAGAAAATATTATTTATAAATTTTGTATTGAAA
 FAD3C' (SEQ ID NO:12)    (2898) A-TAAACTAGAAAATATTATTCATAATTTTTACATTGAAA
 FAD3A'' (SEQ ID NO:9)    (2915) AAATGAAAAATCTATACTTTTATACTCCCTCCGTTTTTTA
FAD3C'' (SEQ ID NO:11)    (2984) TAAGGATCATTGTGTAA----------------------A
   FAD3C (SEQ ID NO:10)   (2336) ----------------------------------------
                                 3281                                  3320
   FAD3A (SEQ ID NO:7)    (1764) ----------------------------------------
  FAD3A' (SEQ ID NO:8)    (2265) TTATAAAATAATACTTATTTTAAAACGAAATT------AA
 FAD3C' (SEQ ID NO:12)    (2937) TTATAAAACGATACTTATTTTAAAACAAAATTTT----AA
 FAD3A'' (SEQ ID NO:9)    (2955) ATATAAGTCGTTTTACAGTTATACACGTAGATTAAGAAAA
FAD3C'' (SEQ ID NO:11)    (3002) ATACAAATAATTTTGAAGTTATGTTTGAAGTTTG------
   FAD3C (SEQ ID NO:10)   (2336) ----------------------------------------
                                 3321                                  3360
   FAD3A (SEQ ID NO:7)    (1764) ----------------------T----AAACAACTG---
  FAD3A' (SEQ ID NO:8)    (2299) TTTACAACGACAATTAAACTGAAACGGAAAGAAATTATTA
 FAD3C' (SEQ ID NO:12)    (2973) TTTACAACGACAATTAAATTGAAACGGAAGAAGTTTATTA
 FAD3A'' (SEQ ID NO:9)    (2995) CCATTAATTTCTTATATTTTCTAGACAAAAACATCATTAA
FAD3C'' (SEQ ID NO:11)    (3036) ----------------TTTTC--GAAGAAAACCACTTTGA
   FAD3C (SEQ ID NO:10)   (2336) ----------------------T----AAACAACTG---
                                 3361                                  3400
   FAD3A (SEQ ID NO:7)    (1774) --ATTTA---------------------------------
  FAD3A' (SEQ ID NO:8)    (2339) ATACTTAATTAAAGAGTTTTT-------AGAAAAATTGAA
 FAD3C' (SEQ ID NO:12)    (3013) TTACTTAATTAAAGAGTTTTTT-----TAAAAAAAATGAA
 FAD3A'' (SEQ ID NO:9)    (3035) TTATTTACCTAACCACAATTCAACCAATATAAAAATAGAA
FAD3C'' (SEQ ID NO:11)    (3058) AACTTTA------------------AATTTAGAGT---AA
```

FIG. 1K

```
FAD3C   (SEQ ID NO:10)  (2346)  --ATTTA---------------------------------
                                3401                                 3440
FAD3A   (SEQ ID NO:7)   (1779)  ------------------------------AATTGTTTATGG
FAD3A'  (SEQ ID NO:8)   (2372)  AGACATGTTTATGCGAAACTCATGTGAAAGTCTTTGAAAT
FAD3C'  (SEQ ID NO:12)  (3048)  AGACATGTTTATGCGAAACTCATGTGAAAGTCTTTCAAAT
FAD3A'' (SEQ ID NO:9)   (3075)  GATATATTACCATTGGTCATACAACATTAATTATTAATAA
FAD3C'' (SEQ ID NO:11)  (3077)  ACTCTATT----------TAGAG----AGTTTTTTTTAG
FAD3C   (SEQ ID NO:10)  (2351)  ----------------------------AATTGTTTATAG
                                3441                                 3480
FAD3A   (SEQ ID NO:7)   (1791)  ----TACT--------------------------------
FAD3A'  (SEQ ID NO:8)   (2412)  AATAGATTTTGGTATAAATATTTCAAATTTTCTT------
FAD3C'  (SEQ ID NO:12)  (3088)  AAAATATTTTGGTATAAATTTTTCAAATTTTCA-------
FAD3A'' (SEQ ID NO:9)   (3115)  ATTTTACATAG-AAAACCGAAAACGACATATAATTTGGAA
FAD3C'' (SEQ ID NO:11)  (3102)  AGGTTACGCAGTAACTCAGAAAATGA--------------
FAD3C   (SEQ ID NO:10)  (2363)  ----TACT--------------------------------
                                3481                                 3520
```

FIG. 1K (CONT.)

```
FAD3A   (SEQ ID NO:7)   (1795)  ----------------------------------------
FAD3A'  (SEQ ID NO:8)   (2446)  -----AAAATAATAATTATATATTAATATAAT--------
FAD3C'  (SEQ ID NO:12)  (3121)  -----AAAATAATAATTATAAATTAATATAATATAAT---
FAD3A'' (SEQ ID NO:9)   (3154)  CAAAAAAATTTCTCTAAAACGACTTATATTAAAAAACGGA
FAD3C'' (SEQ ID NO:11)  (3128)  ----AAAATCTAT--------ACTTTTAT-----------
FAD3C   (SEQ ID NO:10)  (2367)  ----------------------------------------
                                3521                                 3560
FAD3A   (SEQ ID NO:7)   (1795)  ----G---TAGTTAACTTTAACAACGGGCCACTTATATTC
FAD3A'  (SEQ ID NO:8)   (2473)  ----TTGTGATAAAATCTCGTCAAAAACTCACTAATGCAA
FAD3C'  (SEQ ID NO:12)  (3153)  ----TTGTGATAAAATCTCGTCAAAAACTCACTAATGCAA
FAD3A'' (SEQ ID NO:9)   (3194)  GGGAGTAGTACCTAACTTTAACGATGGACCACTTATATTC
FAD3C'' (SEQ ID NO:11)  (3145)  ------AGTACCTAACTTTATCGATGGACCACTTATATTC
FAD3C   (SEQ ID NO:10)  (2367)  ----G---TAGTTAACTTTAACAACGGACCACTTATATTC
                                3561                                 3600
FAD3A   (SEQ ID NO:7)   (1828)  GAGCCATTGG-CATAAAATGATT-CTTCTCGAAATTCGTT
FAD3A'  (SEQ ID NO:8)   (2509)  ATGCTTTTAT-TTTGAATTTCTTACTCCTCTAAATGCATT
FAD3C'  (SEQ ID NO:12)  (3189)  ATGCTTTTATATTTGAGTTTCTTACTCCTCTAAATGCATT
FAD3A'' (SEQ ID NO:9)   (3234)  GAGTCCTTAG-CATAAAATGATT-CTCCTCGAAATCCGTT
FAD3C'' (SEQ ID NO:11)  (3179)  GAGTCCTTAG-CATAACATGATT-CTCCTCGAAATCCGTT
FAD3C   (SEQ ID NO:10)  (2400)  GAGCCATTGG-CATAAAATGATT-CTTCTCGAAATTCGTT
                                3601                                 3640
FAD3A   (SEQ ID NO:7)   (1866)  TACTTTTCT--TAGTATT-TTT-------CAGTTTTGTAG
FAD3A'  (SEQ ID NO:8)   (2548)  TACTTTTATACTAATATTATTTTCTTTCTCTAATTTGGCG
```

FIG. 1L

```
FAD3C' (SEQ ID NO:12)  (3229) TACTTTTATACTATTATTATTTTCTTTCTCTAATTTGGTG
 FAD3A'' (SEQ ID NO:9)  (3272) TACTTTCTT--CATTATT-TTTTCCTTTTCAGTTTTGGCG
FAD3C'' (SEQ ID NO:11)  (3217) TACTTTCTT--CGTTATT-TTTTCCTTTTCAGTTTTGGCG
  FAD3C (SEQ ID NO:10)  (2438) TACTTTTCT--TAGTATT-TTT-------CAATTTTGGAG
                               3641                                3680
   FAD3A (SEQ ID NO:7)  (1896) TTTACGTAGAACTAAT------AA-----AAAG-------
  FAD3A' (SEQ ID NO:8)  (2588) TTT-CGTAATAGTTTG--TCTGTATTTTGAAAACTA----
 FAD3C' (SEQ ID NO:12)  (3269) TTTTCGTAATAGTTTG--CCTGTGTTTTGAAAACTA----
 FAD3A'' (SEQ ID NO:9)  (3309) TTTTCGTAATACTTTTGTCTTCAATCTTGAAAGCTATTAG
FAD3C'' (SEQ ID NO:11)  (3254) TTTTCGTAATACTTTTGTCTGCAATCTTGAAAGCTATTAG
  FAD3C (SEQ ID NO:10)  (2468) TTTACGTAGAACTAAT------AA-----AAAG-------
                               3681                                3720
   FAD3A (SEQ ID NO:7)  (1918) -AAAAAAACTTATAAACACACC------------------
  FAD3A' (SEQ ID NO:8)  (2621) -ACAAAAAATAATAAAAACAAA---------AGCTTATAA
 FAD3C' (SEQ ID NO:12)  (3303) -ACAAAAAATAATAAAAACAAA---------AGTTTATAA
 FAD3A'' (SEQ ID NO:9)  (3349) TATAAAAACTTATAAACACATCACATGCAATGAATTAATA
FAD3C'' (SEQ ID NO:11)  (3294) TATAAAA-CTTATAAACACAT----------GAATTAATA
  FAD3C (SEQ ID NO:10)  (2490) -AAAA--ACTTATAAACACACC------------------
                               3721                                3760
   FAD3A (SEQ ID NO:7)  (1939) ----------------------ACATGCAATGAATA---
  FAD3A' (SEQ ID NO:8)  (2651) ---ACACAT------------A-GCATGCAATGAATATG-
 FAD3C' (SEQ ID NO:12)  (3333) ---ACACAT------------A-GCATGCAATGAAT----
 FAD3A'' (SEQ ID NO:9)  (3389) CGAATACATAACCAGAATGACAAATTTTCAATGAATATTT
FAD3C'' (SEQ ID NO:11)  (3323) CGAATACATAACCAGAATGACAAATTTTCAATGAATATTT
  FAD3C (SEQ ID NO:10)  (2509) ----------------------ACATGCAATGAATA---
                               3761                                3800
   FAD3A (SEQ ID NO:7)  (1953) AATTCGAATATATAA----CCATACTGTTAAA--------
  FAD3A' (SEQ ID NO:8)  (2674) TACGAATATATATATACCAATACATA-TCTAAGTACTATTTT
 FAD3C' (SEQ ID NO:12)  (3353) -------ATATATATCAATACATA-TCTAAGTACTATTTT
 FAD3A'' (SEQ ID NO:9)  (3429) AATACCAGTAAGTACTACTCCGTAATAGTAATAGTAATAG
FAD3C'' (SEQ ID NO:11)  (3363) AATACTAGTAAGTACTACTCCGTAATAGTAAT-----TAG
  FAD3C (SEQ ID NO:10)  (2523) AATTCGAATATATAA----CCATACTGTTAAA--------
```

FIG. 1L (CONT.)

```
                                         3801                                    3840
FAD3A (SEQ ID NO:7)       (1981)  ---TATTAAT--------------------T----AA---
FAD3A' (SEQ ID NO:8)      (2713)  TCCAAGTACT---T--------------AATCTTGATTAC
FAD3C' (SEQ ID NO:12)     (3385)  TGCAAGTACT---T--------------AATCTTGATTAC
FAD3A'' (SEQ ID NO:9)     (3469)  TCATATTAATTTTTTTTTGTCATCAAACAAACAGTAATAG
FAD3C'' (SEQ ID NO:11)    (3398)  TAATAGTAAT----------------------AGTAATAG
FAD3C (SEQ ID NO:10)      (2551)  ---TATTAAT--------------------T----TA---
                                  3841                                    3880
FAD3A (SEQ ID NO:7)       (1991)  -CATTTTAATCTTAATTTTGCATTCCAGTTGCCAGAAAAA
FAD3A' (SEQ ID NO:8)      (2736)  TAAAATTCATTTTAATTGTTCCTTTCAGTTACCAGAAAGG
FAD3C' (SEQ ID NO:12)     (3408)  TAAAATTCATTTTAATTGTTCCTTTCAGTTACCAGAAAAG
FAD3A'' (SEQ ID NO:9)     (3509)  TAATATTAATTATAATTATGTATTTCAGTTGCCAGAAAAG
FAD3C'' (SEQ ID NO:11)    (3416)  TCATATTAATTATAATTATGTATTTCAGTTGCCAGAAAAG
FAD3C (SEQ ID NO:10)      (2561)  -CATTTTAATCTTAATTTTGCATTCCAGTTGCCAGAAAAA
                                  3881                                    3920
FAD3A (SEQ ID NO:7)       (2030)  TTATACAAGAATTTGTCCCACAGTACACGGATGCTCAGAT
FAD3A' (SEQ ID NO:8)      (2776)  TTATACAAGAATTTACCCCACAGTACTCGGATGCTCAGAT
FAD3C' (SEQ ID NO:12)     (3448)  TTATACAAGATTTTACCCCACAGTACTCGGATGCTCAGAT
FAD3A'' (SEQ ID NO:9)     (3549)  TTGTACAAGAACTTGCCCCATAGTACTCGGATGCTCAGAT
FAD3C'' (SEQ ID NO:11)    (3456)  TTGTACAAGAACTTGCCCCATAGTACTCGGATGCTCAGAT
FAD3C (SEQ ID NO:10)      (2600)  TTATACAAGAATTTGTCCCACAGTACACGGATGCTCAGAT
                                  3921                                    3960
FAD3A (SEQ ID NO:7)       (2070)  ACACTGTCCCTCTCCCCATGCTCGCTTACCCTCTCTATCT
FAD3A' (SEQ ID NO:8)      (2816)  ACACTGTCCCTCTGCCCATGCTCGCTTACCCGATCTATCT
FAD3C' (SEQ ID NO:12)     (3488)  ACACTGTCCCTCTGCCCATGCTCGCTTACCCGATCTATCT
FAD3A'' (SEQ ID NO:9)     (3589)  ACACTGTTCCTCTGCCCATGCTCGCTTACCCGATCTATCT
FAD3C'' (SEQ ID NO:11)    (3496)  ACACTGTCCCTCTGCCCATGCTCGCTTACCCGATCTATCT
FAD3C (SEQ ID NO:10)      (2640)  ACACTGTCCCTCTCCCCATGCTCGCTTACCCTCTCTATCT
                                  3961                                    4000
FAD3A (SEQ ID NO:7)       (2110)  GGTAAATCCTAATTCCTCATTTTTCTTCCTGATTATAATT
FAD3A' (SEQ ID NO:8)      (2856)  GGTAT-------------TTTTTAATTCCTAAAATTTACT
FAD3C' (SEQ ID NO:12)     (3528)  GGTAT-------------TTTTTAATTCCTAAAACTTACC
FAD3A'' (SEQ ID NO:9)     (3629)  GGTAAAAAAAAA-TACAATTTCAATTTTTTTCTTAAAATT
FAD3C'' (SEQ ID NO:11)    (3536)  GGTAAAAAAAA--TACAATTTCTATTTTTT-CTTAAAATT
FAD3C (SEQ ID NO:10)      (2680)  GGTAAATCCTAATTCCTAATTTTTCTTCCTGATTATAATT
                                  4001                                    4040
FAD3A (SEQ ID NO:7)       (2150)  ACAATTTTGAATTTTTAGATTTTGAGTATTAA--CTAAAT
FAD3A' (SEQ ID NO:8)      (2883)  ACAAGT----CATTTTAGAC--TGTGTTTTAA--AACAAT
FAD3C' (SEQ ID NO:12)     (3555)  ACAATT----CATTTTAGAT--TGTGTTTTAA--AACAAT
FAD3A'' (SEQ ID NO:9)     (3668)  ACAAAT----GGTTTTATATTTTGAGTTTTAAGCCAATAT
FAD3C'' (SEQ ID NO:11)    (3573)  ACAAAT----GATTTTATATTTTGAGTTTTAAGCCAATAT
```

FIG. 1M

```
FAD3C (SEQ ID NO:10)  (2720) ACAATTTTGAATTTTTAGATTTTGAGTATTAA--CTAAAT
                               4041                                  4080
   FAD3A (SEQ ID NO:7)  (2188) ATAAATTAAATTTGTTTGGGGATGA-CTACAGTGGTACAG
  FAD3A' (SEQ ID NO:8)  (2915) ATAA-TTATTTTTG-TTTGGTTTTA-CTGCAGTGGTACAG
 FAD3C' (SEQ ID NO:12)  (3587) ATAAATTATTTTTTCTTTGGTTTTA-CTGCAGTGGTACAG
 FAD3A'' (SEQ ID NO:9)  (3704) ATAAATTAATTTTGATTGGATTTTAACTACAGTGGTACAG
FAD3C'' (SEQ ID NO:11)  (3609) ATAAATTAATTTTGATTGGATTTTAACTACAGTGGTACAG
  FAD3C (SEQ ID NO:10)  (2758) ATAAATTAAATTTGTTTGGGGATGA-CTACAGTGGTACAG
                               4081                                  4120
   FAD3A (SEQ ID NO:7)  (2227) AAGTCCTGGTAAAGAAGGGTCACATTATAACCCATACAGT
  FAD3A' (SEQ ID NO:8)  (2952) AAGTCCTGGAAAAGAAGGGTCACATTTTAACCCATACAGT
 FAD3C' (SEQ ID NO:12)  (3626) AAGTCCTGGAAAAGAAGGGTCACATTTTAACCCATACAGT
 FAD3A'' (SEQ ID NO:9)  (3744) AAGTCCTGGAAAAGAAGGGTCACATTTTAACCCATACAGT
FAD3C'' (SEQ ID NO:11)  (3649) AAGTCCTGGAAAAGAAGGGTCACATTTTAACCCATACAGT
  FAD3C (SEQ ID NO:10)  (2797) AAGTCCTGGTAAAGAAGGGTCACATTATAACCCATACAGT
                               4121                                  4160
```

FIG. 1M (CONT.)

```
  FAD3A (SEQ ID NO:7)   (2267) AGTTTATTTGCCCCAAGCGAGAGAAAGCTTATTGCAACTT
 FAD3A' (SEQ ID NO:8)   (2992) GGTTTATTTGCTCCAAGCGAGAGAAAGCTTATTGCAACTT
FAD3C' (SEQ ID NO:12)   (3666) GGTTTATTTGCTCCAAGCGAGAGAAAGCTTATTGCAACTT
FAD3A'' (SEQ ID NO:9)   (3784) AGTTTATTTGCTCCAAGCGAGAGGAAGCTTATTGCAACTT
FAD3C'' (SEQ ID NO:11)  (3689) AGTTTATTTGCTCCAAGCGAGAGGAAGCTTATTGCAACTT
  FAD3C (SEQ ID NO:10)  (2837) AGTTTATTTGCCCCAAGCGAGAGAAAGCTTATTGCAACTT
                               4161                                4200
  FAD3A (SEQ ID NO:7)   (2307) CAACTACTTGCTGGTCGATCATGTTGGCCACTCTTGTTTA
 FAD3A' (SEQ ID NO:8)   (3032) CGACTACTTGCTGGTCCATAATGTTGGCAATTCTTATCTG
FAD3C' (SEQ ID NO:12)   (3706) CAACTACTTGCTGGTCCATAATGTTGGCCATTCTTATCTG
FAD3A'' (SEQ ID NO:9)   (3824) CAACAACTTGCTGGTCCATAATGTTGGCCACTCTTGTTTA
FAD3C'' (SEQ ID NO:11)  (3729) CAACTACTTGCTGGTCCATAATGTTGGCCACTCTTGTTTA
  FAD3C (SEQ ID NO:10)  (2877) CAACTACTTGCTGGTCGATCGTGTTGGCCACTCTTGTTTA
                               4201                                4240
  FAD3A (SEQ ID NO:7)   (2347) TCTATCATTCCTCGTTGGTCCAGTCACAGTTCTAAAAGTC
 FAD3A' (SEQ ID NO:8)   (3072) TCTTTCCTTCCTCGTTGGTCCAGTCACAGTTCTCAAAGTA
FAD3C' (SEQ ID NO:12)   (3746) TCTTTCCTTCCTCGTTGGTCCAGTCACAGTTCTCAAAGTA
FAD3A'' (SEQ ID NO:9)   (3864) TCTATCGTTCCTCGTTGGTCCAGTCACAGTTCTCAAAGTC
FAD3C'' (SEQ ID NO:11)  (3769) TCTATCGTTCCTCGTTGATCCAGTCACAGTTCTCAAAGTC
  FAD3C (SEQ ID NO:10)  (2917) TCTATCATTCCTCGTTGGTCCAGTCACAGTTCTAAAAGTC
                               4241                                4280
  FAD3A (SEQ ID NO:7)   (2387) TATGGTGTTCCTTACATTGTAAGTTTCATA-TATTTC---
 FAD3A' (SEQ ID NO:8)   (3112) TACGGTGTTCCTTACATTGTAAGTTTCTTAGTATATCATA
FAD3C' (SEQ ID NO:12)   (3786) TACGGTGTTCCTTACATCGTAAGTTTCTTAGTATATCATA
FAD3A'' (SEQ ID NO:9)   (3904) TATGGTGTTCCTTACATTGTAAGTTTCACA-TATTATTAC
FAD3C'' (SEQ ID NO:11)  (3809) TATGGCGTTCCTTACATTGTAAGTTTCACA-TATTATTAC
  FAD3C (SEQ ID NO:10)  (2957) TATGGTGTTCCTTACATTGTAAGTTTCATA-TATTTC---
                               4281                                4320
  FAD3A (SEQ ID NO:7)   (2423) ------ATTATTATATCATTGCTAATATA---------AT
 FAD3A' (SEQ ID NO:8)   (3152) AAGGGTATATATTTATTATTCAATATATATACTATATGAT
FAD3C' (SEQ ID NO:12)   (3826) AAGGGTATATATTTATTATTCAATATATATACTATATGAT
FAD3A'' (SEQ ID NO:9)   (3943) AAGAG-ATTTATATATTATTAATAATAAA---------TT
FAD3C'' (SEQ ID NO:11)  (3848) AAGAA-ATTTATATATTATTAATAATAAA---------TT
  FAD3C (SEQ ID NO:10)  (2993) ------TTTATTATATCATTGCTAATATA---------AT
                               4321                                4360
  FAD3A (SEQ ID NO:7)   (2448) TTGTTTTTGACATAAA-GTTTTGGAAAAATTTCAGATCTT
 FAD3A' (SEQ ID NO:8)   (3192) TTGTTTTTGTCATATA-TTTTTG--AAATATTCAGATCTT
FAD3C' (SEQ ID NO:12)   (3866) TTGTTTTTGTCATAAA-CTTTTG--AAAT--TCAGATCTT
FAD3A'' (SEQ ID NO:9)   (3973) TGTTTTTTGACATAAA-GTTTTGGAAAATTTTCAGATCTT
FAD3C'' (SEQ ID NO:11)  (3878) TGTTTTTTGACATAAG-GGTTTGGAAAATTTTCAGATCTT
```

FIG. 1N

```
FAD3C (SEQ ID NO:10)  (3018) TTGTTTTTGACATAAAAGTTTTGGAAAAATTTCAGATCTT
                               4361                                  4400
   FAD3A (SEQ ID NO:7)  (2487) TGTAATGTGGTTGGACGCTGTCACGTACTTGCATCATCAT
  FAD3A' (SEQ ID NO:8)  (3229) TGTGATGTGGTTGGACGCTGTCACTTACTTGCATCACCAT
 FAD3C' (SEQ ID NO:12)  (3901) TGTGATGTGGTTGGACGCTGTCACTTACTTGCATCACCAT
 FAD3A'' (SEQ ID NO:9)  (4012) TGTAATGTGGTTGGACGCTGTCACGTACTTGCATCATCAT
FAD3C'' (SEQ ID NO:11)  (3917) TGTGATGTGGTTGGACGCTGTCACGTACTTGCATCATCAT
  FAD3C (SEQ ID NO:10)  (3058) TGTAATGTGGTTGGACGCTGTCACGTACTTGCATCATCAT
                               4401                                  4440
   FAD3A (SEQ ID NO:7)  (2527) GGTCACGATGATAAGTTGCCTTGGTACAGAGGCAAGGTAA
  FAD3A' (SEQ ID NO:8)  (3269) GGTCATGATGAGAAGTTGCCTTGGTACAGAGGCAAGGTAA
 FAD3C' (SEQ ID NO:12)  (3941) GGTCATGATGAGAAGTTGCCTTGGTACAGAGGCAAGGTAA
 FAD3A'' (SEQ ID NO:9)  (4052) GGTCACGATGAGAAGTTGCCTTGGTACAGAGGCAAGGTAA
FAD3C'' (SEQ ID NO:11)  (3957) GGTCACGATGAGAAGTTGCCTTGGTACAGAGGCAAGGTAA
  FAD3C (SEQ ID NO:10)  (3098) GGTCACGATGATAAGCTGCCTTGGTACAGAGGCAAGGTAA
```

FIG. 1N (CONT.)

```
                                      4441                                    4480
FAD3A   (SEQ ID NO:7)   (2567)  GTAGATCAACATT--------AATTTATAA---------G
FAD3A'  (SEQ ID NO:8)   (3309)  TTAAATTAACTATTACAA--GTATTTTAC----------A
FAD3C'  (SEQ ID NO:12)  (3981)  TTAAATTAACTCCTAGGT--GATTTTCCCGTGCTCATGTA
FAD3A'' (SEQ ID NO:9)   (4092)  ATAAATCAATTTTTAAAAAGAAATGTACAG---------A
FAD3C'' (SEQ ID NO:11)  (3997)  TTAAATCAATTTTTAAAAAGAAATGTACAG---------A
FAD3C   (SEQ ID NO:10)  (3138)  GTAGATCAACATT--------A-TTTATAA---------G
                                      4481                                    4520
FAD3A   (SEQ ID NO:7)   (2590)  AAGCAACAATGATTAGTAT-TTGATTAATCTA-AATTATT
FAD3A'  (SEQ ID NO:8)   (3337)  AAAAACTAATGATTAGTATATTTGATTAATCTTAATTCTT
FAD3C'  (SEQ ID NO:12)  (4019)  CGGATATAAATATTTCTAAAGTAAATATACTATAATAATT
FAD3A'' (SEQ ID NO:9)   (4123)  AAGCAATAATGGTTAGTA--TTGATTAATCTT-AATTTTT
FAD3C'' (SEQ ID NO:11)  (4028)  AAGCAATAATGGTTAGTA--TTGATTAATCTT-AATTTTT
FAD3C   (SEQ ID NO:10)  (3160)  AAGCAATAATGATTAGTAG-TTGAATAATCTG-AATTTTT
                                      4521                                    4560
FAD3A   (SEQ ID NO:7)   (2628)  GATGTTTTGTGTACAATAATAGGAATGGAGTTATTTACGT
FAD3A'  (SEQ ID NO:8)   (3377)  GATGTTTTGTGATTAATAATAGGAATGGAGTTACTTACGT
FAD3C'  (SEQ ID NO:12)  (4059)  AATTGTTATTTATTTTTAATTTTAAATTAGTTTATAATTT
FAD3A'' (SEQ ID NO:9)   (4160)  GATGTTTGCATACAATAATAGGAATGGAGTTATTTACGT
FAD3C'' (SEQ ID NO:11)  (4065)  GATGTTTGCATACAATAATAGGAATGGAGTTATTTACGT
FAD3C   (SEQ ID NO:10)  (3198)  GATGTTTT-TGTACAATAATAGGAATGGAGTTATTTACGT
                                      4561                                    4600
FAD3A   (SEQ ID NO:7)   (2668)  GGAGGATTAACAACTATTGATAGAG-----ATTACGG-GA
FAD3A'  (SEQ ID NO:8)   (3417)  GGAGGATTAACAACTATTGATAGAG-----ATTACGG-AA
FAD3C'  (SEQ ID NO:12)  (4099)  GTATGCATGATTTATATTAATAAAATTTATATTACTTTAA
FAD3A'' (SEQ ID NO:9)   (4200)  GGAGGATTAACAACTATTGATAGAG-----ATTACGG-AA
FAD3C'' (SEQ ID NO:11)  (4105)  GGAGGATTAACAACTATTGATAGAG-----ATTACGG-AA
FAD3C   (SEQ ID NO:10)  (3237)  GGAGGATTAACAACTGTTGATAGAG-----ATTACGG-GA
                                      4601                                    4640
FAD3A   (SEQ ID NO:7)   (2702)  TCTTCAACAACATTCATCACGATATTGGAACTCACGTGAT
FAD3A'  (SEQ ID NO:8)   (3451)  TTTTCAACAACATTCATCACGACATTGGAACTCACGTGAT
FAD3C'  (SEQ ID NO:12)  (4139)  TTATAAATATGATTT-TATATATGTTATATCTAATCGGTT
FAD3A'' (SEQ ID NO:9)   (4234)  TCTTCAACAACATCCATCACGACATTGGAACTCACGTGAT
FAD3C'' (SEQ ID NO:11)  (4139)  TCTTCAACAACATCCATCACGACATTGGAACTCACGTGAT
FAD3C   (SEQ ID NO:10)  (3271)  TCTTCAACAACATTCATCACGATATTGGAACTCACGTGAT
                                      4641                                    4680
FAD3A   (SEQ ID NO:7)   (2742)  CCATCATCTTTTCCCACAAATCCCTCACTATCACTTGGTT
FAD3A'  (SEQ ID NO:8)   (3491)  CCATCATCTTTTCCCACAAATCCCTCACTATCACTTGGTC
FAD3C'  (SEQ ID NO:12)  (4178)  TTGTTGTTTTTACAGTCGATTTAGT---TATCATTTGGGT
FAD3A'' (SEQ ID NO:9)   (4274)  CCATCATCTTTTCCCACAAATCCCTCACTATCACTTGGTC
FAD3C'' (SEQ ID NO:11)  (4179)  CCATCATCTTTTCCCACAAATCCCTCACTATCACTTGGTC
```

FIG. 1O

```
FAD3C (SEQ ID NO:10)    (3311) CCATCATCTTTTCCCACAAATCCCTCACTATCACTTGGTC
                               4681                                 4720
FAD3A (SEQ ID NO:7)     (2782) GATGCCGTGAGTGATCTCGCT----CTCTCTC---TAGTT
FAD3A' (SEQ ID NO:8)    (3531) GATGCTGTGAGTCATCTCACTCTCTGGCTAC------TTT
FAD3C' (SEQ ID NO:12)   (4215) -AAATTGGATTGCATCTCAGAATTCAACTGTAATATTTTT
FAD3A'' (SEQ ID NO:9)   (4314) GATGCGGTGAGTGATCTAGCTTTCTCTCTCTC---TAGTT
FAD3C'' (SEQ ID NO:11)  (4219) GATGCCGTGAGTGATCTAGCTTTCTCTCTCTC---TAGTT
FAD3C (SEQ ID NO:10)    (3351) GATGCCGTGAGTGATCTCGCT----CTCTCTC---TAGTT
                               4721                                 4760
FAD3A (SEQ ID NO:7)     (2815) TCATTTGATTAAAA--TTAAAGGGTGATTAATTACTAAAT
FAD3A' (SEQ ID NO:8)    (3565) CATCAAAACCATTTGATTAAAGGGTGATTAATTACTAATG
FAD3C' (SEQ ID NO:12)   (4254) TATTTTAACTATAT--TAAAATTTTGATTAATTTCTTATT
FAD3A'' (SEQ ID NO:9)   (4351) TCATTTGATTAAA-------TG-GTGATTAATTACTAATT
FAD3C'' (SEQ ID NO:11)  (4256) TCATTTGATTAAA-------TG-GTGATTAATTACTAATT
FAD3C (SEQ ID NO:10)    (3384) TCATTTGATTATA---TTAAAGGGTGATTAATTACTAAAT
                               4761                                 4800
```

FIG. 1O (CONT.)

```
FAD3A (SEQ ID NO:7)     (2853) TAGTGATCTTAATTAATGATATGCG-ACAGACGAAATCAG
FAD3A' (SEQ ID NO:8)    (3605) TAGTGATTTTA-ACAAATGGAATGTGACAGACAAAAGCAG
FAD3C' (SEQ ID NO:12)   (4292) T--TCATTT-----AGGTGGTTGTTGTCTTAGAACTT---
FAD3A'' (SEQ ID NO:9)   (4383) TA--------A-TTAATGAATTGTGGACAGACGAGAGCAG
FAD3C'' (SEQ ID NO:11)  (4288) TA--------A-TTAATGAATTGTGGACAGACGAGAGCAG
FAD3C (SEQ ID NO:10)    (3421) TAGTGATCTTAATTAATGACATGCG-ACAGACGAAAGCAG
                               4801                                 4840
FAD3A (SEQ ID NO:7)     (2892) CTAAACATGTGTTGGGAAGATACTACAGAGAACCAAAGAC
FAD3A' (SEQ ID NO:8)    (3644) CTAAACATGTGTTGGGAAGATACTACAGAGAACCAAAGAC
FAD3C' (SEQ ID NO:12)   (4322) -TAAATATATTTTATAAAGATTATGTATAACTTAATATAT
FAD3A'' (SEQ ID NO:9)   (4414) CTAAACATGTGTTAGGAAGATACTACAGAGAGCCGAAGAC
FAD3C'' (SEQ ID NO:11)  (4319) CTAAACATGTGTTAGGAAGATACTACAGAGAGCCGAAGAC
FAD3C (SEQ ID NO:10)    (3460) CTAAACATGTGTTGGGAAGATACTACAGAGAACCAAAGAC
                               4841                                 4880
FAD3A (SEQ ID NO:7)     (2932) GTCAGGAGC----AAT--ACCGATCCACTTGGTGGAAAGT
FAD3A' (SEQ ID NO:8)    (3684) GTCAGGAGC----AAT--ACCGATCCACTTGGTGGAGAGT
FAD3C' (SEQ ID NO:12)   (4361) ATATTGTGCTTAAAATGAAATAAAAAATAAAATAAAGTGT
FAD3A'' (SEQ ID NO:9)   (4454) GTCAGGAGC----AAT--ACCGATTCACTTGGTGGAGAGT
FAD3C'' (SEQ ID NO:11)  (4359) GTCAGGAGC----AAT--ACCGATTCACTTGGTGGAGAGT
FAD3C (SEQ ID NO:10)    (3500) GTCAGGAGC----AAT--ACCGATCCACTTAGTGGAAAGT
                               4881                                 4920
FAD3A (SEQ ID NO:7)     (2966) TTGGTGGCAAGTATTAAGAAAGATCATTACGTCAGTGACA
FAD3A' (SEQ ID NO:8)    (3718) TTGGTAGCAAGTATTAAGAAAGATCATTACGTCAGTGACA
```

FIG. 1P

```
 FAD3C' (SEQ ID NO:12)  (4401) CTGATTCTAAATTACATAAATTAATATAACGATAAT-ATT
FAD3A'' (SEQ ID NO:9)   (4488) TTGGTCGCAAGTATTAAAAAGATCATTACGTCAGTGACA
FAD3C'' (SEQ ID NO:11)  (4393) TTGGTCGCAAGTATTAAAAAGATCATTACGTCAGTGACA
   FAD3C (SEQ ID NO:10) (3534) TTGGTGGCAAGTATTAAGAAAGATCATTACGTCAGTGACA
                               4921                                 4960
   FAD3A (SEQ ID NO:7)  (3006) CTG--GTGATATTGTCTTCTACG---AGACAGATCCAGAT
  FAD3A' (SEQ ID NO:8)  (3758) CTG--GTGACATTGTCTTCTACG---AGACTGATCCAGAT
 FAD3C' (SEQ ID NO:12)  (4440) CTGAAGTCTCATGCATATATATATATAAATTTTACAAAAG
FAD3A'' (SEQ ID NO:9)   (4528) CTG--GTGATATTGTCTTCTACG---AGACAGATCCAGAT
FAD3C'' (SEQ ID NO:11)  (4433) CTG--GTGATATTGTCTTCTACG---AGACAGATCCAGAT
   FAD3C (SEQ ID NO:10) (3574) CTG--GTGATATTGTCTTCTACG---AGACAGATCCAGAT
                               4961                                 5000
   FAD3A (SEQ ID NO:7)  (3041) CTCTACGTT-TATGCTTCTGACAA-ATCCAAAATCAACTA
  FAD3A' (SEQ ID NO:8)  (3793) CTCTACGTT-TATGCTTCTGTCAA-ATCGAAAATCAATTA
 FAD3C' (SEQ ID NO:12)  (4480) AACTAAATTGTAACATTTGGTTAATATTTTACAGTAATTA
FAD3A'' (SEQ ID NO:9)   (4563) CTCTACGTT-TATGCTTCGGACAA-ATCTAAAATCAATTA
FAD3C'' (SEQ ID NO:11)  (4468) CTCTACGTT-TATGCTTCTGACAA-ATCTAAAATCAATTA
   FAD3C (SEQ ID NO:10) (3609) CTCTACGTT-TATGCTTCTGACAA-ATCCAAAATCAATTA
                               5001                                 5040
   FAD3A (SEQ ID NO:7)  (3079) ACCTTTCTTCCTAGCTCTATTTAG----------GAATAA
  FAD3A' (SEQ ID NO:8)  (3831) AACTTTCTTCCCCCTTTTGTTTAGCACTATTATGAATAA
 FAD3C' (SEQ ID NO:12)  (4520) AAATATTTTATAAATTCTAAATA---ACT-TTATGTATTT
FAD3A'' (SEQ ID NO:9)   (4601) ACTTTTCTTCCTAGCTCTATT-AG----------GAATAA
FAD3C'' (SEQ ID NO:11)  (4506) ACTTTTCTTCCTAGCTCTATT-AG----------GAATAA
   FAD3C (SEQ ID NO:10) (3647) ATCTTTCTTCCTAGCTCTATTTAG----------GAATAA
                               5041                                 5080
   FAD3A (SEQ ID NO:7)  (3109) AACAGTCCTTTGGTTTTTACTTATTTCTGGTTGTTTTTAA
  FAD3A' (SEQ ID NO:8)  (3871) A--CCAGTTTTTTTT---ACTTATATATTGTTGTTTTTAA
 FAD3C' (SEQ ID NO:12)  (4556) A--ATTTATTGAATGGAAACTGAAATTTATTTTAAATAAT
FAD3A'' (SEQ ID NO:9)   (4630) A-CACTCCTTCTCTTTT-ACTTATTTGTTTCTGCTTT-AA
FAD3C'' (SEQ ID NO:11)  (4535) A-CACTCCTTCTCTTTT-ACTTATTTGTTTCTGCTTT-AA
   FAD3C (SEQ ID NO:10) (3677) AACACTCCTTTGGTTTT-ACTTATTTCTGGTTGTTTTTAA
                                5081                                 5120
```

FIG. 1P (CONT.)

```
   FAD3A (SEQ ID NO:7)  (3149) GTTAAA--TGTACTCGTGAAACTTTTTTTA-ATTAAATGT
  FAD3A' (SEQ ID NO:8)  (3906) GTTAAAAATGTACTCGTGAAACTCTTCTTAATTTAGATAT
 FAD3C' (SEQ ID NO:12)  (4594) CTTAAAAATGAAAACATATTTGCTTTGGTATTTTGCTTAT
FAD3A'' (SEQ ID NO:9)   (4667) GTTTAAAATGTACTCGTGAAACCTTTTT---TATTAATGT
FAD3C'' (SEQ ID NO:11)  (4572) GTTTAAAATGTACTCGTGAAACCTTTTTTT-TATTAATGT
   FAD3C (SEQ ID NO:10) (3716) GTTAAAAATGTACTCGTGAAACTTTTTTTT-ATTAAATGT
                               5121                                 5160
   FAD3A (SEQ ID NO:7)  (3186) ATTTACATT-------ACAAATC----AAGTTTTTGTTCG
```

FIG. 1Q

```
  FAD3A' (SEQ ID NO:8)  (3946) TATTCCATT------TACA--CTGAAAAACATACAATTTC
 FAD3C' (SEQ ID NO:12)  (4634) GGTTCCATTAAGTTCTACAAACATAAAAACATAACATTTA
 FAD3A'' (SEQ ID NO:9)  (4704) ATTTACGTT-------ACAAAAAGTGGAAGTTTT-GTTAT
FAD3C'' (SEQ ID NO:11)  (4611) ATTTACGTT-------ACAAAAAGTGGAAGTTTT-GTTAT
  FAD3C (SEQ ID NO:10)  (3755) ATTTACATT-------ACAAATCGTAAAAGTTTTTGTTCG
                               5161                                 5200
   FAD3A (SEQ ID NO:7)  (3215) TTTTCTTTATGTTTTTAGTTACAA---TA---AATAAAG-
  FAD3A' (SEQ ID NO:8)  (3978) AAAGGT-TGAAAAGAAAGACAAAATTTTCT---AGAATGA
 FAD3C' (SEQ ID NO:12)  (4674) AAAACTGTGATTATTTTGTAACTATTTGATCAAACAATGA
 FAD3A'' (SEQ ID NO:9)  (4736) CTTTTTCTCTAGTTGCAATCAAAAGG--------------
FAD3C'' (SEQ ID NO:11)  (4643) CTTTTTCTCTGGTTGCAATCAAAAGG--------------
  FAD3C (SEQ ID NO:10)  (3788) TTTTCTCTATGTTTTTAGTTACAAACTTAC--AATCAAAA
                               5201                                 5240
   FAD3A (SEQ ID NO:7)  (3248) ----------------------------------------
  FAD3A' (SEQ ID NO:8)  (4014) C---------------------------------------
 FAD3C' (SEQ ID NO:12)  (4714) TTATTTTTTAATTTTAATTTTAGTTTTTTAATAACTCTTA
 FAD3A'' (SEQ ID NO:9)  (4762) ----------------------------------------
FAD3C'' (SEQ ID NO:11)  (4669) ----------------------------------------
  FAD3C (SEQ ID NO:10)  (3826) AG--------------------------------------
                               5241                                 5280
   FAD3A (SEQ ID NO:7)  (3248) ----------------------------------------
  FAD3A' (SEQ ID NO:8)  (4015) ----------------------------------------
 FAD3C' (SEQ ID NO:12)  (4754) AAAATAAGCAGTGAACAAAAGTGAGATTGTATTTGAAATT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5281                                 5320
   FAD3A (SEQ ID NO:7)  (3248) ----------------------------------------
  FAD3A' (SEQ ID NO:8)  (4015) ----------------------------------------
 FAD3C' (SEQ ID NO:12)  (4794) AATATTATACAAGTAAAATATAATTTTTTAAGTTTATAAA
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5321                                 5360
   FAD3A (SEQ ID NO:7)  (3248) ----------------------------------------
  FAD3A' (SEQ ID NO:8)  (4015) ----------------------------------------
 FAD3C' (SEQ ID NO:12)  (4834) AAAATTCCTTTTTATTATATGTATATGTTTTTTTGGAAAA
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5361                                 5400
```

FIG. 1Q (CONT.)

```
FAD3A (SEQ ID NO:7)  (3248) ----------------------------------------
  FAD3A' (SEQ ID NO:8)  (4015) ----------------------------------------
 FAD3C' (SEQ ID NO:12)  (4874) TTTTAAAAAGGAAACTAAATAAAAAAATAAATAATAGTAT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5401                                 5440
```

FIG. 1Q (CONT.)

```
   FAD3A (SEQ ID NO:7)  (3248) ----------------------------------------
  FAD3A' (SEQ ID NO:8)  (4015) ----------------------------------------
 FAD3C' (SEQ ID NO:12)  (4914) TTTAAATGTAATATTTTTAATTCATTAAGTGTATTAGTGT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5441                                 5480
   FAD3A (SEQ ID NO:7)  (3248) ----------------------------------------
  FAD3A' (SEQ ID NO:8)  (4015) ----------------------------------------
 FAD3C' (SEQ ID NO:12)  (4954) AATCAACTATCGTGAGAGTTAACGTGAGAGCGATACATAG
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5481                                 5520
   FAD3A (SEQ ID NO:7)  (3248) ----------------------------------------
  FAD3A' (SEQ ID NO:8)  (4015) ----------------------------------------
 FAD3C' (SEQ ID NO:12)  (4994) AAAACCGACTTCTCAAATAATATTTTATAGAGATTACGAT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5521                                 5560
   FAD3A (SEQ ID NO:7)  (3248) ----------------------------------------
  FAD3A' (SEQ ID NO:8)  (4015) ----------------------------------------
 FAD3C' (SEQ ID NO:12)  (5034) GTTTCACAAAAAAAAATTATTAGTATTTGATTAATCTTAA
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5561                                 5600
   FAD3A (SEQ ID NO:7)  (3248) ----------------------------------------
  FAD3A' (SEQ ID NO:8)  (4015) ----------------------------------------
 FAD3C' (SEQ ID NO:12)  (5074) TTCTTGATGTTTTGTGATTAATAATAGGAATGGAGTTACT
 FAD3A'' (SEQ ID NO:9)  (4762) ----------------------------------------
```

FIG. 1R

```
FAD3C'' (SEQ ID NO:11)  (4669) ----------------------------------------
  FAD3C (SEQ ID NO:10)  (3828) ----------------------------------------
                               5601                                 5640
   FAD3A (SEQ ID NO:7)  (3248) ----------------------------------------
  FAD3A' (SEQ ID NO:8)  (4015) ----------------------------------------
 FAD3C' (SEQ ID NO:12)  (5114) TACGTGGAGGATTAACAACTATTGATAGAGATTACGGAAT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5641                                 5680
   FAD3A (SEQ ID NO:7)  (3248) ----------------------------------------
  FAD3A' (SEQ ID NO:8)  (4015) ----------------------------------------
 FAD3C' (SEQ ID NO:12)  (5154) TTTCAACAACATTCATCACGACATTGGAACTCACGTGATC
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5681                                 5720
   FAD3A (SEQ ID NO:7)  (3248) ----------------------------------------
  FAD3A' (SEQ ID NO:8)  (4015) ----------------------------------------
 FAD3C' (SEQ ID NO:12)  (5194) CATCATCTTTTCCCACAAATCCCTCACTATCACTTGGTCG
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5721                                 5760
```

FIG. 1R (CONT.)

```
   FAD3A (SEQ ID NO:7)  (3248) ----------------------------------------
  FAD3A' (SEQ ID NO:8)  (4015) ----------------------------------------
 FAD3C' (SEQ ID NO:12)  (5234) ATGCTGTGAGTCATCTCACTCTCTCGCTACTTTCATCTAA
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5761                                 5800
   FAD3A (SEQ ID NO:7)  (3248) ----------------------------------------
  FAD3A' (SEQ ID NO:8)  (4015) ----------------------------------------
 FAD3C' (SEQ ID NO:12)  (5274) ACCATTTCATTAAAGGGTGATTAATTACTAATGTACTGAT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5801                                 5840
   FAD3A (SEQ ID NO:7)  (3248) ----------------------------------------
  FAD3A' (SEQ ID NO:8)  (4015) ----------------------------------------
 FAD3C' (SEQ ID NO:12)  (5314) TTTAACAAATGGAATGTGACAGACAAAAGCAGCTAAACAT
```

FIG. 1S

```
FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5841                                5880
   FAD3A (SEQ ID NO:7)  (3248) ----------------------------------------
  FAD3A' (SEQ ID NO:8)  (4015) ----------------------------------------
 FAD3C' (SEQ ID NO:12)  (5354) GCGTTGGGAAGATACTACAGAGAACCGAAGACGTCAGGAG
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5881                                5920
   FAD3A (SEQ ID NO:7)  (3248) ----------------------------------------
  FAD3A' (SEQ ID NO:8)  (4015) ----------------------------------------
 FAD3C' (SEQ ID NO:12)  (5394) CAATACCGATCCACTTGGTGGAGAGTTTGGTAGCAAGTAT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5921                                5960
   FAD3A (SEQ ID NO:7)  (3248) ----------------------------------------
  FAD3A' (SEQ ID NO:8)  (4015) ----------------------------------------
 FAD3C' (SEQ ID NO:12)  (5434) TAAGAAAGATCATTACGTCAGTGACACCGGTGACATTGTC
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               5961                                6000
   FAD3A (SEQ ID NO:7)  (3248) ----------------------------------------
  FAD3A' (SEQ ID NO:8)  (4015) ----------------------------------------
 FAD3C' (SEQ ID NO:12)  (5474) TTCTACGAGACTGATCCAGATCTCTACGTTTATGCTTCTG
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               6001                                6040
   FAD3A (SEQ ID NO:7)  (3248) ----------------------------------------
  FAD3A' (SEQ ID NO:8)  (4015) ----------------------------------------
 FAD3C' (SEQ ID NO:12)  (5514) TCAAATCGAAAATCAATTAAACTTTCTTCCCCCTTTTTGT
 FAD3A'' (SEQ ID NO:9)  (4762) ----------------------------------------
FAD3C'' (SEQ ID NO:11)  (4669) ----------------------------------------
  FAD3C (SEQ ID NO:10)  (3828) ----------------------------------------
                               6041                                6080
```

FIG. 1S (CONT.)

```
    FAD3A (SEQ ID NO:7)  (3248) ----------------------------------------
   FAD3A' (SEQ ID NO:8)  (4015) ----------------------------------------
  FAD3C' (SEQ ID NO:12)  (5554) TTAGCCCTATTATGAATAAACCAGTCTTTTTTCACTTATT
  FAD3A'' (SEQ ID NO:9)  (4762) ----------------------------------------
 FAD3C'' (SEQ ID NO:11)  (4669) ----------------------------------------
   FAD3C (SEQ ID NO:10)  (3828) ----------------------------------------
                                6081                                6120
    FAD3A (SEQ ID NO:7)  (3248) ----------------------------------------
   FAD3A' (SEQ ID NO:8)  (4015) ----------------------------------------
  FAD3C' (SEQ ID NO:12)  (5594) TATTGGTGTTTTTAAGTTAAAAATGTACTCGTGAAACTCT
  FAD3A'' (SEQ ID NO:9)  (4762) ----------------------------------------
 FAD3C'' (SEQ ID NO:11)  (4669) ----------------------------------------
   FAD3C (SEQ ID NO:10)  (3828) ----------------------------------------
                                6121                                6160
    FAD3A (SEQ ID NO:7)  (3248) ----------------------------------------
   FAD3A' (SEQ ID NO:8)  (4015) ----------------------------------------
  FAD3C' (SEQ ID NO:12)  (5634) TCTTTTATTATTAATCCATTTATACACTGAAAAACATACA
  FAD3A'' (SEQ ID NO:9)  (4762) ----------------------------------------
 FAD3C'' (SEQ ID NO:11)  (4669) ----------------------------------------
   FAD3C (SEQ ID NO:10)  (3828) ----------------------------------------
                                6161                                6200
    FAD3A (SEQ ID NO:7)  (3248) ----------------------------------------
   FAD3A' (SEQ ID NO:8)  (4015) ----------------------------------------
  FAD3C' (SEQ ID NO:12)  (5674) ATTTCAAAGGTTAAAAAGAAAAATAAATTTTCTAGACTGA
  FAD3A'' (SEQ ID NO:9)  (4762) ----------------------------------------
 FAD3C'' (SEQ ID NO:11)  (4669) ----------------------------------------
   FAD3C (SEQ ID NO:10)  (3828) ----------------------------------------
                                6201
    FAD3A (SEQ ID NO:7)  (3248) -
   FAD3A' (SEQ ID NO:8)  (4015) -
  FAD3C' (SEQ ID NO:12)  (5714) C
  FAD3A'' (SEQ ID NO:9)  (4762) -
 FAD3C'' (SEQ ID NO:11)  (4669) -
   FAD3C (SEQ ID NO:10)  (3828) -
```

FIG. 1T (CONT.)

(A) Sequences amplified from the junction of the tGFP cassette from pDAS000341 with Fad3C at the DSB recognized by ZFN 28051-2A-28052

":" indicates deletions at cut-site

5' junction of tGFP cassette with FadC

| Fad3 / ZFN recognition site 28051 | Inserted Bases | ZFN recognition site 28052 / AtUbi10p |
|---|---|---|
| TTCTGGCCTCTTTATTGGGCCGCCCAAGGAACCCTTTTCTGGGCCATCT | | TCGTACTCGGCCACGACTGGTAATTTAATGGATCCACTAGTAA |
| TTCTGGCCTCTTTATTGGGCCGCCCAAGGAACCCTTTTCTGGGCCATCT | | TCGTACTCGGCCACGACTGGTAATTTAATGGATCCACTAGTAA |
| TTCTGGCCTCTTTATTGGGCCGCCCAAGGAACCCTTTTCTGGGCCATC: | CAGTCGTGGCCGAGTACGAAGATGGCCCAGA | :::TACTCGGCCACGACTGGTAATTTAATGGATCCACTAGTAA |
| TTCTGGCCTCTTTATTGGGCCGCCCAAGGAACCCTTTTCTGGGCCATC: | | ::GTACTCGGCCACGACTGGTAATTTAATGGATCCACTAGTAA |
| TTCTGGCCTCTTTATTGGGCCGCCCAAGGAACCCTTTTCTGGG::::: | TATCTCAGTTCGGTGTAGGTCGTTCGCTCCAAGCTGGGCTGCGTGCACGAAC | :CGTACTCGGCCACGACTGGTAATTTAATGGATCCACTAGTAA |
| TTCTGGCCTCTTTATTGGGCCGCCCAAGGAACCCTTTTCTGGGCCA::: | | :::::::::::::GACTGGTAATTTAATGGATCCACTAGTAA |

3' junction of tGFP cassette with FadC

| AtuOrf23t / ZFN recognition site 28051 | Inserted Bases | ZFN recognition site 28052 / Fad3C |
|---|---|---|
| TCCAAGGTTGCGGCCGCGCCCAAGGAACCCTTTTCTGGGCCATCT | | TCGTACTCGGCCACGACTGGTAATTTAATTTTCAATTTATTT |
| TCCAAGGTTGCGGCCGCGCCCAAGGAACCCTTTTCTGGGCCAT:: | | :::TACTCGGCCACGACTGGTAATTTAATTTTCAATTTATTT |
| TCCAAGGTTGCGGCCGCGCCCAAGGAACCCTTTTCTGGGCCAT:T | | :::TACTCGGCCACGACTGGTAATTTAATTTTCAATTTATTT |
| :::::78 bases deleted ::::::::::::::::::::: | | :CGTACTCGGCCACGACTGGTAATTTAATTTTCAATTTATTT |
| TCCAAGGTTGCGGCCGCGCCCAAGGAACCCTTTTCTGGGCCATCT | | TCGTACTCGGCCACGACTGGTAATTTAATTTTCAATTTATTT |
| TCCAAGGTTGCGGCCGCGCCCAAGGAACCCTTTTCTGGGCCATCTTC | | :::::::::::::TGGTAATTTAATTTTCAATTTATTTTT |
| TCCAAGGTTGCGGCCGCGCCCAAGGAACCCTTTTCTGG:::::: | TAGCGGTGGTTTTTTTGTTTGCAAGCAGCAGATTACGCGCAGAAAAAAAGGA | TCGTACTCGGCCACGACTGGTAATTTAATTTTCAATTTATTT |
| TCCAAGGTTGCGGCCGCGCCCAAGGAACCCTTTTCTGGGCCATCT | TACGAGCGTAATGGCTGGCCTGTTGAACAAGTCTGGAAAGAAATGCATAAACATATCCCAGCCACGACT | ::::::::::::::::GGTAATTTAATTTTCAATTTATTT |

FIG. 20A (B) Sequences amplified from the junction of the tGFP cassette from pDAS000343 with Fad3C at the DSBs recognized by ZFNs 28051-2A-28052 and 28053-2A-28054. ":" indicates deletions at cut-site

| Fad3 / ZFN recognition site 28052 | Inserted Bases | ZFN recognition site 28052 / AtUbi10p |
|---|---|---|
| **TAGTTTATTTGCCCCAAGCGAGAGAAAGCTTATTGCAACTTCAAC** | | **TCGTACTCGGCCACGACTGGTAATTTAATGGATCCACTAGTAA** |
| TAGTTTATTTGCCCCAAGCGAGAGAAAGCTTATTGCAACTTCAACT | | :::::::::::::82 bases deleted:::::::::::: |
| TAGTTTATTTGCCCCAAGCGAGAGAAAGCTTATTGCAACTTCAA:: | CG | :::::::::::::68 bases deleted:::::::::::: |
| TAGTTTATTTGCCCCAAGCGAGAGAAAGCTTATTGCAACTTCAACT | | TCGTACTCGGCCACGACTGGTAATTTAATGGATCCACTAGTAA |
| TAGTTTATTTGCCCCAAGCGAGAGAAAGCTTATTGCAACTTCAACT | AT | ::GTACTCGGCCACGACTGGTAATTTAATGGATCCACTAGTAA |
| TAGTTTATTTGCCCCAAGCGAGAGAAAGCTTATTGCAACTTCA::: | | :::TACTCGGCCACGACTGGTAATTTAATGGATCCACTAGTAA |
| ::::::::121 bases deleted::::::::::::::::::: | | ::::::::::::::::AGGTAATTTAATGGATCCACTAGTAA |

| AtuOrf23t / ZFN recognition site 28053 | Inserted Bases | ZFN recognition site 28054 / Fad3C |
|---|---|---|
| **TCCAAGGTTGCGGCCGCAGCGAGAGAAAGCTTATTGCAACTTCAAC** | | **TACTTGCTGGTCGATCGTGTTGGCCACTCTTGTTTATCTATCA** |
| TCCAAGGTTGCGGCCGCAGCGAGAGAAAGCTTATTGCAACTTCA:: | | :ACTTGCTGGTCGATCGTGTTGGCCACTCTTGTTTATCTATCA |
| TCCAAGGTTGCGGCCGC:::::::::::::::::::::::::::::: | GCGCCGACCCAGCTTTCTTGTACAAAGTTGGCATTATAAGAAAGCATTGCTTATCAATTTGTTGCAACGAACAGGTCACTATCAGTCAAA | :ACTTGCTGGTCGATCGTGTTGGCCACTCTTGTTTATCTATCA |
| TCCAAGGTTGCGGCCGCAGCGAGAGAAAGCTTATTGCAAA:::::: | CTTC | :ACTTGCTGGTCGATCGTGTTGGCCACTCTTGTTTATCTATCA |
| TCCAAGGTTGCGGCCGCAGCGAGAGAAAGCTTATTGCAACTTCA:: | GATAAAAGTTGCTCGCCTGTGTGGGTGTGGATGCT | :ACTTGCTGGTCGATCGTGTTGGCCACTCTTGTTTATCTATCA |
| TCCAAGGTTGCGGCCGCAGCGAGAGAAAGCTTATTGCAACTTCAAC | TACAC | TACTTGCTGGTCGATCGTGTTGGCCACTCTTGTTTATCTATCA |
| TCCAAGGTTGCGGCCGCAGCGAGAGAAAGCTTATTGCAACTTCAAC | | TACTTGCTGGTCGATCGTGTTGGCCACTCTTGTTTATCTATCA |

| Sample | Fad3 — ZFN recognition site 28051 | # of Extra Bases Inserted | ZFN recognition site 28052 — CaMV19sp |
|---|---|---|---|
| | TTCTGGCCTCTTTATTGGGCCGCCCAAGGAACCCTTTTCTGGGCCATCT | | TCGTACTCGGCCACGACTGGTAATTTAATGGATCCAACCGACAACCACTT |
| **349711** | TTCTGGCCTCTTTATTGGGCCGCCCAAGGAACCCTTTTCTGGGCCAT:: | 442 | :::TACTCGGCCACGACTGGTAATTTAATGGATCCAACCGACAACCACTT |
| **349215c** | TTCTGGCCTCTTTATTGGGCCGCCCAAGGAACCCTTTTCTGGGCCATC: | 406 | TCGTACTCGGCCACGACTGGTAATTTAATGGATCCAACCGACAACCACTT |
| 349216c | TTCTGGCCTCTTTATTGGGCCGCCCAAGGAACCCTTTTCTGGGCCATC: | 406 | TCGTACTCGGCCACGACTGGTAATTTAATGGATCCAACCGACAACCACTT |
| **349685** | TTCTGGCCTCTTTATTGGGCCGCCCAAGGAACCCTTTTCTGGGCCAT :: | | :::TACTCGGCCACGACTGGTAATTTAATGGATCCAACCGACAACCACTT |
| 346258 | TTCTGGCCTCTTTATTGGGCCGCCCAAGGAACCCTTTTCTGGGCCATC: | 435 | :::TACTCGGCCACGACTGGTAATTTAATGGATCCAACCGACAACCACTT |
| 348918 | TTCTGGCCTCTTTATTGGGCCGCCCAAGGAACCCTTTTCTGGGCC:::: | 378 | :::TACTCGGCCACGACTGGTAATTTAATGGATCCAACCGACAACCACTT |
| 359900 | TTCTGGCCTCTTTATTGGGCCGCCCAAGGAACCCTTTTCTGGGCCATCT | | :::TACTCGGCCACGACTGGTAATTTAATGGATCCAACCGACAACCACTT |
| 346125 | TTCTGGCCTCTTTATTGGGCCGCCCAAGGAACCCTTTTCTGGGCCA::T | 62 | :::TACTCGGCCACGACTGGTAATTTAATGGATCCAACCGACAACCACTT |
| 348919 | TTCTGGCCTCTTTATTGGGCCGCCCAAGGAACCCTTTTCTGGGCCA::: | 378 | :::TACTCGGCCACGACTGGTAATTTAATGGATCCAACCGACAACCACTT |

FIG. 21B

| Sample | AtuORF1-t- — ZFN recognition site 28051 | # of Extra Bases Inserted | ZFN recognition site 28052 — Fad3C |
|---|---|---|---|
| | GTAATACATAGCGGCCGCGCCCAAGGAACCCTTTTCTGGGCCATCT | | TCGTACTCGGCCACGACTGGTAATTTAATTTTCAATTTATTTTTTCTTCAACTTCTTA |
| 346175 | GTAATACATAGCGGCCGCGCCCAAGGAACCCTTTTCTGGGCCATCT | | ::::::::GCCACGACTGGTAATTTAATTTTCAATTTATTTTTTCTTCAACTTCTTA |
| 346102 | **GTAATACATAGCGGCCGCGCCCAAGGAACCCTTTTCTGGGCCATCT** | | TCGTACTCGGCCACGACTGGTAATTTAATTTTCAATTTATTTTTTCTTCAACTTCTTA |

(B)

| Sample | AtuORF1-t- / ZFN recognition site 28053 | # of Extra Bases Inserted | ZFN recognition site 28054 / Fad3C |
|---|---|---|---|
| | GTAATACATAGCGGCCGCAGCGAGAGAAAGCTTATTGCAACTTCAAC | | TACTTGCTGGTCGATCGTGTTGGCCACTCTTGTTTATCTATCATTCCTCGTTGGTC |
| 345888 | GTAATACATAGCGGCCGCAGCGAGAGAAAGCTTATTGCAACTTCAA: | 137 | ::CTTGCTGGTCGATCATGTTGGCCACTCTTGTTTATCTATCATTCCTCGTTGGTC |
| 356731 | GTAATACATAGCGGCCGCAGCGAGAGAAAGCTTATTGCAACTTCAAC | | TACTTGCTGGTCGATCGTGTTGGCCACTCGGTACCTGGAGCACAAGACTGGCCTCA |

| Sample | Fad3 / ZFN recognition site 28051 | # of ExtraBases Inserted | ZFN recognition site 28052 / CaMV19sp |
|---|---|---|---|
| | TTCTGGCCTCTTTATTGGGCCGCCCAAGGAACCCTTTTCTGGCCATCT | | TCGTACTCGGCCACGACTGGTAATTTAATGGATCCAACCGACAACCACTT |
| 1:1 #5 | TTCTGGCCTCTTTATTGGGCCGCCCAAGGAACCCTTT::::::::::: | 3 | :::TACTCGGCCACGACTGGTAATTTAATGGATCCAACCGACAACCACTT |
| 1:1 #39 | TTCTGGCCTCTTTATTGGGCCGCCCAAGGAACCCTTTTCTGG:::::: | 153 | TCGTACTCGGCCACGACTGGTAATTTAATGGATCCAACCGACAACCACTT |
| 1:1 #46 | TTCTGGCCTCTTTATTGGGCCGCCCAAGGAACCCTTTTCTGG:::::: | | :::::::::::::::::136bp missing:::::::::::::::::::: |
| 5:1 #63 | TTCTGGCCTCTTTATTGGGCCGCCCAAGGAACCCTTTTCTGGCCATCT | 370 | :::::::CGGCCACGACTGGTAATTTAATGGATCCAACCGACAACCACTT |
| 10:1 #16 | TTCTGGCCTCTTTATTGGGCCGCCCAAGGAACCCTTTTCTGGCCAT:: | 36 | TCGTACTCGGCCACGACTGGTAATTTAATGGATCCAACCGACAACCACTT |
| 10:1 #64 | TTCTGGCCTCTTTATTGGGCCGCCCAAGGAACCCTTTTCTGGCCATCT | 78 | ::::::::::::::::::52bp missing:::::::::::::::::::: |
| 10:1 #66 | ::::::::::::::::::51bp missing::::::::::::::::::: | | :::::::::::::::::254bp missing:::::::::::::::::::: |

FIG. 23B

| | AtuORF1-t- / ZFN recognition site 28051 | # of ExtraBases Inserted | ZFN recognition site 28052 / Fad3C |
|---|---|---|---|
| | GTAATACATAGCGGCCGCGCCCAAGGAACCCTTTTCTGGCCATCT | | TCGTACTCGGCCACGACTGGTAATTTAATTTTCAATTTATTTTTTCTTCAACTTCTTA |
| 1:1 #5 | GTAATACATAGCGGCCGCGCCCAAGGAACCCTTTTCTGGCCAT:: | 4 | :::::::::GCCACGACTGGTAATTTAATTTTCAATTTATTTTTTCTTCAACTTCTTA |
| 1:1 #39 | GTAATACATAGCGGCCGCGCCCAAGGAACCCTTTTCTGGCCATCT | 112 | ::::::::::::::GACTGGTAATTTAATTTTCAATTTATTTTTTCTTCAACTTCTTA |
| 1:1 #46 | GTAATACATAGCGGCCGCGCCCAAGGAACCCTTTTCTGGCCATCT | 112 | ::::::::::::::GACTGGTAATTTAATTTTCAATTTATTTTTTCTTCAACTTCTTA |
| 5:1 #63 | GTAATACATAGCGGCCGCGCCCAAGGAACCCTTTTCTGGCCAT:: | 234 | ::GTACTCGGCCACGACTGGTAATTTAATTTTCAATTTATTTTTTCTTCAACTTCTTA |
| 10:1 #16 | ::1655bp missing (possible double insertion):: | | ::GTACTCGGCCACGACTGGTAATTTAATTTTCAATTTATTTTTTCTTCAACTTCTTA |
| 10:1 #64 | GTAATACATAGCGGCCGCGCCCAA::::::::::::::::::::: | 9 | :::TACTCGGCCACGACTGGTAATTTAATTTTCAATTTATTTTTTCTTCAACTTCTTA |
| 10:1 #66 | TGTAATACATAGCGGCCGCGCCCAAGGAACCCTTTACTCGGCCA:: | 7 | ::::::::::::::::::::TAATTTAATTTTCAATTTATTTTTTCTTCAACTTCTTA |

FIG. 24A

| Sample | Fad3 / ZFN recognition site 28051 | # of ExtraBases Inserted | ZFN recognition site 28052 / CaMV19sp |
|---|---|---|---|
| | TTCTGGCCTCTTTATTGGGCCGCCCAAGGAACCCTTTTCTGGGCCATCT | | TCGTACTCGGCCACGACTGGTAATTTAATGGATCCAACCGACAACCACTT |
| 5:1:1 #8 | | | |
| 10:1:1 #9 | TTCTGGCCTCTTTATTGGGCCGCCCAAGGAACCCTTTTCTGGGCCATCT | 206 | TCGTACTCGGCCACGACTGGTAATTTAATGGATCCAACCGACAACCACTT |
| 10:1:1 #21 | TTCTGGCCTCTTTATTGGGCCGCCCAAGGAACCCTTTTCTGGGCCATCT | 273 | :::::::CGGCCACGACTGGTAATTTAATGGATCCAACCGACAACCACTT |
| 10:1:1 #37 | TTCTGGCCTCTTTATTGGGCCGCCCAAGGAACCCTTTTCTGGGC::::: | 5 | ::::::TCGGCCACGACTGGTAATTTAATGGATCCAACCGACAACCACTT |

FIG. 24B

| Sample | AtuORF1-t- / ZFN recognition site 28053 | # of ExtraBases Inserted | ZFN recognition site 28054 / Fad3C |
|---|---|---|---|
| | GTAATACATAGCGGCCGCAGCGAGAGAAAGCTTATTGCAACTTCAAC | | TACTTGCTGGTCGATCGTGTTGGCCACTCTTGTTTATCTATCATTCCTCGTTGGTC |
| 5:1:1 #8 | GTAATACATAGCGGCCGCAGCGAGAGAAAGCTTATTGCAACTTCAAC | 229 | ::CTTGCTGGTCGATCGTGTTGGCCACTCTTGTTTATCTATCATTCCTCGTTGGTC |
| 10:1:1 #9 | GTAATACATAGCGGCCGCAGCGAGAGAAAGCTTATTGCAACTTCAAC | 26 | TACTTGCTGGTCGATCGTGTTGGCCACTCTTGTTTATCTATCATTCCTCGTTGGTC |
| 10:1:1 #21 | GTAATACATAGCGGCCGCAGCGAGAGAAAGCTTATTGCAACTTCAAC | 33 | :ACTTGCTGGTCGATCGTGTTGGCCACTCTTGTTTATCTATCATTCCTCGTTGGTC |
| 10:1:1 #37 | GTAATACATAGCGGCCGCAGCGAGAGAAAGCTTATTGCAACTTCAAC | 17 | ::CTTGCTGGTCGATCGTGTTGGCCACTCTTGTTTATCTATCATTCCTCGTTGGTC |

FAD3 PERFORMANCE LOCI AND CORRESPONDING TARGET SITE SPECIFIC BINDING PROTEINS CAPABLE OF INDUCING TARGETED BREAKS

CROSS-REFERENCE TO RELATED APPLICATIONS

The present application is a continuation of U.S. patent application Ser. No. 14/019,211 filed Sep. 5, 2013, now U.S. Pat. No. 9,914,930, which claims the benefit of U.S. Provisional Patent Application No. 61/697,854, filed Sep. 7, 2012, and U.S. Provisional Patent Application No. 61/820,260, filed on May 7, 2013, the disclosures of which are hereby incorporated by reference in their entireties.

FIELD OF THE DISCLOSURE

The present disclosure relates generally to compositions and methods for use in recombinant plant technology (for example, for generating a transgenic plant). More specifically, the present disclosure relates to plant cells and plants including loci within their genomes that may be used for the site-specific introduction of any nucleic acid of interest.

BACKGROUND

Many plants are genetically transformed with exogenous nucleic acids (e.g., transgenes) to introduce desirable traits, for example, to improve agricultural value. Examples of improvements in agricultural value that can be achieved through genetic transformation include: improved nutritional quality, increased yield, pest or disease resistance, drought and stress tolerance, improved horticultural quality (e.g., improved pigmentation and/or growth), herbicide resistance, production of industrially useful compounds and/or materials from the plant, and/or production of pharmaceuticals. The introduction of cloned genes into plant cells and recovery of stable fertile transgenic plants can be used to make a genetic modification of a plant stable through multiple generations, and thereby allow the genetic engineering of a crop plant.

In methods for genetic transformation and transgenic plant production, exogenous DNA is typically randomly introduced into the nuclear or plastid DNA of a eukaryotic plant cell, followed by isolation of cells containing integrated exogenous DNA, and subsequent regeneration of a stably transformed plant. Transgenic plants were typically generated by *Agrobacterium*-mediated transformation technology. Successes with these techniques spurred the development of other methods to introduce a nucleic acid molecule of interest into the genome of a plant, such as PEG-mediated DNA uptake in protoplasts, microprojectile bombardment, and silicon whisker-mediated transformation.

In all of these plant transformation methods, however, the exogenous nucleic acids incorporated in the plant genome are integrated randomly in the genome of the plant cell, and in unpredictable copy number. Terada et al. (2002) *Nat Biotechnol* 20(10):1030; Terada et al. (2007) *Plant Physiol* 144(2):846; D'Halluin et al. (2008) *Plant Biotechnology J.* 6(1):93. For example, the transgenes are frequently integrated in the form of sequence repeats, either of the whole transgene or of parts thereof. Such a complex integration pattern commonly adversely impacts the expression level of the integrated nucleic acid (e.g., by destruction of transcribed RNA through post-transcriptional gene silencing mechanisms, or by inducing methylation of the integrated DNA). Also, the location of the integration site commonly influences the level of expression of the integrated nucleic acid. Moreover, the integration of the exogenous DNA may have a disruptive effect on the region of the genome where the integration occurs, and thereby influence or disturb the normal function of that target region to produce undesirable side-effects. The combination of factors including the foregoing results in a wide variation in the level of expression of transgene or exogenous DNA (and overall agronomic quality) between different transgenic plant cell and plant lines, even those created by the same methods. Because the integration is random, these effects are not able to be controlled by the practitioner while he or she attempts to produce a new plant with desirable characteristics.

The foregoing considerations necessitate that, whenever the effects of introducing a particular exogenous nucleic acid into a plant is investigated, a large number of transgenic plant lines must be generated and analyzed in order to obtain significant results. Likewise, in the generation of a transgenic plant containing a particular integrated nucleic acid so as to provide the transgenic plant with a desired phenotype, a large population of independently created transgenic plant lines must be created to allow the selection of a plant line with optimal expression of the nucleic acid, and with minimal or no side-effects on the overall phenotype and performance of the transgenic plant. These practical considerations take on added importance in transgenic plants created by inserting multiple exogenous nucleic acids (i.e., gene stacking). In such plants, phenomena such as post-transcriptional gene silencing may be amplified.

Several methods have been developed in an effort to control transgene insertion in plants. See, e.g., Kumar and Fladung (2001) Trends Plant Sci. 6:155-9. These methods rely on homologous recombination-based transgene integration, which has been successfully applied both in prokaryotes and lower eukaryotes. Paszkowski et al. (1988) EMBO J. 7:4021-6. However, until recently in plants, the predominant mechanism for transgene integration has been based on illegitimate recombination, which involves little homology between recombining DNA strands. A major challenge in this area is therefore the detection and selective generation of rare homologous recombination events, which are masked by far more efficient integration events via illegitimate recombination. Moreover, even if the selective generation and detection of targeted homologous recombination events is achieved, the event must be targeted to a desirable location in the host genome in order to realize the maximum benefit of this strategy.

For example, an assumed benefit of targeted genetic transformation is the reduction in event-to-event variability of transgene expression, as compared to transformation events that are obtained from random integration. A further assumed benefit is a significant reduction in the number of events required to screen introduced nucleic acids, sort transformation constructs, and produce events that contribute to desirable overall characteristics in the resulting transgenic plant. A critical factor required to realize these benefits is the identification of specific locations in the genome where transgene performance is consistent, and if possible, where adverse effects on the host plant are eliminated or minimized.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination and integration at a predetermined chromosomal locus. See, for example, Urnov et al. (2010) *Nature* 435(7042):646-51; United States Patent Publications 20030232410; 20050208489; 20050026157; 20050064474; 20060188987; 20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) *Proc. Natl. Acad, Sci. USA* 104(9): 3055-3060 describes using designed ZFNs for targeted gene addition at a specified locus. U.S. Patent Publication 20110041195 describes methods of making homozygous diploid organisms.

However, there remains a need for compositions and methods for modifying and/or modulating expression of FAD3 genes in plants, including generation of plants with targeted insertions of desired transgenes at the FAD3 locus.

BRIEF SUMMARY OF THE DISCLOSURE

The present disclosure describes compositions and methods for modulating expression of FAD3 genes (e.g., in plants, algae, and fungi) and the use of these loci as sites for the targeted integration of a nucleic acid sequence of interest (e.g., an exogenous nucleic acid sequence) into a host cell. In some embodiments, a host cell may contain one or more genomes with one or more FAD3 sequences (e.g., homeologues and/or paralogs), any or all of which may be selectively modified and/or disrupted. In specific examples, the present disclosure describes FAD3A, FAD3A', FAD3C' and/or FAD3C genes, as well as corresponding homeologues or paralogs, in *Brassica napus* (i.e., *B. napus* line, DH12075) and their use as loci for targeted integration of a nucleic acid sequence of interest. As described herein, though FAD3 genes are involved in fatty acid biosynthesis in the host, their modification or disruption (e.g., by integration of an exogenous nucleic acid in the FAD3 coding sequence) unexpectedly may have no or minimal adverse effects on the resultant host organism.

Also described herein is the use of one or more particular FAD3 loci in tandem with a polypeptide capable of effecting cleavage and/or integration of specific nucleic acid sequences within the FAD3 loci. Examples of the use of FAD3 loci in tandem with a polypeptide capable of effecting cleavage and/or integration of the FAD3 loci include a polypeptide selected from the group consisting of zinc finger proteins, meganucleases, TAL domains, TALENs, RNA-guided CRISPR-Cas9, recombinases, leucine zippers, CRISPr/Cas and others known to those in the art. Particular examples include a chimeric ("fusion") protein comprising a site-specific DNA binding domain polypeptide and cleavage domain polypeptide (e.g., a nuclease), such as a ZFN protein comprising a zinc-finger polypeptide and a FokI nuclease polypeptide. For example, described herein is a demonstration of the in vitro and in vivo efficacy and specificity of particular ZFNs designed to bind and induce double stranded breaks in FAD3A, FAD 3A', FAD3A", FAD3C. FAD3C', FAD3C", and in combinations thereof without cleaving corresponding homeologues or paralogs. In some embodiments, particular FAD3 loci may be used with any of the foregoing polypeptides to effect site-specific integration of a nucleic acid of interest that is subsequently expressed in the host while having a minimal adverse impact on the agronomic performance of the host.

In certain aspects, described herein are polypeptides comprising a DNA-binding domain that specifically binds to a FAD3 gene. In some embodiments such a polypeptide may also comprise a nuclease (cleavage) domain or half-domain (e.g., a ZFN, a recombinase, a transposase, or a homing endonuclease, including a homing endonuclease with a modified DNA-binding domain, TAL domains, TALENs, RNA-guided CRISPR-Cas9), and/or a ligase domain, such that the polypeptide may induce a targeted double-stranded break, and/or facilitate recombination of a nucleic acid of interest at the site of the break. In particular embodiments, a DNA-binding domain that targets a FAD3 locus may be a DNA-cleaving functional domain. The foregoing polypeptides may be used in some embodiments to introduce an exogenous nucleic acid into the genome of a host organism exhibiting homologous recombination (e.g., a plant or animal species) at one or more FAD3 loci (e.g., a plant or animal species) at one or more FAD3 loci. In certain embodiments, the DNA-binding domains comprise a zinc finger protein with one or more zinc fingers (e.g., 2, 3, 4, 5, 6, 7, 8, 9 or more zinc fingers), and can which is engineered (non-naturally occurring) to bind to any sequence within a FAD3 gene. Any of the zinc finger proteins described herein may bind to a target site within the coding sequence of the target gene or within adjacent sequences (e.g., promoter or other expression elements). In certain embodiments, the zinc finger protein binds to a target site in an FAD3 gene, for example, as shown in Table 4. The recognition helix regions of exemplary FAD3-binding zinc fingers are shown in Table 3. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

Also described herein are methods for disrupting or editing a FAD3 gene. Additionally described herein are genetically modified host organisms (e.g., transgenic plants) produced by methods according to embodiments of the invention. In particular examples, a transgenic organism produced by a method according to an embodiment of the invention may be, without limitation, algae, a fungus, a monocotyledonous plant, a dicotyledonous plant, etc.

The foregoing and other features will become more apparent from the following detailed description of several embodiments, which proceeds with reference to the accompanying figures.

BRIEF DESCRIPTION OF THE FIGURES

FIGS. 1A through 1T, show sequence alignment of FAD3 gene sequences (SEQ ID NOs:7-12), generated using AlignX®.

FIGS. 20A and 20B, show sequence alignments after modification with the indicated ZFNs and donor plasmids. FIG. 20A shows a sequence alignment amplified from the junction of the tGFP cassette of pDAS000341 with Fad3C at the double strand break as recognized by ZFN 28051-2A-28052. The ":" indicates the deletions located at the cut sites. SEQ ID NO:300 to SEQ ID NO:313 are shown in the alignment, respectively, in order of appearance. FIG. 20B shows a sequence alignment amplified from the junction of the tGFP cassette of pDAS000343 with Fad3C at the double strand break as recognized by ZFN 28051-2A-28052 and ZFN 28053-2A-28054. The ":" indicates the deletions located at the cut sites. SEQ ID NO:314 to SEQ ID NO:327 are shown in the alignment, respectively, in order of appearance.

FIGS. 21A and 21B, show sequence alignments of sequences amplified from the junction of the hph cassette of pDAS000340 with FAD3C at the double strand break as recognized by ZFN 28051-2A-28052. "Sample" is a unique identifier for each plant that was assayed. The ":" indicates the deletions located at the cut sites. The sequences shown in FIG. 21A are for the 5' junction and the sequences shown in the FIG. 21B are for the 3' junction. SEQ ID NO:368 to SEQ ID NO:375 and SEQ ID NO:380 to SEQ ID NO:381 are shown in the alignment of FIG. 21A, respectively, in order of appearance. SEQ ID NO:376 to SEQ ID NO:377 and SEQ ID NO:382 are shown in the alignment of FIG. 21B, respectively, in order of appearance.

FIG. 22 shows a sequence alignment of sequences amplified from the junction of the hph cassette of pDAS000342 with FAD3C at the double strand break as recognized by ZFN 28053-2A-28054. "Sample" is a unique identifier for each plant that was assayed. The ":" indicates the deletions located at the cut sites. The sequences shown in the FIG. 22 are for the 3' junction. SEQ ID NO:378 to SEQ ID NO:379 and SEQ ID NO:383 are shown in the alignment, respectively, in order of appearance.

FIGS. 23A and 23B, show a sequence alignment for sequences amplified from the junction of the hph cassette of pDAS000340 with FAD3C at the double strand break as recognized by ZFN 28051-2A-28052. The ":" indicates the deletions located at the cut sites. The sequences shown in FIG. 23A are for the 5' junction and the sequences shown in the box (B) are for the 3' junction. SEQ ID NO:328 to SEQ ID NO:334 are shown in the alignment of FIG. 23A, respectively, in order of appearance. SEQ ID NO:335 to SEQ ID NO:342 are shown in the alignment of FIG. 23B, respectively, in order of appearance.

FIGS. 24A and 24B, shows a sequence alignment of sequences amplified from the junction of the hph cassette of pDAS000342 with FAD3C at the double strand break as recognized by ZFN 28053-2A-28054. The ":" indicates the deletions located at the cut sites. The sequences shown in FIG. 24A are for the 5' junction and the sequences shown in FIG. 24B) are for the 3' junction. SEQ ID NO:343 to SEQ ID NO:346 are shown in the alignment of FIG. 24A, respectively, in order of appearance. SEQ ID NO:347 to SEQ ID NO:351 are shown in the alignment of FIG. 24B, respectively, in order of appearance.

SEQUENCE LISTING

Figure 2:
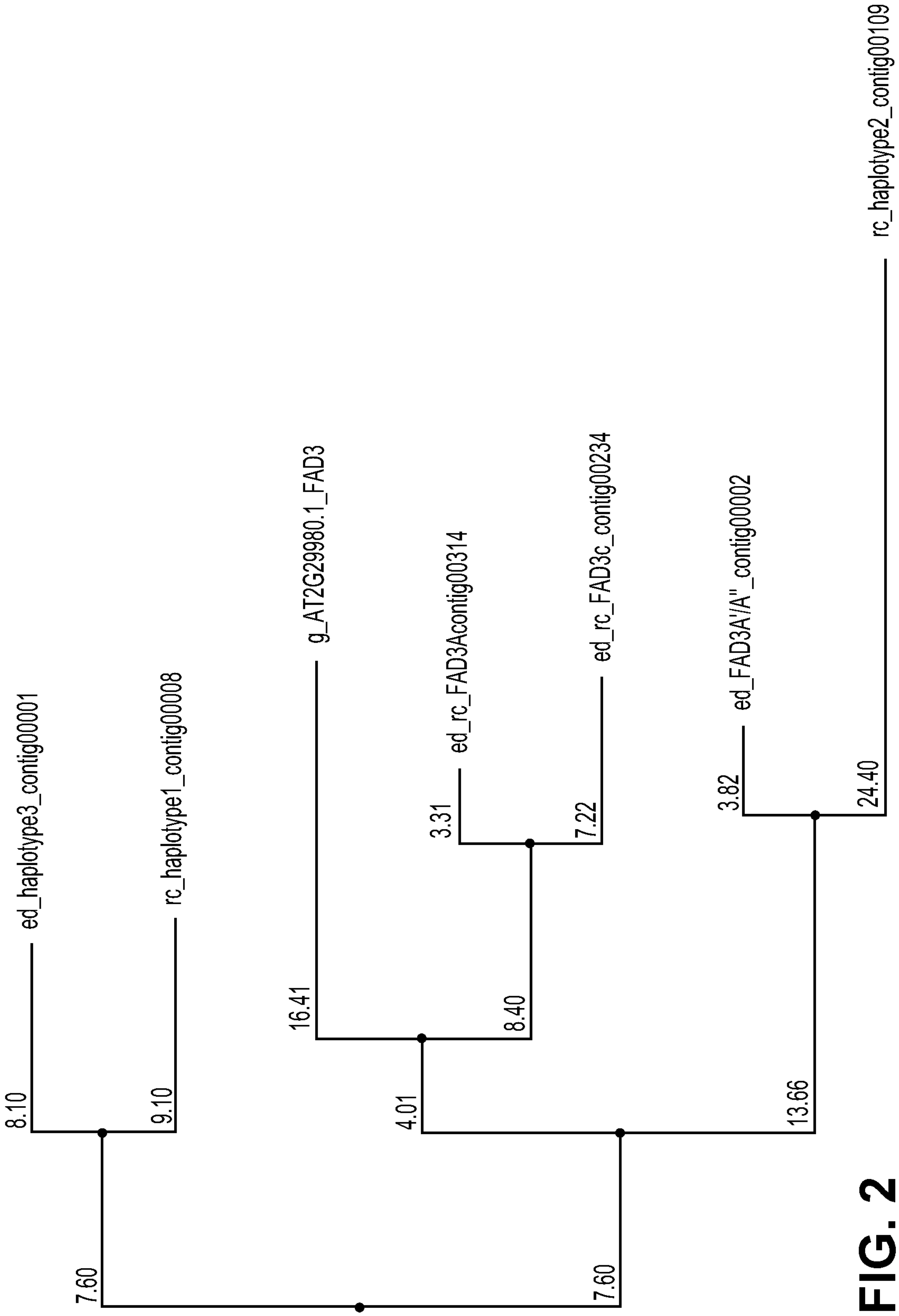
FIG. 2 shows a phylogenetic tree of FAD3 gene sequences generated using Jalview v 2.3 based on neighbour joining distances. The labeled sequences correspond as follows: FAD3A'/A" is described throughout this application as FAD3A'; Haplotype2 is described throughout the application as FAD3C'; Haplotype 1 is described throughout the application as FAD3C"; and, Haplotype 3 is described throughout the application as FAD3A".

The nucleic acid sequences are shown using standard letter abbreviations for nucleotide bases, as defined in 37 C.F.R. § 1.822. Only one strand of each nucleic acid sequence is shown, but the complementary strand is understood to be included by any reference to the displayed strand.

DETAILED DESCRIPTION

I. Overview of Several Embodiments

Embodiments of the invention establish an approach for targeted integration of exogenous nucleic acids (e.g., transgenes) in a host genome without greatly adversely impacting other phenotypes of the host beyond those affected by the integrated nucleic acid. Some embodiments may be used for "stacking" multiple nucleic acids in a single host genome. Such an approach uses the development and deployment of four inter-connected technologies: targeting technologies allowing the introduction of double stranded breaks in specific genomic DNA locations (see, e.g., Puchta et al. (1993) Nucleic Acids Res. 21:5034-40; Siebert and Puchta (2002) Plant Cell 14:1121-31; D'Halluin et al. (2008) Plant Biotechnol. J. 6(1):93-102; Cai et al. (2009) Plant Mol. Biol. 69(6):699-709; Shukla et al. (2009) Nature 459(7245):437-41); Shan et al. (2103) Nature Biotechnol. 31:686-680; Le et al. (2013) Nature Biotechnol 31: 688-691; Nekrasov et al. (2013) Nature Biotechnol. 31:691-693, Ainely et al. (2013) Plant Biotechnol. J. (On Line 19 August); delivery technologies allowing the delivery of an optimized exogenous (donor) nucleic acid (Bibikova et al. (2003) Science 300(5620):764); integration technologies involving modification of the host genes (located either in the homologous recombination or NHEJ pathways) so as to increase the HDR or NHEJ frequencies for targeted donor DNA integration; analytical tools to enrich and characterize targeted integration events; and specific desired host genomic locations ("performance loci") that are genetically well-defined and that support stable gene expression across generations without greatly adversely affecting the transformed host organism. See, also, United States Patent Publications 20030232410; 20050208489; 20050026157; 20050064474; 20060188987; 20090263900; 20090117617; 20100047805; 20110207221; 20110301073; 2011089775; 20110239315; 20110145940; 20080182332; 20090205083; 20100199389; 20110167521. For example, in plants, a performance locus is a locus where the negative impact on the agronomic or quality properties of a transgenic plant wherein a transgene has been inserted at the locus is negligible or non-existent.

Embodiments described herein take advantage of the unexpected finding that plant FAD3 genes are performance loci for the targeted insertion of exogenous nucleic acids (e.g., gene(s); non-coding DNA sequences, such as an Engineered Landing Pads (ELPs) (U.S. Publication No. 20110191899) and Engineered Transgene Insertion Platform (ETIP) (U.S. Publication No. 20140090113); and plant transformation unit(s)). The ubiquitous nature of FAD3 loci in plants, and evidence that alteration or knock-out of FAD3 in canola, corn, sunflower, wheat, cotton, and soybean does not carry an agronomic or quality penalty, identifies FAD3 loci as a broad class of performance loci across commercially-relevant plant species.

Some embodiments utilize site-specific double-stranded DNA cleavage at a FAD3 locus, for example, resulting from the delivery and expression of a target-site specific DNA recognition and cleavage protein. In specific examples, such a FAD3-specific DNA recognition and cleavage protein may be, for example and without limitation, a ZFN; a TALEN; RNA-guided CRISPR-Cas9 system, a recombinase (e.g., Cre, Hin, RecA, Tre, and FLP recombinases); a meganuclease, and an engineered protein derived from any of the foregoing or their equivalents. Cleavage may also be effected using the CRISPR/Cas system with an engineered crRNA/tracr RNA ('single guide RNA') to guide specific cleavage. In some embodiments, such a double-strand break may be repaired via integration of a donor nucleic acid at the cleavage site within the FAD3 performance locus, for example, by Homology Directed Repair (HDR) or Non-Homologous End Joining (NHEJ).

This disclosure exemplifies the utility of FAD3 loci as performance loci, for example, by describing the FAD3A or 3C locus in canola (*Brassica napus*), and corresponding FAD3-specific ZFNs that may be utilized to integrate an exogenous nucleic acid at the FAD3A or 3C locus.

Embodiments of the present invention address many unsolved problems in the art. For example, the selectivity of the targeted integration approach described herein may reduce or eliminate the necessity of repeated field trials required for elimination of unwanted transgenic events, which trials are costly due to the resources involved and the burdensome regulatory requirements in this area. Furthermore, the targeted DNA insertion approaches described herein may be particularly beneficial in the process of transgene stacking.

Although the native nucleotide sequence at an endogenous FAD3 locus may be used to directly target a nucleic acid of interest, in some embodiments, a nucleic acid may first be targeted to at least one FAD3 locus of the host, such that the integration of further nucleic acid molecules of interest into the host is facilitated. In other examples, nucleotide sequences that are not homologous to native sequences of the host organism (e.g., essentially randomly generated nucleic acid sequences) that flank a DNA recognition site (e.g., zinc finger recognition sites) may be utilized.

II. Terms

As used in this application, including the claims, terms in the singular and the singular forms, "a," "an," and "the," for example, include plural referents, unless the content clearly dictates otherwise. Thus, for example, a reference to "plant," "the plant," or "a plant" also refers to a plurality of plants. Furthermore, depending on the context, use of the term, "plant," may also refer to genetically-similar or identical progeny of that plant. Similarly, the term, "nucleic acid," may refer to many copies of a nucleic acid molecule. Likewise, the term, "probe," may refer to many similar or identical probe molecules.

Numeric ranges are inclusive of the numbers defining the range, and expressly include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Cross: As used herein in regard to plants, the term "cross" or "crossed" refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into a plant. This technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a nucleic acid sequence of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred nucleic acid sequence from the non-recurrent parent.

Introgression: As used herein, the term "introgression" refers to the transmission of an allele (or modified allele comprising an exogenous nucleic acid) into a genetic background at a particular locus. In some embodiments, introgression of a specific allele at the locus may occur by transmitting the allele to at least one progeny via a sexual cross between two parents of the same species, where at least one of the parents has the specific allele form in its genome. Progeny comprising the specific allele may be repeatedly backcrossed to a line having a desired genetic background. Backcross progeny may be selected for the specific allele form, so as to produce a new variety wherein the specific allele form has been fixed in the genetic background. In some embodiments, introgression of a specific allele may occur by recombination between two donor genomes (e.g., in a fused protoplast), where at least one of the donor genomes has the specific allele form in its genome. Introgression may involve transmission of a specific allele form that may be, for example and without limitation, a disrupted or modified allele; a transgene; a PTU; and an ELP.

Germplasm: As used herein, the term "germplasm" refers to genetic material of or from an individual plant, a group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells). As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated.

Gene: As used herein, the term "gene" (or "genetic element") may refer to a heritable genomic DNA sequence with functional significance. A gene may be a native nucleic acid, or a nucleic acid that has been integrated into the genome. The term "gene" may also be used to refer to, for example and without limitation, a cDNA and/or an mRNA encoded by a heritable genomic DNA sequence.

Nucleic acid molecule: As used herein, the term "nucleic acid molecule" may refer to a polymeric form of nucleotides (i.e., ribonucleotides, deoxyribonucleotides, and/or a modified form of either of the foregoing). A "nucleic acid molecule" as used herein is synonymous with "nucleic acid" and "polynucleotide." The term includes both sense and anti-sense strands of RNA, cDNA, genomic DNA, and synthetic forms and mixed polymers thereof. The term includes any topological conformation, including single-stranded, double-stranded, partially duplexed, triplexed, hairpinned, circular, and padlocked conformations. A nucleic acid molecule can include either or both of naturally-occurring and modified nucleotides. Such nucleotides may be linked together by naturally-occurring and/or non-naturally-occurring nucleotide linkages.

Nucleic acid molecules may be modified chemically or biochemically, or may contain derivatized nucleotide bases, as will be readily appreciated by those of skill in the art. Such modifications include, for example and without limitation: labels; methylation; substitution of one or more of the naturally-occurring nucleotides with an analog; and internucleotide modifications (e.g., uncharged linkages, for example, methyl phosphonates, phosphotriesters, phosphoramidates, and carbamates; charged linkages, for example, phosphorothioates and phosphorodithioates; pendent moieties, for example, peptides; intercalators, for example, acridine and psoralen; chelators; alkylators; and modified linkages, for example, alpha anomeric nucleic acids).

Exogenous: An "exogenous" molecule is a molecule that is not native to a specified system (e.g., a germplasm, variety, elite variety, and/or plant) with respect to nucleotide sequence and/or genomic location (i.e., locus) for a polynucleotide (and with respect to amino acid sequence and/or cellular localization for a polypeptide). In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A promoter is a region of DNA that generally is located upstream (towards the 5' region) of a nucleic acid that enhances transcription of the nucleic acid. Promoters permit the proper activation or repression of the nucleic acid(s) with which they are operably linked. A promoter contains specific sequences that are recognized by transcription factors. These factors bind to the promoter DNA sequences and result in the recruitment of RNA polymerase, the enzyme that synthesizes the RNA from the coding region of the nucleic acid. Transformed: A vector "transforms" or "transduces" a cell when it transfers nucleic acid molecules into the cell. A cell is "transformed" by a nucleic acid molecule when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Introduced: As used herein, the term "introduced," when referring to translocation of an exogenous nucleic acid into a cell, refers to the incorporation of the nucleic acid into the cell using any methodology available in the art. This term encompasses nucleic acid introduction methods including, for example and without limitation, transfection; transformation; and transduction.

Transgene: As used herein, the term "transgene" refers to an exogenous nucleic acid coding sequence of interest. For example, a transgene may encode an industrially or pharmaceutically useful compound, or an expression product that contributes to a desirable agricultural trait (e.g., herbicide resistance or pest resistance). In a further example, a transgene may be an antisense nucleic acid, wherein expression of the antisense nucleic acid inhibits expression of a target nucleic acid sequence. A transgene may comprise regulatory sequences operably linked to the transgene (e.g., a promoter). In some embodiments, a nucleic acid molecule of interest to be introduced by site-specific targeting at a FAD3 locus is a transgene. However, in other embodiments, a nucleic acid molecule of interest may be a PTU, an ELP, an ETIP, or an endogenous nucleic acid sequence (e.g., wherein additional, exogenous genomic copies of the endogenous nucleic acid sequence are desired).

Elements can also include DNA that encodes for a structural RNA, such as shRNA. Such RNA can modify exogenous or endogenous genes including, but not limited to affecting postings or conferring herbicide resistance.

Recombinant: As used herein, the term "recombinant" refers to a material (e.g., nucleic acid, gene, polynucleotide, and/or polypeptide) that has been altered by human intervention. For example, the arrangement of the parts or elements of a recombinant molecule may not be a native arrangement, and/or the primary sequence of the recombinant molecule may have been changed from its native sequence, e.g., to optimize its expression and/or activity. A material may be altered to produce a recombinant material within or removed from its natural environment or state. As one example, an open reading frame of a nucleic acid is recombinant if the nucleotide sequence of the open reading frame has been removed from it natural context and cloned into an artificial nucleic acid molecule (e.g., a vector). Protocols and reagents to produce recombinant molecules (e.g., recombinant nucleic acids) are common in the art, and their use is routine. The term "recombinant" may also refer herein to a cell or organism that comprises recombinant material (e.g., a plant and/or plant cell that comprises a recombinant nucleic acid). In some examples, a recombinant organism is a transgenic organism.

Vector: As used herein, the term "vector" refers to a polynucleotide or other molecule that is capable of transferring at least one nucleic acid segment(s) into a cell. A vector may optionally comprise components/elements that mediate vector maintenance and/or enable its intended use (e.g., sequences necessary for replication, genes imparting drug or antibiotic resistance, a multiple cloning site, and/or operably linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably linked elements to facilitate cloning or subcloning steps (e.g., a multiple cloning site containing multiple restriction endonuclease sites).

Expression Vector: The term "expression vector," as used herein, refers to a vector comprising operably linked polynucleotide sequences that may facilitate expression of a coding sequence in a particular host organism. For example, a bacterial expression vector may facilitate expression of a coding sequence in a bacterium. Likewise, a plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) may comprise, for example, promoters; enhancers; termination signals; and polyadenylation signals (and other sequences) that are generally different from those used in prokaryotic expression vectors.

Sequence identity: The term "sequence identity" or "identity," as used herein in the context of two nucleic acid or polypeptide sequences, refers to the residues in the two sequences that are the same when aligned for maximum correspondence over a specified comparison window. A value of sequence identity may be determined by comparing two optimally aligned sequences (e.g., nucleic acid sequences and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The sequence identity is calculated as a percentage by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in Altschul et al. (1990) J. Mol. Biol. 215:403-10.

The National Center for Biotechnology Information (NCBI) Basic Local Alignment Search Tool (BLAST™; Altschul et al. (1990)) may be used to align sequences, and it is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with greater similarity to the reference sequences will show increasing percentage identity when assessed by this method.

As used herein, the term "substantially identical" may refer to nucleotide sequences that are more than 80% identical. For example, a substantially identical nucleotide sequence may be at least 85%, at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Locus: As used herein, the term "locus" refers to a position on a genome that corresponds to a measurable characteristic (e.g., a trait). In some embodiments, a locus of particular interest is the genomic position of a FAD3 gene, where disruption of the gene reduces or eliminates expression of the mRNA transcribed from the wild-type gene. A locus may be defined by a probe that hybridizes to a unique nucleotide sequence contained within the locus either during Southern hybridization or PCR.

Marker: As used herein, a "marker" refers to a gene or nucleotide sequence that can be used to identify plants that are likely to have a particular allele and/or exhibit a particular trait or phenotype. A marker may be described as a variation at a given genomic locus. A genetic marker may be a short DNA sequence, such as a sequence surrounding a single base-pair change (single nucleotide polymorphism, or "SNP"), or a long sequence, for example, a minisatellite/simple sequence repeat ("SSR"). A "marker allele" refers to the version of the marker that is present in a particular plant. The term marker as used herein may refer to a cloned segment of plant chromosomal DNA (e.g., a segment comprising a FAD3 locus, or a modified and/or disrupted FAD3 locus), and may also or alternatively refer to a DNA molecule that is complementary to a cloned segment of plant chromosomal DNA. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. Any and all of the above-described varieties of markers may be used in some embodiments of the present invention.

In some embodiments, the presence of a transgene or marker (which are characterized by a "target" sequence) in a germplasm may be detected through the use of a nucleic acid probe; e.g., an oligonucleotide. A probe may be a DNA molecule or an RNA molecule. An oligonucleotide probe may be prepared synthetically or by cloning. Suitable cloning vectors are well-known to those of skill in the art. RNA probes can be synthesized by means known in the art, for example, using a DNA molecule template.

An oligonucleotide probe may be labeled or unlabeled. A wide variety of techniques exist for labeling nucleic acid molecules, including, for example and without limitation, radiolabeling by nick translation; random priming; and tailing with terminal deoxytransferase, where the nucleotides employed are labeled, for example, with radioactive $^{32}P$. Other labels which may be used include, for example and without limitation, fluorophores; enzymes; enzyme substrates; enzyme cofactors; and enzyme inhibitors. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may be an exact copy of a transgene or marker to be detected. A probe may also be a nucleic acid molecule comprising, or consisting of, a nucleotide sequence that is substantially identical to a cloned segment of chromosomal DNA comprising the transgene or marker to be detected. A probe may further comprise additional nucleic acid sequences, for example, promoters; transcription signals; and/or vector sequences.

A probe may contain all or a portion of the target nucleotide sequence and additional, contiguous nucleotide sequence from the genome. This is referred to herein as a "contiguous probe." The additional, contiguous nucleotide sequence is referred to as "upstream" or "downstream" of the original target, depending on whether the contiguous nucleotide sequence from the chromosome is on the 5' or the 3' side of the original marker, as conventionally understood. A probe may also contain a nucleotide sequence that is not contiguous to that of the original target; this probe is referred to herein as a "non-contiguous probe." The sequence of the non-contiguous probe may be located sufficiently close to the sequence of the original target on the chromosome so that the non-contiguous probe is linked to the original marker or transgene.

In some embodiments, a probe is a nucleic acid molecule that is "specifically hybridizable" or "specifically complementary" to an exact copy of the target to be detected. "Specifically hybridizable" and "specifically complementary" are terms that indicate a sufficient degree of complementarity, such that stable and specific binding occurs between the nucleic acid molecule and the target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual,* 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 μg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

Linkage (dis)equilibrium: As used herein, the term "linkage equilibrium" refers to the situation where a marker and a second nucleic acid (e.g., transgene, PTU, and second marker) independently segregate; i.e., the marker and the second nucleic acid sort randomly among progeny. Nucleic acids that show linkage equilibrium are considered unlinked (whether or not they lie on the same chromosome). As used herein, the term "linkage disequilibrium" refers to the situation where a marker and a second nucleic acid segregate in a non-random manner; i.e., the nucleic acids have a recombination frequency of less than 50% (and thus by definition, are separated by less than 50 cM on the same linkage group). In some examples, nucleic acids that show linkage disequilibrium are considered linked.

Linked, tightly linked, and extremely tightly linked: As used herein, linkage between a marker and a second nucleic acid (e.g., transgene, PTU, and second marker) may refer to the phenomenon in which nucleic acids on a chromosome show a measurable probability of being passed on together to individuals in the next generation. Thus, linkage of one marker to a second nucleic acid may be measured and/or expressed as a recombination frequency. The closer two nucleic acids are to each other, the closer to "1" this probability becomes. Thus, the term "linked" may refer to one or more genes or markers that are passed together with a second nucleic acid with a probability greater than 0.5 (which is expected from independent assortment where markers/genes are located on different chromosomes). When the presence of a gene (e.g., a transgene) contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance) the more tightly they are linked. Because chromosomal distance is approximately proportional to the frequency of recombination events between traits, there is an approximate physical distance that correlates with recombination frequency. This correlation is generally known or readily determinable across the major crop plants (Helentjaris and Burr (eds.) (1989) *Development and Application of Molecular Markers to Problems in Plant Genetics*. Cold Spring Harbor Laboratory, Cold Spring Harbor, N.Y.; Gresshoff (ed.) (1994) *Plant Genome Analysis*. CRC Press, Boca Raton, Fla.; Lander et al. (1987) Genomics 1:174-81; Tanksley et al. (1988) "Molecular mapping of plant chromosomes," In *Chromosome Structure and Function*. Gustafson and Appels (eds.) Plenum Press, NY, pp. 157-73) and many other organisms. For example, 1 cM corresponds to about 2.5-3.0 kb in yeast, about 140 kb in *Arabidopsis*, about 400 kb in sunflower, and about 350 kb in *Eucalyptus.*

The term "linked" may refer herein to one or more nucleic acids that show a recombination frequency of less than 50% (i.e., less than 50 cM). For example, "linked" nucleic acids may recombine with a frequency of about 45% or less, about 40% or less, about 35% or less, about 30% or less, about 25% or less, about 20% or less, about 15% or less, and about 10% or less. The physical distances between such nucleic acids on the same chromosome (nucleic acids on different chromosomes are expected to be in linkage equilibrium) that correspond to the foregoing recombination frequencies depend on the host genome, and may be easily calculated as set forth, supra.

As used herein, the term "tightly-linked" may refer to one or more nucleic acids that show a recombination frequency of about 20% or less (i.e., about 20 cM or less). For example, "tightly linked" nucleic acids may recombine with a frequency of 22% or less, about 18% or less, about 16% or less, about 14% or less, about 12% or less, about 10% or less, about 8% or less, about 6% or less, about 4% or less, and about 2% or less.

As used herein, the term "extremely tightly-linked" may refer to one or more nucleic acids that show a recombination frequency of about 10% or less (i.e., about 10 cM or less). For example, "extremely tightly linked" nucleic acids may recombine with a frequency of 11% or less, about 9% or less, about 8% or less, about 7% or less, about 6% or less, about 5% or less, about 4% or less, about 3% or less, about 2% or less, and about 1% or less.

The closer a particular nucleic acid is to a gene that encodes a polypeptide that contributes to a particular phenotype (whether measured in terms of genetic or physical distance), the more tightly-linked is the particular nucleic acid to the phenotype. In view of the foregoing, it will be appreciated that nucleic acids linked to a particular gene or phenotype include those nucleic acids that are tightly linked, and those nucleic acids that are extremely tightly linked, to the gene or phenotype. In some embodiments, the closer a particular nucleic acid is to a FAD3 locus (e.g., a modified or disrupted FAD3 locus), whether measured in terms of genetic or physical distance, the more tightly-linked is the particular nucleic acid to any trait/phenotype conferred by an exogenous nucleic acid integrated at the FAD3 locus (or to a wild-type FAD3 phenotype in the case of an unmodified locus). Thus, genetic markers that are linked, tightly linked, and/or extremely tightly linked to a FAD3 locus comprising an integrated exogenous nucleic acid may be useful in an MAS program to identify organisms (e.g., plants and plant varieties) comprising the integrated nucleic acid, to identify organisms comprising a phenotype conferred by the integrated nucleic acid, and to breed such an integrated nucleic acid and/or a phenotype conferred by the integrated nucleic acid into other compatible organisms.

Marker-assisted breeding: As used herein, the term "marker-assisted breeding" may refer to an approach to breeding plants directly for one or more trait(s) (e.g., a polygenic trait). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships between traits of interest and easily detectable traits available for use in plant breeding. In some embodiments of the invention, marker-assisted breeding comprises identifying one or more genetic markers (e.g., SNP, isozyme, and/or SSR markers) that are linked to a FAD3 locus wherein an exogenous nucleic acid contributing to a trait of interest has been integrated, and following the trait of interest in a segregating, breeding population by following the segregation of the one or more genetic markers. In some examples, the segregation of the one or more genetic markers may be determined utilizing a probe for the one or more genetic markers by assaying a genetic sample from a progeny plant for the presence of the one or more genetic markers.

Marker-assisted breeding provides a time- and cost-efficient process for improvement of plant varieties.

Trait or phenotype: The terms "trait" and "phenotype" are used interchangeably herein. For the purposes of the present disclosure, traits of particular interest include agronomically important traits, as may be expressed, for example, in a crop plant, and the production of transgene expression products from a targeted integration event. The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Quantitative Trait Locus: Traits that are continuously varying due to genetic (additive, dominant, and epistatic) and environmental influences are commonly referred to as "quantitative traits." Quantitative traits may be distinguished from "qualitative," or "discrete," traits on the basis of two factors; environmental influences on gene expression that produce a continuous distribution of phenotypes, and the complex segregation pattern produced by multigenic inheritance. The identification of one or more regions of the genome linked to the expression of a quantitative trait defines such regions as Quantitative Trait Loci ("QTL").

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant.

A "transgenic plant" is a plant comprising within at least one of its cells an exogenous polynucleotide. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally-occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci (e.g., a FAD3 locus). A "subline" may refer to an inbred subset of descendents from a common progenitor that are genetically distinct from other similarly inbred subsets descended from the same progenitor. In some embodiments, a "subline" may be produced by inbreeding seed from an individual transgenic plant selected at the $F_3$ to $F_5$ generation until the residual segregating loci are homozygous across most or all loci.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms “first and second cleavage half-domains;” “+ and − cleavage half-domains” and “right and left cleavage half-domains” are used interchangeably to refer to pairs of cleavage half-domains that dimerize.

An “engineered cleavage half-domain” is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

Means for generating a double strand DNA break: As used herein, the term “means for generating a double strand DNA break” is intended to invoke the special claiming provisions authorized by Congress in 35 U.S.C. § 112, sixth paragraph. Specifically, a “means for generating a double strand DNA break” refers to a molecular structure that is capable of cleaving both strands of a double-stranded DNA molecule. Such structures include polypeptide domains comprised within many known nuclease proteins, for example, the FokI nuclease domain, the catalytic domain is selected from the group consisting of proteins Mmel, Colicin-E7 (CEA7_ECOLX), Colicin-E9, APFL, EndA, Endo I (END1_EC0LI), Human Endo G (NUCG_HUMAN), Bovine Endo G (NUCG_BOVIN), R.HinPll, l-Basl, l-Bmol, l-Hmul, l-Tevl, l-Tevll, l-Tevlll, l-Twol, R.Mspl, R.Mval, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD6l (R.BspD6l large subunit), ss.BspD6l (R.BspD6l small subunit), R.PIel, Mlyl, Alwl, Mval269l, Bsrl, Bsml, Nb.BtsCI, Nt.BtsCI, Rl.Btsl, R2.Btsl, BbvCI subunit 1, BbvCI subunit 2, BpulOI alpha subunit, BpulOI beta subunit, Bmrl, Bfil, l-Crel, hExol (EX01JHUMAN), Yeast Exol (EX01_YEAST), *E. coli* Exol, Human TREX2, Mouse TREX1, Human TREX1, Bovine TREX1, Rat TREX1, Human DNA2, Yeast DNA2 (DNA2_YEAST).

Means for repairing a double strand DNA break: As used herein, the term “means for repairing a double strand DNA break” is also intended to invoke the special claiming provisions authorized by Congress in 35 U.S.C. § 112, sixth paragraph. Specifically, a “means for repairing a double strand DNA break” refers to a molecular structure that is capable of facilitating/catalyzing the joining of the ends of double-stranded DNA molecules, for example, by joining ends generated by cleaving a single double-stranded DNA molecule, or by joining one end generated by cleaving a single double-stranded DNA molecule with the end of an exogenous double-stranded DNA molecule. Such structures include polypeptide domains comprised within many known ligase proteins, for example, Cre recombinase. In some examples, the same molecular structure may serve as both a means for generating a double strand DNA break and a means for repairing a double strand DNA break, where the same structure facilitates both the cleavage and repair of double-stranded DNA molecules (e.g., Hin recombinase).

The induction of the site specific double stranded breaks in the genome induces the host plant cell DNA repair pathway which resolves the double stranded break through homology-directed repair (HDR) or non-homologous end-joining (NHEJ) repair. In plants, the scientific literature reports that precise gene or donor DNA integration into native genomic or at pre-engineered locations have involved incoming donor DNA construct(s) that comprise varying amounts of sequence homologous to the sequences flanking the targeted double stranded break. The integration of such donors into the specific target locus presumably has relied on the HDR pathway. Exclusively relying on the HDR approach for gene targeting in plants can have limitations due to reports that the HDR repair pathway is not the dominate DNA repair pathway when compared to NHEJ. The published plant scientific literature utilizing target specific DNA breaks (ZFN, TALeNs, or Engineered Meganucleases, etc.) the NHEJ pathway has been reported as the method to introduce specific point mutations (insertions, or deletions) into the geneome. Here we report that site specific double stranded breaks (induced by ZFN, TALeNs, etc.) in the presents of various donor DNA design with homology regions of 0 to <10 bp can be specifically inserted at targeted break via the NHEJ repair pathway in plants. A variety of different DNA donor designs with zero homology to small 1-10 bp of ranging from linear to circular, single stranded to double stranded can be targeted to specific locations using the NHEJ pathway. NHEJ based donor DNA plant genome targeting can be based on “sticky end capture”, where the targeted double stranded break in the genome generated by FokI (or other Type II endonuclease domains) and the corresponding sticky ends are on the NHEJ donor DNA designs. The sticky ends donor DNA can be delivered directly to the cell as linear donor DNA with predefined overhangs. An alternative approach is to produce the donor DNA sticky ends in vivo by co-delivering the host target ZFN and a circular DNA donor molecule that contains at least one ZFN recognition site that is identical to the target recognition site. Expression of at least one ZFN cuts the host genomic DNA (native or pre-engineered) and the circular donor DNA to produce sticky ends that are resolved using the hosts NHEJ repair pathway.

It is possible to have one or more ZFN cuts sites on the donor molecule (a single ZFN cut site to linearize the entire donor molecule, 2 of the same ZFN sites to release a smaller donor DNA fragment or 2 different ZFN sites to release a fragment from the donor and a corresponding fragment from the host genomic DNA (DNA replacement).

Thus, the donor polynucleotide can be DNA or RNA, single-stranded and/or double-stranded and can be introduced into a cell in linear or circular form. See, e.g., U.S. Patent Publication Nos. 20100047805 and 20110207221. In certain, embodiments of the present invention may also include linear exogenous (donor) nucleic acid(s), compositions comprising these nucleic acids and methods of making and using these linear donor molecules. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule. The linear exogenous nucleic acid may also include single stranded specific DNA.

IV. FAD3 Performance Loci

The loci designated FAD3 (fatty acid desaturase 3) are included in QTLs involved in the inheritance of the complex multigenic trait of fatty acid content in plants. FAD3 encodes the enzyme responsible for the desaturation of linoleic acid (18:2) to linolenic acid (C18:3). Tanhuanpaa et al. (1998) Mol. Breed. 4:543-50; Schierholt et al. (2001) Crop Sci. 41:1444-9.

Within the plant oil biosynthetic pathway the fatty acid desaturases (FADs) play a key role in plant lipid biosynthesis and their activity significantly influences the fatty acid composition. FADs are abundant in plants, and expression analysis suggested that FAD mRNAs are produced in over-abundance. Furthermore, FAD genes are expressed in various, tissues, and cell types, as well as subcellular compartments including the plastid and endoplasmic reticulum.

The fatty acid composition of plants, and the performance of oils produced therefrom in many applications, is determined by the relative concentrations of the major fatty acid constituents; oleic, linoleic, and linolenic (C18:3). The concentrations of these fatty acids are predominantly regulated by the function of the enzymes FAD2 and FAD3. Oleic acid is converted to linoleic acid and linolenic acid in plants according to the scheme:

$$C18:0 \longrightarrow C18:1 \xrightarrow[FAD2]{} C18:2 \xrightarrow[FAD3]{} C18:3$$

FAD3 genes have been identified in major plant and algal species including but not limited to maize, soybean, cotton, *Arabidopsis*, wheat, forage grasses, rice, sunflower and *Brassica*, and modification of FAD3 expression leads to altered fatty acid profiles in such organisms. Furthermore, plants comprising modified FAD3 genes have been commercialized, and disruption of a FAD3 gene has been shown to be able to improve the nutritional and functional properties of oil produced by a host plant without an agronomic penalty to the host plant. For example, canola and sunflower varieties that have been commercialized under the Nexera® brand (Dow AgroSciences, LLC) are characterized by a higher oleic acid, lower linoleic aced, and lower linolenic acid (and lower saturated fatty acid) composition, when compared to wild-type canola and sunflower profiles. The dominant canola species grown in Europe, North America, and Australia is *Brassica napus*, a polyploid *Brassica* species considered to have arisen from the hybridization of *B. oleracea* (having a diploid C genome) and *B. rapa* (having a diploid A genome). Cytogenetic investigation revealed the AA and CC genomes show a degree of relatedness as being partially homologous to one another. Both the A and C genomes contain a high percentage of homeologous and/or paralogous genes. Thus, it is thought that the AA and CC genomes are derived from a common ancestor genome. Prakash and Hinata (1980) Opera Botanica 55:1-57. Although the genomes of both progenitor species are technically classified as diploids, these genomes contain a high percentage of regions that are duplicative of one another. Song et al. (1991) Theor. Appl. Genet. 82:296-304. A detailed organelle and nuclear RFLP analysis revealed that the AA genome of *B. rapa* contributed ten chromosomes to *B. napus*, while *B. oleracea* contributed nine chromosomes from its CC genome as the maternal donor. Song et al. (1992) Genome 35:992-1001. Through the number of genome duplications in both ancestral genomes, as well as the high percentage of similarity between the A, B and C genomes, there have arisen several copies of FAD2 and FAD3 genes. As a practical matter, this fact makes breeding canola with modified and/or disrupted copies of these genes challenging in order to produce a particular fatty acid profile.

All of the known functional gene copies of FAD3 in canola are located on linkage group N4 of the A genome. Scheffler et al. (1997) TAG 94(5):583-91; Schierholt et al. (2000) TAG 101(5-6):897-901. More recently, a high oleic trait in canola has been associated with a modified and disrupted FAD3 gene that is located on the A genome. U.S. Patent Publication No. US 2006/0248611 A1; Hu et al. (2006) "Identification and Mapping of FAD2 and FAD3 Mutations and Development of Allele-specific Markers for High Oleic and Low Linolenic Acid Contents in Canola (*Brassica napus* L.)," Plant & Animal Genomes XIV Conference, Jan. 14-18, 2006, San Diego, Calif. An inactivating FAD3 allele contributes to the control of oleic acid content by reducing the desaturation of linoleic acid to linolenic acid. This high oleic acid and FAD3 trait was identified in a *B. napus* variety (DMS100) that has a characteristic oleic acid content of about 77%. See, U.S. Publication No. 20060248611. Further, genetic markers have been developed to assist the introgression of the Fad3 and high oleic acid trait into canola.

FAD3 loci may be modified and/or disrupted in a plant without detrimentally affecting the value of the plant, and for many purposes, with an actual increase in its value, including alteration of FAD3 expression, alteration of oil content/ratios and/or integration and expression of desired transgenes. Furthermore, according to the ubiquitous nature of FAD loci in plants, FAD3 loci may be modified and/or disrupted without detriment for at least some purposes in many species, including, for example and without limitation: canola; soybean; maize; wheat; forage grasses; *brassica* sp.; rice, tomatoes, barley; oats; sorghum; cotton; and sunflower, as well as fungi and algae. Embodiments of the invention include FAD3 loci, and the use thereof as performance loci for integration of exogenous nucleic acids. In examples, a FAD3 locus exhibits at least one of several features that have been found to be desirable within the context of its use as a performance locus, including, for example and without limitation: that there is an approximately consistent level of expression during the life cycle of the host organism; and surprisingly, that insertion of donor DNA at a FAD3 locus does not induce a quality or fitness penalty on the host.

In some embodiments of the present invention, at least one FAD3 locus (e.g., a FAD3A and/or FAD3C locus) is used as a target site for the site-specific integration of an exogenous nucleic acid (e.g., a nucleic acid comprising a nucleotide sequence encoding a polypeptide of interest). In particular embodiments, integration of the exogenous nucleic acid results in a modified locus. For example, integration of the exogenous nucleic acid may modify the locus so as to produce a disrupted (i.e., inactivated) FAD3 gene.

In some embodiments, a FAD3 locus may comprise a nucleotide sequence that is specifically hybridizable to the complement of a nucleotide sequence selected from the group consisting of SEQ ID NOs: 20-23, SEQ ID NOs: 25-38, SEQ ID NOs: 40-45, SEQ ID NO: 47 and SEQ ID NO: 49. For example, a FAD3 locus may comprise a nucleotide sequence selected from the group consisting of SEQ ID NOs: 20-23, SEQ ID NOs: 25-38, SEQ ID NOs: 40-45, SEQ ID NO: 47 and SEQ ID NO: 49. In some embodiments, a FAD3 locus may comprise a nucleotide sequence that is substantially identical to a nucleotide sequence selected from the group consisting of SEQ ID NOs: 20-23, SEQ ID NOs: 25-38, SEQ ID NOs: 40-45, SEQ ID NO: 47 and SEQ ID NO: 49. For example, in some embodiments, a FAD3 locus is a FAD3 homologue (e.g., an ortholog or a paralog) that comprises a nucleotide sequence that is at least about 85% identical to a nucleotide sequence selected from the group consisting of SEQ ID NOs: 20-23, SEQ ID NOs: 25-38, SEQ ID NOs: 40-45, SEQ ID NO: 47 and SEQ ID NO: 49. A FAD3 homologue may comprise a nucleotide sequence that is, for example and without limitation: at least 80%; at least 85%; at least about 90%; at least about 91%; at least about 92%; at least about 93%; at least about 94%; at least about 95%; at least about 96%; at least about 97%; at least about 98%; at least about 99%; at least about 99.5%; 99.6%, 99.7%, 99.8% and/or at least about 99.9% identical to a nucleotide sequence selected from the group consisting of SEQ ID NOs: 20-23, SEQ ID NOs: 25-38, SEQ ID NOs: 40-45, SEQ ID NO: 47 and SEQ ID NO: 49. Such a FAD3 homologue may be readily identified and isolated from any complete or partial genome readily available to those of skill in the art for a variety of organisms.

IV. Targeted Integration of a Nucleic Acid at a FAD3 Locus

Site-specific integration of an exogenous nucleic acid at a FAD3 locus may be accomplished by any technique known to those of skill in the art. In some embodiments, integration of an exogenous nucleic acid at a FAD3 locus comprises contacting a cell (e.g., an isolated cell or a cell in a tissue or organism) with a nucleic acid molecule comprising the exogenous nucleic acid. In examples, such a nucleic acid molecule may comprise nucleotide sequences flanking the exogenous nucleic acid that facilitate homologous recombination between the nucleic acid molecule and at least one FAD3 locus. In particular examples, the nucleotide sequences flanking the exogenous nucleic acid that facilitate homologous recombination may be complementary to endogenous nucleotides of the FAD3 locus. In particular examples, the nucleotide sequences flanking the exogenous nucleic acid that facilitate homologous recombination may be complementary to previously integrated exogenous nucleotides. In some embodiments, a plurality of exogenous nucleic acids may be integrated at one FAD3 locus, such as in gene stacking.

Integration of a nucleic acid at a FAD3 locus may be facilitated (e.g., catalyzed) in some embodiments by endogenous cellular machinery of a host cell, such as, for example and without limitation, endogenous DNA and endogenous recombinase enzymes. In some embodiments, integration of a nucleic acid at a FAD3 locus may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically at a FAD3 locus, wherein the at least one nuclease, recombinase, and/or ligase polypeptide is expressed from the nucleotide sequence in the host cell.

A. DNA-Binding Polypeptides

In some embodiments, site-specific integration may be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an $\alpha$-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some examples, a DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 includes 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43(3 Pt 2):729-36. The N-terminal 65 amino acids of GAL4 comprise the GAL4 DNA-binding domain. Keegan et al. (1986) Science 231:699-704; Johnston (1987) Nature 328: 353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that may be utilized in certain embodiments include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-κB; and components of the regulatory system described in Wang et al. (1994) Proc. Natl. Acad. Sci. USA 91(17):8180-4, which utilizes a fusion of GAL4, a hormone receptor, and VP16.

In certain embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) Science 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. Nos. 8,420,782 and 8,440,431 and U.S. Patent Publication No. 20110301073.

In other embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In particular embodiments, a DNA-binding polypeptide specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

B. Targeting Endonucleases

In particular embodiments, a DNA-binding polypeptide that specifically recognizes and binds to a target nucleotide sequence may be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. In some embodiments, functional polypeptides of a chimeric polypeptide may be operatively linked by their expression from a single polynucleotide encoding at least the functional polypeptides ligated to each other in-frame, so as to create a chimeric gene encoding a chimeric protein. In alternative embodiments, the functional polypeptides of a chimeric polypeptide may be operatively linked by other means, such as by cross-linkage of independently expressed polypeptides.

In some embodiments, a DNA-binding polypeptide that specifically recognizes and binds to a target nucleotide sequence may be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR-Cas9, and meganucleases.

As used herein, the term "targeting endonuclease" refers to natural or engineered isolated proteins and mutants thereof that comprise a DNA-binding polypeptide and a nuclease polypeptide, as well as to chimeric polypeptides comprising a DNA-binding polypeptide and a nuclease. Any targeting endonuclease comprising a DNA-binding polypeptide that specifically recognizes and binds to a target nucleotide sequence comprised within a FAD3 locus (e.g., either because the target sequence is comprised within the native sequence at the locus, or because the target sequence has been introduced into the locus, for example, by recombination) may be utilized in certain embodiments.

Some examples of chimeric polypeptides that may be useful in particular embodiments of the invention include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR-Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

In certain embodiments, the chimeric polypeptide comprises a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/trangsenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E)

residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

C. Zinc Finger Nucleases

In specific embodiments, a chimeric polypeptide is a custom-designed zinc finger nuclease (ZFN) that may be designed to deliver a targeted site-specific double-strand DNA break into which an exogenous nucleic acid, or donor DNA, may be integrated (See co-owned US Patent publication 20100257638, incorporated by reference herein). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. In some embodiments, the ZFNs comprise non-canonical zinc finger DNA binding domains (see co-owned US Patent publication 20080182332, incorporated by reference herein). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

The flexibility and specificity of the ZFN system provides a level of control previously unachievable by known recombinase-mediated gene editing strategies. As one example, ZFNs can be easily engineered, for example, to recognize specific nucleic acid sequences. Wu et al. (2007) Cell. Mol. Life Sci. 64:2933-44 (See, US Patent Publications 20090205083, 20110189775, 20110167521 and 20100199389, incorporated by reference in their entireties herein). Randomization of the codons for zinc finger recognition residues allows the selection of new fingers that have high affinity for arbitrarily chosen DNA sequences. Furthermore, zinc fingers are natural DNA-binding molecules, and engineered zinc fingers have been shown to act on their designed targets in living cells. Thus, nucleases based on zinc fingers are targetable to specific but arbitrary recognition sites.

In particular examples, a method for the site-specific integration of an exogenous nucleic acid into at least one FAD3 performance locus of a host comprises introducing into a cell of the host a ZFN, wherein the ZFN recognizes and binds to a target nucleotide sequence, wherein the target nucleotide sequence is comprised within at least one FAD3 locus of the host. In certain examples, the target nucleotide sequence is not comprised within the genome of the host at any other position than the at least one FAD3 locus. For example, a DNA-binding polypeptide of the ZFN may be engineered to recognize and bind to a target nucleotide sequence identified within the at least one FAD3 locus (e.g., by sequencing the FAD3 locus). A method for the site-specific integration of an exogenous nucleic acid into at least one FAD3 performance locus of a host that comprises introducing into a cell of the host a ZFN may also comprise introducing into the cell an exogenous nucleic acid, wherein recombination of the exogenous nucleic acid into a nucleic acid of the host comprising the at least one FAD3 locus is facilitated by site-specific recognition and binding of the ZFN to the target sequence (and subsequent cleavage of the nucleic acid comprising the FAD3 locus).

VI. Exogenous Nucleic Acids for Integration at a FAD3 Locus

Embodiments of the invention may include one or more nucleic acids selected from the group consisting of: an exogenous nucleic acid for site-specific integration in at least one FAD3 locus, for example and without limitation, a PTU, ELP, ETIP or an ORF; a nucleic acid comprising a nucleotide sequence encoding a targeting endonuclease; and a vector comprising at least one of either or both of the foregoing. Thus, particular nucleic acids for use in some embodiments include nucleotide sequences encoding a polypeptide, structural nucleotide sequences, and/or DNA-binding polypeptide recognition and binding sites.

A. Exogenous Nucleic Acid Molecules for Site-Specific Integration

As noted above, insertion of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805, 20110281361, 20110207221 and U.S. Publication No. US-2013-0326645-A1. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally integrated so that its expression is driven by the endogenous promoter at the integration site, namely the promoter that drives expression of the endogenous gene into which the donor is integrated (e.g., FAD3). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one FAD3 locus, so as to modify the FAD3 locus, in embodiments include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the FAD3 gene.

In some embodiments, an exogenous nucleic acid is integrated at a FAD3 locus, so as to modify the FAD3 locus, wherein the nucleic acid comprises an agronomic gene or nucleotide sequence encoding a polypeptide of interest, such that the agronomic gene or nucleotide sequence is expressed in the host from the FAD3 locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass. In some embodiments, the host is a plant, and plant material provided for commercial production of a polypeptide of interest may be a plant, plant part, plant tissue, or plant cell. In some examples, the plant part may be plant seed. Protein extraction from a plant biomass may be accomplished by known methods which are discussed, for example, in Heney and On (1981) Anal. Biochem. 114:92-6.

Likewise, agronomic genes may be expressed in transformed plant cells, plants, and/or their progeny. For example, a plant may be genetically engineered via methods of particular embodiments to express various phenotypes of agronomic interest from at least one FAD3 locus.

In some embodiments, nucleic acids comprising an agronomic gene or nucleotide sequence encoding a polypeptide of interest may include, for example and without limitation: a gene that confers resistance to a pests or disease (See, e.g., Jones et al. (1994) Science 266:789 (cloning of the tomato Cf-9 gene for resistance to *Cladosporium fulvum*); Martin et al. (1993) Science 262:1432; Mindrinos et al. (1994) Cell 78:1089 (RSP2 gene for resistance to *Pseudomonas syringae*); PCT International Patent Publication No. WO 96/30517 (resistance to soybean cyst nematode); PCT International Patent Publication No. WO 93/19181); a gene that encodes a *Bacillus thuringiensis* protein, a derivative thereof, or a synthetic polypeptide modeled thereon (See, e.g., Geiser et al. (1986) Gene 48:109 (cloning and nucleotide sequence of a Bt δ-endotoxin gene; moreover, DNA molecules encoding δ-endotoxin genes can be purchased from American Type Culture Collection (Manassas, Va.), for example, under ATCC Accession Nos. 40098; 67136; 31995; and 31998)); a gene that encodes a lectin (See, e.g., Van Damme et al. (1994) Plant Molec. Biol. 24:25 (nucleotide sequences of several *Clivia miniata* mannose-binding lectin genes)); a gene that encodes a vitamin-binding protein, e.g., avidin (See PCT International Patent Publication No. US93/06487 (use of avidin and avidin homologues as larvicides against insect pests)); a gene that encodes an enzyme inhibitor, e.g., a protease, proteinase inhibitor, or amylase inhibitor (See, e.g., Abe et al. (1987) J. Biol. Chem. 262:16793 (nucleotide sequence of rice cysteine proteinase inhibitor); Huub et al. (1993) Plant Molec. Biol. 21:985 (nucleotide sequence of cDNA encoding tobacco proteinase inhibitor I); Sumitani et al. (1993) Biosci. Biotech. Biochem. 57:1243 (nucleotide sequence of *Streptomyces nitrosporeus* alpha-amylase inhibitor) and U.S. Pat. No. 5,494,813); a gene encoding an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (baculovirus expression of cloned juvenile hormone esterase, an inactivator of juvenile hormone)); a gene encoding an insect-specific peptide or neuropeptide that, upon expression, disrupts the physiology of the affected pest (See, e.g., Regan (1994) J. Biol. Chem. 269:9 (expression cloning yields DNA coding for insect diuretic hormone receptor); Pratt et al. (1989) Biochem. Biophys. Res. Comm. 163:1243 (an allostatin in *Diploptera puntata*); and U.S. Pat. No. 5,266,317 (genes encoding insect-specific, paralytic neurotoxins)); a gene encoding an insect-specific venom produced in nature by a snake, a wasp, or other organism (See, e.g., Pang et al. (1992) Gene 116:165 (heterologous expression in plants of a gene coding for a scorpion insectotoxic peptide)); a gene encoding an enzyme responsible for a hyperaccumulation of a monoterpene, a sesquiterpene, a steroid, hydroxamic acid, a phenylpropanoid derivative or other molecule with insecticidal activity; a gene encoding an enzyme involved in the modification, including the post-translational modification, of a biologically active molecule, e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic (See, e.g., PCT International Patent Publication No. WO 93/02197 (nucleotide sequence of a callase gene); moreover, DNA molecules containing chitinase-encoding sequences can be obtained, for example, from the ATCC, under Accession Nos. 39637 and 67152; Kramer et al. (1993) Insect Biochem. Molec. Biol. 23:691 (nucleotide sequence of a cDNA encoding tobacco hornworm chitinase); and Kawalleck et al. (1993) Plant Molec. Biol. 21:673 (nucleotide sequence of the parsley ubi4-2 polyubiquitin gene)); a gene encoding a molecule that stimulates signal transduction (See, e.g., Botella et al. (1994) Plant Molec. Biol. 24:757 (nucleotide sequences for mung bean calmodulin cDNA clones); and Griess et al. (1994) Plant Physiol. 104:1467 (nucleotide sequence of a maize calmodulin cDNA clone)); a gene that encodes a hydrophobic moment peptide (See, e.g., PCT International Patent Publication No. WO 95/16776 (peptide derivatives of Tachyplesin which inhibit fungal plant pathogens); and PCT International Patent Publication No. WO 95/18855 (synthetic antimicrobial peptides that confer disease resistance)); a gene that encodes a membrane permease, a channel former, or a channel blocker (See, e.g., Jaynes et al. (1993) Plant Sci 89:43 (heterologous expression of a cecropin-β lytic peptide analog to render transgenic tobacco plants resistant to *Pseudomonas solanacearum*)); a gene that encodes a viral-invasive protein or complex toxin derived therefrom (See, e.g., Beachy et al. (1990) Ann. rev. Phytopathol. 28:451); a gene that encodes an insect-specific antibody or immunotoxin derived therefrom (See, e.g., Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments)); a gene encoding a virus-specific antibody (See, e.g., Tavladoraki et al. (1993) Nature 366:469 (transgenic plants expressing recombinant antibody genes are protected from virus attack)); a gene encoding a developmental-arrestive protein produced in nature by a pathogen or a parasite (See, e.g., Lamb et al. (1992) Bio/Technology 10:1436 (fungal endo α-1,4-D-polygalacturonases facilitate fungal colonization and plant nutrient release by solubilizing plant cell wall homo-α-1,4-D-galacturonase); Toubart et al. (1992) Plant J. 2:367 (cloning and characterization of a gene which encodes a bean endopolygalacturonase-inhibiting protein)); a gene encoding a developmental-arrestive protein produced in nature by a plant (See, e.g., Logemann et al. (1992) Bio/Technology 10:305 (transgenic plants expressing the barley ribosome-inactivating gene have an increased resistance to fungal disease)).

In some embodiments, nucleic acids comprising an agronomic gene or nucleotide sequence encoding a polypeptide of interest may also and/or alternatively include, for example and without limitation: genes that confer resistance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) EMBO J. 7:1241, and Mild et al. (1990) Theor. Appl. Genet. 80:449, respectively); glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes (including but not limited to CP4, DMMG, and DGT-28); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. Nos. 4,940,835 and 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European patent publication No. 0 333 033 and U.S. Pat. No. 4,975,374 disclose nucleotide sequences of glutamine synthetase genes, which may confer resistance to herbicides such as L-phosphinothricin. Nucleotide sequences of exemplary PAT genes are provided in European application No. 0 242 246, and DeGreef et al. (1989) Bio/Technology 7:61 (production of transgenic plants that express chimeric bar genes coding for PAT activity). Exemplary of genes conferring resistance to phenoxy proprionic acids and cyclohexones, such as sethoxydim and haloxyfop, include the Acc1-S1, Acc1-S2 and Acc1-S3 genes described by Marshall et al. (1992) Theor. Appl. Genet. 83:435. GAT genes capable of conferring glyphosate resistance are described, for example, in WO 2005012515. Genes conferring resistance to 2,4-D, phenoxyproprionic acid and pyridyloxy auxin herbicides are described, for example, in WO 2005107437 and WO 2007053482.

Nucleic acids comprising an agronomic gene or nucleotide sequence encoding a polypeptide of interest may also include, for example and without limitation: a gene conferring resistance to an herbicide that inhibits photosynthesis, such as a triazine (psbA and gs+ genes) or a benzonitrile (nitrilase gene). See, e.g., Przibila et al. (1991) Plant Cell 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

In some embodiments, nucleic acids comprising an agronomic gene or nucleotide sequence encoding a polypeptide of interest may also and/or alternatively include, genes that confer or contribute to a value-added trait, for example and without limitation: modified fatty acid metabolism, e.g., by transforming a plant with an antisense gene of stearyl-ACP desaturase to increase stearic acid content of the plant (See, e.g., Knultzon et al. (1992) Proc. Natl. Acad. Sci. U.S.A. 89:2624); decreased phytate content, e.g., introduction of a phytase-encoding gene may enhance breakdown of phytate, adding more free phosphate to the transformed plant (See, e.g., Van Hartingsveldt et al. (1993) Gene 127:87 (nucleotide sequence of an *Aspergillus niger* phytase gene); a gene may be introduced to reduce phytate content-in maize, for example, this may be accomplished by cloning and then reintroducing DNA associated with the single allele which may be responsible for maize mutants characterized by low levels of phytic acid (See Raboy et al. (1990) Maydica 35:383)); and modified carbohydrate composition effected, e.g., by transforming plants with a gene encoding an enzyme that alters the branching pattern of starch (See, e.g., Shiroza et al. (1988) J. Bacteol. 170:810 (nucleotide sequence of *Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

In some embodiments, an exogenous nucleic acid is integrated at a FAD3 locus, so as to modify the FAD3 locus, wherein the nucleic acid comprises a PTU or ELP, such that, for example, the subsequent site-specific integration of a second exogenous nucleic acid at the site of the PTU or ELP is facilitated. See, also, U.S. Publication No. US-2013-0326645-A1.

Targeting endonuclease-mediated integration of a nucleic acid molecule of interest into a plant genome via targeted integration requires delivery of targeting endonucleases or targeting endonuclease-encoding nucleic acid molecules, followed by expression of a functional targeting endonuclease protein in the host. An exogenous nucleic acid is preferably also be present in the host cell at the same time as the targeting endonuclease is delivered or expressed therein, such that functional targeting endonuclease protein induces double-stranded breaks at the target site(s) in the at least one FAD3 locus, which are then repaired, for example via homology-driven integration of the exogenous nucleic acid into the locus. One skilled in the art may envision that expression of a functional targeting endonuclease protein may be achieved by several methods, including, but not limited to, transgenesis of a targeting endonuclease-encoding construct, and transient expression of a targeting endonuclease-encoding construct. In both these cases, expression of a functional targeting endonuclease protein and delivery of an exogenous nucleic acid in the host cell may be simultaneously achieved in order to drive targeted integration at a FAD3 locus.

A particular advantage obtained in embodiments utilizing ZFNs as targeting endonucleases, is that the requirement for dimerization of cleavage domains of chimeric zinc finger nucleases imparts a high level of sequence, and hence cleavage, specificity. Since each set of three fingers binds nine consecutive base pairs, two chimeric nucleases effectively demand an 18 bp target if each zinc finger domain has perfect specificity. Any given sequence of this length is predicted to be unique within a single genome (assuming approximately $10^9$ bp). Bibikova et al. (2001) Mol. Cell. Biol. 21(1):289-97; Wu et al. (2007), supra. Furthermore, additional fingers can provide enhanced specificity, Beerli et al. (1998) Proc. Natl. Acad. Sci. USA 95:14628-33; Kim and Pabo (1998) Proc. Natl. Acad. Sci. USA 95:2812-7; Liu et al. (1997) Proc. Natl. Acad. Sci. USA 94:5525-30, so the number of zinc fingers in each DNA-binding domain may be increased to provide even further specificity. For example, specificity may be further increased by using a pair of 4-, 5-, 6- or more finger ZFNs that recognize a 24 bp sequence. Urnov et al. (2005) Nature 435:646-51. Thus, ZFNs may be used such that a recognition sequence is introduced into the host plant genome is unique within the genome.

B. Nucleic Acid Molecules Comprising a Nucleotide Sequence Encoding a Targeting Endonuclease In some embodiments, a nucleotide sequence encoding a targeting endonuclease may be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. In these and further embodiments, the last codon of the last (i.e., most 3' in the nucleic acid sequence) of a first polynucleotide sequence encoding a nuclease polypeptide, and a second polynucleotide sequence encoding a DNA-binding polypeptide, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, consist of any sequence, such that the amino acid sequence encoded is not likely to significantly alter the translation of the targeting endonuclease. Due to the autonomous nature of known nuclease polypeptides and known DNA-binding polypeptides, intervening sequences will not in examples interfere with the respective functions of these structures.

C. Vectors and Expression Constructs

In some embodiments, at least one nucleic acid molecule(s) comprising at least one exogenous polynucleotide sequence encoding a polypeptide of interest, and/or a targeting endonuclease, may be introduced into a cell, tissue, or organism for expression therein. For example, a nucleic acid molecule comprising a polynucleotide sequence encoding a targeting endonuclease that specifically recognizes a nucleotide sequence comprised within at least one FAD3 locus may be introduced into a cell for expression of the targeting endonuclease, and a nucleic acid molecule comprising a polynucleotide sequence encoding a polypeptide of interest may be introduced into the cell, such that the polynucleotide sequence encoding the polypeptide of interest is integrated into the at least one FAD3 locus, e.g., by homologous recombination following introduction of a double strand break at the locus by the expressed targeting endonuclease, and the polypeptide of interest is expressed from the integrated polynucleotide sequence.

In some embodiments, a nucleic acid molecule such as one of the foregoing may, for example, be a vector system including, for example and without limitation, a linear plasmid, or a closed circular plasmid. In particular examples, the vector may be an expression vector. Nucleic acid sequences according to particular embodiments may, for example, be integrated into a vector, such that the nucleic acid sequence is operably linked to one or more regulatory sequences. Many vectors are available for this purpose, and selection of the particular vector may depend, for example, on the size of the nucleic acid to be inserted into the vector, the particular host cell to be transformed with the vector, and/or the amount of any encoded polypeptide that is desired to be expressed. A vector typically contains various components, the identity of which depend on a function of the vector (e.g., amplification of DNA or expression of DNA), and the particular host cell(s) with which the vector is compatible.

In some embodiments, a regulatory sequence operably linked to one or more coding sequence(s) may be a promoter sequence that functions in a host cell, such as a bacterial cell, algal cell, fungal cell, or plant cell, wherein the nucleic acid molecule is to be amplified or expressed. Some embodiments may include a plant transformation vector that comprises a nucleotide sequence comprising at least one regulatory sequence operably linked to one or more nucleotide sequence(s) encoding a polypeptide of interest or a targeting endonuclease, wherein the one or more nucleotide sequence(s) may be expressed, under the control of the regulatory sequence(s), in a plant cell, tissue, or organism to produce the polypeptide of interest or the targeting endonuclease.

Promoters suitable for use in nucleic acid molecules according to some embodiments include those that are inducible, tissue-specific, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); U.S. Pat. No. 5,447,858 (soybean heat shock promoter); and U.S. Pat. No. 7,151,204 (maize chloroplast aldolase promoter).

Additional exemplary promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313: 810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530, 196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7).

In particular embodiments, nucleic acid molecules may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Publication No. 2001/047525 A1); fruit-specific promoters (See, e.g., U.S. Pat. Nos. 4,943,674, and 5,753,475); and seed-specific promoters (See, e.g., U U.S. Pat. Nos. 5,420,034, and 5,608,152). In some embodiments, a developmental stage-specific promoter (e.g., a promoter active at a later stage in development) may be used.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs are provided by: GmHsp (U.S. Pat. No. 5,659,122); PhDnaK (U.S. Pat. No. 5,362,865); AtAntl; TEV (Carrington and Freed (1990) J. Virol. 64:1590-7); and AGRtunos (GenBank Accession No. V00087; and Bevan et al. (1983), supra).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al. (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank Accession No. E01312).

Additional information regarding regulatory sequences that may be useful in particular embodiments is described, for example, in Goeddel (1990) "Gene Expression Technology," Methods Enzymol. 185, Academic Press, San Diego, Calif.

A recombinant nucleic acid molecule or vector may comprise a selectable marker that confers a selectable phenotype on a transformed cell, such as a plant cell. Selectable markers may also be used to select for cells or organisms that comprise a nucleic acid molecule comprising the selectable marker. A marker may encode biocide resistance, antibiotic resistance (e.g., kanamycin, Geneticin (G418), bleomycin, and hygromycin), or herbicide resistance (e.g., glyphosate). Examples of selectable markers include, but are not limited to: a neo gene that confers kanamycin resistance and can be selected for using, e.g., kanamycin and G418; a bar gene that confers bialaphos resistance; a mutant EPSP synthase gene that confers glyphosate resistance; a nitrilase gene that confers resistance to bromoxynil; a mutant acetolactate synthase gene (ALS) that confers imidazolinone or sulfonylurea resistance; and a methotrexate-resistant DHFR gene. Multiple selectable markers are available that confer resistance to chemical agents including, for example and without limitation, ampicillin; bleomycin; chloramphenicol; gentamycin; hygromycin; kanamycin; lincomycin; methotrexate; phosphinothricin; puromycin; spectinomycin; rifampicin; streptomycin; and tetracycline. Examples of such selectable markers are illustrated in, e.g., U.S. Pat. Nos. 5,550,318; 5,633,435; 5,780,708 and 6,118,047.

A nucleic acid molecule or vector may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18*th Stadler Genetics Symposium*, P. Gustafson and R. Appels, eds., Plenum, NY (pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); a xylE gene that encodes a catechol dioxygenase that converts chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone, which in turn condenses to melanin (Katz et al. (1983) J. Gen. Microbiol. 129:2703-14); and an α-galactosidase.

All of the nucleotide sequences that encode, for example, a particular polypeptide of interest or a particular targeting endonuclease, will be immediately recognizable by those of skill in the art. The degeneracy of the genetic code provides a finite number of coding sequences for a particular amino acid sequence. The selection of a particular sequence to encode a polypeptide according to embodiments of the invention is within the discretion of the practitioner. Different coding sequences may be desirable in different applications.

In some embodiments, it may be desirable to modify the nucleotides of a nucleic acid, for example, to enhance expression of a polynucleotide sequence comprised within the nucleic acid in a particular host. The genetic code is redundant with 64 possible codons, but most organisms preferentially use a subset of these codons. The codons that are utilized most often in a species are called optimal codons, and those not utilized very often are classified as rare or low-usage codons. Zhang et al. (1991) Gene 105: 61-72. Codons may be substituted to reflect the preferred codon usage of a particular host in a process sometimes referred to as "codon optimization." Optimized coding sequences containing codons preferred by a particular prokaryotic or eukaryotic host may be prepared, for example, to increase the rate of translation or to produce recombinant RNA transcripts having desirable properties (e.g., a longer half-life, as compared with transcripts produced from a non-optimized sequence).

Nucleic acids may be introduced into a host cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); and by acceleration of DNA-coated particles (See, e.g., U.S. Pat. Nos. 5,015,580, 5,550,318, 5,538,880, 6,160,208, 6,399,861, and 6,403,865). Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely-utilized method for introducing an expression vector into plants is based on the natural transformation system of *Agrobacterium. A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of *A. tumefaciens* (See, e.g., U.S. Pat. Nos. 4,536,475, 4,693,977, 4,886,937, and 5,501,967; and European Patent EP 0 122 791) or a $R_i$ plasmid of *A. rhizogenes*. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as *Sinorhizobium, Rhizobium*, and *Mesorhizobium*, that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one fusion protein of the invention) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers that are specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et al. (2002) Plant J. 32:243-53), and may be applied to genomic DNA derived from any plant species or tissue type, including cell cultures.

A transgenic plant formed using *Agrobacterium*-dependent transformation methods typically contains a single to multiple copies of recombinant DNA. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay).

In addition to direct transformation of a plant or plant cell with a nucleic acid molecule in some embodiments, transgenic plants may be prepared in particular embodiments by crossing a first plant having at least one transgenic event with a second plant lacking such an event. For example, a nucleic acid comprising at least one modified FAD3 locus, wherein an exogenous nucleic acid has been integrated in a site-specific manner, may be introduced into a first plant line that is amenable to transformation, to produce a transgenic plant, which transgenic plant may be crossed with a second plant line to introgress the at least one modified FAD3 locus (and therefore the exogenous nucleic acid) into the second plant line.

To confirm the presence of a nucleic acid molecule of interest in regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two are feasible. Thus, PCR genotyping strategies may include (but are not limited to) amplification of specific sequences in the plant genome, amplification of multiple specific sequences in the plant genome, amplification of non-specific sequences in the plant genome, or combinations thereof. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule of interest, for example, at a sequence corresponding to a coding region within the nucleic acid molecule of interest, or other parts of the nucleic acid molecule of interest. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

VI. Transgenic Plants and Plant Materials Comprising a Nucleic Acid Integrated at a FAD3 Performance Locus In some embodiments, a transgenic plant is provided, wherein the plant comprises a plant cell comprising at least one modified (e.g., FAD3 locus, disrupted and/or targeted integration of an exogenous sequence) FAD3 locus. In particular embodiments, such a plant may be produced by transformation of a plant tissue or plant cell, and regeneration of a whole plant. In further embodiments, such a plant may be obtained through introduction of an exogenous nucleic acid at the at least one FAD3 locus in a site-specific manner, or through introgression of the modified FAD3 locus into a germplasm. Plant materials comprising such a plant cell are also provided. Such a plant material may be obtained from a plant comprising the plant cell.

A transgenic plant or plant material comprising a plant cell comprising at least one modified FAD3 locus may in some embodiments exhibit one or more of the following characteristics: expression of a targeting endonuclease in a cell of the plant; expression of a polypeptide of interest in a cell of the plant (or in a plastid therein); expression of a targeting endonuclease in the nucleus of a cell of the plant; localization of a targeting endonuclease in a cell of the plant; integration at a FAD3 locus in the genome of a cell of the plant; integration of a nucleotide sequence encoding a polypeptide of interest or an agronomic gene at a FAD3 locus in the genome of a cell of the plant; and/or the presence of an RNA transcript corresponding to a coding sequence integrated at a FAD3 locus in the genome of a cell of the plant. Such a plant may additionally have one or more desirable traits, including, for example and without limitation, those resulting from the expression of an endogenous or transgenic nucleotide sequence, the expression of which is regulated by a polypeptide of interest or an agronomic gene integrated at a FAD3 locus in the genome of a cell of the plant; resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid that is subsequently integrated in at least one FAD3 locus according to methods described herein. Accordingly, the plant may be a dicot or monocot. Non-limiting examples of dicotyledonous plants usable in the present methods include *Arabidopsis*, alfalfa, beans, broccoli, cabbage, canola, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, barley, onion, rice, sorghum, wheat, rye, millet, sugarcane, oat, triticale, switchgrass, and turfgrass. Transgenic plants according to the invention may be used or cultivated in any manner.

Some embodiments also provide commodity products produced from transgenic plants of the invention. Commodity products include, for example and without limitation: food products, meals, oils, or crushed or whole grains or seeds of a plant comprising one or more nucleotide sequences integrated in at least one FAD3 locus. The detection of one or more such nucleotide sequences in one or more commodity or commodity products is de facto evidence that the commodity or commodity product was at least in part produced from a transgenic plant produced according to an embodiment of the invention. In some embodiments, a transgenic plant or seed comprising a plant cell comprising at least one modified FAD3 locus may comprise at least one other transgenic event in its genome, including without limitation: a transgenic event from which is transcribed an RNAi molecule; a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

A transgenic plant comprising a plant cell comprising at least one modified FAD3 locus may have one or more desirable traits. Such traits can include, for example: resistance to insects, other pests, and disease-causing agents; tolerances to herbicides; enhanced stability, yield, or shelf-life; environmental tolerances; pharmaceutical production; industrial product production; and nutritional enhancements. The desirable traits may be conferred by one or more nucleic acid molecules integrated by targeted recombination at the FAD3 locus that are expressed in the plant exhibiting the desirable traits. Thus, in some embodiments, the desired trait can be due to the presence of a transgene(s) in the plant, which is introduced into the genome of the plant at the site of at least one modified FAD3 locus. In an additional embodiment, the desirable trait can be obtained through conventional breeding, which trait may be conferred by one or more nucleic acid molecules integrated by targeted recombination at the at least one modified FAD3 locus.

Transgenic plants according to the invention may be used or cultivated in any manner, wherein presence of at least one modified FAD3 locus is desirable. Accordingly, a plant may be engineered to, inter alia, have one or more desired traits, by being transformed with nucleic acid molecules that are subsequently integrated in a site-specific manner in at least one FAD3 locus according to the invention, and cropped and cultivated by any method known to those of skill in the art.

VII. Marker-Assisted Breeding of Transgenic Plants Comprising a Nucleic Acid Integrated at a FAD3 Performance Locus Molecular markers that are linked (e.g., tightly-linked) to Fad2 and Fad3, in *Brasicca* spp. are provided. For example, DNA segments containing sequences involved in the HO trait (FAD3) are identified. These segments are located around and between markers that are linked (e.g., tightly-linked) to the mutant alleles in a genomic linkage group. Thus, nucleic acid molecules comprising a mutant FAD3 gene having an inactivating mutation are also provided. The segments identified, and the markers thereof, are included in the present subject matter, in part, by their position in linkage groups in the *B. napus* genome.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

EXAMPLES

Example 1: Identification of Fad3 Target Sequences from a Bacterial Artificial Chromosome Library BAC Library Construction A Bacterial Artificial Chromosome (BAC) library was sourced from a commercial vendor (Amplicon Express, Pullman, Wash.). The BAC library included 110,592 BAC clones containing high molecular weight genomic DNA (gDNA) fragments isolated from *Brassica napus* L. var. DH10275. The gDNA was digested with either the BamHI or HindIII restriction enzyme. Isolated gDNA fragments of about 135 Kbp were ligated into the pCC1BAC vector (Epicentre, Madison, Wis.) and transformed into *Escherichia coli* str. DH10B (Invitrogen). The BAC library was made up of an even number of BAC clones that were constructed using the two different restriction enzymes. As such, the Hind III constructed BAC library was contained in 144 individual 384-well plates. Likewise, the BamHI constructed BAC library was contained in 144 individual 384-well plates. A total of 110,592 BAC clones were isolated and arrayed into 288 individual 384-well plates. Each of the 288 individual 384 well plates were provided by the vendor as a single DNA extraction for rapid PCR based screening. The resulting BAC library covers approximately 15 Gbp of gDNA, which corresponds to a 12-fold genome coverage of *Brassica napus* L. var. DH10275genome (estimate of the *Brassica napus* L. genome is ca. 1.132 Gbp as described in Johnston et al. (2005) *Annals of Botany* 95:229-235).

Sequence Analysis of Fad3 Coding Sequences Isolated from the BAC Library

The constructed BAC library was used to isolate FAD3 gene coding sequences. Sequencing experiments were conducted to identify the specific gene sequences of six FAD3 gene homeologoues and paralogs from *Brassica napus* L. var. DH10275.

The FAD3 gene sequence was initially identified within the model species *Arabidopsis thaliana*. The gene sequence is listed in Genbank as Locus Tag: At2g29980. Comparative genomic relationships between the model plant species *Arabidopsis thaliana* and the diploid *Brassica rapa*, one of the progenitors of the tetraploid *Brassica napus*, have been previously described. (Schranz et al. (2006) Trends in Plant Science 11(11):535-542). With specific relation to the FAD gene the comparative analysis predicted that 3-4 copies of the gene may occur within the diploid *Brassica* genome. Additional genetic mapping studies were completed by Scheffler et al. (1997) Theoretical and Applied Genetics 94; 583-591. The results of these genetic mapping studies indicated that six copies of the FAD3 gene were present in *Brassica napus*.

Previous sequencing efforts focused on the FAD3 genes from *Brassica napus* had identified and genetically mapped both A and C genome specific copies (Hu et al., (2006) Theoretical and Applied Genetics, 113(3): 497-507). A collection of EST sequences from seed specific cDNA libraries had previously been constructed and sequenced from the plant line DH12075 by Andrew Sharpe of Agriculture and Agri-food Canada, 107 Science Place, Saskatoon, Saskatchewan. As a collection of ESTs from the doubled haploid canola plant DH12075 full length gene sequences were not available, moreover the indications of sequence quality and confidence of correctly called nucleotides was also not available. Consequently, sequence variation between different FAD gene sequence reads could not be unequivocally attributed to different gene copies of the various homeologues and paralogs of the FAD3 gene family, nor was the genomic sequence available. However, when a combined sequence analysis was performed with the ESTs as well as the two FAD3A and FAD3C full length gene sequences described in Hu et al., (2006), ESTs that matched both of the genes were identified along with an additional 4 haplotypes. As a result, a total of six unique haplotypes of FAD3 were identified. Following the assembly of all available data for the various FAD3 haplotypes, high levels of exon sequence divergence in exon 1 was identified. The divergence of the FAD3 sequence in exon 1 was identified as an opportunity which could be utilized for the design of gene/allele specific PCR primers. In addition, exons were identified that were either minimally differentiated between haplotypes (e.g., exons 5, 6, 7 and 8 had 1-3 bp that varied between FAD3A and FAD3C) or that were devoid of sequence variation (e.g., exons 2 and 3).

Sequencing analysis of the BAC library which was constructed from *B. napus* L. var. DH12075 resulted in the isolation of six BAC sequences (SEQ ID NO:1, SEQ ID NO:2, SEQ ID NO:3, SEQ ID NO:4, SEQ ID NO:5, and SEQ ID NO:6) from which the coding sequences for the FAD3A (SEQ ID NO:7), FAD3A' (SEQ ID NO:8), FAD3A" (SEQ ID NO:9), FAD3C (SEQ ID NO:10), FAD3C" (SEQ ID NO:11), and FAD3C' (SEQ ID NO:12) genes were determined. The FAD3A, FAD3A', FAD3A", FAD3C, FAD3C", and FAD3C' gene sequences were identified and genetically mapped.

Sequence analysis of the six FAD3 genes was conducted using a sequence alignment program and a neighbor-joining tree using percentage of identity. The sequence alignment was made via the AlignX® program from the Vector NTI Advance 11.0 computer program (Life Technologies, Carlsbad, Calif.) and is shown in FIG. 1. AlignX® uses a modified Clustal W algorithm to generate multiple sequence alignments of either protein or nucleic acid sequences for similarity comparisons and for annotation. The neighbour-joining tree was created with Jalview v2.3® software and is shown in FIG. 2. (Waterhouse et al. (2009) Bioinformatics 25 (9) 1189-1191). The contigs identified as containing FAD3 genes were used as BLASTn queries against a database of *Arabidopsis thaliana* genes. The region of each of the 6 contigs containing the FAD3 gene was identified through comparison to the *Arabidopsis thaliana* FAD3 gene (Genbank Accession No: At2g29980). The FAD3 contigs were then orientated such that all FAD3 genes were in the 5' to 3' orientation. FAD3 contigs were trimmed to contain as many as 2 upstream (5') and 1 downstream (3') *Arabidopsis thaliana* genes where possible. Once orientated the complete coding region of the FAD3 genes were extracted from each contig and used to generate a Neighbour joining tree to display the relationship between the different FAD3 gene family members. The 6 FAD3 family members were aligned into 3 pairs of FAD3 genes (FIG. 2).

PCR Based Screening

A cohort of PCR primers were designed to screen the aforementioned BAC library. The primers were designed as either universal primers, which would amplify all members of the gene family, or as gene specific primers for targeted allele amplification. The PCR primers were designed to be 20 bp long (+/−1 bp) and contain a G/C content of 50% (+/−8%). Table 1 lists the primers which were designed and synthesized. The clones of the BAC library were pooled and screened via the Polymerase Chain Reaction (PCR).

TABLE 1

Primer sequences used for PCR amplification of FAD3 sequences

| Primer Name: | SEQ ID NO: | Sequence: |
|---|---|---|
| D_uni_F3_F1 | SEQ ID NO: 13 | GAATAAGCCATCGGACACAC |
| D_spec_F3_F2 | SEQ ID NO: 14 | ATGCGAACGGAGACGAAAGG |
| D_spec_F3_F3 | SEQ ID NO: 15 | TGTTAACGGAGATTCCGGTG |
| D_spec_F3_F4 | SEQ ID NO: 16 | GTAGCAATGTGAACGGAGAT |
| D_uni_F3_R1 | SEQ ID NO: 17 | CAGTGTATCTGAGCATCCG |
| D_spec_F3_R2 | SEQ ID NO: 18 | GTGGCCGAGTACGAAGATAG |
| D_spec_F3_R3 | SEQ ID NO: 19 | CAGTAGAGTGGCCAGAGGA |

Two different sets of conditions were used for the polymerase chain reactions (PCR). The first series of PCR reactions contained: 1×PCR buffer (containing dNTPs); 1.5 mM $MgCl_2$; 200 μM of 0.25 U Immolase® DNA polymerase (Bioline, London, UK); 250 nM of each primer; and, about 5-10 ng template DNA. A second series of PCR reactions were developed for the amplification of genomic DNA and contained: 5-10 ng of genomic DNA, 1×PCR buffer, 2 mM dNTPs, 0.4 μM forward and reverse primer, and 0.25 U Immolase® DNA polymerase (Bioline, London, UK). Reagents were pooled into a final volume of 13 μL and amplified using an MJ PTC200® thermocycler (BioRad, Hercules, Calif.) or an ABI 9700 Gene Amp System® (Life Technologies, Carlsbad, Calif.). PCR based screening of specific plates was conducted using a 4 dimension screening approach based on the screening system described by Bryan et al (Scottish Crops Research Institute annual report: 2001-2002) with the above described PCR conditions. Following PCR based screening of pooled BAC libraries; the amplified PCR product was sequenced using a direct Sanger sequencing method. The amplified products were purified with ethanol, sodium acetate and EDTA following the BigDye® v3.1 protocol (Applied Biosystems) and electrophoresis was performed on an ABI3730xl® automated capillary electrophoresis platform.

Following PCR based screening and confirmational Sanger sequencing, a collection of plates were identified that contained the various different FAD3 gene family members. A total of six unique FAD3 homeologous and paralogous gene sequences were identified (Table 2). A total of two plates per each FAD3 gene sequence were chosen to undergo plate screening to identify the specific well and clone within the plate that contained the FAD3 gene (Table 2). The specific wells were identified for both of the plates and an individual clone was selected for each of the FAD3 gene family members (Table 2).

TABLE 2

Identification of the BAC clone plates that provided positive reaction with the detailed PCR primer combinations, along with two plate identities that were taken forward for clone identification within the plate

| Gene Name | Primer Sets | Positive Plate Pools | Chosen Plates |
|---|---|---|---|
| FAD3A (FAD3A-1) | F2 + R2 | 16, 231 | Plate 16<br>Plate 231 |
| FAD3C | F4 + R2 | 18, 27, 136, 178, 211, 232 | Plate 18<br>Plate 27 |
| FAD3C" (Haplotype1) | F4 + R2, F4 + R3, F3 + R3 | 23, 44, 53, 56, 77, 116, 158, 199, 209, 278, 280, 282, 283, 284, 286 | Plate 44<br>Plate 199 |
| FAD3A' (FAD3A'/ FAD3A") | F4 + R2 | 52, 121, 139 | Plate 121<br>Plate 139 |
| FAD3C' (Haplotype2) | F4 + R2 | 144, 188, 235 | Plate 144<br>Plate 188 |
| FAD3A" (Haplotype3) | F4 + R3 and F3 + R3 | 69, 105, 106, 229, 242, 247, 248 | Plate 69<br>Plate 106 |

The single BAC clone, for each identified FAD gene family member, was further analysed via sequencing. The DNA was isolated for the BAC clone and was prepared for sequencing using a Large Construct Kit® (Qiagen, Valencia, Calif.) following the manufacturer's instructions. The extracted BAC DNA was prepared for sequencing using GS-FLX Titanium Technology® (Roche, Indianapolis, Ind.) following manufacturer's instructions. Sequencing reactions were performed using a physically sectored GS-FLX TI Pico-titer Plate® with the BACs pooled in pairs for optimal data output. The BACs were combined in pairs where the FAD2 gene was paired with a FAD3 gene. All generated sequence data was assembled by Newbler v2.0.01.14® (454 Life Sciences, Branford, Conn.). The assembled contigs were manually assessed for the presence of the corresponding FAD gene using Sequencher v3.7® (GeneCodes, Ann Arbor, Mich.).

After the full genomic sequence of all six FAD3 genes had been identified and fully characterized, zinc finger nucleases were designed to bind to the sequences for each specific gene family member.

Example 2: Design of Zinc Finger Binding Domains Specific to Fad3 Genes

Zinc finger proteins directed against DNA sequences encoding various functional sequences of the FAD3 gene locus were designed as previously described. See, e.g., Urnov et al. (2005) Nature 435:646-651. Exemplary target sequence and recognition helices are shown in Table 3 (recognition helix regions designs) and Table 4 (target sites). In Table 4, nucleotides in the target site that are contacted by the ZFP recognition helices are indicated in uppercase letters; non-contacted nucleotides indicated in lowercase. Zinc finger nuclease (ZFN) target sites were designed to bind seven target sites of FAD3. The FAD3 zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and an opaque-2 nuclear localization signal derived from *Zea mays* to form FAD3 zinc-finger nucleases (ZFNs). Expression of the fusion proteins was driven by a relatively strong constitutive promoter such as a promoter derived from the Cassava Vein Mosaic Virus (CsVMV) promoter and flanked by the *Agrobacterium tumefaciens* ORF23 3'UnTranslated Region (AtuORF23 3'UTR v1). The self-hydrolyzing 2A encoding nucleotide sequence from *Thosea asigna* virus (Szymczak et al., 2004) was added between the two ZFNs that were cloned into the construct. Exemplary vectors are described below.

The optimal zinc fingers were verified for cleavage activity using a budding yeast based system previously shown to identify active nucleases. See, e.g., U.S. Patent Publication No. 20090111119; Doyon et al. (2008) *Nat Biotechnol.* 26:702-708; Geurts et al. (2009) *Science* 325:433. Zinc fingers for the various functional domains were selected for in-vivo use. Of the numerous ZFNs that were designed, produced and tested to bind to the putative FAD genomic polynucleotide target sites, fifteen ZFNs were identified as having in vivo activity at high levels, and selected for further experimentation. These ZFNs were characterized as being capable of efficiently binding and cleaving the unique FAD3 genomic polynucleotide target sites in planta.

TABLE 3

FAD3 Zinc Finger Designs

| ZFP | sF1 | F2 | F3 | F4 | F5 | F6 |
|---|---|---|---|---|---|---|
| 27961 | RSDNLAR (SEQ ID NO: 116) | QKKDRSY (SEQ ID NO: 117) | RSDNLAR (SEQ ID NO: 116) | QRGNRNT (SEQ ID NO: 119) | RSDHLSR (SEQ ID NO: 120) | RNQDRTN (SEQ ID NO: 121) |
| 27962 | DRSNLSR (SEQ ID NO: 122) | RQDSRSQ (SEQ ID NO: 123) | QSSDLSR (SEQ ID NO: 124) | DRSALAR (SEQ ID NO: 125) | TSGSLTR (SEQ ID NO: 126) | N/A |
| 27973 | QSSDLSR (SEQ ID NO: 124) | AASNRSK (SEQ ID NO: 128) | TSGSLSR (SEQ ID NO: 129) | RSDALAR (SEQ ID NO: 130) | RSDVLST (SEQ ID NO: 131) | WGRLRKL (SEQ ID NO: 132) |
| 27974 | ERGTLAR (SEQ ID NO: 133) | RSDDLTR (SEQ ID NO: 134) | RSDHLSA (SEQ ID NO: 135) | QHGALQT (SEQ ID NO: 136) | TSGNLTR (SEQ ID NO: 137) | QSGHLSR (SEQ ID NO: 138) |
| 27987 | TSGSLTR (SEQ ID NO: 126) | RSDHLSQ (SEQ ID NO: 140) | CTRNRWR (SEQ ID NO: 141) | RSDNLSE (SEQ ID NO: 142) | ASKTRKN (SEQ ID NO: 143) | N/A |
| 27990 | TSGSLSR (SEQ ID NO: 129) | TSSNRAV (SEQ ID NO: 145) | TSGNLTR (SEQ ID NO: 137) | DRSALAR (SEQ ID NO: 125) | RSDVLSE (SEQ ID NO: 148) | RNFSLTM (SEQ ID NO: 149) |
| 27991 | QSGDLTR (SEQ ID NO: 150) | TSGSLSR (SEQ ID NO: 129) | QSGNLAR (SEQ ID NO: 152) | TSGSLSR (SEQ ID NO: 129) | QSGSLTR (SEQ ID NO: 154) | N/A |
| 27992 | DRSHLAR (SEQ ID NO: 155) | TSGSLSR (SEQ ID NO: 129) | TSSNRAV (SEQ ID NO: 145) | TSGNLTR (SEQ ID NO: 137) | DRSALAR (SEQ ID NO: 125) | N/A |
| 28004 | QSGNLAR (SEQ ID NO: 152) | HLGNLKT (SEQ ID NO: 161) | RSDHLSQ (SEQ ID NO: 140) | TARLLKL (SEQ ID NO: 163) | QSGNLAR (SEQ ID NO: 152) | QTSHLPQ (SEQ ID NO: 165) |
| 28005 | RSDNLSV (SEQ ID NO: 166) | TSGHLSR (SEQ ID NO: 167) | TSGSLTR (SEQ ID NO: 126) | RSDALST (SEQ ID NO: 169) | DRSTRTK (SEQ ID NO: 170) | N/A |
| 28021 | QNAHRKT (SEQ ID NO: 171) | TSGNLTR (SEQ ID NO: 137) | LKQMLAV (SEQ ID NO: 173) | RSDNLSR (SEQ ID NO: 174) | DNSNRKT (SEQ ID NO: 175) | N/A |
| 28022 | RSDNLSV (SEQ ID NO: 166) | QNANRIT (SEQ ID NO: 177) | TSGSLSR (SEQ ID NO: 129) | QSSVRNS (SEQ ID NO: 179) | DRSALAR (SEQ ID NO: 125) | N/A |
| 28023 | RSDNLSR (SEQ ID NO: 174) | DNSNRKT (SEQ ID NO: 175) | DRSNLTR (SEQ ID NO: 183) | RSDVLSE (SEQ ID NO: 148) | TRNGLKY (SEQ ID NO: 185) | N/A |
| 28024 | RSDALAR (SEQ ID NO: 130) | RSDVLSE (SEQ ID NO: 148) | RSSDRTK (SEQ ID NO: 188) | RSDNLSV (SEQ ID NO: 166) | QNANRIT (SEQ ID NO: 177) | N/A |
| 28025 | QSSDLSR (SEQ ID NO: 124) | QSTHRNA (SEQ ID NO: 192) | RSDNLAR (SEQ ID NO: 116) | QRGNRNT (SEQ ID NO: 119) | RSDHLSR (SEQ ID NO: 120) | RNQDRTN (SEQ ID NO: 121) |

TABLE 3-continued

| FAD3 Zinc Finger Designs | | | | | | |
|---|---|---|---|---|---|---|
| ZFP | sF1 | F2 | F3 | F4 | F5 | F6 |
| 28026 | DRSNLSR (SEQ ID NO: 122) | RQDSRSQ (SEQ ID NO: 123) | QSSDLSR (SEQ ID NO: 124) | DRSALAR (SEQ ID NO: 125) | TSGSLTR (SEQ ID NO: 126) | N/A |
| 28035 | QSSDLSR (SEQ ID NO: 124) | AASNRSK (SEQ ID NO: 128) | TSGSLSR (SEQ ID NO: 129) | RSDALAR (SEQ ID NO: 130) | RSDTLSQ (SEQ ID NO: 206) | QRDHRIK (SEQ ID NO: 207) |
| 28036 | RSDDLTR (SEQ ID NO: 134) | QSSDLRR (SEQ ID NO: 209) | RSDHLSA (SEQ ID NO: 135) | QHGALQT (SEQ ID NO: 136) | TSGNLTR (SEQ ID NO: 137) | QSGHLSR (SEQ ID NO: 138) |
| 28039 | TSGSLSR (SEQ ID NO: 129) | RSDALAR (SEQ ID NO: 130) | RSDTLSQ (SEQ ID NO: 206) | QRDHRIK (SEQ ID NO: 207) | TSGNLTR (SEQ ID NO: 137) | DRGDLRK (SEQ ID NO: 219) |
| 28040 | DSSDRKK (SEQ ID NO: 220) | TSGNLTR (SEQ ID NO: 137) | DNYNRAK (SEQ ID NO: 222) | DRSHLTR (SEQ ID NO: 223) | RSDNLTT (SEQ ID NO: 224) | N/A |
| 28051 | RSDNLSN (SEQ ID NO: 225) | TSSSRIN (SEQ ID NO: 226) | RSDNLSE (SEQ ID NO: 142) | ASKTRKN (SEQ ID NO: 143) | RSDALTQ (SEQ ID NO: 229) | N/A |
| 28052 | RSDTLST (SEQ ID NO: 230) | DRSSRIK (SEQ ID NO: 231) | RSDDLSK (SEQ ID NO: 232) | DNSNRIK (SEQ ID NO: 233) | N/A | N/A |
| 28053 | QSSDLSR (SEQ ID NO: 124) | QAGNLSK (SEQ ID NO: 235) | QSGDLTR (SEQ ID NO: 150) | TSGSLSR (SEQ ID NO: 129) | QSGNLAR (SEQ ID NO: 152) | N/A |
| 28054 | TSGSLSR (SEQ ID NO: 129) | LRQTLRD (SEQ ID NO: 240) | TSGNLTR (SEQ ID NO: 137) | DRSALAR (SEQ ID NO: 125) | RSDVLSE (SEQ ID NO: 148) | RNFSLTM (SEQ ID NO: 149) |
| 28055 | QSGDLTR (SEQ ID NO: 150) | TSGSLSR (SEQ ID NO: 129) | QSGNLAR (SEQ ID NO: 152) | TSGSLSR (SEQ ID NO: 129) | QSGSLTR (SEQ ID NO: 154) | N/A |
| 28056 | DRSHLAR (SEQ ID NO: 155) | TSGSLSR (SEQ ID NO: 129) | LRQTLRD (SEQ ID NO: 240) | TSGNLTR (SEQ ID NO: 137) | DRSALAR (SEQ ID NO: 125) | N/A |

TABLE 4

| Target Sites of FAD3 Zinc Fingers | | |
|---|---|---|
| ZFP | Target Site (5' to 3') | SEQ ID NO: |
| 27961 | cgCCGGAGAAAGAGAGAGAGattgagg | SEQ ID NO: 20 |
| 27962 | tgGTTGTCGCTATGGACcagcgtagcaa | SEQ ID NO: 21 |
| 27969 | tcTCCGTTcGCATTGcTACGCTggtcca | SEQ ID NO: 22 |
| 27970 | gaAAGGTTtGATCCGAGCGCAcaaccac | SEQ ID NO: 23 |
| 27973 | tcTCCGTTcGCATTGcTACGCTggtcca | SEQ ID NO: 22 |
| 27974 | tcGGAGATATAAGGGCGGCCattcctaa | SEQ ID NO: 25 |
| 27987 | taGCCCAGAACAGGGTTccttgggcggc | SEQ ID NO: 26 |
| 27988 | ctTCGTACTCGGCCACGactggtaattt | SEQ ID NO: 27 |
| 27989 | ttGAAGTTGCAaTAAGCTttctctcgct | SEQ ID NO: 28 |
| 27990 | acTTGCTGGTCGATCATGTTggccactc | SEQ ID NO: 29 |
| 27991 | aaGTAGTTGAAGTTGCAataagattct | SEQ ID NO: 30 |

TABLE 4-continued

| Target Sites of FAD3 Zinc Fingers | | |
|---|---|---|
| ZFP | Target Site (5' to 3') | SEQ ID NO: |
| 27992 | tgGTCGATCATGTTGGCcactcttgttt | SEQ ID NO: 31 |
| 28004 | aaCGAGAATGAAGGAATGAAgaatatga | SEQ ID NO: 32 |
| 28005 | atACCATGGTTGGTAAGtcatttatttt | SEQ ID NO: 33 |
| 28021 | ccAACGAGgAATGATAGAtaaacaagag | SEQ ID NO: 34 |
| 28022 | caGTCACAGTTcTAAAAGtctatggtgt | SEQ ID NO: 35 |
| 28023 | tgTGACTGGACcAACGAGgaatgataga | SEQ ID NO: 36 |
| 28024 | tcTAAAAGTCTATGGTGttccttacatt | SEQ ID NO: 37 |
| 28025 | cgCCGGAGAAAGAGAGAGCTttgaggga | SEQ ID NO: 38 |
| 28026 | tgGTTGTCGCTATGGACcagcgtagcaa | SEQ ID NO: 21 |
| 28035 | ctTAAACGGTGGTTgTGCGCTcggatca | SEQ ID NO: 40 |
| 28036 | tcGGAGATATAAGGGCTGCGattcctaa | SEQ ID NO: 41 |

TABLE 4-continued

| Target Sites of FAD3 Zinc Fingers | | |
|---|---|---|
| ZFP | Target Site (5' to 3') | SEQ ID NO: |
| 28039 | tcTCCGATctTAAACGGTGGTTgtgcgc | SEQ ID NO: 42 |
| 28040 | atAAGGGCTGCGATTCCtaagcattgtt | SEQ ID NO: 43 |
| 28051 | agATGGCCCAGAAAAGGgttccttgggc | SEQ ID NO: 44 |
| 28052 | cgTACTCGGCCACGactggtaatttaat | SEQ ID NO: 45 |
| 28053 | ttGAAGTTGCAaTAAGCTttctctcgct | SEQ ID NO: 28 |
| 28054 | acTTGCTGGTCGATCGTGTTggccactc | SEQ ID NO: 47 |
| 28055 | aaGTAGTTGAAGTTGCAataagattct | SEQ ID NO: 30 |
| 28056 | tgGTCGATCGTGTTGGCcactcttgttt | SEQ ID NO: 49 |

Example 3: Evaluation of Zinc Finger Nuclease Cleavage of FAD3 Genes

Construct Assembly

Plasmid vectors containing ZFN expression constructs of the exemplary zinc finger nucleases, which were identified using the yeast assay, as described in Example 2, were designed and completed using skills and techniques commonly known in the art. Each zinc finger-encoding sequence was fused to a sequence encoding an opaque-2 nuclear localization signal (Maddaloni et al. (1989) *Nuc. Acids Res.* 17(18):7532), that was positioned upstream of the zinc finger nuclease.

Next, the opaque-2 nuclear localization signal::zinc finger nuclease fusion sequence was paired with the complementary opaque-2 nuclear localization signal::zinc finger nuclease fusion sequence. As such, each construct included a single open reading frame comprised of two opaque-2 nuclear localization signal::zinc finger nuclease fusion sequences separated by the 2A sequence from *Thosea asigna* virus (Mattion et al. (1996) *J. Virol.* 70:8124-8127). Expression of the fusion proteins was driven by a relatively strong constitutive promoter such as a promoter derived from the Cassava Vein Mosaic Virus (CsVMV) promoter and flanked by the *Agrobacterium tumefaciens* ORF23 3'UnTranslated Region (AtuORF23 3'UTR).

The vectors were assembled using the IN-FUSION™ Advantage Technology (Clontech, Mountain View, Calif.). Restriction endonucleases were obtained from New England BioLabs (NEB; Ipswich, Mass.) and T4 DNA Ligase (Invitrogen) was used for DNA ligation. Plasmid preparations were performed using NUCLEOSPIN® Plasmid Kit (Macherey-Nagel Inc., Bethlehem, Pa.) or the Plasmid Midi Kit (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.). Before delivery to *B. napus* protoplasts, Plasmid DNA was prepared from cultures of *E. coli* using the Pure Yield Plasmid Maxiprep System® (Promega Corporation, Madison, Wis.) or Plasmid Maxi Kit® (Qiagen, Valencia, Calif.) following the instructions of the suppliers.

Figure 3:
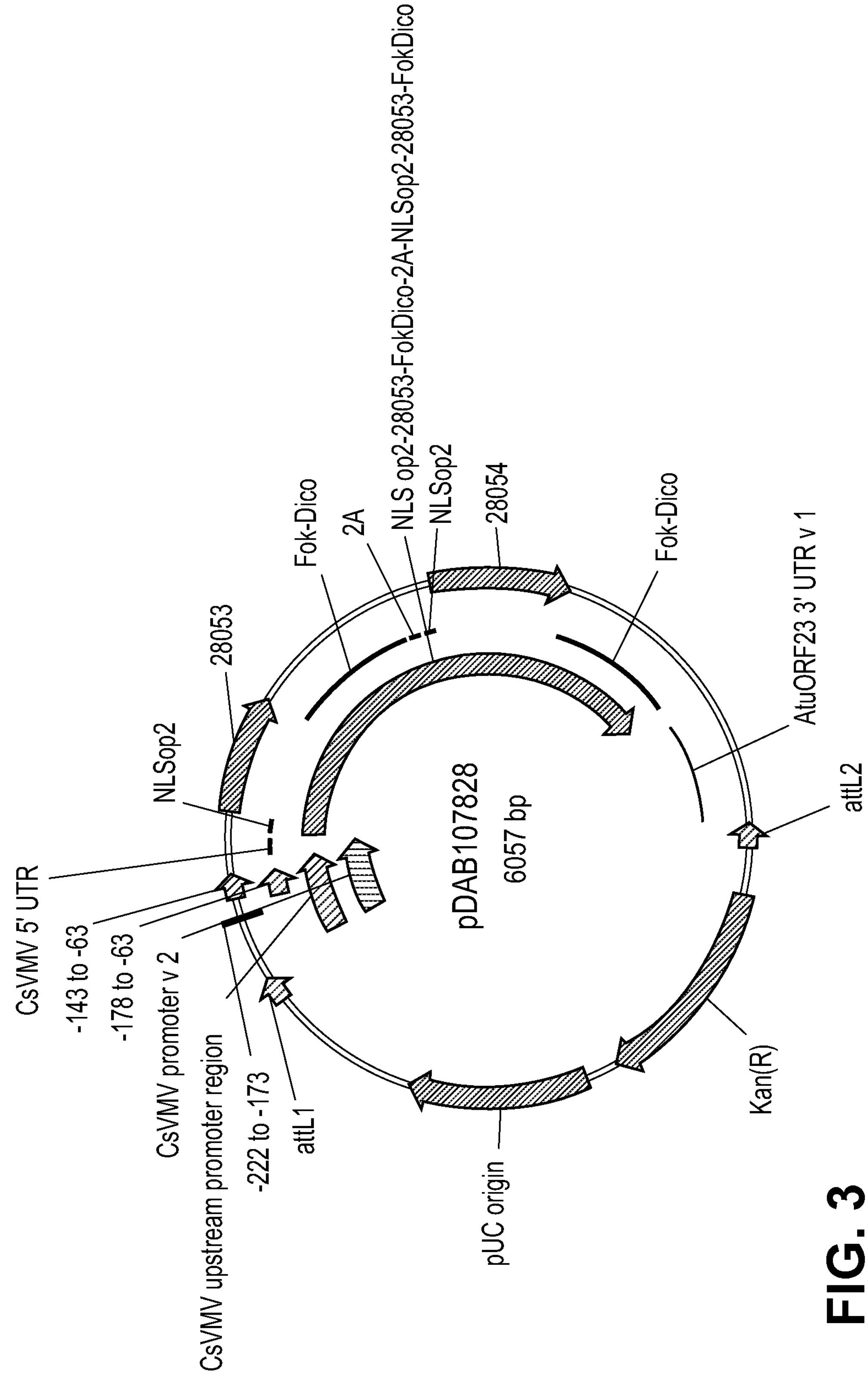
FIG. 3 shows a plasmid map of pDAB107828.
Figure 4:
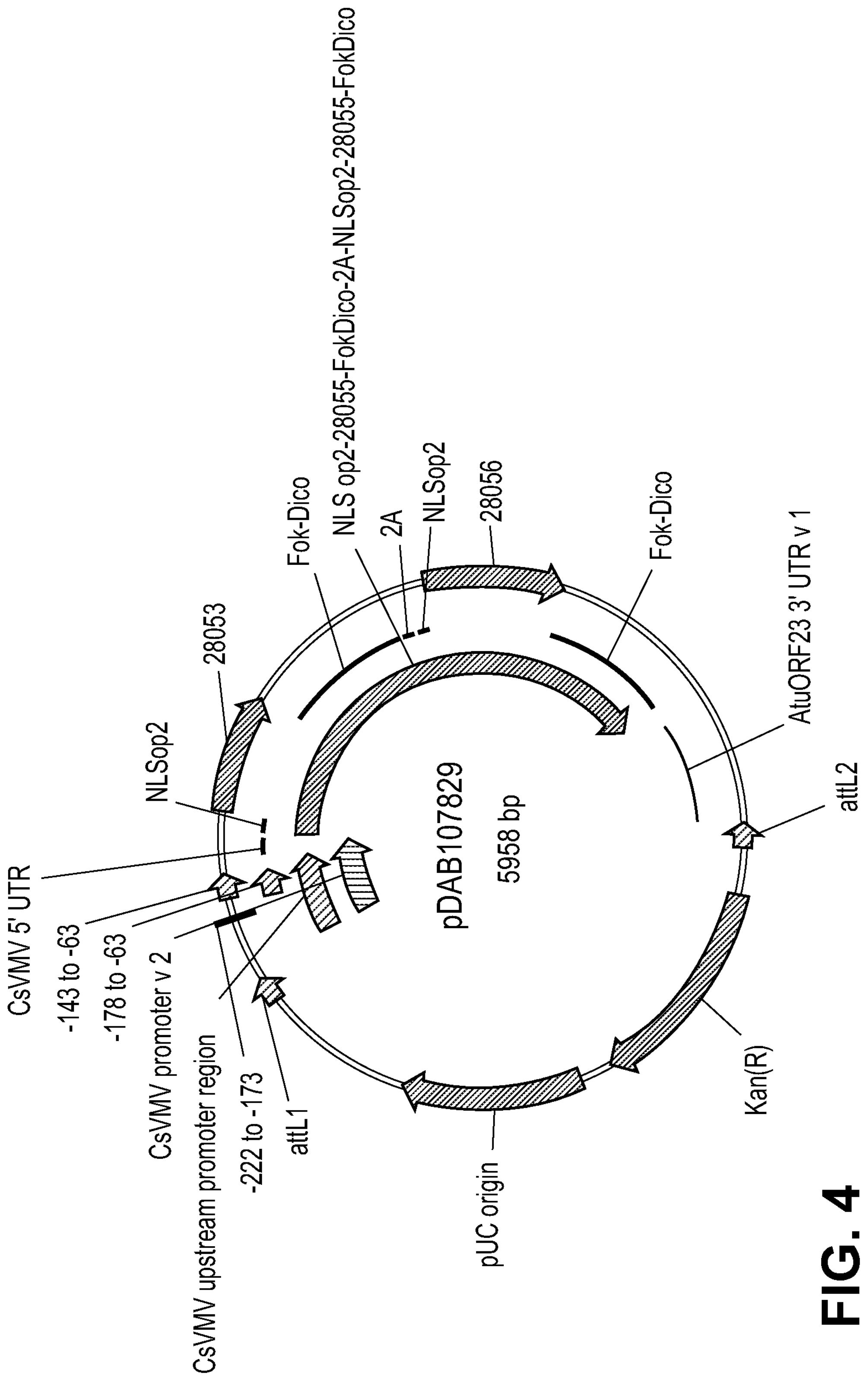
FIG. 4 shows a plasmid map of pDAB107829.
Figure 5:
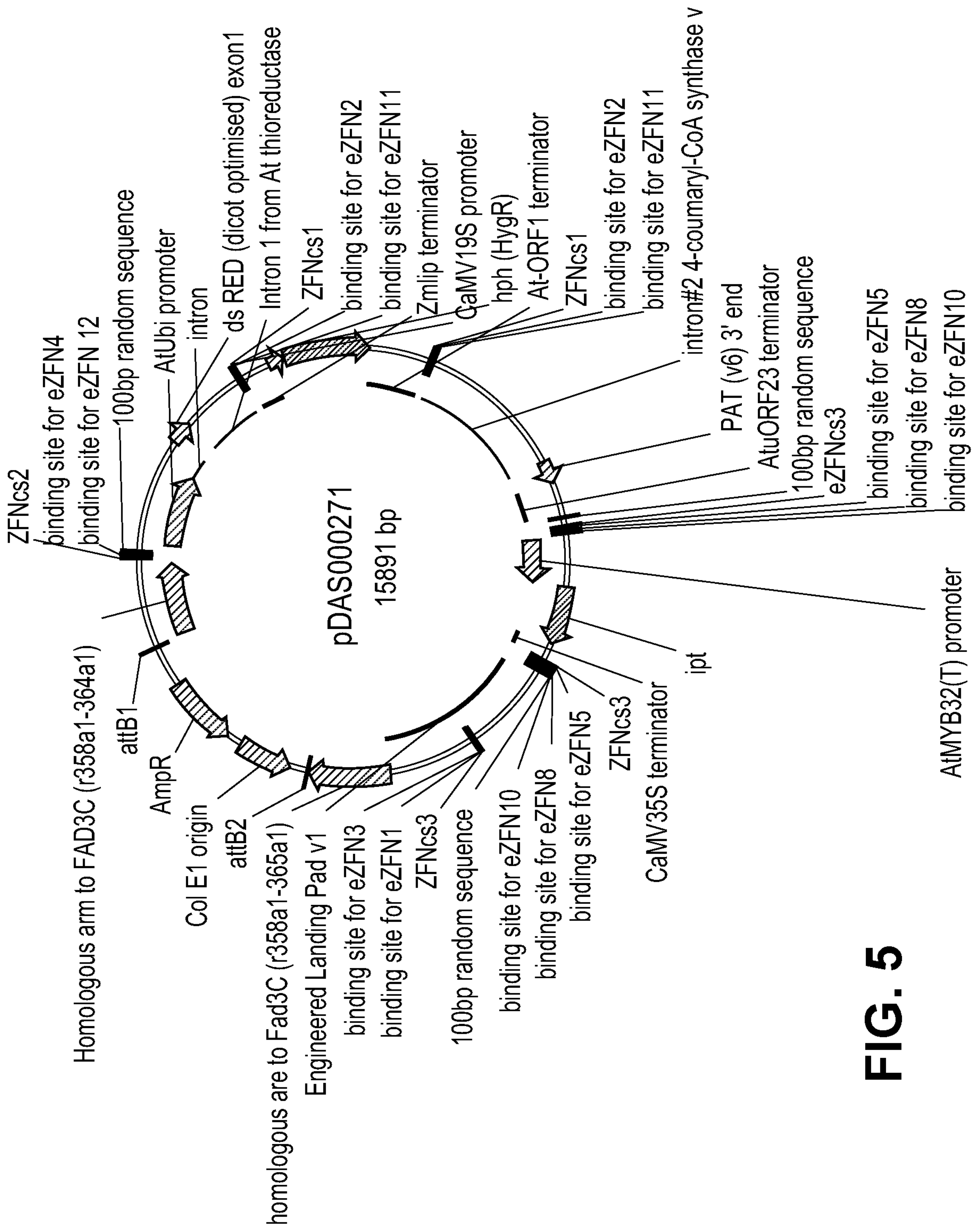
FIG. 5 shows a plasmid map of pDAS000271.
Figure 6:
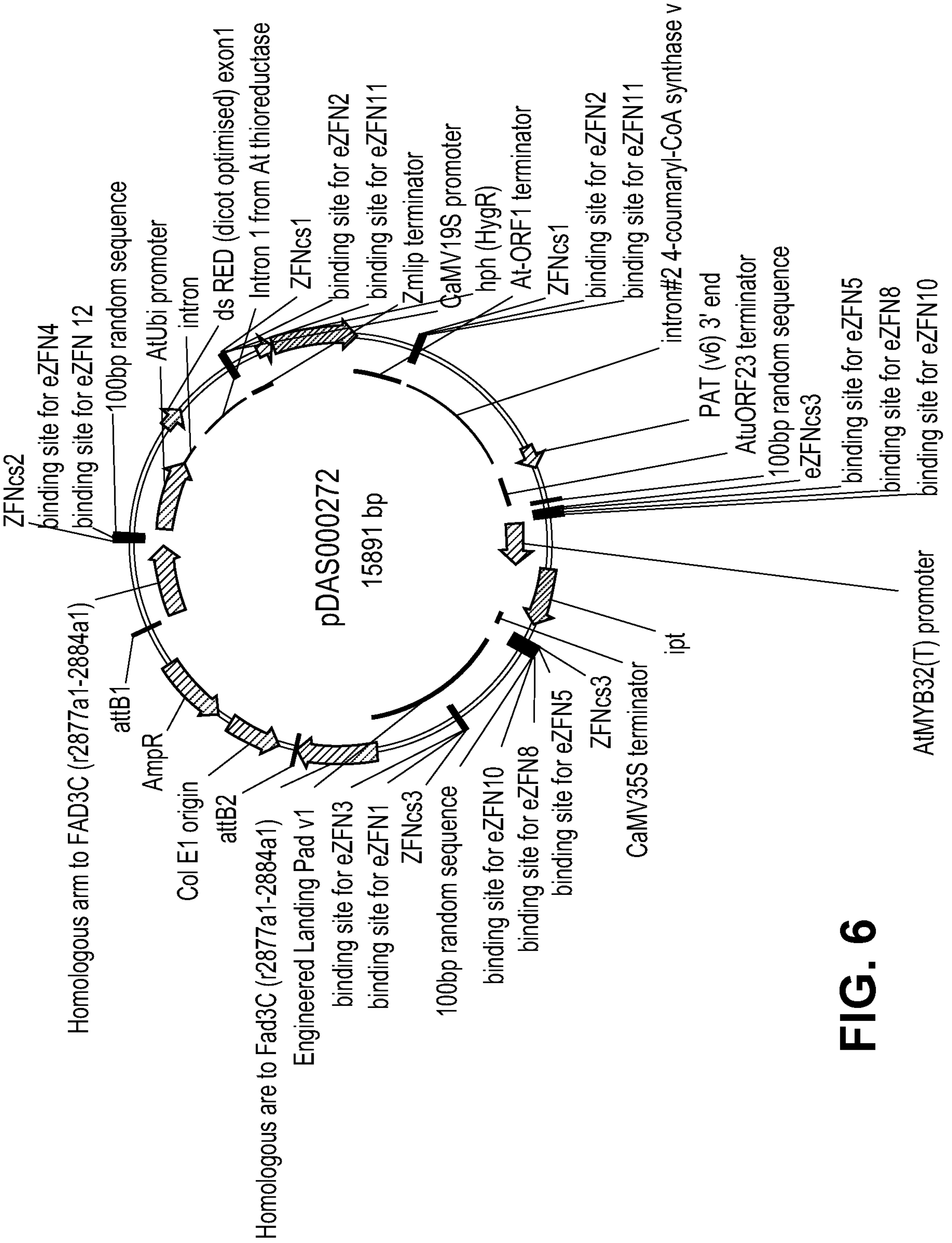
FIG. 6 shows a plasmid map of pDAS000272.
Figure 7:
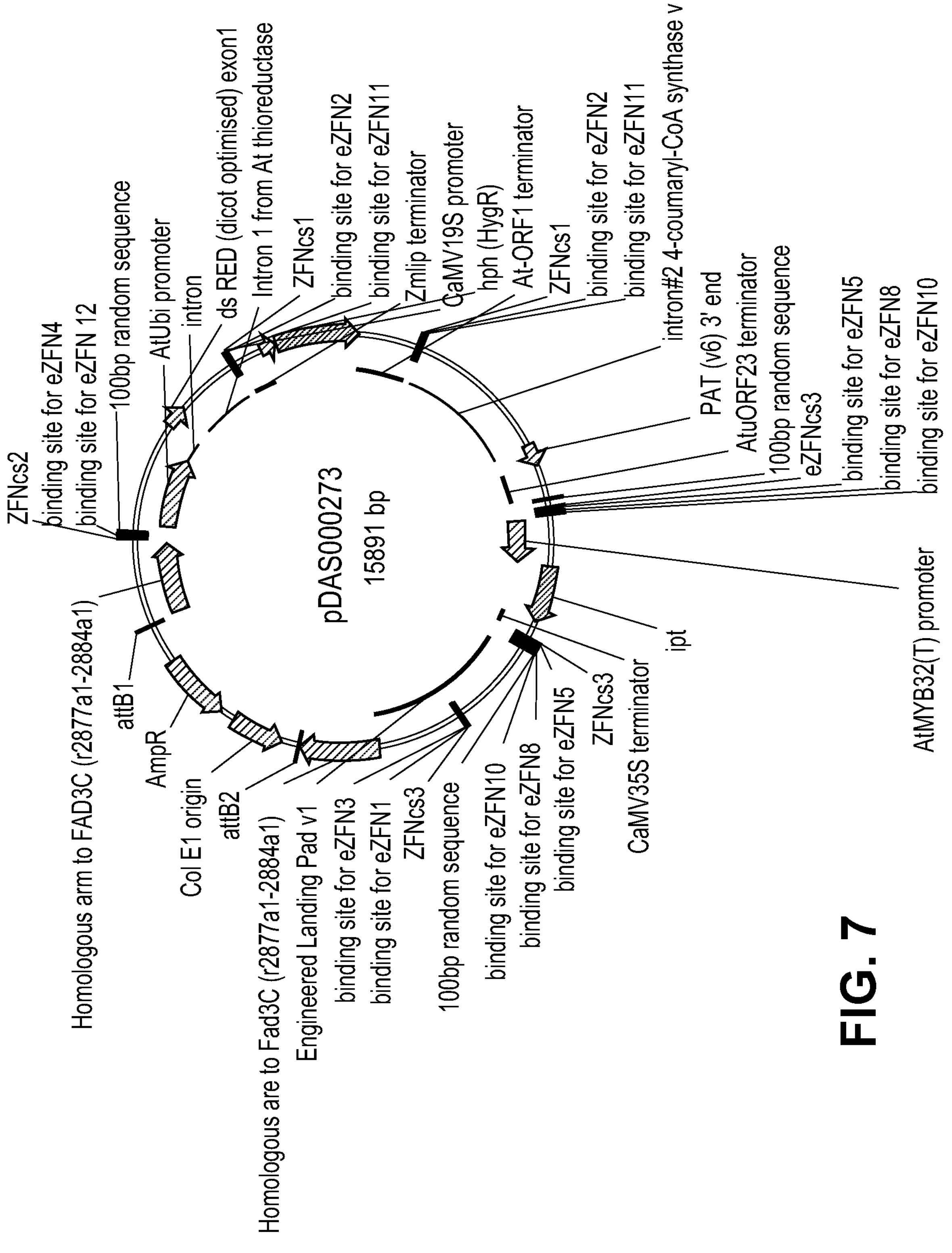
FIG. 7 shows a plasmid map of pDAS000273.
Figure 8:
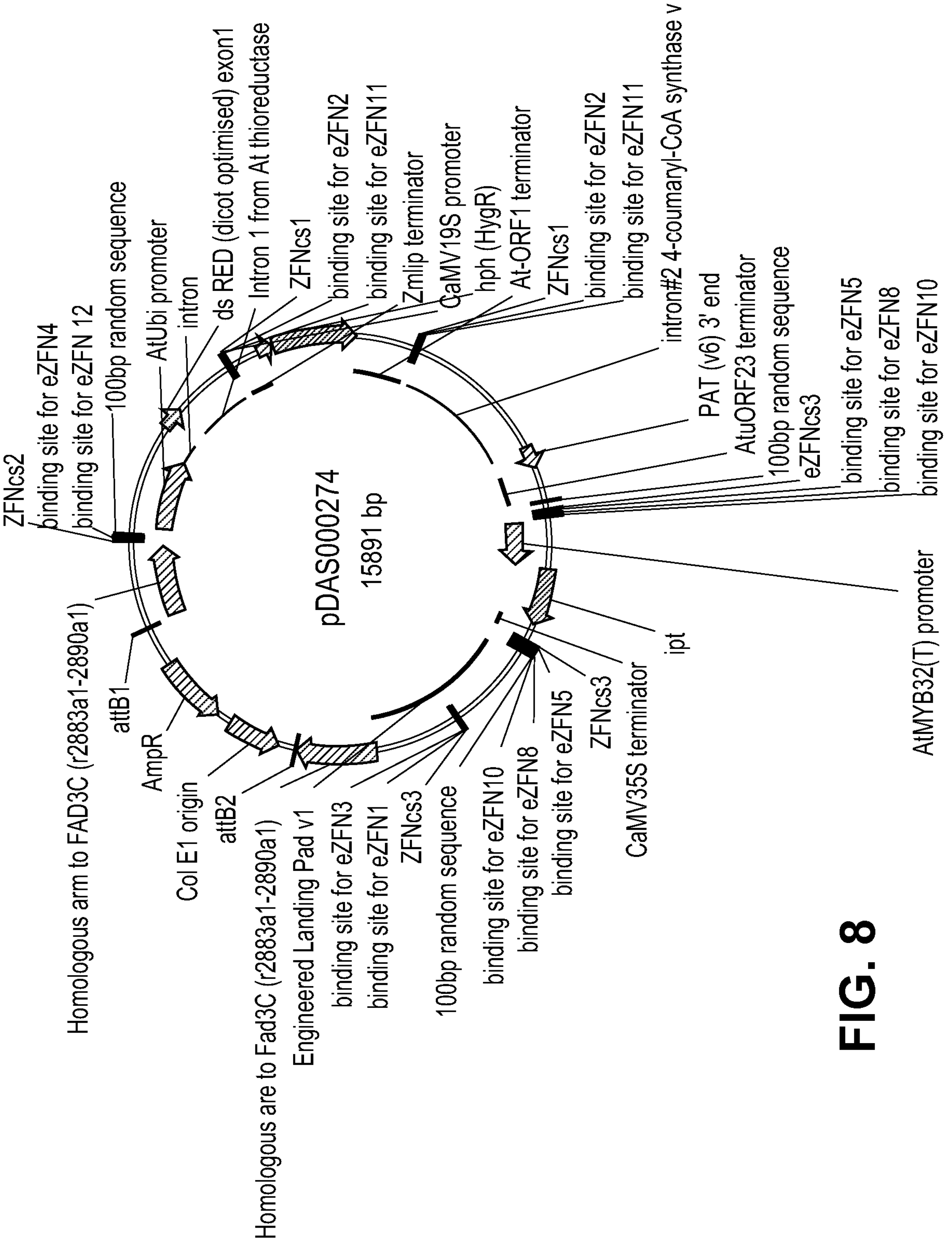
FIG. 8 shows a plasmid map of pDAS000274.
Figure 9:
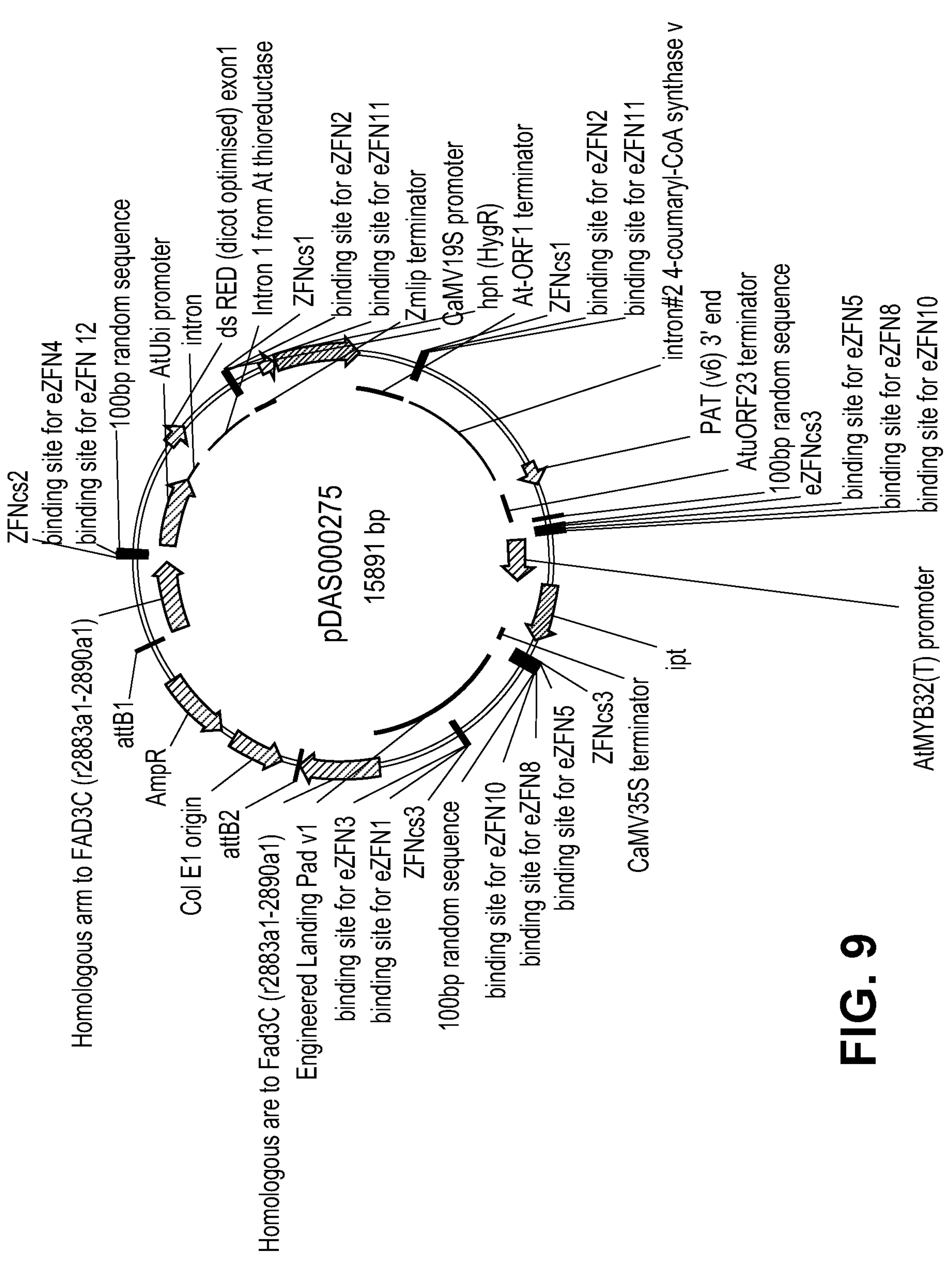
FIG. 9 shows a plasmid map of pDAS000275.

The resulting eleven plasmid constructs; pDAB107824 (ZFNs 28025-2A-28026), pDAB107815 (ZFNs 27961-2A-27962), pDAB107816 (ZFNs 27969-2A-27970), pDAB107817 (ZFNs 27973-2A-27974), pDAB107825 (ZFNs 28035-2A-28036), pDAB107826 (ZFNs 28039-2A-28040), pDAB107818 (ZFNs 27987-2A-27988), pDAB107827 (ZFNs 28051-2A-28052), pDAB107821 (ZFNs 28004-2A-28005), pDAB107819 (ZFNs 27989-2A-27990), pDAB107828 (ZFNs 28053-2A-28054) (FIG. 3), pDAB107829 (ZFNs 28055-2A-28056) (FIG. 4), pDAB107820 (ZFNs 27991-2A-27992), pDAB107822 (ZFNs 28021-2A-28022) and pDAB107823 (ZFNs 28023-2A-28024) were confirmed via restriction enzyme digestion and via DNA sequencing.

Preparation of DNA for Transfection

Plasmid DNA of the above described vectors was sterilized by precipitation, washed in 100% (v/v) ethanol, and dried in a laminar flow hood. The DNA pellet was suspended in 30 of sterile double-distilled water at a final concentration of 0.7 μg/μl for transfection into protoplast cells as described below. The preparation of the plasmid DNA was undertaken to result in supercoiled plasmid DNA for transient transfection and linearized plasmid DNA for stable transfection. The addition of carrier DNA (e.g. fish-sperm DNA) to the transforming plasmid was not required for the transient transfection of protoplast cells. For transient studies about 30 μg of plasmid DNA per $10^6$ protoplasts was used per transformation.

Transfection

Transfection of *Brassica napus* L. var. DH10275 was completed as described in Spangenberg et al., (1986) Plant Physiology 66: 1-8, the media formulations are described in Spangenberg G. and Protrykus I. (1995) Polyethylene Glycol-Mediated Direct Gene Transfer in Tobacco Protoplasts. In: *Gene Transfer to Plants*. (Protrykus I. and Spangenberg G. Eds.) Springer-Verlag, Berlin. *Brassica napus* seeds were surface sterilized in 70% ethanol. The seeds were immersed in 12 mL of the 70% ethanol solution and mixed by gently rocking the cocktail for 10 minutes. The 70% ethanol solution was removed by decanting the solution and exchanged with a seed sterilization solution of 1% w/v calcium hypochlorite and 0.1% v/v Tween-20. The seeds were immersed in the seed sterilization solution and mixed by gently rocking the cocktail for 25 minutes. The seed sterilization solution was decanted and the sterilized seeds were rinsed three times in 50 mL of sterile water. Finally, the seeds were transferred to a sterile 80 mm Whatman Filter Paper Disc® (Fisher-Scientific, St. Louis, Mo.) that had been laid within a Petri dish and the seeds were lightly saturated with sterile water. The Petri dish was sealed with Parafilm® (Fisher-Scientific, St. Louis, Mo.) and the plates were incubated at 25° C. under complete darkness for one to two days. After signs of seedling emergence were observed from the seeds, the seedlings were transferred to Petri dish containing solidified GEM medium to encourage further seed germination. The seedlings were incubated on the GEM medium at 25° C. for four to five days.

A volume of liquid PS medium (about 10 mL) was decanted into a sterile Petri dish. Using sterile forceps and a scalpel, an aerial portion of the four to five day old seedling in the 4-leaf stage of growth and development, was removed and discarded. Hypocotyl segments in lengths of 20-40 mm were determined to produce the highest population of small, cytoplasmic-rich protoplasts. The hypocotyl segments were aseptically excised and transferred to liquid PS medium. The excised hypocotyl segments were grouped together and cut transversely into 5-10 mm segments. Next, the hypocotyl segments were transferred to fresh PS medium and incubated at room temperature for 1 hour. The plasmolysed hypocotyls were transferred to a Petri dish containing enzyme solution. Care was taken to immerse all of the hypocotyl segments into the solution. The Petri dishes were sealed with Parafilm® and incubated overnight for sixteen to eighteen hours at 20-22° C. with gentle rocking.

Protoplast cells were released from the hypocotyl segments. The overnight hypocotyl digests were gently agitated to release protoplasts into the enzyme solution. The Petri dish was angled slightly to aid the transfer of the digesting suspension of enzyme solution and plant debris. Using a 10 mL pipette the digesting suspension was transferred to a sterilized protoplast filtration (a filter of 100 micron mesh) unit to further separate the protoplasts from the plant debris. The filtration unit was tapped gently to release the excess liquid that had been caught in the sieve. The protoplast suspension, about 8 to 9 mL, was gently mixed and distributed into 14 mL sterile plastic round-bottomed centrifuge tubes. Each suspension was overlaid with 1.5 mL of W5 solution. The W5 solution was carefully dispensed over the protoplast suspension at an angle and dispensed drop-by-drop with minimal agitation. The addition of the W5 solution to the protoplast suspension resulted in the production of a protoplast rich interface. This interface was collected using a pipette. Next, the collected protoplasts were transferred into a new 14 mL centrifuge tube, and gently mixed. The yield or obtained protoplasts were determined using a haemocytometer to determine the number of protoplasts per milliliter. The method was repeated, wherein leaf tissue was digested to produce mesophyll protoplasts.

Next, W5 solution was added to a volume of 10 mL and the protoplasts were pelleted at 70 g, before removing the W5 solution. The remaining protoplast suspension was resuspended by gentle shaking. Each tube containing the protoplast suspension was filled with 5 mL of W5 solution and incubated at room temperature from one to four hours. The protoplast suspensions were pelleted at 70 g, and all of the W5 solution was removed. Next, 300 μL of transformation buffer was added to each of the pelleted protoplast suspensions which contained the isolated protoplasts. To each of the tubes, 10 μg of plasmid DNA was added to the protoplast suspensions. The plasmid DNA included the zinc finger nuclease constructs described above. Next, 300 μL of pre-warmed PEG 4000 solution was added to the protoplast suspension and the tubes were gently tapped. The protoplast suspensions and transformation mixture was allowed to incubate at room temperature for fifteen minutes without any agitation. An additional 10 mL of W5 solution was added to each tube in sequential aliquots of 1 mL, 1 mL, 1 mL, 2 mL, 2 mL, and 3 mL with gentle inversion of the tubes between each addition of W5 solution. The protoplasts were pelleted by spinning in a centrifuge at 70 g. All of the W5 solution was removed leaving a pure protoplast suspension.

Next, 0.5 mL of K3 medium was added to the pelleted protoplast cells and the cells were resuspended. The resuspended protoplast cells were placed in the center of a Petri dish and 5 mL of K3 and 0.6 mL Sea Plaque™ agarose (Cambrex, East Rutherford, N.J.) in a 1:1 concentration. The Petri dishes were shaken in a single gentle swirling motion and left to incubate for 20-30 minutes at room temperature. The Petri dishes were sealed with Parafilm® and the protoplasts were cultured for twenty-four hours in complete darkness. After the incubation in darkness, the Petri dishes were cultured for six days in dim light (5 μMol $m^{-2}$ $s^{-1}$ of Osram L36 W/21 Lumilux white tubes). After the culture step, a sterile spatula was used to divide the agarose containing the protoplasts into quadrants. The separated quadrants were placed into a 250 mL plastic culture vessel containing 20 mL of A medium and incubated on a rotary shaker at 80 rpm and 1.25 cm throw at 24° C. in continuous dim light for 14 days and then analyzed to determine the level of activity of each ZFN construct.

Genomic DNA Isolation from Canola Protoplasts

Transfected protoplasts were supplied in individual 1.5 or 2.0 mL microfuge tubes. The cells were pelleted at the base of the tube in a buffer solution. DNA extraction was carried out by snap freezing the cells in liquid nitrogen followed by freeze drying the cells, for about 48 hours in a Labconco Freezone 4.5® (Labconco, Kansas City, Mo.) at −40° C. and about 133×$10^{-3}$ mBar pressure. The lyophilized cells were subjected to DNA extraction using the DNeasy® (QIAGEN, Carlsbad, Calif.) plant kit following manufactures instructions, with the exception that tissue disruption was not required and the protoplast cells were added directly to the lysis buffer.

Testing OF FAD3A and FAD3C ZFN's for Genomic DNA Sequence Cleavage in Canola Protoplasts The design of the ZFN target sites within the FAD3A and FAD3C gene locus were clustered, so that multiple pairs of ZFN were design to overlapping target sites. The clustering of ZFN target sites enabled PCR primers to be designed that would amplify the flanking genomic sequence from all FAD3A and FAD3C gene family members within a 100 bp window so as to encompass all of the overlapping ZFN target sites. As such, the Illumina short read sequence technology could be used to assess the integrity of the target ZFN site of the transfected protoplasts. In addition, the PCR primers designed needed to include specific nucleotide bases that would attribute sequence reads to the specific gene member of the FAD3A and FAD3C gene family. Therefore, all of the PCR primers would be required to bind 5-10 nucleotides away from any ZFN target cut site as non-homologous end joining (NHEJ) activity is known to cause small deletions that could remove a priming site to inhibit amplification and therefore distort the assessment of NHEJ activity.

Primers were designed to bind to all of the ZFN target loci for the FAD3A and FAD3C gene families (Table 5) and were empirically tested for amplification of all gene family members through Sanger based sequencing of PCR amplification products. In several instances primers could not be developed that would distinguish all gene family members (Table 6), however in all instances the target gene sequences of FAD3A or FAD3C, could be distinguished. Following PCR primer design custom DNA barcode sequences were incorporated into the PCR primers that were used to distinguish the different ZFN target loci and identify specific sequence reads to a transfection and ZFN (Tables 5 and 6).

TABLE 5

Amplification performance of the designed PCR primers on the FAD3 gene families. An "X" indicates gene copy detection specificity, a "+" indicates that at the specific locus in question the sequence reads designed by the two primers were unable to be distinguished and an "N/A" indicates that the locus was unable to be amplified from those specific gene copies

| ZFN | FAD Gene Copy | | | | | |
|---|---|---|---|---|---|---|
| Locus | FAD3A | FAD3C | FAD3A' | FAD3C' | FAD3A" | FAD3C" |
| Locus 1 | X | X | X | X | X | X |
| Locus 2 | X | X | X | X | N/A | X |
| Locus 3 | X | X | + | + | X | X |

TABLE 5-continued

Amplification performance of the designed PCR primers on the FAD3 gene families. An "X" indicates gene copy detection specificity, a "+" indicates that at the specific locus in question the sequence reads designed by the two primers were unable to be distinguished and an "N/A" indicates that the locus was unable to be amplified from those specific gene copies

| ZFN | FAD Gene Copy | | | | | |
|---|---|---|---|---|---|---|
| Locus | FAD3A | FAD3C | FAD3A' | FAD3C' | FAD3A" | FAD3C" |
| Locus 4 | X | X | X | X | + | + |
| Locus 5 | X | X | N/A | N/A | N/A | N/A |

TABLE 5-continued

Amplification performance of the designed PCR primers on the FAD3 gene families. An "X" indicates gene copy detection specificity, a "+" indicates that at the specific locus in question the sequence reads designed by the two primers were unable to be distinguished and an "N/A" indicates that the locus was unable to be amplified from those specific gene copies

| ZFN | FAD Gene Copy | | | | | |
|---|---|---|---|---|---|---|
| Locus | FAD3A | FAD3C | FAD3A' | FAD3C' | FAD3A" | FAD3C" |
| Locus 6 | X | X | X | X | X | X |
| Locus 7 | X | X | X | X | X | X |

TABLE 6

Primer sequences designed for FAD3 ZFN assessment of activity. Primers include custom barcodes, along with both requisite illumina adaptor sequences for construction of illumina library for sequencing-by-synthesis analysis. Purchased primer was the sum of all three columns presented

| Locus ID | SEQ ID NO: | Illumina Adaptor Primer Sequence Barcode Locus Primer |
|---|---|---|
| FAD3_ZFN_Locus1A_F3 | 50 | ACACTCTTTCCCTACACGACGCTCTTCCGATCT *ACGTA* CCTTTCTTCACCACATTYCA |
| FAD3_ZFN_Locus1B_F3 | 51 | ACACTCTTTCCCTACACGACGCTCTTCCGATCT *CGTAC* CCTTTCTTCACCACATTYCA |
| FAD3_ZFN_Locus2C_F1 | 52 | ACACTCTTTCCCTACACGACGCTCTTCCGATCT*CTGACG* ATGGTTGTCGCTATGGACC |
| FAD3_ZFN_Locus3D_F1 | 53 | ACACTCTTTCCCTACACGACGCTCTTCCGATCT*TGACTC* GAAAGGTTTGATCCRAGCG |
| FAD3_ZFN_Locus3E_F1 | 54 | ACACTCTTTCCCTACACGACGCTCTTCCGATCT*GACTGC* GAAAGGTTTGATCCRAGCG |
| FAD3_ZFN_Locus3F_F1 | 55 | ACACTCTTTCCCTACACGACGCTCTTCCGATCT*ACTGAC* GAAAGGTTTGATCCRAGCG |
| FAD3_ZFN_Locus4G_F1 | 56 | ACACTCTTTCCCTACACGACGCTCTTCCGATCT*GCTAGC* CGTGTATTTTGATAGCTGGTTC |
| FAD3_ZFN_Locus4H_F1 | 57 | ACACTCTTTCCCTACACGACGCTCTTCCGATCT*CTAGCC* CGTGTATTTTGATAGCTGGTTC |
| FAD3_ZFN_Locus5J_F1 | 58 | ACACTCTTTCCCTACACGACGCTCTTCCGATCT*TAGCTG* GAGCTTCTCAGACATTCCTCT |
| FAD3_ZFN_Locus6K_F1 | 59 | ACACTCTTTCCCTACACGACGCTCTTCCGATCT*TCAGTG* TTTATTTGCCCCAAGCGAGAG |
| FAD3_ZFN_Locus6L_F1 | 60 | ACACTCTTTCCCTACACGACGCTCTTCCGATCT*CAGTCG* TTTATTTGCCCCAAGCGAGAG |
| FAD3_ZFN_Locus6M_F1 | 61 | ACACTCTTTCCCTACACGACGCTCTTCCGATCT*AGTCAG* TTTATTTGCCCCAAGCGAGAG |
| FAD3_ZFN_Locus6N_F1 | 62 | ACACTCTTTCCCTACACGACGCTCTTCCGATCT*GTCAGG* TTTATTTGCCCCAAGCGAGAG |
| FAD3_ZFN_Locus7P_F3 | 63 | ACACTCTTTCCCTACACGACGCTCTTCCGATCT*GTACGA* CTTCAACTACTTGCTGGTCSAT |
| FAD3_ZFN_Locus7Q_F3 | 64 | ACACTCTTTCCCTACACGACGCTCTTCCGATCT*TACGTA* CTTCAACTACTTGCTGGTCSAT |
| FAD3_ZFN_Locus1A_R1 | 65 | CGGTCTCGGCATTCCTGCTGAACCGCTCTTCCGATCT*AC GTA*CGTTCACATTGSTRCGYTGG |
| FAD3_ZFN_Locus1B_R1 | 66 | CGGTCTCGGCATTCCTGCTGAACCGCTCTTCCGATCT*CG TAC*CGTTCACATTGSTRCGYTGG |
| FAD3_ZFN_Locus2C_R1 | 67 | CGGTCTCGGCATTCCTGCTGAACCGCTCTTCCGATCT*CT GAC*CCGATCTTAAACGGYGGTTGT |

TABLE 6-continued

Primer sequences designed for FAD3 ZFN assessment of activity. Primers include custom barcodes, along with both requisite illumina adaptor sequences for construction of illumina library for sequencing-by-synthesis analysis. Purchased primer was the sum of all three columns presented

| Locus ID | SEQ ID NO: | Illumina Adaptor Primer Sequence Barcode Locus Primer |
|---|---|---|
| FAD3_ZFN_Locus3D_R1 | 68 | CGGTCTCGGCATTCCTGCTGAACCGCTCTTCCGATCT*TGACT*TAGCTCATGGATCTCAAAGGACT |
| FAD3_ZFN_Locus3E_R1 | 69 | CGGTCTCGGCATTCCTGCTGAACCGCTCTTCCGATCT*GACTG*TAGCTCATGGATCTCAAAGGACT |
| FAD3_ZFN_Locus3F_R1 | 70 | CGGTCTCGGCATTCCTGCTGAACCGCTCTTCCGATCT*ACTGA*TAGCTCATGGATCTCAAAGGACT |
| FAD3_ZFN_Locus4G_R_uni | 71 | CGGTCTCGGCATTCCTGCTGAACCGCTCTTCCGATCT*GCTAG*TTAAATTACCAGTCGTGGCC |
| FAD3_ZFN_Locus4H_R_uni | 72 | CGGTCTCGGCATTCCTGCTGAACCGCTCTTCCGATCT*CTAGC*TTAAATTACCAGTCGTGGCC |
| FAD3_ZFN_Locus5J_R2 | 73 | CGGTCTCGGCATTCCTGCTGAACCGCTCTTCCGATCT*TAGCT*CTTTTTTCTTCGATKCTAAAGATT |
| FAD3_ZFN_Locus6K_R1 | 74 | CGGTCTCGGCATTCCTGCTGAACCGCTCTTCCGATCT*TCAGT*CTGTGACTGGACCAACGAGG |
| FAD3_ZFN_Locus6L_R1 | 75 | CGGTCTCGGCATTCCTGCTGAACCGCTCTTCCGATCT*CAGTC*CTGTGACTGGACCAACGAGG |
| FAD3_ZFN_Locus6M_R1 | 76 | CGGTCTCGGCATTCCTGCTGAACCGCTCTTCCGATCT*AGTCA*CTGTGACTGGACCAACGAGG |
| FAD3_ZFN_Locus6N_R1 | 77 | CGGTCTCGGCATTCCTGCTGAACCGCTCTTCCGATCT*GTCAG*CTGTGACTGGACCAACGAGG |
| FAD3_ZFN_Locus7P_R1 | 78 | CGGTCTCGGCATTCCTGCTGAACCGCTCTTCCGATCT*GTACG*ACTTACAATGTAAGGAACRCCRTA |
| FAD3_ZFN_Locus7Q_R1 | 79 | CGGTCTCGGCATTCCTGCTGAACCGCTCTTCCGATCT*TACGT* ACTTACAATGTAAGGAACRCCRTA |

Following DNA extraction of canola protoplasts transfected with the ZFN, PCR amplification of the target ZFN loci was performed to generate the requisite loci specific DNA molecules in the correct format for Illumina based sequencing by synthesis technology. Each assay was optimised to work on 25 ng starting DNA (about 12,500 cell equivalents of the *Brassica napus* genome). Multiple reactions were performed, per sample to provide the coverage required to assess NHEJ efficiency and specificity at the appropriate level, about sixteen PCR reactions equivalent to 200,000 copies of the *Brassica napus* genome taken from individual protoplasts. PCR amplification master-mixes were made for all samples to be tested with the same assay and one reaction, performed in triplicate, was assayed using a quantitative PCR method that was used to determine the optimal number of cycles to perform on the target tissue, to ensure that PCR amplification had not become reagent limited and was still in an exponential amplification stage. The experimentation with the necessary negative control reactions was performed in 96 well format using a MX3000P Thermocycler® (Stratagene, LaJolla, Calif.).

From the output gathered from the quantitative PCR platform, the relative increase in fluorescence was plotted from cycle-to-cycle and the cycle number was determined per assay that would deliver sufficient amplification, while not allowing the reaction to become reagent limited, in an attempt to reduce over cycling and the amplification of common transcripts or molecules. The unused master mix, remained on ice until the quantitative PCR analysis was concluded and the cycle number determined and was then aliquoted into the desired number of reaction tubes (about 16 per ZFN assay) and the PCR reaction was performed.

Following amplification, samples for a single ZFN locus were pooled together and 200 μL of pooled product per ZFN was cleaned using the MinElute PCR Purification Kit® (Qiagen) following manufacturer's instructions. To enable the sample to be sequenced using the Illumina short read technology additional paired end primers were required to be attached by amplification onto the generated fragments. This was achieved by PCR amplification using primers that would be, in part complementary to the sequence added in the first round of amplification, but also contain the paired end sequence required. The optimal number of PCR cycles to perform, that would add the paired end sequences without over amplifying common fragments to the template was again determined using a sample pass through a quantitative PCR cycle analysis, as described previously.

Following PCR amplification, the generated product was cleaned using a MinElute Column® (Qiagen) following manufacturer's instructions and was resolved on a 2.5% agarose gel. DNA fragments visualised using Syber® Safe (Life Technologies, Carlsbad, Calif.) as bands of the correct size were gel extracted to remove any residual PCR generated primer-dimer or other spurious fragments, the DNA was extracted from the gel slice using a MinElute Gel Extraction Kit® (Qiagen) following manufacturer's instructions. After completion of the gel extraction an additional clean up of the DNA was performed using AMPure Magnetic Beads® (Beckman-Coulter, Brea, Calif.) with a DNA to bead ratio of 1:1.7. The DNA was then assessed for concentration using a quantitative PCR based library quantification kit for Illumina sequencing (KAPA) with a 1/40,000 and a 1/80,000 dilution and with the reaction being performed in triplicate. Based on the quantitative PCR results the DNA was diluted to a standard concentration of 2 nM and all libraries were combined for DNA sequencing. The samples were prepared for sequencing using a cBot Cluster Generation Kit® (Illumina, San Diego, Calif.) and were sequenced on an Illumina GA2x® with 100 bp paired-end sequencing reads following manufacturer's instructions.

Method of Data Analysis for Detection of Non-Homologous End Joining at Target Zinc Finger Sites Following completion of the sequencing reaction and primary data calling performed using the Illumina bioinformatic pipeline for base calling, full analysis was performed to identify deleted bases at the target ZFN site in each instance. A custom PERL script was designed to extract and sort barcodes from DNA sequences computationally following a list of input sequences. The barcode had to match the reference sequence at a Phred score of greater than 30 to be accepted, to reduce misattributing sequence reads. After the sequence reads had been binned into the different barcode groups that had been used, a quality filter was passed across all sequences. The quality filter was a second custom developed PERL script. Sequence reads were excluded if there were more than three bases called as "N", or if the median Phred score was less than 20, or if there were 3 consecutive bases with a Phred score of less than 20, or if the sequence read was shorter than 40 bp in length. The remaining sequences were merged where both of the paired sequence reads were available using the NextGENe® (SoftGenetics, State College, Pa.) package. The remaining merged sequence reads were then reduced to a collection of unique sequence reads using a third custom PERL script with a count of the number of redundant sequences that had been identified recorded on the end of the remaining sequence identifier. The unique sequence reads were then aligned to the FAD3 reference sequence using the NextGENe® software that created a gapped FASTA aligned file.

Using the gapped FASTA file a conversion of the gapped base position number to the input reference was performed using a fourth custom PERL script. This enabled bases that discriminate the different gene family members (either homoeologous or paralogous sequence variation between the different gene family members) to be identified in the assembled data. Once the conversion of base numbering had been performed it was possible to generate haplotype reports for each unique sequence reads and assign the reads to specific gene family members. Once the reads had been grouped by gene a 10 bp window was identified and assessed that surrounded the ZFN target site. The number of sequences with deletions was recorded per gene along with the number of missing bases.

The data was then graphically displayed as a multiple line graph, with the number of sequences with 1 through 10 bases deleted at the target ZFN site per 10,000 sequence reads. This analysis was performed for all ZFN transfections along with control transfections. In several instances, repeats in the native DNA sequence lead to an increase in sequencing error in the target ZFN site, such an error can be commonly seen as an increase in the prevalence of single base deletions that were reported in all samples, both transfected with ZFN or controls.

From these results highest level of ZFN activity at a FAD3A and FAD3C target site was observed as determined by the greater activity of NHEJ. The ZFNs which were encoded on plasmid pDAB107828 (i.e., ZFN28053 and 28054) and pDAB107829 (i.e., ZFN28055 and 28056) were selected for in planta targeting of an Engineered Transgene Integration Platform (ETIP) given its characteristics of significant genomic DNA cleavage activity and minimal non-target activity.

Example 4: DNA Constructs for Engineered Transgene Integration Platform (ETIP) Canola Plant Lines The plasmid vector constructs described below were built using methods and techniques commonly known by one with skill in the art. The application of specific reagents and techniques described within this paragraph are readily known by those with skill in the art, and could be readily interchanged with other reagents and techniques to achieve the desired purpose of building plasmid vector constructs. The restriction endonucleases were obtained from New England BioLabs (NEB; Ipswich, Mass.). Ligations were completed with T4 DNA Ligase (Invitrogen, Carlsbad, Calif.). Gateway reactions were performed using GATEWAY® LR CLONASE® enzyme mix (Invitrogen) for assembling one entry vector into a single destination vector. IN-FUSION™ reactions were performed using IN-FUSION™ Advantage Technology (Clontech, Mountain View, Calif.) for assembling one entry vector into a single destination vector Plasmid preparations were performed using NUCLEOSPIN® Plasmid Kit (Macherey-Nagel Inc., Bethlehem, Pa.) or the Plasmid Midi Kit® (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Control Vectors

Figure 10:
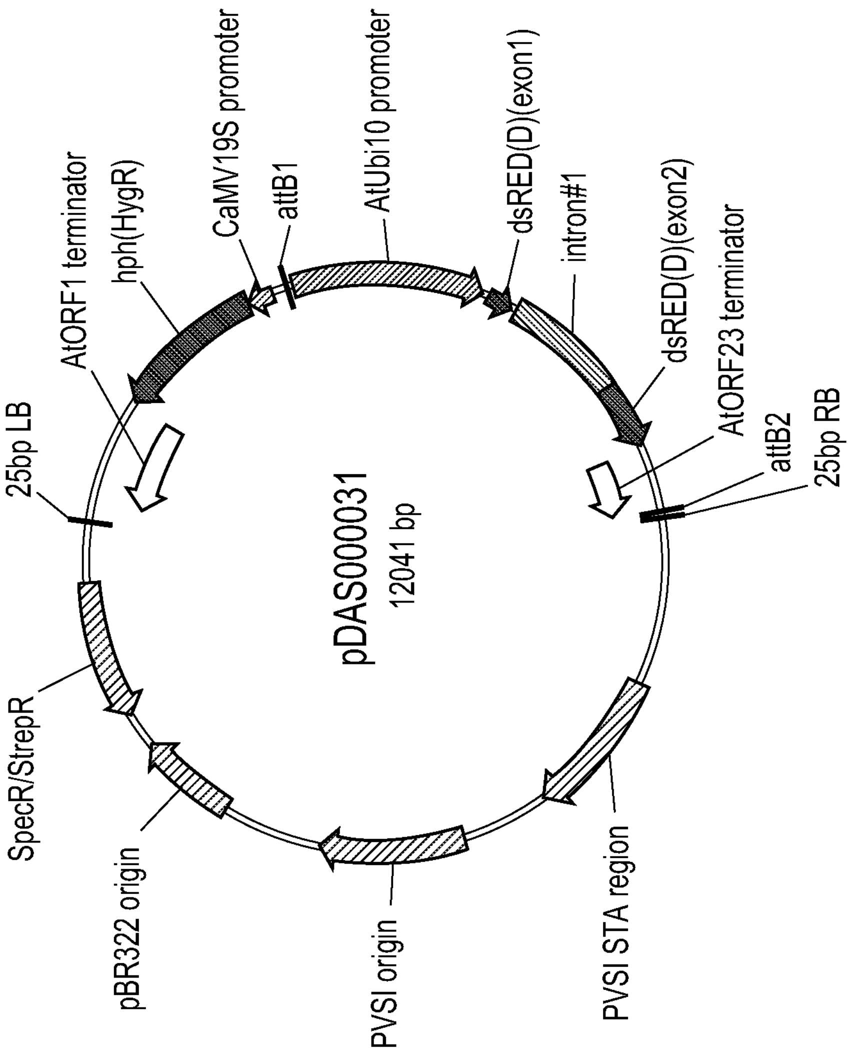
FIG. 10 shows a plasmid map of pDAS000031.
Figure 11:
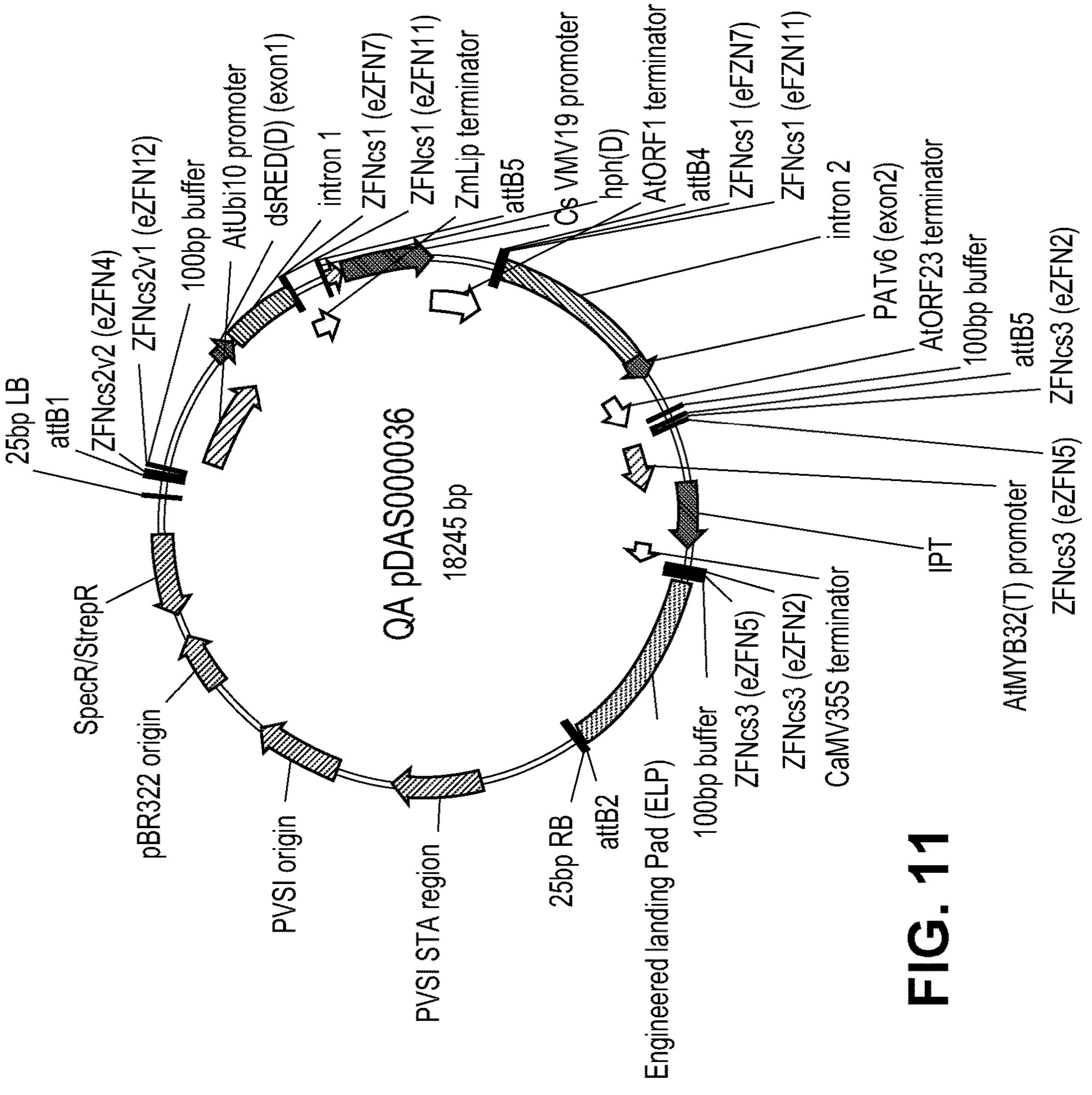
FIG. 11 shows a plasmid map of pDAS000036.
Figure 12:
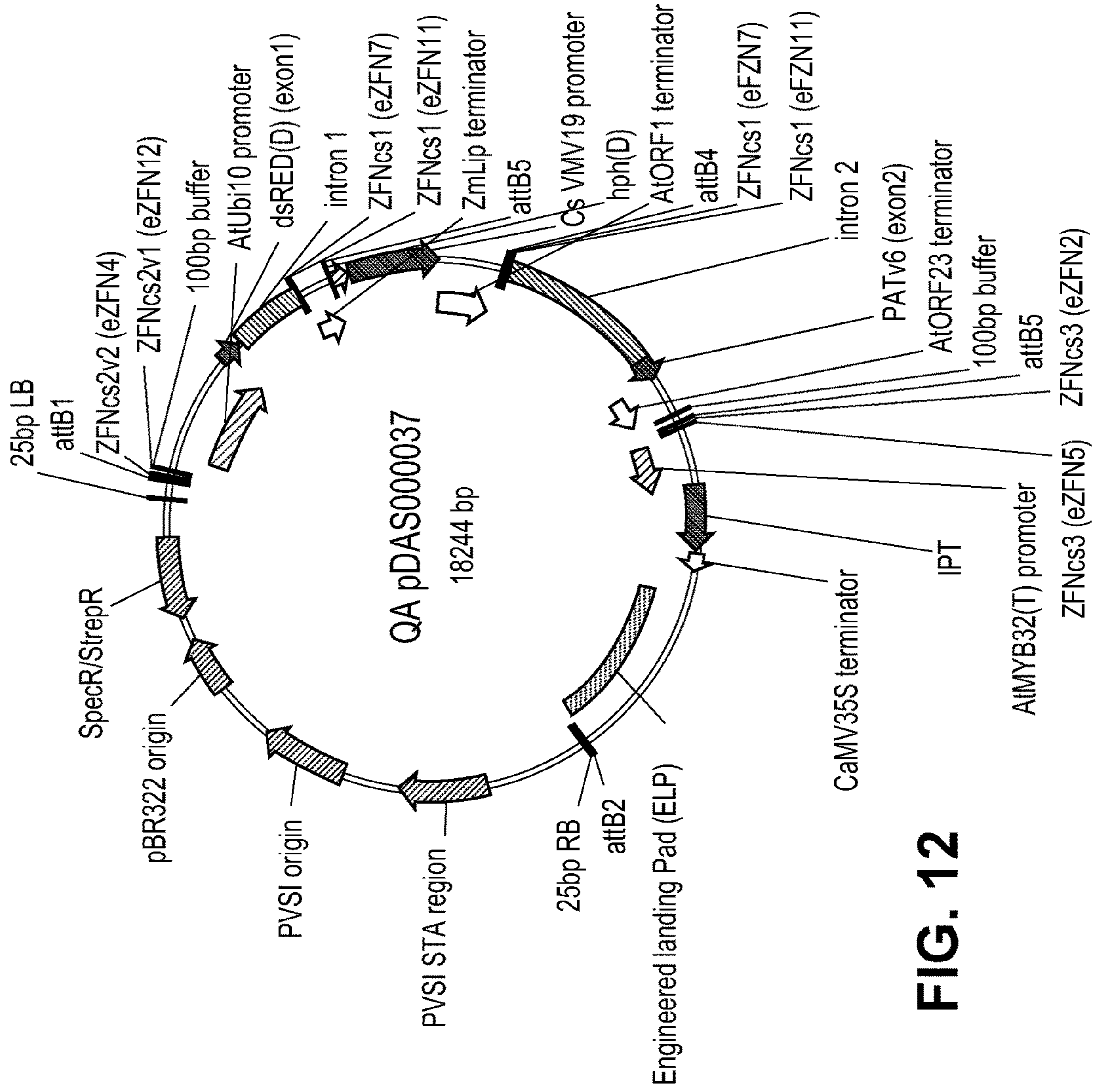
FIG. 12 shows a plasmid map of pDAS000037.

A control vector was used to develop a Fluorescence Activated Cell Sorting (FACS) cell based sorting method. Standard cloning methods were used in the construction of a control vector, pDAS000031 (FIG. 10: T-strand insert as SEQ ID NO:85) including two gene expression cassettes. The first gene expression cassette contained the Cauliflower mosaic virus 19s promoter (CaMV 19S promoter; Shillito, et al., (1985) *Bio/Technology* 3; 1099-1103): hygromycin resistance gene (hph(HygR); U.S. Pat. No. 4,727,028): and the *Agrobacterium tumefaciens* Open Reading Frame 1 3'UnTranslated Region (AtORF1 terminator; Huang et al., (1990) *J. Bacteriol.* 1990 172:1814-1822). The second gene expression cassette contained the *Arabidopsis thaliana* Ubiquitin 10 promoter (AtUbi10 promoter; Callis, et al., (1990) *J. Biol. Chem.,* 265: 12486-12493): dsRED (dsRED (D); U.S. Pat. No. 6,852,849) and an intron from *Arabidopsis* (intron #1; GenBank: AB025639.1) *Agrobacterium tumefaciens* Open Reading Frame 23 3'UnTranslated Region (AtORF23 terminator; U.S. Pat. No. 5,428,147) as an in-frame fusion with a trans orientation (e.g., head to head orientation). The plasmid vector was assembled using the IN-FUSION™ Advantage Technology (Clontech, Mountain View, Calif.).

Example 5: Generation of ETIP Canola Plant Lines Transformation of *Brassica napus*

The ETIP constructs for the FAD3A and FAD3C site specific construct (pDAS000271-pDAS000275) and accompanying ZFN (pDAB107828 and 107829) and the control the DS-Red control construct (pDAS000031) are previously described in Example 4. These binary vectors are transformed into *Agrobacterium tumefaciens* strain GV3101: PM90. Transformation of *Brassica napus* protoplast cells is completed using the transfection protocol described in Example 3 with some modification.

The modifications to the protocol include the use of sodium alginate instead of Sea Plaque™ agarose. The transfection experiments in which both the ZFN construct and the ETIP construct are co-delivered into *Brassica napus* protoplast cells are completed at DNA concentrations comprising a 5:1 molar ratio of plasmid DNA. The other ETIP and control plasmid constructs are transformed at concentrations of 30 μg of plasmid DNA.

Additional modifications to the protocol include the propagation of whole plants from the transformed protoplast cells in medium containing 1.5 mg/mL of hygromycin. The propagation of whole plants requires that the A medium is replaced every two weeks and the growth of the protoplast-derived colonies is monitored. After the protoplast-derived colonies grow to approximately 2-3 mm in diameter, the colonies are transferred into individual wells of a 12-well Costar® plate (Fisher Scientific, St. Louis, Mo.) containing solidified MS morpho medium. The plates are incubated for one to two weeks at 24° C. under continuous dim light until the calli proliferate to a size of 8-10 mm in diameter. After the protoplast cells reach a diameter of 1-2 cm in diameter, the protoplast cells are transferred to individual 250 mL culture vessels containing MS morpho medium. The vessels are incubated at 24° C. under 16 h light (20 μMol $m^{-2}$ $s^{-1}$ of Osram L36 W/21 Lumilux white tubes) and 8 h dark conditions. Within one to two weeks, multiple shoots are visible. The shoots are transferred into 250 mL culture vessels containing MS medium after they reach a length of 3-4 cm. The 250 mL culture vessels are incubated at 24° C. under 16 h light (20 μMol $m^{-2}$ $s^{-1}$ of Osram L36 W/21 Lumilux white tubes) and 8 h dark conditions. The shoots are maintained in the culture vessels until they develop into plantlets at which time they are transferred to a greenhouse to grow to maturity.

Example 6: Molecular Confirmation of Integration of T-DNAs Containing ETIPS in Canola Genomic DNA is extracted from leaf tissue of all putative transgenic plants using a DNeasy 96 Plant DNA Extraction Kit™ or a DNeasy Plant Mini Kit™ (Qiagen). The genomic DNA from each plant is analyzed by PCR using primers designed to amplify virC from pTiC58 Forward (SEQ ID NO:88 CGAGAACTTGGCAATTCC) and pTiC58 Reverse (SEQ ID NO:89 TGGCGATTCTGAGATTCC) to test for persistence of *A. tumfaciens*, primers designed to amplify actin from *B. napus*; Actin Forward (SEQ ID NO:90 GACTCATCGTACTCTCCCTTCG) and Actin Reverse (SEQ ID NO:91 GACTCATCGTACTCTCCCTTCG) to check the quality of the genomic DNA. Primers are designed to amplify the hph gene; HPH Forward (SEQ ID NO:92 TGTTGGTGGAAGAGGATACG) and HPH Reverse (SEQ ID NO:93 ATCAGCAGCAGCGATAGC) encoded by the ETIP. Plants that do not give a product from virC primers, and that produce amplicons of the correct size when amplified with primers to actin and hph are confirmed as transgenic.

A second screen is completed, where gDNA from each transgenic plant is analysed by PCR using five sets of primers designed to amplify the binary vector outside of the T-DNA region [(1F SEQ ID NO:94 ATGTCCACTGGGTTCGTGCC; 1R SEQ ID NO:95 GAAGGGAACTTATCCGGTCC) (2F SEQ ID NO:96 TGCGCTGCCATTCTCCAAAT; 2R SE ID NO:97 ACCGAGCTCGAATTCAATTC) (3F SEQ ID NO:98 CCTGCATTCGGTTAAACACC; 3R SEQ ID NO:99 CCATCTGGCTTCTGCCTTGC) (4F SEQ ID NO:100 ATTCCGATCCCCAGGGCAGT; 4R SEQ ID NO:101 GCCAACGTTGCAGCCTTGCT) (5F SEQ ID NO:102 GCCCTGGGATGTTGTTAAGT; 5R SEQ ID NO:103 GTAACTTAGGACTTGTGCGA)]. Plants from which PCR products of the correct and expected size are amplified with primer sets 3 and 4 are considered to have backbone integration.

DNA from plants with no backbone integration is purified from 20 g of leaf tissue using a modified CTAB method (Maguire et al., (1994) Plant Molecular Biology Reporter, 12(2): 106-109). The isolated gDNA is digested with several restriction enzymes and 10 μg of gDNA is separated by electrophoresis on an agarose gel and transferred to membrane using a standard Southern blotting protocol. Membranes are probed using the DIG Easy Hyb System™ (Roche, South San Francisco, Calif.) following the manufacturer's instructions. Probes to each expression cassette to the ELP and to an endogenous control gene, actin, are amplified from the ETIP construct using the following primers: (IPT-F SEQ ID NO:104 TCTCTACCTTGATGATCGG; IPT-R SEQ ID NO:105 AACATCTGCTTAACTCTGGC; dsRED-F SEQ ID NO:106 ATGGCTTCATCTGAGAACG; dsRED-R SEQ ID NO:107 TTCCGTATTGGAATTGAGG; PAT-F SEQ ID NO:108 TTGCTTAAGTCTATGGAGGCG; PAT-R SEQ ID NO:109 TGGGTAACTGGCCTAACTGG; ELP-F SEQ ID NO:110 ATGATATGTAGACATAGTGGG; ELP-R SEQ ID NO:111 AGGGTGTAAGGTACTAGCC; Hph-F SEQ ID NO:112 TGTTGGTGGAAGAGGATACG; Hph-R SEQ ID NO:113, ATCAGCAGCAGCGATAGC; actin-F SEQ ID NO:114 GTGGAGAAGAACTACGAGCTACCC; actin-R SEQ ID NO:115 GACTCATCGTACTCTCCCTTCG).

The ETIP sequence is amplified and sequenced from all plants containing only a single copy of the ETIP. The sequence of each T-DNA insert is analyzed by direct sequencing of PCR products using the ABI3730xI™ (Applied Biosystems, Life Teachnologies). The T-DNA insert was amplified from genomic DNA, using Phusion Hot Start II Polymerase™ (Finnzymes, Thermo Fisher Scientific). The amplification reactions of the T-DNA are completed with multiple primer pairs to amplify overlapping sequences of approximately 2 Kbp in length. Each PCR product is sequenced with multiple primers to ensure complete coverage. The PCR reactions are treated with shrimp alkaline phosphatase and exonuclease I (Applied Biosystems, Life Technologies) to inactivate excess primer prior to the sequencing PCR reaction. The sequences flanking the T-DNA insert of each single copy ETIP line are identified by digestion of purified genomic DNA with eight restriction endonucleases separately followed by ligation of double-stranded adapters specific for the overhangs created by the restriction endonucleases. Following this ligation step a PCR is performed with a biotinylated primer to either the 3' or 5' end of the ETIP and a primer to each adapter. The PCR products are captures and cleaned on Ampure Solid Phase Reversible Immobilization (SPRI) Beads™ (Agencourt Bioscience Corporation, Beckman Coulter Company). A nested PCR is performed and all products are sequenced using ABI Sanger Sequencing and Big Dye Terminator v3.1 Cycle™ sequencing protocol (Applied Biosystems, Life Technologies). Sequence data are assembled and analyzed using the SEQUENCHER™ software (Gene Codes Corp., Ann Arbor, Mich.).

Results of ETIP Transgenic Canola Transformed with Zinc Finger Nuclease and pDAS000271-pDAS000275 ETIP Constructs The transgenic *Brassica napus* events which are produced via transformation of ETIP and ZFN constructs result in the integration of a single copy, full length T-strand insertion of the ETIP polynucleotide sequence from pDAS000273 or pDAS275 within the FAD3A locus, and from pDAS000271, pDAS000272 or pDAS000274 into the FAD3C locus. Three to four events are fully characterized and confirmed to contain the integrated ETIP. The confirmation is completed using an in-out PCR amplification method, and further validated via Southern blot. The selected $T_0$ events are grown to the $T_1$ stage of development. The $T_1$ plants are rescreened to determine the zygosity of the integrated T-strand. Screened events are categorized as homozygous, hemizygous, or null.

The homozygous events are used to produce protoplasts via the previously described method. The protoplasts are subsequently co-transformed with a ZFN that is designed to target a zinc finger binding site which is incorporated within the ETIP sequence and a donor plasmid which shares homology with specific regions of the ETIP. The ZFN cleaves the ETIP locus and the donor plasmid is integrated within the genome of *Brassica napus* cells via homology directed repair. As a result of the integration of the donor plasmid, the partial DS-red transgene is repaired to a full length DS-red transgene. The expression of the now fully operational DS-red transgene is used to sort protoplast cells with a FACS method. Putative transgenic plants are sorted using the FACS method described in Example 7 and the isolated protoplasts are regenerated into mature plants. The integration of the donor plasmid is confirmed within the ETIP-targeted plants using molecular confirmation methods. As such, the ETIP locus serves as a site-specific locus for gene targeted integration of a donor polynucleotide sequence.

Example 7: FACs Based Sorting of Protoplast Cells

*Brassica napus* protoplasts that were transfected with the DS-Red control construct, pDAS000031, were sorted via FACS-mediated cell sorting using a BD Biosciences Influx-Cell Sorter™ (San Jose, Calif.). The protoplast cells were isolated and transfected as described in Example 3. After the cells had been transfected with pDAS000031, the cells were sorted using the FACS sorter with the conditions described in Table 7.

TABLE 7

Conditions used for sorting protoplast cells transfected with pDAS000031

| Parameters | |
|---|---|
| Drop frequency | 6.1 KHz |
| Nozzle diameter | 200 μm |
| Sheath pressure | 4 psi |
| Recovery media | W5 media |
| Culture conditions | Bead type culture using sea-plaque agarose and sodium alginate |
| Sort criteria | Sorting based on chlorophyll autofluorescence, reporter gene expression (Ds-Red) |
| Sort recovery (%) | 50-75 |
| Viability post sorting (%) | >95 |

The protoplasts which expressed the DS-red transgene were sorted and isolated. The FACS isolated protoplasts were counted using the sorter. About $1\times10^5$ to $1.8\times10^5$ of cells were placed in a well of a 24-well micro titer plate on the first day after the FACS isolation. The cells were transferred to a bead culture for 5 to 20 days. Similar conditions were tested, wherein about $1\times10^4$ of cells were placed in a well of a 2 or 4-well micro titer plate on the second day after the FACS isolation. The various conditions that were tested resulted in the recovery of cells at a viability or 95-98% of the total isolated protoplast cells. The FACS sorted protoplast cells were transferred to a bead culture for 3-20 days. The FACS sorted protoplast cells were regenerated into plants on media which contained 1.5 mg/mL of hygromycin using the above described protocol. The putative transgenic plants were confirmed to contain an intact T-strand insert from pDAS000031 via molecular confirmation protocols.

The FACS sorting method is directly applicable to screen any fluorescent transgene sequence and is used to isolate a proportion of *Brassica napus* protoplast cells that are targeted with a fluorescent transgene via homology mediated repair within a specific site in the ETIP region within a genomic locus.

Example 8: Targeted Integration into and Disruption of *Brassica Napus* Omega-3 Fatty Acid Desaturase (Fad3) Via NHEJ Selection of Zinc Finger Binding Domains Specific to Fad3C and Fad3A The transcribed regions for homoeologous Fad3 genes were identified and characterized, zinc finger nucleases that were designed to bind and cleave these sites for NHEJ-mediated targeting of a donor sequence. Zinc finger proteins (ZFPs) directed against DNA sequences from homeologues of Fad3 sequences were designed and tested as described above. From the ZFNs showing on-target activity, two zinc finger proteins were selected that cut the Fad3 target at high efficiency: ZFP 28051-2A-28052 recognizes SEQ ID NO:255 5'-gcccaaggaacCCTTTTCTGGGCCATcttcg-TACTCGGCCACGactggtaatttaat-3' and was shown to specifically bind and cleave the Fad3C genomic locus. Likewise Zinc finger protein 28053-2A-28054 recognizes SEQ ID NO:256 5'-agcgagagaaAGCTTAtTGCAACTTCaactacTT-GCTGGTCGATCGTGTTggccactc-3' and was shown to specifically bind and cleave the Fad3A and Fad3C genomic locus. Exemplary target sites are shown in Table 8; nucleotides in the target site that are contacted by the ZFP recognition helices are indicated in uppercase letters; non-contact nucleotides are indicated in lowercase. Nucleotides in copies of Fad3 that differ from Fad3C are identified by underlining. Nucleotides in the target sites that are contacted by the ZFP recognition helices are shown in Table 8.

TABLE 8

Zinc Finger Protein Binding Sites specific to Fad3C (28051-2A-28052) or Fad3A and Fad3C (28053-2A-28054)

| | | |
|---|---|---|
| 28051-2A-28052 | SEQ ID NO: | SEQ ID NO: 257 ***gcccaaggaacCCTTTTCTGGGCCATat***<br>SEQ ID NO: 45 ***cgTACTCGGCCACGactggtaatttaat*** |
| Fad3C | 259 | GCCCAAGGAACCCTTTTCTGGGCCATCTTCGTACTCGGC CACGACTGGTAATTTAAT |
| Fad3A | 260 | GCCCAAGGAACCCTGTTCTGGGCTATCTTCGTACTCGGC CACGACTGGTAATTTAAT |
| Fad3C' | 261 | GCCCAAGGAACCCTTTTCTGGGCCATCTTCGTCCTCGGC CACGACTGGTAAAGTTTC |
| Fad3A' | 261 | GCCCAAGGAACCCTTTTCTGGGCCATCTTCGTCCTCGGC CACGACTGGTAAAGTTTC |
| Fad3A" | 263 | GCCCAAGGAACCCTTTTCTGGGCCATCTTCGTTCTTGGCC ACGACTGGTAAATTAAA |
| Fad3C" | 263 | GCCCAAGGAACCCTTTTCTGGGCCATCTTCGTTCTTGGCC ACGACTGGTAAATTAAA |
| 28053-2A-28054 | SEQ ID NO: | SEQ ID NO: 265 ***agcgagagaaAGCTTAtTGCAACTTCaa***<br>SEQ ID NO: 47 ***acTTGCTGGTCGATCGTGTTggccactc*** |
| Fad3C | 256 | AGCGAGAGAAAGCTTATTGCAACTTCAACTACTTGCTGG TCGATCGTGTTGGCCACTC |
| Fad3A | 268 | AGCGAGAGAAAGCTTATTGCAACTTCAACTACTTGCTGG TCGATCATGTTGGCCACTC |
| Fad3C' | 269 | AGCGAGAGAAAGCTTATTGCAACTTCAACTACTTGCTGG TCCATAATGTTGGCCATTC |
| Fad3A' | 270 | AGCGAGAGAAAGCTTATTGCAACTTCGACTACTTGCTGG TCCATAATGTTGGCAATTC |
| Fad3A" | 271 | AGCGAGAGGAAGCTTATTGCAACTTCAACAACTTGCTGG TCCATAATGTTGGCCACTC |
| Fad3C" | 272 | AGCGAGAGGAAGCTTATTGCAACTTCAACTACTTGCTGG TCCATAATGTTGGCCACTC |

Design and Construction of Expression Vectors Encoding Zinc Finger Nucleases Specific to Fad3C and Fad3A The Fad3 zinc finger designs were incorporated into zinc finger expression vectors encoding a protein having at least one finger with a CCHC structure (U.S. Patent Publication No. 2008/0182332). In particular, the last finger in each protein had a CCHC backbone for the recognition helix. The non-canonical, zinc finger-encoding-sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and a sop2 nuclear localization signal. The self-hydrolyzing 2A encoding nucleotide sequence from Thosea asigna virus (Szymczak et al., 2004) was added between the two ZFN fusion proteins. Expression of the ZFNs was driven by the strong constitutive promoter and 5' untranslated region (UTR) from Cassava Vein Mosaic Virus (Verdaguer et al, Plant Molecular Biology 1996, 31(6); 1129-1139) and flanked by the 3' UTR (including the transcriptional terminator and polyadenylation site) from open reading frame 23 (ORF23) of *Agrobacterium tumefaciens* pTi15955 (Barker et al., Plant Molecular Biology 1983, 2(6); 335-50).

Figure 13:
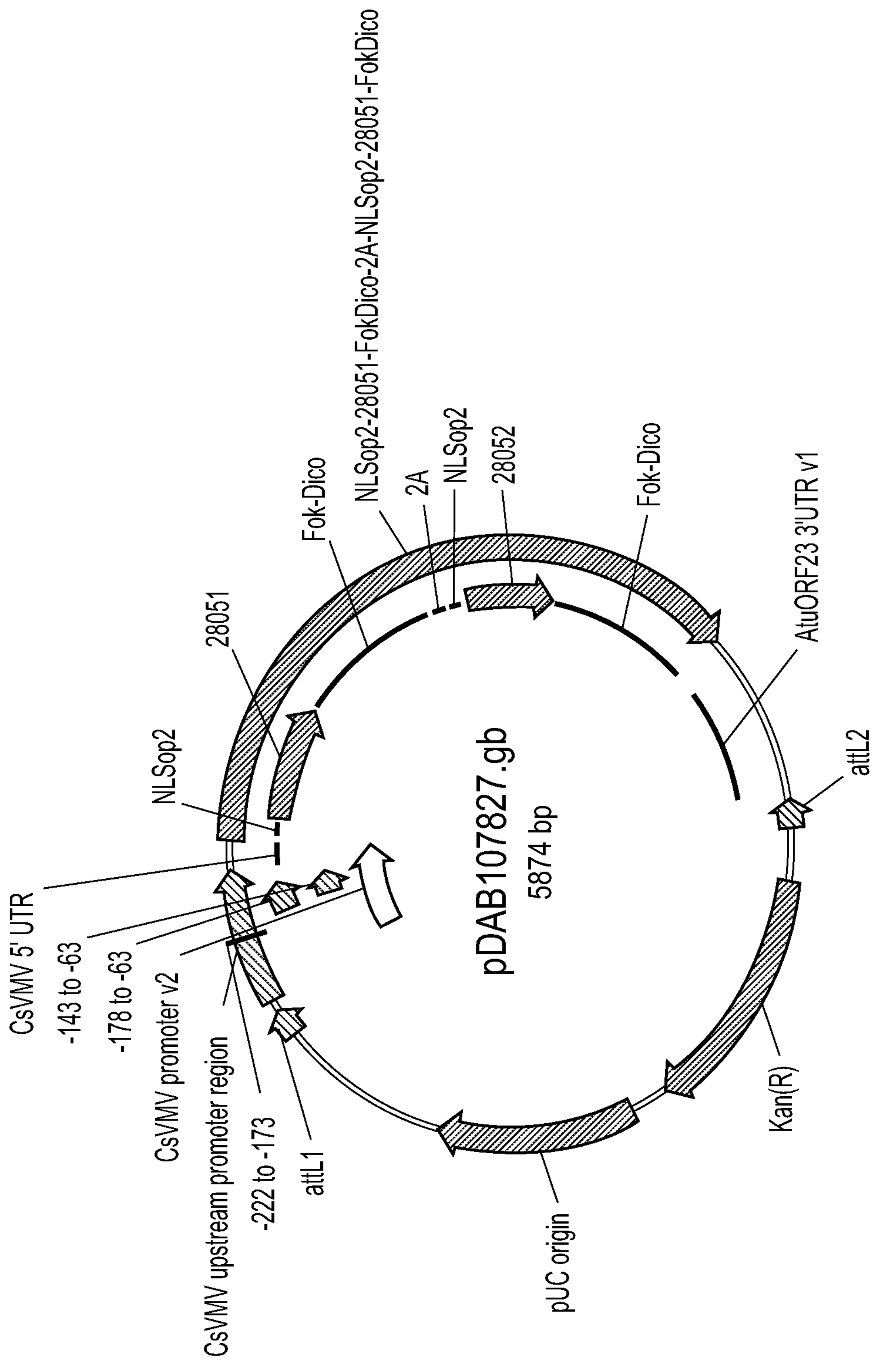
FIG. 13 shows a plasmid map of pDAB107827.
Figure 14:
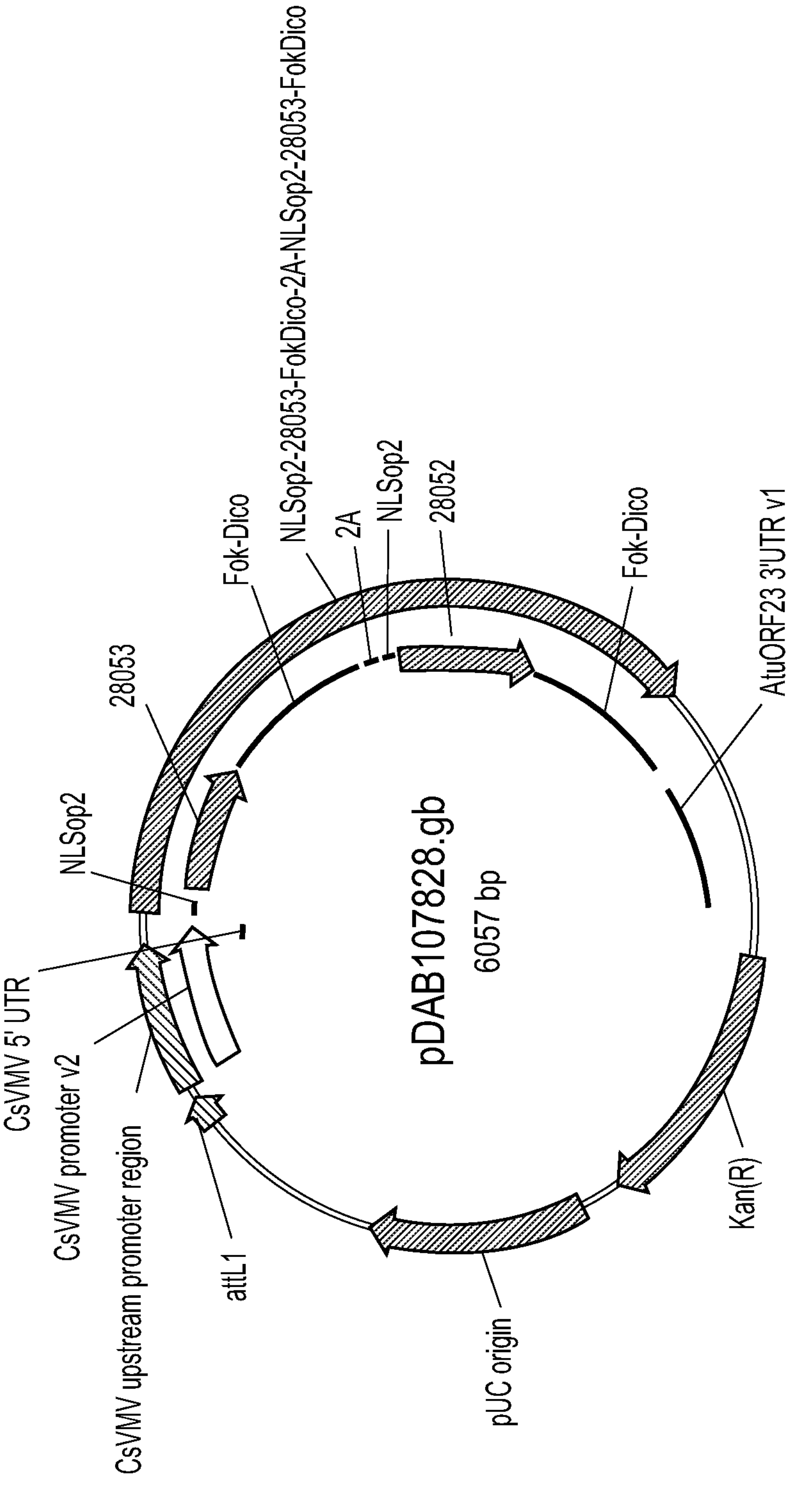
FIG. 14 shows a plasmid map of pDAB107828.

The vectors were assembled using the IN-FUSION™ Advantage Technology (Clontech, Mountain View, Calif.). Restriction endonucleases were obtained from New England BioLabs (NEB; Ipswich, Mass.) and T4 DNA Ligase (Invitrogen) was used for DNA ligation. Plasmid preparations were performed using NUCLEOSPIN® Plasmid Kit (Macherey-Nagel Inc., Bethlehem, Pa.) or the Plasmid Midi Kit™ (Qiagen) following the instructions of the suppliers. DNA fragments were isolated using QIAquick Gel Extraction Kit™ (Qiagen) after agarose Tris-acetate gel electrophoresis. Colonies of assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes, Ann Arbor, Mich.). The resulting plasmid constructs: pDAB107827 (ZFN 28051-2A-28052, FIG. 13, SEQ ID NO:273) and pDAB107828 (ZFN 28053-2A-28054, FIG. 14, SEQ ID NO:274) were confirmed via restriction enzyme digestion and via DNA sequencing.

Design and Construction of "Donor" Vectors for NHEJ-Directed DNA Repair

Two strategies of integration of DNA into Fad3 were undertaken; gene splicing, where an expression cassette was integrated into a single ZFN-induced double-stranded break and gene-editing where a portion of the gene was removed by the use of two ZFN-induced double-stranded breaks and an expression cassette was inserted to repair the gap.

For each integration method, gene splicing or gene-editing, two vectors were constructed. The first encoded a turboGFP (tGFP) gene expression cassette and the second encoded a gene expression cassette to confer resistance to the antibiotic hygromycin. The tGFP expression cassette included the promoter, 5' untranslated region and intron from the *Arabidopsis thaliana* polyubiquitin 10 (UBQ10) gene (Norris et al, Plant Molecular Biology 1993, 21(5), 895-906) followed by the tGFP coding sequence (Evrogen, Moscow, Russia). The tGFP coding sequence was codon-optimised for expression in dicot plants and the 3' untranslated region (UTR) comprising the transcriptional terminator and polyadenylation site of open reading frame 23 (ORF23) of *A. tumefaciens* pTi15955 (Barker et al, Plant Molecular Biology 1983, 2(6), 335-50). The hygromycin resistance gene expression cassette included the 19S promoter including a 5' UTR from cauliflower mosaic virus (CaMV) (Cook and Penon Plant Molecular Biology 1990 14(3), 391-405) followed by the hygromycin phosphotransferase (hph) gene (Kaster et al Nucleic Acids Research 1983 11 (19), 6895-6911). The hph gene was codon-optimised for expression in dicotyledonous plants and was flanked by a 3'UTR comprising the transcriptional terminator and polyadenylation site of Open Reading Frame 1 (ORF1) of *A. tumefaciens* pTi15955 (Barker et al, Plant Molecular Biology 1983, 2(6), 335-50). Both cassettes were synthesized by a commercial gene synthesis vendor (GeneArt, Life Technologies, Regensberg, Germany).

Figure 15:
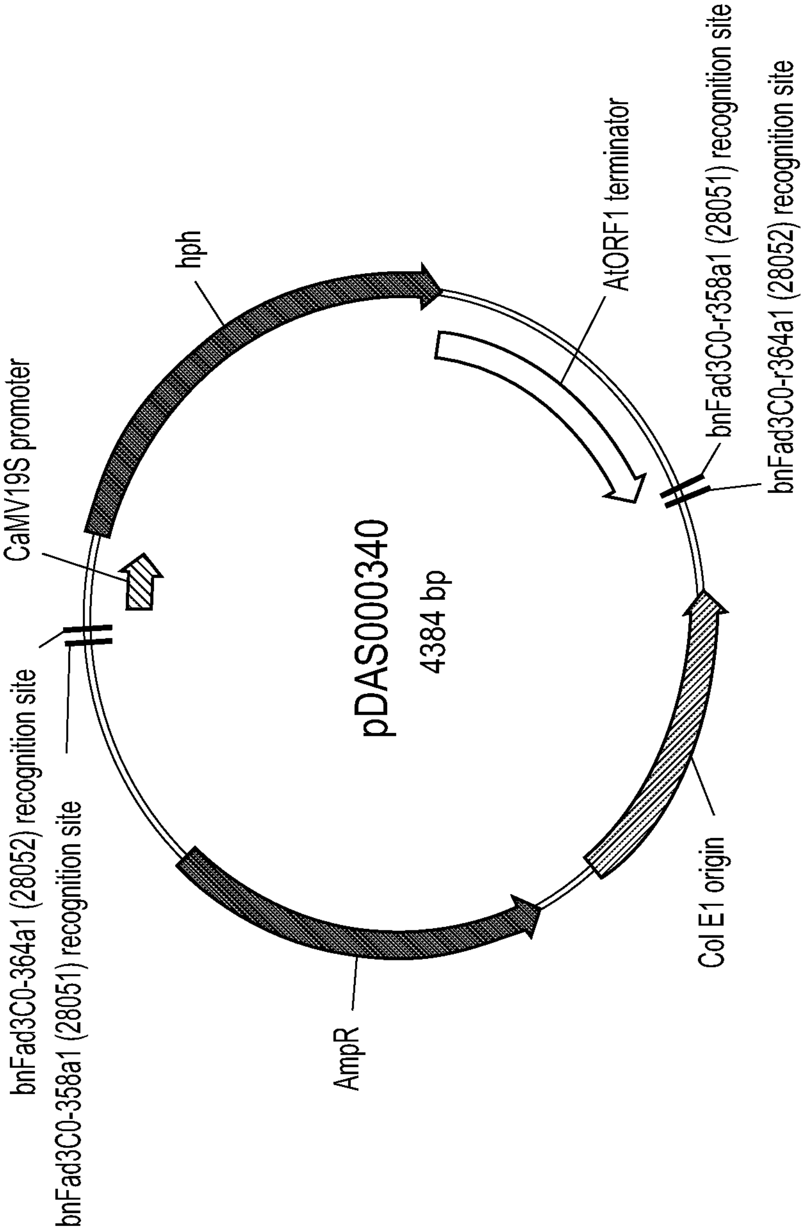
FIG. 15 shows a plasmid map of pDAS000340.
Figure 16:
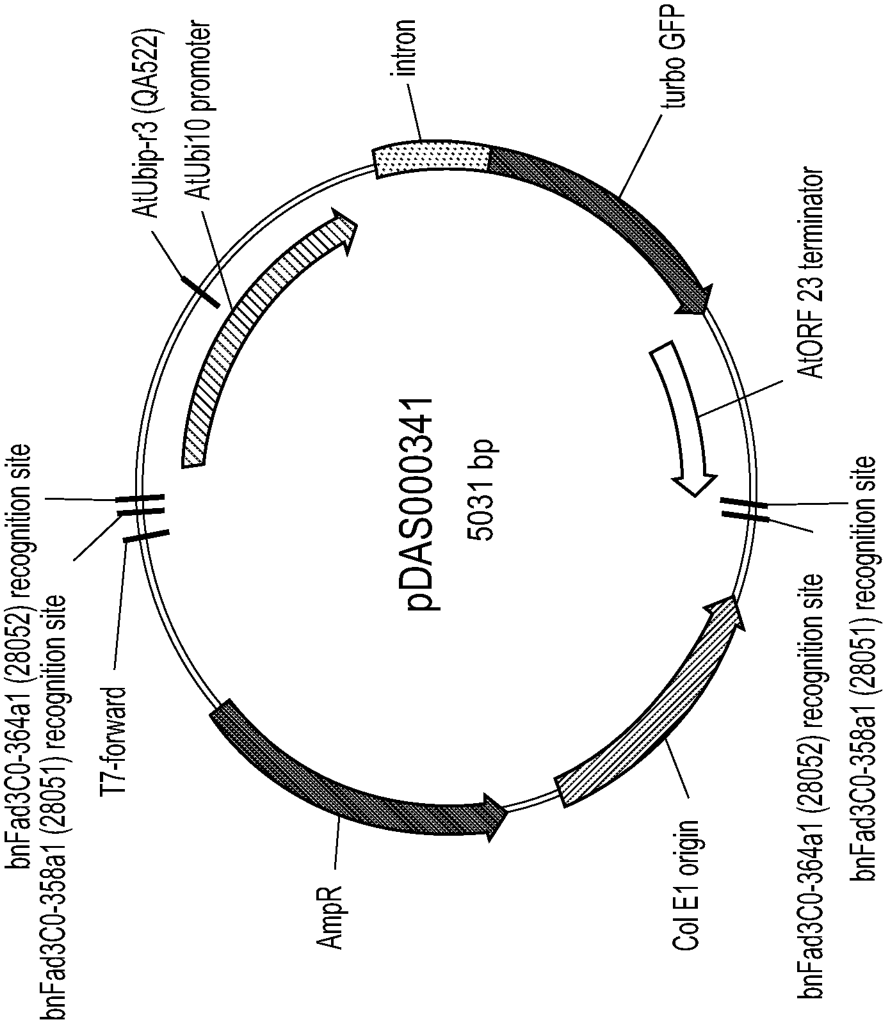
FIG. 16 shows a plasmid map of pDAS000341.
Figure 17:
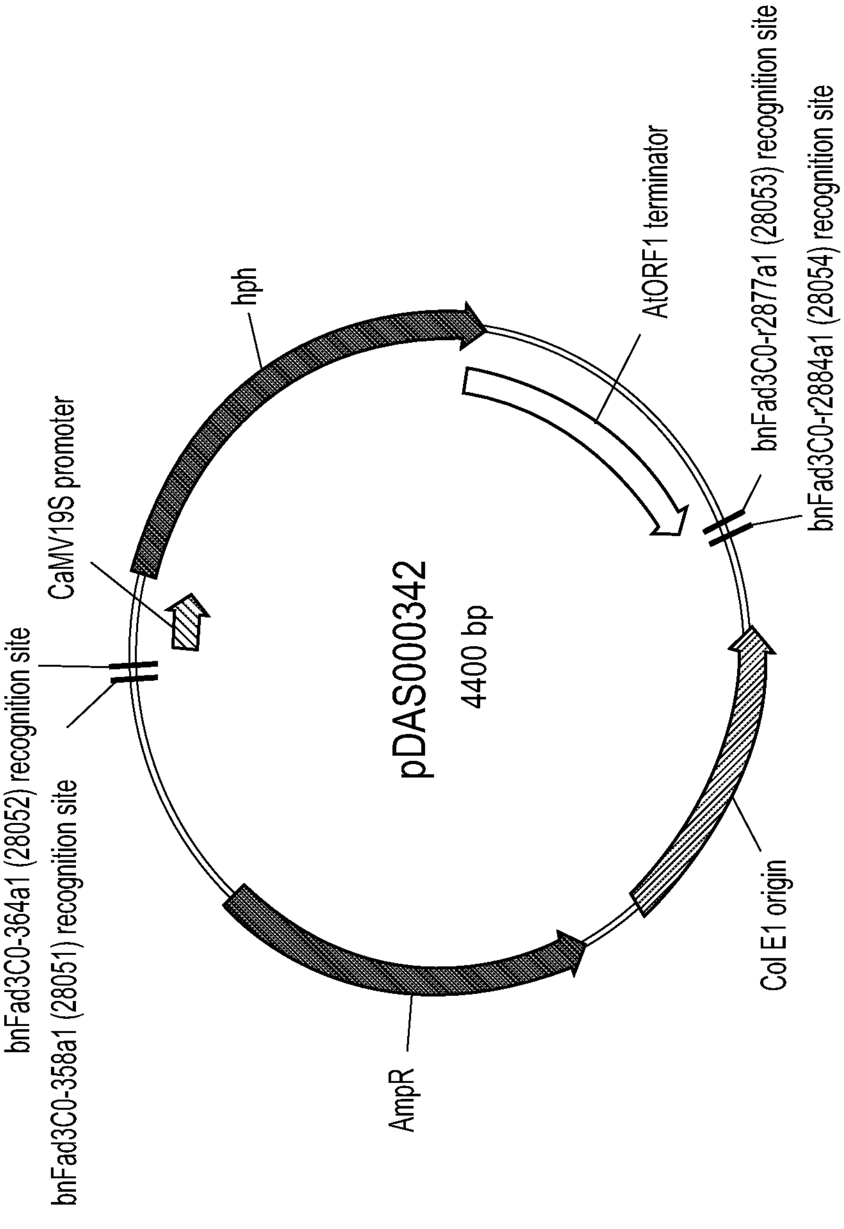
FIG. 17 shows a plasmid map of pDAS000342.
Figure 18:
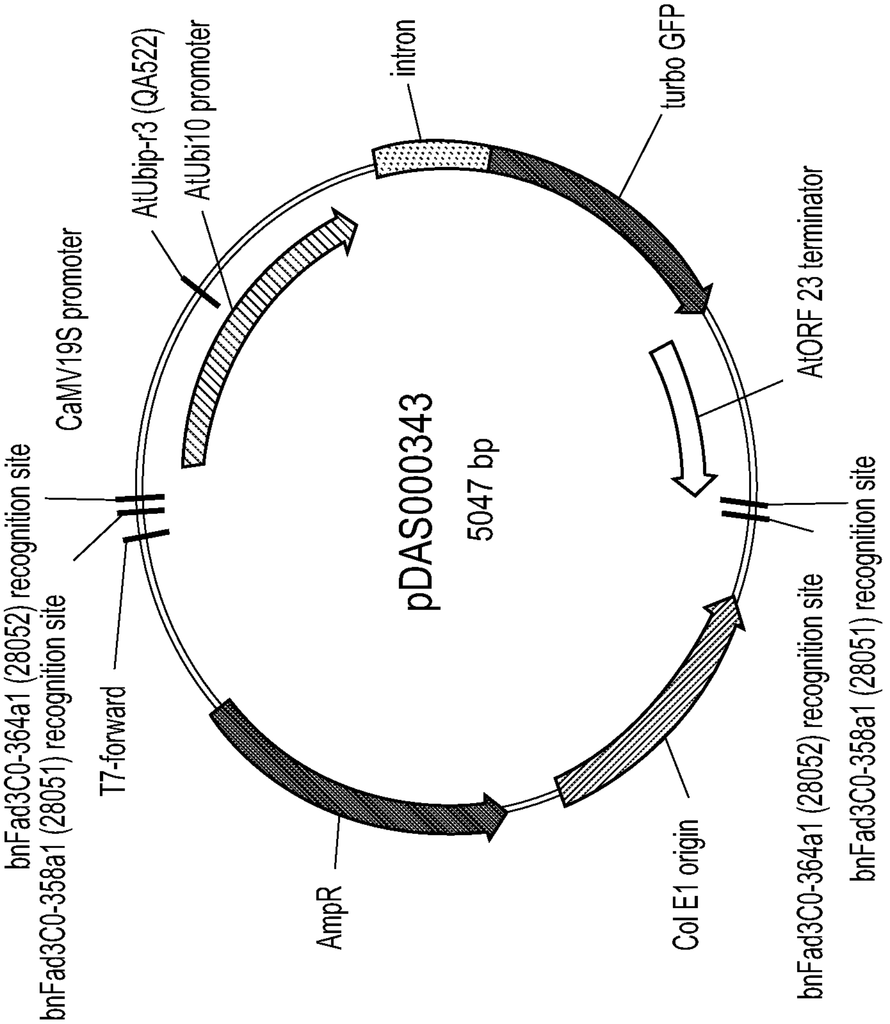
FIG. 18 shows a plasmid map of pDAS000343.

Vectors for the gene splicing experiments were constructed by cloning two tandem copies of the ZFN recognition sequence targeted by the ZFN encoded in the vector pDAB10782. Vectors for the gene editing experiments were constructed by cloning one copy of each of the ZFN recognition sequences targeted by the ZFNs encoded in the vectors pDAB107827 and pDAB107828. In both cases the two ZFN recognition sequences were separated by the recognition sequences for BamHI and NotI restriction endonucleases. The tGFP and HPH cassettes were cloned into the BamHI and NotI sites of each vector resulting in four "donor" vectors: pDAS000340 (hygromycin-resistant gene-splicing donor: SEQ ID NO:275, FIG. 15), pDAS000341 (tGFP reporter gene splicing donor: SEQ ID NO:276, FIG. 16), pDAS00342 (hygromycin-resistant gene-editing donor: SEQ ID NO:277, FIG. 17) and pDAS000343 (tGFP reporter gene editing donor: SEQ ID NO:278, FIG. 18).

Colonies of the assembled plasmids were initially screened by restriction endonuclease digestion of DNA purified from overnight cultures of *E. coli*. Restriction endonucleases were obtained from New England BioLabs™ (NEB, Ipswich, Mass.) and Promega™ (Promega Corporation, WI). Plasmid preparations were performed using the QIAprep Spin Miniprep Kit™ (Qiagen, Hilden, Germany) or the Pure Yield Plasmid Maxiprep System™ (Promega Corporation, WI) following the instructions of the suppliers. After the restriction fragments were confirmed by agarose gel electrophoresis of resulting fragments, plasmid DNA of selected clones were sequenced using ABI Sanger Sequencing and Big Dye Terminator v3.1™ cycle sequencing protocol (Applied Biosystems, Life Technologies). Sequence data were assembled and analyzed using the Sequencher™ software (Gene Codes, Ann Arbor, Mich.).

Maintenance of Plant Material for Protoplast Isolation

Mesophyll derived protoplasts were isolated from three-week old sterile shoot cultures of *Brassica napus* (DH10275). The corresponding seeds were germinated following the methods herein described. The seeds were surface-sterilized using 70% ethanol for 1 minute and gently shaken followed by 3-4 rinses in sterile double-distilled water. The seeds were subsequently sterilized using 20% bleach and 10 μl of Tween 20. The seeds were further treated with the bleach on a table top shaker at approximately 100 RPM, for 15 minutes followed by 3-4 rinses in sterile double-distilled water, seeds were carefully transferred to a sterile filter paper to remove the excess moisture and plated on seed germination medium (½ strength MS/B5 Vitamins+1% sucrose+0.8% Agar; pH 5.8.

Approximately, 50-60 mL of media was poured into each Petri™ dish (15×100 mm) and the plates were placed with a slight angle using a support. Approximately 50 seeds were placed on each plate. The plates were incubated upright at 22° C. in 16 h/d light (20 μmol m−2 s−1) for 6 days. Hypocotyl segments of 0.5 cm size were dissected from the six day old seedlings and cultured on shoot induction medium (MS/B5 Vitamins+3% sucrose+500 mg/L MES+BAP (13 μm)+Zeatin (5 μm)+Silver Nitrate (5 mg/L)+0.8% Agar (pH 5.8). The medium was poured into a 100×20 mm sterile PETRI™ dish, approximately 20 explants were placed on the medium per plate. Shoot meristems that appeared after 3-4 weeks were transferred to shoot elongation medium (MS/B5 Vitamins+2% sucrose+500 mg/L MES+BAP (2 μm)+GA-3 (0.1 μm)+0.8% Agar (pH 5.8) and poured in 250 mL culture vessels) and the cultures were maintained in this medium for 4 weeks with one round of sub-culturing in between. Shoots of 2-3 cm height were then transferred to root initiation media (½ strength MS/B5 Vitamins+1% sucrose+500 mg/L MES+IBA (2.5 μm)+0.6% Agar (pH 5.8) and poured in 700 mL culture vessels) for root development. Rooted shoots were sub-cultured in fresh root initiation media at 3-4 weeks intervals as stem cuttings for two-three rounds before use. The cultures were maintained throughout at 22° C. in 16 h/d light (30 μmol m−2 s−1).

Isolation and Purification of Mesophyll Protoplasts

In vitro grown DH12075 *Brassica napus* plants were used as the explant source for isolating mesophyll protoplasts. To isolate the protoplasts, the 3rd to 4th upper fully expanded leaves from 3-4 weeks old plantlets were cut with a sharp scalpel into small strips (0.5 to 1 mm) for protoplast isolation. Enzymatic digestion was carried out by treating 250-500 mg of leaf material with 25 mL of digestion buffer (1.2% (w/v) Cellulase "Onozuka™" R10 and 0.2% (w/v) Macerozyme® R10 dissolved in K4 media (Spangenberg et al., 1998)). The PETRI™ dish containing the leaf material and digestion buffer was sealed with Parafilm™ and incubated at room temperature for 12 to 15 h in darkness. After overnight incubation the digests were filtered through a BD® cell strainer (mesh size 70 μm). Protoplast suspensions (5-6 mL) collected in a 14 mL round bottomed tube was over layered with 1 mL of W5 washing buffer (154 mM NaCl, 125 mM CaCl2, 5 mM KCl and 5 mM glucose; pH 5.8 Menzel et al. (1981)).

The protoplast suspensions were further centrifuged at 400 RPM for 10 min. After centrifugation, protoplasts that floated in the interphase were withdrawn and washed by centrifugation using 10 mL of W5 buffer at 400 RPM for 10 min. After the final wash, isolated protoplasts were resuspended at a density of 1×106 protoplasts per mL of W5 buffer and incubated for 1 hour before transfections.

Assessment of Protoplast Yield and Viability

Protoplasts yield was assessed using a haemocytometer following the method of Sambrook and Russell, (2006). The cell viability was tested using 400 mg/L of Evans blue stain dissolved in 0.5 M of mannitol as described by Huang et al. (1996) with few minor modifications to the protocol.

PEG 4000 Mediated DNA Delivery

Before delivery to *B. napus* protoplasts, plasmid DNA of each donor and ZFN construct was prepared from cultures of *E. coli* using the Pure Yield Plasmid Maxiprep System® (Promega Corporation, Madison, Wis.) following the instructions of the suppliers. Aliquots of donor and ZFN plasmid DNA were prepared in three molar ratios: 1:1 (30 μg of each plasmid), 5:1 (donor plasmid to ZFN plasmid to a total of 30 μg of plasmid DNA) and 10:1 (donor plasmid to ZFN plasmid to a total of 30 μg of plasmid DNA). Additionally, donor-only and ZFN-only aliquots (30 μg) were prepared as controls. The amounts of DNA delivered to the *B. napus* protoplasts via the PEG4000 mediated transformation are summarized in Table 9.

TABLE 9

Quantities of ZFN and donor DNA delivered to protoplasts

| | Molar Ratio of plasmid DNA | Total quantity of DNA (μg) delivered to 1 million protoplasts |
|---|---|---|
| Splicing | Donor plasmid only | 30 |
| | ZFN plasmid only (pDAB107827) | 30 |
| | 1:1 Donor:ZFN | 60 |
| | 5:1 Donor:ZFN | 30 |
| | 10: Donor:ZFN | 30 |
| Editing | Donor plasmid only | 30 |
| | 1:1: ZFN plasmids (pDAB107827 and pDAB107828) | 30 |
| | 1:1:1 Donor:ZFN:ZFN | 90 |
| | 5:1:1 Donor:ZFN:ZFN | 30 |
| | 10:1:1 Donor:ZFN:ZFN | 30 |

Each aliquot of plasmid DNA was applied to one million protoplasts (viability≥95) suspended in 100 μl of transformation buffer (15 mM MgCl2, 0.1% (w/v) morpholinoethanesulphonic acid (MES) and 0.5 M Mannitol; pH 5.8) followed by 150 μl of PEG solution (40% (w/v) PEG 4000 in 0.4 M Mannitol and 0.1 M Ca (NO3)2 (pH 6-7) Spangenberg and Potrykus (1995). After 10-15 min of incubation at room temperature, 5 mL of W5 buffer was added in a drop wise manner and the protoplasts were gently mixed. Another 5 mL of W5 buffer was added as a slow stream to the protoplasts suspension. Protoplasts were mixed gently and centrifuged at 400 RPM for 10 min and the W5 supernatant was removed carefully leaving behind the protoplasts in the form of a pellet. Transfected protoplasts were then incubated in 1 mL of W5 buffer at room temperature until they were embedded in bead type cultures. The transfected protoplasts were embedded following the sodium alginate method as described below.

Culturing of Mesophyll Derived Protoplasts to Recover Viable Microcalli

Before embedding within the medium, the transfected protoplasts were centrifuged at 400 RPM for 10 minutes and the W5 buffer was carefully removed. The protoplasts were then resuspended in 1.0 mL of 0.5 M Mannitol and incubated on ice. To the protoplast solution, an equal volume of 1.0% sodium alginate was added and mixed gently. The protoplasts suspension was incubated in ice until it was embedded. Bead forming solution (0.4 M Mannitol+50 mM CaCl2 (pH 5.8)) was transferred to a sterile six well plate (3-4 mL per well) using a serological pipette. Exactly 1.0 mL of the protoplasts suspension was added in a drop wise manner using a 1 mL pipette into the bead forming solution and each transfected sample (ca. 5×105 protoplasts) was embedded per well. The protoplasts suspension was incubated for 1-2 hours at room temperature to form sodium alginate beads. After the incubation period the bead forming solution was carefully removed and replaced with 4-5 mL of 1:2 mixture of K3+H:A media (Spangenberg et al 1998) supplemented with 1.5 mg/L of hygromycin. The protoplasts were cultured for 3-4 weeks in darkness at 22° C. in a shaker (50 RPM). After 3-4 weeks the resistant microcalli (0.5-1.0 mm) were released by treating with depolymerisation buffer (0.3 M Mannitol+20 mM Sodium Citrate (pH 5.8)). After removing the liquid media, 3-4 mL of depolymerisation buffer was added to each well containing the bead-type cultures and incubated at room temperature for 2 hours. Using a sterile forceps the beads were gently mixed to enhance the efficient release of the microcalli. Next a sterile 1.0 mL pipette was used to gently mix gelling agent that was released in the depolymerisation buffer and subsequently removed. The microcalli was washed twice using 5 mL of liquid A media and the microcalli was resuspended in sufficient quantity of liquid A (50 mL of liquid A was used for one mL of the settled cell volume (SCV: this was measured after transferring all the released microcalli to a sterile 50 or 15 mL falcon tube and allowed to settle down for 5 min)). After mixing the microcalli uniformly, 0.5 mL of the microcalli suspended in the liquid A media was transferred to B1 media (MS/MS Vitamins+3.5% Sucrose+500 mg/L MES+BAP (5 μm)+NAA (5 μm)+2, 4-D (5 μm)+1.5 mg/L hygromycin+0.7% Agarose Type I (pH 6.0) and poured in 100×20 mm sterile PETRI™ dish) and using 1-2 mL of additional liquid A media the microcalli was distributed uniformly in the B1 media and the excess liquid A media was carefully removed from each plate. The plates were sealed using a micropore tape which enhanced the embryo maturation. The cultures were maintained at 22° C. in 16 h/d light (30 μmol m−2 s−1).

Proliferation and Regeneration of Shoots from Mesophyll Derived Protoplasts

Hygromycin resistant colonies were picked from B1 media (microcalli derived from both SA and SP methods) after 2-3 weeks of incubation and transferred to B2 media (MS/MS Vitamins+3.0% Sucrose+500 mg/L MES+500 mg/L PVP+5 mg/L Silver nitrate+5 mg/L 2i P+NAA (0.5 μm)+GA-3 (0.3 μm)+1.5 mg/L Hygromycin+0.7% Agarose Type I (pH 5.8) and poured in 100×20 mm sterile PETRI™ dish). Approximately 25-30 calli were placed per plate and the plates were sealed using Parafilm™ and incubated at 22° C. in 16 h/d light (30 μmol m−2 s−1). Hygromycin resistant colonies were subsequently recovered after 5-6 rounds of sub-culturing in B2 media at two weeks interval. The number of calli per plate was reduced to 12-15 after a third round of sub-culturing. Shoot primordial that appear after 10-12 weeks were carefully recovered along with the residual calli and transferred to shoot elongation medium (MS/B5 Vitamins+2% sucrose+500 mg/L MES+BAP (2 μm)+GA-3 (0.1 μm)+300 mg/L Timentin+1.5 mg/L Hygromycin+0.8% Agar (pH 5.8) and poured in 250 mL culture vessels). The shoots that survive after 2-3 rounds of Hygromycin selection were transferred to rooting media (½ strength MS/B5 Vitamins+1% sucrose+500 mg/L MES+IBA (2.5 μm)+1.5 mg/L Hygromycin+0.6% Agar (pH 5.8) and poured in 700 mL culture vessels).

Isolation of Genomic DNA from Mesophyll Protoplasts

Transfected protoplasts were transferred from the 3 cm PETRI™ dish to a 2 mL microfuge tube. The cells were pelleted by centrifugation at 70 g and the supernatant was removed. To maximize the recovery of transfected protoplasts, the PETRI™ dish was rinsed three times with 1 mL of wash buffer. Each rinse was performed by swirling the wash buffer in the PETRI™ dish for 1 minute, followed by transfer of the liquid to the same 2 mL microfuge tube. At the end of each rinse, the cells were pelleted by centrifugation at 70 g and the supernatant was removed. The pelleted protoplasts were snap frozen in liquid nitrogen before freeze drying for 24 h in a Labconco Freezone 4.5® (Labconco, Kansas City, Mo.) at −40° C. and $133\times10^{-3}$ mBar pressure. The lyophilized cells were subjected to DNA extraction using the DNeasy® Plant DNA Extraction Mini kit (Qiagen) following the manufacturer's instructions, with the exception that tissue disruption was not required and the protoplast cells were added directly to the lysis buffer.

Isolation of Genomic DNA from Callus Tissue

Individual calli was snap frozen in liquid nitrogen before freeze drying for 24 h in a Labconco Freezone 4.5® (Labconco, Kansas City, Mo.) at −40° C. and $133\times10^{-3}$ mBar pressure. The lyophilized calli was subjected to DNA extraction using the DNeasy® Plant DNA Extraction Maxi kit (Qiagen, Hilden, Germany) following the manufacturer's instructions.

Isolation of Genomic DNA from Leaf Tissue

Thirty (30) mg of young leaf tissue from regenerated plants was snap frozen in liquid nitrogen before freeze drying for 24 h in a Labconco Freezone 4.5® (Labconco, Kansas City, Mo.) at −40° C. and $133\times10^{-3}$ mBar pressure. The lyophilized calli was subjected to DNA extraction using the DNeasy® Plant DNA Extraction Maxi kit (Qiagen, Hilden, Germany) following the manufacturer's instructions.

PCR Assays of Genomic DNA for NHEJ-Mediated Splicing and Editing of Fad3C

Figure 19:
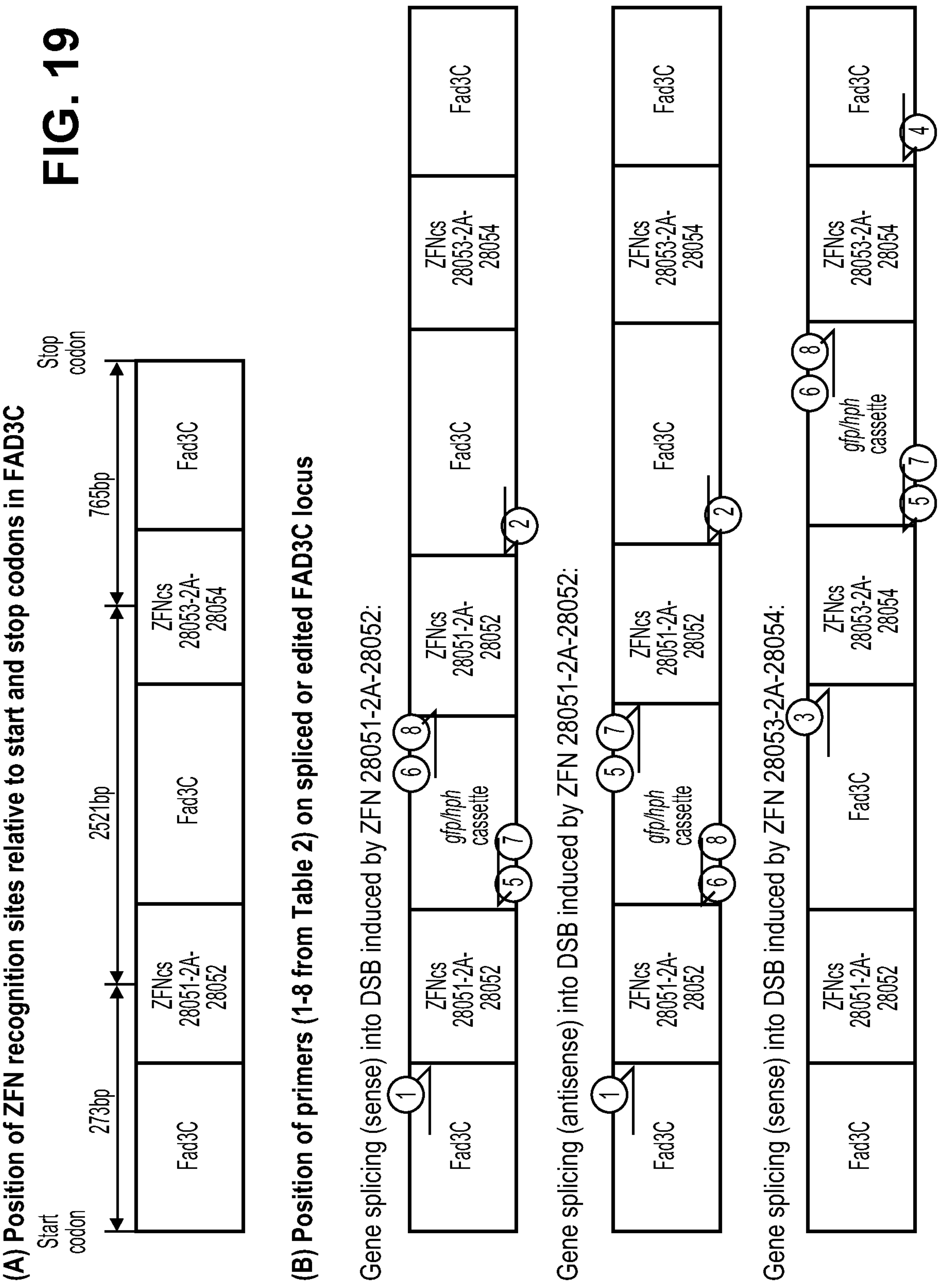
FIG. 19 is a schematic which shows the locations of the primers and their position relative to the start and stop codong of Fad3C. Panel A shows the location of the primer sites for the wild type Fad3C locus. Panel B shows the location of the primer sites to confirm donor integration, and the possible orientations by which the donor could integrate within the Fad3C locus.
Figure 19:
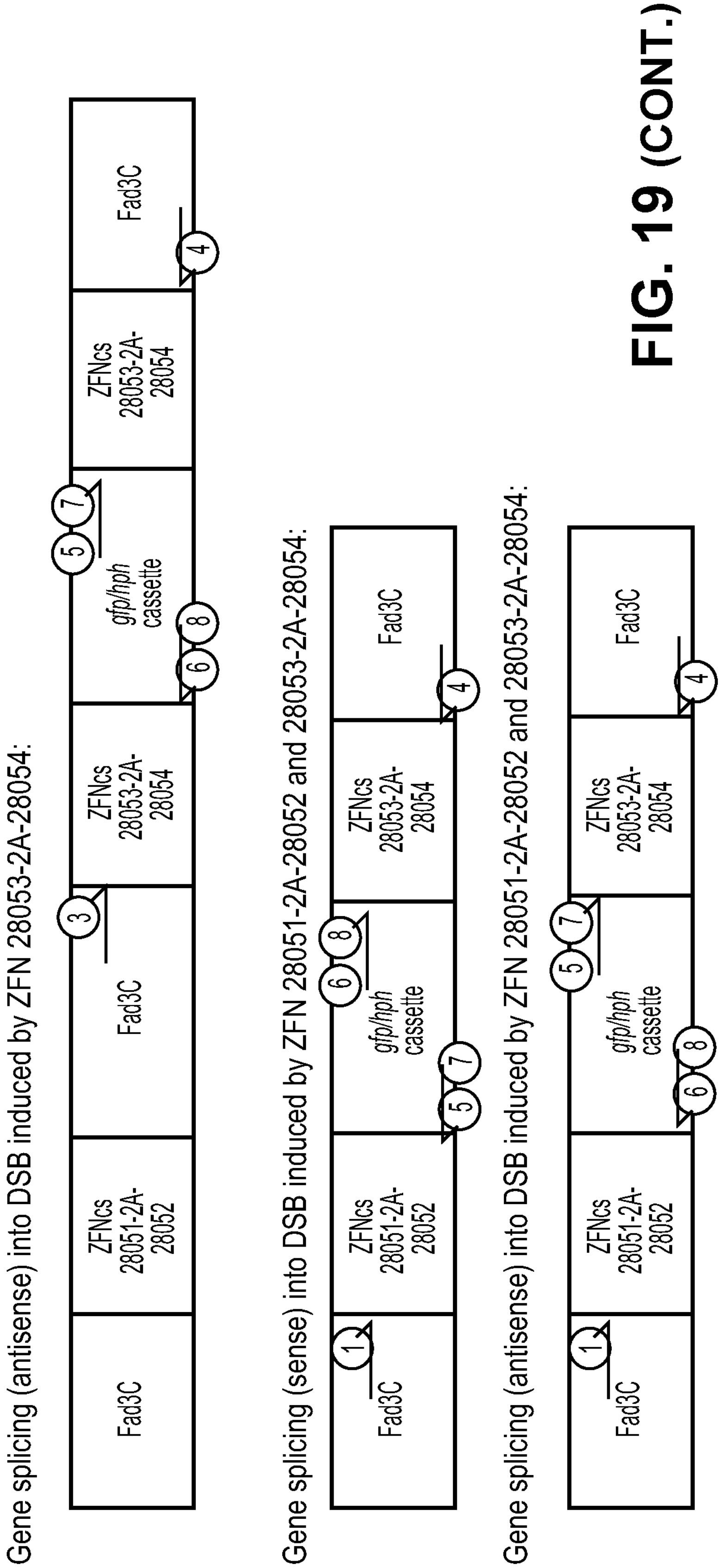

Detection of integration of donor DNA to the Fad3C gene of *B. napus* was done by a series of PCR where at least one primer was specific to the Fad3C locus (Table 10) and a second primer specific to either the promoter or terminator of the gfp cassette (Table 10 and FIG. 19A). Specificity was obtained by designing oligonucleotides where the last base pair aligned to a SNP that differentiated the Fad3C genomic sequence from the other copies of Fad3 genes and included a phosphorothioate internucleotide linkage before this base pair as indicated by an asterisk [*]. This design, used in combination with a polymerase having proofreading activity, directed specific amplification of each Fad3C or Fad3A allele and excluded other Fad3 copies as noted. Each primer set was empirically tested for amplification of the correct gene copies through Sanger-based sequencing of the PCR amplification products obtained from wild type *B. napus*.

TABLE 10

Oligonucleotide sequences used to detect integration of DNA into ZFN-induced double-stranded breaks

| | Primer Name | Primer Sequence | SEQ ID NO: | Specificity |
|---|---|---|---|---|
| 1 | FAD3CNHEJ-L4-F2 | gattectaagcattgttgggt*c | 279 | Fad3C only |
| 2 | FAD3CNHEJ-L4-R2 | gaaaatctcatatcgaacgtgcg*t | 280 | Fad3C only |
| 3 | FAD3CNHEJ-L6-F1 | cgcttaccctctctatctggta*a | 281 | Does not amplify Fad3C' or Fad3C" |
| 4 | FAD3CNHEJ-L6-R2 | ccttgcctctgtaccaaggca*g | 282 | Fad3C only |
| 5 | 19SPNHEJ-R2 | gtgtgtgggaatcttatcttcgg | 283 | n/a |
| 6 | AtORF1NHEJ-F1 | caagtcaggtattatagtccaagca | 284 | n/a |
| 7 | AtUbiNHEJ-R1 | caagaatatcctgatccgttgac | 285 | n/a |
| 8 | AtORF23tNHEJ-F1 | tggcagttgaaatactcaaacc | 286 | n/a |
| 9 | FAD3aCNHEJ-L4-F1 | gtectttgagatccatgagcta*t | 287 | Fad3A only |
| 10 | FAD3aCNHEJ-L4-F2 | gattcctaagcattgttgggt*a | 288 | Fad3A only |
| 11 | FAD3aNHEJ-L4-R1 | tgcgttcaagaaatcaaagac*a | 289 | Fad3A only |
| 12 | FAD3aNHEJ-L4-R2 | gaaaatctcatatcgaacgtgcg*g | 290 | Fad3A only |
| 13 | FAD3aNHEJ-L6-F1 | tctggtaaatcctaattccec | 291 | Fad3A only |

TABLE 10-continued

Oligonucleotide sequences used to detect integration of DNA into ZFN-induced double-stranded breaks

| | Primer Name | Primer Sequence | SEQ ID NO: | Specificity |
|---|---|---|---|---|
| 14 | FAD3aNHEJ-L6-R2 | ccttgcctctgtaccaaggca*a | 292 | Fad3A only |
| 15 | FAD3aNHEJ-L6-R1 | cttgcctctgtaccaaggcaactec | 293 | Excludes Fad3C |

*Indicates phosphorothioate internucleotide linkages to direct specific amplification (with proofreading polymerase) of Fad3C or Fad3A to exclusion of other copies of Fad3 as noted. Each primer set was empirically tested for amplification of the correct gene copies by Sanger-based sequencing of the PCR amplification products obtained from wild type *B. napus*.

Detection of Gene Addition to Fad3C by Non-Homologous End Joining in Protoplasts Genomic DNA was extracted from protoplast pools (one million protoplast per pool) to which donor DNA encoding a functional tGFP reporter cassette (pDAS000341 or pDAS000343), ZFN DNA (pDAB107827 or pDAB107828) or a mixture of donor and ZFN DNA had been delivered twenty-four hours earlier. Quantities of DNA delivered for transformation are described above. PCR products were cloned into plasmid vectors. The genomic editing occurs independently in each cell giving rise to a variety of different insertion events, by cloning into a plasmid vector, each genomic edit can be sequenced without ambiguity. Several clones were sequenced on an ABI3730XL® automated capillary electrophoresis platform. Analysis of gene sequences was done using Sequencher SOFTWARE v5.0™ (GeneCodes, Ann Arbor, Mich.).

Evidence of gene addition to the Fad3C locus by editing or splicing was provided by amplification of both the 5' and 3' Fad3C-cassette junctions from genomic DNA extracted from protoplasts using the primers described in Table 10. Products of PCR amplification with primers “FAD3CNHEJ-L4-F2” and “AtUbiNHEJ-R1” was completed to amplify the 5' junction of tGFP cassette and Fad3C. PCR amplification with primers “FAD3CNHEJ-L4-R2” and “AtORF23tNHEJ-F1” was completed to amplify the 3' junction of tGFP cassette and Fad3C. PCR amplification with primers “FAD3CNHEJ-L4-F2” and “FAD3CNHEJ-L4-R2” was completed to amplify across the double strand breaks induced by ZFN 28051-2A-28052. No amplification was observed from protoplasts to which ZFN plasmid or donor plasmid alone had been delivered. All junction sequences were indicative of insertion of the tGFP cassette at the Fad3C locus via an NHEJ-mediated repair pathway. Deletions of varying lengths from either or both the genome and the cassette were observed as well as the addition of sequences derived from the vector backbones (either from the donor or ZFN) being inserted between the genome and the cassette (FIG. 20A and FIG. 20B).

Detection of Gene Addition to Fad3C by Non-Homologous End Joining in Callus Tissue Regenerated from Protoplasts Further evidence of splicing and editing of the Fad3C locus was obtained from callus tissue regenerated from protoplasts on selection (1.5 mg/L hygromycin, as described above) to which donor DNA encoding an hph cassette (pDAS000340 or pDAS000342), ZFN DNA only (pDAB107827 or pDAB107828) or donor and ZFN DNA had been delivered (quantities of DNA delivered are given in Table 9). DNA was extracted from approximately 80 calli for each ratio, except editing 1:1:1, for which no calli survived, four weeks after protoplast transfection.

Integration of the hph cassette into the *B. napus* genome (fwat Fad3C or randomly) was confirmed by Taqman™ qPCR using primers (SEQ ID NO:294; F-5' CTTACATGCTTAGGATCGGACTTG 3', SEQ ID NO:295; R-5' AGTTCCAGCACCAGATCTAACG 3') and probe (SEQ ID NO:296; 5' CCCTGAGCCCAAGCAGCATCATCG 3') specific to the hph gene. These primer-probe pairs were used in a duplex reaction with primers (SEQ ID NO:297; F-5' CGGAGAGGGCGTGGAAGG 3', SEQ ID NO:298; R-5' TTCGATTTGCTACAGCGTCAAC 3') and probe (SEQ ID NO:299; 5' AGGCACCATCGCAGGCTTCGCT 3') specific to the *B. napus* high mobility group protein 1/1 (HMG FY), which is present as a single copy on the A genome (Weng et al., 2004, Plant Molecular Biology Reporter). Amplification was performed on a C1000 thermal cycler with the CFX96 or CF384 real-time PCR Detection System™ (BioRad, Hercules, Calif.). Results were analyzed using the CFX Manager™ (BioRad) software package. Relative quantification was calculated according to the $2^{-\Delta\Delta Ct}$ method (Livak and Schmittgen, 2001), which provided an estimation of the number of copies of hph cassette inserted into the genome.

Evidence of NHEJ-mediated splicing and editing of Fad3C was obtained by conducting PCR assays with one primer specific to Fad3C and a second primer specific to either the promoter or terminator of the hph cassette (Table 9 and FIG. 19B). Due to limited quantities of DNA obtained from callus tissue, only integration in the sense orientation was assayed. PCR products were gel-purified using QiaQuick MiniElute PCR Purification Kit™ (Qiagen) and sequenced using a direct Sanger sequencing method. The sequencing products were purified with ethanol, sodium acetate and EDTA following the BigDye® v3.1 protocol (Applied Biosystems) and sequenced and analysed as above.

The numbers of calli containing the donor cassette in each experiment are given in Table 11. Evidence of donor gene addition to the Fad3C locus by editing and/or splicing was provided by PCR amplification (with primers shown in Table 10) across the ZFN cut sites and both the 5' and 3' Fad3C-hph cassette junctions. PCR amplification of the genomic DNA isolated from callus tissue recovered from control protoplasts which were transformed with only the hph plasmid (pDAS000340 and pDAS000342) or only the ZFN plasmid (pDAB107827 and pDAB107828) did not result in the production of PCR amplification products.

The PCR amplicons produced from the amplification of the 5' and 3' Fad3C-hph cassette junctions were purified from the agarose gel and sequenced to confirm specificity of the integration within the Fad3C genomic locus. The results of the sequencing analysis of the PCR products indicated that each isolated callus which was generated from an individually transformed protoplast only produced a single PCR amplification product and did not contain cells of mixed genotypes.

In NHEJ-mediated integration of donor sequences within the Fad3C genomic locus experiments the frequency of addition to the target locus (as defined by any part of the donor DNA vector being amplified from the target locus) was 42%, 46% and 32% for the DNA concentrations of 1:1, 5:1, and 10:1 (Donor DNA: ZFN DNA), respectively. See, Table 12. The frequency of on-target splicing was determined by assaying whether both cassette junctions were amplifiable and from the sequencing of the PCR products. These results verified that the cassette was inserted at the target locus in the correct orientation. The frequency of integration was calculated as 4%, 3% and 3% for the 1:1, 5:1 and 10:1 of Donor plasmid DNA: ZFN plasmid DNA concentrations, respectively. In gene editing experiments the frequency of addition to the target locus defined by any part of the donor DNA vector being amplified from the target locus, was 66% and 65% for the 5:1:1 and 10:1:1 of Donor plasmid DNA: ZFN plasmid DNA concentrations, respectively. See, Table 13. The frequency of on-target editing, was determined by both cassette junctions being amplifiable and producing a sequence of PCR products. These results verified that the cassette was inserted at the target locus in the correct orientation at frequencies of 3% and 6% for the 5:1:1 and 10:1:1 of Donor plasmid DNA: ZFN plasmid DNA concentrations, respectively. As observed in the protoplast assays, the base pairs were either deleted or additional bases were inserted between the genome and the cassette as a result of the cleavage of the genomic locus by the ZFN (FIGS. 21-22).

In certain instances the PCR products resulted in an addition of nucleotide sequences within the target locus, no PCR product, or a larger PCR product than observed in wild-type samples. These results which were produced from the PCR amplification using primers flanking the cut site indicated that the locus had been disrupted in both pairs of chromosomes (FIGS. 21-22). In some of the instances more than one band was amplified at the splice junctions (FIGS. 21-22) indicating that different insertions had occurred independently in each copy of the genome.

TABLE 11

| Number of calli positive for presence of hph after four weeks on selection | | | |
|---|---|---|---|
| Vectors delivered | Molar Ratio of Donor DNA:ZFN DNA | Number of calli sampled | Number of calli positive for hph after four weeks on selection |
| pDAS000340 | 1:1 | 88 | 76 |
| DAB107827 | 5:1 | 88 | 35 |
| | 10:1 | 87 | 37 |
| pDAS000342 | 1:1:1 | — | — |
| DAB107827 | 5:1:1 | 80 | 38 |
| DAB107828 | 10:1:1 | 79 | 52 |

TABLE 12

| Number of calli with hph inserted by splicing at FadC locus at the DSB induced by ZFN28051-2A-28052 | | | | | |
|---|---|---|---|---|---|
| Vectors delivered | Molar Ratio of Donor DNA:ZFN DNA | Number of calli positive for hph after four weeks on selection | Number of calli from which at least one splicing border amplified | Number calli from which at least one perfect* border amplified | Number of calli from which both splicing borders amplified |
| pDAS000340 + | 1:1 | 76 | 32 | 0 | 3 |
| DAB107827 | 5:1 | 35 | 16 | 0 | 1 |
| | 10:1 | 37 | 12 | 0 | 1 |

*number base pairs deleted or additional base pairs inserted at cut site

TABLE 13

| Number of calli with hph inserted by editing at FadC locus at the cut sites induced by by ZFN28051-2A-28052 and ZFN28053-2A-28054 | | | | | |
|---|---|---|---|---|---|
| Vectors delivered | Molar Ratio of Donor DNA:ZFN DNA | Number of calli positive for hph after four weeks on selection | Number of calli from which at least one splicing border amplified | Number calli from which at least one perfect* border amplified | Number of calli from which both editing borders amplified |
| pDAS000342 + | 5:1:1 | 38 | 25 | 2 | 1 |
| DAB 107827 + | 10:1:1 | 52 | 34 | 2 | 3 |
| DAB 107828 | | | | | |

*number base pairs deleted or additional base pairs inserted at cut site

Detection of Gene Addition to Fad3C by Non-Homologous End Joining in Plants

DNA was extracted from plants that were regenerated from protoplasts and transferred to potting medium (as described above). The majority of plants recovered were estimated to contain only 1-2 copies of the hph cassette encoded in the donor DNA. Plants were analyzed with the same suite of assays described for callus tissue as well as with assays to determine if the cassette had inserted in an antisense orientation or a donor integration at the Fad3A locus.

TABLE 14

Estimated copy number of plants regenerated from protoplasts. For each ratio three transfections of one million protoplasts were performed

| Vectors delivered | Molar Ratio of Donor DNA:ZFN DNA | # plants with 1-2 copies hph | # plants with 3-4 copies hph | # plants with 5 or more copies hph |
|---|---|---|---|---|
| pDAS000340 | 1:1 | 37 | 16 | 34 |
| DAB107827 | 5:1 | 18 | 14 | 30 |
| | 10:1 | 16 | 13 | 18 |
| pDAS000342 | 1:1:1 | 0 | 1 | 1 |
| DAB107827 | 5:1:1 | 22 | 14 | 18 |
| DAB107828 | 10:1:1 | 23 | 11 | 27 |
| Total | — | 116 | 69 | 128 |

The frequency of on-target splicing for the linear donor design constructs, where the hph cassette was inserted into Fad3C in either direction, was 51%, 32% and 56% for Donor DNA: ZFN DNA at concentrations of 1:1, 5:1 and 10:1, respectively (Table 15). Of these results, 35% 32% and 50% (1:1, 5:1 and 10:1) were inserted in the forward orientation (Table 15).

The frequency of on-target editing, where the hph cassette was inserted into Fad3C in either direction, replacing the area from locus 4 to locus 6, was 2% and 0% for Donor DNA: ZFN DNA: ZFN DNA at concentrations of 5:1:1 and 10:1:1, respectively (Table 16). In addition, when both ZFNs were delivered at 5:1:1, 2% and spliced into locus 4 and 10% spliced into locus 6 and when both ZFNs were delivered at 10:1:1 10% and spliced into locus 4 and 15% spliced into locus 6. The PCR amplicons were obtained and sequenced to determine the insert junction sequences. The resulting sequences for specifically labeled plants are described in Table 17.

TABLE 15

Number of plants with hph inserted by splicing at FadC locus at the DSB induced by ZFN28051-2A-28052

| | Forward Orientation | | | Reverse Orientation | | | Both Orientations (Forward & Reverse) | | Total | | Events Tested Positive |
|---|---|---|---|---|---|---|---|---|---|---|---|
| Ratio | On 5' | One border 3' In-out | Bot 5' | On 5' | One border 3' In-out | Bot 5' | One 5' or | Both 5' & | On | Off-target | for HPH |
| 1:1 | 3 | 2 | 2 | 5 | 3 | 4 | 17 | 4 | 40 | 47 | 87 |
| 5:1 | 8 | 2 | 1 | — | — | — | 3 | — | 14 | 48 | 62 |
| 10:1 | 8 | 2 | 1 | 2 | — | 2 | 9 | 2 | 26 | 21 | 47 |

TABLE 16

Number of plants with hph inserted by editing at FadC locus at the cut sites induced by ZFN28051-2A-28052 and ZFN28053-2A-28054

| | Forward Orientation | | | Reverse Orientation | | | Both Orientations (Forward & Reverse) | | | | |
|---|---|---|---|---|---|---|---|---|---|---|---|
| | One border | One | Both | One border | One border | Both | One border | Both | Total | | Events Tested |
| RATIO | 5' In-out | border 3' In-out | borders 5' & 3' | 5' In-out | 3' In-out | borders 5' & 3' | either 5' or 3' | borders 5' & 3' | On-target | Off-target | Positive for HPH |
| 1:1 | 3 | 2 | 2 | 5 | 3 | 4 | 17 | 4 | 40 | 47 | 87 |
| 5:1 | 8 | 2 | 1 | — | — | — | 3 | — | 14 | 48 | 62 |
| 10:1 | 8 | 2 | 1 | 2 | — | 2 | 9 | 2 | 26 | 21 | 47 |

TABLE 17

| Plant details of single copy hph, target inserted at Fad3C locus at the cut sites induced by ZFN28051-2A-28052 and ZFN28053-2A-28054 | | |
|---|---|---|
| Plant barcode | PCR/Sequence information | Sequence ID Number |
| 349711 | Locus 4 upstream | 353 |
| 349685 | Locus 4 upstream | 354 |
| 346258 | Locus 4 upstream | 355 |
| 348918 | Locus 4 upstream | 356 |
| 359900 | Locus 4 upstream | 357 |
| 346125 | Locus 4 upstream | 358 |
| 348919 | Locus 4 upstream | 359 |
| 349215c | Locus 4 upstream | 360 |
| 349216c | Locus 4 upstream | 361 |
| 346102 | Locus 4 downstream | 362 |
| 346175 | Locus 4 downstream | 363 |
| 345888 | Locus 6 downstream | 364 |
| 356731 | Locus 6 downstream | 365 |
| 346128 | Locus 4 downstream antisense orientation | 366 |

TABLE 17-continued

| Plant details of single copy hph, target inserted at Fad3C locus at the cut sites induced by ZFN28051-2A-28052 and ZFN28053-2A-28054 | | |
|---|---|---|
| Plant barcode | PCR/Sequence information | Sequence ID Number |
| 347359 | Locus 6 upstream antisense orientation | 367 |

The frequency of on-target splicing, where the hph cassette was inserted into Fad3C in either direction for the circular donor, was 51%, 32% and 56% for 1:1, 5:1 and 10:1 respectively (Table 18; FIG. 23). Of these 35% 32% and 50% (1:1, 5:1 and 10:1) were inserted the forward orientation (Table 18).

The frequency of on-target editing, where the hph cassette was inserted into Fad3C in either direction, replacing the area from locus 4 to locus 6, was 2% and 0% for 5:1: and 10:1:1 respectively (Table 19; FIG. 24). In addition, when both ZFNs were delivered at 5:1:1, 2% and spliced into locus 4 and 10% spliced into locus 6 and when both ZFNs were delivered at 10:1:1 10% and spliced into locus 4 and 15% spliced into locus 6.

TABLE 18

| Number of plants with hph inserted by splicing at FadC locus at the DSB induced by ZFN28051-2A-28052 | | | | |
|---|---|---|---|---|
| Vectors delivered | Molar Ratio of Donor DNA:ZFN DNA | Number of plants analysed (positive for hph) | Number of plants from which at least one splicing border amplified (forward/reverse/either) | Number of plants from which both splicing borders amplified (forward/reverse/either) |
| pDAS000340 + | 1:1 | 60 | 21/23/31 | 4/7/8 |
| DAB107827 | 5:1 | 37 | 12/4/12 | 3/1/3 |
| | 10:1 | 46 | 23/12/26 | 4/4/7 |

* no base pairs deleted or additional base pairs inserted at cut site

TABLE 19

| Number of plants with hph inserted by editing at FadC locus at the cut sites induced by ZFN28051-2A-28052 and ZFN28053-2A-28054 | | | | |
|---|---|---|---|---|
| Vectors delivered | Molar Ratio of Donor DNA:ZFN DNA | Number of plants analysed (positive for hph) | Number of plants from which at least one splicing border amplified (forward/reverse/either) | Number of plants from which both editing borders amplified (forward/reverse/either) |
| pDAS000342 + | 5:1:1 | 39 | 17/11/24 | 0/1/1 |
| DAB 107827 + | 10:1:1 | 63 | 27/27/34 | 0/0/0 |
| DAB107828 | | | | |

* no base pairs deleted or additional base pairs inserted at cut site

Targeted Integration of *Brassica Napus* Omega-3 Fatty Acid Desaturase Via HDR

The donor vectors containing the tGFP and HPH cassettes are modified to include 1 kb of FAD3 upstream and downstream donor sequences. The FAD3 upstream and downstream donor sequences are 100% identical to the native FAD3 sequence and are obtained from the FAD3 zinc finger binding site; GCCCAAGGAACCCTTTTCTGGGC-CATCTTCGTACTCGGCCACGACTGGTAATTTAAT (SEQ ID NO:255) or AGCGAGAGAAAGCTTATTG-CAACTTCAACTACTTGCTGGTCGATCGTGTTGGC-CACTC (SEQ ID NO:256). The resulting four "donor" vectors are similar to pDAS000340 (hygromycin-resistant gene-splicing donor), pDAS000341 (tGFP reporter gene splicing donor), pDAS00342 (hygromycin-resistant gene-editing donor) and pDAS000343 (tGFP reporter gene editing donor), wherein the only modification is the inclusion of 1 Kb of FAD3 genomic upstream and downstream sequences. The zinc finger nuclease plasmids (pDAB107827 and pDAB107828) previously described for NHEJ mediated integration are used for the HDR mediated integration.

Transformation of *Brassica Napus*

Mesophyll derived protoplasts are isolated and prepared from *Brassica napus* (DH10275) plants as described above. The protoplasts are transformed with purified plasmid DNA. Aliquots of donor and ZFN plasmid DNA are prepared in three molar ratios: 1:1 (30 μg of each plasmid), 5:1 (donor plasmid to ZFN plasmid to a total of 30 μg of plasmid DNA) and 10:1 (donor plasmid to ZFN plasmid to a total of 30 μg of plasmid DNA). Additionally, donor-only and ZFN-only aliquots (30 μg) are prepared as controls. The amounts of DNA delivered to the *B. napus* protoplasts via a PEG4000 mediated transformation are summarized in Table 20. The transformed protoplast cells are cultured as previously described, wherein the selection medium is glufosinate selection medium, and putative transformants are assayed via qPCR analysis for transgene insertions.

TABLE 20

Quantities of ZFN and donor DNA delivered to protoplasts

| | Molar Ratio of plasmid DNA | Total quantity of DNA (μg) delivered to 1 million protoplasts |
|---|---|---|
| Splicing | Donor plasmid only | 30 |
| | ZFN plasmid only | 30 |
| | 1:1 Donor:ZFN | 60 |
| | 5:1 Donor:ZFN | 30 |
| | 10: Donor:ZFN | 30 |
| Editing | Donor plasmid only | 30 |
| | 1:1: ZFN plasmids | 30 |
| | 1:1:1 Donor:ZFN:ZFN | 90 |
| | 5:1:1 Donor:ZFN:ZFN | 30 |
| | 10:1:1 Donor:ZFN:ZFN | 30 |

Detection of Gene Addition to FAD3 by HDR in Protoplasts

Genomic DNA is extracted from protoplast pools (one million protoplast per pool) to which donor DNA encoding a functional reporter cassette or selectable marker cassette, ZFN DNA or a mixture of donor and ZFN DNA are delivered twenty-four hours earlier. Quantities of DNA delivered for transformation are described above. PCR products are cloned into plasmid vectors. The genomic editing occurs independently in each cell giving rise to a variety of different insertion events, by cloning into a plasmid vector, each genomic edit can be sequenced without ambiguity. Several clones are sequenced on an ABI3730XL® automated capillary electrophoresis platform. Analysis of gene sequences is done using SEQUENCHER SOFTWARE V5.0™ (GeneCodes, Ann Arbor, Mich.).

Evidence of gene addition to the FAD3 locus by editing or splicing is provided by amplification of both the 5' and 3' FAD3-cassette junctions from genomic DNA extracted from protoplasts. No amplification is observed from protoplasts to which ZFN plasmid or donor plasmid alone had been delivered. All junction sequences are indicative of insertion of the cassette at the FAD3 locus via an HDR-mediated repair pathway. Deletions of varying lengths from either or both the genome and the cassette are observed as well as the addition of sequences derived from the vector backbones (either from the donor or ZFN) being inserted between the genome and the cassette.

Detection of Gene Addition to FAD3 by HDR in Callus Tissue Regenerated from Protoplasts Further evidence of splicing and editing of the FAD3 locus was obtained from callus tissue regenerated from protoplasts on selection to which donor DNA encoding a cassette, ZFN DNA only, or donor and ZFN DNA are delivered. DNA is extracted from approximately 80 calli for each ratio.

Integration of the cassette into the *B. napus* genome is confirmed by TAQMAN™ qPCR using primer and probes specific to the donor insert and the genomic flanking sequences. Relative quantification is calculated according to the $2^{\prime\Delta\Delta Ct}$ method (Livak and Schmittgen, 2001), which provided an estimation of the number of copies of cassette inserted into the genome. Evidence of NHEJ-mediated splicing and editing of FAD3 is obtained by conducting PCR assays with one primer specific to FAD3 and a second primer specific to either the promoter or terminator of the cassette. PCR products are gel-purified using QIAQUICK MINIELUTE PCR PURIFICATION KIT™ (Qiagen) and sequenced using a direct Sanger sequencing method. The sequencing products are purified with ethanol, sodium acetate and EDTA following the BIGDYE® v3.1 protocol (Applied Biosystems) and sequenced and analyzed as above.

The numbers of calli containing the donor cassette in each experiment are determined. Evidence of donor gene addition to the FAD3 locus by editing and/or splicing is provided by PCR amplification across the ZFN cut sites and both the 5' and 3' FAD3-cassette junctions. PCR amplification of the genomic DNA isolated from callus tissue recovered from control protoplasts which are transformed with only the plasmid or only the ZFN plasmid do not result in the production of PCR amplification products.

The PCR amplicons produced from the amplification of the 5' and 3' FAD3-cassette junctions are purified from the agarose gel and sequenced to confirm specificity of the integration within the FAD3 genomic locus. The results of the sequencing analysis of the PCR products indicate that each isolated callus which is generated from an individually transformed protoplast only produce a single PCR amplification product and do not contain cells of mixed genotypes.

Detection of Gene Addition to Fad3 by HDR in Plants

DNA is extracted from plants that are regenerated from protoplasts and transferred to potting medium. The majority of plants recovered are estimated to contain only 1-2 copies of the cassette encoded in the donor DNA. Plants are analyzed with the same suite of assays described for callus tissue as well as with assays to determine if the cassette had inserted in the FAD3 locus.

The frequency of on-target splicing, where the cassette is inserted into FAD3 locus is determined using the PCR assays described above. The amplicon bands obtained are sequenced to determine the flanking sequences. Additionally, plants are screened for off-target insertions to determine the frequency of integration of the cassette at sites other than FAD3.

Example 9: Targeted Integration of *Brassica napus* Omega-3 Fatty Acid Desaturase (FAD3) with an Agronomically Important Gene Constructs containing the DGT-28 transgene (International Patent Publication No. WO/2013/116700, herein incorporated by reference) that confers resistance to the herbicide glyphosate are designed and built for integration within the FAD3 genomic loci of *Brassica napus*. The constructs and associated zinc finger nuclease constructs (e.g., (pDAB107827 and pDAB107828)) are transformed into *Brassica napus* cells as previously described above. Transformants are identified and confirmed via molecular confirmation assays as previously described. The FAD3 chromosomal integrants, comprising an integrated dgt-28 transgene are isolated. The integration of the dgt-28 transgene within the FAD3 locus is exemplified via NHEJ mediated integration and HDR mediated integration. The integration within the FAD3 locus can be directed into the FAD3 endogenous sequence or into the previously described ETIP (pDAS000271-pDAS000275) that is stably integrated within the FAD3 locus. The integration within the FAD3 locus via an NHEJ mediated mechanism can be made using linearized donor or circular donor DNA designs. Transformed DGT-28 *Brassica napus* events are obtained and tested for robust expression of the DGT-28 and the subsequent resistance to the herbicide glyphosate.

While certain exemplary embodiments have been described herein, those of ordinary skill in the art will recognize and appreciate that many additions, deletions, and modifications to the exemplary embodiments may be made without departing from the scope of the following claims. In addition, features from one embodiment may be combined with features of another embodiment.

What may be claimed is:

1. A nuclease comprising a cleavage domain and a DNA-binding domain that binds to a target site as shown in any of SEQ ID NOs: 20-23, SEQ ID NOs: 25-38, SEQ ID NOs: 40-45, SEQ ID NO: 47 or SEQ ID NO: 49, wherein the nuclease cleaves a FAD3 gene in a plant cell.

2. The nuclease of claim 1, wherein the DNA-binding domain is selected from the group consisting of a meganuclease DNA-binding domain, a leucine zipper DNA-binding domain, a transcription activator-like (TAL) DNA-binding domain, a RNA-guided CRISPR-Cas9, a recombinase, a zinc finger protein DNA-binding domain, and chimeric combinations of any of the foregoing.

3. The nuclease of claim 2, wherein the zinc finger protein DNA-binding domain comprises from three to six zinc finger domains, each zinc finger domain comprising a recognition helix region, wherein the zinc finger protein comprises the recognition helix regions ordered and shown in a single row of Table 3.

4. The nuclease according to claim 1, wherein the cleavage domain or cleavage half-domain is selected from a group consisting of a cleavage half-domain from a type IIS restriction endonuclease, a cleavage half-domain from FokI endonuclease, a cleavage half-domain from StsI endonuclease, and a homing endonuclease.

5. The nuclease of claim 1, wherein the nuclease binds to some but not all copies of a FAD3A, FAD3A', FAD3A", FAD3C, FAD3C" and/or a FAD3C' gene.

6. The nuclease according to claim 1, wherein the plant cell is a monocot plant cell or a dicot plant cell.

7. The nuclease according to claim 6, wherein the plant cell is selected from the group consisting of *Brassica* sp., *Brassica napus; Brassica rapa; Brassica juencea; Brassica oleracea; Brassica nigra; Zea* sp.; *Zea mays; Glycine* sp.; *Glycine max; Triticum* sp; *Triticum aestivum; Oryza* sp; *Oryza sativa; Triticae* sp.; *Triticae triticum; Heliantheae* sp.; *Heliantheae helianthus; Gossypium* sp.; *Gossypium hirsutum*; and *Hordeum vulgar.*

8. A method of cleaving a FAD3 loci in a plant cell, the method comprising:

introducing a polynucleotide comprising a nuclease according to claim 1 into the cell such that the FAD3 gene in the plant cell is cleaved.

9. The method according to claim 8, further comprising integrating a nucleic acid molecule of interest into the cleaved FAD3 gene.

10. The method according to claim 8, wherein the FAD3 loci is a FAD3A, FAD3A', FAD3A", FAD3C, FAD3C" and/or a FAD3C' gene.

* * * * *

SEQUENCE LISTING

```
<160> NUMBER OF SEQ ID NOS: 383

<210> SEQ ID NO 1
<211> LENGTH: 20890
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

aattgttgta ttttttaaat ataattctca aaaattctat tttaagaaag ttttcatttt     60

tacttaaaaa tattgtagat ttgaagttgt ggtttagtaa tttggataac aataattttt    120

gttgatagat gaaaaacaga agaagatcac gattcgttca cacattccca actcacatta    180

cactaacacc tttgagtaaa gtgagccatt ttattatatt catgcctacc aggctaccaa    240

tatctgtaaa gctctcctca aataaatagc aagcataaga ttttgattat atcccagtag    300

aaaaactaga ctttatcttc taaataatca ttaagcatgc taatgactta gttacaaaga    360

gggtagatca aaagaaatgg atttgatgaa gctctgggaa gcttagtaag agcattggtg    420

attctctggt agttcttgtt aacatttttg tcttctcggt gactctcaac ttcaacatca    480

accttgacag tttcaagaca tttcaaattt cccaagaaat gcttctctga ttcagctctc    540

tacgagttcc tctataccct gaaaccttta gcaccttcac ttgacatgtc gataaacaac    600

atacttcctc ctccttattc ttcctagcga cgcacacaca ggcgtccccg catctatctg    660

taactcggtg cacaagaccc tgaaaagcaa aattcatgta acaacaacaa tcaaacgaat    720

tgtgtgtgtg tctatgtatc aaaacgaaac tggtacctcc tactttgatg acaagagttt    780

ctaggtttgg agagttgttg agaagaagtg gcaccacttg ccatcctttt tctttgtcac    840

tctcaaaaga cagagtaagg agcttgtgaa agaccggcat tgatttacag tataggtgaa    900

acacctggag atttattact attatttatc acaaaccaaa aaaaaaatgc aataactaat    960

aacactaaga ctttgcactt cagattgaca caactagcag aaggaaagat aacaaaacta   1020

acctcaagag acgtaggaga caagtcaagg actttgtttc tataacgtgg atgtactcgc   1080

tttctaagtg aagctccgag aagcttcttc gttccaggac agtgcggatc cagttgtcca   1140

ctcgagaagc gtcgtgagtg tgctcacagc gcaaagagaa tcttttgatg attgaagagt   1200

tggttaggag agctagtgtt ttgtcgacga agtcagggaa gccacgtgga tcaccagttg   1260
```

-continued cagttgcgtc gtcgctcaga tcgaggctgt ctacgaggga aagcagattc ctccaccttt 1320
tggacagaac caatgtggaa gctgcttgat ttgtcggaag caaggacagg actttgccaa 1380
gaacctcatc tgggagactg cttattgaat ctcgttgggg agacatatat taaggtttaa 1440
gatcgaacca gaaacttgtc gattaaaggt cacaagttca gaacaatcga agaaaggagc 1500
aaacgaacga aggtaggtga acttacaatt agaaaggaac cgacgacgag ggagcgaaac 1560
gcagcgtttg acgtggtatt tctaattgtg taatatttat ttttaaaaaa tgtgatttct 1620
tttaaaaaaa gttttacaaa agttgatagg tttcggggca taataattgg gttaattgca 1680
gtgaggatgg gagtaaaatt gagtttgcaa aagtgaggcg gtaaatttgt atggttctgc 1740
atagttgaaa ataaataagt ttatcatgtg tttataattg tttagttata aagtagcgac 1800
taaataaaat aaaaatgatc attttataat atatagctat aaaatagtaa aattagaata 1860
ttatacttag aatataagat atattaattt gatataacta gtaataaatt atttgtataa 1920
tgtttgttta ttttgaaaat tttggtttat cccactatat aaaagaagct aaatttgagc 1980
ttcataaggc tatccacatg tgcacaaata ttcaggacca accaaagtgc catgtcatct 2040
ttgtgagctt gcaattttaa aaaaatttgt cacctacgtg gcccgtatga cccatctctc 2100
ccgagcctct cttcatacca tattggtcgc agcccattac ccatctcttg atacggttcg 2160
ggttatatcg ctgtcctctc tgaaatatca aaatcactaa ccctaatcac cgttctcgat 2220
ctctttgtcg attctcttcc tcccccaaac tcatcccgat ctctttgtcg attctctttc 2280
tctccccaac tcatcccgca taacgtcccc gatgagagtg ctggtacttc aatgtgctct 2340
cataaagcct tcaatgtttt cttcaaccat gctgttgcct gttggtgatg ttttcaattt 2400
aatatgcgga gaggatgaga tcgacttggg gagaggaggt tattgttcgg aattgaaacc 2460
cgaaaatgga tttcacaatc gtaagctctc acttctttgg gctcgcttcg tcttcttaaa 2520
gaggctttat cggctgcgtt gaggctgtat cgtccggtgc cggagttctt caaccccggc 2580
ttgaagggcg acaagataca acatgggact tttgtttcgc agtgatgttt ttgatttact 2640
tggctgggag gatgagatcg actctgggag attttgtttc gagttcaaac cggagggatt 2700
gactttgaaa tcgtacgctc ttagtataca taattatggg ccaatacaca cagattacga 2760
tacaaacaca aacacgaagc tcagcattag agtttcagcc ccggagattc aacagcaact 2820
aaagtaagat tccaaattcg tcctctgttc agcctccagt caatttcttt tactttttta 2880
atctttgcct aatgttcatt actgtgatca aaaataactc gcttgcatat gtcttctttt 2940
tcaggttgtt acttggcttt ctatttcatg aagcacagaa cgtagtatat aaaaggaaac 3000
aggaatacac tttgcaaata ttctctgtgt ctttggatta atctataatc ttgtgatgta 3060
gatagataca aaagcttctt acggatctcc atggagaatt catgaaggta acctgaaaca 3120
actctctatc tcttgcaagt ggatgccaga ctaatgtcat agtttggtaa aattccagat 3180
taagttttgg tgaatgactt tgtgttttgt acagaagata agaactcatg ttcgttatgg 3240
gaagcagtta tcacaataca accttactta tcgaattttc atcaagtaat attacatgat 3300
ttataattag ttgtgtattt tatgacattt tataagtgtg gttgacgata aaaatgacaa 3360
ggctatcaca aaagatacct caagttcagg tattttagat atgggactct ctggaccttt 3420
aatatgtgat aatgtatcga agttttaagt cttcttccaa caatactcta attcgatttt 3480
gtggtgtatc gatacatttc ctgaagggct tactcggaag cttccagtta ccaacaagta 3540
tgtgaagcca atatgtatag gatttggagg ggcggaggac cacgaccttg aaaatctgaa 3600

-continued

```
gaaacagctt gaagatgatg atctcatcag aggtacaata actgcggaac atcaaggcag   3660
tgaaggtaca attttacctg tgcatgtcaa aaccgaactc tgtagccatc tccctacacc   3720
ggtttagtca taactgtcat ttgattaaca aacagagtct ggtgttaatt agctgataca   3780
aaagacaatc gcgcatacag ctgagagggt cacgtggtct aagtcttgaa ttaacgtttg   3840
agttgttctg ttcagtgaca aaggcttctg tccattccaa atcaagcagg tacacatatg   3900
aatccggtcc tgtgtttaga atcaagaaac aaagttcctt cgcgtcaaag gcttgtgtgc   3960
gagtctcttc agtgctctct ttggctttct tatgttcgat tcacacaagt attggtcttc   4020
cacaacaaag actcatccac attattacat cttctgctat aaaccttttc ttttacctct   4080
aggctcattg tcaataccaa aatacagctg cgttttgacc ttgattaggt gtgattgtga   4140
ctctctttca cttcctcgat gcacatggct acacttttct ttgcggtggt tgagatgtcg   4200
atagacataa tcactcttgg gaaaatcaag ggactgctca gcatgggtcg cctcttttgc   4260
ttgaaatatt ggagaccaat gagttagagt ttagagacat caattggtag attcatacaa   4320
tataagctta gagttttgtt tcttctttgt ttttccggtt gattggtttt aagaaatgga   4380
atcctttctc tcaaaagact ataagcatat ttagtgtcag atggcttgat gattcttcga   4440
ttttgaaacc agaaatctat tttcctgcca aatgcttctt tgttattgtt acatagtgga   4500
gtgtttaaaa cattactaaa ccaattccgt caaattttaa tagaacgaag caaaacgatt   4560
agaaccagtt gtatttttat atctttgtaa aactcagctt ctcaggatca atcttatcac   4620
tacgaatcat cattctataa aagaagatga agtcggattt ggaaagcgtt tggtaatttt   4680
tagaagtttg agagaaggta atagaagttg tattaaatag tggatatagt ggacgtttga   4740
attaagtttg tacacttctc ggattgatac atttattcac gttttgaaat tgaacacgtc   4800
tattcattaa acacgttccc aaagtcttag aaacaaatac attatcaatt caaatcccat   4860
tagaataagt tattgttcat acgttctaaa tatttaataa taaattaaac aacaaatttt   4920
ttatatctac aaaattttca tcataacata agtattttta tcacgtaaat taaattgaaa   4980
tgcatttgaa atatttagta agaattaaat atccagtttt ttaatatcac aaaaaaatat   5040
cttttatcac gtaaaaactt gaaaacatcc atgtataaaa ttatatacaa tctgtataga   5100
gatttatctc ttttgaaaaa atattaaaaa ttatatgatg taaaatatat tttaatgata   5160
acacaataca aactatatat aatgataatt atcaaatcaa taaaattcat ttctaattta   5220
tggttaagta tatattaaca aatttaatta tttattaaag ttaataaaga ctttgtaaca   5280
cagtataatt tagttttgga caatgataat tatcaaatta atattttaaa aattttatgg   5340
ttacttatat attaacaaat ctaattattc attaagaata ataaatattt tagccgctct   5400
acattttaaa gtgaaagttt agaagatgaa aaaactcact ccataaataa tattataaat   5460
tatttaaaat aaacataaat aaatgattaa atataagttt gattataaca aacaatccgc   5520
gcagggcgcg gataaaagat ctagtaatta gtaataagtt atttgtataa catgaaattg   5580
agtatttgaa acaaatattt atgttttaga tatttatatt tattaactac ataaatatgt   5640
attccaaata ctcaatttca tacttaaata tgtatgttaa atgcccagtt agatgtaaat   5700
acacattttc ccttatgtgt tgcttttttt tttaacttat gctatatccg caatggccgt   5760
atatattttt caaagttttg ctaattagta aaactttttga aatataaata aattttaaga   5820
taataattta aattaaagta atatatatat cgaattttaa tttattatat taaagttttt   5880
ggtttaaatt tccagcgttt aatttttttt tggtaaagta acagttaaaa cccattaatg   5940
gaaagtattt tcaccgcctt tgagatcttt tcctcagtat taatttccct agacgaagca   6000
```

-continued

```
attccaaaac caaaaacata ataacacata ttcattgctt ttaccaaaaa aaaaaacaca   6060
tattcattgc atgctttaat taccagaaaa cgaataaaaa tctcatttac gttccaaaaa   6120
caaagtacac acaaaaagaa cttctagaag aaaaaacgta taaacacgtg tctctataca   6180
gagtgagaac aggacaaaca aagctggaca gggttttaag taccgtataa accctcgact   6240
acgaacacaa aacagtttca aaagtaaggg taatattgtc atttagttag ccttcaaata   6300
atgttgcccc ggggatcatg gacgctttat attcagctta cacatattta tctaactgaa   6360
tcactcaaga aaataaatca cacagacgtt ttttaaggag agaaacaaac ctctctctct   6420
ctctcagatc ggagaaaaga gccatggcgg ctgcgtggaa cgggagtgag tatttcgaca   6480
tcgacgttga gaccggtaga caatcgttcg cgcggccgtc gaacgccgag actgtcgagc   6540
aagacgaaga agatctgaga tgggcagccg taggaaggtt accgtcgcag agacaaggga   6600
gccatctatc ggttctgcgt cggtcgcaaa cgtcgcaggc gcagacttct ggctacgcag   6660
acgggaacgt cgtgcagacc attgacgtta ggaagcttga tcggtctgat cgtgagatgg   6720
ttgttcgtca ggcactcgcc actagcgatc aggataatta caagctcctc tccgccatta   6780
aagaacgtct cgataggttt gtttctattt ttataggttt gttttgatta ttgatattcg   6840
atggatcttt gatataatct tggtgttgtt ttatttgtag agttggaatg gaagttccca   6900
agattgaagt ccggtttgag catttgaatg ttgaagctga tgttcaagct ggtacaagag   6960
ctttacctac tttggttaac gtatctcgtg atttcattga ggtttgtctc ctcttttttt   7020
gactatcttg ttccacacgt aaccttttgt ttctaatatt gtatctcttt gtttgtgttg   7080
ttgcagcgtc tcttaagcag cttgaggata atgaagacta gaaaacacaa gctaacaatc   7140
ttgaaagata tcagtgggat tatcaaacca ggaaggtgaa tgaaatacaa tgttttgatt   7200
attataacta tgtaacacaa acactaacag tttatatatt ttgctgttct tgaaggatga   7260
ctttgctact aggaccaccc ggttcgggga agtcgacttt acttcttgct ctcgcaggga   7320
agcttgataa aagtttgaag gttagttaat taacccgtga aattatctaa tatgctcata   7380
tatatatcac atgtttgata tctcttttgt tagtattcac atgtatcttg agattcatct   7440
ttttatttgt tataaattta tttttatttt tacagaaaac gggtaacatc acttacaatg   7500
gagagaatct tgatgagttc catgttaaaa ggacttcagc atatattagt caaacagata   7560
atcacattgc tgaactcact gttcgtgaga cacttgattt tgctgcgaga tgtcagggtg   7620
caagcgaagg atttgcaggt tagtatttac actttactat attaacttct gaaattgacg   7680
tgtcctcaag tgtttcttgt ttacattata ggttacatga aagatctaac ccgattagag   7740
aaagagaggg gtatacatcc ttcttctgaa attgatgctt tcatgaaggt cagcatcata   7800
tacctcctaa cttcctttta ctagtttata atttataagc cacaatcacc aacactttct   7860
tcaaatttgt tataggctgc ttctgtcagt ggtagtaagc atagcgtttc cacggattat   7920
gtgcttagag tgcttggtct tgatgtatgt tcagatacaa tggttggtaa tgatatgatg   7980
agaggtgttt caggaggtca aaggaaaaga gtgacaacag gtctctttca ctctctttaa   8040
acctctctat tttcacttat ccattagtct aacttataaa tcttgatgca ggggagatga   8100
ctgttggtcc aagaaagact ttgtttatgg atgaaatatc tactggtctt gatagctcaa   8160
caactttcca gattgtgaaa tgtgttagaa actttgtcca tctaatggat ggaactgttc   8220
ttatggcact tcttcagcct gcaccagaaa catttgatct tttgacgat ttgattcttc   8280
tatcagaagg ttacatggtt tatcaaggtc ctcgagaaga tgtggtggga tttttcgagt   8340
```

-continued

```
ctctaggatt ccgtctccca ccacgtaaag gtgttgcaga ttttctccaa gaggtatcat   8400
acatcctaat ccttttcttt ggttatattc atgacaagat ctgagttttt ggaaattata   8460
aacattttta aataaattta ataaaaaaga aatatatatt ttttaatttg agaacctata   8520
ctatgtaaaa aacttcctaa aactttggag gccaaggcct ggttatattg ttacatggta   8580
gtccaaaaat atattcttat gttttataat gttgttatgc atgcaggtga cgtccaaaaa   8640
ggatcaagct cagtactggg cagatccttc taagccttac cagttcattc ctgtctcgga   8700
catagcagct gctttccgca actcgaatta cgggcatgct gcagattcaa aactggcaac   8760
accatttaat aagtcatctg cggatccttc agctttgtgc cgaacacagt ttgccatatc   8820
aggatgggag aaccttaaag tttgcttcga acgagagata ctattgatca accgtcacag   8880
gtttctttac acgtttagga catgtcaggt attataataa ctctacgtat tttgattttc   8940
attacatcta tttgttgcat aacttctatg tttctgacat ggaacatctt gtatgaaggt   9000
tgcatttgtg ggatttgtta cagccacggt gtttttgaga actagattac acccaacaaa   9060
cgaagcatat ggaaacgagt atctgtcttg tcttttcttt ggcctagtac acatgatgtt   9120
caatggtttc tctgaactgc ctctcatgat atcgcgtctc ccagttttct acaagcaaag   9180
ggataactcg tttcatccag cttggtcctg gtctattgct agctggatct tgcgtgtgcc   9240
ttactctatc cttgaagctg ttgtctggac ttgtgtcgta tactatagtg tgggacttgc   9300
tccctcagca ggcaggttgg tcatttttct agacatcctt ctttttattt tatggtttca   9360
atgtcagaaa ataaaaaaaa tctttttgtt cttttaggtt tttccgatac atgttactcc   9420
tcttctcggt gcatcaaatg gctctaggtt tgtttcgtat gctggcttct gtagcaaggg   9480
acatggtcat tgctaataca ttcggatctg catcaatctt ggcagtgttc ttgcttggag   9540
gattcgttat tccaaaaggt tggttattac tactttactt catacataat aagaattgct   9600
atactaaaac cctcgcattt tttgacagat gatattaaac cctggtggac ttggggcttt   9660
tggatatcac ctttatcata tgggcaacgt gccattgcgg tcaatgaatt cacagccacg   9720
aggtggatgc aggtgtgctc aataatctca tatctaagtt aatataatac ttaagagtat   9780
atacaaatgc ttaacaatag actttttctt gcacatcaag cagccatcag ctatatcgaa   9840
tactacaatt ggattcaact ttctcaagct acgaagtttc ccaacaaatg acaactggta   9900
ttggattgga gttggtgtac tcatttgtta tgcacttctc ttcaacaaca ttgtcactct   9960
cgccttggct taccttaacc gtgagattct ttctattatt atctaatgat catttcttgt  10020
atatatatca ctgtagcaat atattgtgaa gctttttgtc ttttttttctt actcttgcag  10080
ctctaaaaaa ggctcgagca gttgttttag aagatctcaa tgaagaaacc caaactgctt  10140
cagtatcaaa tgcaagacaa ggtagaagtg agaagaaagg aatgattctt ccgttcaaac  10200
cattaacaat gactttccac aacgttaact attatgttga catgccaaag gttacattca  10260
cttcctttgt atataacagt cctaatatat ggttacataa ttatattttt tttggaatgt  10320
caggaaatgc gttctcaagg tgtaccagag actagactac aactgttatc aaacgtgagt  10380
ggagtcttct cccctggcgt tcttacagct ttggttggat caagtggtgc tggaaaaact  10440
acattgatgg atgttcttgc gggtcgaaag acgggtggat ataccgaggg agatatcaga  10500
atctctggtt accaaaaaga acaacaaaca tttgctagaa tctctggata cgttgagcaa  10560
aacgatatac attctcctca agtcacagtt gaagagtccc tttggttctc tgctaggctt  10620
cgtcttccta aagatatcag caaagaaaag aaaaaggtaa gtatgaaaaa agattaactc  10680
attttgttcc tatttaaaca gttttactag taatatgttt ttgtgtgttt gttaggaatt  10740
```

-continued

```
tgtggaggaa gttatgagac tagtggagct tgatagtcta agatatgcat tagtaggttt  10800
acctggtaca acaggactgt ctacagaaca aaggaaacgt ctaacaatag cggttgagtt  10860
agttgcaaat ccatcgataa ttttcatgga tgaaccaaca tctggacttg atgcaagagc  10920
agctgcaatt gttatgagaa ctgttaggaa cactgttgac actggtagaa cagtggtttg  10980
caccattcat caacctagta ttgacatttt cgaggctttt gacgaggttt gccctaagat  11040
ttcttgggtt acaagaaata ttatcaaccg gtgatcttaa cgtgtgttct tttttgccta  11100
cagctgcttc taatgaaacg aggaggacag gttatatatg gcgggaaatt aggtgaacac  11160
tcgcaggtta tggtagacta ctttcaggta ctttgtcttg gccttctcta catagttgct  11220
tgtcacccaa gaaaactatt atttcaaacc ctaaactttc tacagggtat taatggagtc  11280
cctggaatct caagtggcta caacccagca acatggatgc ttgaagtaac cacacctgct  11340
ttggaggaga aatatagcat ggactttgca gatttataca aaaaatctga acagtttagg  11400
taactatcac attacctaca ttttccaatc tcttttaaaa attattataa taaactgatc  11460
tttaaccatt tacagagaag tggaggcaaa catcaagcaa ctcagtgttc caccagaagg  11520
ctcagagcca ataaagttcg actcaatata ttcacaaaac caactctctc agtttctact  11580
ctgcctctgg aaacagaacc ttgtctactg gagaagtcca gaatacaatc ttgtgagact  11640
gatcttcaca acggtcgctg ctattatact cggcacggtc ttctgggaca ttggtaccaa  11700
gagaacttcc acacaagatt tggtcactat aatgggagct ctttactcgg cttgcttgtt  11760
tcttggagtt agtaatgctt catcagtaca accgatcgtt tcgatcgaaa gaacggtttt  11820
ctatagagag aaagcggcgg gaatgtatgg tccaatccca tatgcagcag ctcaagggct  11880
tgtggagata ccttacattc tcacccaaac cattctctat ggtgtcatca catacttcac  11940
cattggtttt gaaagaacgt tgagtaagtt tgttctctac ttggtgttca tgttcctcac  12000
tttcacctac ttcaccttct acggcatgat ggcggttggt ctcaccccga atcagcactt  12060
agctgctgtg atctcctctg cgttttactc tctatggaat ctcctatctg gtttcctcgt  12120
ccaaaaacct gtaagtatat tccactctat caagtgaaaa tgtagttaag atggagaaat  12180
gagtgatcag ttgtgtataa tgttgttgtt gtttcagttg attccagtgt ggtggatatg  12240
gttctattac atatgtccag tggcgtggac acttcaagga gtgatcctct cacagcttgg  12300
tgacgtggag agcatcatca aggagccaat gttccatggc acggtcaagc agtttattga  12360
acagtacttt gggtttaagc cagatatgat aggtgtatcg gctgcagttc ttgtcggatt  12420
ttgcgctctc ttcttctctg gattcgcact ttcagtcaaa ttcctcaatt tccagagaag  12480
atagaagaca agaacaaagg atattttgac tctttcttat gttagcatca ctcacgtgac  12540
aaacttttca tgtttttggc tctttctcac attttagtta gctttctttt ctattttacc  12600
actgatttag agttagtttt gttgacattg acgtaaaata aacctaaata tatatataaa  12660
gaaactgttt ttctctgttt agaaatttct ttgcttttgt aattttttgt ttagttgtta  12720
aaagccttgt ctcaaatact atatgagaaa cggctaaaaa gaatctctgt catcttactt  12780
actccacacg aaattgttta tatacaagtt taaccgatat gctaaaccta gatacacaat  12840
tttataataa aggaatgtag atatgttact ctatgattct tacatgagtc tccctaataa  12900
tactatgttt attatgcctt gctttctttg tttatctctg ctcttagaac aaacaacctt  12960
gatttgttgg gtctccttta gagggacgtc gttgtttttt ttggccaagg agactttttt  13020
ttttgaacta ccggctcaag gagacttaac acagctaaca gagtgtctat gaatagcaat  13080
```

-continued

```
gagtgtaaag tgatgtcttt gcaaatggta gcctcaagag ccctagcatc tccaatggga  13140
cacaaaaatt tactctatat ttcactctaa aatagagtaa ctctattata gagttgaatt  13200
tgcttcaata gttcactcta taatagagta actctattat agagtgaaat atagagtatt  13260
tttgtttttt tactctatat ttggagtaaa aaagcaacaa tactctatat ttcactctat  13320
tatagagtaa ctctattata gaataaacca ttggagcaaa ttcaactcta taatagagtt  13380
actctatttt aaagtgaaat atagagtaaa tttttgtgtc ccattggaga tgctctaagt  13440
ggtagcctca tttgagaata gaatatgctg tcttggtgtt tccactttgt taatatctct  13500
tgtggaggtt ttgaatatac aaatgtcaga gctgttactc ttattttatt tttaatttat  13560
tttatcattt tgttgtattg agcgaccaac ctataagagt acgattatga tttggagtct  13620
gacactcgtt ttctctcttg catcaaataa aactaggaat acaaatttga aaatactgta  13680
ttgaaagaac caaaatctct attaaaatcc aacataggac gaatgaaaat tttctaaaat  13740
tatgtaggaa cagttttacg agcaacacta atagtaatat ctttattatt atttggtcaa  13800
atgatacata ctaaagggtc aatttgtaat taaaaaaaaa gaaactaaaa agaacttcaa  13860
aatcttttta gatatatttt tagattgtgc aaaaaaaata tatttttttt agatatatca  13920
cagtcatgcg catcagaaag gcttatatat atttgggccg taaagtattg tccatcactt  13980
aaaaaagcga caactccgtg acattattgt tgtgctggga cccaaaaacg gcgtgcattt  14040
tgtcgactct ctcagtcgaa ctttttcttt tgtccccacc aacaaaaagt ttttaagacc  14100
tttatttatt gtaactaaaa acataaagaa aacgaacaaa aacttgattt gtaatgtaaa  14160
tacatttaat taaaaaaagt ttcacgagta catttaactt aaaaacaacc agaaataagt  14220
aaaaaccaaa ggactgtttt attcctaaat agagctagga agaaaggtta gttgattttg  14280
gatttgtcag aagcataaac gtagagatct ggatctgtct cgtagaagac aatatcacca  14340
gtgtcactga cgtaatgatc tttcttaata cttgccacca aactttccac caagtggatc  14400
ggtattgctc ctgacgtctt tggttctctg tagtatcttc ccaacacatg tttagctgat  14460
ttcgtctgtc gcatatcatt aattaagatc actaatttag taattaatca ccctttaatt  14520
ttaatcaaat gaaactagag agagagcgag atcactcacg gcatcaacca agtgatagtg  14580
agggatttgt gggaaaagat gatggatcac gtgagttcca atatcgtgat gaatgttgtt  14640
gaagatcccg taatctctat caatagttgt taatcctcca cgtaaataac tccattccta  14700
ttattgtaca caaaacatca ataatttaga ttaatcaaat actaatcatt gttgcttctt  14760
ataaattaat gttgatctac ttaccttgcc tctgtaccaa ggcaacttat catcgtgacc  14820
atgatgatgc aagtacgtga cagcgtccaa ccacattaca aagatctgaa atttttccaa  14880
aactttatgt caaaaacaaa ttatattagc aatgatataa taatgaaata tatgaaactt  14940
acaatgtaag gaacaccata gacttttaga actgtgactg gaccaacgag gaatgataga  15000
taaacaagag tggccaacat gatcgaccag caagtagttg aagttgcaat aagctttctc  15060
tcgcttgggg caaataaact actgtatggg ttataatgtg acccttcttt accaggactt  15120
ctgtaccact gtagtcatcc ccaaacaaat ttaatttata tttagttaat actcaaaatc  15180
taaaaattca aaattgtaat tataatcagg aagaaaaatg aggaattagg atttaccaga  15240
tagagagggt aagcgagcat ggggagaggg acagtgtatc tgagcatccg tgtactgtgg  15300
gacaaattct tgtataattt ttctggcaac tggaatgcaa aattaagatt aaaatgttaa  15360
ttaatattta acagtatggt tatatattcg aatttattca ttgcatgtgg tgtgtttata  15420
agttttttc tttttattag ttctacgtaa actacaaaac tgaaaaatac taagaaaagt  15480
```

```
aaacgaattt cgagaagaat cattttatgc caatggctcg aatataagtg gcccgttgtt  15540
aaagttaact acagtaccat aaacaattta aatcagttgt ttactacagc taaacgacaa  15600
atctgacaag tggtcgtcca agcctcacac tggaaaaagg attgattaaa ataaatacat  15660
agaattctaa gaaaattaaa atgaaagagt ttcaaaaaaa gaaaaaaaaa taatgagagg  15720
gggattaccg gaacccaaga ctcgtcgttt tcaacatggc catggttctg gtggtgtgtc  15780
cgatggctta ttctcctgca accacccccca attataaaat aaactattat tttattttca  15840
taaaaatgaa attggaattg tcaataacat atcgttttcg aggcagatgc taagaatctc  15900
actcgtttaa ctacgttatt catttttga gcaacaaaca aatgtatcta ggaaaatgat  15960
gcatgttcgt agatatttca agctgatgta tccatttaac aataaaataa gccattaaaa  16020
caaatatata taaatattat attaaactta tacattaatt tattcaagga catgtcatat  16080
gataatagct aattggacca taaataggcc catagcatta aataaaagtt tggttctttt  16140
ttcttcgatg ctaaagattt tgatgctttt agtcacatgc attattttac tatgaaaaat  16200
taatatattt tcagttatca gattactgtt tgctaacatg caccaagaat gacaaggaaa  16260
atgtaagaaa tacgaaaaca agaataaatt tgcatgaaaa aagaagttaa aataaatgac  16320
ttaccaacca tggtatggaa cgagaatgaa ggaatgaaga atatgaccaa ccgcagtatt  16380
cagaagagga atgtctgaga agctcccatg tccactgtat tattcaaatg aaattttaca  16440
tcataaacac atttatcatt tattgcacaa tgttaactga actttcctca attcaaacgt  16500
ttcaacaagg taacaaaaat agaatatgac gtgtcacatg actatatttc gaaaatagat  16560
tggaacaaca cacaataatt aaaagaacca ataaacagta attaaattgt tacagaaaac  16620
aataaaatgt gttttattga aaatttcaaa cgtagatcca taaaacgcgg aaacaacaat  16680
aattatagga aagaaaaaga tgtttagtta ggagtgttac gactgatgaa aaagaaccaa  16740
aaaaaaacaa aagaattaaa aatcttagat cccctttttgc ttttaaaata ggccaaattg  16800
gatgaacata ataattaaaa ttgaaaaaag taaacctgaa gagaatcaaa tcttgaagtc  16860
agtgaaaatc tcatatcgaa cgtacggtca agaaatcaaa gacaatgcaa aaaacgaaaa  16920
aaacatataa acatatcaaa attaagaagt tgaaagaaaa attaaattac cagtcgtggc  16980
cgagtacgaa gatagcccag aacagggttc cttgggcggc ccaataaaga ggccaaaaga  17040
accagctatc aaaatacacg gcggcgacgg caagagccac gacggcgaaa atgtctctgg  17100
cgacatagct catggatctc aaaggactct ttacccaaca atgcttagga atggccgccc  17160
ttatatctcc gatcttgaac ggtggttgtg cgctcggatc aaacctttcg tctccgttcg  17220
cattgctacg ctggtccata gcgacaacca tcgccggaga aagagagaga gctttgaggg  17280
atgtttctct ctctctctaa aactgtgtgg gctctgagtg aaatgtggtg aagaaagggt  17340
ctgatggact ttggggtatg tgtggtttgt ttatatagag ggagaagatg tgtagagaca  17400
ccaaactgtt ttctattttt cttaatttaa gaaacttatt tatttctttg aagaataaaa  17460
agtgtatttt tgcggtaacc tgtgcgcaat gtatctttgt tacgtcgttc atttcgatga  17520
aaactaagtt agagaaatgt gttacaaaaa aaaaggcaat gctataaaat ttccagaaga  17580
ttagaaattg cgttattaag tataaggatt ataccaaatt gcattatttt ccttagaaat  17640
aaggattata ccaaatgaat tgttaatgtt tcgtactttt actggatatt tatgcactga  17700
aatggtagtc ctttttggga cttaaacaac ttgtatgatt tttacaattt agcaaaagaa  17760
aaatacatgt agtcgaaaat attttttta gtcttcaata tatagttttt tgctaaaatt  17820
```

-continued

```
tcctcgatta tgtattaatc ataaaaaacg atctatatcg atatcatata gacagtagat  17880
atgacaacat ttatatggat ttaaaaaaac gtattaatgt gagggaaaat agttgccaca  17940
tcactgtgat gtatttgact taagaaacag acttccatca gtttatttat ttgagacgac  18000
ttgattaaat tggcagtcta tacaatagta caatgtatag gtaactttaa ttttatcaaa  18060
aaatttgtgt aaccaatcaa atttaatatt agttatattt tatagttggt tgaataattt  18120
ttaatttata attttaataa tatattttag ataaaaaata ttttttaata aacgtgtttt  18180
atctatagaa tatcttatat ttagaaacgg agagagtata acatatgtat atgagaatca  18240
gttggattta acaaattcac tagatccgga aataacacca ccaaaataga acaagatcaa  18300
aacatgatgt agggtctgaa tgaattgctt aaaaatggta taatattcca attatgttta  18360
ttagtactta taaaattagt gatcggttta actttttaac atataactaa ctttgactgc  18420
tgaatatggt gtcttgatca aaaaagacat ttgtggttag tcaatgagac atcatatttt  18480
agaaatgcag gcaagatggc gtttcctcta cctctttttc tctcttaaat caatttccca  18540
acacgtcttt acgagttaag catcaactaa ttgctacaat tgtatacaga tttgacctac  18600
ttgcctccat taactacatt tcaggctata tgttagtgta tatgtaggca ttaattataa  18660
atacgcattt caactgagct tcaatgcata tattcaaatt ttttgttgga atgatttccc  18720
catctttaag aatcgggtag tgaagactga ggacgtgaac cgtgggttta ctgttttatt  18780
aactctacct atatcagttt ttaatattca attttatatg agaaatcgat taatattact  18840
ataatacaaa cattgttttc ctccgttata ttatggtttt tgtcactgaa tttgaacatg  18900
atttgagaca gagaccaaac aatatatgac gtctgtatac ttaatcaaaa tatgagaaga  18960
ttatatgcac tctatcttta aacgtgagat ctccaaaact gtcataaaaa cgtgaactcg  19020
tttcttcttc caataacaaa tatcaatatt gttcatccaa ttccttcctc cataaaaacg  19080
tgaacacctt tcttcttcca atcgtaatat catgtgttgt tcatccagtt ccttcctcca  19140
caagctttct atcgaacgga acagtctgaa accgtgttaa acaaatcacc ctggaagatg  19200
taatccagct tctgtgagag ttttgaagaa ggaagatctc tttttgtaac gcaaacattt  19260
aattttcctc atatgtgatt cgatgatgtt tgataattaa aaatgtgatg gccttaatga  19320
ataatcttgg tcatgttttt agtaaccact atttcttcta gcagtcatca aaacaatttt  19380
tttttataat gttgatttat tatgatatta attatgaaaa atattacata gacgattcga  19440
caaccgacaa tactacatgt cttatgagga tctacttcta actgtattat ctgagccgtc  19500
ctacgaatat ccactcctga ctagatttac ttgcaccatg ttgaagattc cttgtaagtt  19560
tttcttctgt agtctgcatt aataaatcgt tatattcgga acttgaaaca tggatttcct  19620
gtaatctgca aataattgca tagtctggga ctcgaactcc aaacctgact gtataagtct  19680
ttaaacctta actaataggc tatggtgctt ccacgatcat caaaacagtt taccacatga  19740
gattatatat gacgttggat aacatgtatg attaatttat taaagactca ttaataaaaa  19800
tttaactgta gttttttttt tgaataaaca tagtttcctc gatctcaaag aatctacaat  19860
ttaaaattca aatgtttctc taaaaaatga agtaattcca caatataatt gagtttactc  19920
aaatcgtaat tcattgttag agtgaaaata aagtaataaa taaaaaatac tttttatttt  19980
gaaatgccat tttaaagtaa attacgaagt tggatggaaa atattttaat tactcaaaat  20040
tttataacta tatatctagg tgagccatgg aaaaggaaag gtacaaaatg atgagtgtgg  20100
gcgtagacat gaagcctgca cgtgagagtt gtagctattc gacaaacata tactaatttg  20160
ttgcgtacca tttccacttt atatatattt atatatttgt gtgtgttgag ctgagatatg  20220
```

agaataaaaa ttgagaatat acctcaaaaa tgcaaagaga agtatgtgtt tgttatttag 20280
cagacgcaca tggtggagga catcctcgtg agttccgaag ggctaagtta tacagcttta 20340
accgagctaa ttaattcatc gtccttacat aatttgagca ctatttgaag aagacagagt 20400
atatatacat attagttaat acagttatat atgatccaat tttctttgtt tgacaacaat 20460
gtgttttcaa acaaagaccc tgtaactttt tttgacccgg ttctgatata tgtatgtgaa 20520
tatgtgattc atatatttct ctaactacga gtacgactaa atgtgcttat caattatcat 20580
acacgtctct acgtgcttct ctatcttata ttcttggtat taaccattcg tattttatga 20640
acattcgtgt acgttgaaag gaatcattac gtagatgccc acgatgttac ccaagttgga 20700
gaattatgtt atttagaaaa cccattttta attacgctaa ttaccaaaaa taatatgaag 20760
aatggggccg tgggaatatg ctttcggtag gttttgcgtt ctaaatttac atagcatagg 20820
cagtcaacag ataagaggtt aaatgtatat tagaccgaaa tatttttaac gtgttggggg 20880
gtgggggggg 20890

<210> SEQ ID NO 2
<211> LENGTH: 105998
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
acaactaata ctatatctat tcaacaaaaa aaaaaaaact acccaataaa aaacatttca 60
attgcaataa tgaagataat gatatgactt cagaacaaca tcgtcccatc ttaaacccaa 120
tatgatgtca tctttagatg ataaaatatt ttgattttta tttttagcct tttattagaa 180
agaaaattaa ctgtaataaa ttatacaaat tgaaaaatat ccttacaatt ttattaagct 240
tcaatcagac attaaatttt ttgtggttac aaatttttgc agattatttc aaggaacatg 300
caaaatattc atcaactaat aaattattta aacaaacata ttaactcatc tattatatta 360
aattaggaac atgatctatt aatatatgtt ttgtgctact attttgatat aattattaaa 420
acattttact aatcacttaa aaaaatattt tacaaaaata taattataaa aaaacaccaa 480
tacgattaaa cacacaaata gaaaaattag tttaaaaaat gtaaaacaga aaatataccc 540
gctctttgaa gagcgggtca gaatctagtt cagtgataaa ttagaatatg ttacttttga 600
cgttaaaaca aacagaatat tttttgaaca ctagaatatt tgaatatgtt aattggtatt 660
gatgtttttt tgaaaaaata aaaaaaataa aaattaactc tgtgcttttc tacagtaata 720
gaatcgatgc ctcgagtcga gatacaacca tctggtgcac taaaacttgg gaccattaag 780
ataagaacca agcaaattgc atattacatt atatatatat ataaatatat atatatatat 840
gtatataaaa attacacaga agttgtcact attaattaaa gatatctttg tcaatatttt 900
aatggtgaca tcaataattc tttttttggg ttcttcatcc agctgccagt attcaaaaaa 960
aaaaatctct gaaaatattt cattgattag aaagaaatat acatcagcaa aattagcata 1020
tcaacaaaag aataatcaag gctaatggaa cataacatca aaacaaagaa ctagctaaaa 1080
cagaggagga tctctcattg tcaaaaagat aagagtgccc agaaggatgg ctgagagcaa 1140
cataagatcg cattcggttt tgaaaaatca catgttgaac gatgagatga gcttctctgt 1200
tagcagtatg atgttcgcat acaaccttcc attgatccaa attttccaaa aggagattaa 1260
gctccaccac tttgaagcta aaggatgacc acgctcttgg tctattaatt gcacccacta 1320

-continued

```
aggttcttcc catctaagtc aaaccaaacc ttcaaaagct tatgactaaa tactttcaat   1380
atatagtcca cacaggagag atgaaatgag cttcattttc cgaacccacg gacctgaaag   1440
cccctcggct atgcatagac aagtcaagat attatcggca tcatgccatc ttttgcatac   1500
cacacgtcgg caacaaaata tttccaaata aacatattta agcacaataa ttacatcttt   1560
ttggttaata acgagaatct gttgatagta tggttgaatt agaataaatc ttgcttttct   1620
tcttacattt tctcaccaaa attcaacatg cacgcataaa gtgtgtaaac tgtttagtat   1680
aaaatttcac gcgaagttcg tgtgaaattg gaaaacagac ctaactctgt cttaattctt   1740
gcaaatgcag cttgattttg aagctaaatc ctttaacttg tggttaacgt tgattaccaa   1800
aaaaaacatg tggttaacgt gtaaattaac aacccattta gtggtgaacc taactcagcc   1860
atgtcgcttt ataattaggt caatattaat tacagaactt caattcactt ggttcactta   1920
cctttgattt tccttgttcc acgactcttt tttttgttt tttttttcat acaagaaact    1980
cagatggcac atttttaaag aagagttgaa aggaaaatga acaagcataa atttggtttt   2040
tttcaaccga agaacattat aagtcaagtt ttgaattatc attaacatgt ttcttattat   2100
ggaatagcca tacacattcg gagttcggtc atatgtatca tacatgcgtg ggaacaagaa   2160
tattcgtaga caactaattt taaaaatgtg acgtaaatgt caaactatta gggtatgaat   2220
ggtgaccaag gaatgacgag gaacaaatgc attccctaac attccttaca aaaatcacca   2280
ttcataagga ataattttc cttctcattc cctaccattc ctttttatgt agagaaataa    2340
agaacaaatt aattccttgt taaatatgag atggaacaac cattcccttt cattcctgca   2400
attttattcc tctacattcc tttcctattc gttcctcttg tttccagaat ggttaccagt   2460
cggaccctta gaaaaaatct tacgatattt tttattgaaa gatgacgttt ctttttctg    2520
gagcatgaat attcatatat ctataggact cctgttgaca attaaaaact atcttaggcc   2580
ggggtatttt gatcggattt aagtctatgt atttttattt ataccaatgg gccgggttac   2640
cgtttaagtt taggacaatt tattaaaaat aatccaaaat ttgaaaaatg aaaatctata   2700
catgaaattc aatcaaaagt aaaattaatc taaaataata gtgcaattac aactattttt   2760
atgactaaaa atatataaag acttttaaaa ttatagtctt gaaaattttg cacgggacaa   2820
tgaaatcttc tgagaagtct agttataaat ctaattataa ttactttata aatttttgag   2880
aaaaaaatac tttgattgga aataaattga aatcatgtga atataaaaaa ttctaaataa   2940
tgtaaattga aagttaataa gaataaataa ttatgataca tataagtgaa tatatattgt   3000
aagtcattat tgtccattgg ttagaatttt tgttacatat tcaagtaata tttatatagt   3060
tatattttgg attcttaaat attttttgaa attaaaattt tgcatataag tgttaaattt   3120
tgtgtatatt aaacatttta caaattgatt ttattttaat aaagaggtat ttctagttat   3180
ttcaattatt tgattttagg ctctaaggat aagagacttc gtaaagaatt cggctaagtt   3240
attttgtttc ctatccgttt tgattttta aatctctttg ttgtgaaatc tgttattaaa    3300
tatagcataa tttaaaaata attgtaaata taaaacaagt aacaagtatg aaaaaattgc   3360
tacctggcta tatattactc gaagacatta ttattgctat gaaaagtaaa taatattcat   3420
atatagaaac atccatgttt ttgctcatta ttatcttctg taatgtgcac aaatattact   3480
tttagagtga ttcctgtact cttatagtag agtaaacaaa aaaaatcata tttttttaat   3540
agtattattt aacaaataat tttcaaaaac tctatatact tctaaataac tgacaagtat   3600
ttacaaagca agtaacagaa catgacataa tgtacaagta aatcattatt aagcaagtgc   3660
```

-continued

```
ttgaaataac aaatgattgt ttttaacaaa caaaatacaa atcaaaattt tgatgactcg   3720
tgtaaaacaa gtcaaatatc aaatcaacac aataattagg tttggttttc tccagagcat   3780
gacacctcag attttaaaat agatgtggga ttgacatgtc atcaaatgaa aaaagttgag   3840
taaccaatct aattattttg tacgtccaca tcagtttcgc tcagccgtaa tgagaaaaaa   3900
aaattacgaa gattacttta cctatctctt ctcctctgtc tctcctcttg ctctgtttcc   3960
tcctctcctt actcaatttt tttcagacgt gggctggtca aaccccaacc cttgcaaatg   4020
ggacaccgtc caatgagacg ggaacagctg cgtcacgagg aaccagctca gacagaaggg   4080
gatccgcagc actctccctc cggatctcca taaactctcc gagcttgtcg tcctcgagac   4140
tcacgtcaga cggtcagaga agacagagca gcggcgtcgg agaagacaga gcagcggggt   4200
cggagccgag ctcgtcgtcc tcgagactca cgagtcagac gtcggagaaa acagagcagc   4260
ggggtcggag ccgagctcgt cgtcctcgag actcatcaga cagacgtcgg agaagacagt   4320
gcagcggcgt cggcgaagaa aaagagcagt ggcgtggtcg gcgaagaaga gcagcagcgt   4380
cggagatggt actgaagcgg ggctgattga cggcgtaggt tgaagaagag ctttgtttga   4440
cagctgaatt aggtttaatc aattggttta gttaataaac caatttgtaa ttgtaaccaa   4500
tttttaattg taaaccatgt atccaaattt cgtatcgtaa agaaatacca atttataatc   4560
cgatttagtt acaaataaac ttttatttta tgtttttttt aaaataatta aaagaagtaa   4620
atactataaa attaataatt ttaaaataaa taataacaaa aaaaatgata ttaaataata   4680
tttaatggca gacaaaaaag agaattacac tatgatatca ctaaaaaaag tttctgtcac   4740
aaataaaaaa tatagactct aaagattgaa atgatcaaaa tgtttcatta aagagttaaa   4800
tatacattta tatctctagg gttaactaat tcaaatttta gagtttaaag ttaaaagtgg   4860
agatttgaga ttgagattta aaattttata aaacaaaaaa taaatattaa aaataaaaaa   4920
tttaaaaata gtttcaaaaa ttattttcga attacaaaaa gaaaatttca aaaaaaaatt   4980
aataaaaaaa ttcgaatttg aaaacatata atctaaaact ataacaaaat tttttttaa   5040
attttttaa tttattttaa ttttattttt tatatatcta tggtgttagg gtccttttac   5100
ctattaaata aaatatttg gtcattttct tccttgtggt ctatttttgt gaccaaaaat   5160
tgaaaatgat ctttttagaa gaattgctct acaaaaaatg ctatattaat cataaaaaat   5220
taatcataaa aagtaatgct tatcattata ggataaattt ttataaatatc tattagtgtg   5280
tatgcttttt gaaattgttt aagcaaattt gatacactat caagagctgc agaaattaca   5340
ttatcaaatt agattaatac taattctgta aaaatacaaa atttatataa tatctttgtc   5400
cgcggcgtag cgcgggtatt aacctagtat aagtaaaata gcaaatatca ggtctgtgtg   5460
tgttcccata ttagatggtt ggtccatctg actttgaaag gtactggatt tgattttgat   5520
acccagatgg cgatgtttta aaataattga attattaatc tagttcctaa taattaatat   5580
acgaaatttt gttattcagc taataattaa tcaagtttct ggaagatttt ctttcgggaa   5640
gattgcacat aatgactttc actattaaaa actcgtttca tagctagaac atttttata   5700
tattttgtac ttttattcat ggctgattta caacatgttt tctatatatt ttgaaaacta   5760
acttttatag caaattacta actagtttat tatttctttt tccaaatata ttgagaaaat   5820
ttgatcaaaa tgtaaactag ttttccagaa tcatatataa catcggaaat atatcagaat   5880
atatatagtg ttacaaattt aattataaat tttcaaaaac taattagtct ttctatggga   5940
atagaaaaac agacaagtcc caaaggtttt tttttttgac aaagggttaa gtcccaaagt   6000
tacgatgata aataatgtta caaatgtgtc accaaatttg tgagaaacat tgctaaggca   6060
```

```
tcagcagtct accaattatc aaacgcatga aaactattct catgatctta aaaatggcga   6120
acaaaatgaa ctcaacaaga ttttgattgt ggcctgaaac gatcagcttt tatgatactc   6180
ttataatatc acaagatttt gattgtgggt gatcgtactg atctaatatt agttttatca   6240
agtttgcaga acttttctta tcgatttcgc tattgagttt acacttacct gctgtatagt   6300
attcacatcg ccgagaaggt aaataaacag tactcttatg tttttttgtt tttttggtaa   6360
aatcagtact ctatgttgca aaaatgtgcg actgattcat gtttggcttt acatttttgc   6420
ttcggtagaa atcagaaagc aagtgaatag taaaaaatgg ttcgtatcaa gttggtgtaa   6480
aattttgtga ttgattgaac aatttaattc tgtcgagttc acattgctgc tagcctggta   6540
caaactctcc aataatttaa agaaacgtaa atggactgga catatgcatg cacacggttg   6600
ggaattattt aagaaaatgt aactcaacaa ccaaatcttg taagtgtcct gtcatttggt   6660
ggggtccatc cgtaccatct cttaaaataa aactcaaagt acatgcatgt aaaagtggat   6720
cggaataatt gcactcccaa aacaaacaaa ggctactaga aaatatatgc aaaaataaaa   6780
gaacagaaag aagaaaaagt gagattgcgt gtgtaaaaag taaagtagcc agaaaaaaaa   6840
gaagaaaaaa gtacaaaagc gtccctttga tagatgtatt gtgttcaaag ttctgtatga   6900
tgtttctatg aaatttctag atttgatacc ataatcaata tactcggatc cgatagacct   6960
cataggaagg ttctctgaac actttaacaa ctagtataag aaatagagtt caatacaaaa   7020
tattaaatta caaataaggt ttattgttta gtttcgtttt agacattcgt atctaattat   7080
aatttatagt ctttggtaga ttgatcaggt taaaaggcct acatgtgaca aatcagcatc   7140
atgcattaat gggttcccaa tttttgcgat ccagtttagt aaaagtcaga ttaaagccaa   7200
tgccactatc accccaagaa taccatcatg ggtcctgtca actaatgtga cacatgaccg   7260
aacctgaatc gttatttgtc ccattgtaat aattcacaat ctagagggct tatccatacc   7320
atatctaagc cggtcttgtc gcttcattcc atttttacca ttttactgac taattataag   7380
agttctatct accccctaat ttttttttta aattgatcat ttattaggcc gattgtaacg   7440
ttatgaacat tccaacccgg tccatcctga tctgatcaga tagctaggtg tcggtcatat   7500
cacaactagt gcttggttgt ggatcaaacc cgacaaccca cagattgagt gatttttttt   7560
attcaagaaa tttgacttgt ttaacccgca acaagaaaat ataaaatcta catccgtccg   7620
cttaaacttg cggatgaccc acaagtaatt ttaataataa taaaattgtt attttaaata   7680
ttttttaaaa taataacaaa aatcaattta taattaaaat taaatatttt ttattaataa   7740
tattttcttc ctaatttttt gtggttcaat ttcggctgac ccgcataaaa aactcttgac   7800
ccttacccgc atccgccaat caactttttt tcaaatcact cgaccgcaac aaccacgcgg   7860
cggatccaac agggcagaac ccgccaataa tgactcaaat atctctagcc caatattgat   7920
cggatgatcc ggttttgaag ttcttataga actgcaatac actaatctaa tgtaacacgc   7980
cttgtttaat aaaaaagaca caatccaatg catacatttt gaaaaatcaa aacaaaggga   8040
tattctttcc acataacgaa tcccaaaaca accccagaac ctctcatatg tgtcacatgt   8100
gatactcttg tgacactaac atataaactc gacacgactc agaaagtgaa catgatgaca   8160
ctgacagaac atgtatcaat ttcaagaaaa agaaaagaaa gccaagttat gcgatggatt   8220
taaaacatat caggctgtaa attaactagc ctcgtgtgtt tgttgtatca atgcatgcat   8280
cttacgcaga gggcacagac tcgtcggttt tcttttcttc aacagctttc tctgcctctg   8340
ctgatgctac cttctcgact ggtttctctt ccttcttctc ctcggtgtcc ttctcttcca   8400
```

-continued

```
ctgtcaactt ctcaagaaga ccagcagtat cagaagcctc tttactctct tctttctctt   8460
cttcagaatc ggtaacttcc ttgaactttt gcataaatgc tttgcagtct gataacggta   8520
ttgtaaacaa gacttgatta tttatacaag gtagaaagat ttttaaaaac acaaacaata   8580
aatcacatga aacagtttcc aatactacac gtctactaca ccagctcatt cccaagctac   8640
actgagacag ccaatataaa cactagagct ttcgactgct tttagtctat ccagatcata   8700
cacttgaacc tacacaaatg tccagatacc tctagttgga ttgccacctt taaaaggcta   8760
ccattaagta aacaaccatg atacccttca acaattactg attagtgcaa agggaaaata   8820
actcaaaaac aagtaaaaac tctaaaatgg gtgatactat aagcttgtag aactgaacat   8880
ccaaaacttg tgaccatatg caaatatcac caagttcaag atcctccagt gacctaagcc   8940
ataaatttac attatctaca ctctagaccc cggaaaaaaa ggattagtca tgctcttaag   9000
gtttaagcta ctataagtat gccacacata cacaagggaa aaatccagac tcactctcaa   9060
ctgacgcaaa gtggattaaa aaaaggttta agctttgggg aacatcctaa agatttaagc   9120
tactataaac tatgctacaa tgagaacagt gctaccacaa gcaacaatga gatccaaaca   9180
cacacaatga gactgattcg aactcactct caaccgaagc aaaccggata cagaaaagct   9240
catccttcaa ctccccatcg gagaaatcac gagcgtgcca cacacaagac ttatcattcc   9300
cagcgtgttc ctgaacactc atccccgacg taactgcaca taaggagaag aatcaaacaa   9360
tgagaataac acaaacacag atccatcatt aaaaaatagt cacgatcggt accgagatga   9420
ttagcacaga tcttgagagt tttggactgc ctcataacga gacggatctt cccagactcc   9480
ttatgcttca agaacttgac cgtaccagcg cctctctcct tccactgact cccatcttta   9540
tcgaacctat acagcttcga tttcctaaca gattcgcaaa aaaaaacaat aatcaacaac   9600
cacgatcaga tctagaaccg atctagtagg aggagtagag tttacagatc gaggattgcg   9660
tcttcgtttt cttcgccggt agtgacggcg acttcttcga gtttgatgat gggagcgacc   9720
tgagcgccgg tgtcttcgtc ctcgttggct ccggactctt cttcgtctct gtgctcgcgc   9780
tccggctcgt tgctgatgct cgccatctta tcagatcaga tcgaagcttt gctggttgtt   9840
gttgttggat tacagagtgg gcgtaggagc tagctagatt ggaggagaga atgttgggag   9900
agtttctgtt gacggaaaat gatttgtttt tttataagag agagagacgg cgctttgttg   9960
gaaatggatc tttgatttaa atgggcctac gtcacgttta ttccggagag ctgaatatgg  10020
tggactgtac tggatccatt ctggaaagct gagtatgcag agctcaaatt gaattaattt  10080
gattaggggg catatgcatt tgtcttttca aatcggaatt tgagttagtt cttatcaaag  10140
aaagttcaag aaatctgtaa gagatagttc tgcgtttctt aagaaattat tgattatgta  10200
aattagaccg attttttaa tatttaaacc atttttttag gaaaaaatgt ttcgtttaaa  10260
tactgcttag gcggacgtcc aactgttgcg aacataattt tttagaaaac tggttcttat  10320
catatatgat tttcagatag aaacgttttg aatacattcc atggaatttc cgattggttg  10380
tactcaggtt tcaaatcagt tccaattttt tttatacatg taaatatttg aaaaacatat  10440
tagtcctttt tcttggatac tttgggaaat tctttaaatt tatcttgtta caattatttt  10500
gttacaacta gatcataaat aaaaataatc atgagtatac ggattttggg actgaatgtt  10560
tcaaacaaaa aaaatttaga ttaatatttg ttcacaaaat ttcaaacaca agactaaact  10620
tgacattttt tttcctaacc gaatccagtt aaaccagtat gctaaagtca aatatgacac  10680
aacaagaaca tcatgtgtcg aaagattcag gtagtccagt ttaaaactaa gataatatat  10740
ttcatgaaga tagtgtttca aaaggggaaa acaaaagaaa aagtcgctag gaaagttgaa  10800
```

-continued

```
aatgtccaaa atgttccaaa cccaaattga gaaaaaacca catccacatt ccctcagata  10860
gaccaccaaa ccagcctgag aaaaacgatt cttttgaaag aagactttaa ttcagtaaag  10920
gaaacagcga aacatatcat tccagaacgg tgacttgttc ccactctcca tcaacagcct  10980
ctttccacac cgtcacgttg ttgttcccat cggacacggc caacatgtta cctgtcaacg  11040
accacgacac ccgccacact ggagtcataa agtccttcag aatcttacct tcccattgct  11100
caccttcttt ccccacagtc catatgatca ctttcccatc ctgtgagcca ctggctatgg  11160
tggacttagg gagacccaag ttcggtgccc aagccacatc acgaacccaa tcagtatgct  11220
tctgaagagc cggaaagcaa tccatcttcc acgacccgtt tgagagcttc cacactttca  11280
cagtattatc acacccaccg gaagccagct tgtaaaccgg atcaagcaag ccagagctga  11340
caagagcacc aggggaagtg gcaggtgccc atgagacaga agtgactcca acaggatgcg  11400
cttggtcaat cttcgtcgtg tcccagccac catcagcacg gcctgtgaat accgaaatgt  11460
ttccgtcgga tgacccacaa gccaaggata gtccgaggtc atgaggagcc caagcgatgg  11520
agttgacaga agatttatgg tccgtgaaga catgagcttg ggtccactgg ttttggctgc  11580
cttctttcca gagtatgacc tgaccgtcat aggagcatga agcaaggaat gatccaaact  11640
tagggtgggc ccacgcgacc tgccagacag gaccacggtg gccggttaat gtagctaggt  11700
gctgggatcc accgttgttg ctgactccgg ttatcttgat ggtgcagtca gatgaggcag  11760
ttgcaactct ctttccgtag tagtccattt gcacatcatg gaccatgtct tcatgacctg  11820
tttcgatctt ctgacccggc atgtttccgg attgactttc tctgcttctt aaaagaaaac  11880
acagcgaaac agctcgtaaa cacacagttc aatttcaatg aagtataata acattttaca  11940
cgttgaggat gttcgcttaa ccacgtgttc tcataggctc acacatgtaa tcaagaaaga  12000
ttatataata tgattatgaa cagaatgaag tttcagtcag agaccactaa caatgtacca  12060
ttcaatcctc agagatcaat ttcaacctca actaagaaaa ttacgattga tcaaacgtca  12120
caggggccaa ttgcacaata ctgtataaga gattaacaat agatccgagt agtaaatcct  12180
cagaacgaaa ctctagccgc agatcgactc gattcaaaca caaagatcta agctaagatc  12240
tcgaatccaa agcagaatca aatcgattca aatgttgaga gatagctgta gaaatgagat  12300
tcaattagac ggatcacgag gtcagagtca cgatacaaac cagatcaaac gaagattaat  12360
cacgctgaca aaatcaatca cagattcgaa cagaaaccta gcttagattt accgagacag  12420
cgcagaaaat cgagaaaacg aaattcgcag aagtagctca gggaagagat agcgtacctg  12480
aaggagcggt cggtcgacta agagacgccg gagtgtgagt tggagaagaa gatcgacaga  12540
gaagaaaacg ctagggggaa gcgatggata gttttttttct gtttctaaag aaaaagaaaa  12600
atagatctaa cagagtgatc taaaccgtag tccagactct aaaccgggtg ggtagactag  12660
agatatttta ttataaagcg gttatcagcg cagcttaatt atctaactat tttcttctcg  12720
accttggttt gacccttttt tggttctaga gtttgtataa accgatctca aaactaatta  12780
cagagtaatc taaaccgtgg ccatccagat taaaccggac gttcaaatag atgagagtca  12840
actcccatgt ttttttctg aaccttttg gctattttt tcttttcttt tttttaatca  12900
tctgattata gatgaaatac agagctaacg gaacatacga agcccccgaa tcaaaagcct  12960
aaaacaaggc agcatagagt ttcatttcta cggaatttct atagcataat gcgtttagtc  13020
aattgttttt ttcttttttt gctaaaagta gtcaattgtt agtctcattt aacaaaaatc  13080
atatcttata ttctcacgga tctatattgt aactcttaag tatcatcaat gaatttgatc  13140
```

-continued

```
tcttctacgt tactttggtt gatgtgcact tgcaatatag tagtattata taggttaata  13200
cgttgtcgtc aacttccact gtttaccatg ttcttgttca tggaaacgca caaaccattc  13260
gattcgcctt tcggaaagtc cccatataag tgattcctcg ctgaatgatc tcgttggggc  13320
caacctaaaa gtgcattttg tttactccct agcagtcaaa catttcattc ctgagttcaa  13380
caaaatccag taaattcaat gttttaattg tttggcattc ccgaagaatt ttcccaaatt  13440
gtattatcat tggacattgg ctctcttatt aaatactact atgggtcaaa ccttcattca  13500
actacgaagc tttctcacgt ttacatgctt ctttttttat atatggataa cctacaaaag  13560
agtcgtaaaa tgaaaagggt tgctggactg cactacccta cccacctagg tattggctaa  13620
gttggccaag tatacataat atgtaaatgt attaaacata aactacaata caaatatgat  13680
caactcgtaa agaaatcaaa tatttaatat cgatgcaaaa atatataata ttggaatttt  13740
aagtacaatt atccactaaa aagcaaagaa agtgttgcac aaaaataaaa tagaaaatga  13800
aaaaaggata tgcgatgaag agagtggaat actctaaaag gtagcgtata atctatgttg  13860
atacctttct ccaaattgaa aacttgtgga gttgtggcaa tccaacattg cccaccactt  13920
catagtcata ttccatttgc tcctccttat ttctttgttt attgtctggt ttttaaacat  13980
tgatcaacgt ttatagttca cagactatgc gacctaacaa gtttatctac accaacacca  14040
aaattaaaga gaggctggca atttcaggtt ggcccctaat cacttacttt agtaggccta  14100
actacactac ttgcatggtc ttagttcgtc tctaacgacc ttcaatatat aataaaaata  14160
ataatacttg gtcaagaagc taccactacc aaatcaagat gggattgtgt aaacgagagt  14220
tatcaacaaa aagaggcaac agttgagagt taggacgctc atcacaccac gtaaaagagc  14280
tttcaagaaa tagatagacc gatccgaatc acatgcatta ccgaataaaa agttaaggct  14340
gagaatgaaa gagatttttt ctcgcaactt cttcttatta ttatattcat gatgataaca  14400
aaaatatata acacgaataa taatgctgta aaacttgaca tatatctgaa tattctctac  14460
cacaagtaac agcaatagtt cacacgtcat cgccgacgtg gattcttcat ttcccggcgg  14520
tctaacggac gtgttcaatt ccgattctac ccttgctgaa actagatatt ccccttgtgc  14580
ccctgactct tcgaaagcat tggctctcac ctcaatccaa ccgtttgatt cccattttgc  14640
ccctccggtc gtcgctaatt tactcatcct tgccatcgcc gaaaccgtag actcaactct  14700
agctacatcg ctcacttcat cttcttcgaa atccgagttg acccagtcca atacgcaacg  14760
cggagacgac tcggtgacaa acgagtgatg atcttgacac agaaacggat gctccagaag  14820
ctggccgcag ctccatctct gactccgatc tcgtctcaag catttgtcca agaaatcgcg  14880
accgagctcc gaaactcccg ccggaataaa cggcagctcg tttgaatacc cgatccgact  14940
cagcgagtcg aatccgttat cttcccacgc tggctttctg gtgagcatct cgatgacggt  15000
gcaaccgaga gaccacacgt cactctccgg cccttgatac tctctcctta tcacttccgg  15060
agccatccaa agcggacttc cacgcggcgc aatcccagcc gtcggttttt taaattccat  15120
cgccgatccg aagtccgcca gcttaacgga gcttccgccg ttaacgacca gaacgttctt  15180
cgatttaacg tcgcagtgaa cgattccgtt agagtgaacg tgaccgagag cggagacgag  15240
acaccatacg taacggcgta tgagagtttc gtcaactacg gttccaccgt ttgacaggtc  15300
accttccggt aaatattcca aatggagatt cctgaacgac gtcgttcctt ctttggacac  15360
gtcatcgccg aggaacctca cgatgtgtgg gtgggacttg agagagcgga ggattgtgat  15420
ttcgttctcg agggactcgg attgagaagg aagacacgtg gcgagatcta ctgacttaac  15480
ggcgaaaact ccaccgtcga tcttactcac ggctttggtt accgttccaa agcatcctct  15540
```

cccgatacaa gaacctcgaa tccaaggaga tgaagaagtg tttgtgatgc tctgtttctc 15600
catgtgtttt tgtttgctaa ctaactttgg tgtgtaaaat tatgaagtac acacgacggt 15660
atataactat atatacgtgt gcgaaagtgt caaatgtgaa gcacaaataa agttgggagt 15720
tttattaatt tccgacgtgg acgtttcttt tctacttgtc tttctgacat ttgaaatcgt 15780
gaagccattt taagccattt taaaatacaa taaaaagttt cccacttggg aattcagaac 15840
taactctcga attattgatt ataatatttt aaaattagac aaatggataa ttgggagaac 15900
ggtttgatga agtcagttcg acacttggtg atgttcttgg gatgttctgt aagaaaaccg 15960
agtactttcc atattatcct tatccataat aagattcaag ttgcggtttg atcaggtccg 16020
ttgatctgtt acctcttaga cactgttatt ttatttgagt gtcatataga aaaggtaaca 16080
tatatctttg taaaacgcaa cttcatttta aatcatttat ttactaagaa cagaggaaat 16140
attattttga tttactatta ttttataaat gcaccatttt tatgaatttt tataaaattt 16200
tatatgctga atatgtaaga tgttttcata ttttatatgt aacttttaat tttataaaaa 16260
aatgtaagat tagtgatatt ttataatcta tttataatta gttaaataat ttaaatttaa 16320
attttaataa ttatttttat ataaaaatat atatttttaa tagttgttca ttgacgtaaa 16380
atttcatata ttttagaaca aatggaatgt acaattaagt gtttaaattg ttattttta 16440 tgttttaata gtttttagta ttaatttgta cctttaaatt tgatatacga gtttaatggg 16500
tattgggtac cctttgataa ttatcatgtt cttttttgtg acaagataat tatcatgttt 16560
aagtatcact aggttttgac ccgtgcgccc gcacgggtgt atattttgca taattatata 16620
tttttgttag ttgtagactt gtaagttaat gttttgttat tgagttctta tatatagtgt 16680
atcttgttca ttttgcttgg tgatgaattt taaactatta gttgtattta ttttcaattg 16740
tacttttttt tacctttact tggtaaatta aacaattaag tgtaaaatat tggaatattt 16800
tgtttagatt aggtgtgttt tattaaatta tactataaaa tttttgtgat ttttagagat 16860
aagcattact tggttgacaa gtttttgaa agataattat gtgattgcgt tagttatttg 16920
atcctttttt aaatgctgac tgcgtacaat taagaaacaa tattctttgt tgatttgtct 16980
tttaataatc ataaatttat gagtcgtttt tggaatattt tctcatatgg aagaaaataa 17040
gtttaattag gtacgatttt atatgtaaaa tcttaactaa tatgatattt aaggagcata 17100
ctatacgcat atacaaagta taccaaattg ataaacaata aaaaatattt gactttagga 17160
accaaaatct aaaccataaa acaaccaaac cgtaccttta ttatagaatt aatatactaa 17220
atgttggtat gcatagtcat aaagaatatt attctctgtt tatatcatgc atatgtaata 17280
gaaaacgtga atataatggt atatatacgt tttgatatga aagatatttt gtaaatatat 17340
gttcaatcga ttggtttgca acgggttaac agattttgaa acatttggtt attgattttt 17400
tgtgttcggt tgataaaatt ctaaatttag cattgatctg ggcaattaac aatttctaag 17460
cccaaagcaa tgttatgggt gggtaagaaa gacgaaaagg caaaaatatt tcaaaaaaaa 17520
agaagtaaaa tgacagaatt tgatggcagt ggcatagaga tgtaattttt gtgcaactct 17580
aaggggtaat tactgtttgt acttctgctt taatagttta gatgtttact ttacaaatgt 17640
catacttaca aaaatattaa aatggataag tcaacggctc ttgtttttat gctatctcat 17700 ttccttttc aaccataact tggaaaaaaa atacagtata tgtgtatata tatatattta 17760 tttattttt tgatcaaata tatatatata tatatatata tatatatttt atttttttga 17820
aaaatatatt tctcaacaaa taaaaagttt gttgacattt actgttgagg ccattaggtt 17880
aggggcgaca agtgatgaga tctctccgac gaatcctggg aacggcaagg caaactaaaa 17940
cgtgtcgatt gattttcggt catttgtttc cgttgacttc tgttgatatg cattacagtt 18000
ttctttttct tttgttaaca cgatcagaca tggaatattc ggtggtaatc accaatcaag 18060
tactcactat tcttagaatc gtgatactaa agtatatcac gtaataagcc aatcatatac 18120
gtagaacttt tagcctataa ttacaaaatg acatcaacta taatttataa gcgattgttt 18180
tgtgtcactg tcaagtgtca acaacttaca tgtaaatact tcgattatag ttcagtattt 18240
ttgatagttt tggctcaatt tggaagtcca gtttagtccc agcagaaaag aaaagaaaaa 18300
tctcaaagaa ctttaaaatt ttcaataaac caatcagttc cctttaccaa accggactaa 18360
attgattacc aattttatat aaaaatttgc ccagtggatt ccagcttaaa accgaaccca 18420
aactgaatta actaaacata gactttgctt gatatggtta cgtagtctgt caagccctat 18480
tgcctaatac caatacacat ctcgtcatca taattttaag ttaagactta agacacaata 18540
cgctttgtat acgattaact agagtcgtaa aatatgttta aaatacgcaa ctttttgaat 18600
tgttagcgct taaatcattg tcaacaatca atgtagacga gagtgtatcg gtacactgca 18660
agtacgtgta gcgacagagt tagttgtcca acgaagtttg atccaagaca tgagaaagag 18720
aggttcatca cttaaaactt ttaagcacct aaaaaactac tttggtgggt ctactttgtg 18780
aatctaacgt gtcaagaagc tgttggtcca cgttctccaa cagagcacca gagactccag 18840
ttgtccgaac tcacttatgt ttctgctcga agattgcact attgacgtgc cttcaccacc 18900
tccaccacca catctacttt aaataacatt tttttgttct ttcgttagga aacaaaacat 18960
agaaatgtac tcaacgtgat ccttgaggaa atgagaatga aaaatgctag tttaataatg 19020
ttgaccaaga aaaaagataa tcaaggattt attcaatata cttatcagtt actagcaaac 19080
tcatgagttg acaaaaaaag caagtgaata aataagaact tcaaatactt ctgctgctta 19140
tatagactag ccatctatta tgctatttac atattaagaa aacgtcattt tctgaaagaa 19200
aatccgccgc aactatcata tataaaaggg tggatatatg gagtatgttg ttaaataagt 19260
ttattttgtt tgttagcttc tgggagagat ctgcccctcc atgaacatga agtactatat 19320
caacggtcca ccacttgtag gttatccttt cgcttagagt tcaaaaataa gatatcattt 19380
tgagatttaa tggacccata ccatattacc aagttacaga tcgagcaatc ccacttggaa 19440
aacatattag acaatgcaag tgaaagtgca acatgccatt cgctggtact aactttaatg 19500
tcactttaat gttcttttct aatggaaatc gactcagaca tatgtatagt aatatactcg 19560
gagaagagaa aagtaacaag gtcatgtatt tactcggaaa agagaaaagt atgaaaataa 19620
agttaagata atcaggaact atttgaaatt aagtcgcgtg gttttagaga caatatgttg 19680
atttgcttta ataatttctt taaataaaat aaatagtata tttgggtact ataagatgca 19740
tggcaaagag caaaacacaa tatagacaaa agttgctgtt tatgttgata agtgtcgtgg 19800
gagaagaaga caaaaacgaa gcagaaataa ctctaaacta aggtggccga caatacaaca 19860
tgcttatgtt attgtaactc gggagaaacc tctaaaaaca taatcttcga cttttttttat 19920
ataggatcgg ttcaagatca tgcacactga tcctcgtatc acaaggataa cgatcctatc 19980
gatcggtagt aagaggtgca gtatcatggg tattttactc ataacaaaat tgtggaatct 20040
gaacggtgga agcattataa gcgtagttga ggaggtatgg accgtcacaa tgttatgtga 20100
actgctattg cagtttaata aagttgaatg taaaagtttt atgtatttat gcaaagttta 20160
atatgatgat tttttaaaaa tatgtaagca aaattgtaag gttttgactg taacttcaaa 20220
tgtcaaaagt ccaattaatg atcagtgaag actgcacatt acttcaaatt aataatggaa 20280
gcagcctagt gattctaaaa gtgaataaat ctttttgat acaaagtttt aggcaaatgc 20340
attttagatt aagacattaa actaatgctt agaatcagat aattcgaatt tcagaaacag 20400
gctactataa aaaatgtatt tcttcatgat ttgattgtaa acaatgagat gagaacaaca 20460
aaatgatcaa caaacattta ttagtttagt tacattgaat tggtggaaca catgatgtgt 20520
gtgtgggact gaactgctaa attggcggag actttgtttg gtaaagtaaa ataaccaaca 20580
ataaaaagag aaaagcttaa caacgtgtcg ttttggaatc cattgagaaa acaaagaaac 20640
agcaacgtat tctccgccta caacacaaaa acatgagttt atatttcacg tgttgctttt 20700
tcgttttcac tttgaccatt gtcttcttcc tcttcgtgtc ggtaatcatt atcagcgcac 20760
aaattttaaa tttactttga ataaagttga gttttcaatc tatgaaaatg tttatgacaa 20820
tctcatagtg ttgattcaaa gtaacgtaag tgtccatcat cgatatggtt gaaagtctaa 20880
tgtgaatacg taaaatgtgg acgatgtgat aaatactact actagactaa aaggaccaac 20940
aaaagacaca accaaaagta gtaacggttc tcagttcaag ggttttaatt caaccggtgg 21000
acgaattaat ttagaggctt aacaaagcaa acaaagacta caagaaacag agacttgttt 21060
tggcgcggtg gaggatcttg cttttggttg ttataagtca tacaaggttt ttgtcttctt 21120
aagtaataaa aacaaacgtt tgtggatgat ctcatgtcga agcgtgagaa actaaacatt 21180
ctctaatagt gatatattgg aaatgagttc ttggtcaaaa tataattaag gtatatatac 21240
cagagcccat cccaagttca aacaaagaaa gcttgagctt gtctgcttgt gctttcaatt 21300
caaataaata tttagaggcc gttgaatact gcattatttt tatagtctag ttgtgatggt 21360
ttgtaaatgt gtttaaattg ctgaggagtc gcagctcttt tttacctccc atatccatta 21420
attttgtttg cttccgcggc tttcaaatac ttaggccggc tctagacctt tcatattgat 21480
aaatttgaca taaacctttt ttatgtttgt tccacataat ttctaatcta ttttaactct 21540
tgttgatatg aaatgcatcg aaagttaagg ggttaaatcc atgtcaacat tcaacaacat 21600
tgcttgcata tgtgttctat gtgatgtcag cgtcctaaac ctttgctcag atacatatct 21660
taggtcaaaa agactcccat gacatgttcc agagtccata gggtgaggga aggttccaat 21720
ttatcaatgc aaactgctat tcgcatagta ggctaggaac tcgcatcaag catctggtcg 21780
agagacgaac caacgaccat tatgccaaaa gacgggccac atgaagactt ggtcggccca 21840
aatggaaagt taaccaaaaa atttacccaa ctaaacctcc ataagcctca aactagaaca 21900
tgcaccaaag cttcaggatg accacatggt cgaccatgaa gccaatagga agtaaatgga 21960
ccaagaagat gttttgatca tcaagaacgt ggaagagctt aaagactcga gccaagaaaa 22020
ctctgaggat gatactacta caccaaggac tactcaccaa ataaaccaga acgcatcaaa 22080
acagccaagc accaacctgg atcaagatac atctaaacta ggtattttca atttaaacga 22140
tttatgcaga taagatggac catcctagta gttcctaacg atcattcatc ccatctgaca 22200
caccatagtt ttaggccgca agatagttta tataaatttt cttccttttt tcttgttttt 22260
ttcccgtttt ggtcttaaac cacaaatgtt agttttttgt tttcttttct ttgcaaaagt 22320
ctttttgtct tgaatatacc tctgtgagcg taataataag ggcatctcca accctactcc 22380
attttttact ccaaactcaa ttatggagta aaatcttctc caaccccact ccatatttaa 22440
ctccaaaatg gagtaatagc tagggttact ccatttatgg agtaatctta ctcattactc 22500
cattttggag ttgaattttt tatatttatg aaatggttct tttaattttt aatgttttta 22560
tttcatactt aaaataatat aataacttta aaaaatataa tactccgaaa aagattactt 22620

-continued

```
tatagtttac agaaaatatg cataaactca taaaagtcaa aactaagaat aaataatata  22680
aaataaatat aatataatat gaataagtaa tttaataatt aattcggtaa attgttttcg  22740
aaactaccaa aatcggtgaa tattattcaa acggaataga tgagtttttt aatcttgtgg  22800
gtcaaaattt tgattgataa catttgtact tgttgagctt gatatatgca caaacaaaca  22860
ataagaccca atacataatt caaattacaa aacaaaactt tgtttttttc tttatgttcg  22920
tttaatgcat aaaaatattt ttgaattaga aaaattgcat atgataaaat ctgcacgaat  22980
tgaaattgga agataatctc tagttgtatt tttaatgata aatatttagt ttaaataaaa  23040
tatattatta tggaaatttt gtaaacataa aatagttggg ttaaatgtta atttttttata  23100
agttgaaggt actaataaca attattaact aaataaaaaa aagaatcttt ttgtttggag  23160
taaaaaatgg agtaatacat tggagtaaaa tccaactcta ttttggagtt acaccatttt  23220
aaagtaaaat ttggagtaat acattggaga tgctctaagg ctctgcgtag ctttgtacaa  23280
cacactttta cactagatca ataaaataac agagttcaac ctaaggtcgt cttgttcttg  23340
agttttggga ctttgttctt cgggtgagat tcacctagag ttaagtcttg tgcagtatca  23400
aatatccttt catcattttt gtggtgtcat tcgatccact agcaatctcg tcaaccgttc  23460
cagcaaaaaa atgagagtca acttgttaga tctcattcca caagttttgt ccaaaaaatc  23520
ttgtgtccgt ctttcatcca tccaactgcc acgagaaaga gcatagtagc cagcttatgt  23580
gttccatttc actattttca aaggctcacc accgagtctt atttcacaat gaattttatt  23640
tcttaggtgg tttcattagt ttcaatgtct aaaggattga aagtagagag cacgaatgaa  23700
taaacagatt caacgacatt ccaacaacta gacaaaatca aaacacatat tacctttaca  23760
tggaaactag tttgagatac aaatacaact gataatcaaa attaaactac ttgtgtggaa  23820
ataattgatt tccagtttgg cccaatgctg gtgaaatttt ttagaaattg tttaccggaa  23880
tagcttgggt cctttcattc tttataaatt ctaaggtaaa gagcaaatta agcttaaaca  23940
catccccaat acacacgtct acaccacaaa tcatgttcta attttcagat acgatccaca  24000
acaaactcac ccacaaatca gaatacacat actcattgtt tttcgttcaa actttcatat  24060
acgttgccat cattcttctc taactattct ttctatccac cccgtgtttg gatttaacat  24120
agacaaattc ggaggataat aataataagg aactgataat tagattaaat tcgaccaaat  24180
gctcgtttca tacaagtacc tcttcaagtt agaaagaatg aataaatgaa ttatatcaaa  24240
agtcaaatta ataaaggtaa atggacgcaa gcccttcaga tttctatcta aaatatctaa  24300
ggatctctct tatatgaact ggtccaaagg gatcagcatc acactaatat catccaatga  24360
gcctcgtgaa gccgaaagat cgacaagctt cttacagccc aacaacaatg gcttctcctc  24420
ggttcctagg cagaagggac gagcaatgtc tactgcttct tggttactca ctttgtccca  24480
tagaccgtca gatgccaaga tcaagaactc atggtcctgc tcgattctca acgtctttgt  24540
ctctggttcg gctataaccc atttcttgag atgagcatca ccgatccctc ttgacacagc  24600
caaagatcct tcaactctcc atacacctcg aaacgtatca acgtatccac cctgcacaaa  24660
aaaaaaattg aatctacttt tagaaactat actttccatt tgtataaaac attaaaaacc  24720
gagattctca ccgtggtttc aattcttgtc cgttcatcgt ccctagacgg gcggtggtcg  24780
gaagaaagag cctccgcgac tcctccaaca ctcatgacgg cgcgacaatc gccggcattg  24840
gcaaccacga ggttcccgtc gctgaacata gccgtgacgc agcaggaacc gcctttaacg  24900
tcattctcgt tgagaaacgc agcgtctgtg gtcaagtaac cgcgtttcac cgcgtctgcg  24960
atcgctgact cgtcgttttt accagcaacc gcttccaaaa cgttcttgtc taagttcttg  25020
```

gccgcaaact cagccgcttt agctcctccg tgaccatcgt aaacaccgaa gatggcatgt 25080
ttgcgatctc cttggagatt ggttacggca gagaagcgat cctccatagc ttctctcctt 25140
cctctcttgc aataaacaga atagccatcg ccttccctct ccacctctct accttcctcc 25200
ctcggcgtcg ccggagcaac gaacccggtg gtaccgatcg gtatatcaag cctcgtgggg 25260
cgtttgcgtt tcagaacccc tccgggaggt gattggccgg tacacgacgc cggagagaaa 25320
ccggtcggag gtttctgtaa acggagacgg aacggcgagt tgagggacgc cgcggcggcg 25380
gaaggagagg aaggtttgag atgagaaaga gtgagagaga tggtttcttg cggcgaagag 25440
aggatgatag aaggtttgct gcagaaaaga gacgacgacg gagaaaaaac cggagagtta 25500
cagacggaac aagacatcgt gtaagagaat tctgagttcg aagattgatg tgtttctttc 25560
tctctacctt tgagatattt gttttaggag aggaaaagag gtttctatta atataaagag 25620
agagagagag agagaggtaa tgaatgttga agactttcaa agtggtaata atggagtccg 25680
tgagggtaat acggacattt aaaagtaagt caaaaacacg tctaaaagga aagaggaaga 25740
gagtgttaag gaaataaaca aagaatttgg gcatgtggtg gtttaacgta tcagtgttaa 25800
agaagtgttt ggttgatgac tcttcacgtt ttttcaattt attcttttgt ttttaataat 25860
aaaaacagat tctatgaacg ttgtcggtcc gttagagctt atgagttgta ttttgatggg 25920
attactttct tttgtttctt ggtggtccca gtcgcagctt cttagcaagt gaccgttgtg 25980
tggactgaga ggagccttct ttctttcttt ggtttttcat ttgatgacct ttgtaaaatt 26040
atctatctca attcactcga ggtcttctaa ttaaaactaa caagtcttct aatgacatca 26100
ataataacgg ctacttcttt ttccttataa aacggtattt gtttatggat ttatgtgctg 26160
actgctgaag atcaaacatt ggcatccata aggatcaaat tatcttattc tctactagca 26220
acttttaaaa caatgcttta acaagctact gattttgagt acccaataca tattttctgt 26280
ggtttttttc taacactgaa actaatccat tatttagttt gaatcatgta ttatcaagga 26340
tctcaataag caaaagtatg aataaaattt atgattctat tcaaaatata ttttttagat 26400
attctctttt cgttcaggaa ttccaactac tattacagac ttgtgatggg gattcagtgg 26460
gttttttttat aaatagcaat catatgtata acatcattat ttgctgcgaa ttgtaccgtc 26520
attagtttga gtatttacat taataagtaa tggtatgatt ttctgttgtg ttcaaatact 26580
gtttatgaag aatgagtcat atattttacc ctacttttac gattagactt ggtcattaag 26640
atagttgacc agataaaatg attaatcaag caaagaagct tcccactcca taattattgt 26700
ggtcacttgg ttcactttga agttgtcttc gaacgtcttt ttaatagtac taggggttat 26760
ctgtgtttta cgcatgaatt tttttattga catttatttt tagtttaagg ggttaattat 26820
ataattgtga accattattt ttgtgtgagc ttttttttata ctccatatgt tttaaaatgt 26880
tgtatatttt agatttttca cacattttaa taaaacacat taaatttcta tttttttttgt 26940
gattatcttt tttttcataa aagattagtt aataaaatat acattgaaaa tgtaaaaaaa 27000
tagatcttct tgatacaaaa tttttctcta taagtaactt tataaaacgg aagaaatata 27060
agaagacata agaatgtgtt taaaaaaaag acataagact atcgagagcc gaactcgttg 27120
tagttgagta aattgcataa tgttatagtt gttaatttta atggtataaa ttttatttag 27180
aggacttata atttgtttga tattttaaga tcatccacta ttatgtgatt tttgtcagtt 27240
tattacaatc atattctgct atttaaaaaa aaaattgaat tcactttttt ttagttttcc 27300
acaattattt ggacaaaata atcttacatc ccattgttaa attgtgagaa caaaactttc 27360

-continued

```
atctatctac aatagtagca agcgtcgcat ttgtttctga tgttcttaca ggtggatgtt  27420
atcgttacgt catcgtgtga ttgttgtttt tgtatttcta taaattctta aataccgtgg  27480
tatgattact ctagtttcat gaaatgattt cctgaaacgt ttccagcatc agtccccttt  27540
atacattacc catgcatgtc taaatataca ttaccaatct ctaaatatac attacccttt  27600
gttattatgt gaagatgttg tagttcaatg cctactccgt aatgttgata catccatgga  27660
cttgagaacg ggcagaaagc accagcacct tttgttataa cagtatattt tccagaggaa  27720
tttggtggta aacataaata catcattaat cctaatcaaa acgactaatt attattgtca  27780
aaagatcatg cgactagtcg tatgtcaact tacgaagcct gcaacaaaag aatatctttt  27840
tgtaaatgtg gattatttca aggggtgggt cggacacatg aacagtaatg ttaagaagta  27900
aacctattgg gccaaatgag accgacgtag gcccatagaa aacccatgac gacccgtaca  27960
ctagataaat gcatattaac ttcgaagaca ataaatacag aggggtccac gtttccgttg  28020
caaattgggc agtagacatc ctccccgtga agcaaattca aagtcttacc agtagcgaag  28080
aacacaaaaa ctaactcgct acaatcttct ctttttcttt ttttttcaa tgttctctct  28140
cgacgaaggt acaaagatct tgtcttaaat agatatatat ttttatttaa tctaagcata  28200
gttattacac agcccctcag ccagagagag aactaagatg tacaacgtgc atctttatca  28260
gggggttaaa ctgacatagg ttatttgtta attatatgtt tttaatttcg attaaccgcc  28320
gagtaaaggt ggttaattaa gctgcgaaaa gtaaaaccta cataggttat ctttagatta  28380
tatgtttctt attttgatta accgccgagt aaaggtggtt aattaagcag cgggagagtt  28440
acaggaagat tgatgtcgga gatttgtcca gatgacatct ctatattatc agcttcggct  28500
ccctcaagat ttttcttctc aatctgtaaa gataattata ggtcaaaaac atattcactt  28560
ctctttttgc cttctatgac ttattaatac aagagaatat ttttttccta ccaaccatca  28620
tatatatagc aatctggatt tcaaaattta gtttttcttt tcctaccaac catcaaatat  28680
atagcaatct ggatttcaaa atttagtttg tcttgtttct gactttcaag cttctaggtc  28740
tttcaagttt aaagaacatg catctttctc caaagcaggt atctagcttt tccagtttat  28800
aatcaacctg gctgaactag ctaggaaagc tatggctaga tacttgaacc taccaatctt  28860
acccaagcca acctaaacca tataacaaca aaaaccccaa tcggttccat aaatctcaaa  28920
ccaaattacc aaaacccaat tatgtccaac aacagggaag agattttact atatcaaaat  28980
tatatatcta tcaaaaccca ggcttcattg gatatataat tggggaaaac ctcaaaaccc  29040
caaagtataa aaagactgaa tcatttatat ttaaagaact ataccacttc ttaatttttg  29100
gggtaacagt atcaaggttt atgaaatagt tttgaattta cttttagggt tcagggttag  29160
gttttaaact gttgtgctca tctaaaataa ttttattatt actttacttt aaaatttaga  29220
ctattttcat aaacgttctt atatatatat acacaatatt agaaccgaat cgagattttc  29280
ctcaaccaat accagaccaa agaaaaagag aataaacatt ggcacacgaa aacagaataa  29340
acaaaatcta atcaaaaacc aaaatgctct tattaatctc gagatgtttt tttatattaa  29400
aagtgcttat atatgtatat atctgcaagt aagtgtgtgt atatgtgcaa gaagtgctta  29460
ttagcttttg catatttata aagaatgtag cttttcgtta cctgactagc caaaacctgg  29520
ttctcttctt tcagcagatt ctcctgtttt taaaaggaca acatgtacat caattaattt  29580
cagattttgg tatccaaaac atttgcaaca tccctaatag acaagatgca ttgtgaaatg  29640
tgaagaagtt tgatgtagac ctgcgagctc ataaagcaca cttagagaaa ctaatacaac  29700
aattgtgcca aaaaaaaaaa aactaataca acacacaagt gttttgaggc tctcaacacg  29760
```

agaatatatc tataagtgct ataaaatcac aaatctaacc ttttctttga gactttcaac 29820
aagctttaac attagttctg cctgcaacaa attaaatata agtgcacaat cgttttcgac 29880
aaacaaagta aacaaagaga acacattatg gagtcgatgt accttccgag ctctagttac 29940
agagagggca gtctcaaggt gatcttctag ctcaacgagg gaatccacgc ttacatcatc 30000
aattgattcc acaagcttgc tgcatatatg cacagattga caggaaaccc taatatattt 30060
gtaatgaaag gaggagagca aaaatagtct cagttagtac taacctttcc acaagttcta 30120
gtagctcatg gtgtgaacta tagttcagag attttgactg aagatcctgt tcacggagaa 30180
ggataaaaga ggcggtaaaa gaccagtgta tttaagaaat ttgatatgca cgtggaccaa 30240
taacctcaca caggatcatt tggcgaataa tagttcataa caaactcaag ttttaagaaa 30300
tttgttctca acatgtgttt acattatagt tcaaaaaaaa aaaacatgtg tttacatatg 30360
tttatcgaaa aactactcta aaggaagcat cgatagataa cctcttccat gttgaaaaca 30420
atatttgaca actacagctc tcaaatagga atgatacacg cagtttaaat gcccgtgagc 30480
catgcccaca aaaagtaagt tgaaacatga cgctgcgagt tggttctgac cagtatatat 30540
ggagctctct aagccttact tatatcctta aatactgcat gaggaaatat tcaaaatgtt 30600
tgtattacca gggcattgag atcatcagca tgttttttcc catatcgatc aaggatcttc 30660
tccagtctgg agaaaagata aataaaaatg ttaactgaga tcaaaagtca aaactacttg 30720
ttaacccttg aagacaccac tggaatctat caaaacatta aaagagaaat gaaacaaaag 30780
gttaattttc gcaccctaga atttgctaac aattcagaaa aaaccgtagt aatcaggttt 30840
aagcagcagc acatttggat ttccatttct tatttttaac atgctctgat cctttctaag 30900
caatctcaat aataataaaa aagtcctcta aaattaccaa gtatttcaag tttaattttc 30960
caatagttgt gttaggttac atgtatttat ttatatactt gatagactga aaatggcatt 31020
cttttgacaa agaaaagtca taatctatac tatattaaaa gggttatatg agctccatac 31080
agcatgtcca cgtaggacaa ttaaatcgac caatcacgtt gaagcgttta gccatgtcac 31140
taatatgttg ggctcacggt ttttcttttg tgtatttgtt acgattgggc tcaagcccat 31200
gaaaccatta taacaaacaa tcgcactctt tcacgttttt tcgaaaccaa aatcagaacg 31260
attctcatcc cctttcctct tcctcttctt tgatccgttt cacgatctga ttcatgagca 31320
attgattcat cctccacttc gttctccctt tactctcatt tatggattcg tttttctctt 31380
cttttgttta taaaactctt gaacggagtt tcgtttcgat taagcttcgt cgtaaatttt 31440
cattcgtaca ttgcaatgag tttcaccgga aaatccaact cggagaaacc acaacgcgtt 31500
gagggtgact cctttcccgg accgatcaat cccatcggcg atccccactc gaagcaagcc 31560
aaagtcgaag cgtcgttctc ctccggtctg acgaaattaa aggctgacac ctttcccgga 31620
ccgattaagc ccatcggcga tccccactcg aagcaagcca aagccgtagc ctcgatctcc 31680
tccggtctta cgaaattaaa ggatgactcc tttcccggac cgatcaagcc catcggcaca 31740
cctgattcga agaactgcaa aggtaagaaa ccttatcgtt tcttatcaaa ttatatagtc 31800
cgtttgattt ccaaaaaaaa atctgaagct ttgagattta aaaccatgag acgaacaaat 31860
ttttttttta atagataatt tttatacaac cgcaaaggta agaaccctta tcgtttctta 31920
tcaaattata tagtccattt gcttacgaaa aaaaaagtct gaagctttga aatttaaaac 31980
catgagatga acaaaatact ttttttttata atagattatt tttatactat agaaaataga 32040
aaatcatata aattgtggta cggagtttag tatccttttt tgatgatgag aacgttcgta 32100

-continued

```
ttcctatgca ggtacgatca atcacaacac gaagactggt ttctcttcag gcgttagagg  32160
caaagccgct gtctcctctg ccgtcaaggg aaaagccatt gtctccgcca aagtaatggc  32220
tttcaaagat gtgaaatacg gacttcatga cggcgagctg aggtttcggt tgatccattt  32280
ttgggaagct cgaaatgttg tgacgaaggt gcttctcggt ctcaagatgc ttctcatcga  32340
ctaagaggta taaaccgaat tcttgattgc gatttagttt agaaattgtt cagacaagat  32400
gctgataaac attttagatt caaacttatc gctctattat ttatagcaag tgtttgcttt  32460
tgtttgacag gagggagctc agatatttta ggaaagatgg gcacaaccgg aggaagaaga  32520
aagatggtaa aacgatgaaa gaggatcacg aaagctcaag gttaataata tatttacatt  32580
catgttacct cagtttttaa taaatatttt agagtaatat tgtttaagta tatatctagg  32640
ttggaagcat tgatgtgtta cattgttact aggcacatgg ggaagacaat gagaatttcg  32700
agaggctttg ctactggatg cttgaacagt gagtcctatg ttttccatat ttcacatttt  32760
taccggttta gtgtaccgta aatgttactt tgagaacaga aggaaaatga aatgtgaatt  32820
gttactttta gtgcttatgt cctctgtttt tttatgggta cagggaactg atgcatattg  32880
tttttgttca atacttggag gttaaggtgt agcttttctc ttggtgctgt actaatatat  32940
tctttagaat ataaacatcc attcactcaa cattatattg tttcttttta aagtgggttc  33000
tctttttttt aatggtggct ttgataagtt cacgctattt atacagggta ataggataag  33060
ctccagtgga ataaaagaaa acaattcaaa ttctgtgagt ggctccactt ctgtgaatat  33120
tgattcaatg gcaaacacat ccagaacatt gtcaccacta tgtgaagatg ctgattagta  33180
tttgccggag ctttaccgtg gagtccgttg tggccgtgtt attgacgttt tagatttgaa  33240
tcagcctaca cggacctaac agcaacaggg attccagcgg actaacagaa gcagccgtgg  33300
agaggcaagg cagggacgag attagcggcc agaaatttga aaggaaatct tcagaagaat  33360
cagatagtaa gatagttggt gaagaagaga aggaagatat gtcgcttggt aatgatagtg  33420
gtggctctat caaggcggct acacatgaca aagacagaga tacttctcct tcccatgaag  33480
ggataaagct ttctctgtga ttgtgctgtt taaaatgatc atttatgcat agccttggtt  33540
tagtattttt ggtttataaa ggtcatgact acaattcaac agggtattgg aacgagctac  33600
tatgggcagc ttcgtgttct ctctggaggt caagcacctg gtgggcacac tgctatatat  33660
ggaccattcg gtaagtgttt aaaatacatt tttgtgtgtt ttaaaatgat gctttacatc  33720
ttagtcatat acttaattaa gaaagcagag tagcaggatc actcttattt caaaatatgt  33780
gcgcttttta gaagtttaca tttgatgtca taattttgtg aatcagtgtc tcgagtaatc  33840
aaatttgatg tcaccctaac ttcaaacttt gctattcaca tccctcaaaa cttattctct  33900
cagtgtttgc atgcagggtg atccgaagat tatcacctgc aagttttcat gctgctgtag  33960
caaagacatg ttttgaggta cggtaatatt ctcaaaacac cagactttga ctccctttgc  34020
ataacaaatt cttctgcagt tttctgattc taagtatctc cactttgtta ttcactcagc  34080
tgaagaatca actcatcact gctagctatg ttgatgatga aacatccatg tagatggcta  34140
agaaatactt ggattatgat tcttggtgaa gtgacatcca caacttggat aattgagaat  34200
gaggctcata tcagcaaggg gaaagtgaag tctttcacgc tcttcctgtg gtagcattcc  34260
cttttcttct gcagcagata atttattagc acagattgaa ttacttcaat ctgatgtatt  34320
caaatcatgc aataatgtga tcaagagctc acattcacct tccactttgt aatatttatt  34380
atgtatcttt ttttttggga atcataataa gcaataatat tttacagtac atatgcatta  34440
caattacaac caaaagaaaa ttaaagaaaa acagtgaaca tataaagtta gcttaaaaag  34500
```

-continued

```
ggaccccata gagaaaatac atttaaaata tatagtaaat tattaaataa acaaaataaa  34560
attggaacaa atttaaatag taaatatatt taatgtataa ttttaaatag taatgaccac  34620
tattaaattt ttatgtagtt tacctgattt aattatattt tcagttaaaa tggattaaac  34680
ttcacaactt attacttata acttcattaa actcatcagc aatttttaaa aactaattct  34740
aactattaat atagttaaac taaaacaaac attaaaatga atagtcaaat aaacagaatt  34800
tttttatagt aaaaaacatg tcggacgttc gacaactgtc tcgcaacgag cttctaccaa  34860
gagatataaa tgttacttgc acagctcgtg aagtcctctg aaaccgactt acgttacgca  34920
atggcgtcga ccccggttct ggggttggca gcaggagact cacgtatata caaggacctg  34980
gatctccaga cgcatacatt ttcctgattg gcttctatca accgtttctg tgatcttatg  35040
gatcgatgtc ttgctagcgg taacatccag gcacactacg tgcaaggaat tcatgaatat  35100
ttttgcaaca acacaatcaa tggcatgcac catttacgcg tctcagcagg tggttcttac  35160
gcagatggtg taatcatgtt gtgcagaggt gagcgagctg tcggtcatgc ctacatatac  35220
atgcttggtt ggagggagtc cccaactaaa ttagacgaat actggagaag aattaaaact  35280
tcgcttcatg gtattgttgt tgcgagactc ccggtttaca tgacgacgta ccaagaaaca  35340
agagctgcta ttactagcct ttgccaaagg aacctgcgga agctcgagcc accggaaaga  35400
tgccatgtca atgacatgga caattactgc gagctttgct tatgctacaa gtaaatcaag  35460
cagttcattg ctatcctttg agatcacatt agtgttttgc agttcgttgt tatatcgaat  35520
cgtattccgt accaaatcca tggtaatcgc aggaaaattt gatttccggt tttggctgga  35580
agtttgcttt ttgtggtgga aaaattgatt tcgtggtttt gactgcaaat tttgattttc  35640
tcggctttgg caaaaatatt cgattttgtg gttctggcgg agaaaaagaa tttgctgttt  35700
tagcgggctg gaaattttgt gtttacgatt ttggcgggaa gattcaagtt cacggctttg  35760
gcgaaaattt taattttgtg attttggcgg aaaattttgc tcttgcggtt gtgacgggaa  35820
aaaaacaatt ttttattttg gcagtaaatt tcaattttat tttattttat cgagaaaata  35880
caatttgtgg ttttagagga aaaatctaat ttgctgtttt agatggaaat ccgatttgcg  35940
gtttagagga aaattttaat tttacgggtt tgccgaaaaa atcgactttg cgttttttga  36000
aaaaaaacaa ctaaaacctc attttccata atcaatcttt aaatattttt ataatatttt  36060
taaaaagtgt ttttttcttc caaatagtct tacattaaaa ataaatatta aaaacagaag  36120
atcatatatc attttaaatt ggtcaaaaca agtttaaatg agtcaatgta atatttgagg  36180
gtctaaatga aaaattctaa tagatctatt ttaaaattaa tctaacggca tagctattga  36240
atggggtgag tcttaatttt ttttttgaca acatgggatg tgtcttaaat ggggtgggtt  36300
ttcccatttt aacatccata tactccaatg taaagaatat aaccattaga ttattttggt  36360
ttgacattag aagttcggta gctcatataa atctaacacc atgttatgtt gtcaaaggtt  36420
tcggacatta gtaaattaat aaaaatgtag caatcaataa tgtgaattta ttatagtata  36480
tattgttatc agtctaagta taaaaatata tttatattca gatacaaatt ataaagtaat  36540
ttaaatttaa ttaaaatata tggaaaataa cccgggcgta gcccgggaaa atctctagta  36600
acattaatac ctgtacatgt tatccattaa tctatcaatt aattcatatt caacgctggc  36660
ttttgagtca cttaaataaa aattaactaa ggtacataag aaccctatac tcaagtcaaa  36720
tacactttgt tttgcctctg cacccacaac tgtttctttg cattcaggtt tgtgttccat  36780
tttataataa tttgatacta taacaggaac gacgactgag gcttaaatga gagtgtatat  36840
```

```
atattacata gaggtaaaat aaagtgtccc aagtgaaaga aactttgttt tgattctcac  36900
ttggtgcata tagaaaagta ttccataaaa cgaagacata caaaataagg ggaaacaaat  36960
actacatttt ctatttatga ggttacagag acgtctaacg catttcgaaa aaaattacca  37020
acgcagttaa cagtttgtat taataggttc agagttccat tgtgaagtta atcttttgca  37080
cattttcatg tgcaaaacta ggagtttgac tactccaagg ctgaacctag cattcagtct  37140
aaggcgaaca aatcctagca aagtatgcat cgagtgagaa tcaacgatct tcaccaaacc  37200
actagtacga cttggttata ctagagggtg ttagtacaaa cttcatcgat taatttgaca  37260
atgtaggatc atactgaatc tagagagata ctaaaggggt tggtattttt tatgaagacg  37320
aatgtttttt gtggggttgt cgatttccag gaggagccaa agaaacaggg cgtgtgttgc  37380
tgcacttccc aagacaaaag acccaagatt tcatatacca aagcgacaac gttaatttaa  37440
tatagttcag agagaatagg aacaaagtgt tgatatataa tgcagacaat gacaatgaaa  37500
ataagaaaga tgaacgaata tccagtcaca ttaatatgta gcatataaat gtatatcaca  37560
ctgcgaggat gggaaactaa aaagtagaaa ctagtagaaa cttgtaggat agaaattcct  37620
tgaaaccata tatccacatt aatcttagtc catagataca caatctatca tacatttgaa  37680
aaaagttaat gatctatttt accatcaact ccatactatt tttataacaa atctcccgga  37740
agtgcattgc aatgtatagg aatccaagag aacaatgaat taaaattagt ctaaagttag  37800
accaactgat gcacattacg tgctgcacaa agtatcaaat atatgcacac acacaacgat  37860
tgccgattaa agaatcgaag tcgatactgc atcacataaa taatatagca tatgtgagtt  37920
aattaagaac taattgtgag gttaaatttt cttaaataaa aaaatactat atatatatat  37980
atatatatgt atgtgtgtgt ctgtgtgtga aaatcaagaa tcagttagaa accttaaaat  38040
tcggataatc ttaagtaata attcatggta aaaaggataa aaattttgaa gatctaaaat  38100
tatcttttag tcaatagctg cacaatgtcg catacattca aatcaaaact cttgatctag  38160
tatccagcat taaccccaca tcagttttaa ggatctcttc gcagtgcatt gcatacagat  38220
ctgagcgaac caatgattgt agttacgata aaggcagaca gattaattaa ttttctgatg  38280
caaaatccct aaagccaatg aactaaaaga tggcttgaaa cattactaaa gaacatcaag  38340
tattcatcac aacgtatcga gaagatcttg acggacatgc aaatttttaa caaataaaat  38400
aaaatccatg cagaaaaata gaaaaaaaac gaagaaaata agagagaggg agattgagta  38460
agaagcttta gctcatcaca acattgttct tcctcaattt tggttatatc atgtatagag  38520
gaaacaataa caaacaaaac cgaaaaatcc ataagagatt cgccgggtaa atctaagtgt  38580
cttttaatta ttttatttta attattttat tagtaaagta aagagaagaa agcttaaagg  38640
gcaaaaaaat aagagagaga ggagaagtcc tacctatccc cggaggagaa gctgtagagt  38700
ttgtcggagg cggagacaac gagaagccca acagatgcct cgcagagaac agaaagctga  38760
cgagctttct cgatgagacc gttgcgtcgt ttgcagaagg tgacttgtct gctactgttt  38820
ttctcgattc gcttgatttc tagttttttt cttcccatag cttctgtctc cgagaggtct  38880
ctgtgcccta atttgattct gaggtacggt taaagtcgcc ggagagacta agcgttttat  38940
tctttcttct ttttcttcct ttttttttct ttaatttcta cctatttttc ctcgggtagg  39000
gttttttggg gcgggggtaa acgagagaaa taaaaataaa aatatgaaag ttaaaacgat  39060
gcgttttaac gacaagacag ccacgtgcac cgcaggacga actccctgtg gacgcgttgc  39120
gtttgactac tcgactctac catacataca cacaggtagt gctgggaata tgaatcatta  39180
tccgcgggcc ccgccccatt tgatccgctg cggggcaggt gcggatcgag tgatttgaaa  39240
```

aatttggttc gcgggtgcgg gtgcggattg agtgattttt atgcggagcg ggtgcggatc 39300
agccaaaatt cagtgcgggt acccgccaac ccgcaaaaac taaaaaagaa aagatttttt 39360
taaaaaaata ttatttttaa atagaaaatt tttaaaaaat aatttaattt taattataaa 39420
tagattaata tttattattt taataaaaat atttaaaata ttaaatttta ttgttatttt 39480
taataaaaaa atatttaaaa tattaaattt tattgttatt ttaataaaaa atatttaaat 39540
taataatttt taatattatt aatattatcc gcgggtctag cggatcaccc gcgggtttta 39600
gcggggcggg tgcggatttc atattttttt cttgcgggtc aagcgggtca aatttttga 39660
gtaaaaaaaa tcagtttatc cgcgggttgg cgggtcagcg gggcgggttt gacccgcaat 39720
ccagctctac acacagggtg tgagtgaaag gtattaatag agtaaaagtt tattctatat 39780
caatatttac tctaggttga gctaaaatgt taccaatcaa gtggaacata aatttttgtt 39840
atttactcta tgtactgtac acaaagagaa aaagagacac taaatattac tcttgattat 39900
gctagaggta tatgatttta ctctatatag atttttcttc tcatattttc atcttttaca 39960
tttttcactg agtttcactt tttcatttcc tcctttattt accaatcaca ctcatatagt 40020
aatttgcagc acttaaatat ataaaaatca aaatcaattt tcatgttttt tttgtatagg 40080
tgatatatta gtttttaagt aaaactcata taattctaaa atatgtggcg caattttaga 40140
gcatatattg ataatttctc gaaaagcctt ccataaataa aaaattaaga aaaatataag 40200
aattgtagac attactactc ttgctcattt cacatttatc aaatatgtta taactgaatt 40260
tattttaata ttattaattt ttttgtcttg agaaactaag agtatcatta ctggtcagtt 40320
agctaagaat cgtttctagt ataacaacaa tagaatttga tatttgtaat taatttttaa 40380
acacaaaaaa gtttaatcag tgatattgtg acaagtaagc aaattagttt ctcaattttt 40440
ttacgtctct ttccattgat aatttggtat tctatccatt ggaattgaca tttactatcc 40500
aagaaaatta ttctaaacac attaaacaac caaaccctag cttatatgta cgttatgctt 40560
ttgaacagat acactcaggt gatatatggt tagatctaga taactagaga ataaccctct 40620
tgaatttctg caaaaaataa taatttatgt attttttaga gttaatttac tttaaagtag 40680
gaatttagtc aactatccta aacagtaaaa ctagacaatt ggatgtaggt actggacact 40740
taaaatgaca attatatcct tgacaagcaa tttcaattct agttcaaaaa acttcgtcca 40800
aaaaacatta aaaaaaaaca caacttgtga gtaaagagag aagacggtta aacggaagga 40860
ggaaagaaaa atatccacgt cggagagaga agaaagctgg gagaggagct tggggtggcg 40920
agagacaacg tcgtggcgga gctgggcatc gaggaggcgg atcgcttggt ggagacgctc 40980
gacggtggag gcagaggatc cggaagcgag tgccatccgg aggcgagtgc ggaggaaaaa 41040
gaagtggaga ggaatggaga gacggtgggt tcgaaggagt ctagaggtga tgaaaaagat 41100
gatggttgtg ggatgataca tgtaggggat aggagtatta gcgtcattag attttaaaca 41160
tagttcgtaa tagtgtcgaa tggtagatca ctaattagga aatattgttt gtgtatacaa 41220
tgcaaatgct ctatctatta tattaaaatc gaagtataaa ataatacttg attattttaa 41280
atggtttttt acggttttca ttttaaaaaa ctaactttaa cacttctttt gttatctttt 41340
ctaattaatt tgaaaaattt atcatacatt atgaatcaaa acttacttat ttaaagtgtt 41400
tattacatat tttacattta tttccacttt tcttaactat ttcattaatt gtctttatca 41460
taatattttg ataacattta gtttacatgt caaccataat aatttgacat gtttgaataa 41520
aattatttca tttgtgacaa aaattcaaaa aggttaacaa ataatttttt tattttctta 41580

-continued

```
aagaaatagt taatcatggg tgttcggatg ccagtttggg tatatatcgt ttctttcgcg  41640
tatcaagttt tttgggttca aaattaggct ctgatcacgt attataaatt tttgggtgta  41700
tttcaagtcg tgttctccta tgtccagatg gattcggttc tgatgtataa aaactttaag  41760
atatccaaac aaccaaaagt gatttcatat tacggttcaa gtattttgta ctaaaaataa  41820
tcatattacg atttgagtat ttttttattc aaactaaaaa taatttaaaa ataaccaaat  41880
aactaaaagt aaccatatta tctgattgga tttgagttta attctaattt gtaaaaacta  41940
gttatccaaa taatcattat acaattattt atacggtgac acatgtaaaa tatataacgc  42000
tatacatgaa aataaatatc aatttataaa agaggataaa aaccaacact agtcaacaat  42060
taaatagatg ataagtaaca gatttttttt caaaaacgaa atcgggtctc ttgtttgagg  42120
gacaattatt tattcctctt tattcctctt tctccacttt ttttaatttt tgtattttag  42180
tatgagaaac ttgtaaaaag actgtatgtg attgttgtac ccctaaaact ttttctcagt  42240
atactttttt ggctggctgt ggagagaacc atttttctcc atacgtttaa tcaaataaat  42300
gttattgaaa atgtttatat taacaaatgc aaatgaaatt agctcattgt acactactct  42360
tacttctaca taatcgacac atataaacct cgatttaaaa ttcaatcatt tgttcttcca  42420
tctcctctcg aaactcaaac tcttgttata atttacgtat taagttttta ataatccttc  42480
catatacgaa tgagtcttaa actttcagct agacaagata atatgagtct gataagataa  42540
tacctgtagt ttatgatata acaattcgat tcacggattc tgccatctcc acttgttttt  42600
tttaaagcta ctgataaagt ggaaacaaat aaatgcccaa taagaaaaca gcagcatcta  42660
gtccattact cattacaatt cattgtcatt tactgcttcg ccacctgcag cattaagtac  42720
tattacagga ataatcattc gtcacttcat cttgagatat ttttatttct tggcttgttt  42780
agacagagta taattccact ccgtttttta ttaaatggag taaaagttaa aatagagtaa  42840
aaattaattt aactcaactt taaatctcat tctataataa aatttatttc ataaatagaa  42900
taatttattt tttgtttgtt catttagagt agggttgaaa tatttttact ttatttttac  42960
ttttattcta ttttaaaaga aagaatagag tattgtattg tttttctccc tcttcatctc  43020
cttagccata tgaacaatct catattttaa agttagtcac tttaaaaaga tactcggtta  43080
caatcattat cgccaagatt attcgagaat atatgtttac aaaccactga accagcatct  43140
cctcgatcaa cgagttgaat cgccgttacg cgagtacgtc cgtatttgta tcccgtgggt  43200
attacgtggg ctaagtgtcc ttgtataaac gcccattcta gactcaacaa aaaaaggccc  43260
atatagttat ccaatttcac accattattt cggttgctaa gccctttcaa agccccttcc  43320
ttcaacagct tttggttgct ataagggacg ccacgcgcgc attttgcttt cataatcctg  43380
taaataaggc atgcaaaagt ctttggagaa gagccaaggc ttatgatatg ttaggtttgc  43440
taaacaaatt ttgttattag cgattatgat caacacattg tctaatttca gtttagttaa  43500
tagtttttgg tgccaatatc tatggatttt gttcaggtat gaggcataga cacggcataa  43560
acctacctga agggcaaatg tgaagaatcc ctagaacaat ggatacaaca aggtccttga  43620
aagaagttga gaagacaaga aagaaatgtt tttttttttt ttgcttttaa cacagacagg  43680
aaatgtcttc gtatggggtt ttaatcaact tgaaggagta aagatgaaag gaagatattt  43740
ttttttgtat gggtgtgtat gttactaaag gacttttcgt agtggaaagc gggtataatt  43800
tgcctcggta cggcttgaaa tattttttga ttaaacaaat gacatttcac ctgcagagaa  43860
aataatatta catgcacccg cactatttaa ttctgtggat gactcgtggg attatcatgt  43920
ttttttttg ctaaactaaa ggaaataatc gtgggattat catgttatat caatatttat  43980
```

-continued

```
aaaaataatt tagtaatatt tataattcat ttttacaaaa aaaaaaaaaa tatttataat  44040
tcaatatata tttttgaaag tttttagttt actgatgggc aagtatcata acttaaatcc  44100
ggccgtccta cacttgcctc gcataaaata aatcaacatg cacgcgcatt tcaaatattt  44160
aaaattgttt gattcaaaca tgctcagtgg caggtttaac ctgcgggttt tgagtcaatt  44220
ttccaactct tgtcgttagg tttgtctatc tattatcttt atttagatga ctcttaaagt  44280
gttgttcatg agtgttcgtt tctttatcta gttggttcat ttgttgtgat gaattgtttt  44340
ggttgaaaat atttttacat gaggttttaa gcagcaacca aaaattgatg tttggtggcc  44400
catcgtggcg acaaggtgat aatcggcgtg gttagatggc gaggaaattt attccttaat  44460
aaactgcgta ttgagaaaat tggggcctaa cggtaacatt aaacattgaa tgcaacacta  44520
actacagaat aagtttgcta agcaaatttg tttaaaagct tcgcaaactt tctattgatt  44580
cgctgactca tctgggcgta tgctttacgt gatgcataca tatgtccttt tttaatcgtc  44640
catgtagaac gcttacgcac agtttgctca acttcctcac ttcctctatg catttcagct  44700
tttgctttct gttatgtagg aaccaatgtt tcaagttaga gttgagtgtg gaaattttta  44760
agatctaaag aaatctaacc cacaagatta ctatttattt tcactaccaa aaccaaaaat  44820
aatatcttcc taacatatat atgctgacaa caaaaaaacg tctctctcgt tgctagtcat  44880
tctcatctct ctcacgtttt tttcttcgga gaaaaaacaa ggcggcacaa atagaggtgg  44940
gaaagtttgg tgatgcaaat aaaattacac aaataatatg cgtttcttaa gaagaaagta  45000
aaacttgaaa atgacgtgac gtgacgtgac acatgtcata tattgtacgg aactgacagt  45060
ggaaccacgt cggggaccag tgctagggat ggcgttttat tacgctgtta agccacggtg  45120
ttacgatatt ttgatggggc cacgagctct gctcaattat ataagagacc catctttttt  45180
ttttgaaact aagaccaacc atctttcttg ttttggaata accgtttggg tttctattaa  45240
gtttgcggtt tgctaaaaac ggttgtttcg gttttatact caacttttgg aaacttctta  45300
tgacagtttt ttttataatg ccaatgccag tgttgacact cgtccgaaga gttacataaa  45360
gctttatcag actaatagaa ttctctcact aatctgattt acttttgttt tcttgattag  45420
aacatccgca aaaaaacttt ataacttcaa atttgctcta aaaaaagttt caaaattagt  45480
ttaacaaact tcaaaaagaa acttcaaatt tgctcttcaa aaagaaacaa ccgtttagca  45540
aaaactacta tatagagttt ttcctttcta aaaataaact tcaaattttg aaatttgaag  45600
tttttagaaa tgaaacttta tatttgaagt ttcactactc aaaatttcaa atttgaggtt  45660
tcatattttt atttacattt taaaataaag agaaacattt cttactttga aattgatcat  45720
atacgagagc cttatgaaaa taattttatg aaataatatg atattttgct cgtattttaa  45780
tatttaataa tgtaatttta tttataattt tatatattag tgtaatatct tttaattaaa  45840
attgatgtaa tatttttata tatgtgttag ttatttataa aatatttcta tatttaatta  45900
actttgacaa atataagaac catattataa aatacaaata atttaaagtt aaatttaaag  45960
ttttaatttt ggaaaaaaac acatttaaac tttcgatata aaatcttgca aacttcaaaa  46020
tagatagtct ttttggagat actgttagca gttgatatgt attaagtttt actctcctgc  46080
taacttgtta ttgtaaaatt actccaagga aaaggtttgg ttattgattc gatccgatat  46140
gtgaacccac gttttgttta cctggtttgt attaaaggaa acagtaccaa aactttaggt  46200
tctcaatggt gataataaaa cagttttagt aatataaaca ataaggaata tgagtatact  46260
gtaatccaac caagatttag gcgttacacc caataagtaa aattttcata aaataagcgg  46320
```

tacggaataa tggtgattag atatattttt tggtacaaaa taaatatttg attaaaagaa 46380
tatcaaaatt gttcgaacat tcacgaaact cacataaatt ttatttttgt ttgtttgatt 46440
tggtttaggt aataataata gaaatatata ttttgtttga attaaaaata tgaaatagta 46500
aatatctttc ttagtgaact attctttcaa aagtatatta tttttgtaaa gatatttata 46560
tgtttttcaa atcaaagtta tctaaattta tatataaatt ctaaattatt tttaaataaa 46620
aatataatat aatacatgta agataaatata tctttagttg tatttaattt aataatctgt 46680
tttctctagt aatatagtaa ttagtttttt ttgttaatta ctctatatgc taaaatagag 46740
tataattgaa atatagtcca attctattat aaaattatct taaagaaaaa aaaatgaatg 46800
tgtcattgga gatagaatta aggtatcatt ggtagagtat atatctagaa aagtttccta 46860
ccattattat tatattgata tttaacagta accttttata tgttttaatc ttaatcaaaa 46920
actagattat gacctggtat taaaaaatat ttttttaaa aaattcattt tactaattaa 46980
tatgttttaa catttatttt attgtatttg aaaatattat tttgtattta ttttatatat 47040
atgaaattat atatatatat atatatatat tacttaattt tgtttttcag ttatctcaac 47100
cttattcgtt atgatttttt taataaaacc tctccaaatt atttagataa ttatatgata 47160
tatattttga catattttaa gttatacaac ttttttaatg tcaagttatt gactttaata 47220
ttttatttat atacaaattt taatttaata tgaaatattt ttaaatttaa atgaatgtat 47280
ttttatttat taaaatataa ataaattaat tcattgattt aatttatttc atgtataaaa 47340
gaattattat ttttaaaaaa tatagttgta cttattttca aaattttctt gaattatttg 47400
agtgttttaa tcaattattt gatttactaa ataattaaaa aacaatatta ataaaaagtt 47460
attaaaaagg taagatataa ttttttttggt cacaaaatca attagtatct tatttgaaaa 47520
caaatttatt agtatgatgt tattttccat agctatcttt aacgaagttc taatgttttt 47580
ttttttaagt tttaatgttt ttattaatta ctaataacat taaaaataat atattgtatg 47640
acgaaaaatt agattcaaat gaatgtgtct attttaataa gatagattat ctaagaaacg 47700
acacatgaca tgttggtgac tttttaataa gaagagattc ttttatgtca tctctcatac 47760
tttaaaaaat aaaattattg tggttaagag attcaaagtt ttttacacca ctgctgggtg 47820
tgctctttaa gttgttgatt aatgacgatg tctagagttt taattttacc tcaaagaaaa 47880
ggtttgggct gtggatttga tgtgatgtga ccccacgttt tgtttatctg gttcacgttt 47940
ttgaaatcca tcgatataac ttataagcag cagcatgcat cgactgtagt ctttagctgt 48000
catcaagacg tttaccactc acggaagtgc tcagagatct tttgctactc ttttttcttt 48060
gttcaacgga tcttttgcta ccaaaagaga aaaaatatca aagcatagca acttttgcaa 48120
tttgaaaatg cacccaaatt ttctattatt taccaaagag cttcagagaa ttttttggct 48180
atttatggct ccgaatggta acagcggatt gagcggtgcg agacaagcgg tttgactgca 48240
gtgcagttct gacaattata aaaacgtata gatatatggt atatgtagag atttttgtta 48300
ctgtggactg cagtgcggtg cgggacgaat gttaccattc gaagcctatg aagcatccaa 48360
aaaaatttct gtacctaaat ttgttgtctt tcaaaataat tttgggaaac tcgtatatta 48420
accatacaat agtcaccttt gaactataca tgaaaatttc atacatatca ggacaaatca 48480
tggccttgta agaacgagaa ttatacataa tgaaacataa acaaattaaa attaacaact 48540
aacaactcta caaacataaa aaacattatt caaagtttaa tataaaataa cattgtttaa 48600
acttcaaaaa atattcataa ttgagcgtca agtgcagttg tgaagacata aaaacatcaa 48660
tattgaccaa ataccaaaaa tagttattaa agtaagtatt ttaattaatt atttaagtaa 48720
aacataatta ttttaggcat atgataatat catagtatac tttggataca tattaaggat 48780
tgagattgag tttggtataa attttttttt cggattttga aattttcaag ttttttttcg 48840
gatatccatt cgggttcata gtcgaatctg gtaaaattca taacttgaaa taccagagaa 48900
catgatccat tcagtattta tattgggttt ggatcggttc aaatttattt ctatcgagtc 48960
gggtttgatt tggattttcg gattcagttt agttgtccac cactaatttt ctatctaaat 49020
ttgaaatatt ttcaattatt gaactgccta ataccttcac tatttacaaa aggttttgaa 49080
acttatcgcc tatacttgtt gttctattca cacacacaca aaaaagcccg gaatttttat 49140
tttgttttct aactgtactt aacttttgat atttactatt ttaccaagag gtttccctat 49200
aatttgtgct attcataatg atgcacataa atttttctat ttattagata ccccgtaatt 49260
tttgctaaaa gaagtaacaa ctgaagtgtt ccattccata tagtttctat atacaataat 49320
acccctgctc taaaattcat ttaactcggc tgcctagggg gcgagtacac atgaatcggc 49380
caaccactgt ggtgaatcaa cataattggc catattactg gagtattttc atttttgttt 49440
ggatttttttg ttaaaactca atgtacttta gttacatttt tactgtgaaa aattacgaaa 49500
agctgtacga aatttttttca gagtttgagc ctaagttcaa ttggacgtaa gtcactcagt 49560
taccacttag accaaagagt ttttttgtat tagctacgca aataccctta tataaatata 49620
aaaagttgaa aaactaatcc cgactaattt ctgatttttt gataactcac cgaaactaat 49680
ctcatgactt ggtattcaca aaagatttat aaactttttca catttaccga gtcgcaacat 49740
tgttacagat acactcgctg tcacaacacc aacaaaatat acaaaaaaata aaggatgtcc 49800
tataaaaagg aagaatccaa aaatccaaaa aaagtactgt attatacaaa aaccggaaat 49860
aaaaaatctc tgtattaata actccaaagg gacacgtcgg tatctccgtc aaagtcatag 49920
ttatattcga attgtacgga cggtggcggc aaaagcatcc cttcggccat gctagccaac 49980
aaggtcggca tcccgaacat ggactcctcc tcgtccatat aaaacccatc gctgttttcc 50040
tccgtaaaaa tagcctccac gatcgtctcc tccacgtcca agccatgatc cttcgtcgta 50100
tcatttatct cagcctgaaa agccaccgcg gcttcagcag ccgccttctg gatatccttg 50160
gggcatgttg tctccgggat acggagccgc caagccgagt cggcgaaatt gaggcaggcg 50220
gatttgccac ggagggctat ggcggcgacg tcgtgagcac gagctgcgat ctcggcggtt 50280
aggaaagtac cgagccaaat cctagacttt ttgtttggct ccctcacctc acacacccac 50340
ttacctgagt ttctcagacg tactcctctg taaattgggt gacgcgtctc ccgaaacttc 50400
ttccgacccg caggtttctt cggacagctc gcggccagcg tcggacaata ctccccgctt 50460
aatgtaggag actcgtactc ggagcccaac atttcagaga aggcagaaaa tgaggtcatt 50520
gttaactgga taaggttgag tatagtaagg aactagaaag atctcggttc tgatgggttg 50580
ataaatgttt attttatctc tcaggtggat tctaaagttt gtagttcgat aaaaagttgg 50640
gagtgagagt tggtgtttat attggcctct ggaactagag gcgaacaaac atggagtttc 50700
tggttcctgg agtgacaagt gcgagtgtgt gacttgacac ggctaagcca tcccacggtt 50760
agtgtatgcg ctgtttttat tcactaagaa tctcacacgt gttctactga cccacaagaa 50820
atgactttttg agttttgact cttcattcgt tattaagtat ataaatttat taattttgaa 50880
aataatggac ataaacaatc tgcaaagaag atattttttag tgttctcttt ttgttttctt 50940
ccttgatatt tttaatgctc tccctatgcc ttttttttgt caataatctc catgatttta 51000
tttttcattg atattgaata tcctgtctat gtgtttttttc ttgatacatt acaaatatat 51060
aaatttatca atcgtggatc tagaaattat tttaactaga agcatatata tattaagata 51120
ataaactatt taaataaact atttttataa aaataatata actatgtaat gtttttgga 51180
cgaaatttat taaaataatt ataaaaaatt agtttatagt attaaactat atttaaactt 51240
agtatctaca acatacacat acagtaatat aatatcaaat cattcacaca tcacagagta 51300
gaaaacgaat gattttatag tatattgaaa acaagagagt tttctttcaa aacatttcta 51360
tctttctctt tctttttatg tcgtttcaat ggaaaaaaaa actagatgaa atatttcgtt 51420
tgaacttgcc ctagatcttt tcatttattt ttcaatatac aatacaaaat cacttatttt 51480
cttttctcat gatactggtc caatagtaat ttggagtagg taaagaacaa tttgtaaaat 51540
atacagttat gattagttct gttcaaataa aaacatagta ttcgattgcg tttctcttat 51600
ccagtcagat ggttcttaaa gtactaggta gtataatata ataatataag ttaatctaag 51660
atgaattgag cgaataattg agcgaaaata attgaccaca ggattagacc gatagaaaag 51720
caaaaaaaaa catcactctc atttgctaaa aaaaaacatc actctcaatc tcaaaatata 51780
tcgataaaat atctgaaatc aaaataatat ctttttcttt tttttgaaca catcaaaata 51840
atatctatga aaaaaatcgt ggtctaaacc taaatcacgt ggtgtgagta tttaaagccg 51900
gacgatcgat caaacttaca agattttata ttcttactat aaatccagaa agtagtttat 51960
attcctaagt ataatggaaa caagaactta accaaaccaa aaaaaaactg aataatcttt 52020
tttctgtaaa ctaaatacaa aactgtgtca aattttatac atatctattt ttttaaaaaa 52080
tatccaaaat ttagaagaat tgaatcaaaa accaagtgga atatcaaaga ttttattagt 52140
atagatatct ttatcaacat gtatctaaaa tttcttctaa ttaaattaat aacaagggat 52200
gataaaaaca tgggaaatgg tgggaatgca accattatca tgagagtaac tgagatctta 52260
ttatggtaag tttaagaata ggtataatta taagattaat ggtttattaa gtagtgatat 52320
aattatataa gatttgaatg gtacatgtga gaattatata acatgaagca acattgttat 52380
aatttacggt gtcgggtcca gactcttccg gcgtttaaag cagataaaaa aactgatgcc 52440
ccttaactat agtaaaattt tactatattt taaatttata atcaaaataa tgctaaatat 52500
tattacaatt tatgatattt ttaaagaaat aaaatgcaaa acatcaaaac attttgcagc 52560
tcctctagac tgtttttcct tctcattgtg ttcataaaat ttcacaaaaa ttgtttatat 52620
atgggtttat tcagttgaac tcatcagagt attattatca tagtccaacc accaagcatg 52680
aatcttgtgc attcttttca aacttataat ggtttataca ccatctttta tattatatta 52740
tttcgaagct ttttttaccg taagtttttt tctgactcta catctagctt attcagtttc 52800
ggaatcaaaa agataaaaac gttttctttt ctaaaatagt agtgtttttt aaaccagacc 52860
ggtctgatgg ttgaaccggg tttgaccatg aaccggttgc atagcagggt tggaactaat 52920
aattggtttg accatgaatc ggttacgtag ccggattcga tctcaaagtt attaaactga 52980
taaaaatcat taaaactatc aaaaatcaat ataccattca tttaaacata aaacaagttt 53040
atatttttaa tattttatca tatttcattt atatttttaa ttatgtatca tatttactaa 53100
cattaatttt aaacttatac actaaaacat agaaagatta tagaaaacaa actattaaat 53160
ttttttgaca cacacaaaag aaaaggatta taccaacatg ttttattatt tctggtatca 53220
ttcataaggt gaaaacaaaa atcaaatata accataatag ttgtaaaata tactagttaa 53280
atacgtttta attataccaa ttataccgat tgtaatagct atattcgttt tagttgtact 53340
agttatatta tttttttgtc ataacaacca atgaaaaatt attgattgaa gaagattatg 53400
agttaatata ttttcgttga attgtatttt tttggtgaat catgtttttg aaagtattat 53460
aagatgaaga agatgaaaat agattttttt ttgatttaat gtaaaaaata tccagaaatg 53520
aactggtttg gtgatagata gcaaaaataa atttaacaat gtatcacctt tcgttgacaa 53580
aaaaaaaaaa aacaatgaat cacctttctc atttaaaaat aataaaaata ataagaaata 53640
taagtattgt agaattttaa taagccacta cgggcacata agaatttgat cccacacctt 53700
tgtgacaacg cctcggcgct ctggaacttt ctcgtcgcaa cattctcttg actggctcaa 53760
gtttgacctc ctgttaatcg taagatcttt ttcatgaata cgattcctct agatttgttt 53820
tcgtttcctt tttgtttctt gattttgttg ctacgaactc ttagggtctg cgatgcttgt 53880
gctttgcgat agctctctat atctcttaga ttcttttcaa gaaagttgat agcttcatag 53940
attaagtatt agatctctga aaaatttgca actttggaat aacagtgttt cggcttaaat 54000
tgctgcacat aagatgttcg acgatattcc tctgagaaga taactactag acatgctttt 54060
gttttccaag tttcggtttg attttactga acagtaatca catacgcatc tctttatgga 54120
tgagacccac cacatgtata aggaagtgac cattttattt tggcaggttc actgtttcag 54180
tagccatggc aaagcatcac cctgatctga tcatgtgccg gaaacaaccc ggcattgcca 54240
tcggacgact gtgtgagaaa tgcgacggga aatgcgtggt gtgtgattct tacgtgcgtc 54300
cctgcactct ggtgcgtatt tgcgacgaat gcaactacgg gtcgttccaa ggacggtgta 54360
ctatttgcgg aggggttggg atctcggatg cttactactg caaagagtgt acgcagcagg 54420
agaaagacag agatggttgt cccaagattg tcaaccttgg gagtgccaag acggatctct 54480
tctatgaacg taagaagtat ggattcaaga aacgatgaag atgtattggt ttgcccgatt 54540
gctggatctc ttatgctatg tctgttgcat gataaaacta atatgtattg ggtataaaaa 54600
acccatacat tatgctttct ttttcttgat aatctagact ttattggact tatcttagtg 54660
tctaaatagt ctcttgcgtt gtgtatcgtg tttgatttca tcacaccaca gtagaagtag 54720
gcatgttctt ggactcttaa tcatgttttg attgaataca aaattactaa actacatgta 54780
ccgctcaaat gcaatcatgt taaaacataa taaattttag tttatccaaa ctgtgcgagt 54840
ttaaataaat aaaaatgtta ctaaatactc aatccgttcc acaaagatcg attttttttag 54900
tatttttacg tatattaaaa aaatacatta aaccgtcata attagtgtat cattttcaaa 54960
aaaattaatt gattttattg aattatcatt ggttaaaagt tattaaaaca taaaacaaat 55020
ttttttttcta aaaagtctat catgacggat ggagtaatcg aaaggactgg tgtaacaaac 55080
aagagtgttt gaggaattgt tgtgatcact tgattagcgg atgcagtagt ggttgactga 55140
tcattttctt atataaactt gggtctgttt caaatgtaaa tcgtgggtct atttatttgc 55200
agtggtttaa aaatgaaaga tcatcgcatg aactaatttg atgattatgg gctatctctt 55260
ttttctaaac ccagaaaagt ttataagata gatgggccca aagcctgtta agaatcgtat 55320
tatattattt taaaaataga agcaagaaaa gaagaaagat gaaacttctc cttcagctga 55380
tacagatctt ctagacagag acatattcaa atgcttccaa agctcaggga aaattcctaa 55440
atcagattcc atcactttga ccaaatacta agaagaagaa agatgttctt gatcaagaac 55500
ctcagacgaa tctcgccgac aacctcctcg gccctgatcg gcttccgaaa caccggatca 55560
ccccctctct cctcccgttt ctgcaccact ctgaatcaac cccaacaggt ccagactccg 55620
gctcccaatg gattggatcg gagccgttac gaaggtttgg caccgacgag agaaggagag 55680
aaaccgagag tggtggttct cgggtcgggc tgggcgggtt gtcgtttgat gaaagggatc 55740
gatacgagca tctacgacgt cgtttgcgtt tcccctagga accacatggt cttcactcct 55800

-continued ctcctcgctt ctacctgcgt aggcactctc gagttcaggt ccgtcgctga gcctatctct 55860
cgtatccagc ctgccatctc gagagagccc ggctcgttct tcttcctcgc taattgctct 55920
cgccttgatg ctgattctca tgaggtatta ttactgtggg aatcatctga atctcagcat 55980
ttgtaactga accggaaaat tcgaattgaa ccgatccata ccgaaattga ttttgtaggg 56040
ttgtatttgg gatgtcccaa aaaaaaccaa acaggaaaac ccaaaaaaac tgaacctata 56100
taaatactct ttttttagga acacctatat aaatgcttta aatattcaat cttataagtt 56160
attttgatgg attttgtaat aatatccgaa tccgaagtat tattaatcaa acttgaaaag 56220
gttcagatct tagacaatgt tataaaattt actagaatcc gaagtattat taaccgaatt 56280
atgatccaaa cgtatatttt ttccgtttct aaaaaattca tattttagga ttttcacatt 56340
tattaagaaa atatatcaaa ttttagttac ttatacatta ttttccgtaa ccaactattt 56400
cccacaagtt ttcaccaata gaattttaat aaatacaatt atgtttttttg aagtttacaa 56460 tttacattta atttatgcat tgaaaatatg aaaatctatc tttttgaaac aatttttttt 56520
tctaaaacat ggatatttta ggaacggaga gagtataaaa attcttctgg aaccgaaccc 56580
gaaagctcat gcacttttga tgaaaaatat ctttgcacgc tttcttaaat gtttgtcatt 56640
ggggataggt tcactgtgag actttaactg atggcttgaa cacattaaag ccgtggaagt 56700
tcaagatagc ttatgacaag cttgtggtag cttgcggtgc agaggcctcc acttttggaa 56760
tccaaggagt tctagaaaac gccatctttc tccgtgaggt tcaccatgct caggagattc 56820
gcaggaagct tcttctaaac ctcatgctct ctgatactcc tggtaagtga taaacaaata 56880
atgttatatt tctcatgaag aatcaaaatt attagcacag aacactttgt tttaaattag 56940
gaatatcgaa agaggagaaa cagaggctgc tccattgcgt tgtggttgga ggtggaccaa 57000
ctggggtgga gttcagcggt gaactcagtg acttcatcat gaaagatgtt cgtcaacggt 57060
atgctcatgt gaaggacgat gttcatgtta ctttgataga ggtttgtttt caagaagctg 57120
cttcttcagg ttcctcctta tgtgtgtttc atcacttcac aattgtctct gttttatgtg 57180
attatttaca ggccaaggat atactttctt cattcgatga tcgtctcaga cgctatgcta 57240
tcaagcagtt gaacaaagtg agttcattaa tggttttaaa aatcaatcta ggcggcaaat 57300
cgtagtcgaa acattttttt tttaaatccg attatacgat tcaaaccagt ataaaccatt 57360
cttaatcggt ttaaattgat ttaaaatagt ttaaatctgt taaattaaat aatcatgtta 57420
gtacagattc acaacttgtc ttaatttttt tgttttgtat tatctaattt tgataataca 57480
tcgaaataat tatataatta aatccaaaaa ctaagtatct tatataaata taaaataaat 57540
caataattca cttaatcatt agttttctac attataccgc ctagcgattt cttgtggtta 57600
atttataaga cgtgaaatgt ttctgtgctc attattatgc tgcattcata tacattatta 57660
gtctggagtg cggtttgtgc gtgggattgt gaaagatgtg aagccgcaga agctaatcct 57720
tgacgatggc acagaagttc cctacggact cttagtatgg tccactggtg taggtccttc 57780
tccttttgtt agttctcttg atcttccaaa agctcctggt ggaaggttag ctcatcaaca 57840
tcactacatt agaccctttt ttttttgcga aaaatattcc acatcggcta agactttttc 57900
tatctttttg tccctgtata gaattggtat tgaccaatgg atgcgtgtac cttctgtaca 57960
agacgtgttt gccattggtg actgcagtgg atatcttgag accactggaa aaccaaccct 58020
tcctgctctt gctcaggtaa actttttaga tagataagct tcataatcgt ctataccttc 58080
tcatgccttg ttatactacg ttactgctca attaaggtag ctgagagaga aggcaaatac 58140
ttggcgaatc tactaaatga gattgggaaa gccaatggag gacgagccaa cagtgcaaag 58200

```
gagatagcac ttggagttcc ttttgtgtat aagcaccttg gaagcatggc aacaatcggt  58260
agatacaaag ccctagtgga cctccgcgag agcaaggtaa caaatatttg actatgattc  58320
acctcgtaaa acaatgtggg gttgagagag attacttggg caggacgcaa aagggatatc  58380
aatgactggt ttcgtgagct ggttcatatg gagatccgct tatctgactc gagtcatcag  58440
ctggagaaac cgcttctatg ttgctattaa ctggttcact actttcgtct ttggccgtga  58500
cattagccgt atctgatgtg tccgaatcca ccagtgtgtt ttgacctcgg tttactttac  58560
acgtcgtcgt tttttgtaca aaattacaat aacacaatct tctgaagact gagaaggttt  58620
taaattatcc tcttttttt ttgttgttac taataatatc tttggttgtt gcgatttcgt  58680
ttgaagaaaa aagaataatt cagggttaaa tattttttc agggttaaac aataagtatc  58740
tggaaaataa ttatcagtta tggattagac agatgcccta aagagtttat atttaaagtt  58800
tctattttga ttgaattaga aaatattatt tatagtttta atatgatatc ttaaacaatt  58860
ttttgcatca aagtaggata gttgctgttt taatttttaa tgtaaaatca agttggtctg  58920
caagggaaga catccaagcg accgcttagg acatataatt ttaaaagaca tatttttata  58980
tatttatttt tattcagaac ttcgatagtg tttatatgta aaaatattta taatattttt  59040
gataataata atatttgtaa gaatttttac cctcgttaat agaactctca ctaacaaata  59100
aattggaaaa atgtattgat aaataatgat tattttaaaa tgtaaaattt tgcgtgaaat  59160
atttatggta atgttaacta atattgatgt gcagttaatt tattaaaaat atgtttacca  59220
attagtagtt gaccaaattg gtttatcaag ttttaatgtg atttatatca tatagatatg  59280
atattagata aaacataaac atatatatta tttgcagaaa ggctaaccta aaaagaaaat  59340
ggataaggat catgatgact atcccaccat gcttgttgag atagtacctc ttaagatatt  59400
ttgaatttca atttatcaaa tagatacttt attgattgaa aatagcaatg ttagtagctt  59460
aaggtatagt attaaagatc aaatgggctt tgaatcattc ggactacgta tgtccaatag  59520
aggtttatcg gctctatacg ctgaaatgaa aggactatta tgacagtatc atgcatgaga  59580
gacgagaggg ttcctttggt ctggtttcaa atggattgct cagatttagt ggatatgact  59640
acgagatcga tagactggct gtttttgct ttggatattg gtgtgtttcg gagtttacat  59700
gatgattttg agagcatgag catgtacttt ttagaaaaac gtctcatcta atccatatat  59760
ggtctagtga tatgaatagc tgataaaaaa aaagataaat tgatttttaa ttttaatctt  59820
tctggttctg aaccggattg tagatttatt tatttattta ttttagttgc tttttctttt  59880
tttccacaaa ttttttatt ttaataccaa aaaatttaac atatctaatt tgaaaacttt  59940
tgtcaaaaaa atcttagggt atccaaagat gttagatcaa cactatgtaa atttacacga  60000
tttatattag gtttgttttg tagatagatt ccctaaggct aaaacatcag aaaataaagg  60060
taatatttag ttgcccaaaa aaaaaggtaa tgttaaatat tggatcttat atattcacat  60120
gttcatgtca gttgccacgc atgctcatgt actactatgt gtgtgcttgc aattcaataa  60180
acaatgtcgt cgtatttaat atttctgaaa agtctttgta gtttgttatt cttaaaacta  60240
tataaaaaga tgttttttt ccaaatcgtt ttacacggaa acataatgca aagtaatatt  60300
attttaagaa aaggtctcat gtacagttaa cgaaaggaca agatagggaa taaagtgaga  60360
aaatacaata ataaacaaag aaatgaatat tgaaatattg gtctataaaa tctcaggacg  60420
gctacggtga caatgtctaa aactcatttg gtctctctta tgtccaaatc agattttttt  60480
tctctgaaag aaggtctacc aaatcaaact tcttctctac cgattgctaa acgactcaca  60540
```

-continued

```
ttcatcacgt acataactaa tattttctct gtttcaaaaa aaagatgcat gttttataat  60600
tcttatacat attaaaaaaa atatgaaatt ttgattacta atatagatta atttttgtaa  60660
ctaactattt ctcctaattt ttaatcaata gaattttaat aaacacaatt atatttttca  60720
aagtttataa tttatcatta attaatacat tgaaaatata aaaaatacat ttttagacaa  60780
tttttttcta aaacatgaac tttttggaa cagaagaaat aattgtcttc gtaaatatct  60840
ttttgcctaa tcgttataaa actttaaata tataaatggg agaatatatc gtttagatcc  60900
gataccaaag ggtttgtca attatttacg aacgaaaatg gcatgaaaat gcctatgtat  60960
ttcaatcaag gcccttaaat caactgtttt ctctcagcaa aagtaagaaa aaacgatttc  61020
aagactccag actcatgatg ctatttgaga aaataattac ctcttattca tctagttcat  61080
gtttttaatg catatatgta aaaagatgaa agtgaccaaa tgtgccagca aaaacaggac  61140
tatgacttta cctttcagct ctattattta aactttgctt atctttcccc caaccaacta  61200
agaaaccttt gtctactttt ttgtagacat ttgcgcaaga gtcagtgtga acttattgat  61260
tcggggaagc aaactcatta ctaaaggcat cattatcagt ggatttctac agctgagtat  61320
ttagacattc gtttattaat attttaaaat aaaagaattt ttataatcat tctacagctg  61380
agtttatgaa cattaacagt agatttctac agagaagttt gaaatagtct tgtatcagtg  61440
acaaaatgcc taatgaattt atggtttctc aatatctcta aagagtttct cagcaaaaag  61500
acaattctca ttttttactt ttatgatatt tttaatacaa aaaactcatg aaagaaatgc  61560
caataaaaca aggggcaatt tgttggataa ccatagtagg aaaacaatta acaggtaata  61620
aaagaatata aactctgaaa cgtttggttg attgaagcaa tgtagtaaat ctgaaactta  61680
tttggttgat ccaaaccgaa acctgttctc tctaatggga gtatgcgtcg ttgtaagata  61740
ttcaccgtga tcatttacaa gttgacagaa acaaaaactt tttcctaggg aaaatattga  61800
tgaatcgaaa aaaggagaaa gcctcgaacg agatgtcatt gtttagggcc aaataattaa  61860
ctggataatt agagatttgt tagaaagtaa agccattgct tctttaggaa tagaagacaa  61920
cgtgtttcgt cgtttacacg tgcacgtaca acatcccatc tttctttttc ttgtccaaag  61980
ccatcactct ttttttctga acaactcttt gaattgttta atttacatct aattatcttc  62040
aaaaattggc ttgattaatc acatgagatt ggtctaatgg tatgtagact acagagagat  62100
ccgggttcac taaacctgta taatcataag gatatggacc attgtttaca acccatttaa  62160
aatatgaaag aaaatcaatc catgacttcc ccttagaaaa ttaatatgga ctcttccata  62220
atagtatctt tgaaaaatat atactctgtt agatataaac catacatata aatggtttgt  62280
gatgctgaag agacatgtat tcatgaagtg atcgtgatct ttaactgttc tttttcttaa  62340
tggttgtatc tttaactgtg ctttgtattg atagattagc cacgttttta ttcaacgcac  62400
acatattatg acgaatatta agggctttaa tgtacgcctt tcacctttgg tggaccacta  62460
atccatgtta atgattttgt tatgagaagt atagaagcaa ttcacttatg acaaattgac  62520
aatatagggt ttcggaactt cggttccgcg cgaatctcct ccaaaacaat gaaaaaaact  62580
cagtttgtat gggcctagct agaaacaatg gtctctggtg ctatgaattc gaacattctg  62640
gtgctatgaa ttcgaacatt cttttgaatt catatgatcc tctacaaggt ctgaaccaag  62700
ctactctacg gtccatgact ggcttgcgca actttagtgt agtccagggt ttttttgtc  62760
gtggtgatga gtctatatgt ggttggaagg ttcatgcagt acaataaatc tttgttttag  62820
cgagctgttg tatatgtggt acacgaaaag acatcattct tacgacgtgt tctataccaa  62880
ctacattccc tcaacacttg tattggtttg ttcgtctgaa tcaacaattg tgtcttttaa  62940
```

atgattttta tgattagttc aaaacccaaa atagttaact aacggggcaa aaatggtaac 63000
gaatagctta actgattata ttttccttta taaccctaca cattagagat atttcagtgt 63060
aatatataag ttactagata ataacccgcg cattgtgcgg gatgtgatta ttagttttct 63120
tatttttaat aaaaagacat taaatctatt taatctagat attagttcgg ttttaagttt 63180
ttttttggat tttaatcttc taaaataaac tattatttta aattaatatt cattttagtt 63240
tattcggtta aaatgtttga ttttttttta tccggtaaaa accaaaaatt aatattattt 63300
atttattttc atgttatgaa ttttagatag tcgtcatgtc aaaccaatag attcatatta 63360
ttgtttctaa acagataata gttaagaaaa ttattaagac aaattatttc actacaattt 63420
ggttggtagt gaaagaagca ttaagaaaaa atattttaac tttcaaaaaa aaattagata 63480
cttcagttgt ggtgaatact tagttataag gtgctcacat caaaatgcac atgtatgtgt 63540
atgtaaaagt atatataaat agttgacaaa tatataaaga tattgttagt taataataaa 63600
tgacattttt ttttcaaaac aatacatgaa agataaaatt aaaattaatt taaaataaaa 63660
aggcattgac gttagtcatt tttttatata aataaattaa aattggatcc gtaaatagag 63720
gtggacacat atcgaatatc tgggtatttg gaaacattcg tgtcgattcg atctttagcc 63780
acctagatat tcggtgactc ggatatccaa aatattttag aattttaaag aatatccgat 63840
ttgatccgta aataaaataa aattttaaaa ataattttaa taataaaatt ttattacaaa 63900
aataaaacat tatttaactt tttaaattat agtacctaat ataataaatt taattcatta 63960
aaatattgta aaactaatat aaagtataat atataacgta tatatataat tctgtacata 64020
tatgtatata tatgcatata acatagcaaa ttagatattt gttcctaaaa atattggtat 64080
ttgtgatttg cttctttttg gatattgtat tttagtattt gatttatttc ctagagttaa 64140
gtatatccag attttttggt tcaaatcaaa acggataaca aatcgaatcg aaatttatga 64200
atattttgct caattttatc tgtaaacaat aaaaataaca tatatatatg gtttggcttt 64260
tgatttgtta tctattttta ttcgaaccga aaaatctaga gttttattga aaccatgtat 64320
gtgagattta tgttaaaaaa aatgcaaaat acatagtgtg cacacattta tgaatatagt 64380
atgaacgcgt tagtatattt attatcaaat cattgtgagg ctgccacgtg tctattatag 64440
tgtgaatgta tttattacaa tgcttctctt ttaatataca agggattttc attgtaattt 64500
gcaaatttat aacaggcagc atattccccg ggcctactct tcatattatt tttggtgagt 64560
agcgtaatca tagatagttt tcttaattct tgaacttggg taacatcgtg ggtatctacg 64620
aaatgattcc tttcgacgta cacgatttat agataaacac gtagagacgt gtataataag 64680
cgagaaactt atttagcagt gttagagaaa tatttgagtt aacagactat agaaccttta 64740
taaattagta ttcaataaat taatattttt aatattcaat aattaatatt ttaatcttca 64800
gtaaaaaaat ataatattcg ataacttagt attcaataaa ttaatatttt caataaatta 64860
atattcaaaa aattaacatt tataaaaaat cattaaatta tattgtctca ttacaattgt 64920
aaattaataa ctgatgtata aaaattatat aaacataaca aaatattgtt atgtatggtt 64980
tttatttaaa atgaaactaa ttctaatttt ttcaacactt caaagtattt tataattata 65040
tatttaaaaa tattaacatt atgtgattca tattatatat atgtcaaata atttaataaa 65100
cactatgaaa gctaagttta caaaacttaa ttaatatata attcacgaaa aaatctattc 65160
cttttatttt acatataaac atattttaaa atatataaat ctaagtatga tattttgata 65220
aattactaat tttataaatt aaatattata gttcattaag tattttgaat aattattgga 65280

-continued

```
tctttaagta ttttgaataa ttattcaaaa ttgactcatt ttgtttttta agatttttaa  65340
aaaattgagt tttttttttcg atttccgtta gaatttgatt tgggtaaaaa ctaaaatctg  65400
aaataccata gaataataac catttggata cttatgtcga attcaaaaca gtttaattct  65460
caggttcaaa ttttcatatt gtttttttcat accatagaat aatagccatt tggatactta  65520
tgtctaaaag taatataatc tgagacaaaa tataaaaata taaggattta tatatttcaa  65580
ccatatggat atggttgtgt gatacgaaag tgttagacat tatcgatttg aaatctatca  65640
ttcagatttg tcttttacat ggttaaaggg tgtgtgaata taaaactttc acgtagaaca  65700
acggatttat ctgttgcctg aaaaacaggc taaacactct attatgatta gtcttagatt  65760
taggacaccc ctggtccata aaaaaggtct tacatattta ctttcgcata catatttttc  65820
taatttaatt tcactgaata gaacgatgta acaaagtaac aaacccattg catttaaaat  65880
tacagcaaat tatccttttt ttaaatatat aattatttct ttaaatatat atatattttt  65940
ttattttttt ttcaacaaat atataattat taaaaaaaac agttttgagt atctcaatca  66000
attctacaga cttacacatc ctccttcccc tttatataaa gaaacttcag acctcaaaat  66060
acatcgaacc ctttcttcac cacattccac ttcccacact ctcttttttt ttgaattata  66120
gagagagaat cctcctccaa atctctctct ctcccaggat ggttgttgct atggaccaac  66180
gcaccaatgt gaacggagat gccggtgccc ggaaggaaga agggtttgat ccgagcgcac  66240
aaccgccgtt taagatcggg gacataaggg ctgcgattcc taagcattgt tgggtgaaaa  66300
gtcctttgag atctatgagc tacgtagcca gagacatttg tgccgtcgcg gctttggcca  66360
ttgccgccgt gtattttgat agctggttcc tctgtcctct ctattgggtc gcccaaggaa  66420
cccttttctg ggccatcttc gtcctcggcc acgactggta aagtttcttc cattttgcat  66480
tgcatcgatt tattgaatgc acgttctacg agtattgttt gtcagttact tcgtaaaatg  66540
attcttttga tgttcatttt ttgaagatct aagatttttt ttttagattt tctttttaaa  66600
tcattgttcc accaccacct ttcatcggtc gtacgactcg ttacaacacc acatctttat  66660
tttctataat tactactgct tccgcatttt atggatctct caacttataa ttaaagtata  66720
atatcaagaa tatctattat ttttcttaaa caagaaagat aatattgttt ctttgttatt  66780
ttggtgtatt tccaatctat ttcgagattt agaaatgtga cacgtcatta ccttgttgaa  66840
gtgtttaaaa caaacatgga aagtttaaat aaatagtgca ataaatgata tatatgtata  66900
tgatgaataa tgatgtgaaa tataattgaa taatggcagt ggacatggga gtttctcaga  66960
cattcctctg ctgaatagtg tggttggcca tattcttcat tccttcatcc tcgttcctta  67020
ccatggttgg taagtcagct tatcaaccct ttttactata ttattaatta ttaaacttgc  67080
atttgtatac ttggtgcaag ttggtaaatg taatctgata actgaaaatc tattcattgc  67140
tcgttctatt tttttttttgg ctagagacaa ttttataatt aaataatgca tgtgagaata  67200
tgactattta tgtgaggtag cttttcttat tcctgtcgaa aagcatcaaa tctttagcaa  67260
cgaaggaaaa aggaatcaaa tttttttatta aatgcaatgg gtctatgtct tggtcattag  67320
tttttttgcat ataatttatt tatattttttt tcttaacagc agctaattta attataatta  67380
aatattcatt ttataaataa tattagacca attattaaag gttagatatt ttaagaatta  67440
ttcatgactt tgtttattgg aactcctttt atcttttaat cttttctatt tctccatttt  67500
taataatgag aaactgactt caaatctcca ataaagatgg tcttatgtag taacagtata  67560
atttttttgtt tggtaaatgt aacatcatct tcaaatatct ttgaaaatag acttacatgc  67620
attattttgc tgcgacatta ttgtcactta ttcctggcaa taaattagtt tattactgaa  67680
```

-continued

```
cttttttttg gtcaatttat tactagtaac tttaaactta aaagagtgag attgtttgat  67740
caaaaaaaat aaaaatagag tgagatagtt agaatctgcc atgaaagcaa cactatatag  67800
acaatttaat ttttatgaaa acacatttaa taatttgagg ctgcaggaga ataagccatc  67860
ggacacacca ccagaaccat ggccatgttg aaaacgacga gtcttgggtt ccggtaacat  67920
ttccctcttt aataatttct atttttctgt caaaataatt agtttttcga aatttgaggc  67980
cagaacgacc acttgtcaaa tttgattttt agctgtagta aaaacagttt gctagtgtca  68040
cagttaaccg gtaattgatt ctttttaacg atttatagaa gtaacatttt tgtaaaataa  68100
aatatacatt atggtatgtg acaacggacc acgcttattt gtattggtga atcttttaat  68160
tactccctcc aatttatttt agttgcagat ttagatttat gcacatagat taataaaaat  68220
attttgcaca ttttcaaaat aaaaacacca ttacttatac aactaaccat atttcaacca  68280
ataaaaataa attagaaaat attatttata aattttgtat tgaaattata aaataatact  68340
tattttaaaa cgaaattaat ttacaacgac aattaaactg aaacggaaag aaattattaa  68400
tacttaatta aagagttttt agaaaaattg aaagacatgt ttatgcgaaa ctcatgtgaa  68460
agtctttgaa ataatagatt ttggtataaa tatttcaaat tttcttaaaa taataattat  68520
atattaatat aatttgtgat aaaatctcgt caaaaactca ctaatgcaaa tgcttttatt  68580
ttgaatttct tactcctcta aatgcattta cttttatact aatattattt tctttctcta  68640
atttggcgtt tcgtaatagt ttgtctgtat tttgaaaact aacaaaaaat aataaaaaca  68700
aaagcttata aacacatagc atgcaatgaa tatgtacgaa tatatatacc aatacatatc  68760
taagtactat ttttccaagt acttaatctt gattactaaa attcatttta attgttcctt  68820
tcagttacca gaaaggttat acaagaattt accccacagt actcggatgc tcagatacac  68880
tgtccctctg cccatgctcg cttacccgat ctatctggta ttttttaatt cctaaaattt  68940
actacaagtc attttagact gtgttttaaa acaatataat tatttttgtt tggttttact  69000
gcagtggtac agaagtcctg gaaaagaagg gtcacatttt aacccataca gtggtttatt  69060
tgctccaagc gagagaaagc ttattgcaac ttcgactact tgctggtcca taatgttggc  69120
aattcttatc tgtctttcct tcctcgttgg tccagtcaca gttctcaaag tatacggtgt  69180
tccttacatt gtaagtttct tagtatatca taaagggtat atatttatta ttcaatatat  69240
atactatatg atttgttttt gtcatatatt tttgaaatat tcagatcttt gtgatgtggt  69300
tggacgctgt cacttacttg catcaccatg gtcatgatga gaagttgcct tggtacagag  69360
gcaaggtaat taaattaact attacaagta ttttacaaaa aactaatgat tagtatattt  69420
gattaatctt aattcttgat gttttgtgat taataatagg aatggagtta cttacgtgga  69480
ggattaacaa ctattgatag agattacgga attttcaaca acattcatca cgacattgga  69540
actcacgtga tccatcatct ttttcccacaa atccctcact atcacttggt cgatgctgtg  69600
agtcatctca ctctctggct actttcatca aaaccatttg attaaagggt gattaattac  69660
taatgtagtg attttaacaa atggaatgtg acagacaaaa gcagctaaac atgtgttggg  69720
aagatactac agagaaccaa agacgtcagg agcaataccg atccacttgg tggagagttt  69780
ggtagcaagt attaagaaag atcattacgt cagtgacact ggtgacattg tcttctacga  69840
gactgatcca gatctctacg tttatgcttc tgtcaaatcg aaaatcaatt aaactttctt  69900
ccccctttt gtttagcact attatgaata aaccagtttt ttttacttat atattgttgt  69960
ttttaagtta aaaatgtact cgtgaaactc ttcttaattt agatattatt ccatttacac  70020
```

tgaaaaacat acaatttcaa aggttgaaaa gaaagacaaa attttctaga atgaccctaa 70080
aatccctttt atcacaaata tagtcttcaa ggatcaaaat taccaacata tttcattaaa 70140
aagtaaatag acacttatac tcttagagtt aaaaaatagc ttcaaaaaat ttttgaattt 70200
caaaataaaa ttttgaaaca aaattcgaaa aatgtttcat gcacctatgt atatgtgtct 70260
gtgtctgtgc catcgttgtc caaatgtaag tttgcacgat cagtagtatt cgtgacttga 70320
gcatctatgt catgctctcc attcccacat gattttagag agttatgttt catgtcacag 70380
cgggggatct agagtttgca tgggttgatt gcgggttcag aaccttcgtc cagttcccct 70440
agctgcggtc aaagtagagt tttctctttg gaggaccatg tactctgctt cgagctgagt 70500
tagtctctaa gcactttatt ctagcggttt ggaatttctt tccatctgct attttaagtt 70560
ttgaacctct gaggtgactc ttggattgca tgtagtggta ttattgtttg ccgtagctga 70620
gttcatctct tcaacttact tctccaaggc ttcaagataa gcttggaaaa ttgctcatgt 70680
attaatctat gtgactatgt ctagcaatgt acgcacaatc ggtataaaat tttaatagtt 70740
tattttttgg tcaacaaatt tttaatagtt tttttgacca aaatattttt aatggttttt 70800
aatatgtatt tctaatggaa aaactgatta aaatggtttt ccaaaaacgt caatgaaatt 70860
attaattttg taaataaaat ataggattat ataaattagc gttatgtgag tattgactta 70920
gtaataacaa taatcaatta taagtctaag ctcaatgtga tgattttttt tttttgcttg 70980
aaatgtaatg acgatgatga aaaaaattcg caatataaat aaaaagttaa tactttgtaa 71040
tcataaattt atctttagaa aatttattgc attgtattaa agctttacat tgttttgtct 71100
cttcataaaa aaattaccaa atttttttaa gtaatcttat aagaaaagaa aagtctgtaa 71160
caaatataca aagctggatt atttcaatat attatttgag aaatattaca atatttgagc 71220
tatgtcatgt gtcattatta gaatgctttt taaattatct agaaacataa gttgatctat 71280
ctaaacatat attatacttc tcattagact aattatacaa tcaaattaat aatctacaat 71340
taatattttc attctttcct tagaaaaaac tacggaatta cctaatgtga ttcaaatata 71400
tatttgacaa ataatgactt ataataataa gtatttgata acaatttgtc tatcctcaat 71460
cattttgttt aattttatat tattaaaata aagtaaacaa tcacattaac catataataa 71520
aatttagatt tttagtatat aaccacatta aaatgtgacc agtgatttaa atttcttgtt 71580
ataagaatat ataaatgatt ataaaaccat atgagtgaaa atttcattta ataatcattc 71640
agatatatat ctacatatta aactatatac catataaaat aaataaatat tttaatttca 71700
attgcattga agaagtattg aaaacttaaa attttaattg caaaattttc attgaatttt 71760
tataaattat taaaactatt aaaaatcaca cattgaaaat ttgttagtat tggttttgaa 71820
atttgctat aagcatatat aaataattat aaaaatatat aagtagaaag tctgatttaa 71880
tagatagtca tattaaaata tatattatat atctatgttg ttattatata aatttaatta 71940
tatatcacat aaaatagata aaagtgattg cttgaattta tttagcataa aattattcta 72000
aacaaataag agtaattgtt ttggtttatg tgtttgcgct ggtttaaata tatatacaat 72060
agttaatggt ttctcaatta ttcaatatat atatatatta tttcataata tataaaaaat 72120
aaaataaata ataatatata aaaataattt gtatatacaa taatcattct gtgaaggaat 72180
tttaaactag taaattatat tacttcagtt tgactttcct tttcgaggta ttaatagttg 72240
ttgcttggta aggaatgtca aaagtcaaaa ctaatagtca gagtcaaaaa catatcatct 72300
ccagtatagt atataatcaa aaaggatcca tatatttaaa gaatatttca aatatatata 72360
tgaaaggttt tagactcttc atattcataa gaaaaaacta aaacaataaa gacaaaaaaa 72420
tcaaaatgat atcaataaga aaatgttatt ttttggcgtt cttgtgtttg gcgattctct 72480
tgactctaag tatgcaatat atgttgatta ttttgtttct atttgttatt atattatata 72540
tcccttcatg tatgtagtgt aacatattat ataggtttcg gttaaagtat atacatttgt 72600
ttgttatagg ataagtcttt gagatattga attgtacact aacaaaaaaa tcatgttctt 72660
aaataactcc ctaatttctt tttaaaaata tatgctcaga tcttgcggaa gctcaagata 72720
ggagtaagct aattcctata ggtccttgcg cacagattcc gaactgcagt cagacatgca 72780
aaaattcagg ctttgctaaa ggcggacaat gcatcaaatg gtatcctaat tctattaagt 72840
atacatgtgc gtgctttgta aacgctgcta caccggctgt ttaagataat aactcttcaa 72900
atttgaacta aaaagatctc aaatgactat ttaaatagaa tattgaagaa atatgtttta 72960
tgcaaataaa agtgcatttc aattttaatt atgttctcaa tgtggactgt tatatgatca 73020
tatatatata tatatatata tattctgtat gaaataaacc gaattaataa agtttagaat 73080
tgttgtcaag tttgcaatca taaattttca attaataaca acgaattcaa gatatgagtt 73140
atctagttca cataactaac atgagccccc caaaaaaaca tgagccacac atcttattgt 73200
tttggttgtt cgattctaca aaaatgaatt ttatttatta acaatataaa caatttaaat 73260
gaaatttttt gtgaagtact gttttattaa taagatacag aatttcagaa aaagataaca 73320
aataaaaata aataaaggta ctgctaatca atttataaac cataattatc taaacatgtt 73380
gatctccttt attgttctgc tcttaaccat tccagaattt gtttgttatc ctattttgta 73440
tagaaaaaca ttatttatct taatacttgt ataattaaaa aacaaacatt tgattcctta 73500
tataataagg tcaattatat aatttggggt catcgtcaat gtctacttca taaaatgata 73560
tgcgcctgat tccaaaattt gaggaaaagt cttttatgta aaattctttt tattttttct 73620
aatgtgttaa gtttatgttg gatttgaacc aatcaattct agtgataaaa ttatacttga 73680
cagctaatct ttcactctga atatttttat taaaatttg gaaagaaata gaactatgta 73740
tattatttta actctatcaa aaataaaaga agtctttcgt gcctccagaa aaattaatgt 73800
gttttatcac ctacctaaca ccttgtaaca tagaactatg tatattattt taactctatc 73860
aaaaataaaa gaagtctttc gtgcctccag acaaattaat gtgttttaac accttgtaac 73920
acatactcca tttgcgatat cgtaaaacta aagtacaaaa aaatttatgt agtgattgta 73980
aggtcaatac actagtcttc ctaaactcaa agataaatta atgtactgac catcgccatg 74040
aaattgaccc atatgccaag tgaacaggcg tgaaaaatcc attagcttaa ctgccgatgg 74100
tcggatatta aaaatttctt tatcatatcc cttatatatt aattaagtaa cattacaaca 74160
ttgttttgta gcaacgtgtc accgtgaaaa tgaaattcag aattcttata gaaatatgta 74220
ggttcatctt aacttatact atacttttta ctaaactagc tattaaatta ataaatagtg 74280
tacaaaagaa tattttagta ctttctttat ataaaaacta cagaattgtc taatatgatt 74340
aacgtatata tgacaattaa tgattatgaa taatatattt ttgataataa tttttgtatc 74400
ttagcttttt tttctgttta attttagatt attaaaatat attaaacaat cacattaacc 74460
atatattaaa aaatattttt ttatatgtta tatttttaaa tttttaaaac gactacaaat 74520
tattaaaaac gttaaatgtc tcacactaaa attttgtgat caatggttta actttttttgg 74580
taataacaag aaacaaatga tcataaatcg tatgaatatg aagtctcact cactagacat 74640
taatattata tattaaatat agcttaaaat tatagtttaa aattaaacta taaaacatag 74700
aaaaatactt aaatatgata atttctaaat ttgtattgaa aaagtattga aaccttcata 74760
ttttaatatt gaaatttgca ttcaaaaatt cgcacattaa aaattttgtg tttatcatat 74820
gattataaat tctcaataat aaatatttat attaaaatat actatatatt tatatccatg 74880
tcattgaaat ttagttatat accatataaa ataaataaaa ttattgtttt ttaatttact 74940
aaaaaagtat cgtaaataaa caagatgtat tgttttgatt tatgtgctta atctaattta 75000
attatatata taatatgtaa atgaatataa ataaataata atatatataa tatttttata 75060
tataacattc attctgcgca attgcgcggg tcttaagcta gtatatatat taagtcagat 75120
gatagacaat tgagaatctc tcgacagttt tgttctcaaa aggtgatcaa agtgatccaa 75180
gaaattcggg gaagatagtt gatggtaaaa atggcagtga aacctttaat tggctctctc 75240
aatcaatggg tgtgagtgac tctctcaatc aatggtgaac cagaatttct agaatcgcac 75300
aacaatccta atccagtgat caagagcaac aaatgaataa ctcaaataat aaagacaaga 75360
tacactcttt gaagaaggaa gcaatttctt ttataaaact ttttggttga ttgaaagtgc 75420
tttgtacaag gacgaccatg agcttaaata gactctgaag acaaagattg ctaagccaaa 75480
atcaaataga gatcaaagaa aataaaggga aagagctgtt ggccttaaat ggctttcttg 75540
gccaaaaata agaaaggtga tgattatttt gcgtcttgag agttttgtgg agaaagccta 75600
gtgtcttggg acgaccatgt gaattgcaag tgtcttcata aggctgtggt tgaagtgata 75660
tagccattgg tcatcaaatg gattccagcc caaccattag ccgggggaca atatgataag 75720
aagccggcca tacaattttc aaaggttgca gcattataag ctgtaaccat ggaggcaaca 75780
agagatggat atgttctgta tccaaaggtt taaaaatctg agcatgtgct ggacgaagat 75840
ggtgagtcta tgattggtca taacttaaac cgacatagac caaacttagt atatttattc 75900
aaccacatta tggttcaata tgtttttcca aaaatttagt aaagttctgc tttaaacgta 75960
attgttgaaa cttgcatcat gctacaacag tgtactgctt ataaattaca aaactttgaa 76020
aaactagaga gaaagagaag agaatagaga acgagacgac gcagacaaac atctttctga 76080
ttctatctac cagtgaaacg gagggaaggt ttgtggaaga ggtacagcct cattaccgga 76140
tccatcagag actgcactcg cattctcaaa caaaccggac ccataaaaaa cagtctcttg 76200
ggacaaagaa agtggtggct gtggctgaag caaatgagag gaagatgatg acagaagaga 76260
gagagcgcaa tcagagtcat ggatgcaact cgtcattctc gagctgtcct cttcttcttg 76320
caagaaaggg aactgtttcc ctctgctgtt tggagaagaa gatatcggga acgtaatgcc 76380
tgtctttgca ggaaaagaac caacatagct ctggttctgc ccgtaacttg aaccattggc 76440
catagctacg cttacaggac cgcttcccca gctcggactc acaacagatg tagttggaaa 76500
cacgtgtgga gagcttgaaa aatccagcaa tttgctacct gttaacaaga tggtgcttag 76560
ggactcttaa gtctattgga tccaaaaaaa aaaagaattt attttttatt ttttaaaaga 76620
agaaaagcaa aaaccttgga agaaagttgc agtacgatcg gtatggtcgg gctgaggctt 76680
ccgtcttctt cgattgtgtc catcaagacg tttcctacaa cttttcttac cttcatcaaa 76740
ctcttccaaa ccatgaaacc tatctcaaaa acaaagtgga ccatgagcta aattttttttg 76800 ttttttggaa ttcatttctt taaataaaat atatattttt aaaaaattag gctttaatct 76860
aggctaaaat aacacaaaaa aactgtagta tgtgcaaatg caccctcagc aatatataca 76920
cagatgttaa cattatccaa catatgaata caatcagttt ttacctgctg cattgttgac 76980
aaaacctctg attattgcca ttgattgtaa ccacaggagt tttagaatgg acatcacaga 77040
ctttatgtct tttatgatac tctctacagt tactaaaatc agaatcacat ccatcaacca 77100
gacaaatcgg gatctggttg ttccctcttg tcctcttgga gcttcttgaa gcctcagagg 77160

-continued

```
cgctctcttt caacttacta agacttatca ctttctctgt cttgccaaaa gcagaggagg  77220
aggaggaaga agaggagttt acaatgtttc ttccaagttt cagatcaaat ggtaaatttc  77280
cttttggctg caatcttctt ggtggtgagg atgacccacc gaacgagatc gatgcatcga  77340
ctggggttaa atccggtaca gattcttggt cgaattcaga gaaataaccg gagctgagtt  77400
tgaagttcca atccatttaa agcttttttc cttctccttc ttcactcact aaaagaagac  77460
atacatagaa acaaaaatat caagatttat ccttttggtt ttgttaatct aaattgacag  77520
gtttaagaaa aggatacaat aaattcaact ttcaaacatg aaatttttta actcgattaa  77580
tcttgaattt tgaagaattt tttttaaaa aaattaaaaa atcccaaaaa tgggcaaact  77640
tactgtactg aaaaaacaaa tgggaagtgc agatatatag aactagaaca gatcccatgt  77700
aatgggaaga aagcaaaaca aaataaaaat aaagcaaata tataaacttg cagttttgag  77760
tttcacttca tcataaaacc cctctctctt ttttatttat gtcactcact tgaaagcaag  77820
aatttaatgc aataaagaga cagagattaa agaaagatga aacatgttat tcataaatta  77880
taaaataaga aaagcttggt atttgaaggt tgagaaatct gaccaaatcc atgcacctac  77940
caatggtcag tagaagaaac tcaaaaaaga gaagagcgaa atctacaaaa tattgacaag  78000
tgagaaagag agttgatggg tttagcgaga gaaagtggag acaacgagag tggctgctgc  78060
tgcaataatg cacaagagaa agtgaagaaa aaagtaatat attactaagt ttaaaaatga  78120
agcttaattt aattgtttat ttgctttcct aatataggaa ttgttgatat ccttctttag  78180
agagagagag agagtggagc aaagggacag ctgttattgt tgtttgttca tttgctaact  78240
tttgcgtttt tttaattaaa aaattcttta ttagtttgct tacgaaattt ttaattttgt  78300
aacaagtttg ttattatttt aaaaatttat ccttaattga taattatttt attaaatact  78360
tcaaattttt gacaaaaaat aaattaactc ttttaaatta tttataatgt ttaaggatag  78420
tttataaaac atttataaaa atttataaac ctaaatctta aacaataatt actaaaccat  78480
aaattcaaat gttaaaatat ttttattgaa tataaaattt aaaaatgata gacaacttaa  78540
tgtatataac caatttttct ttatcaattt gtttgccatc caacaagtct gaatttatga  78600
taattaaatg aaatgatatg aaaaatacac agcatcatta gttaattttt tatatatttt  78660
atatgaaaaa acattaaaca tgtaactcat cagtttatgt tagtagtttg gtatctaatt  78720
tagacctgat atgttgttga gaaaagcaaa ttatactaaa attttaatat cgttgaaaat  78780
agtatagaat ttaatgtgta tgattaaaca atatttgttc ttcatggaac tagaatttga  78840
aaattttaag ctgacattta catttttcaa aactgaaaat cttccaaaca taagttagag  78900
atgatagagc acaacctttt taaaaagtca taagattgtc gttagcctga atttcacttg  78960
gtgtgaacaa taatttaatt ataccaacta attctgttaa cgtcattata tccaattaaa  79020
attacaatca atcaaactgt gacaaaaaaa aatcacaatc aatctaaata taaattgtat  79080
aaagcatctg attatccaaa attttactct gttttttttac tttagtatat ttcaagttca  79140
tgtagatgtc caaactaatc tctaaacgag tggtatggct tttttttttt tttgacagca  79200
agaaattcac agactcatga tgactctgta aaccatgttg gtaactccgc atccatgtga  79260
acgaacgagt ggtatgatct acaaatagac tttcattcta gctattcaaa tggaccataa  79320
aataaattta tatttgtata gtcacaaagt aaagtgtagt ggaatgccat caactctatg  79380
ttgattggca attccaaagt tcgcctacaa gatttttatt actaaactat cactttatgg  79440
ttaaaatttt attttgttcc caataactat caagatcttt attttaattt gttatagtac  79500
```

atagcaatcg tttgcaatat atatagcatc tatccaattt taatagcttt caaacatggt 79560
caccttgttt ctttgaaaat aagaataaga cagacagggt tttctaatat gctcttgtaa 79620
ataacaaaaa aaaaattgga aagtaataaa taagaggtat atgatgctta tttgcttacg 79680
gcaaaacata gcatgtgaac gtcgtggttc gcattacaca aacatcttct tctgttttta 79740
actttttatc atctctttct ttctttcccc gatacgcgct atttcttcga ccaacattta 79800
ctccttcacg ggtcacaact cacaagtcga caaataatat gttttttgc caacaactaa 79860 taaacatatt ttgtttcctt ttcttaaata acatgtcttg tcttcaaaga atcaaactag 79920
ccttctactt cttctaaaga gtatcatcac tttaacactt ttcatataga ttaaaatatt 79980
aaaatatatt actattttta ttaattaaat ctatttaacc actagtattt gagataaata 80040
aaactatttg tagaatcaat atattttata attaatatta aacttcaaat aagtataaat 80100
tgctttaaaa tataaatgtc aatctttgtg taacaaaaaa gtatcaaatg atactatttg 80160
taaaacagag aaataattag aaatggctga ttaacaccct cgttaaaaat ttctccaaaa 80220
tcaatttatt tttgaagaat aagttagttg tagaaataaa aataaaaaat ttagttgcat 80280
gtttgactat ttaaatatat tgatttatct tgaattcgga tgttgcaact aagcgatgga 80340
tgttgaatca agtacataca tactggatta catcaaatgt gttatatcaa attgttgtgg 80400
atgttacacc tgatagtgag tttagttcca tgaggttgta tgtactaaag tattaagatg 80460
catgatactg gtgtatatat attttgtatt caaaataact tttattttgt actcgataag 80520
cttaatatcg cctataataa taaaatctca ctttctctgt ggacgtatcc aaattggacc 80580
acgttaaacc tttttgtctt tgttacatcg ctttatccat ctgtttttgc atatgttcat 80640
tttcatgtat gtaacaacaa aagtggcatc acagcttcgg gtctatgatt tggtgagaag 80700
atggctggta taaatgcgaa gatagaaaag tttgatggga gaaataattt caatctctag 80760
tattgcaaac gtttccgaaa caccatggca tatgcgggcc gctgtcagga aagaagtcta 80820
atgttgctgt tttagatact taggaagaaa aggcattctc taaattttgg ttgtgtttaa 80880
cagatgagtt catcatcgaa gtatcggatg agaaaactgt tgctagtttg tgacagaagt 80940
tagagagttt gtaaacaagt tacttctaaa gcaacgcctc tttgccttgc atatgcaaaa 81000
atatatatat tgagatttgc gaccatcctg gcaagttaaa tttgatacta ctagagatgt 81060
gtaacatcga tgttaaggtg gaggatgaag acactacagt aatcatgttg gtatctatgt 81120
cgaacttatt tgaaaatttc gtgcaatcgt tcattattgg caaagataca atgaaactgg 81180
aaaaagttag atcatcgctt catagtcaaa aattttatta gaacaatcca gttaaaaacc 81240
caaaataaaa ataatttagg tattttcttt atatatccca aaagaagagg agtaaagaaa 81300
aatatttacc tttgaaaatc tttataagat attacttaaa gagatttgaa atgtataaaa 81360
gaaataatgg ctatgagagt tgaaaagaat ccgcaatatc tgctagttaa gccctctagt 81420
acaccaagat ttagttttaa acaattcaag gaatataatg ttaaagttta tggtattatt 81480
tttagaagtg acttgaattt aaagccttgt aaattaagat ctttgtagaa ctaacttgaa 81540
tataaattct tgtaaagaaa gttttctgga gatcgtcagg cctcaaaact cagatctaac 81600
cactaaatga gtaaatgtac agccataagt gaattttggc ccttttaggg acgactttgt 81660
ttgtgttcag aaaaaataga ctggatggct tttttttag atcaccagtg tgatgatttg 81720
tttggcattt ttattttaga tcaccagtgt gatgatttga gaataagtga tgcatatggt 81780
gagaaagtat ggcatactta taaaaagaaa caaaccgagc ataacaattt aaactggtaa 81840
tatattaaaa ataatatttt tgacgtcaga ctgaactttt cacataggtt caagcagacg 81900
gctcataaga aatgaaatta caatcatatc atcaacttgt aaacgcattt ttccgtaaat 81960
taaataggag agaaagacag aagtaaagca tcaaatatta gagactgaag gaaccaacac 82020
taaagcctct ttgtgtcccg tgcattctct ttttagtcac tcagtctggt gtcgttcctg 82080
tattccaaac accaaattaa aaaaaaagac cgtcaatata tatacaatag tgtttctttt 82140
tgtttcacat gtagtattac aaacctagac aaccattcta gtactttttg caaagaaaaa 82200
aaatctcatt atgaaggaaa gttaatagtt ttcattggta taattattta ttttcccttt 82260
atgcaaatgc aacctatggt gcttttgttt ccctgaattt gacatcattt tttgaatcaa 82320
gattatagtg atagattgtt gctccgctgc acttgaacca aatccgtttt gatcacactt 82380
tagatccagt tcgtttgaac cttaagtatt aaaaaccggt tatcattttg gcacgttaca 82440
tgcctagtag actctttttt ttttaatgaa aggcccttgc acttacatag tgaagctcaa 82500
acaaatccgg aaaaatgacc aaaccatatt cgaaggatga taactcagct atcatgtgga 82560
ccaacctatt taggactagg tttgccctca caaagatttt catcaccacc ataaattttc 82620
aaatcaagtg gatatgctat atgagttcaa gatatatatt tacgttatag taacctatag 82680
gaagatagga aaatggttaa agatgaaata gttgacctta ggtttgagga tgccatactt 82740
cctaaactgt tccctcacga ctctgttgta tatgaaagct gctcctctga attgcggcaa 82800
aaccaaccat gctaccaaca ctagcttcgc cgtgtaccat atcggtatcc tatatacatt 82860
ttcacacaaa aattcaattt ttgtttctca cattatttcc aggacaaata aaaatacata 82920
gttagtatta ttgttaccac tctaggagcg attgaaggat gagttctgag agagttaaga 82980
aagagtagat aatccaataa gcaagccatt gctcatcatc tgcttttgat gggctctcta 83040
ttgctagcac cgacgcatat cttaccaata ttataaatat aaaaaaaaca atttgaattt 83100
aatcattgaa ataaaacgaa acaaaatgtg aatttatcaa agaaacaata gtaagttact 83160
tacaacggat aaagcagcat caccacagga ctgcatatgg tcgtaaaaag taaacaaaac 83220
acgaaatcac gttgttattt taataataaa aatgctatta taaaagaaaa acaattcagc 83280
cataaattga tggagataag tattaaatcg agaaaataat atgaaaagtc aagtaagtac 83340
ccagcgatgg aatgaagagc agagaggaaa gtccaaagct tagtcattgt aagaggaaca 83400
caaaaaaaat ccaaaccaat caaaggaaga ataaaagaga agtttcgaaa cccttttgtt 83460
ttctaaccaa cacgcccaaa gatggaagga gatcttctta tttataatat caaacttaga 83520
cattaaaaca gtttggcacg tggttcagcc cctggtttaa gccgggacaa ctatatttca 83580
atattttgga taccaaaccg atgaaaaaag ttttgtgaga gcatctacaa taatgaaata 83640
acaccaaatt tgttattttg atgttaaaat agttaccatc tctaacaatg acaccaaatt 83700
ttacaccaaa aataatatta tatattatta atattttaaa ttttaaattt ttttttatta 83760
tttataatta ataaatatct agaatattat ttatattttt gttattttta agtgataaat 83820
gataatagtc atttaattat ttattttgaa aaaaattaat tttttaatta tgcgaaaata 83880
aatttaaaat acaaataata caatatattt atgtctaatt acaaatttta tagtaattaa 83940
attatattat ttattggtgt gctttacatc aaatttggtg agtgttaatt ttagtatttt 84000
attgaagatc aaattacacc aaatttgatg gtttagtgag acggccttat tcatataact 84060
aggcgatcaa aatcgagttt attagtccgg tttacatatt ttggtggctt aagtttcaat 84120
gagttaccgg acacgtgggc tgaagagaca agaggtatca gattctaact tgagcgtgtc 84180
cgacatgtca ccggccaata gagtcccgat gtcggtggga ttctctttat tgttattttc 84240

-continued

```
catgctttcc ctactatatt gatttatcat taattacaca tacaaatatt tttgttgtag  84300
caacactcgt aaaaatagtt taatatgcta taatatttag aaaaatatct gatatatgct  84360
aaacactttt gttagaaatt atatacaaaa tttttcata tacttctttc attttctttt  84420
gaaagtatta aatattttta tcaactagat acatggaaga aagacacatg aaaccatata  84480
tctgtaaaca catttgagat atacaatacc gtaaaaaaga caaaaattat tgaagataca  84540
aatatgcttt tcaaatgaat gaatgttaat aaatatattt tgaaaaacat gttgaaactg  84600
tatctaaacg ataagccttt tctcaaaaaa aaaaaactgt aactaaacga atgaaaatta  84660
tattttggaa aaggtgatcg atctttgaga gcatcccatg atgatgtgat agaaaaaatt  84720
tcttgggaat tcgtaaactc aatgatgtat gactaacctc caggttttct ctatgtttac  84780
tagttgatat caacgatcag aaaccatcac cgcaagatgt attcgcaacc gtaaaaccaa  84840
acaatttttt aatagaatgt aacactcaaa tatctcttta atagacaaag cactgcgatg  84900
agttgcataa gttgtttgga aaatgtgttg agggttttgc agtggaaagc tcaaaatttg  84960
tgtatattag ttacgaactt ccacacatta aactacatgc aaaacagcaa aagtattttt  85020
tttttggaac aaaaaagcaa aatccataca tctcaaatgg aggaagcagc gagataagtt  85080
gcaaaaaaaa aaactgtttg agagtgtttt gaaagttttg caagaaagca caaagatagt  85140
atataatgta ttaggacatt ttaaacatga cgtagtattt acttttacta tttagagatg  85200
aagactttta gaaacatgta agtgcattta tattgagttt gtatcaagag tgcttcaaca  85260
atgagttcct aagaaagttc aaatgaataa gtcgtaaaaa ttgggtattc ttgttttcaa  85320
gtcagttgtg cgagtgaaac gaattcgtga gattaagcca tcaatataat ttcgtattat  85380
tggagatcga tttcgaggct caaatctctg catggagaat tttttatgtt acaatactaa  85440
caataacatg atcatctaat aagcttgaaa taagaaagaa tccatttaac gacataaata  85500
gagtaaaaat tctaacttct taagcaaacg atttactaca tcatggtaca agcgttgggg  85560
ttctcgtcac tgaatatctg tggtggataa gcaaacatct ccacaggata cctcggtggc  85620
tggtattgat attcattctt ctttaaatcc accactttgt catctccctc cgctgcagca  85680
cctccatctc cggccgccga tttggccact ccaccaccgt cttccttagc ctctttgctt  85740
tctttgggtt gttcttcttc ctttttcttc tcgtctttgt cttttgtttc tttttctttc  85800
tccggtggtt ttggcgatgg atcttgcttg acaatcgcag catgcttccc gatttcttg  85860
ttaacgtact caactagctt ttccggtata aaaactcctt tcacgctcac ttgtgatgct  85920
ttaaagtctg gttccacaga ctccactcct gtatagtaaa aggtagttgc tttattttt  85980
tttaataata caatattcaa ggaattaata atcgaagaaa gtcgaacttt caaattgcat  86040
tacaaatatc gaatgcgcaa aactaatttc aattcttaag caaccaatgc tattctttgg  86100
cccttagaac tcgattagtt gatagcattt atgtgtatat atctatcaag cataaaaata  86160
tccacacttt ctagaaacaa caatttgtac aacttatagt tagcatatac acatacgtac  86220
tggaatttta gataactccg catacgagga atgtattcac taactaacta aaaaagtgtt  86280
tagaactttg agatccttgg gaaatataat aggtgaagta aatacaaagc acttgacttt  86340
agttgactct attcaaaccc actacagttt catgtaacct tgaaatacta aaagaaacaa  86400
aaaaaaaata ttcgggacaa ttttgttaaa atatatgatt atagtaacaa ataatctggt  86460
gaatgagttt ctttttaaag gaggaaatgc tctaacggtc taaacgcatg gtcttgtata  86520
ttgctctttt taaagggcct acatagtaca cacaatttta aagatggaat caacttatga  86580
catacataag agtccaaaac gtaatgtccc aattaagtga agtcagagaa aacttcgatt  86640
```

-continued

```
taataggagt catacccagt tgaggatatt ataattaaaa ttttgaataa gaagatgaaa  86700
aagaaaacaa acctttcatt ctcatgattc tcttttggat ctccatggca catgcttcac  86760
aatgcatgtg aactctcaac accactgtca ctacctgttt ttctcagtgc ccacaaaatt  86820
ttaatgttaa ttacacaaaa ccaacttact ttcttcaaat tacaaatcta tcctcaaaag  86880
tcttaacctc ttcttttttt tcttgaggtt ttggtttctc ctcttttttc tccggttcat  86940
ctgaaaccgg tttaggctct gggataggag aaaggagctc cactggacgg tggctctttc  87000
tttgcagtct ctgcaacact tttagtggat ctgccttctc tcctttcacc acaactttac  87060
tatttttaca atcagttgtt acatcctcca cccctaatca cattttcaat tatcccaaaa  87120
ttaactaaac cattacacaa atggatatga aagaaatgtg tttagttgta ccttcaaagc  87180
ctttaagaca tctatggatt tttttagcac aaccttcaca atgcataaag atcttaagaa  87240
caatctcttg tggctctttc ttcttctctt cttctttctt atcatctggt tttttcactt  87300
gtggctcttc agctttttc tccattttct cttctgattt cttcttatct tcctgaaaat  87360
ggtaaaaaag gagaaaaaaa gtttaggaat agtgtttgga tttgtgaatc tgaaagtttg  87420
aaatacaaac ctctcccatt gattttagtg ccagtgttga ctgttgagac ttgagagagt  87480
tttttagtgg ctcacttatt taagtttttt cctcttcttt ctacggactt gagagagatc  87540
tggttatata aaagacacat actatttctt ttatttcttt tttttcaccc cacaaccaca  87600
agtacagaga cttattagta tttttcccat ccaattattc atagattttg aagatctttt  87660
ataaaatgtt tcttctcagt gttttgtttt aactgatttt tttctcagtg tttttagcta  87720
ttttgtatat ttgaccaata ttgggtactc tctaatcgta tattcgtatt gtttccaaaa  87780
tttgaataca gttttaaacc ttatctacca taactcaaac cttatcggtt gaagtaatta  87840
atcggcttga ttgtcaacat attaagtctt ctacaaaaaa taattgcatt actattcggc  87900
agaacctaca tatctaactg aaatatactc tttatgtttt acaaagatat cactctgaca  87960
ttttttttaa ttaaacttct aatactccac atgttttaag acgatccatg ttttagaaaa  88020
atgtgtttca aaaataaatt tttacatttt taatccatat tttatcacat aataattgtt  88080
aattataaaa ttcaaaaaaa taattgtgat tatttaattt atgctgactt aaaattgtgt  88140
caaatagata atcacaatta atacattttc ataaaaaatt atgttttctt aatatatata  88200
aaaaaattaa acataaataa ttgtgaaacg gatagaatat tattttagtg aaatgacatt  88260
atgaaatcag tcaatatgtc tctttcttgg aaaaccccaa taaatctagt atttattatc  88320
atttaatatt gctgatattt aatactccct ctgtttttta aagatggatg ttttaggaaa  88380
atattttgtt tctaaaagat gtatttttca tgttttcaaa gcatattttg tcaattaata  88440
atgaaaaatt gtgtgtttca aaaatattaa ttacatttct tttaatccta ttggtttaaa  88500
aatataggaa atataaagtt acaaaaaact atgcattaat aactaagttt taatatggtt  88560
tcttaataag tgtgaaaatc ctagaacatt catctttaaa aaacagaggg agtatttaaa  88620
attattttga ttgttttatt acattatttt ctttttttaac tagttattat catttatttt  88680
cagctaactt tttattatct atacaaataa atattcctct tagttataaa ttcagattaa  88740
ataattttat acaatctttt caaaaataaa attttctttt ggaaatctat tctatcaggt  88800
tgcatatgca cattttattg taaaaacaaa agcacttatt tcacccaaaa tatttttaga  88860
attttctttg tatagtttta tatatatttc ataataaaac tttaagaatg ttttgttagt  88920
gtattttcat tcattcattc attgtcttgt ttacttgaca aaccacaaag agttatgact  88980
```

aattaatttt cagaaaatat tcaaagtttt tcagactgaa ataattgttt ccaacaaaat 89040
atgataataa taataataat gtagttttat taataattat aacaaagttt aacactaaat 89100
gtttttacgt taaaatataa cgaaggtcac actattttct tgctttaagc cacaaaaaat 89160
actgtctggc atgctttttt tttccttatt gctagacttt tgttgatgat gtagacttca 89220
ttaatgtttg attcaagtca cgactactaa ggctatgtac aataggtggc tttattcaac 89280
accataattt acgcttacac atcatctttt atttcatcca cctattagtt taatattttc 89340
ttatttttat atttacgata atttatttaa taaaatacaa cactataatc caccatttta 89400
tctcatattt tccttttttat aattatattt tgtaagcaaa aaattgaaaa atattttttt 89460
taaactataa taactaaaac ttaataaatt gtaaattttt aataaaaaat atttatgttc 89520
cacttaatat aaaagattaa aaatagactt ttatatatca aaataaaaaa acctaatctt 89580
tatttaagga acacaaaaat aataaatttt aatataattt atttctacaa aaatattatt 89640
tgatataaaa taattaatct caagttatta ggatgtaaca accaataaaa tagttataca 89700
tatatcaata tataatcttt tattttttaa aagaaatttg cttatattca tattcgatta 89760 tgtttttttcc cgaacgtagt ttaaagtgaa gcaaaaccaa catagtggat cttacataaa 89820
atactttcaa catgtagaaa atattcaaca acaaataatc cacctcattt ttttaggttt 89880
tcaacagatc cattgcaggt attcaatagt tgaaagtaaa attcaacaaa cccattgcat 89940
atggtataat agtgacattt gtatacaatg gtgcgtgtat attgtatata tatgaaattt 90000
gttggcccag tgcgtttgta aagtattcta cataatttaa tatatatagg aaatttgaag 90060
cacatacaaa atgtgatttg aagaaagagt tcataatgct agacgttaac ggctttataa 90120
ttgagcatga aagtcttgtg agtacactat ttgaaaccta gtcagcgtac atgattatgg 90180
gtgtgattgt aagtcatgtc tagagtaaat attgaagaaa aaatatcagt tattcttatt 90240
tattctgaaa tcttatcaat caggtaaaaa cacttttctt cctcctacct ctaattgcta 90300
tttacaagag aataaaacac gttaatagtt ttactccaat tcaaacaaga gtaaatgtgt 90360
ttacctagtt tattctctct ctcatttttt tcttttcatt ttcatctttt ttcttttcct 90420
cttatttact ttatattttg atattttcca tccatgctct atatgtgaca acggtttaaa 90480
cgttatattc cttacgaata tttttttttgg taaaaatgaa tgatttattt catatagtac 90540
tatacattag atcaaattta ccccgtcaaa aaaataattt ttctaagaat aattgcagtt 90600
aatatttggc agacctttca tatttaactg acatataccc tttatgtttt ataaatttta 90660
tcattttgat attcttttta atatacaaat aacgccactt taaattttta atacaattta 90720
tactcatttt aaaatattaa ttattaaaaa ttttgattta taaaaaaatt tattcatctg 90780
aaagattatt aattaaacaa atgtaattac taaaaatata tgcattttaa tcatttcatt 90840
atttatgtaa aatgttaaaa taatattttc atgaaatgaa aggaacataa ttgtcttttt 90900
ctttggattt tccaaaatgt ccggcggacc gagactcaac cgactaatcc atgagatata 90960
tttaccggcg ttaaatagat ctgattgttc acagtggaca gtagatactt ctgttgcatg 91020
accacacaaa cgacatatct aaaatggtga gtttaaatat gaaatgctta ctattttcca 91080
agtccccgta ccattcaact acggttgtgt taatataatt gttttgcaaa tggcagaaca 91140
gaaaactaga tgtaaattca caatgcaagg ggcaatgcga tgatagatgg tattctttcg 91200
atgtccgaat aagccataat gtaactactg tctccttaag aagattagaa aaatcttaaa 91260
tgagtaaaat ccatgaattc tactttaaca cttttaactg gagaaaactc tattaaaaac 91320
aacgaagcta catgagattt actttatttt aacatgcata gccgacatct cgaatatttc 91380

-continued

```
tggagcggta aataaggcat tcttgcctac gccaatctcc tgtatattat ttgagaagaa  91440
ttgtaacatt tttttgtagc cagatgtcat cactataatg atttttagaa ttcttagaaa  91500
aatacgttgg ttcatctaaa tatataataa gccttttatt aaaccacaat aaatacatta  91560
ttaatgtcat tcattatttc cttaaataag attacagaat tatctaatgt gactagagta  91620
tataagacaa ttaataattt tgaataataa agatttgata aaaataagtg tgtattctaa  91680
ttatatttgt ttaattttaa gttattaaaa taaattaaac aatcatagta accatataat  91740
aaaaatttaa aaaattattt atatattata ttttgaattt ttaaaaacga gtataaatta  91800
ctaaaactgt taaaagtttc acattcaaat tttgtgatct atgatttaaa atttttgtta  91860
tgacatgata caaataatta aaaaataata taggttgaaa gtctcattta ataagtatca  91920
aaaataaaag atatagaaat atatgtaaca ttttaaattt aactatatgt catataaaaa  91980
tacataaata tcttaatttt aaaatttact ttcaacattt ttttgataaa aaatttgaaa  92040
aaatattgac aatttaattt tttaaaatat tataaattat ttaaaacatt aatcccacag  92100
tgaaaatttt ggtatcacta atttagactt tttgctataa cagatacaaa tgataaaaaa  92160
aatgagcaaa aatcatcatc taataaatat taatattaaa atatatcata tatatgttac  92220
tatcatttaa atttaattat atatcatatc aaatagaaaa aatatttttt cgatttataa  92280
gatttattta tatgttcaca ccaatttaat tatataagta gtacataatg acattttaat  92340
tattcaatat atatttatta tttcataata tgttataaac atataatata taaattaatt  92400
tatatatata atgttcatcc cgcgcaaggc gcgggtctta acctagttaa caagataaaa  92460
ggcatatatt tacttctttt ttacagataa cagaaacaga ctaatagtaa aacaaaaaat  92520
cataaataaa ataaaataca aaattacaca aatttaaaaa aaaattggaa aagtacttcc  92580
gtttattttt tactttaaaa atatcattgt ttttcatttg tagtactctc agataaatgt  92640
aatgtacata aatccagtgt acattctgca tattagatta aacaattttt gtttaacttc  92700
gtttaagact agcgccattg cgcggattaa tgttagcaag accgctttgg acgcaaggga  92760
gtacaaggaa gaccggttaa agcaaagcga ttaacacgtt cgtgaaccta aagaaagagc  92820
acaagtgagt tcattggcaa gaagatatgg ttcctttctt ccggaacgtt tgtctctcca  92880
aaaaacccta caccggtgct agtcctaaga tattttaggt ctaataggaa attaaaaata  92940
taaactctaa aaaattaaaa tttgataaaa attaatttta cgattaaaaa ttaaaaattc  93000
ttcaaaagta tacatagcta ccagatttaa aagttatttt cgttttcttt ttatgtaaat  93060
aagaaactaa acttcaaaaa ttattttgtt aaatgtttga aatatatttt agatccaact  93120
tttatatttt tctactaaca acaataacaa aattaagcct taaaagcttt aaaaattatg  93180
ggccgcatac ccatgttttt tagttatagg ctcaggaccg gcctgccacc actagatgct  93240
atatggagtt gtccaagatg acaaaacagc ttgctaaagt tgatcctttg agaaattggc  93300
tgatgcaatg atcgcttgga ctgaggcgtg ggaggagctt aaccccttcag ttggtggaaa  93360
agatgtcacg gccaagtgat gaaaaattga cgattataag tgatgcctgt tattgctgca  93420
tgaataaggt ttgttattgt tgtgatcttc tatttatata tctcattctg gaagtgtgct  93480
tcgtacaata acgtaatact gtgtgttatt gttgacgtta acgttgctcg acatgtattt  93540
aagccttatt ggtgaaatga tgtgtgctac tttaaattac atggatgaaa tgattgtttt  93600
aacaggaaag taccagagga cttgatacca tcctatatcc aagtaatcgc ttgtccggga  93660
cgtcgaaata ctcgtttatg ttggcctccg acaagcttct aagccttgat tatttcattg  93720
```

-continued

```
ataatgatat aaatgttgta atttacaaaa ttatgcttag agatttttta aaatattact  93780
tgtgatcagt tttaaaacta aattaggttt gattacgaaa attaagagaa aacattaatt  93840
ttgtgactga gagcatctct aaccccactc tatttttcac tctaaaatag agtttagagt  93900
aaataatgct ccaatggtac tctatttctc actctataat agagtaataa ataggtttac  93960
tccaaatata gagtaatttg tttttttatt gttcatcact ttattttcta ctctaaaata  94020
gagtaccatt ggatcaaact caaactctat tatagagtta ctctatttta tagtaaaaaa  94080
tagagtaaac cattggagat gatctgagat ggaagacttc atgtgatcca atggtcaaga  94140
atcaaccact taaggaggca tgtgtcttta actaaagagt tttgtttgtt tgtcaggttt  94200
aggtggcact aaattggtgg atatttgcct catcatgcat gacatcctta gagcatgatt  94260
agtgaaggag atccatttgg gattcttaaa ctatgatttg acatttttct gctaaaaata  94320
tttttattat ttttattaat ttttttttta atatttctta gttaaaaact aaaagatata  94380
tatttttgct tgtagcctca aaataatctc ggagaaaaca tagctatttt cgaattaatg  94440
acatatcgtg aaatacaaaa cgtgcctaac catttcaaat tcattattaa gaaaaccacg  94500
aaatatttac taaaaatgtg acaaaagcag acatgatttt ggtcacgaaa tattcctata  94560
gcaattaggt tagtcatatt catatagctt ctaagaaata tggcacaatt gtgattaaaa  94620
tgaattcatg gcaactatga gtgttactgg ccatagaaaa tgctttgaca tttttttttt  94680
ggctaactaa aatgctttga gttctaaata ctgaatatgg caactcacaa agatcatttt  94740
tcacttctat ttatgaacaa atgcttgaga cattatctaa ccacccttac tattattttt  94800
caagtggtta ttcaagtttc tttcaaattc tcatccttct agatgacaac aataagaaga  94860
tgatattcat ttgtccttat agcacttata cttaccgtag aatatgattt ggcttgtgaa  94920
atgcaccaac atacgatgtt tatttttact tatccgattg aagatataat ggaagttttc  94980
aaggaagata ttttcgtcta taagaacaac ttttatgtct atttatcaaa tttatgcagg  95040
atgttccaac gctgtgaaaa aaaaacattt tctgctaaat cggaggaaat gcactttcac  95100
ggtgagagat agaatcgtgc tgagacatca gacttcaaaa aatgactgag gtgaacaaga  95160
caaaaatcaa ggttatgaga actctatgac caacgaattc tattatagcc gacgaatttt  95220
attaaagaga tttagaggtt ttttgggaca tggtttcttt catcaaggat ttctttaaga  95280
tcgcaagacc tttcacccag ctgttgtgca agaattgttt ttctgaattt aagagtactt  95340
ttttttataa atgcaagtta tatgtattta ttttttaaaa taaattttac aacattaatg  95400
gttgttttcc taaatttgat aaatatatta tacatattta gaaatatata tcttcataaa  95460
ttttagaaaa tgttatatat tcaatattat ttttctaaaa aatattggtc aaattcaaga  95520
agattttata cacattcatg aagatttttc ctagaaaatg ttatacatat tcaaaaatat  95580
tttactaaat atacatctaa ttcaaattta ttaaattatt cttatatatt catgaaaatt  95640
ttcttacaca catttgagaa ttatttataa atacatattt gagtttacct aaattttatg  95700
aagatattat atatatgtat taatatattt ttcagtaata cttttataaa tatgcatata  95760
actcaaattc aggatatcat atatatttag gaatgtcttc ctaagctttt taataaaaaa  95820
gatttttcaa aaaataaaaa aaaataaaaa tcattttttt aaatatcatc tttgagaaaa  95880
ttcatttaaa tatttattta ttttatatat ctaaaaaata ttgtcattta cctcattaat  95940
gaatgctaac ttggtcattt taccgttata ggatcttttt ttttggtagg accgttatag  96000
gatcatttga gatttgtatt taagaccatt tgaaaccatt tttcaaacta aaatatatta  96060
tacatatttt atattatgca acataaatat tttaataaac tttctatttt tttttgcgta  96120
```

tgacacgagt cattacttaa ttatatatta taaattaggt attagaatac cacataaatt 96180
tggttgcggg gcgcacattt agtaccggat attccttttt ctcaaaagta tttaataata 96240
ccaaacatag caagttgctt taaacatagc aagtcgcaag tagaaaattt cctttttaca 96300
aacatcagcg gtagttagcc agtgacggac gggtgtgtcg aacaatatac aaaaaaaacc 96360
cggaacatta gaatacaaat ttgataaaaa caaacttcca aacaaagttt atcaatgatc 96420
tatcgaatat cacaattcac agcaaaatga tatcctaacc tctttgaaat gtatttgttt 96480
gtaacttgtc attctattat ccattaagac aatgattttt ggtttttgga ataattccgc 96540
ttttcatgtt ttaagtatat tttatatcag tgatttgtga tatataaaaa tgtctatctg 96600
tgatagaaat atttaataat ttataatagt tacatttgtt aacaattgtt aagagtttcc 96660
attaagtaaa tttattgtct tatagtgatc atttttggct caacaaacta attaatttta 96720
aaacagaact acaaaattat caaaataaaa attattgcat agatattaat tacatgcgcc 96780
gaatagtaag gtggatacaa ctttaaaaga attagaccca aaaaaaaact ttaaaagaaa 96840
aaaatggtgg atacaacttt tgtggataca acaaacaaag ttcgcatatg ctttttacaa 96900
atgttcgtca attcatatga atttaaacaa gtcaacacgc tcacgttatc accttctcct 96960
tcggtagtgt ctttctaggg tagctgtaat atgaggaagg tttttcacag cagtaatttt 97020
ttctgtcaac ggataaagta acaaatagaa aaaaaattaa ttatttgaca gatgttgact 97080
ttttggtatt tatagatgaa cttgtggaaa atgtggaaag cataaacctt tttagtgcct 97140
ctcccttatt acaaaataat aactataggt atatatatat atatatatat tatttttttt 97200
taactatagg tatatgattc catattaaat tggactagaa ccaacctcga acattgacgg 97260
caaaaaattt aaattttttt aacactgata atcgattata tcattatata atatcttttt 97320
atgtttcata tgataattac aacatatgta attatgatga gaatttcaaa gacaaagatt 97380
tcacaatata gtttaccctg taacattcga attgattggc ggttctacgt gtactacata 97440
tgaccataac aaatgattct gtattcagca ctgaaatttc cgataatctt gtgttctata 97500
actgtaagaa attattttc tgaaatcgaa ccccaaacat ggtatagaaa cctttaaact 97560
ttgacaaatg aattacaatg ctttcacaat ttttttttat catctaccaa aaagaaaaag 97620
agaatataag aagtgttgga ccatagttac acagattcta aggaaaataa agtatataat 97680
ctttttaata aagtctatac ttatctatca aaaattgtct ttggatactt ttagaatcat 97740
caaaaaccat ttaaataccc attgaaatgc ttaaatattt taaaaagccc aggagaacag 97800
atgacgtgtg ttatgtagtt gttagatatt gaaaataata ggtatgcacg aaaggaaaat 97860
caggtggtat ccatcttgga aaggcgacta aaccctttcc gttgacaaaa ctgaataaaa 97920
caaacatacc agatcaccaa taaccttgaa tatatatctt tttttttatc aaggactata 97980
ttataaaaaa aaactcaatt attagaccat gagttcgtat atggtgaagt aagggttata 98040
ttgaaaagtt aagcccgccc tcttctgatt gtcattgact tcaaagtaaa cctatatctc 98100
ttcttttcca atcaagattc tctatatata aaagagattc aagaaacata taactacaga 98160
aagaaaaaaa acaaagaaac aaatggagac atggagaaaa atgaaatctt ttgggcataa 98220
gagctcttca agcacggctt cgatcaccaa gagcaagtct tggaatggct ctgctcatct 98280
cgagaatgct aataacaagg aatcaacagg aaagatcaag aaaaaatcgc cgccgccgcc 98340
accacacgga tgtttcacag tttacgtggg tcccacgaaa gagagagtcg tggtgaaaac 98400
gaaactgttg aaccatcctt tgctcaagaa cttgttagaa gaagcagagg ctgaatatgg 98460
atatagacgt gatgggccta ttgttcttcc ttgcgaggtt gacttcttct acaaggtttt 98520
ggctaatatg aagtttaatg gtgatgagta cgatgaagaa gatgatgatg atgatggtat 98580
gattaaccct ccgatttgcg gtttgggtag tccctataga tgtgctggtc tcgagtccat 98640
gggcgtgaga cgtagcggct cgtacaagct tcttcgatct ccatctttgt tcaaattaag 98700
taggttttga ttttttgtt tggtttttg aaaatgatat ataggttttg attttcttt 98760 ttcccttctc cataatacta ggtatctaag atcttgttca taccattacc ttatgcataa 98820
aagaaaaatg cgaggaaaaa aaagaaccct cacatttccc taaattatat tccatttgtt 98880
tttctgagat tttgatgtct gattttgtat cttaatttac atgtgagtgt ttttggatga 98940
cgcaaacttt gaattaaaga aattactaaa aacactaacg aaacaaacgc ttgtaaaccg 99000
aattgtttgt tgttgaactt aaagccacta catcaaagat acaagaacat caaaaataaa 99060
aagactcctc actaagattt tgattggtag aacctttaca agaacattat attctttatc 99120
taatcactat ttttattaac ttgatatatt attcaagttt gaggtggtat gaaaaaccag 99180
aaacagaatc tttacatatt taaaatagca tctattagat gtaaatgctc tttatgtaac 99240
gatctcttat gcttttgatg agagcattta actttaaaat ataaaatact aaatataaaa 99300
taaagattat ttaaattaaa ttaaaaatat acttatataa aaattaaatg gtatttaaaa 99360
taaaatttat aattaatata tttaaatcat ttaaaataat agtattttag attaagaata 99420
tgatgatttt atttatgaat cacttacccg tactctgcac tcacttataa taaaaaaaat 99480
ttgtcatcca ctttaataat tttattaatg aaattatata atatttgcaa catagtacac 99540
ttttatagca tagtgctaga attttatcag caactccata tctatacgga tggtaactgg 99600
gtcattcgaa cacatcatta tattttgcta gttatataat tgttctttga ataaatttag 99660
tgcattttta atttagctga cttcaagttt atatttaatc gtatcatatc taattaattt 99720
taatatgcaa tccttttagc caattaattt tatatttaga ttttctgtaa ataaattatg 99780
taatttcatt atcctaaaga taaaaataat taaatttcgt atgattcatg aattcaatcc 99840
tgatttactg agaaaacaac tatgaagatt aatccaattt gggaattcat agattgaatt 99900
caccttttgc aatcaaactt ttataaagag aaaaaggaat taaatttcgg tatggttcat 99960
agatttaatt taattttatt ggaaaaaaca actaagatgc tggtccagtt aattctctgt 100020
taattaggat gttatgaggc aagtattata gaatgaattc accattgcaa tcaaaccttg 100080
tgacaattca tcttatgttg gaaaagagag caaagccact aatagatttg gggataaagc 100140
aaaaagtgca ttcaggttat gagattatgt tttgagaaga tccatggatc tcaacaagtc 100200
ttgttgagtt attacacatg ttgttcatcc aataatgata gtgagtgact taatggagag 100260
ccaaaaacat ggaagatgga aaaataagga actttaccgc ggaagatgac aatccttgcc 100320
tataagtcaa ttgaggcatc aagatagttt tgttcgagtt atacgaataa tagtctatgt 100380
atagtcaaat tgggatattg agtagctaat aatacactta atcatgaagt tgatgtcatg 100440
aagttaatac agcttcaaac atttgtttag aaaattaatg atatgtcatc ttatgtgact 100500
tgacaagcac atgaaacctt atgtaactat gaatttaaca aatcactcat gagatgtgat 100560
aatcattgtc ctcaatgcgg gactaaatat gaatccataa acaataatat ttttgagtgt 100620
ccatcaactc ttcaaacttg ggttttaaca acatcatttt cttaattttt ggttttctct 100680
attttaagtt tatataccaa tatgaattat ttattttatc ataagaacaa tattgaagac 100740
tcaaaaatgg atagatatcc ttacccataa ataatatgat atatttaaaa agtgcaaaag 100800
gctaaagatc tgatatcaac agtaaaagac ttagtaacgt ggtatagctt tcctacaaag 100860
ttaaaggagt tatatatcct gaagagtaga tttgtgtaga aataaaagtt gtagattcat 100920
tagttagaag acataaacat ctcagagatt tatatttcgt ttgttgtttt atttcgatat 100980
agtttttcaa acgacttcaa gttcaaactt aagtaataaa tgagtcatat gatttgatat 101040
tttttttaaa aaaaattatg gtaaatgatc tagccatata aaagagaatg gtttagtaca 101100
attatatgtt aactctttat taaaattgac taacgatcgg ctcggcctct gcctaatgtt 101160
tgaagtagct ctgcggtttt gtccgaaccg aaccgaacca aaatttttgg ctttcggttt 101220
agttacggtt ttgggttcgg taagcttttg aaaaataatt tgatttttgg ttcggttcgg 101280
ttcgttttcg attttcaaaa aaaactaaaa aaaaaacaaa atcactgaaa aaccaaacca 101340
aaaaacccaa atttaaccga aaatatccaa aaaaaattag aaaactttac cgaaattaac 101400
cggaaacaaa aaaaaatcgt tatttcagaa ataaaagtga aaaccaaaaa taatcgagaa 101460
ccaaaccaaa cgaaaccgaa tcaaaatttt gttcagttaa tttcgaaatt ggtttccaaa 101520
aattcggtta accgaaaacc gacgattcgg ttgggtctct ggcagggcta atttgaagtg 101580
ctggagagaa agaaaagtaa agaaacggca ccgtttcgta tcattttttt ttcctcggca 101640
ccgtttcgta tctatcatta agcttttta acctttaat gcagtctcca ttctcgggag 101700
agatcaatta atacttttc caataaagtt cttttgaaga aaaaacagac tcgccttcct 101760
cgtcatcagc ctttcttctt taacctaaaa atggatgatg atgatgctat tcgcgtaaag 101820
ctagagaatc tcccgactcc tacttccgtc aacggaatca aaccctccgt aatcgatctc 101880
tgcagcagcg acgaagaaga caacgacggc atcgatgctt ccagaaccgt cggcgagaag 101940
agagcgcgaa gggactgtga tatcaatact ccggcgaaga gggtggcggt agaggaaggg 102000
cttgggcaat cgtcgtcgat agtggctctc caggctacgc cttgtaacgt cgtgaggcct 102060
tcttcgtcgg cggcgtcttg caagcagttc tggaaagcag gggattacga aggaacctct 102120
ggtggtcact gggaagtctc tgcaggtagc gaatctcgaa ccgtgggttg tatacttctc 102180
tatttatttg gggtaaagtt tgttgagatg ttaattggtt caggtgggtt tgatcatgtg 102240
agagtacatc ccaagttctt gcattctaat gctacaagtc acaagtgggc tcttggaggt 102300 atcttttta tattttttaa tcaaagtttt catttttatt atttttagca gtgttttatg 102360
aagttggttg gaataagaat gtttgtttga tttttgcag catttgctga gcttttggac 102420
aatgctctgg atgaggtgtg gaatgttttg tttctatttt taatattttt tctgtttggt 102480
ggtaatgttt tttttttttt ttctgttttg ggttatcagg tacacagtgg agctacttat 102540
gttaatgtca acatgctaac caataagaaa gatggaagca ggatgctctt gatcgaaggt 102600
atataatagt ttatttagta ttttttctt tctgtttgta ttcacgtttt gatgatgttg 102660
tgtttgggaa attttcagat aatggaggcg gtatgaatcc tgagaagatg cgacactgca 102720
tgtctttagg atactctgcc aagagcaaac ttgcaaacac tattggacag tgtaaggcaa 102780
ctcttttacc tgcaagatta tatttttaaa tgcttcttcc atcaagaata cacttaaagt 102840
tcatatgctt tttttttgaa gatggcaatg gattcaagac tagtactatg agacttggag 102900
ctgatgttat tgtattctca cgttgccctg gcaaagatgg agataggtta gttggtttta 102960
atgattttac tgggatatgt gttgtgtatt gaaagagatc aacaaaagct ttacaatgtt 103020
ctgtttgctt gatgttggtt ttagctttac acagacaatt gggctgttgt catacacgtt 103080
tctgaagagc acagggaaag aggacattgt tgtacccatg gtaagctaac tgtatgaaat 103140
aaccattcat ataacccttg ataatctgga atatttgata gcatgtgact gatttgtaag 103200
cataagaaag ttaggtaggc cagacactgt ttcagagtag cttttgtctg aaatactgtt 103260
agaaaatagg cgtcaaactc cttgaaacct ttgtctgctt cagagttaac tgtttgtcca 103320
aatttaatta gaattagcca attttaatct ctcttctaat cttcttctga tggtgattta 103380
aatgaaagct cgactacgaa agggaaggtt cagaatggag tccaatagta cggtcttcag 103440
ctagtgactg gaataagaac gtggatacga ttgttcaatg gtccccattc tctactgaag 103500
acgagcttct ttgccaggta aaaaacaaag gagttgtttc ataatattta tagctacttg 103560
tttattttga gaatatttcc acttatctgt gctctatggc tgttgtagtt caatctaatg 103620
aaggagcatg ggacaaggat aatcatatat aacctctggg aagatgacca aggactgcta 103680
gaacttgatt ttgacacgga tccacatgta tgtgtttttt tttactgtga ttttgatctg 103740
caacgatgta aaagctttct gtattcgtat actttgacac acgtttggtt gcaggatatc 103800
caacttagag gggtcaatag ggatgagaaa agtatcagta tggctgctca gtaccctaac 103860
tctagacact tcctcacata caggcattca ctcagagtat gaatcttcta tccgtctttc 103920
cttaacagtg gcagttgaaa ttgttttttt ttgttttacg aaattcattt gttaccttgt 103980
gaattgttgt ctccagagtt atgtatcgat tctatacctg agagttccac ctgagttccg 104040
tatcattctc cgaggaagag atgttgagca tcacaacatt gtgaatgaca tgatgcacac 104100
aaaccaaatc acttatcgtc caaaagaagg acccggtgga caatctaatt tctcaaatgt 104160
aatgtttttc acaacttagt tatactcaaa agacttcttc ctgcaaattt tatttgaaga 104220
acttgcgcag tttctaaata tggttgtgtg gcaatattta taacagatgt ctgctgttgt 104280
gacgattgga tttgttaagg atgcaaaaca tcacgttgat gtacaaggct tcaatgtcta 104340
ccacaagaat cgccttatta aggtttctct cgctcttttc ggcttatatt acctttgttt 104400
ctgtcagttt tttaactgtc ccactttgtt tttgtcagcc attttggagg atatggaatg 104460
cagcaggaag tcaaggtcgt gggattatag gtaatcgtta ttttgcagga aggtctataa 104520
tacatgattg gctcttttaa tgtgaagtct aatgcgttag tttgctaaaa ggtgttttgg 104580
aagctgattt cgttgagccg gctcatgata agcaaggttt tgagcgtaca acagttttgt 104640
ctagactcga gacacgtctt cttgtaatgc agaagaatta ttggtttgtt gctctcttct 104700
cttgcttttt agaaaattgc cgatgcttca ctgaactctt tgcgcttctg atttattcag 104760
gaggttgaac tgtcacagaa ttggatatgt ttcagcacat ggcaaaaagt ccgctaaaga 104820
ctctgaagac agaggtacta acatcttctt cttttttttt taaacaatcg ggttttaaa 104880 acgtgtgcta ataaacaaat ctcttggaca tttgtgtaga atcatcacca gagtatgcag 104940
tcccaaccag gaaaagagct gctgctgctg catcgttgag ctttaaaact ccaactggtg 105000
caaggacagt tgtgaatcga ggaggaaaag gaaaaggatc tgttagagat tctaatgggg 105060
tcggttcatc agagaaaagt ggtaaacatg gaaacacctc ttccaaattt aatggacgag 105120
caaaggctcg aggagctcct ccagctttag aagatatcaa cagtgatgag gactctgatt 105180
acgatcctcc gggtgaagaa aatgtcactg agcttcctga gaaggtcctc caatgctctt 105240
tcttttattt ttctccggta aatagaatta tgaacgtaac cttttgtgta cttgttctcg 105300
cagagcttcg aaccaccaac caagccacgt tctactgatt cacgtaccct cagtcaacta 105360
gagcaagaga atgaaacgtt aaaagagagg ttttgttacc ttacgttacc atgttatgat 105420
tcatgtttct cacttgtttg aacaacactg taagctttgt gttttcctta attctcaggc 105480
taaataaaaa ggaagctgtt tacttgctgt tgcaagaaga gctgcgacgt gagaaagagc 105540
ttcgcaaaaa acttgaagct gaggtataaa ttctactctt taacattttt actgtgtctg 105600

```
cttgcaaacc tataagcaac aatcagttag tcaccaatgg atgattcctc tttggtattg 105660

ttaggttcaa agaacaaaag acgagttaga agacgtgaag aaagagcaag agagtttaat 105720

cgacatattc tcagaggata gagacagacg cgacaaggag gaagaagatc tcagaaataa 105780

gctagaggtt ccttctttct tcttatcacc tttctctact aaatcttctc tcagattcag 105840

gaaatgtaaa ctttttcttg tggttgcagg aggcgtcaaa gaggatccaa gcgttgttag 105900

atgaaaaatc ccgagggaga cgctagaggt ctggagctag ctcggaagga tagtcactgc 105960

atggaggagg ataccattga ctcgtttagt tttttttt                        105998
```

<210> SEQ ID NO 3
<211> LENGTH: 59642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gtagataaca aaataaaact agtggttaat agacaaaata atatatatat atatatatat     60

atatatatat atctatggtt tgttattttc tgtaaatttt tagtttttct aaaacaaatg    120

atataaaaat aataaagatt tattttaaat tttggttttt tattttagtg tagttttagt    180

ctaaatatat tttataactt tggtaaaaat gtataatttt ttgtaattta aatattatat    240

aataaaatta aaagctgatt taaaaaaaaa ttccagtgta ataaatgtat aatacttata    300

actaaagaaa ttatttaact tttctttaag atttatggta tacatattga ctaaaaatta    360

taaattaact tacataaaaa ttaaaattac ttaattcata gagaagatta ttatttgtaa    420

gtttttttgt ttgttttcta gaagggcaga tataattata tatatgaaaa attaatttct    480

tgaaagaaaa tgaagtcagt cgtttggaaa ccacaaaagc acataaaaag tggattttgg    540

tttctatgta taaaatagtg taggagttga aaaactgggt tcccaaaaat acagggaatc    600

tgttttagtt aaatcttgat tgggtaaaaa gtagctttta gtgtctccgc tggtatcggt    660

ctttctcgtt ttttgggtgt aaaatgttaa gaaaaatgtt tggaaaaact gcggtgagcg    720

tgtcattctc attttgttat agaacaaaac ttaggttcac tctctagact ggatttttaa    780

attcaccaca tctcctatca ctaatcaaat tgttacctag ataaataata aaaatattat    840

ttttaaaaga acaaatctaa aataatagaa aaataataat gacgtcaatt ttaatgacgt    900

taacgccgtt atctaaaccc taaaccctaa atcttaaact tcaaacctta aatttaaatc    960

ttaaaatgta aatctaaacc ctaaacctta aactctaaaa ccaaacccta taccctaaac   1020

cttggatcct aaactcaaat cgtaaatcct aaacctaaac cctataccat aaaggtttga   1080

gttaatgttg atgtttttct tttagggttt aaggtttggg tttaaggcct aggatttggg   1140

tttatggtct aggatttaag tttagagttt acgatttgga tttagggtct aggatttagg   1200

tttagggtat atgatttggg tttcaagtct agagtttggg tttagaattt aggttgaggg   1260

tatatgattt cggtttcaag tctagagttt gggtttagaa tttagggtat agtatttggg   1320

tttaggggtt aggatttaga tttaaggttt agaatttagg gtttaaaatt taggatgagt   1380

tttgttagtg gtgttaacgt tattaaaatt ggcaatcatt attttttatt attattttaa   1440

tttttataaa aaaatattaa taatattttt attaatttag gtggtacttt gattagtgat   1500

aagagttgtg gtgaattagg atgaaccaaa attttgttct ttgttatata ctagtggcaa   1560

acccccgcgg agctttgatt taagttgttc tatttatcct gaagtgtata atagtatgac   1620
```

-continued

```
aaatgtgtat cgtattcatg gtagcatatg ccactctcga gctctgaatg agaatgaaaa   1680
ttttctcgaa aacattgatg aattgatata tgtgagagct tgttagcttg acaatttagc   1740
aatataagaa tgttattatc agccttcatt tcatttttat agtgaaagaa agaatatgaa   1800
cggtaattag caataaagaa cggttgcgta gtttccaaat aagtttttt ttgtgattct   1860
tgaaaaatac agcgaaacat atctacaatg ctagattaac tttagctcat ggttcaattt   1920
tctggcaaca gttacagcac gagcagaaat ccttaacaaa caaaaataag caaaaccgcc   1980
accaccggtt ctaaccacta aaatgagtat ctcatttttt aaattagacc gtttgataga   2040
attgcataac tgtctaacta agcatttgaa accacatggg tgttctcggt ttcttgatct   2100
ctttctgagc attttgaaat tcaatcttaa aacattgtga ctgagagata ttacttggac   2160
aggagcaaaa gggatatttc cagagctggt tcatatggaa attggcgtat cttactcgag   2220
cccaggggcg gatctactaa gggagtagtg ggatctgacc ccattaaaat gaacaaatag   2280
tttgttttgt ataagaaata ctaaagaatc ttcagctcaa ttgttgttag ttctagttct   2340
gacctctata aattagggtt cagttcccta attgacactt tttcagtata tttttgcaga   2400
tttcttttct tatttagtga catctacagt ccacgtaaca tattattaag aagaatcaaa   2460
gcccatgtaa catttttaaa gcttattaca tttttatata gtgaaaacac tacttattct   2520
ttaaaaatac ggccactata atacactata accccggtaa aaacatttct agatccgcca   2580
ctcctcgagc cattagctag acaaacgagt tatatgtcgc tatcaactgg tttactactt   2640
tcgtctttgg ccgtgacatt ttccgtatct gattgtgttt gattccaagt gttttcttct   2700
tagtttactt tacacggcgt ggtttataca gaagcacaat aacataactc ctgagggtat   2760
ttaaagtttc tatttttatt gaattataaa atattagggg tgtgtgaggt ggtgtatttg   2820
ttgtatttta tgtattttat gtttgttatt atttttgtt atgaaaatgt ttgaaagtac   2880
agttttatat attttttgct atagttaatt gatgttatag gatgatatta tcttatacca   2940
atattttgaa tcccggtccg gatccgcggt tgaaccgata aatccagtaa tccgaatata   3000
attcggtttg agttttatga agaaaccatt atttaaaaac ccaataaaac tcggaactcg   3060
acaaccagtt gaatactggt caaaccaata agtaactttt atttattttt taaattcttt   3120
aattatgtta ttaaattttt ttatttaaat taaaaaatga gattttctga ttttacttat   3180
tttttttctg ctgccggata tcgactatgt atcttttct ctttttttt tcgtacatct   3240
catttacact atttaatttg tgatttattt gttatttttt aagattttga tgaagatcca   3300
tgccatttga aaaaaataaa gtgaacgatg ataaggaaaa cctgaattag ttgttgtgat   3360
ttggtcggta ttagtttttt tggttatcga tattctatta ttatagttta atttttaact   3420
tttgtttttt tatttaaagt ttaactttac ctttcacatt taaatactat ggatttcaag   3480
tattaatatt tttttattag atgtcataac gtctaacttg ttaattgtaa aatagtctga   3540
attaaatttt gatgttttgt atgttaaatg aaataaaaat aagaaaattt aagtgttttc   3600
taaatattct taaaacataa atatgtatta tttttaatac ctaataagtt attatttaat   3660
aaatttaatt aatatattga actgcggttc gtccgcggtc catcgagtaa tccgatgatc   3720
cggtaaggtt cagtgtccgg tttcgggttt caaaacattg cttatacttt atacattatt   3780
tgtttgtatg aaaatgtgca gtatattttg tattgtattt aattaagatt ttactgctta   3840
tgatagatat tgttggagct taattggtgc ttacgtagtt atctaatata acgtaagaca   3900
agagattgac ccgcacgcca gtgcggatgc taatttttac ggttttataa atttttattc   3960
```

-continued

```
gttattttat aattagtgta agatgtgtcg tcgtataact aattgtattc aaaagatttg   4020
gactgaatct ggtaaaaaga ttatttatcg tacaattata gtaacccatt tcagatacat   4080
tggttattta gatattttta tgtttctaca catcagaatc aaaatcattt agacccggga   4140
tgatccaact caaacctcat acataaattt ataatatcca agtggcgcct aatttcaaaa   4200
tccaaaaaaa ttaatcccga aagaaacaac ttgtacctca atgagtattc gaatgtccat   4260
acttaactga ttctgcaaat aaattaaaaa gaaaactctt tttatatatt aggcaaaaat   4320
aagaaaaata gaaagaattt tttatttagg aaaatagtta tatgaagtga aacattaagt   4380
gacaataaat gtaatacttt ttaattattt tgatttaaaa ttattatttt gtttacataa   4440
actatgtctc gaaactgaga attttgactc ctgatacatg taatatttgt ctatttcttt   4500
tttttggtc atattggcta acaactttgc tgcaacaaaa ggcaagcaaa aacacaaaga   4560
tagaatcaat cattatacat aaacaactaa cattgcagag acgtcctcgt atatcgacaa   4620
cactaggctt aagcagtgga atgacgccat ggaaaacaaa gaacacaatc aatgatctaa   4680
tgcttgtgat tggttccaca actagtgcag aaataacaat cttaacactg gctacaatag   4740
cagaggcgat gtaacaccaa aatgccgagc ttttaaacag tacagagagt aaatcatctg   4800
tagagcaatc ttccaaccca aaggctgagc ttgcaataca tgagcagcaa cgatacaaaa   4860
gccatgataa taggaaagtt gaagttggtt caaaagaatg ttaataatca agtctgaaac   4920
cacaaccaag ctaaaaatct acaatttaac attgagtact ccattctaga ggaagttaaa   4980
aagatctgaa accaagaagt gatagacaac agacactcta taacagagta gaatgtagta   5040
attaataagc aaagaacact ctttagcaga gtagaggaag gactctaaaa catgtttgtt   5100
aatagacata aaatttatat tttgctttag attaatacac atattgatca ggcctgagta   5160
tgcatgtgag caaatgcata ttaatttatt atcctctgtt atagagtagt tgtaaatgtt   5220
aaaaagaaat tatgatggta attatttatt aaaaaaagat ctagtttttt ttataattct   5280
gattaaataa ttcatttagg ctccaaatgt ttccaaccgc tccgtcccac accgcactta   5340
acagtaacaa aaatctctac atatattata tatctatacg tttttataac tgatataacc   5400
gcacctcagt tgtaccgctt gtcccgcacc gcttaatccg ctgttaccat tcggagcctt   5460
agttagacca tatagttttg tattttcttg tgaatgtaca catatatagt acatactaca   5520
taatgtctag aattagattt attggggttt ttaggtaata aaccataaaa tcttttttag   5580
tacgtttaat acagaatcat aatgcaaaag aatgatattt taagaaaagg caatgtcatg   5640
tacagttagc gaaaggataa gagagggaac aaagtgaact gagaagatta agatataata   5700
atggacaagt gacattgtcg tggctatgtc tttaaaactc atatatggtc tctctttgtt   5760
tggctttatg tccgattccg atttcttatc tacgttcaca tgcataacta ataatagtct   5820
tcataaatat cttctccttt cctcattata attttttta aatacaaaat cgaatttatt   5880
gggagaatat ttcgtttaga tccgatatct tttctaatta tttatggaac aaacgttatt   5940
ttatattaac tcaaatccac tatatgaatt atgtatgtaa gaacaaatat gaaaggtgag   6000
gatgaatata attaaagact tgatgctaag tttggttaaa caaaactaag tgatggtggt   6060
ttagggggcg actggttttc tcgttaccac ccgcaaacgc agcttttgcg attggtcgcg   6120
gttgtcggcg atttgtaaca attactcaaa tcgctctaaa ccgcttcaaa ccgttccgaa   6180
tctcataaat tcaaaagctg gctccagcta gcatttgcgg ttgcgaacgg ttgcgggagg   6240
gtgaattttt ttttcttttt ttaaaacaat atatatacaa aagtaaaaat gtttaataaa   6300
aaatttaaaa tttaaaattg acattatgaa aatattaaaa tatatctatt atattttaat   6360
```

```
taaaataata aaattttata ataaaaacaa tttcaataaa ttttcgaaaa ttaaaattat   6420
aactttctaa atataaattt tatatttatt ataattttat gatttttgat atttttataa   6480
ttatattaaa tgtaaatatt gttaatttat tatttgattg ttaccgcatt tggtagttaa   6540
ccagtcataa gtcacccgca aacgcaccaa tttttaaccg cagtacgagt cgtacaaatc   6600
tcttaaaacc gctagaaacc gcaaccgccc gcatccacaa actcctgcaa ccgcaaccgc   6660
tacgtttgaa ccagtcaggc ccttagtgat aaaaatgaag atgcagaatg ctgagatgat   6720
atgtatcagt tcgcgaagta ctagaggagg tactacaggc gtgtgtcatg aagatggagc   6780
ttaatgtgag tttgggtttt gtgatgtgcg tgggcttgct gagcttggaa aaggaaagat   6840
gatatgtgtt taaagacata tggacgtttt ccataatgca aaagggagtt tgcttgaaga   6900
tgaagttttc cattaatgaa aatggaaagt taccttaagt gtatttggaa gacttgagga   6960
gcaagttaag gacgtggaag gcaagttctg gtctactata taaggaggga cgtgccttct   7020
gagaaagcta gacctgagag aataaagaga gagaggtttc cttggtgtgt gttactgctt   7080
ggtgtcgaag gacattctga agcattgtct gatggagtcc gatgtggact tagtttggtg   7140
gcgttggagt tggcgccttg tgtggtggag ttagccattg tgtatagctc gtgtgagctt   7200
tgtgtgtgct tgggtgatca agcgttttgg tgtcactggt gtgcgttggg tgctgacgta   7260
cttggtgaag tacttccgag aagtgaaaga tcgaagcata gactcagggg gagtttagta   7320
gaggcggttt cattgaagag atcagtggag attgcagctg tagaagacag tgtgctccga   7380
tgcatcggat ggtgatctat gcatgcgtgc ttgattccta atctttgtag attgcctact   7440
tagaaaagag tggtagacac tagtgtgtgt gtgtgtgtgt gttgtatcat atagcaattg   7500
taggttgctc cttgttctaa gtcaatgaaa tctggacgag gtcccgagga tgtaggaaac   7560
gaaccccgtt aacaaacttt gtgtgtttta ctttctgcac ttgtttattg tcgcctcatc   7620
tgcactaaca attggtatca gagcgggtca cctaagttac tggtgagatc atggatgatg   7680
aggacgaaac ttgttcagaa agtaggacaa agtttgattg aagatcgttg aagatggcgt   7740
gatgggattt cttcctaggt ttggaaggtg atgatcttcg agttggtttt tgaccatgat   7800
gtgattcata gggggagatg gaagacgtgg ttttcaagtc ggttatgatg agtgcacatg   7860
catagtcaaa aagagggaga ttgaagatgc agtatgctga gatgatctgt atcagttcgc   7920
gaagtactac aggcgtgtgt catgaagatg gagcttaatg tgagtttggg ttttgtgatg   7980
tgtgtgggct tcctgagctt ggaaaatgaa agatgatatg tgcttgaaga catagggacg   8040
ttttccataa agcaaaagag agtttgcttg aagatgaagt tttccattga tgaaaattga   8100
aagttacctt aagtgtattt ggaagacttg aaaagcaagt taaagacgtg gagagcaagt   8160
tctggtctgc tatataaaga gggaaatgtc ttctgagaaa gctaaacctc agagaataaa   8220
gagagagagg tttccttggt gtgtgttact gcttggtgtc gaaggacatt ctgaagcatt   8280
gtctgataga gtccgatgtg gacttagttt ggtggcgttg gagttggcgc tttgtgtcgt   8340
ggagttagcc attgtgtata gctcgtgtga gctttgtgtg tgcttgggtg atcaagcgtt   8400
ttggtgtcac tgatgtgcgt tgggtgctga cgtacttggt gaagtatttc cgagaagtgg   8460
aagattaaag tctagactca gggggagttt agcagaggcg atttcattga agagatctgt   8520
ggagattgca gctgtagaag acagtgtgct ccgatgcgtc ggatagtgat ctatgcatgc   8580
gtgcttgatt cctaatcttt gtagattgct acttacacta atgtgtgtgt gttgtatcat   8640
atatcaattg tagattgctc cttattctaa gtcaataaaa tctggacgag gtcccgggaa   8700
```

-continued

```
tatagaaaat gaaccccgtt aacaaatttt gtgtatttta ctttctgcac ttgtttattg   8760
tcgcctcatc tctactaaca aaatatacct tacaacatga tgctactgac tcagttttcc   8820
tccaggtttg atttttataa aactctttca cacctcttat gggcaagttg aaatggggtt   8880
atatttcaaa ttcataaaaa aatttattac tcatggttac tctcaccttg aaaaaaataa   8940
taattgaatt gtgttaaaat ccaaatcaca gaatatatat atatatatat atgtatatat   9000
atgtaagaac ttatttttca gcaaaacaaa atttgatttc aagattccac ctcatgatat   9060
taacagagaa aacattacct cttatttaac tggttgatat tttatacgag tatggaagtt   9120
cctaaaagtg atcaaatgtg tgaaataaat atgccggcaa aaggcagaac tatgacttta   9180
gctttcagct ctgtttacct ttgcttatgt ttttccccaa ccaactaaga aacatttgtt   9240
tacttttgtg tgacattact cattaagtga ctgagaattt tctaactccg gcaaacaaaa   9300
tcatttctaa agaatgctgt attaaactaa agtgattgga cccactagtc aagttacttt   9360
taccgtgaac tactgtttca ctctattttg gcttcatgct tagtgttcta aaattatgtt   9420
tgagtgtcct aattaagaac aagagaacta attccacagc cggaaattcc aaactgaaac   9480
ctgttttctc aaatctccaa atctatgaag ccatatatgt aaatttcgta gtggcgaatc   9540
ggaatatgtg ttgctctatg gttgtagttg attttcgact tgatcacttt atttaatgac   9600
aagaacagca atgttttgtc ctaagaaaag gttgatgagc ctgacacaaa aagggaggaa   9660
gccaagaatt tgttggggtc gaacgaagtg tcatgctaca gaaaagaaat gtcatggttt   9720
aagggtccgc taattcatta gatagttcga tgtttttata tagtagagag acagtgcctc   9780
acacgtgcat gtacgtccca tctttttctt gtcctgtaag ccatcctttt aaacactatt   9840
gttaatccac aaacctaact tttaactatt taaatggttt tagttttcat ctagttatca   9900
agaagtaact taaaaacatc tccaaaaagt attctataac tttaaatatg aagtttttttg   9960
cattccaaaa aataaatttc aaaactttaa atttgaagtt tcatatattt gtttgcattt  10020
tactccctac aattacacat cacatttaaa aattcttgtt tattgtttta atcttttaaa  10080
aaaatatctc ataaatattt tgactttttt ataaatttaa tttttacata taaaattaaa  10140
taaaacttta aaataagatt taaaatgttt taaaactaga tttaaacaac aacaatatac  10200
aaaagaaact taaaagaaaa ctttaaaatt acatgaagac ataactacta cacaaattta  10260
aatattacaa tagttatgta aatttgattc ggaacctcca aaatctttaa aatattgtcc  10320
aaacaaattt tgtttaacca aaaatggttg ttgttgtttt tgatgttttt cgtacgattt  10380
tttcttgttc agattgaatt tatgcacgag tattaacatc atcaatagaa gttaagtctt  10440
ttagcaatat tttattttc tcttttacat tttttagat ctaatgtatt tataatatta  10500
gtttcactag atttaaataa tttttagctc gtattctaca aattacaaat aaagatagtc  10560
atttttactt caaaatacac tagattatca tatatgcatt acaaaaaataa ttttatagaa  10620
tattatggta ttttccttaa atattaatat taattatgtt atttctattt aaaattttac  10680
taattaatat tttgtaatac gtttatatat gtgttagtaa aagtttgatg aatttaaatt  10740
aataataaca aatatagtac tccaaagctc tattcatgca taacatggcg ggtggcaatc  10800
caaaaaatat tcacatcacg tatgttttca gtgttgacta tacgaggatt cactacaaaa  10860
aaaatagcca tattgttacg aatttttttg tcacaataaa gaataattcg taacaataaa  10920
aatattgtga ccagtttgtg acgttcttta aacggtgaca atatgatcgt cacaaatttt  10980
gttggtaaca aaaaacgtca ctctgtttat gacgatatat attgtaacta tttcgtcaca  11040
gatagcaact atttactaaa gtaagaaaaa cgttagaatt accaaccaca attaacatca  11100
```

-continued

```
caaaattgtc atattatgtg actgtctaca agtcttaatt tcgtctctag ttaccactaa  11160
aataaagttt caaaccgtcg caagaaaata cgaaaaaata attactaatc catcttcatc  11220
gtgacttttc gtggccttaa actttgtaac attttattac taaataattg tcactaattc  11280
atattacttt tttatatttc atcgctaatt tatcatcaaa cttctggctt aactaattat  11340
taatttgtca tctcaaaagt ttcaacattg atcactatat tattgatgat ttgtagttta  11400
aatacatagt aatgaaaaca ataccaaaat aaactgataa cataaataat aaaccacaat  11460
aaaagaatat tctaatatgc gatcagattc agtttagcga tctccagttg tgactcatga  11520
taaaaggctt cttgattttt agcatcggtt gattcttgca cacgaagcga aaggtacgac  11580
tgctaacttg tattctttaa agtgaccacc ttgtaactgg cttcttcttc catgatttta  11640
ttaccaatgg ctcagatctg cttcacctct gctgtcttta agcttaagat ctactctcta  11700
ttgaactctc cttaatgtcc cagatacgca taccaccaca gcgccagaaa cgactgttgg  11760
tgacaacacc gtcaacacaa atctctcacg cttttccatt tttacgctct cgctcttcct  11820
aaggtgcctc tgcggctttt cttttggagg aaatatatac actttttatt tagggtttct  11880
aggctaatgg gctctaagcc tctacttatt agtctaaggg ttccggctta aaatagagat  11940
acggtggatt cagattaaag tatttttacc tatattacga tccatcttca atagaaatag  12000
ttgatatttt ctattgttta tcatttttac atataaatat aatcttctat ctaatacaaa  12060
ctatatatgt attgtttttt ctttaaactg atttacataa ataataaaat tttagtttat  12120
acataattta aaacttatca taaaatgata tataaaacat ccatattttc aattagtatg  12180
agaaaaagta ctttttgaaa tccttcacgt ttatacatag gggcatataa atcgactata  12240
taaacattgc taaatcaatt tctaaatatt tcatggattt cttacatctt tgagtagaag  12300
tttattacaa aaaaaatttc atctacgata tgtaccagtt agaaactatt attttgttat  12360
tataccgtca caaagtaaaa ctaacttttc catcacaagt tcgtaattag tgtgacgaga  12420
catacagtca taatatggta acagatgtta accaattgtt aatttgtcac aattttgtca  12480
ttgattgcga caaaacttag ataccatttg aatcatcaca atattgtgtc aaaaaagcta  12540
ctcatctgtg acacaaaaat ttggtcacca taacgtatct aaaatgtcat aaatttgtga  12600
caaatatttt tttgtatcaa aatttagtca caatataatc attttctcgt agtgattgga  12660
ctgaaatgca taagacacta aacctttcgg agatgcgtgg attggggctt atttgccaaa  12720
taaccaaaac agaggtaatt agatctgtag tgagaagtta gagagatata gaaagagaat  12780
tgaagagaaa gaggatgttt ttggttagat agtgtatttg tgtttttgta tctttagagg  12840
ggcaaatttc ctttggttaa ttccggatat gtatcactat cagtccactt ctttaacatg  12900
ttttttttta acatgttaat tttcagctgt ggtggatcat gtactaatct tctcacatac  12960
aataaacaaa ttggtaaact agacatagag gatcattagt attaagatgt cttatagtaa  13020
aataaagaca attttataag agttagatat tagtagttat gagaagtata taattaattt  13080
atgacggttc ggattggcac gagttcatca caaataaata aaaagctatc agtttattat  13140
gggattagat aacatagtct tgaaggctat gaactcgaac attctttaac tatggtccac  13200
tacaaggcct gagtaaagta ttctctacgg ttcatgcaag actagcttgc gcaacttgat  13260
tgtggtccag gatccttttt tgcttgtagt ggacctattg gtgactcaaa atgtgtttgt  13320
caggttcatg cagtacaata aatcttttta tttttcaagc aagggtcatg gactatatta  13380
ttgtgctttg ttactatgca tgagccacgt gaatgcatca atattgatag ggccgtttct  13440
```

-continued

```
ttttttttct ttttttttc gagcaacaag ggctgttctt atatatacaa aataagcatt  13500
agtgttgaaa atcccactca tgagtgattt aatggtagat ggattttggg aaactaaaca  13560
atccagattc gaatcaaccc cacgatatta aacagtgtag tcacgcagat atgaaactat  13620
tatttgagtc ccatttgaat attcagaaaa aaaattcata tttagaccat gtatctccac  13680
ttgagagact agtttgagtt tttctatagg tttgggatac tctcaagtta atcaacaaaa  13740
ctccaaatat tttagttata taaagtatat aatctcaaat cattaaaaca aaattttata  13800
tttagcctct aatattaaat gtgaaaatgt atatttgggt taggttgtga atggttaatg  13860
gccctttcat ttttttccca gctggacgat ccatttctta cgggttttgt ggtctaaata  13920
aaaatgataa tgtatgtctg catgcacgcc gatggaacat gtaattctta tccgtgtaat  13980
ggtggcctct atagcactta tatgataaag aaaaattaaa ggtgaattcg aatacttcca  14040
tgttgcaaat ttatgctaat attttcgaat acattttcca tccgactgag agaaaaagtg  14100
ttgtggggtt gggttacaaa caaatgcgag gtaggtgcat gttcgataca cgaaaagaca  14160
tcattattta cgacgtgttc tataccccgt ccattccctc aacacttgta ttgtttaaat  14220
caagttaaga attgtatttt tatgattttt actatgatta gttggaaatc caaaataatt  14280
cattaaagat gagaaattag taacgattag ctttcactaa tccatttttt ctttataacc  14340
ccacacgttg agttatttcg gtctaatacg taagcttcat atgttgtcct ttgaaaattt  14400
agaaaaccta cggatgcata ttctctcggc cccactcttt gttttttgg taattagctt  14460
aatgataaat ggtttttaag aaaactaggt gactgatctg caccctgtgc ggacataaga  14520
acatgatcgg cccgcaccat gtgttctctt tcggtctgca cctcacgaga gggaacacag  14580
taacgtcagt atgaagaggt agatattgtg tgtatgtata attgcaacgc cacaaaatat  14640
tttgtgtgtt tacgaagata ttttcattca aaaaatgaaa taaatagtgt atagttttag  14700
aaataacata ttttatatta ttattaatta gaattgtatt gtatatgtgt cgtaactctt  14760
tattttaggt gaataatatt atttttccat aaataataaa caaacattta tgtagacata  14820
ttaaaagaaa atataataaa aatcaaaata ttatccataa ataatataaa ttatgaagta  14880
tatttctcga taaagaaagc aaattcaatt agaaacctgc aaaaattaaa taaattttgt  14940
aagcaattgg acgggttaac attatttgat agatttataa atttttaaat tttattgaac  15000
atgaaataat attaaattga cataccgtca tcggtctcct aactcatcac aacccatcta  15060
acaaatacaa aaaataaata attgtaacag tttatatatt ttaaaatttg tatttgaaaa  15120
aaaagtagat taaatttacg taccgtaact acgaaatatt ctgaaaaact tgtttgtaga  15180
caacattcaa tgtttttgtc tgtggcttcc cttctttacc agttattagg atttttaatc  15240
cagatctcga cttaactctt gaaagtgcaa ctttgccttg cattttgtaa gcattttata  15300
aattatgata aattatgata aatttattct ttaaacaacg ataaataatt taaaaataat  15360
attaataaac atttttggat tttgtaatat tgaaaatagt tattatataa ttatattcga  15420
acacaattca tcaagtagag tataaaacta ttataattat cttatataaa atttcgttca  15480
ttgtatttta tagtttataa atattaaaac aaataaatgg tagagtatgt aacacctgtt  15540
ttctaccagc gtgagttaga acaccgccgt atttaagaat cataagggcc tctacaggtc  15600
tttcttcttc gccttcacca tcccacttta gcggcttcag ttaaaccttc ttgtatatcc  15660
ctgagaaatt tcctccctgc gccattccaa aaggttctct gctgtgagaa aatgacctca  15720
tgaattaaat aaaaaatgca taatgctagc ttacttataa gatagtatat tcaacaaaaa  15780
aatgatataa gatagtatta cttgtcccct ggtcacattt atgtattata tacatagatc  15840
```

```
ctttgatcct tcctgtatat tcaacacaaa ctcttcacca actcaagcat gaattcttgt  15900
cctctggtca caaaaattat aagagtttta taaacgcaga ataagtatat aaacaatgct  15960
tctaaaaaat gtattttgtg tgatgtatac ttacttcttt atcaacaacc accatttcaa  16020
tggtgtttcc tgattctttg ttatagttta tccacaagcg aacaatccta atttcttttt  16080
ttttgacgct gatttattaa gatattacaa ttacgatatg agaaagatta catagacgat  16140
tcggcaaccg gcaatactac ctgccttatg aagacctacg cctaactgca tcacctgagc  16200
cgtcctatga aaatccacgc ctggccagat ttatttgcac catgttgaag atcccttgta  16260
tgtctttctt ctgtagtctg cataattctt taataaactg ctctctccgg gacttgaaac  16320
ctggatttct tgtaatctgc aataaattgc atagtctgag attcgaaccc cagacctggg  16380
tgtagaagcc tttaaacctt aaccagtagg ctagggtgct tccacaacaa tcctaacttc  16440
aatacgcgac gtatctttac ggggttttaa ttctctcaca taagaaacaa tatttttttt  16500
tgctcgcacc attgccattg ttcttgtaag agctgaatgt ttgtaattta agcattcggg  16560
tttctcatat atatattaag ccgatttatt tatcatatta atgaccccta ataaatatta  16620
aaatcgttta aagaaagata ttaattgtgt attgtcataa attgatttgc atatgatatg  16680
attttaactt gcgcaagtaa tgtaataaat atgataacaa ccggcgcaag caattgattc  16740
gaataataag gaaagttatt aatatgcaaa ttagttaaca atcttgcgca agttatctaa  16800
ttattatccc caaatcgaat aaatatatgg gcttaacatc taccgacaat atatttgggt  16860
ttttctaaac aggctattca catttttctc ataaataaga agaccaaact tgaaaatccg  16920
aaaaccaaca gaccggaaac cgcaaggaat gaaactgact gactaaatta gtaatgtgaa  16980
gctctaaatc atgctgcaat tagtgatgca acagactatc gcaattagta atgtgaagct  17040
caaaatcgtg ctaatgaaac aaaaaccaaa cttgaaaatg tcaagagagg actgtctaaa  17100
tgcttgttga gttattaagg agaagataat cttacagtcc ttcttcagag actgaagtcg  17160
aattgccgat tgttgtaaat gtcagttgtc tcttcttgtt ccatcagtag acagtccgca  17220
aaatacatct ctggtcgtgg caatggtctt gtttaagaga atcaagaact caacaacaag  17280
aagattaatc agtcaattag atacaaagat tcaaagtgtt aataagcaaa tcgtagttta  17340
tagcttaaca tatgtcgaat ctaatcagtg aaatccaaaa atctttgtat catagcttaa  17400
aagtcgaatc caatcagaga aaccgaaaaa tcttcgcatt atagcttaaa agtcgaatcc  17460
aatcagagaa accaaaaaaa ctataaattc cgagagtatc gacaaacttc acctcgtctg  17520
gttgtcgctt caattgtttt catcggtttg aaaccatatc tcccttcaat tgatacgcga  17580
ttgaaaaaaa aaaaaaaaaa aaacttcatg acatacgacg gtgttttcaa atccgtggag  17640
gggagtgaaa aaaataaatg aaaaagaaaa attccaaaaa atcagccaat agaattataa  17700
ggattttccc gagaagctct atatgagtgc cacgtcagca gaaatcacta aagtgacttc  17760
tcttttaatt tttaggagga taattctcta gcttgggtaa aatcgtggat atctacgaaa  17820
tgattccttt ctacgtacac gacttttcat caaatacgaa tggttagtac aattaatagt  17880
ccatccgttc ctaaaagatc tatgttttag aattttcaca ctttttaata aaacactagg  17940
ataagacctg cgccttgcgc agggtgaatt tatttatata tattatcgat aatttttttta  18000
tatattggat cattttattt atacttatat aatgtttttt tgttgttatt atataatttt  18060
tttccgatga ccggatcaat ttttattaaa aattatggaa ctaaactata aataataaat  18120
catgggttga tcggattgga cattaagcaa attatgacac aaaaatttta tttttttccac  18180
```

cgaacacatt cttgaaaaaa ttcaacagta ttattttcac agttgaatta ttttgacatt 18240
tatcttccat atggttttga aaggtctcag atcaaccatc gaattgatac atgtcatttt 18300
aatgttttta atcgtattct taagggaaaa ctaacatttt tgtaatttaa agtggtttta 18360
aaaaattcaa aatataacat ataagaaaaa aatctaatat ataagaaaag tataacatat 18420
aaggtttact catttttgta atataaagtc gttttacgaa tttaaaatat aacatataat 18480
gtctcctcat ttttgtaatt taaagtcatt ttagaaaatt caaaatataa catatgagaa 18540
aaaaaatcta actttttatt atatggttaa tgtcactgtt tattgttttt taataatata 18600
aatttaaaca aaaattcaga aggatgtaaa aattgttatc aaatctttat tattcataat 18660
cattaattat catatttatg ttaatcacat taggtaattt cgtagttttt atttaaggaa 18720
ataatacact cttcttatat tttagattaa tataatgttt tctagtaatt aaattttgaa 18780
ccaacatttt ttcaatattg atttttaagc tgtcacgtaa gttaaattat tatcctaatt 18840
aaatgacacc gaatcagagt ctttttttaat tagtacaaac ttagagttat aatttttaaa 18900
tgattttcaa ttaatatacg tacatgagaa actaaaacag cttgttatat aactaccgag 18960
atatttgatc ggattagcat aagcaatatt taatagcctt ggccgcaaat tctcaattga 19020
tacgccctca catataagct ctatatatta tttagtttcc attagttcct taggcttaat 19080
taatagtctt ggctataaag tctcccacta cgatgaattt ccataggtta atgtgttagt 19140
ttataaaata tattaataat atattgcctt ggccacaaag acttaacaaa catattttat 19200
ggatctcaca cgattattaa tatttccatg ggcagctttt ccttgaagaa aaatgagaaa 19260
taaaaaaaat tgattaaatt cgtttaacat aaataccaaa actggtaatg attgatttaa 19320
cataacccta aattagtttg tgatatgaac cggttaaatt gtagagcagt actttttgaa 19380
tcacatgaaa ctcaaaagta atctgccgtt tttatatacc tcacttacag taataattac 19440
atgattttag aacaaaaatt ctctagaacc aactgaagaa ggactcccca accattgttt 19500
tacaaaaaaa aggacccccc aaccattcat gcaaacagac atagttatga ccctttaaac 19560
aatatcatag tacagattat aaagtttttt atcaagtgac tgaattttttc tggtaaacca 19620 cgtttgctac atatacaata taattaataa agtggatatg agaaaatcag gaagattaac 19680
tgaaacttgt gtagcatagt tctattacag tggtgaatgt tcttattaat caaggtagat 19740
aatattaact gacgataatg ttctaacgat aatgttcctg tcaataattt ttgtaagtga 19800
tgtaggtctg tttattttcg tacataatgc atagaaaatt acatgttcta ttttctacaa 19860
acttgaagta aaatgagaac atttaatatt tattccctat aaaatgtatt cgtagacgtt 19920
attacatagt tatgcttaca tgataagaaa aacatacaca ataaataata ctgatggatt 19980
acactatggt tttacatagc ataggcgcac ctgccgtctt atttttagac tatgtatatg 20040
tgactgtcaa aaattgtatt tcgctaggga gttaatttat aaactatgct atttcttaat 20100
gtgttataat tctgacacgt cagattttag aaggcttaaa caactgccac ataggatggg 20160
gtcttttttt aatttttaca aaattcaggt tataactttt taaaagatcc tcaattaata 20220
tataggggat attaagactt agttataaat acatagtttt ttttgtaatt ttatatttta 20280
tatattttta aactaataag attctaaaaa ataaaattaa tgttcttgaa ctttacaatt 20340
tctcactatt gttgacaaaa ttacattgaa aatataaaat atgtatattt ttaaagcaaa 20400
agttttctat agaatatgaa tcttttagaa acggaaagag tataagatat gtcaacacgt 20460
caagacgtgt atgataattg ataagtacat ttactcgtag ttaattaggg aaaatatgaa 20520
actacatatc atatatacat aacattatta aaatagaata aaactgtaat catatggagg 20580
tggttcagtg gtaaacggac ttcagaaaac ataaatttga ataaattcgt gtggtcaaac 20640
agatatgaaa ctatatctta aacttcattc taatatctag aaagacagtc catctatagg 20700
ttttaccttc atgtttatag caaaaaaaaa gagaatgaaa aatgtcaaaa aaacatcata 20760
aaaatgtcat tataacctaa gaaatcgtaa tatcattttc atctcgctat caattcaatt 20820
caacctaagt cataactgta tcaactaatg tgtatatata tattgtctcc ttcaaataaa 20880
gctcgaaata tgtaacgatt tattcgttaa ttgtttaaag ttcatactta aaacaaagtg 20940
gcccttcgga aatcacgagg aaatcgaagg atgttctcca ccatgtgcgt atgctaaata 21000
acaaacacat acttcttttt acattttagg atttattctt aaactattat tctgatatct 21060
aaacacacat atataaatag tagaaatggt acatagcaag tcgcctacat tagtttctta 21120
ttcttgaaga gcttcattcg tgaggaaaat taactatagt tctctaagtt tggcaatctt 21180
tgatgtgaaa aaaactatgg aaaaattccc tctaattagc accagtccca cgtttcacac 21240
cttcattaag agaaaattgt aatgtgcact caattaattc catagtttat aggaaaatat 21300
gatagtcttt taagccgggc tacaactaga cgcttgtgga tgtgagcaat ctaagttaga 21360
tattacccgg cagatactat gacttacaaa gtacatccta tgtttctaat tacttgtaaa 21420
cggtgcgctt taggttgcca actctggtca tagagtgtca caaccatgtg aaaatgtttt 21480
atccaaataa agaaaagttg ttacaagtaa ttttaatgag taactagatc tcgatccgcg 21540
cacatgtgct gatttttatt ttcatttctt tttatataaa tattttgttt taaattctaa 21600
attagtatat attataatat atatgtgtct atcaattttt aaaacataat aagtttacgg 21660
tatatttttt cattgaataa tttgtttcaa actttcacat atatttgtat ctttttctat 21720
atatattttc gaataattat tttattatta aactcgtaac tatatatata aagattacta 21780
aaatattatt ttattgtcat attcaaagat attgtaacat ttcacaaatt tagaaagttt 21840
ttaaaaaatt aaactttttc gtttcataga tttatattat cgagtaaata attaaacatt 21900
tagtttttgt tttaattttt aaaataaact atatagtttg aaatttgttt tcattggttt 21960
aaggtagtaa atattaatca ttgttagata atatgatttt tgttatttaa attttttttt 22020
ataattttaa aaattaacat cgacaaatat ttaattattt aacatatgga ggtatagtat 22080
tataatatta aattatatct attttattta tactatatat aaatccaatg gatcatctat 22140
tgtttaaatt caattattga tagttcaata aaattttctg gtaggcctaa aattttaata 22200
ataagattat agattaaatg taatatgact tttttagaat aaattcatta ggtccatttt 22260
ttaaaaaatt acacatgaat cgaagttgtg acttatgttt taatatatat ataagattgc 22320
atatagtccg aacgtactta atgcaactaa gtccaatata tatacaatta tattaagtcg 22380
ttgatgattg aatcgcaaag gcgtgttgga aaacaatcga agagagaaga agaggtatgt 22440
tcaaaaaaaa gaaaagaaga agaggtagat gaaaccctca attttaaaat tcaatggggt 22500
gattaggtta gaagtaaaat aaaaaaaaat tgtgtagaat ttagtttgta tgattttttt 22560
atttaactgt aaggaaagta ttttaaaatt ttattgctgt agcattattt tttctacagc 22620
taaaaattgt tgttttagaa aatatagttt ttttacatct atttttaatc ttcctgttgt 22680
agttttcaga actattctaa agcataattg ataattttaa aggttataga taaaaattaa 22740
aactaaaaac agctactata acacaatcca ccaccccaag tctccaccac tagccacatt 22800
aaatgaattg attttagttc attcaccatt tataatctta ttatatattc ttaataaaat 22860
acaaaatata tatattagaa atgatgctat tttttttttg taactggaga aatgatgcta 22920

-continued

```
tttttaatca accatttaac ccacttgacc cacacaatga atttgttctg tttttgtgtt  22980
gttatttccg gataaagtga attagttcca tccaactgat tcttctacgt atgataggtt  23040
tctaagcatc taactagtat gcagtattat attacgtgat gaatgaaaaa caaaaaacca  23100
ccaactacgt tatgccaaaa atagaacttt tttttccgcg ggggggggg gagaggggta  23160
acaaatacaa aaaaaaaag ttattcttgg gttcaccccc tagagtgaac ttctaggttc  23220
accaaccaat atgattttat tatttcaaat tcgatatttg ttaaaaaagg aaataaaata  23280
ttgtcaagtt atattatgct tttaaaataa aaaggtaaaa aaaaatagtt acaaaaaaaa  23340
gaagttttta aaaaaaatac tgttaacgtc gccagcaaaa cactaaactc taaatcctaa  23400
tccctaaacc ctaaatctga aaccctaaac ctttgggtaa accctaaacc cttgggtaaa  23460
ccctaaatcc ttggataaat cataaattct aaatcaaaaa cactaaacac taaaatccta  23520
aacccttgag tgttttagtg tttagtgttt ttgatttaga gtttatgatt tatccaaggg  23580
tttagggttt cagatttagg gtttaggaat taggatttag ggtttacttt tttcctgacg  23640
acgttaaaaa tattttttg taattactac tatttttatt ttttattttt tatcttttta  23700
ttttaaaaac ataatataac ttgacaatat tttgtttctt tttttaaaag atattgaatc  23760
tgaaataatg aaattctatt ggttggtgaa cctagaaatt caccctaggg agtgaaccca  23820
agaataagtc aaaataaaat cgctattaaa gcaagacatc ttccaaaaat ataaaaaaaa  23880
taaaaaaaac caaagtcatc tcaaataaat aaaaccgctg gatacatgtt tagtaagtca  23940
aacaaatcat agtgatgtgg caactgtttt ttcctcaact ttcctcaatt taatttgcta  24000
gcaatttcta ctcaattcaa ttctaagcta ctacccatta actacttcat ttttttttta  24060
gattttctta tttattggga agttttatta atcactttta tgatgaacta attccttata  24120
tattatttga gaaaattaca atatttaaaa cgtgtagtgt atggttctca gattacctaa  24180
agaaataaat tggtcaatct aaatatacac ggtagttctc attaaattaa ctaaaaaact  24240
aattactaat gtaccaaaag aaattattat ttagtttctt aaataaaagc tacaaaatta  24300
ttaaatgtga tcaatatata tacatgacaa ctagtgattt tgaataataa aaaattgata  24360
acaatttgtg tttcttctat attttgtttt atatttttaa aataaattaa ataatcatat  24420
taatcataga ataaaatttt aaattttttc ttatatgcga tactttgatt tttttaaac  24480
aactataaat tattaaaact gtaaaaaata ttacattaaa aattttgtga gtaatggctt  24540
aaatttttg ttatacaata tataaatata caaatgatca taaaatcata tgaataaaat  24600
atcttattta atagattttc atattaaaaa tatgttttta ctatcgttta aattaaacta  24660
tataccatat aagaacataa tagtttaatt tgaaatttgc attgaagaaa tattgagaac  24720
ttaatattct aattttatat tttgtattaa atttttaaaa acaattataa attactaaaa  24780
ctattaaaag tatcccattg agaattttat tttcaatatt ttaaaaaata cgaattgtca  24840
taaaactata taactataaa gcattattta acagatattt taaaatatac ttctatatat  24900
taatattatt taaatttaat tatataccat agatataatt gaatttttag atttttata  24960
tcaaaattat tttaagtaaa aagagtgttt gttttgattt atgtgttcgc gtcaacttaa  25020
ttatatacat aatagttata gacttttcag tttattattt tattatttca tgtaaaaacg  25080
taaaataaat aataatttat atacacaatg tccatcccgc acatataaaa ataattcatg  25140
ttgatcttag cctagtcaat aaataatcga caaaatttta gggaacaaaa tatatatgct  25200
agaggatcgt tatgtttgtc ttccattcca ctgcatctac atatggcatt tgattctaga  25260
gtaagaaaca caaataaatt tatttggtac aatccttccg tccaaggaaa atctaaaaat  25320
```

```
ataaaagaca tcttagtgaa gttatagatt atggtagcat tctatttata cccaagttta  25380
aatatgattg tcgtataacg tattgaatag caaatatctt cgaatctcat atatatgaaa  25440
ttagtgtaaa ttttaaacgt aaacaattta tacgaccaca gttcgaaaat aaaaacaatt  25500
tatacgacca gaaatggcaa aatgttgttc ttagcatttt tttttttaac tttacttttg  25560
cgtaaaacac atttctccaa tttggtttca ttgcgttgaa cgacgtaaca aagtaataca  25620
cctaaccctt ttttttggaa cattatacac ccaacccatt gtacaaaagt tacagctaaa  25680
ttaccctttt tattcttttg ataaataaaa aataaattat taatcattaa aaaataattt  25740
ggagtatttt ctcaatgtcc atatatacat cttctccctt tatataagcc aacctcacac  25800
acccaaaaaa tccatcaaac ctttcttcac cacatttcac tgaaaggcca cacatctaga  25860
gagagaaact tcgtccaaat ctctctctcc agcaatggtt gttgctatgg accagcgcag  25920
caatgttaac ggagattccg gtgcccggaa ggaagaaggg tttgatccaa gcgaacaacc  25980
accgtttaag atcggagata tcagggcggc gattcctaag cattgttggg tgaagagtcc  26040
tttgagatct atgagctacg tcgccagaga cattttcgcc gtcgcggctc tggccatggc  26100
cgccgtgtat tttgatagct ggttcctctg gccactctac tgggttgccc aaggaaccct  26160
tttctgggcc atcttcgttc ttggccacga ctggtaaatt aaattttctg ttttaattat  26220
tttgactctt tttgttcaat ttattaattt cttgaatgca cgttcgatga gtatcgtcgt  26280
cactgacttc aagatttaat tcttttgagg ttaccttttc atgttcaatt attaaaaaat  26340
aaaataaaat ataggatcta agattttttt cttcatcagt tcaagcatca tcactcatca  26400
gtcgtaagac tcgtaacaaa atatcttctt ttctataatt aatattattt ccgcatttaa  26460
tggatctacg ttttgatgtt ctcaaatttt gtttctcttt ctctagatcc ccggaacttt  26520
taattataat tatagtatag tataatatca agaaaatata ctgtttattt tttttggcaa  26580
caaatatatt actcttgttt ctttgacaag aaaaaaatat attgtttttt tcttcttttt  26640
gtgttccaat ctattttcga gatttagaca agtgacacgt catataccgg atttgttacc  26700
ttgttaaaga gtttgggtta aaacaaatgt agaaaagtta aaataaattg tgcaataaat  26760
gataaatacg tttttatgtt aaacaatgat gtgaaaataa aattgaataa tggcagtgga  26820
catgggagtt tttcagacat tcctctgctg aacagtgtgg ttggtcacat tcttcattca  26880
ttcatcctcg ttccttacca tggttggtaa gtcatttatt aactatttcc atgtaaacta  26940
ttagtacttg ttttcgtatt tcttacattt tcgtttgtca ttcttcttgg gtgcatgcta  27000
gcaaactgta atcagtatta actgggaact accaactgtt tttttttgc tagagtagca  27060
attttataat taaataagaa tcctattaaa caatgcatgt gacaatatga ggttgctttt  27120
ctgttcaaaa caaatcttta gaagccaatg aaaaagaatc caaaactttt ttttaaatga  27180
tatgcgccta tctattggtc ctgactcctg agttttctta ctttcttaag tataattaga  27240
ttttgatttt tttttatagg ttttcactat tgttatttgt ttacatcagc ttcagatatc  27300
ttcgaaaaag atttacatgc atcaatttca tgaggattta tagtttttct tttacttatt  27360
tccgacacaa tgtttagtag taaaaagcat taaatgtttt tttgctcaaa aaaaaaagaa  27420
tgggattgtt agagcactct attgttagtt gttcaataaa tataccaact aaaaaaacaa  27480
aataaatata aaatgagtga gattgttaaa tcattataga gacaatttca ttttcacaaa  27540
aataaataaa tacataactt tttataattg gggtttgcag gagaataagc catcggacac  27600
accaccagaa ccatggccat gttgaaaacg acgagtcttg ggttccggta atctttccta  27660
```

```
ctctcgtagt ttctcttgtc ttttatttat ttgtttgttt ttcggaattt attcttatgt  27720
ctatgttctt aggattctat atgtttattt tattagttta tgttttcagt ctgaggtcag  27780
accgaccact tgtcagatct gttttctagc tgtagtaaaa aacaatttgc aagtgtaata  27840
gttcagcata attgatcttg ttagagcatt tccaaaacaa actttataat tttaaatata  27900
cagtttttttg ttctctaaaa aagaatttaa aaattttaaa gtttgaggga cgaaacttca  27960
aatttgaact ttcactactc aacttcaaat ttgaaatttc atcttttta tttacatttt  28020
gatcattata attaattata cattacattt atgattctta agtattttct catttattgt  28080
tttaattctt aaatttttta tacatcataa atatttccaa tttgttttta taaattcaaa  28140
ttttacacaa aaaagtaata aaaattttaa ataagattta taatatttta aaactataat  28200
taggcaaaaa aaatattaca aaaaaatgta ataaaaactt taaaataaga tatatcaaga  28260
cataattatt agaaatttta aatattataa caatattaat aatctggtaa atttgctcca  28320
aaacctcaaa aatttctaaa ttattgtcca aacaaatttg tttaaccgaa tatggagcat  28380
tacaaaaata attttatgga atagtgtggt attttgcttg tagttaatat ttaattatgt  28440
atttctattt ataattttat atatttaatg taagattttt ttaattaata ttactgtaat  28500
atttttatat atgtactagt tatttataaa agttttatag atttgtatta gttataacaa  28560
aaataaggat cattgtgtaa aatacaaata attttgaaat tacgtttaaa gttttggtta  28620
tgaaaaaaat actttgaaac tttaaattta gagttttgca aactttaaaa tgttagatag  28680
atagtttttt tggagatgca tttagtggtt atggtagtaa ctcagaaaat gaaaaatcta  28740
tacttttata ctccctccgt tttttaatat aagtcgtttt acagttatac acgtagatta  28800
agaaaaccat taatttctta tattttctag acaaaaacat cattaattat ttacctaacc  28860
acaattcaac caatataaaa atagaagata tattaccatt ggtcatacaa cattaattat  28920
taataaattt tacatagaaa accgaaaacg acatataatt tggaacaaaa aaatttctct  28980
aaaacgactt atattaaaaa acggagggag tagtacctaa ctttaacgat ggaccactta  29040
tattcgagtc cttagcataa aatgattctc ctcgaaatcc gtttactttc ttcattattt  29100
tttccttttc agttttggcg ttttcgtaat acttttgtct tcaatcttga aagctattag  29160
tataaaaact tataaacaca tcacatgcaa tgaattaata cgaatacata accagaatga  29220
caaattttca atgaatattt aataccagta agtactactc cgtaatagta atagtaatag  29280
tcatattaat tttttttgt catcaaacaa acagtaatag taatattaat tataattatg  29340
tatttcagtt gccagaaaag ttgtacaaga acttgcccca tagtactcgg atgctcagat  29400
acactgttcc tctgcccatg ctcgcttacc cgatctatct ggtaaaaaaa aatacaattt  29460
caattttttt cttaaaatta caaatggttt tatattttga gttttaagcc aatatataaa  29520
ttaattttga ttggatttta actacagtgg tacagaagtc ctggaaaaga agggtcacat  29580
tttaacccat acagtagttt atttgctcca agcgagagga agcttattgc aacttcaaca  29640
acttgctggt ccataatgtt ggccactctt gtttatctat cgttcctcgt tggtccagtc  29700
acagttctca aagtctatgg tgttccttac attgtaagtt tcacatatta ttacaagaga  29760
tttatatatt attaataata aatttgtttt ttgacataaa gttttggaaa attttcagat  29820
ctttgtaatg tggttggacg ctgtcacgta cttgcatcat catggtcacg atgagaagtt  29880
gccttggtac agaggcaagg taaataaatc aatttttaaa aagaaatgta cagaaagcaa  29940
taatggttag tattgattaa tcttaatttt tgatgttttg catacaataa taggaatgga  30000
gttatttacg tggaggatta acaactattg atagagatta cggaatcttc aacaacatcc  30060
```

-continued atcacgacat tggaactcac gtgatccatc atcttttccc acaaatccct cactatcact 30120
tggtcgatgc ggtgagtgat ctagctttct ctctctctag tttcatttga ttaaatggtg 30180
attaattact aatttaatta atgaattgtg gacagacgag agcagctaaa catgtgttag 30240
gaagatacta cagagagccg aagacgtcag gagcaatacc gattcacttg gtggagagtt 30300
tggtcgcaag tattaaaaaa gatcattacg tcagtgacac tggtgatatt gtcttctacg 30360
agacagatcc agatctctac gtttatgctt cggacaaatc taaaatcaat taacttttct 30420
tcctagctct attaggaata aacactcctt ctcttttact tatttgtttc tgctttaagt 30480
ttaaaatgta ctcgtgaaac ctttttttatt aatgtattta cgttacaaaa agtggaagtt 30540
ttgttatctt tttctctagt tgcaatcaaa aggatcttta aaactttttt gatttggaca 30600
gaaagaaaaa gacagttcca ctgaaagtcg acaaaatgca cgccgttttt gggtcccagc 30660
acaacaacaa tatgtcacgg agttgtcgct tttttaagta atgggcaata cttttcggcc 30720
caaatatata aaagccttct taaattgcgt caggtatctc acgcaggacc taaataatta 30780
tacaaacatc tcattcgtcc ccatatatta aagagttgat tacctagtag gccacttttt 30840
gagttttctt tgcacccaaa gctactttcc gcttgtagca taaacattca cggaaactga 30900
aagagttttt ggattatttt gcccttactg aaacgaaacg gaaaattgga atattgtttg 30960
tgttgttttt gttcggttag cttttagaca tttattagat taggtttctc gatagttaga 31020
tttttataag gaccacaaga tcgtaaaaaa aatgttaatc caacaatcac gttaaaatga 31080
ccagtttagc aagttacagt catccatatt tcatggatgt ggatgctatc atgtccacaa 31140
atacatgttc ggtggttatg gatgctttcg tgtccatgta aggatgttat ggttactcag 31200
atttgtggat ggagaaagtt ggataaacat tacttggata gataaacatt atgtggacgg 31260
acgaacatta tggatacaaa aatagtggac atgtaagttg tgggcagaca aatgttacaa 31320
gaatgagtta tagacgagaa cacaacatgt aagggaacaa aagttattta acttaacttt 31380
gtggacaaga ttttatattc tacaattagg cggtaaatta acaaattttg tcggaactgt 31440
ttatcggaaa gtgatctgat gattccgaag cacttctgag aaatattggc gatgatcata 31500
taaaaatcaa tattttaaaa taaaaaataa attttggata agaagtataa aacatattgt 31560
agacaagttt ctgcaagaaa atgtgtgaaa atggcctgcg aaaactaaaa tcaatataaa 31620
aaaaagactt attcttaggt ccactcccta gggtgaacct ctaccaatag gattgtttta 31680
ttttatattc aatatctttt aaaaaaagaa acaaaatatt atcaaattat attatgtttt 31740
taaaattaaa aggtaaaaaa atagtaataa ttacaaaaaa aatattttac gtcgtgagca 31800
taacattaaa ccctaaaacc taaattctaa tccctaaacc cttaatccta aaccctaaac 31860
cattggataa accctaaact ctaggataaa tcctaaactc taaatcaaaa tcactataca 31920
ctaaaacatt caagcgttta ggatttaggg ttttagtatt tttttattta gagtttagga 31980
tttatccaag ggtttagagt ttacccaagg gtttagggtt tacccaaggg tttagggttt 32040
acccaaaggt ttagggttta tccaagggtt tagggtttag ggattaggat ttaggattta 32100
gagttttgtt gagaacatta aaaatatatt attttttttta attctttttt ctgtaactat 32160
tatctttttt tactttttta ttttaaaaac ataatataat ttgagaatat tttgtttcta 32220
tttttaaaag atatcaaatt tgaaataata aaatcctatt ggttggtgaa tcaccctagg 32280
ggtgaaccca agaatgactc aaaaaaaaac tataaagttt cttctgaatg agcttgcatg 32340
tttttttctc tacgatcagt gatgttaaag ttcttccttg taaagagata atctctccag 32400

-continued

```
caatttgctt tggctccttc ttgacgcctt atccttcgct gacaacaaag gtcttcctca  32460
ctatctgaaa aaaaaatcta aacattggtt gagagagttt gatggtgaag ttagagaaag  32520
aggccaaagt taaaaccttt gatttaatgg ggcgttggat aagagaccac agatctggaa  32580
ctgaaaaatg aacaaaaccc aatgatgtta gtagctagcc aacgagtaac caccacaagt  32640
tgctggctct tcaccattat cagcaatgaa ctagggtttt gttcccacca ttggtgaatc  32700
tgaatcgcag cattgagggg ctccacaacc atggcggtga catggaagaa tttgttacgt  32760
ttcgtcacac agtctcgtct ccaccctttg attactacat ctcttgaaat catccattgg  32820
acaagacaac gacagagaaa acagcttcgt tgccacaact gtcatcaagg ttgtgtggac  32880
aaataaaaat ggagataaca acctttgagc tcatctactc tctgaaactc cagccaacaa  32940
atcccgaact caaccacatc cgatctcgag ctcacccacg gcgagttcca agctcatcca  33000
ttctctgaag taaagcgaat ttgggattaa gagagaagaa gagaataaaa gaagcgttga  33060
ttaggtttta tcaatttggg aatttggtaa ttagagttcc aaaagagatt gtcggtatct  33120
tccactcctc taaggcaggc cgcaaacgag aaattaggag acttttcgag agagatgggt  33180
ttcgtggctg agagaaaaga tgaaataagg gattagggtt tgaaagttga ttttgaaaaa  33240
gtgaagtgaa cagatagaaa aaagatgggc tccattaatt ttgaaaacct aaagtgaaaa  33300
tagagaagaa agacaggccc cgtgtaactc tagtttggtt gctggaagtt ggttctttct  33360
ttagttagag ggcactaaga ccatgtttat ccctaaaaca cttagtgggt tttctaattt  33420
ttattttatt ttattttgtc tgatttaaaa aaaaaaatta aaaagtatac taatcgcggg  33480
ccgtcacgtg ttggtggggt ccgcgcacag tgctaaaaac ccacaacaat ctctattatt  33540
aaaagagaag tacccataaa aaataaccct aaaagttaca caatatttac agtcaaatgc  33600
cattgagaat taaattaatc ttacactaaa aatgattgtc ttttccacat attaattgtt  33660
tttctaaaat aactcaaaca aactacaaaa gaaagaaaca tattattaat aactcaaaca  33720
attacatatt attaaataaa ggaataagca taaataattc tcctgcaata tcaacactgt  33780
aacattcctt attatatgag tcccatcctt tttttttgtc atcatatgag tcccatcctt  33840
agcttacgta acctgtacga acatcaaatt atataagctt tataagaaat taaactaaga  33900
aaaactaaca atgattttca tatgagtttg aacaatttca attcacttta tttcacggtg  33960
gtgtatgtag cttattttta accaccttat tatattgaaa tattccactg acttctatat  34020
gtccaaataa ttaataatca ttattattaa ttaaaatcta ataattagga aaataactgt  34080
agttttgaga acactggcga cggcgaatgc gaatttttag ggttttgaga tgtttcatgg  34140
atgggatccg gggtctagtg gatttttctg gaattgcaag gagctctatc ttaatgagca  34200
aatcgggaga ttatggaagc aaaatggtct tcttgtcata aggagaaagg gagatctggg  34260
aattttattt ggctttgatc ttgtactgtc aaagatcgga atcgcggaga ttcgattgag  34320
aagggagaaa agtaaggcat tcgttaacat caaagcgaga tcttttctac taatattggg  34380
gatttctttt tgctttttgg tgcttagata tctggtaact ggttatagga aattcgggat  34440
ttggggtttg atgcgatttg atattcagga aagtcggaat ctaaggatta atggggttag  34500
agggagtatc aatagagagg atctcctgat tgattttctt tacgatttgt gttattatat  34560
aaaggagggt gttcagagct tcagtagcac aaacttacaa atctccttct ttctcttacg  34620
gatttcgttt ctggttgttt tttctttggt atctatgagt cagggacaat tggtgggaaa  34680
ggggggagcc tcgaaggagg gagaaggagt tcgcaaaaga ttgaagatct ccgttcctca  34740
tttcgataac tcggacctta tcaagagcta tgcaatgact ctgattggga ggtgtatgaa  34800
```

cccggttgcg caaaaagtca actcgttgct ggtgatgttg ccgaagatat ggaaggtgga 34860
agagagggtg actggtgcag atttgggaaa ggggatgttc cagtttcatt ttgagaagga 34920
agaagacatt gaagcggttt tggagtcaca gccgtaccat tttgattatt ggatgatctc 34980
gatagctcgg tggcaaccaa ggatgacaag gagctttcct tcggagatcc ctttttggat 35040
caaagtggaa ggtcttccaa cagagttttg gtcaactcca gcgcttcaaa gcataggcga 35100
tgccattgga gagactacgg atgtggatct ggactatgga aagatgcgag tggtgcttga 35160
tggcttcaaa gagttaacac tggaaacatc cgtggagttc aaaggaggtg aattctatga 35220
tgaggaagag gtcccggtat ctcttaaata cgataaattg tttggcattt gcaagctctg 35280
ttctagtcta tgccatgacg aggatcattg tcctcttaat cctaaaagtg tggacaagaa 35340
aacagatagc agagaggagc tggctaataa gaaagaggac agggcaagga gctacaaagg 35400
agtggtgatt catggagagg agagtcaaca ggagaggggc acagatcaac ggaattatta 35460
tggtaagggg aaagggaaaa tgcatgagga ccaggactca aagtgggtac gagttcctga 35520
aagaggaaac aagaggtact cgtcttacca cgataacaac agaaacgatg agggaaataa 35580
cagacacaag aacactcgtt gggaacagcc taggagttac gtgcaggaat cgcgggagaa 35640
ggggcatcgt ggcacaagac gggagaggag tcctccgcat tatgcacgag aggagccaaa 35700
ggaggaaggg gagctgcaag acacaggcag tgctaacaaa ggatctcaaa tggaaggaaa 35760
gacttctgca tctaacaacc tgcagattga atcgaatggg gccagggcaa atttgattaa 35820
gcttcctcct aaatccgtgg aaatggagaa tggtgcaata gctgcgatag tttcaggaac 35880
ggttggggcg gggaaaggaa cggagccacc attgggtgac aatggaaagg atatggaaga 35940
gaatgaagta atggacctag ctgagaatgt gattccatct gcaggggaca aaggttgcat 36000
gggtgaggat gaagctttcg aaaatcttac tgatggagag atggaggaac tgaatggatc 36060
acaagaagtg gtgctggaga ccgttgagga agaatcacga ccaacggatg tcgaggagaa 36120
ggaactacaa gttggagagg aggaaaaaaa gaagggcgct cgcaagatac taaagcacac 36180
aatggcggca ggagcttcaa agaagaagtt cgttcaggca ctcctttcac agaacaaaaa 36240
tactcaagct agacagggaa agcgtcaggg agacggaagc aaattgcagg aggataaggg 36300
ttcttcatac cccaaacaaa cttcctcaaa gaactcaact gcatcccatg gttaatacaa 36360
ttcatataga attgaggagt ggacttctgg ttgcgtcggt ttctgcttac tgttggttta 36420
tttcaataag ctctaggagc tttcttctac ggttcaattt gatttttgca ttgctggttt 36480
tatgtttcag tggcaattgc ctatctttta ttgtatttgg ttatggtttt ggtattaaga 36540
ataataattg tctttctggt ttctatgatc ttgatatggt taaatattgg tatggtgtta 36600
agacccttta ttcaggtcag atggcgttag tggcttggct gtgtgtaggg atgcatttgg 36660
ctcacttcat acaatggatg ttggacctga tctctgtaaa acaagttcag tggaagaatg 36720
atacaaggag ggttttggac aaggtacttg ggtctggttt cattatttgg tataaggtgg 36780
cacttaatta ctcatttctg gatagtacta agtgcacggt agtttggaga tgtttgttgc 36840
ttggtctttc taaggaacct agatgctctc gagtggctat gtatttgaac acattatatt 36900
gttatggtta tgggtttaat ttcagggata gagatctgag atggtcctta attatgggtg 36960
gagggggaag aggtagagtc atggacacgt cttggatcat tgcaggggag cacactcttg 37020
gcttggtctc attaaaccaa gtgcagagaa cctttggatc catgatcggt atcaagctgg 37080
ctttctcagt gccgctgcaa gatggaagtg gatacgacaa atatacggtg tctaactctt 37140

```
ggcgtttatt taggacatgt tcaaaatatg caaggttatt gtcctttgga gtcataatat  37200
gggatataat atggtgggtg aagttttggt ttcctttggt tactggttta tatgtacagg  37260
tcgaaatgat aatgtgtttt ggtatcctga gtgtacaata tggaactgat gagtattgga  37320
taattgatct agttcgtaaa aaaattatat cttctcctac aatcttatat atcgttacat  37380
acattgttaa ttgggcctta tggtttatta ttagaagtgg tgaatgtgat cgtatagtta  37440
ctggtgggct ggagagttgg ataaattata agatcacatg gcctttttg gtctttcgtt  37500
tttgtcacca aaatttgagt ttcttaatca agtggataat tttatgggtc ttgggatgcg  37560
aattgtgttt attggttaca gttggtatgg gaatggttat aggatcatgg gtatgtgatg  37620
gtgatcaaga gtctttatat ataattgtcc ttacaagcga ttgtgaagta tctgaagttt  37680
tttcagatag gatgattagg cttattgagg ttaaatcttt tgtcggtatc atcaaaccta  37740
tcttttctgg ttcgaacgat aaatatatat atatatatga agatattaag ctggaattgt  37800
agaggtcttg gaagtcactg gacaataagt tatcttcggg agatatggca ccaacacaaa  37860
ccggagtttt tatttttgtc tgaaacgaaa caggatttcg atttcgtaca aagatttcag  37920
tctcattttg gctatgatag cctggttact gtggatccaa atgggcggag tggtggttta  37980
gctctttttt ataataatga gtatcaagtt agagtcatat attctagcaa tagaatgata  38040
gacgtggagg cggtggttaa aggaaaacaa gtttttctta cttttgtata cggggatccg  38100
gtaccaaagc taagagaaca ggtatgggag agattaactc gatatggatt agcaagatcc  38160
gaaccttggt ttattattgg tgatttaaac gagattactg ggaatcatga aaaggatggg  38220
ggatccctaa gatgtgcaac atcttttatt ccgtttaaca atatgatacg gaacagtggg  38280
ttactggaat tcccggctcg tggaaataaa ttttcatggc aaggaaggcg tggcaaagga  38340
aaggatgctg tgacggtcag atgtcgattg gatcgagcct tggcaaatga agaatggcat  38400
acgttgttcc cgtgctccta cacagaatat ttgaggttag tgggatctga ccaccgtcct  38460
gtaatcgctt ttttggagga caagttattg aggaaaagga gaggacaatt cagatttgat  38520
aagagatgga taggtcagga ggggcttatg gaatcaatag tgacaggatg gacggagaat  38580
cagggtgggc aaattgagga ttttgttaca aaaattagta attgtcggca tgagatttct  38640
tcatggcgaa aggataatca gccatatggg aaggataaaa ttagggagct tcaacatgca  38700
ctcgaggaag ttcagacaga taatagcaga tcccaggaag agattctgga agtttccagg  38760
aagctacaag aggcttataa ggatgaagag gaatattggc atcagaaaag ccggaatatg  38820
tggtattcat ctggagatct taataccaag ttttaccatg ctctaacaaa gcagcgaagg  38880
gtccgcaata aaatagtggg tctccacgat gaaaggggta attggattac tgaggacaat  38940
ggaatcgaga aggtggccgt tgattatttt gaagacctgt ttagtacgac cactccaaca  39000
gaatttgatg gtttttgga tgagatcgtt ccgtctattt ctccccaaat gaatcaagtt  39060
ttgttgagaa tagcaacaga ggaagaggtc cgacaagctt tatttatgat gcatccggag  39120
aaagcgccag gtccggatgg aatgacagcc ctctttttcc agcattcctg gcatgttatt  39180
aagaaggatg tggtagaaat ggtgaacaat tttttggtta caggtgctat ggattcaagg  39240
ctaaatacta ctaatatttg tatgattcct aagacagaga gacctacaag aatgacggaa  39300
ctgaggccga taagtctttg taatgtgggt tacaagatta tctcgaaagt tttgtgtcaa  39360
cgcctgaaaa tttgtctccc tctcttaata tcagagacac agtcagcttt tgtggaaggc  39420
aggttaatat cggataatat tctcatagcg caggaaatgt ttcatggatt gagaaccaat  39480
aagtcatgtc aaaataagtt tatggcgatt aaaacggaca tgagcaaggc ttatgatagg  39540
```

atagaatgga gttttattga ggctcttcta tataaaatgg ggtttgatgc acattggatt 39600
aagctaatgg tggaatgtat atcctcggtt caatatagag tacttcttaa tggtcagccg 39660
cgaggcctta taattcccca gcgagggtta cgtcaggggg atcctttgtc tccttatcta 39720
tttattatgt gtactgaggc tttaattagg aacatcaaga aggcggagag agacaaacgg 39780
ttaaccggta tgaaggtagc aagagcttgt ccagcagtct ctcacttact attcgctgat 39840
gatagccttt tcttttgtaa ggcaaataag gaagagtgtc aaactattct caggatttta 39900
aaggaatacg aagcggtttc agggcaacaa attaattttc agaaatcctc aattcaattt 39960
ggccacaaga ttatagaatc cagtcggcaa gaaatgagag atattttggg tattcaaaac 40020
ttaggaggaa tgggatctta tttagggttg cccgaaagtt tgggaggatc taaggtacaa 40080
gtgtttggtt ttgttcaaga acgcttgaat aatagggtta atggatggac ttttcgattt 40140
tttactaaag gaggaaaaga ggtgattatt aaatcagtgg tcacggcttt accaaatcat 40200
gtgatgtctg tttatcggct accaaaagca acagtaaaga agttaacaag tgcagtagct 40260
cagttttggt ggagcccagg aggaagcaca aaaggcatgc attggaaatc atgggataaa 40320
gtgtgtgtcc ctaaagacaa tggtggccta ggattcaagg atctcatgga ttttaacaca 40380
gcgatgcttg gtaagcaaat gtggaggcta atagacaagc cacattctct cttctctaga 40440
gtttttaaag gacggtatta caggaatgct tcacctcttg aaccgatccg ttcttactca 40500
ccgtcatatg gctggcggag tatcatatct gctagatctc tggtttgtaa aggactaatt 40560
aaaagggtgg gaacaggttc atctatttcg gtatggaatg atccttggat cccagccact 40620
cgcccgagac cagcaaacaa aaaccttcaa aatagttacc cggaccttac agtggattct 40680
ctcattaata tggaatttcg aacttggaac cttcaggcaa ttagggctgt ggtggatcct 40740
catgatgtaa aaatcattga gagtatgcca ttaagcagaa atctgatgga agatagaaat 40800
ggatggcatt ttactaacaa tggaaaatat tcggtaaaat caggatatca ggtggaacgg 40860
gtttatcctg atagagaaaa accaccagag gtttatgggc ctacagtgga tgtccttaaa 40920
gccttctgtt ggaaaatacg gtgtccgccc aagatacaac attttctatg gcaacttctt 40980
tcaggttgta tagcggtgtt gaaaaatcta aaggcgagag gaatccatgg ggatatatgt 41040
tgtgctcgat gtggggatcc ggaagaatca ataaaccatg tatttttcga atgtccccca 41100
gtacgtcaag tatgggcttt atctaaaatc ccttcgagcc tcagtttatt ccctacagga 41160
tctttttttg gtaatatgga tcatcttttt tggcgagtta atccaaaaat ggatgatcat 41220
caatttgctt ggattttatg gtatatatgg aaaggtagga ataataaagt tttcagtaac 41280
ctggatgtcg atccaaggga aacccttaga ctagcagaat tggaatctac actttgggct 41340
gcggcacagg tgaacaacga ccaaaaacgg gaattacagg tacataccag acccatattg 41400
gtaacttcag gacgctggtg ttttatagat ggatcatgga aagataagga tctattttca 41460
ggacagggct ggtatagtat cctaccgggt ttcgatggct tattaggggc acggaatgta 41520
agggcatgtc tttcaccact acattcagag gtggaggcgc tgatctgggc aatggaatgt 41580
atgaggaatt taagacagct tcatgttacg tttgcaacgg attgttctca actggtgaag 41640
atggtttcgg aaccagaaga atggccagca tttgaaagtt acctgaaaga tatcaaagtc 41700
ctacaaggaa gcttcaacaa ctcagagatt gttcatgtac ctcggacgga gaataaaagg 41760
gcggatagct tagcacgtag tgttaggaaa caatcgtctt tcgtcgttca catggatgca 41820
gagttaccga tttggtttac agagtcaagt tgagtctgtg aatgtcttgt tgtcaaaaaa 41880
aaaaataatt aaaatctaat atttttgaat tgaaaatctt ttccctcccc caacaatctt 41940
ctacttagat ttcggaaaaa aaaatagaaa catttgcgga atctactaat ttgtttctaa 42000
acaagatttc cccttcaatt tcggaacaaa gaagatatat ataaaatttg atccataact 42060
actaaacaat aaacacaata ttcgaatttc accaatataa tcttactctc tcctattttg 42120
ttagtttcac aataacacac aataaacaaa gtattctaaa tattaatgca aacaagagat 42180
gccttgcgag ggtggttaag atatttcctc aactttaggg ttttgtattg cgttaaaaaa 42240
attgacccac acacttgcgg aacaagcaca agatcttatc atttcctatt tcaaatcata 42300
accattaaga ttttaccata atttcaaaaa caataaacag aatcaacaaa atattctttt 42360
catttatttc gcctaatatg tcttgcaaaa taagcaaaga tatttattct caactagggt 42420
attgtccctc tactatatat tctacccgag tacaaaccca ttctacacat tcttttacca 42480
cttacgctga tgaaacatta caaatggttt tagctgatga aactgttagt tctataatat 42540
ttgtattttt tttttgaatt ttataaagta gactttgaac aaaatcatct cttcctattt 42600
ttgaatgttt ttttgtaact tagtttcatt attattttttg gtttgtctaa ataatgtatt 42660
tgttttcaaa aatttcaata aaatatttga actttatatt caactttaaa ataaaatatt 42720
tataatttaa tttaataaaa ccccaaatat acttaaacct ccgatacttt actatttaat 42780
ttaccaaata aactaaataa aaatacaata aaagaaaaac acaatctcat agtttaaaaa 42840
tgatggctaa tcatattgaa caagacacac cgaaatcaaa cctgaaaaac atatgaatct 42900
ataacataat aagtacaaac aattaaattt atcaaatttt caaaagttaa aaatatatga 42960
ttatgaaaaa caaaatcatc ctttttttgaa caagaagaaa gcccccacgt tctgtcttgg 43020
atggtattac caatatttca cattctttat ctaatggaaa cgaagaaaca acaacaaaca 43080
tacatcgtga tatcaatcaa gaggataatg attttgttag aggatgatga ttttattcat 43140
agcctttgaa aaaattaatt tccgtaaaag ttatacctta tttatctatt tcatatatca 43200
tactaactca taattttttta tttcatcata ttttaatggt tttcaataga aatgtggtcc 43260
aaattatatt accttatcac agtatgatca attttgttgc caccgtgtga tcaaattatg 43320
ttacagcaat atttgtatta tgtgatgtat ttttgtcatt atttgtatta aaattttgat 43380
atattatata atggtgtaaa aaaatttaat tacattaagt aaacagaaaa aaaacacccg 43440
cccggtcggg cgggaccaga tctagttggt tattatttca tcaactttgt taccggtttt 43500
tgcataaaac atgggaccca acactgtaag aaaccctata attacctccg ataaacatgc 43560
cctaagagca tctgcaatag tgagtctcac catgaaattc ttagcattat tataatatac 43620
tagagatttt ttccgcgctt cgcgcggatt gtatcttata aatttatttt atttataata 43680
ttatttgttg gtttttttat attaactttt tgtttttccg atgttagttt tttttaattt 43740
aaatttatat gtttatattt ttatattttt cttgttgtag atggagaatt atattttttta 43800
ttgatggttt tttgtatgtg acataaactt tttgaaattt taaaataatg ttatatatag 43860
tacgattaac acattaaaga agagaaacat attcagacac attttacaca ggttttatat 43920
gcataatttt aaacattata tatgtatata ttataagttt gaaacatgta aatgctttct 43980
aaagctaaat acttgttctg agtttacata acttatcgag agttttatct ctttttaaat 44040
ttaaatcaca gaaaaaaaaa tatcaaaaag tcagtataaa tggatttttt gggcttttaa 44100
atcaacactg aaaaattaca tgaattagat aacaacactt ttataaacaa ctcgataaaa 44160
tttgaccgag ctaaagattt tcacacaata tgttctttct tcttcaaatt gcgaagagcc 44220
tataggcaca aggaaaaaaa ttataatttt tgctttcact tatataacat tttttctcct 44280
ttacacacga agtttattac actgctataa gcaatggaaa actctattca tataagattc 44340
acatctatgc attttgacaa agaagaattt aagccatctt tagtttcgga atggacaaac 44400
ttcagtcata tacactatat tttctctatg attcaaatct tacaatttta atatatgtgc 44460
agatttccat gtaaaaaagc acgcacgcca tctatcattc aacctattac tttttccaaa 44520
gtaaacacta taatcctcgt ttgattagct ccacaaacta atctctttgg atcagtttac 44580
taaaaaatat ggatactaat gttagaaaag aatataaaca ctatcaacaa taaatattgg 44640
cacaagacta tttggttcaa ggaacatatt caacgtaatg cgtttatatc atggctggtt 44700
ttgcggagaa gactgccaac caaggatcgc ttgaggcgtt gggggttaaa tgtctccgga 44760
acgtgcgtcc tttgtaatct ggaaatagag actcaccatc atctcttctt tgagtgctct 44820
ttctctcgct tgatatggga gccttttgct actgaaattt ggatttttcc tccggctgat 44880
ctacactctg ttgcagcctg gatcaatcaa cctcgcgtca acgcagatgc gcatgctact 44940
tcagtcatca atctctactt tcagtccgcc atctacctgc tgtggaaaga gcgtaatgct 45000
cgtatgttca cagctgtctc ctcaccttca tcagtcatcc ttgcctcttt cgaccgtatg 45060
atgcgtgacc gtctcttctc ttacccggca aattcttctt tctcctattc tctacttctt 45120
tttatctttc ttgtataaga cctccttaag gctttttcta ccttgagttg ttgttggttg 45180
tttttgtttc cttgctgtaa caagttgttt aaaaacaaca gtgtaacttt tcagaaaatg 45240
ataatcttaa catcttacca aaaacaacaa caaatattga cttatttatg tgaatatata 45300
ttttatttta aatcattata gtggacgaag aaaacaccat aatttgtaca acaaattttc 45360
ttagattcac ctcatcatac tcaccatttt actattttat ttacataatt ttacatgagc 45420
ttcttcaccc tccccggtta ttttatcttt atttataact acgatataaa gttataaact 45480
atattataga ttaataattt atttatcctt gaagtctaac gattaaaaat agaacataat 45540
ttaatataga tatatgattc tattaataaa ttagtagtta caaatttgaa atttctagaa 45600
atatcaaaag tcgtatgtta gttaattatc ttcttagtga catttatttt taattttttt 45660
tggatgaaaa tattttggct gaggtagata ctctcaaaaa ccttgaattt agtccctttt 45720
atatagtagg atatattttt ttaaatagtt aaagatccta atccaaaagg tacgtacaat 45780
ggtgttatct aatttagagt cttcaggtct gaagctataa aacatatttc agaaaatggt 45840
tttgttctaa agaacttggc gatctattaa atttttaatc agagtttgat ctaaaaaact 45900
tgtattatat tctatcttgt attatattct atcttcttct gtttccatat agtcttagag 45960
tcagaatagg atgtacaagt tacaaacata tatgcttatt aactaacaaa ttaattttat 46020
gtgttttggt agtaaccact catcttcttg aagaaccaat gaaggagaat gatagtaagc 46080
agaaaaacca tgaagatgca gcaagattgt ccacttccac gtcttcttcc ttcacccgtt 46140
gtagtgtcct ttatttcact acactcctcc tccgtcaacc ttactggaac attcagtgct 46200
gaagaaccgc agatttcaca tacactacaa aaaagagaaa cagaggtttt acacaatcca 46260
tatggttact aagctaatga actgaataga gtacctgttt cctcttagct taaaccaagc 46320
ttcagcgcaa tgaaaatgag caaggccaag ctcatttttg catttgcaac caatctaaat 46380
caagtctaca cttacaaact tgccagaaac tctatctggc gtttgatcag aaccaaaatg 46440
acaaatcctg cagattcttt gtccattatc actttcttct cctccaccac tcagatcaat 46500
catgtgaaac tccttctcct ttgctttttc tgaagcatca ctctcgtgac accatctttc 46560
cccattcttg aatcattctc tttttgatct tccatcaata catggtttga gagagagagt 46620

-continued

```
cactggtctc acccttgagg ccagagacta caatcacagc ctcagggaca gatccactcg  46680
aactttcaca aacagtgatc gaatttgaac aaggtatctg gtccatttca ttcatataca  46740
caccaaaaac aaaaccagga gtggttgtat caagatcaag aatgattgta tcagacaaag  46800
agttaaacat aaacccaaaa ctgaaaacct gtaacagcta gaacatactc aaattattgg  46860
tacgcagagt cctaaagtac aataaagatc gaaactttac cagaatcaag atctagtaga  46920
gtgacaaggt ttcgttttta tttcagaaga atgataaatc agacaattga atctaaaccc  46980
tttgccggaa acggatgcgc gccgctacaa gtgctctcta atctgttgct cttcggtttc  47040
agtttgtgtt ttttctttca taagatgcct cagctagatt ttaggccaga ctcgagaatc  47100
aatttttttc tctgcatcgg tcgagactcg agtatgacga cttttttttc cccactagga  47160
aacacaaaaa ccttcccatc cattcacaag tagccacgta ccataaggat caagtcctaa  47220
aattccttag ttatatatgt tccagtcctt agttttatta agcaaaatat tattattata  47280
tgtgtattta cctaagatta agccctaagg attggtgatg ttactccgtt gcgggtggtc  47340
taagaatatg attattgaga gtttttatgg tggattttta gcggaatata agaactccac  47400
tctaaaaatt tctgctctaa gagcatgatt atccctaaat acacattaga ttagttaatg  47460
actatttaag tattaaattt tagtgaagga atttagttaa gataggattg gagaaagaaa  47520
aaacacatta aaagagagga aggattcaag aatgaagaga agtgttaatg gaaggttctt  47580
catcaatata cacttcagtt cttatcagta tacatatagt ttgtactata taaatcatac  47640
aaaagagaag tattctcaac catttggtga tgtagttttt attaccatac aaaaacaatt  47700
ctaatacaag cgtgtctcaa gaacacaaaa atcgtttcag tttttattat ctttcgagga  47760
gcttgtactg agtgtcgttc aagtaaaacg actgagccgt ctccatgatc catttcgcct  47820
cctcgtcagt gagtttgctt gtgaacaaaa catcacctcg gataaacacc aaggtgtgtt  47880
acaagctgtc aaacatactt agatcattaa gcatgatata cacaaaacaa aacaaaaaac  47940
attgaaaaga gaacaagaaa aacaaaaaac aaaaaacatt gaaaaaattg agaatgaaga  48000
atatgacgac aatgatacaa aagtttgtat actgataata cactagcata caaaacgtga  48060
gtgacgacaa tgacatttct tcactaggcc gatgatacaa aacgttactg ctcccacaga  48120
agcatacaaa acgtctaacg acaaactatc atgaaacagg gagcaaggca tcgactcaaa  48180
ttggccatca cctctttcaa atcgtctgtt tgtttagtaa ggagaaaata aagagtctag  48240
acccaaattg gctatgtacc tcctataaaa cgttatttat tttgcaaaac aggaaacatg  48300
gaacggtggt tatgcaaatg caaaacactt atatactgta taacagtaaa atttcaaagg  48360
aatgacattg tgaaccattc actatagaaa attcaaattc ataatctcgt aatgctgtca  48420
acatccatgt aaagctcagt gcgccatcta aacaaaattt cttcataatc cacatttcat  48480
tagaaatata aaaagggtca agactcaact tcgaactatt aaaaaggaaa aattcatttc  48540
gtgtagaaac gttgtaataa acaattttgg aatggactta gtgatatcat attagttgcg  48600
tttttaataa aatccttaat tacttgttaa ttaattgaaa gagagtaaca gaatgggtct  48660
tcatatacaa attaagcaca ccgaaaaatg cagaatccta atatgaaact gatactcata  48720
tgataactaa taacgttaca caaaatatac agaaaaccgt aaaatgatag aaagaacaat  48780
agcaactatg gtaaaaacca actaaaacca aaacatgtgg caatttggcc ctccattaaa  48840
agctatatac cacagtttag ctcagctata agcttataat aatatacact agggccgggc  48900
ccgcccttcg ggcgggaagt ttgaataaaa caatttcata tgatttatat ttatttatga  48960
ataatttata attatgatat agatgatatc atatacaaac aacacaaatg agaactttta  49020
```

agttataata tactggttat gagttcaatt ttagtatcat atattactat gagagtaatc 49080
ttcgctatta tttcaaaagt ttagttttag ctatcctcca ttagactaac ttataaattg 49140
atttaggtga gtacgaccca aacccccaaa gcatcctttt attattcgag gccttttgtt 49200
ttttttcat gatgcatata tacacatgtg aattttgtac ggaagaataa tgtataaatt 49260
ggagaaatct tattatttgt tattaagctt gatgcaaaag tttaatttaa ataatgtttc 49320
aataaatttg gcgggtttgt ttacggtttc tttgtgcgta tgtagtcaat aaattaaaat 49380
aataacaatc ttcgcatgcg ctgtccatat catgctggtg acattctgct tcgggctcca 49440
tcctggctgt atttgctaaa taccttgtct tcaaaataac tttgatcgat ttaagtgaag 49500
ttttaataat aagtatatta gcttgtggac gacagacgta cactcatgca cgtaaccaaa 49560
gttttgtaat acataatatg attatggacg tcagtttatg cacacaattt aaagaacatt 49620
aaatattttc acactcatat acataattat attagaccgt ggactgtata catacactca 49680
tactaacgta cccaaagttt ttgtagtcca taatatgatt atggacgtcc acttacgtac 49740
acaattaaaa taaacactaa ctcttttaat aaaataatca ctaacattta ttaactcatc 49800
ggaatcaaat aaagcatcaa cttgttcctt ttttaaactt atgtcaactc aatataaaaa 49860
gcattcataa caaccataaa gtagagagtt tgaaaaaaaa acaactggaa tgtagaaaat 49920
ccataacata gatagaaaaa agatgacaat aaagtagaat gcagaaacat tattaagctg 49980
cagaatatcg agagatgatt atcgaagatc catcttaagc aatacgcgcc ctcttacgca 50040
cattaccgac tggctccttt ccagctctct ttgatgtctc acaattgccc ttgccggaac 50100
cagactccac acggttgtta ggcccgtctg gcgcatcatc atcatcattg tcatcacctt 50160
cctgttacat tcaaattgtt atacgctgca tatgctaatg gcgaaatatc ataataagta 50220
ttgcacttac atcatcgaca aattctggag ctggtgcacg ctcaacctca ttgatgatac 50280
gcgacacggt gaacgtctgg tggttgacgg tgaagttgta gggcgtgaca cggacttgga 50340
aagtgtaggt cttgcgttcc attcctgcaa cgaacggagg catcacggaa tcctcagggt 50400
tcactccttc ttcagccttg tcattaaatg gaagcatcga gagtatcaac aacattatat 50460
aataaccaca taagtaatca aactatatat taccagtaac tggaccgcct cacttgcccg 50520
gagattatgc aacttcgtca taacaccatc aaagcaaaca aatgtccctt cagcagtatc 50580
atcagttaca accatctcaa cgcgataact aaaagagaac aaataaaccg aaatggaatc 50640
agtgtgacgc aagggataaa gaaggcgacc aactatcata ttataacaaa tcgatacata 50700
ccgtaaagat ccgaccgcat gagggttatt acagcgtgca cattcgaaag aagtgacagt 50760
gcgttgcaat ttcttgctgc acttagaaca cgcaacatag caccaccctt tgtccgattc 50820
aacccgagaa actctcgcag tgcataagaa atctatttcc tgctgcttaa acatcaacat 50880
tgcgtgcagt caaaaaacaa tctttatata taaacacacg aatgagctaa ttgcatatac 50940
ataactcatt acctgtggcg aatccgtagt gataaaatgg ttaagctctg caattgtcac 51000
agtctcaacc ttcgcataag acttcaagag aggtgcggca gacggaagac cagtgtctct 51060
agccaccaat ctgaacaaaa gttcacgaaa ttaacatcac aaactctcaa cgtctgatta 51120
catactcaga acagaccaaa cttaccggta aaataaagac tctcctgcat gtgtctcctt 51180
atcataataa acatgtgttc ctgacgttgc gttgaggaat aaacgaccta cacaaaatag 51240
taaaaatttc tgaaaaagga attacacata ttaatttatg ccacatcttt aaataagcaa 51300
cgaagtacct ccaaccatct tcgggtttat gcttgtggca acaatcactt taggatcatc 51360

-continued

```
acgcatgcct ccaagcttct ggtggaataa aacggcttga gcgtcaaaca gactaagagt  51420
gacagacaca tcactgcaca tatataacaa acgttagtgc agctaaaatg attaagcaaa  51480
tatgaaagtt gttaaagaaa caaataaatt acttttctaa tttgacggtg accatgacac  51540
ggttcttatc ctccggaggg tcagacacgg tgctcttcac cgccacgatt tcaccaataa  51600
tatctacagg ttcaatattg agatcagaga gctcagtgac ttaatacata aagcacaaaa  51660
cccatacaga taaatataca tatgtacgat acgatcacat ctgtacctgg aagctgagtg  51720
tttgtattgg ctaaaccaac caactcggtc tggttacgga accggaatcc ctctgccggt  51780
attggcgaga ccggatcaga taacacgtca aactcggtgg aatcgttaaa ccggatcatc  51840
aaagaagagt ccacaagctt gaagttctga gcacagcgag ccacgtcaaa gccagaaaca  51900
gagtacatcg tcccggcggc gagcctatct cggaaccttg gaagccgatt cgcgttgata  51960
gtagcttgga tcaaagtcga ctgaaacaga taaaatttag aagtcagaaa ataacgtaaa  52020
cagatctaag gagaccagga agaatcaaac ttacattcac gtccataagt agcatatcga  52080
cccacatcag ctcgccaccg cgtttgacgt tcctcgcctc ccagaaccgt agaagccggg  52140
cctcgacgac ggaggagcat ttgccggact tcaggtcaga gaagaagact ctcgaaatag  52200
acatagcaac aggaatcaga aagtctcaag agaaagaaag agatgatgcg ctggagatct  52260
atagatactt acatatttat acagatctgc tcgggttcaa atggcgcatc gaagagtctg  52320
agggagggat tgaatgagcg agggattgaa tgcaattgga ataaagacga cgacataact  52380
ccggccgttt catcgaagag gaaggaatcg aagacgtcac gcgtcgccgg cgcagaaaag  52440
ggttacgcga gagtaatgtg tcttagggtt ggagacgtcg tgacatcgtt cgggctgtga  52500
gtgtaaaggc ccatcacaga aagatcgagc gaggcccaga agataacatg ttcagtttaa  52560
tgaaacgcag cacctcgtcg tcagtgacac gtgtcgacgc gagaggaagt gaacgtggat  52620
ggcctaagaa gagattaaac tgtcttttat atatatacat ttagttgaca aagctcaaac  52680
tcaaaccaag ccgatgacaa aaactctcag gagatctaca tataactatc atcacacact  52740
atatatatat atatgataaa ataaaaaccg aaatgattag atcacttcaa ctctcgccgg  52800
taactgtatt cccgccgttt cctcttcagc ggtagaatct tgagaggcga caagtttcac  52860
agcgaaagaa aaattggaat tatacttttg tctcgcttca gcgaagcttg aagaaagaac  52920
ggtttgcatc cactgatcaa ccgttttctc ttcatctggt gaccatctca aggcagctag  52980
aatctgaagg atcgcatcgc tttcgatctc tagacgtgtt tcatgtccaa acgaccgacg  53040
aaaatgcgac aagatgctcc tttgtatgtt cttcgctaac ccatcaaagt cgatcgtttt  53100
gaacgtcact ttcccgtcaa cttgctcgaa aaaatcctca agccaagctt tactgttctc  53160
ggacattgca tgcgcttctt catctgcgtt tgcttctgtc tcatccactg gaagattcag  53220
atcgagaaac gaacgttgag actttacagc tcgaagctct gtaccctctg ttcctaactc  53280
ctgtcttcgc ttattcagac cgttcttgtt agcattgtcg gcgagtttta tctggagttt  53340
acatttttta ggggtgagaa ctcttccctc ggagtattcg acacgctcat caagaatatt  53400
cgaagtagta gctaaaacta taacattctt cataccgatc tctcttccgt gcgagtcacg  53460
gagcttacca gttctcacag catcagacag tcttacctga tcaggaaact cagctttgtc  53520
cacgttctcg atgaaaacaa cagactccac acgcttggac acttctccgg cgatgtagtc  53580
aacaactgtt ttccctctga atctatcgtc gagccggtcc tgtgccttga aatccacgca  53640
aacgcagttt tctcgcccgc cgaagaaggc ttcagcgaga gttgttgcta ctttcttctt  53700
cccgacttga tctggtccaa gaagagcgag ccagacatta cttgtggctg aagctagctg  53760
```

gcttctatca tctctgtatc cgcagatgat ctcgctaacg gcgttcacag cttcgttctg 53820
aaaccctact ttccgagaga gtaattctct gagagacttg aagtctttgc agtaccgtga 53880
caatggtttc tctttgctca gctcaaagcc tctccggtta agtgataccg gtgtgcttga 53940
ctcctggtag attgttccta gccctagatc tgttgtaaca cagctcaaag gcgagttcgt 54000
tgttgtgcga gttgtgtgat cttctatatg ttttggcttc gagattctta cagataaacc 54060
gggttggtgt ggcggattct cagcttgaag ggttgaaaca agctgaagtg ggaactgtgg 54120
tctaacaggc tggaagctga gtttaggaaa cgccggagtt tgatggattc gttgacaaat 54180
gtcgtcccat ttcttctgca cagaagctag tgtgtttgga tcatctttag cctgcactga 54240
atgagaacta aacactctca agatagtaac tgagagattc gaattcagag aagaagttgg 54300
ttcataaaag cagcacctgt ctgagaatcc ctttgtcttg ttcagattcc acattacgta 54360
accaacaagg caacttctct gaacactgat caccggactt acctaaggct gtgacttctt 54420
gctcacactt ctcgttacag agatgacacc gaggaagacg agactggttc attgagttac 54480
taaacggtac tctgaaatct gatgttgatg agaagaagcc tccaaatgga acaaatgatc 54540
ccatcaaact gtagatgaaa ccacaaaacg tcacgtttca atcaaaaata ttttagactt 54600
tcccaacact aaataccagt gttataaaag ttgggctcag aaagcgccta tgcggcaaat 54660
catgtataaa gctatttctc taaagcgatt ttttttaaa ttcagtccgt tcgttaaaaa 54720
attggtctac acgcccgtct aaacattagt ttcttgtaaa atgcataatt atagcttaac 54780
tattttaaac attgctaaaa acaaaaacat tcatcccgaa aattcggtta aaaaatcggt 54840
gtagacaccc atctaaacat cagtttcttg taaaatgcat tattatagct taactacata 54900
ttttaaacac tgctaaaagc aaaaacattt atccggaaaa ttcaaatcat ccgataaata 54960
aaaaaatctt aattatccaa actttttact gaattgacta taattatata gaaatatatg 55020
aatctaacca aacgaaatta aatcggagaa tttttcaaac acagtattag agatttctag 55080
tttcgaaaaa aaacaaaata aaacgaaaat aaagccacta taaaagacat taccttgact 55140
tgggataaac tccttgattc gaagatgtaa taggaagaag atgaatattc cagtctttgt 55200
caatcgtggg gaacctctcg atcagtttca aatacatctc gttgctcgac acactcccga 55260
cgaaccagag cttctcacaa tgaagcttca acagctccga gagcctcgac acgagagcat 55320
cactggttaa gaccttgagc tctcctagat tcaaaaccgt ccccgtttta gatttcgagc 55380
agctttgctc cacgattctc cccaactcat cgagtttcat ctcaccgatc tctttcgcta 55440
cactaacgac gcttaaccca ctaatctcca gaggcagaaa ccctaccttt cctctgttga 55500
tcgagtcact aaacgttttg agcgctttac cgccgcaagt tccgacaaga agaggattct 55560
tcttgtcttt ccgacccaac acttccccga ttctccgaca gttctcgtcg aagtcaccgc 55620
tatacccgaa tctcgcccga ccagagccag attcggttac gttacataga aacagtggag 55680
gacagcgaga acgcgggaac cgcgtcaccg gaggatgaag cacgtcgagc tttatgtccg 55740
tgctccgaaa cccggcttcg ccgaacaccc ggctcacgat cgggtcatcg agtatcgaca 55800
atatgaagta cttaagctca accttcaaaa ccgacgtcgt ttgagtaacc ccaccgtgga 55860
gctgatggag atggtaagtc tccgggtgcc ttctctgagt cgcctgagag cgtttgatcg 55920
ccgccatgag ggagttagac accggcggct cttcctccgc ctcgttctcc gtcgtcgtcg 55980
tcgtcgtcgg agaaggtttc gaggaaggga gtctgtcgag agatacgccg acgcagagct 56040
cgagcgcgcg gaactggagg cgggaagagt acggcgtgct gtgagcggcg cgtgaaatgc 56100

-continued

```
aaacttcgcg gagaatcgaa gaaggcatgg ttaagagacc ggagatggcg tggagagacg  56160
tcgtttgcgc gtggcttctc ctacgcgcga cggctaccgc gtcgtctagt gcgcgtgctg  56220
tttcttccgt taaacattgc ctcgccgtgg taaccggtgt cggcatcgtc gcccgctttg  56280
atcaatttca aactacacca accaacaaac aaagatcgta aaagaataag gagaatgctg  56340
agaaatgtat aaacaaatcg cgcgtgaaat ttctcgaaat ggattttacg acaaagatat  56400
caaactgagt agtcgctttt tttgaaaaag aagtattttt atttattttt atgttttgtt  56460
tacttctgtt gctttggttt cagacctcag gcttacgctt agatatgtaa gaaagaagag  56520
tcgctgttta actggtctat tgtgaatagg tcccactaat atgtaatatt tatgtttttt  56580
tcttttcaat ttataatcat atttttgtat ttttgttgtt gcccccaatc ctcgtgtata  56640
ttgaaggagc aaaggcacat gtatagtgag catagattct ctatggccca agtgaaagat  56700
ctcctttttac ttctattggc ttatactctt tcaaatttca attaatttta gatttgacaa  56760
tcccaacagt ttttcacaat tattctcttt cataattttc tctctaattt ttttaatatc  56820
ctcttctttt attcttatct ttaagaatct gttcattcag ctgataaaaa tatctaaata  56880
taagtatcca tgcatatctt cttcttcttt tcgttatttt tccaactttg tatccgtatt  56940
atacacatta cacttccaca ccaactcaat ataagttttg gtccttcggt ttaagtatct  57000
tgaatctaga tgcaagtttt attccttttt tgcaagcttt cttttagttt tgttatacca  57060
ctattcttaa atatttgaga aaataattaa aatgacttaa ttcatgctaa ccaactaaaa  57120
tcaggtaata aactaagaaa aatatataaa gcatcaacac tcatctaaaa atgaatcgac  57180
aaagcattaa ccataagatc atattgagtt atacagggaa gcacaaaagc cattataata  57240
tttcagaatc attacaattc tcacgtcaaa taaagggatc agtcaagatc aatagatgtt  57300
gtactaatcg attagttttt tttttaaaga gaaaacaaaa catgatgatc atggttaaaa  57360
aatgtttgct tcaaaaaagt tctgaacttg attgatttga atagaaaatt gatactttat  57420
gtaaaggatt ttgaattatt atgcatttta aaaagataat aagaatgatt aattagacag  57480
gtcaacttaa attataatta agaatatatt cagtggtaga cagtgatata attttacttt  57540
taagagatta gatggatgtg atatggtaaa gaataaaaac aggagtaagt gattaggccc  57600
caaccccctt tataaattcc accaccacca tttatatgct acttttgtgt cgttgtcatt  57660
gcaaaagtct tttattaata ataatgaaga agaaaataaa acttcctttg tgttctactt  57720
tttatattct ccattgcaaa ggcctccttt tgtctttccc cttttggaaa aggagattta  57780
ctcaacgagc aataattatt accagtgaaa tagtttttga tattatcaca ccagttaagg  57840
acaaacaaac atcgatcacc ggaacatcgg cttaataaaa ttttttagat ttatttttgt  57900
ttcaaaataa taaatttttt aaaattaaag tacttttatt agttaatgct taaaaactgt  57960
atatttttaa gaaacatatt aattgaaaat atttgaattg gttaaatact atcagttgat  58020
atttattaga aaatatataa taacataaat aataaattta attgtaaata tttattatat  58080
ttttaatatg cgtgaatact ctagaaaatc tgtttttcag aaacagaggg agtagtaagt  58140
actacaagtt agtaaattca gttttaaaac taaattgacg gcctatacta tagccagata  58200
taatttccag acgcatgatc caaaatttcc agaatcgcga acgaacaaca tctgattgtt  58260
gcatccagtt actgtgcgcg gatgccgcgt ctggaattct catccagttt acgaaacgaa  58320
cagggccata ttgtgagtca acctcttcat agctccatat tgcttcttgc aagagttgaa  58380
cttgttccta aactttatcc atggatgcct caccccatat gtatcataaa acttgtctgc  58440
aattgtcttt ctcgcagtct catggagaac cttatttttc acattgcctt tcagttcttc  58500
```

ttcaattctt agttgaagca caaaccgtgt ttgttcatca ctccacaata cagtctatga 58560
acaacacaag aggaccatct aagtcaagac taaactaaat tcaatgcatt aagaccatat 58620
ctaagtcaag actaaactaa attcagtgcg taaagaccat ctaagtcaag actaaatgca 58680
acacagaaac accaaaatag agtgttgaga atgacttaca tcacttccag ggacagatgc 58740
cattcaaact tgaacagata gtcactgaaa caaaaataaa aacgagttaa tacaagactt 58800
taagactctt aagcgcaaac aatgaaacaa gaagaccata ctctacaaag acacagcaac 58860
aaaaacaaga agaccatact aataaaacaa gagcttcctt gtattaagag ctacggttaa 58920
atgaaggtgg gaaagtaatc attttcttcc ctcagaacac aatgaaacaa gaagaccata 58980
ctaaaagatt gttaccttac taaaagatct gttctgtctt attttgtttt cttgtctgaa 59040
tgtaataatg aatatacaaa cgacacaaca cattcattag ctctaagcaa ccttactaaa 59100
gattgttacc ttactaaaga gagtctgagc ttgagagggt ttgaacttga gagagcctga 59160
gcatggagag ggtttgaact tgagagagcc tgcgacctgc aagaaaaaaa ataacagacc 59220
ttttgaagct ggcaaatgac agtacatgtt ttgtgactta aaaccacttg gtaagagagc 59280
tcaaatgctc aaatatacaa gaaaggacgt attggtgatg taattcagct aattaatcac 59340
aaactcactg atgagaataa aacaaatgca tcacaaatat acacataacg tcataccgtg 59400
agagagtgag cttgagaggg tctcgagaga gtgacttgag aggagcaaca gctttacaca 59460
aacctaagca tcaaaaaccc aatgctatca tcacttcatc aacccaaaaa cccataagac 59520
tcaaatcaat gtggtatcag agatagttac ctcggagaag agagagctcg agagagatag 59580
ctcgagagag agaactcggg agagagagcg agagagagag agagagagag agagagagag 59640
ag 59642

<210> SEQ ID NO 4
<211> LENGTH: 28086
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (27461)..(27461)
<223> OTHER INFORMATION: a, c, t, g, unknown or other
<220> FEATURE:
<221> NAME/KEY: modified_base
<222> LOCATION: (27463)..(27463)
<223> OTHER INFORMATION: a, c, t, g, unknown or other
<220> FEATURE:
<221> NAME/KEY: modified_base
<222> LOCATION: (27465)..(27465)
<223> OTHER INFORMATION: a, c, t, g, unknown or other
<220> FEATURE:
<221> NAME/KEY: modified_base
<222> LOCATION: (27467)..(27467)
<223> OTHER INFORMATION: a, c, t, g, unknown or other
<220> FEATURE:
<221> NAME/KEY: modified_base
<222> LOCATION: (27470)..(27470)
<223> OTHER INFORMATION: a, c, t, g, unknown or other

<400> SEQUENCE: 4 ttttttttt tgcttaaatt ttaaaaaaaa aattaaaaac taaccaactg cgaaccgcca 60
cgtgtcagta tggtccgcga acagtacaag aactacacca aattcgcctc ttgagaaaag 120
aagaaaatag tgggttttag ttttttgtgg gcccacactt cttaagaacc ccttaaaaat 180
cagggataaa gatagctcta agtggtagcc tcatttgaga atagaatatg ctttattggt 240

```
gtttccactt tgttaatttc tcttgttctc ttgcatcaaa taaaactagg aatacaaatt    300
tgaaaatact gttttgaaag aaccaaaatc tctattaaaa tccaacatag gacgaatgaa    360
aattttctaa aattatgtag gaacagtttt acgagctaca ctaatagcaa tatctttatt    420
attaactggt caaatgatat acatactaaa agtttgattt gtaaatcaac acgccttggg    480
ctagtggtat ttgagagata atttcaatac agtgaacccg cagttcgatc tctgttggcc    540
ataaaataat ttaacattgt acttttgaga tctacagaat aatcggttga tcatattgtg    600
gttaattcaa aaaaaagttc aatttgtatt taaaaaaaaa acttaaaagg aaaatcaaaa    660
tcttttaaga tatatcgcag acatgcgcat cagaaaggct tttatctatt tgggccgtaa    720
agtattgtcc attacttaaa aagtgacaac tccgtgacat tattgttgtg ctgggaccca    780
aaaacggcgt gcattttgtc gactctcagt cgaacttttt cttttgtccg tcccaccatc    840
aaaaagtttt taagaccttt ttgattgtaa gtttgtaact aaaaacatag agaaaacgaa    900
caaaaacttt tacgatttgt aatgtaaata catttaataa aaaaaagttt cacgagtaca    960
tttttaactt aaaaacaacc agaaataagt aaaaccaaag gagtgtttta ttcctaaata   1020
gagctaggaa gaaagattaa ttgattttgg atttgtcaga agcataaacg tagagatctg   1080
gatctgtctc gtagaagaca atatcaccag tgtcactgac gtaatgatct ttcttaatac   1140
ttgccaccaa actttccact aagtggatcg gtattgctcc tgacgtcttt ggttctctgt   1200
agtatcttcc caacacatgt ttagctgctt tcgtctgtcg catgtcatta attaagatca   1260
ctaatttagt aattaatcac cctttaatat aatcaaatga aactagagag agagcgagat   1320
cactcacggc atcgaccaag tgatagtgag ggatttgtgg gaaaagatga tggatcacgt   1380
gagttccaat atcgtgatga atgttgttga agatcccgta atctctatca acagttgtta   1440
atcctccacg taaataactc cattcctatt attgtacaaa aacatcaaaa attcagatta   1500
ttcaactact aatcattatt gcttcttata aataatgttg atctacttac cttgcctctg   1560
taccaaggca gcttatcatc gtgaccatga tgatgcaagt acgtgacagc gtccaaccac   1620
attacaaaga tctgaaattt ttccaaaact tttatgtcaa aaacaaatta tattagcaat   1680
gatataataa agaaatatat gaaacttaca atgtaaggaa caccatagac ttttagaact   1740
gtgactggac caacgaggaa tgatagataa acaagagtgg ccaacacgat cgaccagcaa   1800
gtagttgaag ttgcaataag ctttctctcg cttggggcaa ataaactact gtatgggtta   1860
taatgtgacc cttctttacc aggacttctg taccactgta gtcatcccca aacaaattta   1920
atttatattt agttaatact caaaatctaa aaattcaaaa ttgtaattat aatcaggaag   1980
aaaaattagg aattaggatt taccagatag agagggtaag cgagcatggg gagagggaca   2040
gtgtatctga gcatccgtgt actgtgggac aaattcttgt ataatttttc tggcaactgg   2100
aatgcaaaat taagattaaa atgtaaatta atatttaaca gtatggttat atattcgaat   2160
ttattcattg catgtggtgt gtttataagt ttttcttttt attagttcta cgtaaactcc   2220
aaaattgaaa aatactaaga aaagtaaacg aatttcgaga agaatcattt tatgccaatg   2280
gctcgaatat aagtggtccg ttgttaaagt taactacagt actataaaca atttaaatca   2340
gttgtttact acagctaaac gacaaatctg acaagtggtc gtcctagcct caaactggaa   2400
aaaggattga ttaaaataaa tacatagaat cctaagaaaa ttaaaatgaa agaatttcaa   2460
aaaaaagaaa aaaaatatga gagagggaaa gattaccgga acccaagact cgtcgttttc   2520
aacatggcca tggttctggt ggtgtgtccg atggcttatt ctcctgcaac caccctcagt   2580
```

```
tataaaataa actattattt tattttcata aaaatgaaat tggaattgtc aataacatat   2640
cattttcgaa gcagatggta agagcatgtt taacggggtt tttaagatgg gattcttatc   2700
agaatataaa actcaacccc aacatgaggc catgattaaa actgtttttt ggtttcttaa   2760
tttttttctc cgattaaaaa aataaattaa attaaaaaag aaaccaatcg cggaccacca   2820
ccagtgggat ccacaaacag tacaagtaaa agaccaaaat cgatccttct ttcgcgactt   2880
ttgtaaccgg ttttttgttt tttttgggcc cacactatat cttattatta atattttgtt   2940
aaggaccctt cttagagcac taagagcatg attattgaga agttctcagg gtggagttct   3000
tagcggaata taagaactcg tctcttgatt tttaactaaa aaaactaaaa aacggttctt   3060
aaatacgagt tttaaaagcc ggttcttaat ttttttagtt aaaagttaag agatagattc   3120
ttatattccg gtaagaacct cactctagga acttctcaat aatcatgctc taagaaaccc   3180
catagaacat gctcactcgt ttaactaagt tattcatttt tgagcaacaa acaagtgtat   3240
ctaggaaaat gatgcatgtt cgtagacatt tcaagctgat gtatccattt aacaataaaa   3300
taagccatta aaacaaaaat atataaatat tattaaactc acatatgaag ctacattaat   3360
ttattcaagg acatgtcata tgataatagc taattggacc ataaataggc ccatagcatt   3420
aaataaaagt ttggttcttt tttcttcgat gctaaagatt ttgatgcttt tagtcacatg   3480
cattatttta ctatggaaaa ttaatatatt ttcagttatc agattacagt ttgctaacat   3540
gcaccaagaa tgacaaggaa aatgtaagaa atacgaaaac aagaataaat ttgcatgaaa   3600
aagatgttta aataaatgac ttaccaacca tggtatggaa cgagaatgaa ggaatgaaga   3660
atatgaccaa ccgcagtatt cagaagagga atgtctgaga agctcccatg tccactgtat   3720
tattcaaatt gaattttaca tcataaacat gtttatcatt tattgcacaa tgttaattaa   3780
actttactca attcaaacgt tccaacaagg taacaaaaat agaatatgac gtgtcacatg   3840
actatatttc gaaagtagat tggaacaaca cacaataatt aaaagaatca atatacagta   3900
attatattgt tactttcaaa caataaaatg tgttttattg aaactttcaa acgtagatcc   3960
ataaaatgcg gaaccaacaa taattatagg aaagaaaaag atgtttagtt aggacttatg   4020
agtgttacga tttgatcaaa aaaaaaagtt agcagtgtta cgactgaaaa agagaagaat   4080
taaaaatctt agatcccctt ttgcttttaa aataggccaa tttgggtgaa cataataatt   4140
ttttttttta aaagtaaacc tgaagagaat caaatcttga agtcagtgaa aatctcatat   4200
cgaacgtgcg ttcaagaaat caaagacgat gcaaaaaacg aaaaaacata taaacatatc   4260
aaaattaaga agttgaagaa aaaataaatt gaaaattaaa ttaccagtcg tggccgagta   4320
cgaagatggc ccagaaaagg gttccttggg cggcccaata aagaggccag aagaaccagc   4380
tatcaaaata cacggcggcg acggccagag ccacgacgga gaaaatgtct ctcgcgacgt   4440
agctcatgga tctcaaagga ctcttgaccc aacaatgctt aggaatcgca gcccttatat   4500
ctccgatctt aaacggtggt tgtgcgctcg gatcaaacct ttcgtccttg gaatctccgt   4560
tcacattgct acgctggtcc atagcgacaa ccatcgccgg agaaagagag agctttgagg   4620
gatgtttctc tctctctaaa actgtgtggg ctctgagtga aatgtggtgg agagagtttg   4680
atggactttg gggtatgtgt ggtttgttta tataaaggga gaagatgtgt agagacacca   4740
aactgttttc tttttttctt aatttaggaa acttttttat tctttgaaga ataaaaattg   4800
tatttttgcg gtaacctgtg cgcaatgtat ctttgttacg tcgttcattt cgatgaaaac   4860
taagttagag aaatgtgtta caaaaaaaac aatgctataa aatttacaga agattttaaa   4920
attgcattat cgagtataag taaccatggt aatggtatca aaatttacca agattttctt   4980
```

```
cttttgtttc tctttagttt ttccttagaa gtaaggattg tgcaccgaaa tggtagtcaa   5040
cttgtatggt ttttcatttt cactgattga tatttacaat ttcgcaaaaa aaatacatgt   5100
agtcgaaaat attatgttag tcttcgtact ctattttgtt tctgctaaaa tttcctgact   5160
atgtataaat cataaaaaac gatccatatg gatatcatgt agattgtaga catgccaaca   5220
tttatataga ttttttttaa aacgtattaa tttgagggaa aatagttgcc acatcactgt   5280
gatgtatttg acttaagaaa cagacttcca tcagttttta tttattttag acgacttaaa   5340
ttggcggttt atacaatgta attgttattt tccccagttt gtcattaatt agttaatggg   5400
aaaatcagtt ggattgattg aaccgattca cttgatcccg aaataacaac accaaaatag   5460
aaccaatgtg tggggtaggg tttgaaagaa tttcttaaaa aaatggtaca atttttttttg   5520
gactaaaaac atggtataat tccaactata ttttatcggt ttaacttttg acatataatt   5580
aactttgaat ggtgaataaa gtcataaact aagatcaaaa catttatggt gttttgataa   5640
taaaagacat ttatgggtta gtcaatgaga catcatattt tagaaatgca ggcaagatgg   5700
cgtttcctgg ccagcctcga gatttcgggg gcttatgcga tattggtaaa gatttcatta   5760
aaaaaattta aaaaaatttg gaggtctttt taaaaaattt gggggcctat atttatgtag   5820
ttttttttcaa aaaaattagg ggtcctaaac gaatgtttca tccggctttg cccaggaaca   5880
gctctgctct acctcttctt ctctcttaaa ttaattttcc aacacgtctt tacgagataa   5940
gcatcaacta attgctacaa ttgtatacag aatttactta gctgctgcct ccattaacta   6000
catttcaggt tatatggtag tgtatgtgca ttgattataa atacgcagct tcattgcata   6060
tattcaaact ttttgttgga atgatttccc catctttaag aatcgggtaa tggacgtgaa   6120
ccgtgggttt actgtttaat ttattaacta tacttatatc agttttttaa tatttaattt   6180
tatatgagaa atcgattaat attactaaaa cacaaaaaat tgttttcttg cgttatttta   6240
tggtttttgt cactgaattt gaacatgata ttttctcttt cattaaaggc aaattaccct   6300
gttatggttt gagccagaga ccaaatacta tatattacgt ctatatatac ttaatcaaaa   6360
taagagaaga ttatatgcac tctaccttta aacgtgagat ctccaaaact gtcataaaaa   6420
cgtgatctca tttcttcttc caataacata tatcaatatt gtacatccaa ttccttcctc   6480
cataaaaacg tgaacacctt tcttcttcca atcgtaatat caatgttgtt catccagttc   6540
cttcctccac aagcttttta tcggaagaat ctgcaagcgt gttaaacaaa ccaccatgga   6600
agatgtaccc cagcttctgt gagagttttg gagaaaggag atctacatgc aatttcttct   6660
agcaatcttt tttaacgtaa aacatttaat tttctcatat gtgattctat gatgcttgat   6720
aattaaaata tgatggcctt aatgaataat cttgatgatg tttttagtaa gtcaacagtt   6780
tagcatatga gattaacttt ttaaatattc atttataaaa tttactgcag tttgtataat   6840
aactaattac ataacaccat attcttggat ctaaaagcat ctccaatata aaattctatt   6900
ttttcttcta aaatagaata attcgattgt atagttagtt tactccaatc ctactcattt   6960
ttggagtgaa agcaatgatg aacaaaaaaa taaaaaaaaa tctatttatt ctattataag   7020
tggaaaatat aatgtggttg aagcatttat ttactctaaa ctcctttttg aaataaatta   7080
tgaggtggga ttggaactat tctaattgct caaattctta tgactatata tctaggtaag   7140
ccatggaaaa ggaaaggtac aaatgatgag tgtgggcgta tacatgaagc ctgcacgtga   7200
gagttgtagc tactcgacaa acgtatacta atttgttgcg taccatctcc acttcatata   7260
tatatttata tatctatgtg tgttgagctg agatatgaga ataaaatttg agaatatacc   7320
```

-continued

```
tcaaaaatgc aaagagaagt atgtgtttgt tatttagcag atgcacatgg tggaggacat   7380
ccttcgattt cctcgtgaat tccgaagagc taagttattt tcttttaatt atacagcttt   7440
aaccgagcta attaattaat cgttacataa tttgagcact gtttgaagaa ggcagcgtat   7500
atatacacat tagtatagta atacagttat ataggatcca gttttctttg tttgaaaaca   7560
ctcatatgaa taatatatac ttttaaaaca cgacctgtaa catttttttga cccggtttat   7620
atgtatgtga ttcatatatt tctctaacca cgatcgagta cgactaaatg tgcttatcaa   7680
ttatcataca cgtctctacg tgttcatcta tcttttatta tttttatcaa ccattcgtat   7740
tcgtgtacgt tgaaaggaat cattacgtag atgcccacga tgttaccgaa gttggagaat   7800
tatgttattt agaaaaccca tttttaatta cgctaattac caaaactaat atggggtcgt   7860
aagaatatgc tttcggtagg cttcgcgttc taaatttaca aactatagca gtcaacatat   7920
aagaggttaa atgtattaga ctgaattttt tttaatgtgt ggtgtggggt tacaaagaaa   7980
taaaaacggg attagtgaag cttattggtt actaatttcg aaataatcat gcatggtaaa   8040
aaatcatgtt atacattgtt gtatcagacc aaaaaaatgc tatctcggat tttgaatatt   8100
ttacagtcaa aataagtaga tttaaaagaa tcttgtatta ctgaagttgg aatttagaga   8160
ttattttgaa aattagatag ttgaaaattg attagatcgt tgtagtgatg agttgacaaa   8220
aaataaggtg gtctaaatat atggaaattt cgtcctgaag ataacaaagg cctttgatct   8280
tgcatctagt gcattattaa tagaagaata ttcacaagaa tcttgtgctg tgtgaccatt   8340
tttgtagaac aatggccaca ggaaatgtta tgtttcttgt atctagaaca atagtatcgg   8400
gaggactaat tgtcaccaaa actgaaaaaa taacaagtta actaagtgta tcgatacata   8460
ttcacagtcg aaataattaa tagaggacaa cttgtccatc agttgttaat cttggtggaa   8520
aaggttgctt gttaattgtg ttaaatgcga gtagagtata agcggattta catgtaggaa   8580
aatataggaa gaacataaat attggttgaa aaattgcatc acatttttac caaaaaaaaa   8640
ttgcatcaca tgcatattat tcgcatgaga tgtttaaaga aaggcccacc gcacgcgagt   8700
ttaatctcca atggaaagac ttacagaaag gtcaaagttc tttatcaaca gacaacagga   8760
tatgtgtgcg tagattgtaa aacacgtagt tatctataca taaactaatt cttaaattcg   8820
ttatgtatag tttttttggc aggaaaaaag catagaacca taaagaagaa gaacggttga   8880
agatcacgat ctattcatga atacgtgtcc tcagctttaa accactcaca tggacggttt   8940
aatatctaac aaagcattgt ttttccaaag atactttatt actgtactag gcggcaatcc   9000
agctgataat tagatgaaaa ctaacaccat ttaaataatt taaagttagg tttgtaccaa   9060
taataatgtc taattggacg gcttagagaa gaaaaagatg ggacgtacgt gcacgtgcgg   9120
accgacgaaa cacgttgtcc tctgttcaca taagcaatgg ctctcggctt tctaaaaata   9180
tctctaacta tgcagtgaat tacttgacct aaaccatgtc atttcgtgca accccaacaa   9240
attcctggct tcctttttttt gtggttcatc aatcttttct taggacaaaa cgtttttttt   9300
gtttatgtca gttaataaat gatcaagtcg agtctcgttg acaactagat atcaacgcat   9360
atctggtaga tcactataaa actcagatta tgggtgcatg ttttggatat taaagcaaat   9420
atgtttaggt ttggaatatc agggtatata aaaagatata gtttttgttc ttacggaaaa   9480
gaaactcaaa ttaatgaaca ttaggcttga agtcatataa tcaaacgtgt aaatgacatt   9540
ctttagtaat gattttgttt cccgcagttt aaaaagaaat ctcactcatg actaatgtct   9600
acaaaagtag acaaaggatt cttagttgat tctttagtaa tggttgaata gagctgaaag   9660
ctaaagtcat agcatacatt tggtcacttt catgaattta catatataga taaaaatatc   9720
```

aactagttca ataagatatg attgttttat caaacagaac atcatgagtt ggagtcttga 9780
aatcatttta acctgttttg ctgagagcaa aaatattgat ttaaataaca attgtgagat 9840
aggcaaataa tctcacgtct tacttttcac atatataata cacatatagt tcatatagtg 9900
ggtttgcgtt aaaatagaaa taccattttc atccacaact aattgataaa agaaacattt 9960
ggtatcggga tctaaacgaa atattcacca atcaaattta attttatata tagttttata 10020
atgaggagac gagaagatat ttatgaagac aattattaat tatgtatgtg aatatgattc 10080
gttttctttt ggatttatag agctatagta gcaatccgta gagaagaaat ctgaatcgga 10140
tataacgcca aaagagagat catatgagtt ctaaaaactt aaccacgaca atgttatctg 10200
tccatattat ccatcttcgc acttcatttt gttccatctc ttgtccattc tctatctcta 10260
catgacatta cgtttcctta acatacatgc ttccattatg tttctgtgta aaattaatta 10320
cggttacatt atttattgat ttgcattaca tgtatgattt ggagatgcat acacttggaa 10380
ggagtatacg agcatgcgtg acaactgaca tgaacatgtg aatatttaag atccaaactt 10440
ccaagtatct tataattcaa tcagaataga aactttaaat tataactctt tgttgccaaa 10500
aaaattataa ctccttcagg gatctatcca caaaatccaa atatagcaca aactaataat 10560
tagtttatca gaatgcttaa tgcttgacta ttaaatattt cttctgattc ttttcccttc 10620
aaacaaaacc acagcaacca aaattatcat taaaaaacga caattttaaa accttctctt 10680
tctccgggaa ggttatgtta ttatattatt gtaaatcaaa ccgagacttt ggtctctggc 10740
acaagtcagt tatacggcta atgtcacggc caaagaagaa agtggtaatt tagctgatga 10800
agatagtagg agtttctcc agcttatgac tcgatctcca tatgtaccag ctcacgaagc 10860
cggtcactgg tattcctttg gcgtcctgac caaataatct atctcaacca cattgcttac 10920
gagtgaagtt cattcaaaaa gaaatctcga gtcaaagtga tggatttcgt tttaagaatt 10980
ttccttgagc tcaatgagca tttaaaatgt cccaggccaa aagttctttt cttaataaaa 11040
tttgtgaacc gaaacaaaac attcttctct taacaggtct ttgggcctgc tgttgaaaga 11100
aacagatatt taggcccata tatagtaaaa tttttatggg gcttatagaa atcagatatg 11160
agatattcca taattatcaa attagttcac gagaacctca agtgataggt agaagttgaa 11220
taagattatc agtccagatg aatgccttaa tcttgggaaa gtcatcactt catatgtctg 11280
agaagacgtt tactaacttc aaagttttgt ttgtaaaaaa aaaatcaata tgtgaaatca 11340
aataaactgc atgaacacac acaaagtgaa gtatacaaaa agctgaaatc tagtaagatt 11400
aaataaagct gaaatcgatg tagaaacaga aaatacaaat aaaggtttta tttttgagtt 11460
atttttattg ctctctcagt atacatacat tatttgtaag cttgcaagta aaattaagaa 11520
gacaaaaaag attatcaccc tctcaacgtt tgcgtcctcg gccgccgcga ggtggatcgt 11580
gtctgccgtt agctgaaggt tcaccgtagt cgttggtgct caccatcaat gaccgttctc 11640
tcaccaccct catttcattt tctgtcatat atgcatatac gttacaagtt agaacatagt 11700
gagaatataa aatgttgtac ataagaacct cttattaaca aacgatttat taattaagta 11760
tctatacaaa cgtcaatacc ctcgttttca ttttgtttta actacatcga catgcattca 11820
taatctttta actttatttg cacataaatt tataaacgta tattgatata tatgtttcga 11880
tggttgtgtt ataaacttaa atttataaac atatattgat atctgctaaa aagaatagat 11940
ttaaacacac ccaaattcga cctttttgtg tgtgttggat gtcggtttca caaatcgaaa 12000
tctttgcttg gatttttcac agatagtcag atacgatgga ctaagatcca tttcaacttg 12060

-continued ctattttatg caatttaata ttatctgtaa acttcaatta tatagtcgtg atcttatctg 12120
tcattgtctt tttcaaataa tgtcaacgct tttgaagtgt gaacacaaat taaatatcaa 12180
gcttttatat tacatggttg tactttacaa aaactcataa tacttcaaaa aaatatttaa 12240
aatactttgt tttcttcatt agatttatag tttataattt tatatgacgt tttcttactg 12300
gattcgtcgt tatcacagat atgttctttt aaaagaacaa gtcatcggcg aaaggaaaga 12360
caatctcgag catcgtgatt catgtttgct tgaatttgaa tacaaacaag ctggaaacag 12420
agcgcataaa actaaggata tatccaactt gttttaacaa tatatatttc aacacttatt 12480
caagtaataa ttgtaataat ttagttgtgg gtttctgtag tgatttaaaa tgaaaggtca 12540
atgaagttca catgaactaa ttagtgtgtt attcttttgt tatttgtatg ggttcatcat 12600
gtgttattct tttgttaatc agagtatgta tgcatatcta gggataattg gtatcatgta 12660
aatacgaagg ataaatatac atacaattat ttattttgct tgtgtaattg agattttctt 12720
gttttcttta ttaaaaaggt aaaaactgtt aaggctttct tcttctcctg gtgatatatt 12780
tgaacatact cttaagatat acacagattt acagatatag atcatgtgac taccaccaca 12840
tatcaccgat cagtgatcca ataattgtgg ttgtaaaata tttgattctg agatctcatc 12900
caataacaca taaaatagta aactagatta gttttaacgt taaacaaaga tgatatatgt 12960
agttattagt gaagaaatcc ttatgagttg ttaacaggat atggattatg aagaacttgt 13020
tagcttatat atagtgcttg gatattagat aaccaataca tattaccata caaaaagcta 13080
gtaaacactt gaaactaata gagaaacgaa gggagggaag aagagtatac ctggaaatga 13140
aagactgagg cgagcagaag aagagacgaa agcaaatgtg aagaagagta acaaacataa 13200
cacaaccgag gaagatgatg cataacccat tctctctata tatatatttc tctctctcct 13260
cccttcttct atatatatag accacaaaat gtctcatacc ggcccttcgt tttcagcctt 13320
tctcactatt taatcatttt gatttttatt aatatacccg cttccaaacg tttagttttt 13380
acataattgc gtttgaaagg aacatattct ctataatcta atggttttgt attcaatgcg 13440
tgtatatgca tgtgtttgtt gttgacaagc acaaaaacaa gggaacatga ttgcatttac 13500
atacggtagg tttgacaaga ctgaagtggg atccctttaa accatcaacg aattaaaatt 13560
catttttcca ttgtattggt tacaacagaa ctcaaatgcc agcttaaaat ccaacccatt 13620
gctatttttg attttataat agctttagag gcacaatgat tccaaatcca ttactatttc 13680
ttattctaaa atagaaatta ctattttttg ccaaaaaaaa atagaaatta ttattttgtc 13740
ctctatttat agaggaagaa ataacagtct ctatttttac tctatatttt gaagattgct 13800
attataaaga aatacattag agtaaacttc accttttttat aaagattttc tattttagag 13860
gcaaaaatag caaaatacat tggttttagt aatgggtttt agtagaataa tttaatactt 13920
tcattgtaca aattaaaaaa ctttgttagt tatcacatac attcaattag gataatcata 13980
acataaaaac aagtacagac cacccgagtc tagattatca agaacaagaa agcattatat 14040
gtctggtttt gtacccccat caacttaaga ttctcttgaa cataggcaac acacaagttt 14100
acacatacat agcataagag atccaagtac ttcaagaaag cataggatcg gataaatcgg 14160
aaaatacatc atcgtttttt gaaaccatat ttcttacgtt catagaagag atcggtcttg 14220
gcactcccaa ggttgacgat cttggggcaa ccatctctgt ctttctcctg ctgcgtacac 14280
tctttgcagt agtaagcatc cgagatccca acacctccgc agataacaca gcggccttgg 14340
aatgacccgt agttgcattc gtcacagata cgcaccagag tgcagggacg cacataagaa 14400
tcacaaacca cgcatttgcc gtcgcatttc tcgcacagcc ttccgatggc aatgcctggt 14460

```
tgtttccggc acatgatcag atcagggtga tgctttgcca tggctagtga aacacagacc  14520
tgcacacata agtcacttgt cttgagctca tatgatcgta aagagtacaa aactagaaac  14580
tgaagaacaa gaagcaactt aaagtcctgt tttcacttgt gtctgaacaa tcaattaaaa  14640
gaaaaagaga gtaaaaaaat tggaaaataa agtttgtgta gcagtgttaa cttctcagag  14700
gaatatcatc gaacacctta catgcacaag tctcagccga acattactct ttcaagattg  14760
cagattctag agacatgatc aatcactcta cgaaatataa ttaataatgg gctgagaaaa  14820
caaattgaac aaaagaagga aatcaagaag ctatcacaaa ccctaaaaat tcaaaatcaa  14880
gaaacaaacg aagacgataa ccaatctgga ggagtcctct ttagagataa aaaaaaaaaa  14940
ccaaagctta cagttaacgg gagatcaaac tcgagcaaat caagagactg ttgcgacgag  15000
aaatttccag agcgccaaag atcaaccaac caagaaaggt ctggaacgaa cgaggcaagg  15060
aggaaattta tcacgagtag agctttttaa atcggtccac ttgttatggg ctttttactt  15120
tgggcttaca aactcttcat caaaccaaac caagccggta agcaatgtaa aatccagggc  15180
ctaaaccaaa ccaggttaaa cagcaatctg agttgcgact aaaagtgtcg gtctcggtct  15240
ccgtctccgt ctcagaccca atttttattt catcagccgt tagctttgac ttctgactag  15300
cataacgtga ctttgttgct acaatggtac acaatatact tcttttttta attgggaaaa  15360
tcgcattttt aaccttcaaa gtgacatttt ctaacacttt aaacctccaa cctttttcac  15420
tagcacttca atacctcaac cctcaaaact tatcatatta aaccttgaag tcgtttcccg  15480
ctcttaagcc tccaggcgat ttgacggtaa tgttcacgcc gtcatcctca ctaaaaacgt  15540
gtgtcgtttt tttaattaaa aaacaccaga tacgtttttt atcttttta tctgttctaa  15600
atcgaattgg ggatctaggg tttactcaaa atcaaaatca gaaggagaaa gctcgatact  15660
tggcgacgag caagagattc gaacagagta cgtcgtctca attgatttgt taagcatctt  15720
agtatagcaa gttgtttctg ggctttgttt ttcacttcat aaatcatgta tatgtgtaga  15780
tagcgataat tgtctgagtt agaattggtt tcacttcgtg aatcatgtat atcaagttgt  15840
gtagaagctc ttttacatgt ttatatcaga taatggtgtt gtatatgtgt agatggcaca  15900
cagttcaagt tcatcaaacg ttgtgtacaa aaacgaaaaa ggtgtggttt gcaattgtaa  15960
ctgcttagca aacgttgttc aagcttggac tgatgacaat cccgggagga ggttctatag  16020
ctgcgaaaaa cgcaagactg gagatgaata tgattgttgt aactttttttc agtggtatga  16080
tgttgagaag cctcatggat ggcagcgtga tgcattgatt ggtgctagaa atgttaatcg  16140
ccaacaaaga gaggagatta agagtctgag gaacaagata agagcactta gggaaaacat  16200
gggaccaaat tcaatagatt tgaaggaaaa aactgaagca tgtgacgcat gtgaagggct  16260
caaaagggag gtgctgatac taaacgagag gagcagagtg tatcgcaatg ttctcataac  16320
gtcatcagtt ggattcactg ttgttcttgg tgtgttcatt ggtgtgttga agtggtagaa  16380
ggttattcaa agttgtttga tgattttatg actatgttat gactatgtaa gctatttgat  16440
gttatgacta tttatgcttg tttgaaggtg ttaagactaa gatgattatt atgtttcaat  16500
gttatatttt tgtcatataa agtaaaaaaa catcaagatc ataaaaccga accaaacaaa  16560
ctacattaag tcatgtcatg agaacaacaa aagacaaatt ttaagtcatg agaacaacaa  16620
aagacaaatt ccaagtcatg tgaacaacaa aagtcattga cacaaaaaaa gacagattcc  16680
gagaagacac ataaacaaca tcaagatcat acatagattt aatcactctt gtggaggagg  16740
ttgtgggttt aggtcggacc tatcataaac tcgatctcca agcacctcaa aaggtcgatt  16800
```

-continued

```
tgtgaatgga ctccataatg tcccaacacc atgaggaata ttagttatct tccttacctt  16860
caaaggaagt cctcttggag ctttcttggc atgaggcttt ggatcagtgg atgaaactga  16920
tggctgtgga gcagtagagt gagttggtat ctgagaggat gattcagcag cttgaacagg  16980
ttgagaagag cttgttcttt ttcttcttgt tgaaggaggc ttaggcggac cctgaatcaa  17040
aaataaatgt taacatagat gcattgtgta taaattaaag agtatacgag taacttacca  17100
ctggatgtat acgaggtcgt acacgtttgt tctttggacc ctcataaacc acttgttcat  17160
ttttgcagcc acttttaatg tgacccatct gaaggcaacg gctacatttg ggcacacgtc  17220
cgtgtcttgt cgattttcca gcgttttcaa ggtcttcaaa tggctctttt ctcctctctc  17280
ttgttcttgg tctacctctt ggcttcctta actctggtat tcctattgat ggttttccta  17340
gcctcttcca caagttttca ccattgacgg gcttgatgtt ctcgttgtat gttttcttca  17400
tcttatgggt gtagtaatac tcggatgtat acttcacagg gtcttcttga ttatcatcaa  17460
acacacagac atcatgtttg caaggtatac cagtaagatc ccatcgcctg caagcacact  17520
gatgtgttgc caaattcact gtgtaaccat tatcacactc attaacctca tacaaacttg  17580
agctgcttcg tagtgttgaa caatatttct tggcaatcct tgctttctcc aataaagcaa  17640
gtgtgattgg tgtaacaata gtatcccact tatctgccat aaaccaccgc cttgaattcc  17700
tcttcatagc ttgtcttcga atgtcctcca acatagttat cacgggtttc gcccttgcca  17760
tctttatggt tctgttgaag ctctcagata agttattatg cacgtcagga cagtgtgaat  17820
caacactgaa atatgctcta caccacctct tagggtctgt cttgagtaac tcttggtgtg  17880
ctacaacatt atatgcctct aatagactca acttctcttc atactctcct ttagtgtagc  17940
tgtaagcaac tccccaaaac aaagatttaa actctgatct cgcaaaccca agcttcttcc  18000
aattcgcata aatatgtcta gcacacatgc ggtgttctgc atcagggagt tccaactgta  18060
tggcatgaac aagacctttt tgtttatccg aaatgatggt cagatccttg ccatttccca  18120
agtcgagatc catctttagc ttcttcacaa accagcccca agtgtctttg ttttcccctc  18180
ttacaactgc ccaagcaatg ggaaacattc tgttatcagc gtctctacca actgctgcaa  18240
gcaaatctcc atttaaatcc cactttaaga agcatccatc aagacctatt acaggtctac  18300
aacaactctt ccatgattca cgtaattcct tgaagcaaat ataaaagcag tcaaacatct  18360
gaacaccgtt agcctctctt gtgcataatt cagtgcttat accaccattt gatctatgta  18420
actctgcttc ataatcccat atcttgaata gtcggatttt catcctctga ttcttcaggc  18480
tcatcgtctt cctttggtct gtcaacatct tcatcttcat cactacacga acgctcgtct  18540
tgttcggtgt ttggtatgtg ttccacgaac acttcaacaa catctactcc tagcttcccc  18600
gcagaacgaa gtatacgcat ctcctcatcc aagtaatcat atgcatatct caggtctttc  18660
atctcctctt tctcgaactt gaaccaaagc agtccaattg gtgctcgtat cagtgaatct  18720
tccttgcaaa acagactgaa cctctcccat gtgatctcgt caatcttcca ctccacattt  18780
ttggtgcccg tttcaccaac atacgcatat ccttcaccat ccttcttcat tgaacctcca  18840
aaatgaatct ttaacttcat ttatgttgct tccctgtaat caattgctta aactttagac  18900
aatttcgaga gataaaacga atgtaaaact cgaaattttt gaaagaatag atcaaatcga  18960
tgactcgcgg acccttaccc catatttgct ttgattcacg aaatttccta tcacttaatc  19020
gagctttctc cttctgattt tgattttgag taaccttaga tccccaattc gatttagaac  19080
agataaaaaa gataaaaaaa cgtatctggt gttttttaat taaaaaaacg acacacgttt  19140
ttagtgagga tgacggcgtg aacattaccg tcaaatcgcc tggaggctta agcgcggaaa  19200
```

```
acgacttcaa ggtttaatat gataagtttt gagggttgag gtattgaagt gctagtgaaa  19260
aaggttggag gtttaaagtg ctagaaagtg tcactttgaa ggttaaaaat gcgattttcc  19320
ctttttttaat tagtatactt tctctatatt tcactccaat agcatctcca atgtacacct  19380
ctataatttt ttctaaaata tagatttcta ttataaaggt gaaaatgctc caatatatgc  19440
ctctataata tagttcatct atttatacgg gaaaatatat aaatatattt tttctatatt  19500
ttcttttaaa atagaagaac tctattatag aggcatacat tagagcattt tcacctctat  19560
aatagagttt ctctatttta gagaaaaaat atagagatag aattagaggc gggttggaga  19620
aggtctaata gtataactct ttggatttgt tccatggttc attctaacat aattactaga  19680
tctcgatccc cgcaaccgcg cagatttttg ttttcattta tttttatata aatattttgt  19740
tttcaattct aaattggtat atattataat agatgcgtct atcaattttt aaagcataat  19800
aaatttaccg tatatttttt tctttgaata gattgtttca aacattcaca tgtatttgta  19860
ttttcttcta tatatatatt tcagattatt atttcattat taaaatcgta actatatatt  19920
taaagattag taaaatattg ttttattgtc atattcaaag atattgtaac atttcacaaa  19980
tttagaaagt ttttaaaaaa ttaaaatttt cgcttcgtag atttatatta tcgagtaaat  20040
aattaaacat ttggtttttg tttaattttt aaaataaact atataattta aaatttgttt  20100
tcattggttt aaggtagtaa atattaataa ttgttagata atatgatttt tgttatttta  20160
aaaaaaatat ttataatttt aaaagttaac atcgacaaat atttaaatat ttaacatatg  20220
gaggtatagt atattacaat attaaattat atatatttaa gttatactat ctataaatcc  20280
aatggataat ctattgttta aatccaatta ttgatagtcc aataaaaatt tctggtaggc  20340
caaaaattta aatgatataa ttatacttta aatgtaacat gacttcatag gaataagttc  20400
attaggtcaa ttttttttaaa aatcacatat gaatcaagtt atgacttcta ttttaatata  20460
taagatattt tcacaaaaga tagagatcat ctttttctgc gctgggaatg gagtgctgat  20520
ctttggaaca tttgtctgcg aagaatgggg tattccaatg tggagttcca taaatggtta  20580
gccttctacg aatggtaagg ctgcatgaca aagttgtgcc aaggcttctc agacccttgg  20640
tagtctcaac aacaatctat ttcatttgct ctcagagaaa cgagcgctat tatgttaata  20700
tctcatcgca gccaacaatc attttcaagc tgcttgaccg tttcattaca aatgcacttc  20760
tattcattag aaatcaaaaa cagagctgcg gactgatgca agtatgcaac attggctttc  20820
caagtatgca acattggctt tccagggaat taaaaccata gtctgaacta tacccatttt  20880
aatggaattt acatatgtgg caaaaaaaaa atacaagtca agaggcagac atatatactt  20940
ctttttttta attagaagca agagttttaa ataaactgaa atttttcata aaatttaaag  21000
taattattta caaaaattaa atttaagcta attattaaaa attaaaaatc aaaattaagc  21060
atgccactga atataaaact atgtaaatgc taatctaact agatgttgtg gctgatttgt  21120
tgaactttgt agaaatgatg ctgataaaaa tgttataaat gatctgatgt aactagggat  21180
tctttttgtt ttattttgta ataaatgaag aaaaatattt ttaccattat aattttttat  21240
atatcttaga aaataaggtg ttcgttatat cccaacagta gtttttaatt ggactagatc  21300
tttttgtgtt tgtatatttt tcgtcttttt tatgtattgg tttatttttt tgttatttta  21360
ttgatttcaa atatttttttt gtctcaaatt tcttatttag attagttacc atttttaaat  21420
tttgtacttc tgaatattta gttatactct ttattttctt agttatttta atatagtatt  21480
gcatatttag atacaaagga aaatagtacg tgtaaaaatt aaataatgta gacatatttt  21540
```

tccttgtctg gttttcttca tcccatgtaa aaatccacct aactttgatg taggtttttg 21600
tcatgttcca atatacgtat aaagtttttt gttggtaaaa atttacgtat aaagttgttt 21660
cattattttt tcttggagct tcgaataact tttattgact taccaaaata aaatcttgag 21720
tgattttaag gtgaaaacta acatttctgt taaacagtta ttattttttt acatcgttaa 21780
ataattatat taaacattgc atatggttat ttgatatacc aaaatgtatt atttataact 21840
gagactatga gaaacagaat agatgttaaa tgcattactt gtaacctttg gcatcatctt 21900
tgctatatac tcgaattata ttatattaag tattttattg gtctttaaca tttattttaa 21960
tcctgttcta aattgtaatg tattaattat tatttttata tttgtttgtt ttttttttct 22020
cattgtgttc ttttcttaca tatgttttag attaaatatt tttagcatgt attttaaaaa 22080
acctgccttt ctaaaattaa agttatgttg aaccaaataa agttatatat gtagtaaatt 22140
aaaatatact taaagtataa attaaatata atatatatta tttaattgtt gtttaatcta 22200
ttgtgtttgt tatagttaat aatccacatc taacatattt ttaatgttgg tgggaaaaat 22260
aaccttacac atgataaaac caattaaata tgaagtacat gatatcaaat gtgccaaaaa 22320
ctatcctgaa aaactaacat taatcaaaaa ctaaagtaga ttatcttaag tctttactga 22380
tgaaaaaaaa aaaaaaaaaa aaaagtcttt actatatggt acacgaagct actcttctaa 22440
aatgattttt ttctaattaa tatcacttta tgaacaattt tagtttactt attattgtat 22500
tgttttctac tatatcctca aatctaagtt caactggaat ttaattttaa tgaatctttg 22560
tattttttat tttatttgcg ttggcaaatc ctcctgttaa ttttttttta atgtatattt 22620
catattctag taaataactt ttagttccac tcattggtca atagaaaaga aatatttatt 22680
taggaagcta agacgaaatc tgaaccatgc aacaaaaaca aacataaagt cattaaaatt 22740
cagagacaat ttataagtta atcaacatgc aatagaatca gcaatataac cttggcccaa 22800
caccaatggt gatgggagtg atctgcttca ctacatccgg agagcctgct tgcgtacacg 22860
gtgtgaaaat tttcccatat gttggttcct taattatata taacaaaaaa aacatgcagg 22920
ttcctcattc gttagcgtaa gctttgcagc cacatatgat agatatgtca accaaatgtc 22980
aaactctgac caaattcgtt tctaaagcac ataacaatta agactggaaa ctggaagata 23040
tatattcact atcttacaat gactttcata aggtgctcac ttatagaacc aagtgtaata 23100
taaattactc acatatatgt cttctactca catattctca cctgatccct gagcaggtgg 23160
tttgtattga tctagcagtg tgtgtgaaac tggatttggt tggttgagtt ggctgacttg 23220
agacgtctct cacggataaa ctttggcttt gttccaaatc ctattttgta attcatcaca 23280
caaacctatg aagattgatg gaaaaactat catgaaatat atcaattgat gaaaaagtta 23340
gattaatctt accgtaatac atttgaatca gattgaaata gatatatccc accatataaa 23400
ctaaacacta agctgcgtcc cctagcttct gactcctagt gacaataaca aagggaagac 23460
ataagatgga cattcatata gtgaaatctg taactatacc aatatcaata gcttcagaaa 23520
ccatttgtag ggtctgtgga tcatatgtat ttgcagctgt taaagatagc aagatgattc 23580
catggaccac aatcagcttc tggctcactt gtgctccgat tttctcacaa cttttagccc 23640
gtgaaccata tacgtttgtc ttaattacta tatagaacaa agaaaatcaa tatctgctaa 23700
aaatatattt tctttttctg ttgattatgt tctaatccat gtatttttag tttataaacg 23760
ttgaatacaa gatatcttca tatcctaggg atgcttatat aatgcatcct caatgttaat 23820
ttaaataaac aaattagaga gggaagtaag gcaaacgttt catgaaaaaa aattgtagtc 23880
atcgcatacc tcttgtcaat cttccagatg caaagtagat ctataccagc cattgatctc 23940

-continued

```
cactgttctg cgcaagaata attgactcac attccaacac tgagtcctct caacaatacg  24000
tagaacaaag aacagttcct atgggaaagc ataccactta gaacattatc acgttagttt  24060
ggcattaatc actttgttac cagcacgtgg tgctttactt acctcaactt atatctttta  24120
attcgagaag tcatctgtga aaggttgcaa aactgtatga ccagctggca tctttgtgtc  24180
gaaaagtgtt tgtgggaacc gtagaagttc ttgctgctca ttctcaaact tggccagttt  24240
atgcaaacca attcccctga atatccacca taactaaaga gttattttgc tattttagct  24300
cttccacgga cctagaagtg aaaccacaaa ccataacatt gttcagaact accaacctat  24360
atagtgcaaa ggtcctacac atccttggta ttatagtcga attcaaaaca cgcaccgttt  24420
cattctgact ctgaaaggga ttcccaggcc tccactgcga accagataca ctatttgagc  24480
ctgagatttg tgtctttgat atcaaagttt gcttaacaca tccaaacagt gctcacctcg  24540
gaaatctctt tctattatga tcatcgacat caagaaggaa agatcaatca gtaagggttc  24600
taagcaattt cagatataaa cagaaacgcc agtggtgttt agatttaatt tagaaactac  24660
tgaatcagaa aagcgattat taagttaccg gcaatggagg agcaacaacg taaccaatat  24720
tggaggccat ggcgggaatt tgtgttctga aaattgtcat cgtctgtgaa gaaacattgg  24780
attttgagtg tagccgtcgt ctatatagtg aggatggcga gaaggatgga aaatgaagag  24840
gcttcaatat aatgtcaaga aggcttaaaa ggatttgtac ggtgaaagaa aaagagatga  24900
agagctagat agttatggtc tggttcaaga gaaaacgaat ggaattgatg aaacaaagat  24960
aaagaaaata agaatgtgat gatgacgtgg caataaactc tgacctaatc ggttgatttt  25020
ttaatctgag ctggcatcct ctccattcag catatctgct ttttagtatt gttagattat  25080
aattaaattt aaaattaata aagcatattt agtaaattta aaagttgtaa aaaatattat  25140
aaagatatca cgtacaatat cattttacat aacattccaa atatcttatt tttggaaagg  25200
attctgattc aatctggatc ccgcataata agcctcagcc ctgttcctaa caagaaaggt  25260
ctggaacgaa cgagggaagg aggatattta gcacgagtag cgctttttaa gtcggtccac  25320
ttattacggg atttttactt ttggcttaca aactcttcat caaaccaaac caaaccaaac  25380
caaaccggta agcaatgtaa aatccagtgg ccaaaccaaa ccaggttaaa cagcaatttg  25440
agttacaacc aagtgtcggt ctcggtctca gtctcaggcc catattttat ttcatcagcc  25500
gttagctttg acatattatg actaatacga ctggacacag attggatatc cagatttttt  25560
aagatatttt tgatttgatt cgtatgttac agatatctaa tttattgatt tgctttgttc  25620
caaaaaaata cggatattcg gaaagacgga tatccgaaaa ataaatacat agttgcggat  25680
atttacgaat acctacggat atctcatcca ttttgattaa tacaaacaat cttaaaaatt  25740
cgatacaaat ttgtatttaa aaatattttt tgcatgatat ataaaacaaa aattaaaaga  25800
aatagtgaaa ctatatattt ttaaaatttt aaaacttaat taacaattat aataaaataa  25860
aacttaagaa aaaattataa ttgttataat tatttctcgt atattttatg taatactttt  25920
atataagtaa taatgtgaat aaaatttgtc aaatcatatg ttagaataat aattatataa  25980
atacatttaa aacttttaag tataatcaag atatacatgt atttatatat taccggattg  26040
gagcggatat ccgcttccca aaattttaat atttgtgatt tacttcgatt ttaacggata  26100
ttaattttag tatttgtttt ccttcaaaaa tttacggata tcactacaag aaaacataag  26160
tttaacgacg gtggttttcc tcgtgagttt gtcgtaaaag agagtttacg aggaattagc  26220
gaggaatcac gtttcgtcgt tatatgttcg tcgtaaatca tattttctcg ctaattcgtc  26280
```

```
gtaaactagc gagaaaacca tttcgtcgta aagacgaaga aaacaaatcg tcgtaaagac  26340
cacgtagata gtccatgtaa gaatgtcgct agcattcctc gtaaatacca cgaaagcatt  26400
tcctcgtaaa cgacacgtac atatctcgaa aatatttcct cgtaaaattc acgtaattac  26460
cttgaaattc tttcctcgta acattcacgt aaataccttg aaagtatttc ctcgtaaaat  26520
acttgtttac catttctcgt gatttcctcg taaactttca acgtaaataa atcgtagatt  26580
agctacgaat ctacttcgtt ttattgtttt acagaattta aaaatataat taaaaaattt  26640
aaaattatta aatttattaa taaaattaaa attttaaaaa aatacgcaaa tattttatat  26700
ataaataatt tttgaattta taatacaacc acgggaaaaa aaaagaacta agagtcgtgc  26760
atcgcccgga ggaattcatc actcctcctg tctacatcct cctcggcatg tgtgtcgtcg  26820
gatggttcct cgcctgaaat gagattttgt tgtcgcatgt tcctcaacat ggtctcccat  26880
tccggatttg tggccgctat aacgtccaag aagctctcga gtccacccac acgagctctg  26940
aacgcagatt gcttcgaagc caactcgtta tgcagctgag tgacttcatc atcccgtcgc  27000
tgaccataag acaatgtcgc tctcggaaca tcgttgacgg aaccaatccc caacgtccat  27060
ccctttttt aaagacaatc ttaaaacaaa aaataaatat tgttagtaaa aatttaaagt  27120
taaattaaat gaataataaa aaattaaaat tttagaaaat ttacctcctc gtaaatctta  27180
tccacttcaa gtgtggataa ggtgacgagt aatccgtcgg tggacagctg gatctggtgg  27240
tcttcaaccc gagcaaccaa gtcgttgtag atttgcttgg acttgccatc tagaaatacg  27300
cctgccttgt tcttgtgggt cctctcgtaa agttccataa gagacgggag atgtgccgtt  27360
tctttggcct taaaaacatt taagaaagtt agaataaaaa tatatatata tatatatata  27420
tatatatata taataaatat atatatatat atattattat ntntntnttn ttttattatt  27480
ttttttttt tttttttgaa gaaaacatat ataaaccgaa atcgaatata tacactgcga  27540
tgcaatcaca cacttacaac acccaatttt tccatttaca cctctagaca cacaggtccg  27600
tgtctaacca cctaaatgtt ccgatcctac ctaaacagtc ggatgaacca tgtctaccct  27660
aatctctcca ttgtttttgc acatgtatgc acatataatc agtgtgtaag aatgcatgga  27720
gatgaaataa aagtgtacgg tgtaggtgtg gtaccaaact attgatgagt ctggccattc  27780
aggattatta aagagtggta aaatgtggta aagaaaatcc tgaatgtgta tatggtgtac  27840
cgtttcctga tgttgattcc tggtcaaaag aaattaaatt cattaatggt caaaattatt  27900
tgagtcgatt acaattcacc gagacttgat aaaagattta aggagaggtt gcttggtcaa  27960
gtagttcctc ggtttgtctg cgctaacagt cctgaaaaat ggtcaatatg aaatgtaata  28020
cacaacacac aaggaaatag tctaataatc atcacagggt ctgagaaaaa cacgtagtag  28080
tttttt                                                             28086
```

<210> SEQ ID NO 5
<211> LENGTH: 10653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
aggtcgagta tctttgtagt ggtcgagttg cgggcgatca gattgttctt atttgaacca     60
agagtcaaga atgccactag gccatggttt gacaatgcct tagattgatc agatggatgt    120
tttggaacca agcacgacgg aatagaagca cgacgggaaa actcgaaatt ggacggaaac    180
```

-continued

```
cctaatttcg gtattatgga agtttctgat caagccgaag aatcaagaaa tatttaccgc    240
caaggtcaga gttcagattg gagtttatta aaaatattca gctcatcaga atgggagtag    300
aaaaatattt gggattgatc gcgggtcaga aatttaccgg aatgaccgaa atcagaccaa    360
tggaccgaaa agctcgaggt ggctcgttgc atgggttcag aacgtggtgt aaaccatcta    420
acaagctgag tgtctacaga agctcgaggt gtcatcgtac atggaagttg tacatgcagc    480
ctgacatgta gaagcacgag gtggatcgac caagcacgag gtggatcgac caagcacgag    540
gtgtctccgc gcatgcaacc gaagcatgct gatcgacatg tgtgtgctgc tgtggcgcct    600
tgcatgagtt ctagtcatgc agcctgacat ctgggaggag tggtggcgtc ctgcatatgt    660
cctggacatg aagccagcca tgtggagcac gaggtgccgc cgcgcatgtg tccggagcca    720
tgcgaagcga cacacaggct gccactaacc tgaagctgat tggttgctgt cttctataaa    780
tagcccacga ccccagctca tttcatcaca tccatacctg tacaaaccac cttagaaacg    840
tgagagaaaa gtagaaaaag aaagcaagag tttccgatct atttcgagaa ttttagagag    900
attgcgaggt cagttctcta ctgatttcga gtcagcgcct agggacggtt ctgtccaact    960
gaattcgtcc agaccactca gttcctttga tgatcaacta gatatgctgt ccggagttag   1020
ttcagttcta cgggttcaga tcagtcgaag ttttgctcga tactccgccg ggaagtccga   1080
agaactgtcc agaagctaga ggaggttctg tccgagtcca tatcagcctg tcgaggcctg   1140
tcagtttctt catggtgaag ccgaggttgt gtccaagaca agatcagtcc agtccactcc   1200
agtcatgtcg tcaattgggt tttggccaag tcttctccga tcaaccagct gcttatcagc   1260
aaagaacact gtgagttatg atcaattgat tgctgacttg ttttcatgca ggttcccgtt   1320
acttagaagt tggatcatgg caggaggtcg gctctaactg agtcacggtt tgactagtta   1380
ataattgagg ttatgttgat tgagttgata gcatgctggt tattgcttga gaaccgtagt   1440
agcatgctaa tggttaggtt gattggttag ttagcgaatg cggaatgctt agatgatatc   1500
gctaagttgt ggatagttag atattctgga attagttttt atgctagatt ctggaatatg   1560
attgattctg ttaatttgcg attaatacta ggaaccttgt gttattttac cgggtttagt   1620
attagtcatg tattggccat atagcatttg tgtaaaccac aatgctatgc atgtttgagg   1680
tggattagtg tttcctcgac ctcgtaccca gcgggtttaa ggttactctt ccaactccgt   1740
tgtccttttt gcaggtcgct ttaggtaagg atgatcggat agcttggtgc tcgacgttag   1800
gaccgccgga gtagatttca tgccttttgt aaacggtatt gcgttatgtg ttttgttggc   1860
tcgatttggc attaggccgg gcccagtctt gaattatttc aatgtatgga tatttcttga   1920
atcaataaag taaatgtttt atatgcgctt catgagtact ctgatatctg actagtccgg   1980
tctaacacaa cgttaggtcg tggtacgggt tgaaaagcct taggcctcga tctaacggaa   2040
aacgctaact ctaggtacgg gttgcaaagc cttgtgcctt gacgcagcag gacgagttag   2100
tggaggaact ggtcgaggtc gtggagtaaa ttttgtgact ctggccggat cgtccctagc   2160
ccgtcacgta gcgcttccgg accatggtgt tgggttggac ggtcagtcat gttcttgttt   2220
gattgttggc tggccgattg gcctttcatc tccaaccctt ggtgtgggtc atccgtcggt   2280
catgttcttg tttgattgtt ggccggtggg tcgacctata cctaggacgg ttcgggggtg   2340
ttacactaat catgtaagct cattcagaag aaagtttata gttttttat atagatttta    2400
gttttagcag gcaatgttca tagattttct tgcaaaacct tgtccacaat acgttttata   2460
cttcttatcc acaatttatt ttattttatt ttaaaatatt gatttttatc caatatttct   2520
cagaagtgct tcggactcat cagatcactt tccgataaac agttccgaca aaatttgtta   2580
```

```
atggaacttt tcacctaatt gtagaataca aaatcttgtc cacaaagtta aattaagggg   2640
gtgtattcaa tttaacattt tatgtgattt gatttttaat gggattttag atgatttcaa   2700
taagttgcag agatttatgt gagttttgtt aaactactct agaatatcat ctaaaaccat   2760
gagatttgag ttttaatttt ttttaactaa gaaactctac ctaaacaccc taaaatcatc   2820
tgaaagcttt aaaactccac aacttaaaat attttcaata acaatggatt taagagtact   2880
ttacgaaata tcaaattcaa taacattgta ttttaaatga gtttttaaaa ttcatgtttg   2940
aataacagtg aatttgttat tttaatacaa atcacctaaa actagcagtg gaatacaccc   3000
cgcctaaata ttcttttgtt cccttaattg tgttctcgtc tataactcat tcttgtaaca   3060
tttgtctgta cacaacttac atgtccacta tttttgtatc cataatgttc gcctgtccac   3120
ataatgtttg tctatccacg taatatttat ccaactgagt aaccataaca tccttacatg   3180
gacacgaaag catcaacaac cagcgaacat gtatttgtgg acatgataga atccacatcc   3240
atgaaatatg gatgactgta acttgctaaa ctgttcattt taatgtaatt gttggattaa   3300
cagttttttt acgatcttgt ggtccttatg gaagtccaac tatcaaaaaa cttaatctaa   3360
taaatgtcta aaagctaact ggaaaaacaa cacaaacaat attccaactt tctgtttcgt   3420
ttcagtaaga gcaaaatagt ccaaaaactc tctcaatttc cgtgaatgta tgtagtgctg   3480
ggttcgcggg tcaacccgcc ccgacccgcc ccgccccgcc ccgggtcgaa tcattttttc   3540
gattcaaaaa ctcgacccgc ataacccgca aacaaaaact tttatatccg cacccgcccc   3600
gccaaaaccc gcgggtaacc cgccaaaccc gcgggtaata ttaattatat taaaaatagt   3660
tattttaatt aaaaatgatt attttctaat tatataataa ttattttaat taaaaataat   3720
tatttttat ttatataata gttattttta aaaaatacta ttaaaaaata tatttataat   3780
taaaattata caaatattta ttgtttttta tatattttac gaaaaaatgt ttttttcaa    3840
aatttttttt tttttaattt tgcgggttgg cgggtacccg cgattcaaat tcggctgacc   3900
cgcacccgcc ccgctcaaaa taatcttgac tcgcacccgc acccgcgatt taaaattttc   3960
aaatggttcg acccgcaccc gccccgcggc ggatcaaatg gggcgggacc cgcaggcaat   4020
gattaaaatt tccagctcta aatgtatgct acaagtggaa ggtagttttg ggtgcaaaga   4080
aaacagccta ttaagtaatc aactctttaa tatattggga cgaatgagat gtttgtaaaa   4140
ttatttaggt ccagatactt ggcgcaattt aagaaggctt ttatatattt gggccgaaaa   4200
ggttcgccca ttacttaaaa aagcgacaac tccgtgacat attgttgttg tgctgggacc   4260
caaaaacggc gtgcattttg tcgactttca gtggaactgg ctttttcttt ctgtccaaat   4320
caaaaaagtt ttaaagatcc ttttgattgc aaccagagaa aaagataaca aaacttccac   4380
tttttgtaac gtaaatacat taataaaaaa aaggtttcac gagtacattt taaacttaaa   4440
gcagaaacaa ataagtaaaa gagaaggagt gtttattcct aatagagcta ggaagaaaag   4500
ttaattgatt ttagatttgt cagaagcata aacgtagaga tctggatctg tctcgtagaa   4560
gacaatatca ccagtgtcac tgacgtaatg atctttttta atacttgcga ccaaactctc   4620
caccaagtga atcggtattg ctcctgacgt cttcggctct ctgtagtatc ttcctaacac   4680
atgtttagct gctctcgtct gtccacaatt cattaattaa attagtaatt aatcaccatt   4740
taatcaaatg aaactagaga gagagaaagc tagatcactc acggcatcga ccaagtgata   4800
gtgagggatt tgtgggaaaa gatgatggat cacgtgagtt ccaatgtcgt gatggatgtt   4860
gttgaagatt ccgtaatctc tatcaatagt tgttaatcct ccacgtaaat aactccattc   4920
```

-continued

```
ctattattgt atgcaaaaca tcaaaaatta agattaatca atactaacca ttattgcttt   4980
ctgtacattt ctttttaaaa attgatttaa ttaccttgcc tctgtaccaa ggcaacttct   5040
catcgtgacc atgatgatgc aagtacgtga cagcgtccaa ccacatcaca aagatctgaa   5100
aattttccaa acccttatgt caaaaaacaa atttattatt aataatatat aaatttcttg   5160
taataaatatg tgaaacttac aatgtaagga acgccataga ctttgagaac tgtgactgga   5220
tcaacgagga acgatagata aacaagagtg gccaacatta tggaccagca agtagttgaa   5280
gttgcaataa gcttcctctc gcttggagca aataaactac tgtatgggtt aaaatgtgac   5340
ccttcttttc caggacttct gtaccactgt agttaaaatc caatcaaaat taatttatat   5400
attggcttaa aactcaaaat ataaaatcat ttgtaatttt aagaaaaaat agaaattgta   5460
tttttttttac cagatagatc gggtaagcga gcatgggcag agggacagtg tatctgagca   5520
tccgagtact atggggcaag ttcttgtaca acttttctgg caactgaaat acataattat   5580
aattaatatg actattacta ttactattac taattactat tacggagtag tacttactag   5640
tattaaatat tcattgaaaa tttgtcattc tggttatgta ttcgtattaa ttcatgtgtt   5700
tataagtttt atactaatag ctttcaagat tgcagacaaa agtattacga aaacgccaaa   5760
actgaaaagg aaaaaataac gaagaaagta aacggatttc gaggagaatc atgttatgct   5820
aaggactcga atataagtgg tccatcgata aagttaggta ctataaaagt atagattttt   5880
cattttctga gttactgcgt aacctctaaa aaaaactctc taaatagagt ttactctaaa   5940
tttaaagttt caaagtggtt ttcttcgaaa acaaacttca aacataactt caaaattatt   6000
tgtattttac acaatgatcc ttatttgtta taactaagag catgattaac ctgggattct   6060
taggatgggg ttcttaccgg aagttaagaa actgtttctt aacgtttaac taaaactcca   6120
ctctaagaac tccgggttaa tcatggtcta atataaatcc ataaaaaaaa ttataaataa   6180
ctagcacata tataaaaata ttacagtaat attaattaat aaaaatttac attaaatata   6240
taaaattata aatagaaata tataattaaa tattaaacta gaagcaaaat accatattat   6300
ttcataaaat tattttcgta atgctccatc ttcggttaca caaaatttgt ttagacaata   6360
attttagagg ttccagagca aatttaccag attattagta ttgttataat atttaaattt   6420
tctaatagtt atgtcttcat gtatcttatt ttaaattttt tattattaca tttcttttgt   6480
aatattttgt tgactaatta tagtcttaaa tattataaat cttatttaac atttttatta   6540
cttttatgta taaaatttga atttataaaa acaaattgga aatatttata atatataaaa   6600
aatttaagaa ttaaaacgat aaatgaaaaa atacttaaga attataaatg taacgtgtaa   6660
ttaattataa tgatcaaaat gcaaaaaaaa aacttcaaat ttgaagtttc gaagttcatt   6720
tttgaaaaac aaaaaaatct ttatatttga agttataaaa ttttttttttg agatagatcc   6780
gagaacatta attaccgctg aactattaca cttgcaaatt gtttttttact acagctagaa   6840
aacagatctg acaagtggcc ggtctgacct cagactgaaa acataaacta ataaaataaa   6900
catatagaat cctaggagta tgattattgg ggtttttagg aagaggttct tagcggaata   6960
taagaacccg tttcttaact tttaactaaa aaaattaaga acgtgttcat aaaactctta   7020
tttaaaagct ggttcttagc ttttttagtt aaaagttaag agacaggttc tcatattccg   7080
ttaagaaccc caccttaaga acttcaataa tcataagaac ttagacataa gaatgaattc   7140
ccaaaaaaga acaaataaat aaaagacaag agaaacaatg agagtaggaa agattaccgg   7200
aacccaagac tcgtcgtttt caacatggcc atggttctgg tggtgtgtcc gatggcttat   7260
tctcctgcaa accccaatta caaaagttat gtatttattt atttttgtga aaatgaaatt   7320
```

-continued gtctctataa tgatttaaca atctcactca ttttatattt attttgtttt tttagttgat 7380
atatttattg aacaactaac aatagagtgc tctaacaatc ccattctttt ttttgagcaa 7440
aaaaacattt gatgcttttt actaataaac attgtgcaga aataagtaaa aaaaactata 7500
aatcctcagg aaattgatgc atgtaagtct ttttcgaaga tgtttgaagc tgatgtaaac 7560
aaataacaat aagtgaaaac ctaaaaaaaa atcaaaatct aattatactt aatgaactaa 7620
gaaaactcag gaccatagat aggcgcatat catttaagaa aaggtttgga ttctttttca 7680
ttggctgcta aagatttgat gcttttgaac agaaaaagca acctcatata gtcacatgca 7740
ttgtttaata ggattcttat ttaattataa aattgctact ctagcaacaa aaaaaagttg 7800
gtagcttcca gttaatactg attacagttt cctagcattg cacccaagaa taacaaacga 7860
aaatgtaaga aatacgaaaa caagtactaa taatttacat ggaaatagtt aataaatgac 7920
ttaccaacca tggtaaggaa cgaggatgaa tgaatgaaga atgtgaccaa ccacactgtt 7980
cagcagagga atgtctgaga aactcccatg tccactgcca ttattcaatt ttattttcac 8040
atcattattt aacataaaaa cgtatttatc atttagtgca caatttattt taacttttct 8100
acatttgttt taactcaaac tctttaacaa ggtaacaaat ccggtatatg acgtgtcact 8160
tgtctaaatc acaaaataga ttggaacaca aaaagaagaa aaaaacaata tatttttctt 8220
gtcaaaaaac aatatatttg ttgccaaaaa aataaacagt atattttctt gatattatac 8280
tatactataa ttataattaa aagttccggg gatctagaga aagagaaaca aaaattgaga 8340
acatcaaaac gtagatccat aaaatgcgga aataatatta attatagaaa agaagatatt 8400
ttgttacgag tctgacgact gatgagtgac gatgcttgaa cattgatgaa gaaaaaaatc 8460
ttagatccta tattttcttt tattttttaa taattaaaca tgaaaaagta acctcaaaag 8520
aattaaatct tgaagtcagt gacgatactc atcgaacgtg cattcaagaa attaataaat 8580
tgaacaaaaa gagacaaaat aattaaaact gaaaatttaa tttaccagtc gtggccaaga 8640
acgaagatgg cccagaaaag ggttccttgg gcaacccagt agagtggcca gaggaaccag 8700
ctatcaaaat acacggcggc catggccaga gccgcgacgg cgaaaatgtc tctggcgacg 8760
tagctcatag atctcaaagg actcttcacc cagcaatgct taggaatcgc cgcccttata 8820
tctccgatct taaacggtgg ttgtgcgctt ggatcaaacc cttcttcctt ccgggcaccg 8880
gaatctccgt taacattgct gcgctggtcc atagcaacaa ccatcgctgg agagagagat 8940
ttggacgaag tttctctctc tagatgtgtg gcctttcagt gaaatgtggt gaataaaggt 9000
ttgatggatt ttttgggtgt gtgaggttgg cttatataaa gggagaagat gtatttatgg 9060
acattgagaa aatattccaa attgtttttt aatgattaat aatttatttt ttatttatca 9120
aaagaataaa aatggtaatt tagctgtaac ttttgtacaa tgggttgggt gtataatgtt 9180
ccaaaaaaaa gggttgggtg tattactctg ttacgtcgtt caacgcaatg aaaccaaatt 9240
ggagtaaatg tgtttctttt ctatttttag attttccttg gacggaagga ttgtaccaaa 9300
taaatttatt tgtgtttctt actctagaat caaataccat atgtagatgc agtgaaatgg 9360
aagacaaaca taacgatcct ctagcatata tattttgttc cctaaaattt tgttgattat 9420
ttattgacta ggataagatc accttgggcg ggatagacat cgtttatata aagtggttaa 9480
gaaaatacat cgtgtatata aattattttt acatattacc atttatttta catgaaataa 9540
taaaataata aatatatatt aaataaattg aaaagtctat aactattatg tatataatta 9600
agttggtgta aacacataaa tcaaaacaaa cactcttttc tatttaaaat aatattgaga 9660

```
taaaaaaatc taaaaaatca attatatcta tggtatataa ttaaatttaa atgatattaa   9720

catatagaag tatattttaa aatatctatc cgttaaataa tgcttcatac tcatatagtt   9780

ttatgacaat ttgtattttt taaactattg aaaataaaat tttcaatttg atacttttaa   9840

tagttttagt aatttataac tgtttttaaa aattcaataa aaaatttgaa attaaaatat   9900

taagttctca atatttcttc aatggaaatt tcaaattaaa ctattatgtt cttatatggt   9960

atatagttta atttaaacga tagtaaaaac atatttttaa tatgaaaata tattaaataa  10020

gacattttat tcatatgatt tttatgatca tttatatatt gtataacaaa aaaatttaag  10080

ccactgatca caaaattttc aatgtaatat ttttaacagt tttagtaatt tatagttgtt  10140

taaaaaaatt caaattataa catataagaa aaaatctaaa tttttattct atgattaata  10200

tgattgttta atttattttt taaatataaa acaaaaaata atagaggaaa cacaaattgt  10260

tatcaatttt ttattattca aaatcactaa ttgtcatata tatattgatc acattaaata  10320

attttgtagc ttttattcaa ggaactaaat aaaaaaaatt ttggtacatt aataattagt  10380

tttgtagtta ctttaatgag aactactgtg tatatttaga ttgaccaact tatttctgta  10440

agtaatccga gaaccattct agtgattaga gatgacaatt atggatctgg accgcgggcc  10500

tggcccgtaa aggactgtcg cgggacggta ttgggacgag gttttctagg cccgaaaatt  10560

tgcgggcttc gcgggacagg tctttacggg actgggcctt ttgcgggatg ggccgaaacg  10620

ggtcttgcgg gattacatgg acccgcattt ttt                              10653
```

<210> SEQ ID NO 6
<211> LENGTH: 23648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
cccattcgaa aataaacatc aaacccaaga aaccctagaa acagaaagac accgtcgcca     60

tcgccttcaa agaaatataa aaaattatat tttatattcc attaaaaatt attgaccaaa    120

aaataaacta ttaaaatttt aaaccgctgg tacgtacatt gctaagacat agattaatag    180

atgagcaatt ttccaagctt atctcgaagc cttggagaag taagttgaag agatgaactc    240

agctacggca aacaacaata ccactacatg caatccaaga gtcacctcag aggttcaaat    300

cctaaaatag cagagtacat ggtactccga agagaaaatt ctgccttgac cgtagctagg    360

ggaactagac gaaggttctg aacccgcaat caacccatgc aaactctaga tcgcccgctg    420

tgacatgaag cataactctc taaaatcatg tgggaactgg agagcatgcc atagatgctc    480

aagccacgaa tactgatcgt gcaaacttac atttggacaa cgatggcaca gacacggaca    540

catgtgcata gatgcatgaa actttttgaa tttttttttg aatttttttt ttgaaactat    600

tttttagctc taggagacta tatttgaaat atttagatga aatatttagg taattttaat    660

ccttgaagac tatatttgtg acaaaaggtt ttttagggtc agtctagaaa atttattttt    720

ctttttaacc tttgaaattg tatgtttttc agtgtataaa tggattaata actaaagaag    780

agtttcacga gtacattttt aacttaaaaa caccaataaa taagtgaaaa aagactggtt    840

tattcataat agggctaaac aaaaaggggg aagaaagttt aattgatttt cgatttgaca    900

gaagcataaa cgtagagatc tggatcagtc tcgtagaaga caatgtcacc ggtgtcactg    960

acgtaatgat ctttcttaat acttgctacc aaactctcca ccaagtggat cggtattgct   1020
```

```
cctgacgtct tcggttctct gtagtatctt cccaacgcat gtttagctgc ttttgtctgt   1080
cacattccat ttgttaaaat cagtacatta gtaattaatc accctttaat gaaatggttt   1140
agatgaaagt agcgagagag tgagatgact cacagcatcg accaagtgat agtgagggat   1200
ttgtgggaaa agatgatgga tcacgtgagt tccaatgtcg tgatgaatgt tgttgaaaat   1260
tccgtaatct ctatcaatag ttgttaatcc tccacgtaag taactccatt cctattatta   1320
atcacaaaac atcaagaatt aagattaatc aaatactaat aatttttttt tgtgaaacat   1380
cgtaatctct ataaaatatt atttgagaag tcggttttct atgtatcgct ctcacgttaa   1440
ctctcacgat agttgattac actaatacac ttaatgaatt aaaaatatta catttaaaat   1500
actattattt attttttat ttagtttcct ttttaaaatt ttccaaaaaa acatatacat   1560
ataataaaaa ggaatttttt tataaactta aaaaattata ttttacttgt ataatattaa   1620
tttcaaatac aatctcactt ttgttcactg cttattttta agagttatta aaaaactaaa   1680
attaaaatta aaaaataatc attgtttgat caaatagtta caaaataatc acagttttta   1740
aatgttatgt ttttatgttt gtagaactta atggaaccat aagcaaaata ccaaagcaaa   1800
tatgttttca tttttaagat tatttaaaat aaatttcagt ttccattcaa taaattaaat   1860
acataaagtt atttagaatt tataaaatat tttaattact gtaaaatatt aaccaaatgt   1920
tacaatttag ttcttttgta aaatttatat atatatatgc atgagacttc agaatattat   1980
cgttatatta atttatgtaa tttagaatca gacactttat tttatttttt atttcatttt   2040
aagcacaata tatatattaa gttatacata atctttataa aatatattta aagttctaag   2100
acaacaacca cctaaatgaa aataagaaat taatcaaaat tttaatatag ttaaaataaa   2160
aaatattaca gttgaattct gagatgcaat ccaatttacc caaatgataa ctaaatcgac   2220
tgtaaaaaca acaaaaccga ttagatataa catatataaa atcatattta taattaaagt   2280
aatataaatt ttattaatat aaatcatgca tacaaattat aaactaattt aaaattaaaa   2340
ataaataaca attaattatt atagtatatt tactttagaa atatttatat ccgtacatga   2400
gcacgggaaa atcacctagg agttaattta attaccttgc ctctgtacca aggcaacttc   2460
tcatcatgac catggtgatg caagtaagtg acagcgtcca accacatcac aaagatctga   2520
atttcaaaag tttatgacaa aaacaaatca tatagtatat atattgaata ataaatatat   2580
accctttatg atatactaag aaacttacga tgtaaggaac accgtatact ttgagaactg   2640
tgactggacc aacgaggaag gaaagacaga taagaatggc caacattatg gaccagcaag   2700
tagttgaagt tgcaataagc tttctctcgc ttggagcaaa taaaccactg tatgggttaa   2760
aatgtgaccc ttcttttcca ggacttctgt accactgcag taaaaccaaa gaaaaaataa   2820
tttatattgt tttaaaacac aatctaaaat gaattgtggt aagttttagg aattaaaaaa   2880
taccagatag atcgggtaag cgagcatggg cagagggaca gtgtatctga gcatccgagt   2940
actgtggggt aaaatcttgt ataacttttc tggtaactga aaggaacaat taaaatgaat   3000
tttagtaatc aagattaagt acttgcaaaa atagtactta gatatgtatt gatatatata   3060
ttcattgcat gctatgtgtt tataaacttt tgtttttatt attttttgtt agttttcaaa   3120
acacaggcaa actattacga aaacaccaaa ttagagaaag aaaataataa tagtataaaa   3180
gtaaatgcat ttagaggagt aagaaactca aatataaaag catttgcatt agtgagtttt   3240
tgacgagatt ttatcacaaa ttatattata ttaatttata attattattt ttgaaaattt   3300
gaaaaattta taccaaaata ttttatttga aagactttca catgagtttc gcataaacat   3360
gtctttcatt ttttttaaaa aaactcttta attaagtaat aataaacttc ttccgtttca   3420
```

atttaattgt cgttgtaaat taaaattttg ttttaaaata agtatcgttt tataatttca 3480
atgtaaaaat tatgaataat attttctagt ttatttttta ttggttaaaa tattgttagg 3540
tgtataatta gtgatgtttt tattttaaaa atggacaaaa tattttattt tttgtaatct 3600
atgtgtataa atctaaaact gtaactaaaa taaatcggag gaagtaatta gaagattcac 3660
cgatacaaat aggcgtggtc cgttgtcaca tactattatg tatattttat tttacaaaaa 3720
tgttacttct ataaatcgct aaaaagaatc aattaccggt taactgtgac actagcaaac 3780
tgtttttact acagctagaa atcaaatctg acaagtggtc gttctggcct caaatttcga 3840
aaaacaaatt attttgacaa agaaaaatag aaattattaa agagggaaat gttaccggaa 3900
cccaagactc gtcgttttca acatggccat ggttctggtg gtgtgtccga tggcttattc 3960
tcctgcagcc tcaaattatt aaatatgtgt ttacataaaa attaaattgt ccatggaggt 4020
gattggttgg gttttatcta cctactttag ctttattttt ttctaaatca ttaaacttta 4080
ccaatcatgc tttacgttta cttttcaaaa ttaaagtcta catcaaattt ctattaattt 4140
ttaccaatca tgctttaact ttaaaaataa agctacagca aaaaaaaaac caaacatttt 4200
tcttatgtat tttagttaaa caacttacat ctttcattta taagctgtag aaactgtaag 4260
aacaaaaaat atctataata ttaaataaat aagataatca taataaaaaa acatctataa 4320
atattttact ctaattttgg gtgcttttaa attattgaaa tattttaaat aatatagatt 4380
atttacatat cacattttaa ataacagtaa actttgataa ttttaaaaaa tattaatata 4440
aattatttta agtgataaaa ataataatta ttttatatat acatgcatca catattttac 4500
atattttatt ttaaaatatc tgcagcctat agcttacagc tacaacaaat ttaactacag 4560
caaaagtctc tgcaaaaata atcaacagta acaactttac aactacaacc aatttatcta 4620
cagctaaaat tctacggcca cagtcgaacc aatcatcacc tatatagtgt tgctttcatg 4680
gcagattcta acaatctcac tctatttttt ttctcttttt ttttgatcaa acaatctcac 4740
tcttttaagt tttaagttac tagtaataaa ttgaccaaaa atagtttcca gtaataaatt 4800
atttttattg ccaggaataa gttacaataa tgtcgcagca aaataatgca tgtaagtcta 4860
ttttcaaaga tatttgaaga tgatgttaca tttaccaaac aaaaaattat gatgttacta 4920
caggaaacca tttttattgg aggtttgaag tcagtttctc aatattaaaa atagagaaat 4980
agaaaagaat aaaagataaa aggagtaatt tcccaataaa caaagtcatg aataattctt 5040
caaatatcta acctttaata attggtttaa tattatttat aaaatgaata tttaattata 5100
aataaattag ctgttgttca aaaaaaatta taaataaatt atattcaaaa tactaatgac 5160
cagatatagg cccattgcat ttaataaaag ttttgattcc tttttccttc gttgctaaag 5220
attcgatgct tttcgtcaag aataagaaaa gctacctcac atatatagtc atactttcac 5280
atgcattatt taattataaa attggctcta gccaaaaaaa aaaagaacga gcaatgaata 5340
gattcttgca ccaagtaatt catttaacat ttaaaccaaa aaaagtataa caaatgaaag 5400
tttaataatt aataataata ataaaaaggg ttaataagtt gacttaccaa ccatggtaag 5460
gaacgaggat gaaggaatga agaatatggc caaccacgct attcagcaga ggaatgtctg 5520
agaaactccc atgtccactg ccattattca attatatttc acatcattat tcatcgtaaa 5580
tatagtatat catttattgc actatttatt taaactttcc atgtttgttt taaaagcttc 5640
aacaaggtaa tgacgtgaca catttctaaa tctcgaaata gattggaata caccaaaata 5700
acaaagaaac aatattatct ttcttgtttt agaaaaacaa tagatattct tgattttata 5760
ctttaattat aagttgagag atccataaaa tgcggaagca gtcgtaatta tagaaaataa 5820
agatgtggtt ttgtaacgag tcgtacgacc gatgaaaggt ggtggaacaa tgatttaaaa 5880
agaaaatcta aaaaaaaaaa tcttagatct tcaaaaaatg aacatcaaaa gaatcaattc 5940
ataaagtact gacaatactc atagaacgtg cattcaataa atcgatgcaa tgcaaaatgg 6000
aagaaacttt accagtcgtg gccgaggacg aagatggccc agaaaagggt tccttgggcg 6060
acccaataga gaggccagag gaaccagcta tcaaaataca cggcggcaat ggccaaagca 6120
gcgacggcac aaatgtctct ggctacgtag ctcatagatc tcaaaggact tttcacccaa 6180
caatgcttag gaatcgcagc ccttatgtcc ccgatcttaa acggcggttg tgcgctcgga 6240
tcaaaccctt cttccttccg ggcaccggca tcttcgttca cattggtgcg ttggtccata 6300
gcaacaacca tcctgggaga gagagagaga gatttggagg aagattctct ctctataatt 6360
caaaaaaaag aaagtgtggg aactggaatg tggtgaagaa agggttcgat gtattttgcg 6420
gtctgtgaag tttgtttata taaaggggaa ggaagatgtg tagtctgtag acattgagat 6480
gctcaaactg ttttattaa ataattatat atttaaagaa taaaaagggt aatttgctgt 6540
aattttaaat gcaatgggtt tgttattttg ttacatcgtt ctattcggtg aaattaaatg 6600
ggaaattgaa ggctataacc acaaaaaaaa cgtaattcac cgtctagcca tttaacctaa 6660
cgatcttata cacgctgtta caaatataaa ataatactgt aatattccta aaacacaacc 6720
ggctcaacct gctacaaaaa aataattaaa tattttaatt attcaccgtt gaaaagtaac 6780
tcgtgtctta cccttgttca catcttcccc ttttaacttc tctggtaatt ttgctgcagt 6840
cgaacggtct ccggcaccgc tttcttccat cgcctccact ctgcatgcaa tcgacatctt 6900
ttccatctct tccgtcctct gttttcaatc ttcttcggcg ttacagttct tggttaaggt 6960
ttcagcgacg gtagtaagaa accctttcta cccaacttca ccacttcgat tcttgtcaaa 7020
tctctgaacc ttccgtaagt tctcattcta tttcgtagat tctcttcact gtgtcgtcct 7080
ctgtgcttat tttctttcaa attggggctc gtctcataat cagagtgtta taatttctag 7140
gtctatatca ccggcagatg tgaatatcga tcgtccccga tacggaatta gtctctccca 7200
ctttccaatt tgatttaggt tttggtgttt cccgggttgt gtgaggttcc ttgaatttga 7260
attttcttcg tagaggatat gcaacgtatt tagtttagta ctttatgtat ttcgtgtgga 7320
atatcattgc ttacaaaggg tttgtcgata atacatagta tgttattttg attctccatt 7380
ccatttggaa tgtaatagta cacttaccca attaagctat tccattgtgt aacgcatcaa 7440
ttcattcctt tgtttgtaat gtacttatgg agttgctcat tctaatttat ggttcccctt 7500
tatgttcttc ttctttctta atcgtgaatt gatgtttctg tatcagtgct ttttaaaaat 7560
agtgtatgaa tatcgactac cgtgtggaat atcgtctctt gtacatagtc tagaaattat 7620
gctttcttgt atggaatatc atctttatgt catagttgtc ttgtgtttta tttgcaacat 7680
tacatttggt ttatctacat catgtcacgt tgaataaaca ctacaagaaa acacatgctt 7740
aacgacgaaa attaacgagg aaaaacaatc ctcgtaaatt tgcgtcgaat ttacgacgaa 7800
tttacgtgaa aaactaaagt catccttatt tcctcgtaac gtaacgacaa aactgtttcg 7860
tcgtaaagtg gatgtaattt tacgagtatt ttacgaggaa aaactatttc ctcgtaaata 7920
cgacgtaaat tttgcgtggt atttacgagg gaatagttta cgtgtattta gcgaggaaat 7980
ttttgaatcc accaacttca taggtgttac acgttttttt tgcccaccta attaattttc 8040
gtcgtaaatt catagcaaaa ttacaactac cagattcgaa ttttcctata aatatggatg 8100
tttgaacatc attttaaaca caccaacaac aaaaaacgtg aaagaaaaaa aatggctggc 8160

```
tccgggacta tttacgagtt gcggaagtgg atgtatatgc atagagatgc taacgggaga   8220
gtgacgaaag aataccttgc gggtctggag acatttatgc atcaagcaga ttcaacaccg   8280
ctcgcccaag aaagtggtaa gatgttctgt ccttgtcgga aatgcaacaa ttcgaaactg   8340
gcaaaccgtg aaaatgtttg gaagcattta ataaatagag gtttcacggc aaattactat   8400
atctggtttc aacatggaga aggttttaat tatgatcaga atgaagctag tagtagtaat   8460
agcaattctc aggaaaaaga accggttgat catcatttgc ataatgaaca tagttaccat   8520
caggaggaga tggtagatta tgatagggtt catgatatgg tagttgatgc attcgtagct   8580
catgatgaag atgaagaacc taatataggt gcaaaaaagt tttacgaaat gttaaacgcg   8640
gcgaatcaac cactttacag tggttgtaga gaaggtctct ctaaattgtc gttagctgct   8700
agaatgatga atattaaaac tgatcacaat ctacctgaaa gttgcatgaa cgaatgggcg   8760
gacttgttta aagagtattt gccggaagac aatgtgtctg ctgattctta ttatgagatt   8820
cagaaactgg tttatagttt tgggttgcct tcggagatga tagatgtttg catcgacaac   8880
tgcatgatct attggggaga tgatgagaag ctagaagaat gtcgattctg caagaagcca   8940
cgattcaagc cgcaaggacg gggacgtaat agggtaccgt accaaaggat gtggtaccta   9000
ccaattacag acagattgaa aagattgtat caatcagagc agactgctgg aaagatgaga   9060
tggcatgccg aacatactca gacggatggt gagatggctc atccatcaga tgcaagagcc   9120
tggaaacatt tcaacaaagt acatccagat ttcgctagca atatccggaa tgtgtatctc   9180
ggattatgca cagatggatt tagtccgttc ggaatgtcag ggagacaata ttcattgtgg   9240
ccagtctttc ttactccata caacctgcca ccggagatgt gcatgcaacg ggagttacta   9300
ttcttgacca tattaatacc tggtccgaac catccaaaaa ggtccctgga tgtttcccta   9360
caaccactga taaaagagtt gaaggatttg tggtcaacag ggtgaggac gtatgactgt    9420
tcaacgaaga cgaattttac gatgcgagcg atgcttttgt ggaccataag tgatttccct   9480
gcctatggga tgttgtctgg atggactaca catgggagat tagcttgtcc atattgtaat   9540
ggaacgacag atgcgtttca actgaagaat ggtaggaaga caagttggtt tgactgtcac   9600
cgtcgatttc ttcccattgg ccatccttac cgaagaaaca agaatttgtt taggcacaaa   9660
agggttgtga gagacactcc tcctccatat ctaactggag aacaaattga agcgcaaatc   9720
gactactacg gagctaacga aacagttcgt tggggtggta attggcatgt ccctcgtaat   9780
atgccagatt cttacggtgt tcatcacaac tggcacaaga agagtatatt ttgggagttg   9840
ccatattgaa aggatcttct tctgcgccac aacctcgatg tgatacatat agagaagaat   9900
ttctttgaga acatcatgaa tacaatattg aatgtcccag ggaagacaaa agacaacata   9960
aaatcgaggt tggacttgcc agatatttgc tcaagaagcg agttacatat taaaagcaat  10020
ggacaagttc ccgttccgat attcagatta tcttcagaaa aaaagtcggt gttgttcaac  10080
tgggtggcat cagaagtgaa gttccccgat gggtatgttt cgaatctctc tagatgtgtt  10140
gaaaagggtc aaaagttctc cgggatgaag agtcatgatt gtcatgtatt tatgcaacga  10200
ctactgccct ttgcatttgc ggagctattt ccaacaaacg tacatgaagc acttgcaggt  10260
acgtagtgta ttatatcaca ataatttaca aaataatata tgactaacaa tgtgtttatt  10320
ttttttgaat ataaaaggca ttggagcatt tttcagggat ctgagcacac gcactcttaa  10380
agaagaagtt gaggaacagc ttcaggagaa cattcccatc ttattgtgca acttggagaa  10440
gatatttcct cccggatttt ttgacgtcat ggagcatcta gctgtccacc tcccatatga  10500
```

-continued

```
ggcattgctt cgtggacctg tacattacgg atggatgtat cagtatgagc gagccatgaa  10560
atatttgaag ggaaaagcaa agaacctcgc caaagttgaa ggttctataa ttgctggaag  10620
tttgacggaa gaagtttctc acttcacatc gtactacttt gcgtcaaaag tacgtacacg  10680
gagaagagct ccaagaagat atgatgatgg tggtgttgcg ccaacatatg cagttgctgg  10740
tgttccagac atctttagcc agattgggcg actcggtggg aagtctaaag aggtttggtg  10800
gtcgagtgaa caagacgctc atagtgcaca cacctatatt ctactcaatt gcgaagatcc  10860
attgatgcgt tattttgaaa ggtaacatat attgacactt cgaaacacat ataagtataa  10920
ttaattgtat aattgcgaga gattcattcc tataaaatgt gattttacag cctatttgtt  10980
tctcaagtcg aagaaacatt tcctggtata tccacaagtg acgtagacaa aaggaaagat  11040
caacatttca ttaagtggtt gcggaatcag gtattaacta aaactttttt ttcatacatt  11100
atctgtattt cattaacatt ctctttattt ttgcaggttg attatgacga cgacgatgca  11160
gattattcta agtggttaca cgaagtaatt caatctccac ttgtaaaggt caccacatca  11220
cagatgtatt tcacacgagg ctatactttt catacatatg actatggtag acagcgggcg  11280
accagtaact atggagtatg tgtgaaaggg aaaacagatt tctacgggat cttgacggag  11340
attattgaag tcgaatttcc agggatactg aagctgaaat gcgtcctctt caaatgtgaa  11400
tggttcgacc ccgttgtcaa cagaggtgtt cggtctaaca aattcggtgt agttgatgtc  11460
aacggtggac gaaggtacaa caaattcgag cctttcatct tagcttcaca agcagaccaa  11520
gttagcttcc ttccataccc tcggatgaga gattcaggta ttaattggtt agcagtaatc  11580
aaagttacac ctcgaggacg aatcatcagt ggagaagaac caccattgca agaagaacag  11640
ataaatgaag ttgaggaacc tgaacaagaa attgatgaca tccttctcat tgatccgcat  11700
aatcacgagt acgaagatct taccgatgat gccacagacg aagctgttga agacgagttt  11760
aatgaaaatg atgatgtttc tagtgatgac gagaatgtcg atgtatccga ttgatgtatt  11820
tgttttatga ataagatgag agagtttgtt ttatgaataa gataatgtgg ggtttgtttt  11880
atgaataagg taatgtggga gtttgtttta tgaataagca aatgtgggaa ttgtggtttg  11940
gaatggaaat aaagatgggg tttggaatat atgaagtaga aaataaggaa tataaggttt  12000
ggggtttcgg gttttggatt ctagggattt aaacataaca gtcgttaatt ccacgtaagc  12060
ttaaatcgtc gtaaagtcct cgtattccaa ctagtaaata acgacgaagg actcgttaat  12120
tccacgtaag actaaatcgt cgtaaatacc acgtaggatg aattcgtcgt aaaaaccacg  12180
taggatgaat cgtcgtaaat ataacgtaac ataacgagga aataacgacg aaacctaaaa  12240
ataaatatgg aatatgggat ttggggtttg gggtttcagg tttcgggttt cgggtttggg  12300
gtttggggtt tcgggttttg gatttcgggt ttcgggtttc gggtttttgg tttcgggttt  12360
ggggtttcgg ggtttggggt ttcgggtttt ggatttcgag tttcgggttt cgggtttcgg  12420
gtttcgggtt tggggttcta gggatttaac cataacactc gttaaaaata acgacgaaac  12480
ttaaaattaa atatggggtt tggaatatat gaagtagaaa attaaagatg ggggtttggg  12540
tttcgggttt cgggtttcgg gtttgggggt tggggtttgg ggtttcgggt ttgggtttcg  12600
ggtttcggat tctagggatt taaacataac actcgttaat tccacgtaag cacaaatcgt  12660
cgtaactacc tcgtaggatg aaatcgtcgt aactaccacg taaaatgatt taaacaaaac  12720
actcgttaat tccacgtaag cacaaatcgt cgtaaagtcc tcgtaggatg aaatcgtcgt  12780
aactaccacg taaaatgatt taaacaaaac actcgttaat tccacgtaag cacaaatcgt  12840
cgtaaagacc acgtaaacgg atttatacat aaacccgtta attccacgta agtacaaatc  12900
```

```
gtcgtaaata tctcgtagtg tacaaacttg gaaaaaaaag gaaaaggaga aaaataccag  12960
attaacatgt ggcaagactt ccaacaatta taatacgtaa gtctcgccca catgaattct  13020
aatatcttct ccttttccta ttttttcaa atatttataa tttgaatagg atttttttga  13080
ggattgtgat ttgagataag gtgtgatttg ggagtttgtg tgtggtttga gagtgagagt  13140
tgtgggtata tttataggaa agcaagcctc gttaattcct cgtaaagtaa atcgtcgtta  13200
atacctcgta taaaaaaaca cgggcctttg tgattactcg caatttcctc gtaaaaaaaa  13260
agacgggcct ttgtaactgc tcgctatttc gtcgtaaact tacgaggaat ttgcggcgat  13320
atgtaatctt atatatacac ccgagcgctc attctttctt tcctctctac ttcctctcta  13380
cttcctctcc atttcgtagc aatagtaagc ctctctgatt cctctctaat ttggttagtt  13440
taggatagat taggtggtta gtatagggaa tttagatagg tttgcggatt ttatgttatt  13500
tagtgttgat taggtggata atgttgggaa atatattgtt gatgttaatt ttaaaaattt  13560
catttttttc ccaggttcga aaaggaagac ttactgccca ttacagagag atcttcggtg  13620
agccgggtag tcgtttagac caggcctctt cttccgctcc cagttcttcg ggccaggaga  13680
ctgtccccga gactcagtac actcagagag tctctgggtc tacttcttct agtgcaccat  13740
cggctcctca tgtgcctcct ccgatgcctc ctcctgtgcc tcctccgatg gcacctccga  13800
tggtcgccga tattcatcct gatctgatgg tgcctccgag tgctccttac tcgcagtaca  13860
ctgtagagga cattctccgt ctgccaggca gagaaggttt accagtcatc gacccagacc  13920
gaccggacgg aacgttgtgg tatgttgcat taattttttt taattcgttt aaatttcttt  13980
tataacatta aaaataattt atattttaaa tttgtatttt ccaggtgggg ggttgacgga  14040
tgtcttgcat cggacgtaac cgacacaatc aagggttact tctccatggc acatccaaac  14100
tggagtaaga cgcctcacta cgtcagaaag acgtggttca aaatttacgc tgtaagtttc  14160
tattaattaa ttatatatat tttaattttt tcatgattta tatatatact ttctaaaaaa  14220
ctaattgtta atttattttt tccaacagca aaaatataat tgggccttgg gaatcactga  14280
gagggtgagg aagaagttta acgcgaaagc gaaagttcgc ttgttggaca cggtctccaa  14340
ctggaagggt gactggatcg tgaaggggta tgagtgtggc aaacccgctg agctcaccac  14400
ggatgtgtgg gatggcctca tccgttattg gcgccttcct gattccatta gaatcgccca  14460
ggcttactct aactcccgta acacggtcga tgagcacggg aacgggccga tgcttcacac  14520
tacgggccaa aaaccccacg ccggtgtccg tttggaaatg gtaattaaat attttattaa  14580
ataatttttt taatatatat attaatttat tctaactttc ttaaatgttt tttaggccaa  14640
agagacggga catctcccgt ctcttatgga actttacgag aggacctaca agaacaagac  14700
gggcgtattt gtagatggca agtccgagca aatctacaac gatgtagttg ctcgggttga  14760
agaccgccag actcagctga cccagcaatc taccgacgga ttacccgtca ccttatccac  14820
acttgaagtg gataagattt acgaggaggt aaattttcaa aaaaattaat tttttattat  14880
tcatttaatt taactttaaa tttttactta caatatttat ttttgttttt aaggttgtcc  14940
ccaaaaaaag ggacggacgt tgggtattgg ttccgtcaac gttgttccga gagcgacatc  15000
gtcttatggt cagcgacggg atgatgaagt cactgagctg cgtagagagt ccgctcagct  15060
gcgtaacgag ttgaccgcga caaaatctcg tatgggtgga gtcgagggct tcttggacgt  15120
tattgcggcc acaaatccgg aatgggagtc catgttgagg aacatgcgac aacaacatcc  15180
cattcaaggc gagtcatctg acgtacataa cgaggcggat gttatgagga ggagtgatga  15240
```

```
attctaccgg gcgatgaacg accctaagtt ttttttttgg ttgttgtatt atataaattc   15300

aaaacttatt tatatataaa atattttcat attgatttat ttttattttg aattttaatt   15360

tattattaaa ttaaataatt ttaattattt tttaattata tttttaaatt ctgtaaaata   15420

ataaaaacga agtaaattcg tagccaatgt acgacctctt tacgtggaaa cctcacgagg   15480

aaatgacgag aaacatttaa cgagtatttt acgaagaatc atttacgagt aaataagagg   15540

aaaagtttac gaccatttta cgaggaaatc atttcgtggt tgttacgtgt attttgcgag   15600

gaaactcttt caaggtattt gtgtgtaggt tacgaggaac tattttcgag gtatttacga   15660

ggtattatgg cgacgtcctt acgtggaata ttgacgtggt ctttacgacg aatcgtccta   15720

cttcgtcttt acgacgaaat atattcctcg ctaagttacg acgaattagc gaggaaatat   15780

gtgttacgac agacgtgtaa cgagcaaacg cgtttcctcg ctaattcgtc gtaaagcctc   15840

tcttacgacg aattagcgag gaaaaccgcc ctcgttaaga ttatgttttc ttttagtgaa   15900

aatgaaaata taaggttgtt gtattctact ttacatggaa ttgtagcttt atatctcatg   15960

aacatatcat tcctcttcgt tcttgttctg tcttaagtga taattcattg atatatttaa   16020

tattttagct tccaccttcc tcactatttc caactcttac tttgaatctt caggtttggt   16080

atgaacgagt taggccttcc aagcagattg cttgagaccg gctgtgaacc cattggcaag   16140

aaaagggtta acaattattc aatctccggt ggattgaagt gataaagagt gcattagagg   16200

atgaagacct agcgatgttg aatgcgtcac agtttgggtg agtcttgcag atggggaccc   16260

ataccttctc ggttacgttt cttcacttta ttctatcccg ccagctggtc actgtgaagg   16320

aattctagct gtggtggctc tttgtgggga aacctattcg ctatgttaca actgttctgc   16380

agtataaatg gtaggtgggt ttaagttccc gaatagttgg attgccaatg gagtagggtt   16440

tatatttctc tattttgggt ttagtttttt ctttcacatg ttatcttatc attcccatta   16500

catttgtatt tcatattgct ccatccttgc tgaactatgg cgacaatagc cttgcaatta   16560

tgaataagac aaatatgtac gtaacactat accacatatc tagtaatgga ttgtgtttta   16620

tgttttcttg cggggttcag tgtttaattt caagtgttct cttatcttcc ccattacatt   16680

aatattgtat gtaaaatact cctatatgga atatgaaaaa tagaaaataa catagtttat   16740

attatatgaa atagaaaatt gtacgtgata ttgtccctac gtttcctatt gccaacgaat   16800

ttggggttgc tttaccaatg gattgaagtt tatatttctc taacttgggt ttagtgttta   16860

cttccaaatg atgtctactc attcctctta gctttgtatt gtatgttgcc cagttgtgga   16920

tgtaatatac ctagcatagc actttttaaa aggattgtgt ctataggaaa ttaaatgtct   16980

tcagtactca tctttgtatg aattttccgg tttgaaaacc catcgtttat gagggtcgat   17040

atcccacgcc ccaacaacaa gtaatactct atcttcagta ctcatatgcg ataagaagta   17100

aatgaagatt catttatata tcagtctcta ttccatgtaa aacttgtttt tagtacatat   17160

tctcactgca aattagctgg ttgttacttc caggcagtaa ctccttaact ttcttcacct   17220

ccttgctttg agtttcttca gatggactta cagtgataag tagatggaat acaacattta   17280

ttgctacaac tactaattta caccacttgt ttaactccat acagtaaaaa tatctttact   17340

aactccacct gtttacgtag cttcctccca ctctttaata tggagtagct gtaagccatt   17400

actggacatt tactccatta attacgtcac cgtctgtccc caaccgtaga agtcattgtc   17460

tttgtaagtg attatgttgg taaattacat tcccaagttt atattctatt tgttcatgtg   17520

gcatggaacg tacactcata taaatttgat ggtttgtatc ataccgttgc attcaaatgg   17580

ttttggttga ccagacctaa gcctgacgtc gacgttgtta tattagaaat accccacgct   17640
```

atatgtaccc acctcctcat ccaactccat gtatcgtact ttctaactcc cacgcaactg 17700
tagctatgat attgttttat accatatgga atagtttggc tgtacaataa atagtaactg 17760
ttgattttgc cgatctgaag ctagcaacat gagtatttgg cttcatttgg gtaaagtttt 17820
acgtactttc cttgcgtcat gcacatttca actgtaccaa aagtatttac caaaatattt 17880
acatgctttt tcaattggaa ctacatttat agggatacta ttacttttat actatgtagt 17940
atggatcttg tgtaactgct atagaataca cttgtttcat cgtcgacaat tcgccatttg 18000
tttatggtac acttgcgatt cttatctact cctacatctg catctccttc cataatgtgt 18060
tgaatacatc tcagttacgc gctccgtaag tttttgtgat tgtaaaccca ccacgtcgtt 18120
tactttgtaa tatagaaccg gtaacctgtt gctttaaggg gcataaccgg gtgggaggaa 18180
tcacaaaagc ctgacaatga attatgtcaa aatcaacgct gctttttaa tttattccca 18240
gaaaatggct atttcgccaa ttaaccctta attgaattag aaaaatatgt atgcgaaagt 18300
aaatatataa gacatatttt atggaccggg gatgtcctag gtcgaggact aatcataatg 18360
aactgtttag catgttttc aggcgacaga taaatccgct gttctacgtg gaaattagat 18420
atccacgccc tttaacaacg taaatgagta aatctgaatg ataggtttca aaacgataat 18480
gcctaacact ttcccgccgt atcacacgac catatccata tggttgaaat atataaattc 18540
ttctatttat attttgtctc agattatatt acttctagag gcggatgaaa aaaatatgaa 18600
aatctgaacc tgagaattca aactattttg aatttgacat aagcatccaa atggttattg 18660
ttctatggta tttcagattt tagtttttac ccagatcaaa ataatggaaa tcgaaaaaaa 18720
aactcaaatt ttttaaaaac ctttcaaaat acaaaatgga tcaattttga ataattatcc 18780
aaaatactta aagatccaat aattattcaa aatacttaat gaactataat atttaattta 18840
taaaattagt aatttatcaa aatatcatat ttagatttat atattttta aatatgttta 18900
tatgtaaaat aaaaagaata gatttttgt gaattatata tataattaag ttttataaac 18960
ttagcttcca tagtgtttat taaataattt gacatatata tatatatata atatgaatca 19020
cataatgtta atgtttttaa atataatctg ataaataatt ataaatactt tgaagtgttg 19080
aaaaagtttg aaatgaattt cattttaaat aaaaaccata cataacaata ttttgttatg 19140
tttatataat ttttatacat catttattaa tttataattg taatgagaca atataattta 19200
tgattttta taaatgttaa tttactgaat attaatttgt tgaaaatatt aatttattga 19260
atactaattt attaaatatt aaaatatgat tttattgaat attaaaaata ttaatttatc 19320
gaatactaat ttataaagct tctggtagtc gtctgttaac tcatatattt ctctaactac 19380
tactgaataa gcttgtgact tattatacac gtctatacgt gtttatctat aaattgttta 19440
cgtcgaaaga atcatttcgt agatacccac gatgttaccc aagttcaaga attaagaaaa 19500
ttaactatct atcattacgc tacttaccaa aaataatatg aagagtaggc ccgcgggaat 19560
atgctgcctg ttataaattt gcaaatgaca ataaaaataa cttatatatt acactgaaat 19620
atctctaatg tgtagggtta taaagaaaaa tataattagt taagctattc gttaacattt 19680
ttgccccgtt aattaactat gtattttggg ttttgaacta atcataaaaa tcatttaaaa 19740
gacacaattg ttgattcaga cgaacaaacc aatacaagtg ttgagggaat gtagttggta 19800
tagaacacgt cgtaagaatg atgtattttc gtgtaccatg ggccggccct ggcataaagc 19860
ccataaaaca agtactttag gcaccaaata taataaaaaa ttcatgggca ccaaattttt 19920
ttaaagtcac cttagtctaa tgcattttac gttatcctct tgagcaacaa gacacgagtt 19980

-continued

```
tgacgcgtac tttcttttct tcctttttg ataataatgt catttttgat aatactaaca 20040
atttaatatg atttattcat ggatacatat agacacggtt agtttcttaa tctgccgaca 20100
aaaaaattac ttaatctaac aactattttc tttaattata catcttatat taaattgtgt 20160
gacactagat aaataaattt aattaaacaa aaaacttttt ttggcaaata acaaacctat 20220
gtattagtaa caactaacaa tcatttagat tcttgacgtc ttttgtgtat ttcttgcgtt 20280
gatctttgct ataatagctg aagaagttat aacaattaac tcaaatgatc aattcttcat 20340
attccaagtt tgttttaatt gatatccatc ggaatagctg gcatatgtca tgtaagtttt 20400
cattttttt ctacttgttg gtttctattg cttaaaaaaa taaaatttta ataaacaaaa 20460
aattattgtg agattttaac attcgatgct gacaaataat ttttgaaaaa aaaaaaactt 20520
cagaaaataa ggttttcatt ttttcttaaa gtaaataaat tttaatatga tttaatgcta 20580
ttttattaaa taacaaaaat aaagcaaaaa ttaatatatt gaaagggcat atttgttaag 20640
tacgctttag gcaccagtta agtccggagc gacactgcca catatacaac tcgctaaaac 20700
aaagatttat tgtactgcat gaaccttcca accacatata gactcatcac cacgacaaaa 20760
aaaaaaaaaa cctggactac actcaagttg cgcaagccag tcatggaccg tagagtagct 20820
tggttcagac cgtgtagagg atcatatgta aaggaagttc gaattcatag caccagagac 20880
catcgtttct agctaggtcc atacaaactg agtttttca ttgttttgga ggagattcgc 20940
gcggaaccga agttccgaaa cccgatattg tcaatttgtc ataagtgaat tggcttctat 21000
acttctcgta acaaaatcat taacatggat tagtggtcca ccaaaactga aagataacat 21060
gttaaagaag tggactacta catagtccca gactcccaat caacataagt tacataacca 21120
atagatgaca aatggtccat caattatcaa atttgcttgc ttttgttttg caggtgttat 21180
ttagtgtatc catcccgaaa cgcattttct aaactcgtag tcttgtgcag ttttctagtc 21240
caatcttcat attgttacca agaaaaatac ttgttatgtg aatatttttt ggattgcatg 21300
ccactagccg aaatttcatg gatcaatgga tctttggcgt acatatattt attagaacac 21360
tttcattaca gaggatcctc aggaaaatat ctcataataa aataaaaaca ataaaaagag 21420
aataagatag gatttttaaa tgattatttt tgaaaaaact catgaaaact ccatgaaata 21480
cttgtctttt ccatataggt tcaattttta ttttaaatta ttcttaatca attatttaaa 21540
tttcatttaa atactgatat tttgtttgag aatcaatgat gctctaagtg gcaataattg 21600
taaccagtac tagtttcttt attgaccaac tgatatgaaa cgagaatttt ctattttcta 21660
tttttgtttt agtatttatg tttctgttgc catgacaaag aaagagtgct aaaagatgag 21720
agatgttgct tgttaattgt tatatacgag tagagtataa ccatatcccg atttacatag 21780
ataggattag gaagcgatac gttatacata tcaggataga aatattagtt gaaaatgagc 21840
actacgcgag atgttaaaga aaaaaaggcg tacattaaag cccttaatat tcgacataag 21900
agcaccagca tcagcattag aggttcgtgg acagtggcgg agccagacga aagttttacc 21960
aggggcaatg taaaatttat cttcagttta tagggagcag tataagaaaa ttcaccatta 22020
taatcatata attctcaaat aaacaatgga aaaaaatatt ataatatgct acagtaatga 22080
tcctgtctcg ccacgctcct tccgtatgaa cccgagttgt cactgttcag cgggctccac 22140
gccacgtggc ggtctgctat tggtcaattt atttatttat tttttaaaaa aaaaacaaaa 22200
taaaaataat agtaataaaa taataaaaaa ttcaaattat gaaccccaac cgtgggttca 22260
ttaatgctgg tgctctaata tgtgtgcctt aaataaaaac gtggctaatc tatcaataca 22320
aagcacagtt aaaggtacaa ccattaagaa aaagaagagt taaagatcac gatcacttca 22380
```

```
tgaatacacg tctcttcaac atcacaaacc attcatatgt atggtttaat atctaacaga  22440
gtatatattt ttcaaagaga ctattatgga agagtccata ttaattttct aaggaggggt  22500
gcatccacag attgattttc tttcatattt taaatgggtt gtaaacaata attcatatcc  22560
ttatgattat ataggtttag tgccgtggag tttattcgaa cccggatctc tctgaagtct  22620
acataccatt agaccaatct catgtggtta atcaagccaa tttttgaaga taactagatg  22680
taaattaaac aattcaaaga gttgttcaga aaaaaagagt gatggctttg gacaagaaaa  22740
agaaagatgg gatgttgtac gtgcacgtgt aaacgacgaa acacgttggg ttctattcct  22800
aaagaagcat tggctctact ttctaacaaa tctctaatta tccaattaat tatttgatcc  22860
taaacaatga catctcgttt gaggttttct ccttttttcg attcatcaat atttccctag  22920
gaaaaagttt tgtttctgtc aacttgtaaa tgatcaccgt gaatatctta caacgacgca  22980
tattcccatt acagaagaac aggtttcagt ttggatcaac ctaataagtt tcagacttta  23040
ctaccttcac tacaagaaaa cacaaattta acgacggcca aaatcgtcgt tatttcctcg  23100
gaaaagaagg cttacgagga aatggcgatg aaaggcgttt cgtcgttata tgattgtcgt  23160
aagagaagat tcgtcgccat ttcctcgtta attagcgagg ttatattttc ctcgtaaaga  23220
agaattaagt tttcgtcgta aagaccacgt ggggtttcca cgtaacgcgg tcgttgtgct  23280
tcctcgtaag aaactcgtaa atgattcgtc gtaaaagacc cgcaaaaacc tctaaataaa  23340
ttcgtcgtaa taaaaacgta agaaacacgg aaacaattcg tcgtaataga atcgtaacta  23400
aatccacgta aaatcctcgt taattgttcc tcgatatttc gtcgttaatt ttcctcgtta  23460
atacatcggg aattagcgac gcaattactt tgttttctat ttactgaatt tataaataaa  23520
aattatattt atttaattta ttaataaaat tttaattgaa attaaatcga atagaaaata  23580
tttttttggc cgaattaaaa tgaaattata taatatataa ataagttttg aattttaaaa  23640
tacaataa                                                           23648
```

<210> SEQ ID NO 7
<211> LENGTH: 3247
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
catcagaccc tttcttcacc acatttcact cagagcccac acagttttag agagagagag     60
aaacatccct caaagctctc tctctttctc cggcgatggt tgtcgctatg gaccagcgta    120
gcaatgcgaa cggagacgaa aggtttgatc cgagcgcaca accaccgttc aagatcggag    180
atataagggc ggccattcct aagcattgtt gggtaaagag tcctttgaga tccatgagct    240
atgtcgccag agacattttc gccgtcgtgg ctcttgccgt cgccgccgtg tattttgata    300
gctggttctt ttggcctctt tattgggccg cccaaggaac cctgttctgg gctatcttcg    360
tactcggcca cgactggtaa tttaattttt ctttcaactt cttaattttg atatgtttat    420
atgttttttt cgttttttgc attgtctttg atttcttgac cgtacgttcg atatgagatt    480
ttcactgact tcaagatttg attctcttca ggtttacttt tttcaatttt aattattatg    540
ttcatccaat ttggcctatt ttaaaagcaa aaggggatct aagattttta attcttttgt    600
tttttttggg ttctttttca tcagtcgtaa cactcctaac taaacatctt tttctttcct    660
ataattattg ttgtttccgc gttttatgga tctacgtttg aaattttcaa taaaacacat    720
```

```
tttattgttt tctgtaacaa tttaattact gtttattggt tcttttaatt attgtgtgtt    780
gttccaatct attttcgaaa tatagtcatg tgacacgtca tattctattt ttgttacctt    840
gttgaaacgt ttgaattgag gaaagttcag ttaacattgt gcaataaatg ataaatgtgt    900
ttatgatgta aaatttcatt tgaataatac agtggacatg ggagcttctc agacattcct    960
cttctgaata ctgcggttgg tcatattctt cattccttca ttctcgttcc ataccatggt   1020
tggtaagtca tttattttaa cttctttttt catgcaaatt tattcttgtt ttcgtatttc   1080
ttacattttc cttgtcattc ttggtgcatg ttagcaaaca gtaatctgat aactgaaaat   1140
atattaattt ttcatagtaa aataatgcat gtgactaaaa gcatcaaaat ctttagcatc   1200
gaagaaaaaa gaaccaaact tttatttaat gctatgggcc tatttatggt ccaattagct   1260
attatcatat gacatgtcct tgaataaatt aatgtataag tttaatataa tatttatata   1320
tatttgtttt aatggcttat tttattgtta aatggataca tcagcttgaa atatctacga   1380
acatgcatca ttttcctaga tacatttgtt tgttgctcaa aaaatgaata acgtagttaa   1440
acgagtgaga ttcttagcat ctgcctcgaa aacgatatgt tattgacaat tccaatttca   1500
tttttatgaa aataaaataa tagtttattt tataattggg ggtggttgca ggagaataag   1560
ccatcggaca caccaccaga accatggcca tgttgaaaac gacgagtctt gggttccggt   1620
aatccccctc tcattatttt tttttctttt tttgaaactc tttcatttta attttcttag   1680
aattctatgt atttatttta atcaatcctt tttccagtgt gaggcttgga cgaccacttg   1740
tcagatttgt cgtttagctg tagtaaacaa ctgatttaaa ttgtttatgg tactgtagtt   1800
aactttaaca acgggccact tatattcgag ccattggcat aaaatgattc ttctcgaaat   1860
tcgtttactt ttcttagtat ttttcagttt tgtagtttac gtagaactaa taaaaagaaa   1920
aaaacttata aacacaccac atgcaatgaa taaattcgaa tatataacca tactgttaaa   1980
tattaattaa cattttaatc ttaattttgc attccagttg ccagaaaaat tatacaagaa   2040
tttgtcccac agtacacgga tgctcagata cactgtccct ctccccatgc tcgcttaccc   2100
tctctatctg gtaaatccta attcctcatt tttcttcctg attataatta caattttgaa   2160
tttttagatt ttgagtatta actaaatata aattaaattt gtttggggat gactacagtg   2220
gtacagaagt cctggtaaag aagggtcaca ttataaccca tacagtagtt tatttgcccc   2280
aagcgagaga aagcttattg caacttcaac tacttgctgg tcgatcatgt tggccactct   2340
tgtttatcta tcattcctcg ttggtccagt cacagttcta aaagtctatg gtgttcctta   2400
cattgtaagt ttcatatatt tcattattat atcattgcta atataatttg tttttgacat   2460
aaagttttgg aaaaatttca gatctttgta atgtggttgg acgctgtcac gtacttgcat   2520
catcatggtc acgatgataa gttgccttgg tacagaggca aggtaagtag atcaacatta   2580
atttataaga agcaacaatg attagtattt gattaatcta aattattgat gttttgtgta   2640
caataatagg aatggagtta tttacgtgga ggattaacaa ctattgatag agattacggg   2700
atcttcaaca acattcatca cgatattgga actcacgtga tccatcatct tttcccacaa   2760
atccctcact atcacttggt tgatgccgtg agtgatctcg ctctctctct agtttcattt   2820
gattaaaatt aaagggtgat taattactaa attagtgatc ttaattaatg atatgcgaca   2880
gacgaaatca gctaaacatg tgttgggaag atactacaga gaaccaaaga cgtcaggagc   2940
aataccgatc cacttggtgg aaagtttggt ggcaagtatt aagaaagatc attacgtcag   3000
tgacactggt gatattgtct tctacgagac agatccagat ctctacgttt atgcttctga   3060
```

caaatccaaa atcaactaac ctttcttcct agctctattt aggaataaaa cagtcctttg 3120
gtttttactt atttctggtt gtttttaagt taaatgtact cgtgaaactt tttttaatta 3180
aatgtattta cattacaaat caagtttttg ttcgttttct ttatgttttt agttacaata 3240
aataaag 3247

<210> SEQ ID NO 8
<211> LENGTH: 4014
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
catcgaaccc tttcttcacc acattccact tcccacactc tcttttttttt tgaattatag 60 agagagaatc ctcctccaaa tctctctctc tcccaggatg gttgttgcta tggaccaacg 120
caccaatgtg aacggagatg ccggtgcccg gaaggaagaa gggtttgatc cgagcgcaca 180
accgccgttt aagatcgggg acataagggc tgcgattcct aagcattgtt gggtgaaaag 240
tcctttgaga tctatgagct acgtagccag agacatttgt gccgtcgcgg ctttggccat 300
tgccgccgtg tattttgata gctggttcct ctgtcctctc tattgggtcg cccaaggaac 360
ccttttctgg gccatcttcg tcctcggcca cgactggtaa agtttcttcc attttgcatt 420
gcatcgattt attgaatgca cgttctacga gtattgtttg tcagttactt cgtaaaatga 480
ttcttttgat gttcattttt tgaagatcta agattttttt tttagatttt ctttttaaat 540
cattgttcca ccaccacctt tcatcggtcg tacgactcgt tacaacacca catctttatt 600
ttctataatt actactgctt ccgcatttta tggatctctc aacttataat taaagtataa 660
tatcaagaat atctattatt tttcttaaac aagaaagata atattgtttc tttgttattt 720
tggtgtattt ccaatctatt tcgagattta gaaatgtgac acgtcattac cttgttgaag 780
tgtttaaaac aaacatggaa agtttaaata aatagtgcaa taaatgatat atatgtatat 840
gatgaataat gatgtgaaat ataattgaat aatggcagtg gacatgggag tttctcagac 900
attcctctgc tgaatagtgt ggttggccat attcttcatt ccttcatcct cgttccttac 960
catggttggt aagtcagctt atcaaccctt tttactatat tattaattat taaacttgca 1020
tttgtatact tggtgcaagt tggtaaatgt aatctgataa ctgaaaatct attcattgct 1080
cgttctattt tttttttggc tagagacaat tttataatta aataatgcat gtgagaatat 1140
gactatttat gtgaggtagc ttttcttatt cctgtcgaaa agcatcaaat ctttagcaac 1200
gaaggaaaaa ggaatcaaat tttttattaa atgcaatggg tctatgtctt ggtcattagt 1260
tttttgcata taatttattt atattttttt cttaacagca gctaatttaa ttataattaa 1320
atattcattt tataaataat attagaccaa ttattaaagg ttagatattt taagaattat 1380
tcatgacttt gtttattgga actcctttta tcttttaatc ttttctattt ctccattttt 1440
aataatgaga aactgacttc aaatctccaa taaagatggt cttatgtagt aacagtataa 1500
ttttttgttt ggtaaatgta acatcatctt caaatatctt tgaaaataga cttacatgca 1560
ttattttgct gcgacattat tgtcacttat tcctggcaat aaattagttt attactgaac 1620 tttttttttgg tcaatttatt actagtaact ttaaacttaa aagagtgaga ttgtttgatc 1680 aaaaaaaaata aaaatagagt gagatagtta gaatctgcca tgaaagcaac actatataga 1740
caatttaatt tttatgaaaa cacatttaat aatttgaggc tgcaggagaa taagccatcg 1800
gacacaccac cagaaccatg gccatgttga aaacgacgag tcttgggttc cggtaacatt 1860
tccctcttta ataatttcta tttttctgtc aaaataatta gtttttcgaa atttgaggcc 1920
agaacgacca cttgtcaaat ttgattttta gctgtagtaa aaacagtttg ctagtgtcac 1980
agttaaccgg taattgattc tttttaacga tttatagaag taacattttt gtaaaataaa 2040
atatacatta tggtatgtga caacggacca cgcttatttg tattggtgaa tcttttaatt 2100
actccctcca atttatttta gttgcagatt tagatttatg cacatagatt aataaaaata 2160
ttttgcacat tttcaaaata aaaacaccat tacttataca actaaccata tttcaaccaa 2220
taaaaataaa ttagaaaata ttatttataa attttgtatt gaaattataa aataatactt 2280
attttaaaac gaaattaatt tacaacgaca attaaactga aacggaaaga aattattaat 2340
acttaattaa agagttttta gaaaaattga aagacatgtt tatgcgaaac tcatgtgaaa 2400
gtctttgaaa taatagattt tggtataaat atttcaaatt ttcttaaaat aataattata 2460
tattaatata atttgtgata aaatctcgtc aaaaactcac taatgcaaat gcttttattt 2520
tgaatttctt actcctctaa atgcatttac ttttatacta atattatttt ctttctctaa 2580
tttggcgttt cgtaatagtt tgtctgtatt ttgaaaacta acaaaaaata ataaaaacaa 2640
aagcttataa acacatagca tgcaatgaat atgtacgaat atatatacca atacatatct 2700
aagtactatt tttccaagta cttaatcttg attactaaaa ttcattttaa ttgttccttt 2760
cagttaccag aaaggttata caagaattta ccccacagta ctcggatgct cagatacact 2820
gtccctctgc ccatgctcgc ttacccgatc tatctggtat tttttaattc ctaaaattta 2880
ctacaagtca ttttagactg tgttttaaaa caatataatt atttttgttt ggttttactg 2940
cagtggtaca gaagtcctgg aaaagaaggg tcacatttta acccatacag tggtttattt 3000
gctccaagcg agagaaagct tattgcaact tcgactactt gctggtccat aatgttggca 3060
attcttatct gtctttcctt cctcgttggt ccagtcacag ttctcaaagt atacggtgtt 3120
ccttacattg taagtttctt agtatatcat aaagggtata tatttattat tcaatatata 3180
tactatatga tttgtttttg tcatatattt ttgaaatatt cagatctttg tgatgtggtt 3240
ggacgctgtc acttacttgc atcaccatgg tcatgatgag aagttgcctt ggtacagagg 3300
caaggtaatt aaattaacta ttacaagtat tttacaaaaa actaatgatt agtatatttg 3360
attaatctta attcttgatg ttttgtgatt aataatagga atggagttac ttacgtggag 3420
gattaacaac tattgataga gattacggaa ttttcaacaa cattcatcac gacattggaa 3480
ctcacgtgat ccatcatctt ttcccacaaa tccctcacta tcacttggtc gatgctgtga 3540
gtcatctcac tctctggcta ctttcatcaa aaccatttga ttaaagggtg attaattact 3600
aatgtagtga ttttaacaaa tggaatgtga cagacaaaag cagctaaaca tgtgttggga 3660
agatactaca gagaaccaaa gacgtcagga gcaataccga tccacttggt ggagagtttg 3720
gtagcaagta ttaagaaaga tcattacgtc agtgacactg gtgacattgt cttctacgag 3780
actgatccag atctctacgt ttatgcttct gtcaaatcga aaatcaatta aactttcttc 3840
cccctttttg tttagcacta ttatgaataa accagttttt tttacttata tattgttgtt 3900
tttaagttaa aaatgtactc gtgaaactct tcttaattta gatattattc catttacact 3960
gaaaaacata caatttcaaa ggttgaaaag aaagacaaaa ttttctagaa tgac 4014

<210> SEQ ID NO 9
<211> LENGTH: 4761
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
catcaaacct ttcttcacca catttcactg aaaggccaca catctagaga gagaaacttc 60
gtccaaatct ctctctccag caatggttgt tgctatggac cagcgcagca atgttaacgg 120
agattccggt gcccggaagg aagaagggtt tgatccaagc gaacaaccac cgtttaagat 180
cggagatatc agggcggcga ttcctaagca ttgttgggtg aagagtcctt tgagatctat 240
gagctacgtc gccagagaca ttttcgccgt cgcggctctg gccatggccg ccgtgtattt 300
tgatagctgg ttcctctggc cactctactg ggttgcccaa ggaacccttt tctgggccat 360
cttcgttctt ggccacgact ggtaaattaa attttctgtt ttaattattt tgactctttt 420
tgttcaattt attaatttct tgaatgcacg ttcgatgagt atcgtcgtca ctgacttcaa 480
gatttaattc ttttgaggtt accttttcat gttcaattat taaaaaataa aataaaatat 540
aggatctaag atttttttct tcatcagttc aagcatcatc actcatcagt cgtaagactc 600
gtaacaaaat atcttctttt ctataattaa tattatttcc gcatttaatg gatctacgtt 660
ttgatgttct caaattttgt ttctctttct ctagatcccc ggaactttta attataatta 720
tagtatagta taatatcaag aaaatatact gtttattttt tttggcaaca aatatattac 780
tcttgtttct ttgacaagaa aaaaatatat tgtttttttc ttctttttgt gttccaatct 840
attttcgaga tttagacaag tgacacgtca tataccggat ttgttacctt gttaaagagt 900
ttgggttaaa acaaatgtag aaaagttaaa ataaattgtg caataaatga taaatacgtt 960
tttatgttaa acaatgatgt gaaaataaaa ttgaataatg gcagtggaca tgggagtttt 1020
tcagacattc ctctgctgaa cagtgtggtt ggtcacattc ttcattcatt catcctcgtt 1080
ccttaccatg gttggtaagt catttattaa ctatttccat gtaaactatt agtacttgtt 1140
ttcgtatttc ttacattttc gtttgtcatt cttcttgggt gcatgctagc aaactgtaat 1200
cagtattaac tgggaactac caactgtttt ttttttgcta gagtagcaat tttataatta 1260
aataagaatc ctattaaaca atgcatgtga caatatgagg ttgcttttct gttcaaaaca 1320
aatctttaga agccaatgaa aaagaatcca aaactttttt ttaaatgata tgcgcctatc 1380
tattggtcct gactcctgag ttttcttact ttcttaagta taattagatt ttgatttttt 1440
tttataggtt ttcactattg ttatttgttt acatcagctt cagatatctt cgaaaaagat 1500
ttacatgcat caatttcatg aggatttata gtttttcttt tacttatttc cgacacaatg 1560
tttagtagta aaaagcatta aatgtttttt tgctcaaaaa aaaaagaatg ggattgttag 1620
agcactctat tgttagttgt tcaataaata taccaactaa aaaaacaaaa taaatataaa 1680
atgagtgaga ttgttaaatc attatagaga caatttcatt ttcacaaaaa taaataaata 1740
cataactttt tataattggg gtttgcagga gaataagcca tcggacacac caccagaacc 1800
atggccatgt tgaaaacgac gagtcttggg ttccggtaat ctttcctact ctcgtagttt 1860
ctcttgtctt ttatttattt gtttgttttt cggaatttat tcttatgtct atgttcttag 1920
gattctatat gtttatttta ttagtttatg ttttcagtct gaggtcagac cgaccacttg 1980
tcagatctgt tttctagctg tagtaaaaaa caatttgcaa gtgtaatagt tcagcataat 2040
tgatcttgtt agagcatttc caaaacaaac tttataattt taaatataca gttttttgtt 2100
ctctaaaaaa gaatttaaaa attttaaagt ttgagggacg aaacttcaaa tttgaacttt 2160
cactactcaa cttcaaattt gaaatttcat cttttttatt tacattttga tcattataat 2220
taattataca ttacatttat gattcttaag tattttctca tttattgttt taattcttaa 2280
atttttttata catcataaat atttccaatt tgtttttata aattcaaatt ttacacaaaa 2340
aagtaataaa aattttaaat aagatttata atattttaaa actataatta ggcaaaaaaa 2400
atattacaaa aaaatgtaat aaaaacttta aaataagata tatcaagaca taattattag 2460
aaattttaaa tattataaca atattaataa tctggtaaat ttgctccaaa acctcaaaaa 2520
tttctaaatt attgtccaaa caaatttgtt taaccgaata tggagcatta caaaaataat 2580
tttatggaat agtgtggtat tttgcttgta gttaatattt aattatgtat ttctatttat 2640
aattttatat atttaatgta agattttttt aattaatatt actgtaatat ttttatatat 2700
gtactagtta tttataaaag ttttatagat ttgtattagt tataacaaaa ataaggatca 2760
ttgtgtaaaa tacaaataat tttgaaatta cgtttaaagt tttggttatg aaaaaaatac 2820
tttgaaactt taaatttaga gttttgcaaa ctttaaaatg ttagatagat agttttttttg 2880
gagatgcatt tagtggttat ggtagtaact cagaaaatga aaaatctata cttttatact 2940
ccctccgttt tttaatataa gtcgttttac agttatacac gtagattaag aaaaccatta 3000
atttcttata ttttctagac aaaaacatca ttaattattt acctaaccac aattcaacca 3060
atataaaaat agaagatata ttaccattgg tcatacaaca ttaattatta ataaatttta 3120
catagaaaac cgaaaacgac atataatttg gaacaaaaaa atttctctaa aacgacttat 3180
attaaaaaac ggagggagta gtacctaact ttaacgatgg accacttata ttcgagtcct 3240
tagcataaaa tgattctcct cgaaatccgt ttactttctt cattattttt tccttttcag 3300
ttttggcgtt ttcgtaatac ttttgtcttc aatcttgaaa gctattagta taaaaactta 3360
taaacacatc acatgcaatg aattaatacg aatacataac cagaatgaca aattttcaat 3420
gaatatttaa taccagtaag tactactccg taatagtaat agtaatagtc atattaattt 3480
ttttttgtca tcaaacaaac agtaatagta atattaatta taattatgta tttcagttgc 3540
cagaaaagtt gtacaagaac ttgccccata gtactcggat gctcagatac actgttcctc 3600
tgcccatgct cgcttacccg atctatctgg taaaaaaaaa tacaatttca atttttttct 3660
taaaattaca aatggtttta tattttgagt tttaagccaa tatataaatt aattttgatt 3720
ggattttaac tacagtggta cagaagtcct ggaaaagaag ggtcacattt taacccatac 3780
agtagtttat ttgctccaag cgagaggaag cttattgcaa cttcaacaac ttgctggtcc 3840
ataatgttgg ccactcttgt ttatctatcg ttcctcgttg gtccagtcac agttctcaaa 3900
gtctatggtg ttccttacat tgtaagtttc acatattatt acaagagatt tatatattat 3960
taataataaa tttgtttttt gacataaagt tttggaaaat tttcagatct ttgtaatgtg 4020
gttggacgct gtcacgtact tgcatcatca tggtcacgat gagaagttgc cttggtacag 4080
aggcaaggta aataaatcaa tttttaaaaa gaaatgtaca gaaagcaata atggttagta 4140
ttgattaatc ttaatttttg atgttttgca tacaataata ggaatggagt tatttacgtg 4200
gaggattaac aactattgat agagattacg gaatcttcaa caacatccat cacgacattg 4260
gaactcacgt gatccatcat cttttcccac aaatccctca ctatcacttg gtcgatgcgg 4320
tgagtgatct agctttctct ctctctagtt tcatttgatt aaatggtgat taattactaa 4380
tttaattaat gaattgtgga cagacgagag cagctaaaca tgtgttagga agatactaca 4440
gagagccgaa gacgtcagga gcaataccga ttcacttggt ggagagtttg gtcgcaagta 4500
ttaaaaaaga tcattacgtc agtgacactg gtgatattgt cttctacgag acagatccag 4560

```
atctctacgt ttatgcttcg gacaaatcta aaatcaatta acttttcttc ctagctctat   4620

taggaataaa cactccttct cttttactta tttgtttctg ctttaagttt aaaatgtact   4680

cgtgaaacct tttttattaa tgtatttacg ttacaaaaag tggaagtttt gttatctttt   4740

tctctagttg caatcaaaag g                                              4761
```

<210> SEQ ID NO 10
<211> LENGTH: 3827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
catcaaactc tctccaccac atttcactca gagcccacac agttttagag agagagaaac     60

atccctcaaa gctctctctt tctccggcga tggttgtcgc tatggaccag cgtagcaatg    120

tgaacggaga ttccaaggac gaaaggtttg atccgagcgc acaaccaccg tttaagatcg    180

gagatataag ggctgcgatt cctaagcatt gttgggtcaa gagtcctttg agatccatga    240

gctacgtcgc gagagacatt ttctccgtcg tggctctggc cgtcgccgcc gtgtattttg    300

atagctggtt cttctggcct ctttattggg ccgcccaagg aacccttttc tgggccatct    360

tcgtactcgg ccacgactgg taatttaatt ttcaatttat tttttcttca acttcttaat    420

tttgatatgt ttatatgttt tttcgttttt tgcatcgtct ttgatttctt gaacgcacgt    480

tcgatatgag attttcactg acttcaagat ttgattctct tcaggtttac ttttaaaaaa    540

aaaaattatt atgttcaccc aaattggcct attttaaaag caaaagggga tctaagattt    600

ttaattcttc tctttttcag tcgtaacact gctaactttt ttttttgatc aaatcgtaac    660

actcataagt cctaactaaa catctttttc tttcctataa ttattgttgg ttccgcattt    720

tatggatcta cgtttgaaag tttcaataaa acacatttta ttgtttgaaa gtaacaatat    780

aattactgta tattgattct tttaattatt gtgtgttgtt ccaatctact ttcgaaatat    840

agtcatgtga cacgtcatat tctatttttg ttaccttgtt ggaacgtttg aattgagtaa    900

agtttaatta acattgtgca ataaatgata aacatgttta tgatgtaaaa ttcaatttga    960

ataatacagt ggacatggga gcttctcaga cattcctctt ctgaatactg cggttggtca   1020

tattcttcat tccttcattc tcgttccata ccatggttgg taagtcattt atttaaacat   1080

ctttttcatg caaatttatt cttgttttcg tatttcttac attttccttg tcattcttgg   1140

tgcatgttag caaactgtaa tctgataact gaaaatatat taattttcca tagtaaaata   1200

atgcatgtga ctaaaagcat caaaatcttt agcatcgaag aaaaaagaac caaactttta   1260

tttaatgcta tgggcctatt tatggtccaa ttagctatta tcatatgaca tgtccttgaa   1320

taaattaatg tagcttcata tgtgagttta ataatattta tatatttttg ttttaatggc   1380

ttattttatt gttaaatgga tacatcagct tgaaatgtct acgaacatgc atcattttcc   1440

tagatacact tgtttgttgc tcaaaaatga ataacttagt taaacgagtg agcatgttct   1500

atggggtttc ttagagcatg attattgaga agttcctaga gtgaggttct taccggaata   1560

taagaatcta tctcttaact tttaactaaa aaaattaaga accggctttt aaaactcgta   1620

tttaagaacc gttttttagt ttttttagtt aaaaatcaag agacgagttc ttatattccg   1680

ctaagaactc caccctgaga acttctcaat aatcatgctc ttagtgctct aagaagggtc   1740

cttaacaaaa tattaataat aagatatagt gtgggcccaa aaaaaacaaa aaaccggtta   1800
```

-continued caaaagtcgc gaaagaagga tcgattttgg tcttttactt gtactgtttg tggatcccac 1860
tggtggtggt ccgcgattgg tttctttttt aatttaattt atttttttaa tcggagaaaa 1920
aaattaagaa accaaaaaac agttttaatc atggcctcat gttggggttg agttttatat 1980
tctgataaga atcccatctt aaaaaccccg ttaaacatgc tcttaccatc tgcttcgaaa 2040
atgatatgtt attgacaatt ccaatttcat ttttatgaaa ataaaataat agtttatttt 2100
ataactgagg gtggttgcag gagaataagc catcggacac accaccagaa ccatggccat 2160
gttgaaaacg acgagtcttg ggttccggta atctttccct ctctcatatt tttttctttt 2220
tttttgaaat tctttcattt taattttctt aggattctat gtatttattt taatcaatcc 2280
tttttccagt ttgaggctag gacgaccact tgtcagattt gtcgtttagc tgtagtaaac 2340
aactgattta aattgtttat agtactgtag ttaactttaa caacggacca cttatattcg 2400
agccattggc ataaaatgat tcttctcgaa attcgtttac ttttcttagt atttttcaat 2460
tttggagttt acgtagaact aataaaaaga aaaacttata aacacaccac atgcaatgaa 2520
taaattcgaa tatataacca tactgttaaa tattaattta cattttaatc ttaattttgc 2580
attccagttg ccagaaaaat tatacaagaa tttgtcccac agtacacgga tgctcagata 2640
cactgtccct ctccccatgc tcgcttaccc tctctatctg gtaaatccta attcctaatt 2700
tttcttcctg attataatta caattttgaa tttttagatt ttgagtatta actaaatata 2760
aattaaattt gtttggggat gactacagtg gtacagaagt cctggtaaag aagggtcaca 2820
ttataaccca tacagtagtt tatttgcccc aagcgagaga aagcttattg caacttcaac 2880
tacttgctgg tcgatcgtgt tggccactct tgtttatcta tcattcctcg ttggtccagt 2940
cacagttcta aaagtctatg gtgttcctta cattgtaagt ttcatatatt tctttattat 3000
atcattgcta atataatttg tttttgacat aaaagttttg gaaaaatttc agatctttgt 3060
aatgtggttg gacgctgtca cgtacttgca tcatcatggt cacgatgata agctgccttg 3120
gtacagaggc aaggtaagta gatcaacatt atttataaga agcaataatg attagtagtt 3180
gaataatctg aatttttgat gtttttgtac aataatagga atggagttat ttacgtggag 3240
gattaacaac tgttgataga gattacggga tcttcaacaa cattcatcac gatattggaa 3300
ctcacgtgat ccatcatctt ttcccacaaa tccctcacta tcacttggtc gatgccgtga 3360
gtgatctcgc tctctctcta gtttcatttg attatattaa agggtgatta attactaaat 3420
tagtgatctt aattaatgac atgcgacaga cgaaagcagc taaacatgtg ttgggaagat 3480
actacagaga accaaagacg tcaggagcaa taccgatcca cttagtggaa agtttggtgg 3540
caagtattaa gaaagatcat tacgtcagtg acactggtga tattgtcttc tacgagacag 3600
atccagatct ctacgtttat gcttctgaca aatccaaaat caattaatct ttcttcctag 3660
ctctatttag gaataaaaca ctcctttggt tttacttatt tctggttgtt tttaagttaa 3720
aaatgtactc gtgaaacttt tttttattaa atgtatttac attacaaatc gtaaaagttt 3780
ttgttcgttt tctctatgtt tttagttaca aacttacaat caaaaag 3827

<210> SEQ ID NO 11
<211> LENGTH: 4668
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11

-continued

```
catcaaacct ttattcacca catttcactg aaaggccaca catctagaga gagaaacttc     60
gtccaaatct ctctctccag cgatggttgt tgctatggac cagcgcagca atgttaacgg    120
agattccggt gcccggaagg aagaagggtt tgatccaagc gcacaaccac cgtttaagat    180
cggagatata agggcggcga ttcctaagca ttgctgggtg aagagtcctt tgagatctat    240
gagctacgtc gccagagaca ttttcgccgt cgcggctctg gccatggccg ccgtgtattt    300
tgatagctgg ttcctctggc cactctactg ggttgcccaa ggaacccttt tctgggccat    360
cttcgttctt ggccacgact ggtaaattaa attttcagtt ttaattattt tgtctctttt    420
tgttcaattt attaatttct tgaatgcacg ttcgatgagt atcgtcactg acttcaagat    480
ttaattcttt tgaggttact ttttcatgtt taattattaa aaaataaaag aaaatatagg    540
atctaagatt tttttcttca tcaatgttca agcatcgtca ctcatcagtc gtcagactcg    600
taacaaaata tcttcttttc tataattaat attatttccg cattttatgg atctacgttt    660
tgatgttctc aatttttgtt tctctttctc tagatccccg gaacttttaa ttataattat    720
agtatagtat aatatcaaga aaatatactg tttatttttt tggcaacaaa tatattgttt    780
tttgacaaga aaaatatatt gtttttttct tctttttgtg ttccaatcta ttttgtgatt    840
tagacaagtg acacgtcata taccggattt gttaccttgt taaagagttt gagttaaaac    900
aaatgtagaa aagttaaaat aaattgtgca ctaaatgata aatacgtttt tatgttaaat    960
aatgatgtga aaataaaatt gaataatggc agtggacatg ggagtttctc agacattcct   1020
ctgctgaaca gtgtggttgg tcacattctt cattcattca tcctcgttcc ttaccatggt   1080
tggtaagtca tttattaact atttccatgt aaattattag tacttgtttt cgtatttctt   1140
acattttcgt ttgttattct tgggtgcaat gctaggaaac tgtaatcagt attaactgga   1200
agctaccaac tttttttgt tgctagagta gcaattttat aattaaataa gaatcctatt   1260
aaacaatgca tgtgactata tgaggttgct ttttctgttc aaaagcatca aatctttagc   1320
agccaatgaa aaagaatcca aaccttttct taaatgatat gcgcctatct atggtcctga   1380
gttttcttag ttcattaagt ataattagat tttgattttt ttttaggttt tcacttattg   1440
ttatttgttt acatcagctt caaacatctt cgaaaaagac ttacatgcat caatttcctg   1500
aggatttata gtttttttta cttatttctg cacaatgttt attagtaaaa agcatcaaat   1560
gtttttttgc tcaaaaaaaa gaatgggatt gttagagcac tctattgtta gttgttcaat   1620
aaatatatca actaaaaaaa caaaataaat ataaaatgag tgagattgtt aaatcattat   1680
agagacaatt tcattttcac aaaaataaat aaatacataa cttttgtaat tggggtttgc   1740
aggagaataa gccatcggac acaccaccag aaccatggcc atgttgaaaa cgacgagtct   1800
tgggttccgg taatctttcc tactctcatt gtttctcttg tcttttattt atttgttctt   1860
ttttgggaat tcattcttat gtctaagttc ttatgattat tgaagttctt aaggtggggt   1920
tcttaacgga atatgagaac ctgtctctta acttttaact aaaaaagcta agaaccagct   1980
tttaaataag agttttatga acacgttctt aatttttttta gttaaaagtt aagaaacggg   2040
ttcttatatt ccgctaagaa cctcttccta aaaaccccaa taatcatact cctaggattc   2100
tatatgttta ttttattagt ttatgttttc agtctgaggt cagaccggcc acttgtcaga   2160
tctgttttct agctgtagta aaaaacaatt tgcaagtgta atagttcagc ggtaattaat   2220
gttctcggat ctatctcaaa aaaaaatttt ataacttcaa atataaagat ttttttgttt   2280
ttcaaaaatg aacttcgaaa cttcaaattt gaagtttttt ttttgcattt tgatcattat   2340
aattaattac acgttacatt tataattctt aagtattttt tcatttatcg ttttaattct   2400
```

```
taaatttttt atatattata aatatttcca atttgttttt ataaattcaa attttataca   2460
taaaagtaat aaaaatgtta aataagattt ataatattta agactataat tagtcaacaa   2520
aatattacaa aagaaatgta ataataaaaa atttaaaata agatacatga agacataact   2580
attagaaaat ttaaatatta taacaatact aataatctgg taaatttgct ctggaacctc   2640
taaaattatt gtctaaacaa attttgtgta accgaagatg gagcattacg aaaataattt   2700
tatgaaataa tatggtattt tgcttctagt ttaatattta attatatatt tctatttata   2760
attttatata tttaatgtaa atttttatta attaatatta ctgtaatatt tttatatatg   2820
tgctagttat ttataatttt ttttatggat ttatattaga ccatgattaa cccggagttc   2880
ttagagtgga gttttagtta aacgttaaga aacagtttct taacttccgg taagaacccc   2940
atcctaagaa tcccaggtta atcatgctct tagttataac aaataaggat cattgtgtaa   3000
aatacaaata attttgaagt tatgtttgaa gtttgttttc gaagaaaacc actttgaaac   3060
tttaaattta gagtaaactc tatttagaga gttttttta gaggttacgc agtaactcag   3120
aaaatgaaaa atctatactt ttatagtacc taactttatc gatggaccac ttatattcga   3180
gtccttagca taacatgatt ctcctcgaaa tccgtttact ttcttcgtta tttttttcctt   3240
ttcagttttg gcgttttcgt aatacttttg tctgcaatct tgaaagctat tagtataaaa   3300
cttataaaca catgaattaa tacgaataca taaccagaat gacaaatttt caatgaatat   3360
ttaatactag taagtactac tccgtaatag taattagtaa tagtaatagt aatagtcata   3420
ttaattataa ttatgtattt cagttgccag aaaagttgta caagaacttg ccccatagta   3480
ctcggatgct cagatacact gtccctctgc ccatgctcgc ttacccgatc tatctggtaa   3540
aaaaaataca atttctattt tttcttaaaa ttacaaatga ttttatattt tgagttttaa   3600
gccaatatat aaattaattt tgattggatt ttaactacag tggtacagaa gtcctggaaa   3660
agaagggtca cattttaacc catacagtag tttatttgct ccaagcgaga ggaagcttat   3720
tgcaacttca actacttgct ggtccataat gttggccact cttgtttatc tatcgttcct   3780
cgttgatcca gtcacagttc tcaaagtcta tggcgttcct tacattgtaa gtttcacata   3840
ttattacaag aaatttatat attattaata ataaatttgt tttttgacat aagggtttgg   3900
aaaattttca gatctttgtg atgtggttgg acgctgtcac gtacttgcat catcatggtc   3960
acgatgagaa gttgccttgg tacagaggca aggtaattaa atcaattttt aaaaagaaat   4020
gtacagaaag caataatggt tagtattgat taatcttaat ttttgatgtt ttgcatacaa   4080
taataggaat ggagttattt acgtggagga ttaacaacta ttgatagaga ttacggaatc   4140
ttcaacaaca tccatcacga cattggaact cacgtgatcc atcatctttt cccacaaatc   4200
cctcactatc acttggtcga tgccgtgagt gatctagctt tctctctctc tagtttcatt   4260
tgattaaatg gtgattaatt actaatttaa ttaatgaatt gtggacagac gagagcagct   4320
aaacatgtgt taggaagata ctacagagag ccgaagacgt caggagcaat accgattcac   4380
ttggtggaga gtttggtcgc aagtattaaa aaagatcatt acgtcagtga cactggtgat   4440
attgtcttct acgagacaga tccagatctc tacgtttatg cttctgacaa atctaaaatc   4500
aattaacttt tcttcctagc tctattagga ataaacactc cttctctttt acttatttgt   4560
ttctgcttta agtttaaaat gtactcgtga aacctttttt ttattaatgt atttacgtta   4620
caaaaagtgg aagttttgtt atcttttttct ctggttgcaa tcaaaagg               4668
```

<210> SEQ ID NO 12

<211> LENGTH: 5714
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
catcgaaccc tttcttcacc acattccagt tcccacactt tcttttttt gaattataga 60 gagagaatct tcctccaaat ctctctctct ctctcccagg atggttgttg ctatggacca 120
acgcaccaat gtgaacgaag atgccggtgc ccggaaggaa gaagggtttg atccgagcgc 180
acaaccgccg tttaagatcg gggacataag ggctgcgatt cctaagcatt gttgggtgaa 240
aagtcctttg agatctatga gctacgtagc cagagacatt tgtgccgtcg ctgctttggc 300
cattgccgcc gtgtattttg atagctggtt cctctggcct ctctattggg tcgcccaagg 360
aacccttttc tgggccatct tcgtcctcgg ccacgactgg taaagtttct tccattttgc 420
attgcatcga tttattgaat gcacgttcta tgagtattgt cagtacttta tgaattgatt 480
cttttgatgt tcatttttg aagatctaag atttttttt ttagattttc tttttaaatc 540
attgttccac cacctttcat cggtcgtacg actcgttaca aaaccacatc tttattttct 600
ataattacga ctgcttccgc attttatgga tctctcaact tataattaaa gtataaaatc 660
aagaatatct attgtttttc taaaacaaga aagataatat tgtttctttg ttattttggt 720
gtattccaat ctatttcgag atttagaaat gtgtcacgtc attaccttgt tgaagctttt 780
aaaacaaaca tggaaagttt aaataaatag tgcaataaat gatatactat atttacgatg 840
aataatgatg tgaaatataa ttgaataatg gcagtggaca tgtgagtttc tcagacattc 900
ctctgctgaa tagcgtggtt ggccatattc ttcattcctt catcctcgtt ccttaccatg 960
gttggtaagt caacttatta accctttta ttattattat taattattaa actttcattt 1020
gttatacttt ttttggttta aatgttaaat gaattacttg gtgcaagaat ctattcattg 1080
ctcgttcttt tttttttgg ctagagccaa ttttataatt aaataatgca tgtgaaagta 1140
tgactatata tgtgaggtag cttttcttat tcttgacgaa aagcatcgaa tctttagcaa 1200
cgaaggaaaa aggaatcaaa acttttatta aatgcaatgg gcctatatct ggtcattagt 1260
attttgaata taatttattt ataattttt ttgaacaaca gctaatttat ttataattaa 1320
atattcattt tataaataat attaaaccaa ttattaaagg ttagatattt gaagaattat 1380
tcatgacttt gtttattggg aaattactcc ttttatcttt tattcttttc tatttctcta 1440
tttttaatat tgagaaactg acttcaaacc tccaataaaa atggtttcct gtagtaacat 1500
cataattttt tgtttggtaa atgtaacatc atcttcaaat atctttgaaa atagacttac 1560
atgcattatt ttgctgcgac attattgtaa cttattcctg gcaataaaaa taatttatta 1620
ctggaaacta tttttggtca atttattact agtaacttaa aacttaaaag agtgagattg 1680
tttgatcaaa aaaaaagaga aaaaaaatag agtgagattg ttagaatctg ccatgaaagc 1740
aacactatat aggtgatgat tggttcgact gtggccgtag aattttagct gtagataaat 1800
tggttgtagt tgtaaagttg ttactgttga ttatttttgc agagactttt gctgtagtta 1860
aatttgttgt agctgtaagc tataggctgc agatatttta aaataaaata tgtaaaatat 1920
gtgatgcatg tatatataaa ataattatta tttttatcac ttaaaataat ttatattaat 1980
attttttaaa attatcaaag tttactgtta tttaaaatgt gatatgtaaa taatctatat 2040
tatttaaaat atttcaataa tttaaaagca cccaaaatta gagtaaaata tttatagatg 2100

-continued

```
tttttttatt atgattatct tatttattta atattataga tatttttgt tcttacagtt   2160
tctacagctt ataaatgaaa gatgtaagtt gtttaactaa aatacataag aaaaatgttt   2220
ggtttttttt ttgctgtagc tttattttta aagttaaagc atgattggta aaaattaata   2280
gaaatttgat gtagacttta attttgaaaa gtaaacgtaa agcatgattg gtaaagttta   2340
atgatttaga aaaaaataaa gctaaagtag gtagataaaa cccaaccaat cacctccatg   2400
gacaatttaa tttttatgta aacacatatt taataatttg aggctgcagg agaataagcc   2460
atcggacaca ccaccagaac catggccatg ttgaaaacga cgagtcttgg gttccggtaa   2520
catttccctc tttaataatt tctatttttc tttgtcaaaa taatttgttt ttcgaaattt   2580
gaggccagaa cgaccacttg tcagatttga tttctagctg tagtaaaaac agtttgctag   2640
tgtcacagtt aaccggtaat tgattctttt tagcgattta tagaagtaac atttttgtaa   2700
aataaaatat acataatagt atgtgacaac ggaccacgcc tatttgtatc ggtgaatctt   2760
ctaattactt cctccgattt attttagtta cagttttaga tttatacaca tagattacaa   2820
aaaataaaat attttgtcca tttttaaaat aaaaacatca ctaattatac acctaacaat   2880
attttaacca ataaaaaata aactagaaaa tattattcat aatttttaca ttgaaattat   2940
aaaacgatac ttattttaaa acaaaatttt aatttacaac gacaattaaa ttgaaacgga   3000
agaagtttat tattacttaa ttaaagagtt tttttaaaaa aaatgaaaga catgtttatg   3060
cgaaactcat gtgaaagtct ttcaaataaa atattttggt ataaattttt caaattttca   3120
aaaataataa ttataaatta atataatata atttgtgata aaatctcgtc aaaaactcac   3180
taatgcaaat gcttttatat ttgagtttct tactcctcta aatgcattta cttttatact   3240
attattattt tctttctcta atttggtgtt ttcgtaatag tttgcctgtg ttttgaaaac   3300
taacaaaaaa taataaaaac aaaagtttat aaacacatag catgcaatga atatatatat   3360
caatacatat ctaagtacta tttttgcaag tacttaatct tgattactaa aattcatttt   3420
aattgttcct ttcagttacc agaaaagtta tacaagattt taccccacag tactcggatg   3480
ctcagataca ctgtccctct gcccatgctc gcttacccga tctatctggt atttttaat    3540
tcctaaaact taccacaatt cattttagat tgtgttttaa aacaatataa attatttttt   3600
ctttggtttt actgcagtgg tacagaagtc ctggaaaaga agggtcacat tttaacccat   3660
acagtggttt atttgctcca agcgagagaa agcttattgc aacttcaact acttgctggt   3720
ccataatgtt ggccattctt atctgtcttt ccttcctcgt tggtccagtc acagttctca   3780
aagtatacgg tgttccttac atcgtaagtt tcttagtata tcataaaggg tatatattta   3840
ttattcaata tatatactat atgatttgtt tttgtcataa acttttgaaa ttcagatctt   3900
tgtgatgtgg ttggacgctg tcacttactt gcatcaccat ggtcatgatg agaagttgcc   3960
ttggtacaga ggcaaggtaa ttaaattaac tcctaggtga ttttcccgtg ctcatgtacg   4020
gatataaata tttctaaagt aaatatacta taataattaa ttgttattta tttttaattt   4080
taaattagtt tataatttgt atgcatgatt tatattaata aaatttatat tactttaatt   4140
ataaatatga ttttatatat gttatatcta atcggttttg ttgtttttac agtcgattta   4200
gttatcattt gggtaaattg gattgcatct cagaattcaa ctgtaatatt ttttatttta   4260
actatattaa aattttgatt aatttcttat tttcatttag gtggttgttg tcttagaact   4320
ttaaatatat tttataaaga ttatgtataa cttaatatat atattgtgct taaaatgaaa   4380
taaaaaataa aataaagtgt ctgattctaa attacataaa ttaatataac gataatattc   4440
tgaagtctca tgcatatata tatataaatt ttacaaaaga actaaattgt aacatttggt   4500
```

taatatttta cagtaattaa aatattttat aaattctaaa taactttatg tatttaattt 4560
attgaatgga aactgaaatt tattttaaat aatcttaaaa atgaaaacat atttgctttg 4620
gtattttgct tatggttcca ttaagttcta caaacataaa aacataacat ttaaaaactg 4680
tgattatttt gtaactattt gatcaaacaa tgattatttt ttaattttaa ttttagtttt 4740
ttaataactc ttaaaaataa gcagtgaaca aaagtgagat tgtatttgaa attaatatta 4800
tacaagtaaa atataatttt ttaagtttat aaaaaaattc ctttttatta tatgtatatg 4860
tttttttgga aaattttaaa aaggaaacta aataaaaaaa taaataatag tattttaaat 4920
gtaatatttt taattcatta agtgtattag tgtaatcaac tatcgtgaga gttaacgtga 4980
gagcgataca tagaaaaccg acttctcaaa taatatttta tagagattac gatgtttcac 5040
aaaaaaaaat tattagtatt tgattaatct taattcttga tgttttgtga ttaataatag 5100
gaatggagtt acttacgtgg aggattaaca actattgata gagattacgg aattttcaac 5160
aacattcatc acgacattgg aactcacgtg atccatcatc ttttcccaca aatccctcac 5220
tatcacttgg tcgatgctgt gagtcatctc actctctcgc tactttcatc taaaccattt 5280
cattaaaggg tgattaatta ctaatgtact gattttaaca aatggaatgt gacagacaaa 5340
agcagctaaa catgcgttgg gaagatacta cagagaaccg aagacgtcag gagcaatacc 5400
gatccacttg gtggagagtt tggtagcaag tattaagaaa gatcattacg tcagtgacac 5460
cggtgacatt gtcttctacg agactgatcc agatctctac gtttatgctt ctgtcaaatc 5520
gaaaatcaat taaactttct tccccctttt tgtttagccc tattatgaat aaaccagtct 5580
tttttcactt atttattggt gtttttaagt taaaaatgta ctcgtgaaac tcttctttta 5640
ttattaatcc atttatacac tgaaaaacat acaatttcaa aggttaaaaa gaaaaataaa 5700
ttttctagac tgac 5714

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gaataagcca tcggacacac 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
atgcgaacgg agacgaaagg 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tgttaacgga gattccggtg 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
gtagcaatgt gaacggagat 20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
cagtgtatct gagcatccg 19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
gtggccgagt acgaagatag 20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
cagtagagtg gccagagga 19

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
cgccggagaa agagagagag ctttgagg 28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
tggttgtcgc tatggaccag cgtagcaa 28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
tctccgttcg cattgctacg ctggtcca 28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
gaaaggtttg atccgagcgc acaaccac 28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
tctccgttcg cattgctacg ctggtcca 28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
tcggagatat aagggcggcc attcctaa 28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
tagcccagaa cagggttcct tgggcggc 28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
cttcgtactc ggccacgact ggtaattt 28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
ttgaagttgc aataagcttt ctctcgct 28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
acttgctggt cgatcatgtt ggccactc 28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
aagtagttga agttgcaata agctttct 28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
tggtcgatca tgttggccac tcttgttt 28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
aacgagaatg aaggaatgaa gaatatga 28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
ataccatggt tggtaagtca tttatttt 28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
ccaacgagga atgatagata aacaagag 28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
cagtcacagt tctaaaagtc tatggtgt 28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
tgtgactgga ccaacgagga atgataga 28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
tctaaaagtc tatggtgttc cttacatt 28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
cgccggagaa agagagagct ttgaggga 28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
tggttgtcgc tatggaccag cgtagcaa 28

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
cttaaacggt ggttgtgcgc tcggatca 28

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
tcggagatat aagggctgcg attcctaa 28

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
tctccgatct taaacggtgg ttgtgcgc 28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
ataagggctg cgattcctaa gcattgtt 28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
agatggccca gaaaagggtt ccttgggc 28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
cgtactcggc cacgactggt aatttaat 28

<210> SEQ ID NO 46

-continued

<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
ttgaagttgc aataagcttt ctctcgct 28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
acttgctggt cgatcgtgtt ggccactc 28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
aagtagttga agttgcaata agctttct 28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
tggtcgatcg tgttggccac tcttgttt 28

<210> SEQ ID NO 50
<211> LENGTH: 58
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
acactctttc cctacacgac gctcttccga tctacgtacc tttcttcacc acattyca 58

<210> SEQ ID NO 51
<211> LENGTH: 58
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
acactctttc cctacacgac gctcttccga tctcgtaccc tttcttcacc acattyca 58

<210> SEQ ID NO 52
<211> LENGTH: 58

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
acactctttc cctacacgac gctcttccga tctctgacga tggttgtcgc tatggacc 58

<210> SEQ ID NO 53
<211> LENGTH: 58
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
acactctttc cctacacgac gctcttccga tcttgactcg aaaggtttga tccragcg 58

<210> SEQ ID NO 54
<211> LENGTH: 58
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
acactctttc cctacacgac gctcttccga tctgactgcg aaaggtttga tccragcg 58

<210> SEQ ID NO 55
<211> LENGTH: 58
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
acactctttc cctacacgac gctcttccga tctactgacg aaaggtttga tccragcg 58

<210> SEQ ID NO 56
<211> LENGTH: 61
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
acactctttc cctacacgac gctcttccga tctgctagcc gtgtattttg atagctggtt 60
c 61

<210> SEQ ID NO 57
<211> LENGTH: 61
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
acactctttc cctacacgac gctcttccga tctctagccc gtgtattttg atagctggtt 60
c 61

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
acactctttc cctacacgac gctcttccga tcttagctgg agcttctcag acattcctct 60

<210> SEQ ID NO 59
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
acactctttc cctacacgac gctcttccga tcttcagtgt ttatttgccc caagcgagag 60

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
acactctttc cctacacgac gctcttccga tctcagtcgt ttatttgccc caagcgagag 60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
acactctttc cctacacgac gctcttccga tctagtcagt ttatttgccc caagcgagag 60

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
acactctttc cctacacgac gctcttccga tctgtcaggt ttatttgccc caagcgagag 60

<210> SEQ ID NO 63
<211> LENGTH: 61
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
acactctttc cctacacgac gctcttccga tctgtacgac ttcaactact tgctggtcsa 60
t 61

<210> SEQ ID NO 64
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
acactctttc cctacacgac gctcttccga tcttacgtac ttcaactact tgctggtcsa 60
t 61

<210> SEQ ID NO 65
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cggtctcggc attcctgctg aaccgctctt ccgatctacg tacgttcaca ttgstrcgyt 60
gg 62

<210> SEQ ID NO 66
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cggtctcggc attcctgctg aaccgctctt ccgatctcgt accgttcaca ttgstrcgyt 60
gg 62

<210> SEQ ID NO 67
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cggtctcggc attcctgctg aaccgctctt ccgatctctg acccgatctt aaacggyggt 60
tgt 63

<210> SEQ ID NO 68
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cggtctcggc attcctgctg aaccgctctt ccgatcttga cttagctcat ggatctcaaa 60
ggact 65

<210> SEQ ID NO 69
<211> LENGTH: 65

<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
cggtctcggc attcctgctg aaccgctctt ccgatctgac tgtagctcat ggatctcaaa 60
ggact 65

<210> SEQ ID NO 70
<211> LENGTH: 65
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
cggtctcggc attcctgctg aaccgctctt ccgatctact gatagctcat ggatctcaaa 60
ggact 65

<210> SEQ ID NO 71
<211> LENGTH: 62
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
cggtctcggc attcctgctg aaccgctctt ccgatctgct agttaaatta ccagtcgtgg 60
cc 62

<210> SEQ ID NO 72
<211> LENGTH: 62
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
cggtctcggc attcctgctg aaccgctctt ccgatctcta gcttaaatta ccagtcgtgg 60
cc 62

<210> SEQ ID NO 73
<211> LENGTH: 66
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
cggtctcggc attcctgctg aaccgctctt ccgatcttag ctcttttttc ttcgatkcta 60
aagatt 66

<210> SEQ ID NO 74
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
cggtctcggc attcctgctg aaccgctctt ccgatcttca gtctgtgact ggaccaacga 60
gg 62

<210> SEQ ID NO 75
<211> LENGTH: 62
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
cggtctcggc attcctgctg aaccgctctt ccgatctcag tcctgtgact ggaccaacga 60
gg 62

<210> SEQ ID NO 76
<211> LENGTH: 62
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
cggtctcggc attcctgctg aaccgctctt ccgatctagt cactgtgact ggaccaacga 60
gg 62

<210> SEQ ID NO 77
<211> LENGTH: 62
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
cggtctcggc attcctgctg aaccgctctt ccgatctgtc agctgtgact ggaccaacga 60
gg 62

<210> SEQ ID NO 78
<211> LENGTH: 66
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
cggtctcggc attcctgctg aaccgctctt ccgatctgta cgacttacaa tgtaaggaac 60 rccrta 66

<210> SEQ ID NO 79
<211> LENGTH: 66
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79

```
cggtctcggc attcctgctg aaccgctctt ccgatcttac gtacttacaa tgtaaggaac     60

rccrta                                                                66


<210> SEQ ID NO 80
<211> LENGTH: 13462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

taaataaaaa ctgatggaag tctgtttctt aagtcaaata catcacagtg atgtggcaac     60

tattttccct caaattaata cgttttaaaa aaaatctata taaatgttgg catgtctaca    120

atctacatga tatccatatg gatcgttttt tatgatttat acatagtcag gaaattttag    180

cagaaacaaa atagagtacg aagactaaca taatattttc gactacatgt attttttttg    240

cgaaattgta aatatcaatc agtgaaaatg aaaaaccata caagttgact accatttcgg    300

tgcacaatcc ttacttctaa ggaaaaacta aagagaaaca aaagaagaaa atcttggtaa    360

attttgatac cattaccatg gttacttata ctcgataatg caattttaaa atcttctgta    420

aattttatag cattgttttt tttgtaacac atttctctaa cttagttttc atcgaaatga    480

acgacgtaac aaagatacat tgcgcacagg ttaccgcaaa aatacaattt ttattcttca    540

aagaataaaa aagtttccta aattaagaaa aaaagaaaac agtttggtgt ctctacacat    600

cttctccctt tatataaaca aaccacacat accccaaagt ccatcaaact ctctccacca    660

catttcactc agagcccaca cagttttaga gagagagaaa catccctcaa agctctctct    720

ttctccggcg atggttgtcg ctatggacca gcgtagcaat gtgaacggag attccaagga    780

cgaaaggttt gatccgagcg cacaaccacc gtttaagatc ggagatataa gggctgcgat    840

tcctaagcat tgttgggtca agagtccttt gagatccatg agctacgtcg cgagagacat    900

tttctccgtc gtggctctgg ccgtcgccgc cgtgtatttt gatagctggt tcttctggcc    960

tctttattgg gccgcccaag gaaccctttt ctgggccatc ggtaccgcct tttgcagttt   1020

atctctatgc ccgggacaag tggagtccat gctcaacacc gtgcaggatg aggatgacca   1080

ccgcggtagc gacttcgtgg gcgaggaaag cctttcgtcc aaggtggtcc ctcctcgcaa   1140

tcttgttgga tggtgaatat tataaaagcc tgcccttctc gcgggtgttt aaacgtcgac   1200

ctgcaggtca acggatcagg atattcttgt ttaagatgtt gaactctatg gaggtttgta   1260

tgaactgatg atctaggacc ggataagttc ccttcttcat agcgaactta ttcaaagaat   1320

gttttgtgta tcattcttgt tacattgtta ttaatgaaaa aatattattg gtcattggac   1380

tgaacacgag tgttaaatat ggaccaggcc ccaaataaga tccattgata tatgaattaa   1440

ataacaagaa taaatcgagt caccaaacca cttgcctttt ttaacgagac ttgttcacca   1500

acttgataca aaagtcatta tcctatgcaa atcaataatc atacaaaaat atccaataac   1560

actaaaaaat taaaagaaat ggataatttc acaatatgtt atacgataaa gaagttactt   1620

ttccaagaaa ttcactgatt ttataagccc acttgcatta gataaatggc aaaaaaaaac   1680

aaaaaggaaa agaaataaag cacgaagaat tctagaaaat acgaaatacg cttcaatgca   1740

gtgggaccca cggttcaatt attgccaatt ttcagctcca ccgtatattt aaaaaataaa   1800

acgataatgc taaaaaaata taaatcgtaa cgatcgttaa atctcaacgg ctggatctta   1860

tgacgaccgt tagaaattgt ggttgtcgac gagtcagtaa taaacggcgt caaagtggtt   1920
```

-continued gcagccggca cacacgagtc gtgtttatca actcaaagca caaatacttt tcctcaacct 1980
aaaaataagg caattagcca aaaacaactt tgcgtgtaaa caacgctcaa tacacgtgtc 2040
attttattat tagctattgc ttcaccgcct tagctttctc gtgacctagt cgtcctcgtc 2100
ttttcttctt cttcttctat aaaacaatac ccaaagagct cttcttcttc acaattcaga 2160
tttcaatttc tcaaaatctt aaaaactttc tctcaattct ctctaccgtg atcaaggtaa 2220
atttctgtgt tccttattct ctcaaaatct tcgattttgt tttcgttcga tcccaatttc 2280
gtatatgttc tttggtttag attctgttaa tcttagatcg aagacgattt tctgggtttg 2340
atcgttagat atcatcttaa ttctcgatta gggtttcata gatatcatcc gatttgttca 2400
aataatttga gttttgtcga ataattactc ttcgatttgt gatttctatc tagatctggt 2460
gttagtttct agtttgtgcg atcgaatttg tcgattaatc tgagtttttc tgattaacag 2520
atggcttcat ctgagaacgt tatcactgag ttcatgaggt tcaaggtgag gatggaaggt 2580
actgttaacg gacatgagtt cgagatcgag ggtgagggtg aaggtagacc ttacgaggga 2640
cataacaccg ttaagcttaa ggttacaaag ggtggacctc ttcctttcgc ttgggatatc 2700
ctttctcctc aattccaata cggaagcaag gtaagtttgt ggattcttcg tccatgtgat 2760
ctttgagttt ctttagagct tgtgagggat tagtaagtaa caatgcttga gtttttttgct 2820 gctgggcttc gaaaagtttg tcacttgttg gtttgatcca caaggtcttc ttctccatag 2880
ctactagaca tgttttagct taagattcaa gtttatatat gccttgtgga ttaatcattg 2940
cctgattctt ccgtgtcatc tctgagttta tttagagctt ggaagtggtg tagtaataac 3000
taacaatact cttgataagt tgtagcaatg ctcttgatta gtggatgtaa tatgatgttg 3060
ataagatata tgaggcacag aaccaaaagt ggtgcttcca ctagacccgt ttttagccta 3120
aggttcaagt ttataccttg tagatgtttc tgtattgtct gattcttccc tgtgatattt 3180
gaatttctta gagctttgga agtgatatag gaacaatgct cttgtgtgtt tgtctctatg 3240
aagattatcg ctgtcgtgtt tcatccgagt gtgcgggatt ttttgctgct gggtttagcc 3300
tttcttcaaa aagttattac ttgttagttt tattgttttg gtcttgataa gagatgttag 3360
gacagacatg gtgcttcttg tctatagcca ctagacctat tttagcataa ggttaacgaa 3420
attctctcta catacccttgt ggatttgttt acattgcctg atctttcctg tgatcgctgt 3480
catgtttctt tggaatgatt gatgtttata aatggaaaaa tctttgtgca gaagactccc 3540
gcccatctct ctatgcccgg gacaagtgcc accccacagt ggggcaggat gaggatgacc 3600
accatggggt cgcagcgtgt gcgtgtccgt cgtacgttct ggccggccgg gccttgggcg 3660
cgcgatcaga agcgttgcgt tggcgtgtgt gtgcttctgg tttgctttaa ttttaccaag 3720
tttgtttcaa ggtggatcgc gtggtcaagg cccgtgtgct ttaaagaccc accggcactg 3780
gcagtgagtg ttgctgcttg tgtaggcttt ggtacgtatg ggctttattt gcttctggat 3840
gttgtgtact acttgggttt gttgaattat tatgagcagt tgcgtattgt aattcagctg 3900
ggctacctgg acattgttat gtattaataa atgctttgct ttcttctaaa gatctttaag 3960
tgctgtttaa acaaccgaca accactttgc ggacttcctt tcaagagaat tcaataaggt 4020
taattcctaa ttgaaatccg aagataagat tcccacacac ttgtggctga tatcaaaagg 4080
ctactgccta tttaaacaca tctctggaga ctgagaaaat cagacctcca agcatgaaga 4140
agcctgagct tactgctact tctgttgaga agttcctcat cgagaagttc gattctgtgt 4200
ctgatcttat gcagctctct gagggtgagg aatcaagagc tttctctttc gatgttggtg 4260
gaagaggata cgttctcaga gttaactctt gcgctgacgg attctacaag gatagatacg 4320

```
tgtacagaca cttcgcttca gctgctctcc ctatccctga agttcttgat atcggagagt   4380
tctctgagtc tcttacctac tgtatctcaa gaagggctca gggtgttact cttcaagatc   4440
ttcctgagac tgagcttcct gctgttcttc aacctgttgc tgaggctatg gatgctatcg   4500
ctgctgctga tctttctcaa acttctggat tcggaccttt cggtcctcag ggaatcggac   4560
agtacactac ttggagagat ttcatctgcg ctatcgctga tcctcatgtt taccattggc   4620
agaccgttat ggatgatacc gtttctgctt ctgttgctca agctcttgat gagcttatgc   4680
tttgggctga ggattgtcct gaggttagac atcttgttca cgctgatttc ggatctaaca   4740
acgttctcac cgataacgga agaatcaccg ctgttatcga ttggtctgag gctatgttcg   4800
gagattctca atacgaggtg gccaacatat tcttttggag gccttggctt gcttgtatgg   4860
aacaacagac tagatacttc gagagaaggc atcctgagct tgctggatct cctagactta   4920
gagcttacat gcttaggatc ggacttgatc agctttacca gtctctcgtt gatggaaact   4980
tcgatgatgc tgcttgggct cagggaagat gtgatgctat cgttagatct ggtgctggaa   5040
ctgttggaag aactcaaatc gctagaagat ctgctgctgt ttggactgat ggatgtgttg   5100
aagttctcgc tgattctgga aacagaaggc cttctactag acctagagcc aagaagtgaa   5160
gatcggcggc aatagcttct tagcgccatc ccgggttgat cctatctgtg ttgaaatagt   5220
tgcggtgggc aaggctctct ttcagaaaga caggcggcca aaggaaccca aggtgaggtg   5280
ggctatggct ctcagttcct tgtggaagcg cttggtctaa ggtgcagagg tgttagcggg   5340
atgaagcaaa agtgtccgat tgtaacaaga tatgttgatc ctacgtaagg atattaaagt   5400
atgtattcat cactaatata atcagtgtat tccaatatgt actacgattt ccaatgtctt   5460
tattgtcgcc gtatgtaatc ggcgtcacaa aataatcccc ggtgactttc ttttaatcca   5520
ggatgaaata atatgttatt ataatttttg cgatttggtc cgttatagga attgaagtgt   5580
gcttgcggtc gccaccactc ccatttcata attttacatg tatttgaaaa ataaaaattt   5640
atggtattca atttaaacac gtatacttgt aaagaatgat atcttgaaag aaatatagtt   5700
taaatattta ttgataaaat aacaagtcag gtattatagt ccaagcaaaa acataaattt   5760
attgatgcaa gtttaaattc agaaatattt caataactga ttatatcagc tggtacattg   5820
ccgtagatga aagactgagt gcgatattat ggtgtaatac atagtttaaa cgggcccaag   5880
actcccgccc atctctctat gcccgggaca agtgccaccc cacagtgggg caggatgagg   5940
atgaccagtc agttttactt cccttaattt tctatgtact ttcataatta cttatgttat   6000
tttcttcatg agttttaatg caaattacta tatggactct agtgaaaacg ttcagaatcc   6060
tataaacatg actactgaga cgaacttgag agtagttttg atcatacaca cgtttcatgt   6120
ggtacttgag agttactaat ttttgtcatc ttcgtataag tagtaaaaga tactacaaga   6180
atagtttagt agaaaatact agcggtaggt gaagatttgt cgctatgtac tattattgtc   6240
tagtaacttg agtaacaatt tcgtggtcta aatatcaaat aaaaatggat gagtggttca   6300
ccaaatctag gcatcaaaac tattaatgtc attgtctaga tcttaggtga caccacattt   6360
cgaatattta ttggtaattg agatgttaaa gtaccaatat ttgacttaat aaactaaaag   6420
attttggctt tatcaaatgt agacattgat gacatatcgt tgtcattatc ttgagtatat   6480
acaagtcgat caattaggtg aaagtttagt gtctcgtggt tggtaaacga ttaatacagt   6540
agtatatttt atccaaagac aaaatccaaa tcatttcacc agtatgaata gtattatttt   6600
atcttaaaag ctaaaatctt aaaaaccaag gtagcaccca cgttgagcta gacgatcaaa   6660
```

-continued

```
tcgatttctg ctttgtccaa tttaccaagc tatttaaagc caaataattg aaatataggt   6720
aggtcgttat attaggctaa gatttatctc aaatgcttaa ctaaaggaat aacaagggat   6780
tctagttgtg tggttttata agattggtcc aatttcactt aagtttgttt attgtagaat   6840
tttatatgtg aataatttga attccaattg aaaagatatt atagtaaaag aaaaaatagt   6900
gcgaacaaaa aactttaatc ccataaaaag aaaaagaaaa atgaaaagtt cttctaacat   6960
ccatattttg catcatatca taaagataag aaagatacat atcatagacg tacagataaa   7020
caaacatatc atcatttgtg aaatacatag tacaataatt tgcttttaaa tagagtttaa   7080
gtcacacaca ctgacacaca cgataaaacg ataatgtctg caaaaacact ttaatcccat   7140
tgcctagagg acagcttctc cactttgtct ttaaggttgg ttttgccgtg ttgtttttat   7200
ctttatataa tgatctattt tttggattat gaaatgaatt cacacatttt aattatttaa   7260
gaagatccat atacaggttt ataacagtac taagtgatga ttattttttg tttttgcata   7320
gtttagttta ttgggtaaac attcattacg tgtctcttta tacgaatcac ccatccaaaa   7380
tttcaagtag tcttttagtt catttattat ttcataacta tttgacttat tgatttgaca   7440
agaaacaaca aaagtgttga cttattgata gattgtggga tcataaaagt aattaagcgt   7500
caaccacgac ccacaacaac aaagcacatg ttatacatta atatctcgtt tacttaatta   7560
cagttttcag aatgccgttt catgtcttgt cactggcgat gttattatca tgttggacaa   7620
tattcgactg ttgtcgtttt tacattttcg tattgactaa aactaaaaaa acaaaactct   7680
gtttcaggtt gggcctagga tccacattgt acacacattt gcttaagtct atggaggcgc   7740
aaggttttaa gtctgtggtt gctgttatag gccttccaaa cgatccatct gttaggttgc   7800
atgaggcttt gggatacaca gcccggggta cattgcgcgc agctggatac aagcatggtg   7860
gatggcatga tgttggtttt tggcaaaggg attttgagtt gccagctcct ccaaggccag   7920
ttaggccagt tacccagatc taatatcaaa atctatttag aaatacacaa tattttgttg   7980
caggcttgct ggagaatcga tctgctatca taaaaattac aaaaaaattt tatttgcctc   8040
aattatttta ggattggtat taaggacgct taaattattt gtcgggtcac tacgcatcat   8100
tgtgattgag aagatcagcg atacgaaata ttcgtagtac tatcgataat ttatttgaaa   8160
attcataaga aaagcaaacg ttacatgaat tgatgaaaca atacaaagac agataaagcc   8220
acgcacattt aggatattgg ccgagattac tgaatattga gtaagatcac ggaatttctg   8280
acaggagcat gtcttcaatt cagcccaaat ggcagttgaa atactcaaac cgccccatat   8340
gcaggagcgg atcattcatt gtttgtttgg ttgcctttgc caacatggga gtccaaggtt   8400
gtttaaacat ttaaataccc tgccaagctt gaggtagcct ccaatttgac ggtgccgcca   8460
gcgacgccgt ctggaactgt cctttttgag gaccactccg tttgtggaga tcatgagagt   8520
ccatgctcaa caccgtgcac tagggacagg attgaagact cccgcccatc tcactaggga   8580
caggattgcc accccacagt ggggcctaga aagactggag ttgcagagtt tgtgtcttct   8640
agattaatcc tccaaacttt tgattaacca aaaaaattat caaactaaca tgttctcctt   8700
ttttctttag aaattctaac gaatttatct ttatactgat ttgaatatac ttaatttggt   8760
catttggatg ccctttacaa cctccttacc aaactattga tcacagtttc tattgctaaa   8820
atcaccaaca aaacgcatgt cgccattcat aattatggtt tcacacctac aactaggcta   8880
ataagtaaat aagtagacaa ctagactcag gtttgaaaaa accataaaag ccatatagcg   8940
ttttctcatt gaaactgcga acacgatcgt gtgaatgttg cagtttctag ttttgataca   9000
aacaaacaaa aacacaattt aatcttagat taaaaagaaa aaagagaacg gagcccacta   9060
```

```
gccactcctt caaacgtgtc ttaccaactc tcttctagaa acaaattagg cttcaccttc   9120
ctcttccaac ctctctctct ctctctctct ctttttctca aaccatctct ccataaagcc   9180
ctaatttctt catcacaaga atcagaagaa gaaagatgga cctgcatcta attttcggtc   9240
caacttgcac aggaaagacg acgaccgcga tagctcttgc ccagcagaca gggcttccag   9300
tcctttcgct tgatcgggtc caatgctgtc ctcaactatc aaccggaagc ggacgaccaa   9360
cagtggaaga actgaaagga acgacgcgtc tctaccttga tgatcggcct ctggtggagg   9420
gtatcatcgc agccaagcaa gctcatcata ggctgatcga ggaggtgtat aatcatgagg   9480
ccaacggcgg gcttattctt gagggaggat ccacctcgtt gctcaactgc atggcgcgaa   9540
acagctattg gagtgcagat ttcgttggc atattattcg ccacaagtta cccgaccaag    9600
agaccttcat gaaagcggcc aaggccagag ttaagcagat gttgcacccc gctgcaggcc   9660
attctattat tcaagagttg gtttatcttt ggaatgaacc tcggctgagg cccattctga   9720
aagagatcga tggatatcga tatgccatgt tgtttgctag ccagaaccag atcacggcag   9780
atatgctatt gcagcttgac gcaaatatgg aaggtaagtt gattaatggg atcgctcagg   9840
agtatttcat ccatgcgcgc caacaggaac agaaattccc ccaagttaac gcagccgctt   9900
tcgacggatt cgaaggtcat ccgttcggaa tgtattagaa atcaccagtc tctctctaca   9960
aatctatctc tctctatttt tctccagaat aatgtgtgag tagttcccag ataagggaat  10020
tagggttctt atagggtttc gctcatgtgt tgagcatata agaaaccctt agtatgtatt  10080
tgtatttgta aaatacttct atcaataaaa tttctaattc ctaaaaccaa aatccagtgt  10140
ttaaacgagt ccatgctcaa caccgtgcac tagggacagg attgaagact cccgcccatc  10200
tcactaggga caggattgcc accccacagt ggggcctaga aagactggag ttgcagacat  10260
taaggatgac cagttcgtaa aggtcctgcg gtgtctattg cttttcatag gttaataagt  10320
gtttgctaga ctgtggtgaa aggcctatcc gaagtaaggc cggccggatc cttcatcttt  10380
ggacaaggga ataaagactc cccacttgct actaagaaca atacctaagt tgcccagaca  10440
tgactgtacc cattcagaga cctaccaccc attagggcta tgacactaac actagcccct  10500
ggaggttgac catgctaggc agtgggggtc tcacctatga cccactcaga taggggttta  10560
aaccagtggg tgggatctca gcctcatata ggtgtttgtg gtgagctttc tcctagacaa  10620
gagaaccctg aagaacagca agaaccagct aatatgatat gtagacatag tgggttgctc  10680
aaattttgtg tttagtcata ttagaattga cctcagtgac cactcagaaa gtgcccaagc  10740
ccatctatag gggccaaagt gctattgact ggtgtgtctg tgaattgttc ctccctacag  10800
agttggtgct gatatatcct agcattcttt ggaaaaccta gctagggact gtcaagtgta  10860
agatacctcc tgaattggag ggaacactag ctgccctgta ccttctggct agtaccttac  10920
accctgaatg ggttaggggg tctattattt gctggaaata taccagtttc agtagggctg  10980
ctgccttagg tcccacaagg tgtaacatgt gctcaatagt tgcactacca catgcacgtg  11040
aacttaatga tgttatagcc acaacaccaa ccttggtttg cagtttgaca tccctctgga  11100
atgggtgtag tcatcttgct ctggatctgc ctgaatcatt ggggctgtat gcagcctggg  11160
cttaaagtga agaatgggat gtcccagaaa tattttgggt gagaagaatc ctggagtaga  11220
tggtgacctg actatccctg tcctatgggc acaatctatc atcagatatt gcattcaaag  11280
ggctatcatg ggatcaagtc ctaagtcaac tgttgtttac ctggcagaca ttcatctagg  11340
agttctcttt tatgccaccc cacagtgatc cgccttttgc agtttatcca ctagggacag  11400
```

-continued

```
gattgccacc ccacagtggg gcctctatgc ccgggacaag tgtaaaatat agagtatagg  11460
ggttatcatc acagagaagc tattgctgga gggcctctgt tatttcctct ccatgccact  11520
cccattttta acctaccaac tgaaatccca agggagactc caccctgtaa ctagagtcct  11580
cagaggtgag ccatcccata ttaacaaatg ggcattaggg ctaggatgcc aagggatacc  11640
tgaaatggga agttgtgggg ctgagtcctc ctgggaatca gagataatat gtaaacagtt  11700
tgttgagaga ttgatgagag ctgactttga gaggtggcca tgctccctgg tcctcaatag  11760
ggaaggcact acacaagaaa cctgggtttg atcaactgca ctgtgtccta ctcacacatt  11820
gtgtgcctgg aaaaatgtta cttagtattt ggagggcctc cagaaccccc ctgggtgcaa  11880
gactgggtgc tagtgactgg gtgaatgagt cttggacaca gtggccttgt ctaggttgtg  11940
tgaggtggct aggcatcatg gcaatacctc ataattgatg agtgaggaaa caagactaag  12000
tccttgactc ctcttattac atgacctggt ggatattatg tttaaactct gcaagctgga  12060
atgagtactg ggtgcagatc ccctgggatt ctggctacaa aggtgaatga tagctagtct  12120
gtttattagt agccaaaaaa gtcagtgagg ggtgagtgcc ctgggatgtt gttaagttca  12180
cattgcacac ttggagaccc tctccatcca gtaacatacc agagaaaact gaccaagccc  12240
tcatgggtgt atgggaacaa caaacctcct ggctacttca agggcacata acaccagcaa  12300
ggagcctgtc ataaccacca tctcaaacaa tagaacttcc taagtgaagc aatgacttca  12360
aatctacttg aaggcatgga gtataagcca tgttcctttc agaggggact gtacttctgt  12420
agattacttt ccctcattaa ccagatctgg ccggccgcat gcgtactcgg ccacgactgg  12480
taatttaatt ttcaatttat tttttcttca acttcttaat tttgatatgt ttatatgttt  12540
tttcgttttt tgcatcgtct ttgatttctt gaacgcacgt tcgatatgag attttcactg  12600
acttcaagat ttgattctct tcaggtttac ttttaaaaaa aaaaattatt atgttcaccc  12660
aaattggcct attttaaaag caaaagggga tctaagattt ttaattcttc tctttttcag  12720
tcgtaacact gctaactttt ttttttgatc aaatcgtaac actcataagt cctaactaaa  12780
catctttttc tttcctataa ttattgttgg ttccgcattt tatggatcta cgtttgaaag  12840
tttcaataaa acacatttta ttgtttgaaa gtaacaatat aattactgta tattgattct  12900
tttaattatt gtgtgttgtt ccaatctact ttcgaaatat agtcatgtga cacgtcatat  12960
tctatttttg ttaccttgtt ggaacgtttg aattgagtaa agtttaatta acattgtgca  13020
ataaatgata aacatgttta tgatgtaaaa ttcaatttga ataatacagt ggacatggga  13080
gcttctcaga cattcctctt ctgaatactg cggttggtca tattcttcat tccttcattc  13140
tcgttccata ccatggttgg taagtcattt atttaaacat ctttttcatg caaatttatt  13200
cttgttttcg tatttcttac attttccttg tcattcttgg tgcatgttag caaactgtaa  13260
tctgataact gaaaatatat taattttcca tagtaaaata atgcatgtga ctaaaagcat  13320
caaaatcttt agcatcgaag aaaaaagaac caaactttta tttaatgcta tgggcctatt  13380
tatggtccaa ttagctatta tcatatgaca tgtccttgaa taaattaatg tagcttcata  13440
tgtgagttta ataatattta ta                                          13462
```

<210> SEQ ID NO 81
<211> LENGTH: 13462
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 81

```
ggtttctttt ttaatttaat ttattttttt aatcggagaa aaaaattaag aaaccaaaaa     60
acagttttaa tcatggcctc atgttggggt tgagttttat attctgataa gaatcccatc    120
ttaaaaaccc cgttaaacat gctcttacca tctgcttcga aaatgatatg ttattgacaa    180
ttccaatttc atttttatga aaataaaata atagtttatt ttataactga gggtggttgc    240
aggagaataa gccatcggac acaccaccag aaccatggcc atgttgaaaa cgacgagtct    300
tgggttccgg taatctttcc ctctctcata tttttttct ttttttgaa attctttcat    360
tttaatttc ttaggattct atgtatttat tttaatcaat ccttttcca gtttgaggct    420
aggacgacca cttgtcagat ttgtcgttta gctgtagtaa acaactgatt taaattgttt    480
atagtactgt agttaacttt aacaacggac cacttatatt cgagccattg gcataaaatg    540
attcttctcg aaattcgttt acttttctta gtatttttca attttggagt ttacgtagaa    600
ctaataaaaa gaaaaactta taaacacacc acatgcaatg aataaattcg aatatataac    660
catactgtta aatattaatt tacattttaa tcttaatttt gcattccagt tgccagaaaa    720
attatacaag aatttgtccc acagtacacg gatgctcaga tacactgtcc ctctccccat    780
gctcgcttac cctctctatc tggtaaatcc taattcctaa tttttcttcc tgattataat    840
tacaattttg aatttttaga ttttgagtat taactaaata taaattaaat ttgtttgggg    900
atgactacag tggtacagaa gtcctggtaa agaagggtca cattataacc catacagtag    960
tttatttgcc ccaagcgaga gaaagcttat tgcaacttca ggtaccgcct tttgcagttt   1020
atctctatgc ccgggacaag tggagtccat gctcaacacc gtgcaggatg aggatgacca   1080
ccgcggtagc gacttcgtgg gcgaggaaag cctttcgtcc aaggtggtcc ctcctcgcaa   1140
tcttgttgga tggtgaatat tataaaagcc tgcccttctc gcgggtgttt aaacgtcgac   1200
ctgcaggtca acggatcagg atattcttgt ttaagatgtt gaactctatg gaggtttgta   1260
tgaactgatg atctaggacc ggataagttc ccttcttcat agcgaactta ttcaaagaat   1320
gttttgtgta tcattcttgt tacattgtta ttaatgaaaa aatattattg gtcattggac   1380
tgaacacgag tgttaaatat ggaccaggcc ccaaataaga tccattgata tatgaattaa   1440
ataacaagaa taaatcgagt caccaaacca cttgcctttt ttaacgagac ttgttcacca   1500
acttgataca aaagtcatta tcctatgcaa atcaataatc atacaaaaat atccaataac   1560
actaaaaaat taaaagaaat ggataatttc acaatatgtt atacgataaa gaagttactt   1620
ttccaagaaa ttcactgatt ttataagccc acttgcatta gataaatggc aaaaaaaaac   1680
aaaaaggaaa agaaataaag cacgaagaat tctagaaaat acgaaatacg cttcaatgca   1740
gtgggaccca cggttcaatt attgccaatt ttcagctcca ccgtatattt aaaaaataaa   1800
acgataatgc taaaaaaata taaatcgtaa cgatcgttaa atctcaacgg ctggatctta   1860
tgacgaccgt tagaaattgt ggttgtcgac gagtcagtaa taaacggcgt caaagtggtt   1920
gcagccggca cacacgagtc gtgtttatca actcaaagca caaatacttt tcctcaacct   1980
aaaaataagg caattagcca aaaacaactt tgcgtgtaaa caacgctcaa tacacgtgtc   2040
attttattat tagctattgc ttcaccgcct tagctttctc gtgacctagt cgtcctcgtc   2100
ttttcttctt cttcttctat aaaacaatac ccaaagagct cttcttcttc acaattcaga   2160
tttcaatttc tcaaaatctt aaaaactttc tctcaattct ctctaccgtg atcaaggtaa   2220
atttctgtgt tccttattct ctcaaaatct tcgattttgt tttcgttcga tcccaatttc   2280
gtatatgttc tttggtttag attctgttaa tcttagatcg aagacgattt tctgggtttg   2340
```

```
atcgttagat atcatcttaa ttctcgatta gggtttcata gatatcatcc gatttgttca   2400
aataatttga gttttgtcga ataattactc ttcgatttgt gatttctatc tagatctggt   2460
gttagtttct agtttgtgcg atcgaatttg tcgattaatc tgagtttttc tgattaacag   2520
atggcttcat ctgagaacgt tatcactgag ttcatgaggt tcaaggtgag gatggaaggt   2580
actgttaacg gacatgagtt cgagatcgag ggtgagggtg aaggtagacc ttacgaggga   2640
cataacaccg ttaagcttaa ggttacaaag ggtggacctc ttcctttcgc ttgggatatc   2700
ctttctcctc aattccaata cggaagcaag gtaagtttgt ggattcttcg tccatgtgat   2760
ctttgagttt ctttagagct tgtgagggat tagtaagtaa caatgcttga gtttttttgct   2820
gctgggcttc gaaaagtttg tcacttgttg gtttgatcca caaggtcttc ttctccatag   2880
ctactagaca tgttttagct taagattcaa gtttatatat gccttgtgga ttaatcattg   2940
cctgattctt ccgtgtcatc tctgagttta tttagagctt ggaagtggtg tagtaataac   3000
taacaatact cttgataagt tgtagcaatg ctcttgatta gtggatgtaa tatgatgttg   3060
ataagatata tgaggcacag aaccaaaagt ggtgcttcca ctagacccgt ttttagccta   3120
aggttcaagt ttataccttg tagatgtttc tgtattgtct gattcttccc tgtgatattt   3180
gaatttctta gagctttgga agtgatatag gaacaatgct cttgtgtgtt tgtctctatg   3240
aagattatcg ctgtcgtgtt tcatccgagt gtgcgggatt ttttgctgct gggtttagcc   3300
tttcttcaaa aagttattac ttgttagttt tattgttttg gtcttgataa gagatgttag   3360
gacagacatg gtgcttcttg tctatagcca ctagacctat tttagcataa ggttaacgaa   3420
attctctcta catacccttgt ggatttgttt acattgcctg atctttcctg tgatcgctgt   3480
catgtttctt tggaatgatt gatgtttata aatggaaaaa tctttgtgca gaagactccc   3540
gcccatctct ctatgcccgg gacaagtgcc accccacagt ggggcaggat gaggatgacc   3600
accatggggt cgcagcgtgt gcgtgtccgt cgtacgttct ggccggccgg gccttgggcg   3660
cgcgatcaga agcgttgcgt tggcgtgtgt gtgcttctgg tttgctttaa ttttaccaag   3720
tttgtttcaa ggtggatcgc gtggtcaagg cccgtgtgct ttaaagaccc accggcactg   3780
gcagtgagtg ttgctgcttg tgtaggcttt ggtacgtatg ggctttattt gcttctggat   3840
gttgtgtact acttgggttt gttgaattat tatgagcagt tgcgtattgt aattcagctg   3900
ggctacctgg acattgttat gtattaataa atgctttgct ttcttctaaa gatctttaag   3960
tgctgtttaa acaaccgaca accactttgc ggacttcctt tcaagagaat tcaataaggt   4020
taattcctaa ttgaaatccg aagataagat tcccacacac ttgtggctga tatcaaaagg   4080
ctactgccta tttaaacaca tctctggaga ctgagaaaat cagacctcca agcatgaaga   4140
agcctgagct tactgctact tctgttgaga agttcctcat cgagaagttc gattctgtgt   4200
ctgatcttat gcagctctct gagggtgagg aatcaagagc tttctctttc gatgttggtg   4260
gaagaggata cgttctcaga gttaactctt gcgctgacgg attctacaag gatagatacg   4320
tgtacagaca cttcgcttca gctgctctcc ctatccctga agttcttgat atcggagagt   4380
tctctgagtc tcttacctac tgtatctcaa gaagggctca gggtgttact cttcaagatc   4440
ttcctgagac tgagcttcct gctgttcttc aacctgttgc tgaggctatg gatgctatcg   4500
ctgctgctga tctttctcaa acttctggat tcggaccttt cggtcctcag ggaatcggac   4560
agtacactac ttggagagat ttcatctgcg ctatcgctga tcctcatgtt taccattggc   4620
agaccgttat ggatgatacc gtttctgctt ctgttgctca agctcttgat gagcttatgc   4680
```

-continued

```
tttgggctga ggattgtcct gaggttagac atcttgttca cgctgatttc ggatctaaca   4740
acgttctcac cgataacgga agaatcaccg ctgttatcga ttggtctgag gctatgttcg   4800
gagattctca atacgaggtg gccaacatat tcttttggag gccttggctt gcttgtatgg   4860
aacaacagac tagatacttc gagagaaggc atcctgagct tgctggatct cctagactta   4920
gagcttacat gcttaggatc ggacttgatc agctttacca gtctctcgtt gatggaaact   4980
tcgatgatgc tgcttgggct cagggaagat gtgatgctat cgttagatct ggtgctggaa   5040
ctgttggaag aactcaaatc gctagaagat ctgctgctgt ttggactgat ggatgtgttg   5100
aagttctcgc tgattctgga aacagaaggc cttctactag acctagagcc aagaagtgaa   5160
gatcggcggc aatagcttct tagcgccatc ccgggttgat cctatctgtg ttgaaatagt   5220
tgcggtgggc aaggctctct ttcagaaaga caggcggcca aaggaaccca aggtgaggtg   5280
ggctatggct ctcagttcct tgtggaagcg cttggtctaa ggtgcagagg tgttagcggg   5340
atgaagcaaa agtgtccgat tgtaacaaga tatgttgatc ctacgtaagg atattaaagt   5400
atgtattcat cactaatata atcagtgtat tccaatatgt actacgattt ccaatgtctt   5460
tattgtcgcc gtatgtaatc ggcgtcacaa aataatcccc ggtgactttc ttttaatcca   5520
ggatgaaata atatgttatt ataatttttg cgatttggtc cgttatagga attgaagtgt   5580
gcttgcggtc gccaccactc ccatttcata attttacatg tatttgaaaa ataaaaattt   5640
atggtattca atttaaacac gtatacttgt aaagaatgat atcttgaaag aaatatagtt   5700
taaatattta ttgataaaat aacaagtcag gtattatagt ccaagcaaaa acataaattt   5760
attgatgcaa gtttaaattc agaaatattt caataactga ttatatcagc tggtacattg   5820
ccgtagatga aagactgagt gcgatattat ggtgtaatac atagtttaaa cgggcccaag   5880
actcccgccc atctctctat gcccgggaca agtgccaccc cacagtgggg caggatgagg   5940
atgaccagtc agttttactt cccttaattt tctatgtact ttcataatta cttatgttat   6000
tttcttcatg agttttaatg caaattacta tatggactct agtgaaaacg ttcagaatcc   6060
tataaacatg actactgaga cgaacttgag agtagttttg atcatacaca cgtttcatgt   6120
ggtacttgag agttactaat ttttgtcatc ttcgtataag tagtaaaaga tactacaaga   6180
atagtttagt agaaaatact agcggtaggt gaagatttgt cgctatgtac tattattgtc   6240
tagtaacttg agtaacaatt tcgtggtcta aatatcaaat aaaaatggat gagtggttca   6300
ccaaatctag gcatcaaaac tattaatgtc attgtctaga tcttaggtga caccacattt   6360
cgaatattta ttggtaattg agatgttaaa gtaccaatat ttgacttaat aaactaaaag   6420
attttggctt tatcaaatgt agacattgat gacatatcgt tgtcattatc ttgagtatat   6480
acaagtcgat caattaggtg aaagtttagt gtctcgtggt tggtaaacga ttaatacagt   6540
agtatatttt atccaaagac aaaatccaaa tcatttcacc agtatgaata gtattatttt   6600
atcttaaaag ctaaaatctt aaaaaccaag gtagcaccca cgttgagcta gacgatcaaa   6660
tcgatttctg ctttgtccaa tttaccaagc tatttaaagc caaataattg aaatataggt   6720
aggtcgttat attaggctaa gatttatctc aaatgcttaa ctaaaggaat aacaagggat   6780
tctagttgtg tggttttata agattggtcc aatttcactt aagtttgttt attgtagaat   6840
tttatatgtg aataatttga attccaattg aaaagatatt atagtaaaag aaaaaatagt   6900
gcgaacaaaa aactttaatc ccataaaaag aaaaagaaaa atgaaaagtt cttctaacat   6960
ccatattttg catcatatca taaagataag aaagatacat atcatagacg tacagataaa   7020
caaacatatc atcatttgtg aaatacatag tacaataatt tgcttttaaa tagagtttaa   7080
```

gtcacacaca ctgacacaca cgataaaacg ataatgtctg caaaaacact ttaatcccat 7140
tgcctagagg acagcttctc cactttgtct ttaaggttgg ttttgccgtg ttgtttttat 7200
ctttatataa tgatctattt tttggattat gaaatgaatt cacacatttt aattatttaa 7260
gaagatccat atacaggttt ataacagtac taagtgatga ttattttttg tttttgcata 7320
gtttagttta ttgggtaaac attcattacg tgtctcttta tacgaatcac ccatccaaaa 7380
tttcaagtag tcttttagtt catttattat ttcataacta tttgacttat tgatttgaca 7440
agaaacaaca aaagtgttga cttattgata gattgtggga tcataaaagt aattaagcgt 7500
caaccacgac ccacaacaac aaagcacatg ttatacatta atatctcgtt tacttaatta 7560
cagttttcag aatgccgttt catgtcttgt cactggcgat gttattatca tgttggacaa 7620
tattcgactg ttgtcgtttt tacattttcg tattgactaa aactaaaaaa acaaaactct 7680
gtttcaggtt gggcctagga tccacattgt acacacattt gcttaagtct atggaggcgc 7740
aaggttttaa gtctgtggtt gctgttatag gccttccaaa cgatccatct gttaggttgc 7800
atgaggcttt gggatacaca gcccggggta cattgcgcgc agctggatac aagcatggtg 7860
gatggcatga tgttggtttt tggcaaaggg attttgagtt gccagctcct ccaaggccag 7920
ttaggccagt tacccagatc taatatcaaa atctatttag aaatacacaa tattttgttg 7980
caggcttgct ggagaatcga tctgctatca taaaaattac aaaaaaattt tatttgcctc 8040
aattatttta ggattggtat taaggacgct taaattattt gtcgggtcac tacgcatcat 8100
tgtgattgag aagatcagcg atacgaaata ttcgtagtac tatcgataat ttatttgaaa 8160
attcataaga aaagcaaacg ttacatgaat tgatgaaaca atacaaagac agataaagcc 8220
acgcacattt aggatattgg ccgagattac tgaatattga gtaagatcac ggaatttctg 8280
acaggagcat gtcttcaatt cagcccaaat ggcagttgaa atactcaaac cgccccatat 8340
gcaggagcgg atcattcatt gtttgtttgg ttgcctttgc caacatggga gtccaaggtt 8400
gtttaaacat ttaaataccc tgccaagctt gaggtagcct ccaatttgac ggtgccgcca 8460
gcgacgccgt ctggaactgt cctttttgag gaccactccg tttgtggaga tcatgagagt 8520
ccatgctcaa caccgtgcac tagggacagg attgaagact cccgcccatc tcactaggga 8580
caggattgcc accccacagt ggggcctaga aagactggag ttgcagagtt tgtgtcttct 8640
agattaatcc tccaaacttt tgattaacca aaaaaattat caaactaaca tgttctcctt 8700
ttttctttag aaattctaac gaatttatct ttatactgat ttgaatatac ttaatttggt 8760
catttggatg ccctttacaa cctccttacc aaactattga tcacagtttc tattgctaaa 8820
atcaccaaca aaacgcatgt cgccattcat aattatggtt tcacacctac aactaggcta 8880
ataagtaaat aagtagacaa ctagactcag gtttgaaaaa accataaaag ccatatagcg 8940
ttttctcatt gaaactgcga acacgatcgt gtgaatgttg cagtttctag ttttgataca 9000
aacaaacaaa aacacaattt aatcttagat taaaaagaaa aaagagaacg gagcccacta 9060
gccactcctt caaacgtgtc ttaccaactc tcttctagaa acaaattagg cttcaccttc 9120
ctcttccaac ctctctctct ctctctctct ctttttctca aaccatctct ccataaagcc 9180
ctaatttctt catcacaaga atcagaagaa gaaagatgga cctgcatcta attttcggtc 9240
caacttgcac aggaaagacg acgaccgcga tagctcttgc ccagcagaca gggcttccag 9300
tcctttcgct tgatcgggtc caatgctgtc ctcaactatc aaccggaagc ggacgaccaa 9360
cagtggaaga actgaaagga acgacgcgtc tctaccttga tgatcggcct ctggtggagg 9420

-continued

```
gtatcatcgc agccaagcaa gctcatcata ggctgatcga ggaggtgtat aatcatgagg   9480
ccaacggcgg gcttattctt gagggaggat ccacctcgtt gctcaactgc atggcgcgaa   9540
acagctattg gagtgcagat tttcgttggc atattattcg ccacaagtta cccgaccaag   9600
agaccttcat gaaagcggcc aaggccagag ttaagcagat gttgcacccc gctgcaggcc   9660
attctattat tcaagagttg gtttatcttt ggaatgaacc tcggctgagg cccattctga   9720
aagagatcga tggatatcga tatgccatgt tgtttgctag ccagaaccag atcacggcag   9780
atatgctatt gcagcttgac gcaaatatgg aaggtaagtt gattaatggg atcgctcagg   9840
agtatttcat ccatgcgcgc caacaggaac agaaattccc ccaagttaac gcagccgctt   9900
tcgacggatt cgaaggtcat ccgttcggaa tgtattagaa atcaccagtc tctctctaca   9960
aatctatctc tctctatttt tctccagaat aatgtgtgag tagttcccag ataagggaat  10020
tagggttctt atagggtttc gctcatgtgt tgagcatata agaaaccctt agtatgtatt  10080
tgtatttgta aaatacttct atcaataaaa tttctaattc ctaaaaccaa aatccagtgt  10140
ttaaacgagt ccatgctcaa caccgtgcac tagggacagg attgaagact cccgcccatc  10200
tcactaggga caggattgcc accccacagt ggggcctaga aagactggag ttgcagacat  10260
taaggatgac cagttcgtaa aggtcctgcg gtgtctattg cttttcatag gttaataagt  10320
gtttgctaga ctgtggtgaa aggcctatcc gaagtaaggc cggccggatc cttcatcttt  10380
ggacaaggga ataaagactc cccacttgct actaagaaca atacctaagt tgcccagaca  10440
tgactgtacc cattcagaga cctaccaccc attagggcta tgacactaac actagcccct  10500
ggaggttgac catgctaggc agtgggggtc tcacctatga cccactcaga taggggttta  10560
aaccagtggg tgggatctca gcctcatata ggtgtttgtg gtgagctttc tcctagacaa  10620
gagaaccctg aagaacagca agaaccagct aatatgatat gtagacatag tgggttgctc  10680
aaattttgtg tttagtcata ttagaattga cctcagtgac cactcagaaa gtgcccaagc  10740
ccatctatag gggccaaagt gctattgact ggtgtgtctg tgaattgttc ctccctacag  10800
agttggtgct gatatatcct agcattcttt ggaaaaccta gctagggact gtcaagtgta  10860
agatacctcc tgaattggag ggaacactag ctgccctgta ccttctggct agtaccttac  10920
accctgaatg ggttaggggg tctattattt gctggaaata taccagtttc agtagggctg  10980
ctgccttagg tcccacaagg tgtaacatgt gctcaatagt tgcactacca catgcacgtg  11040
aacttaatga tgttatagcc acaacaccaa ccttggtttg cagtttgaca tccctctgga  11100
atgggtgtag tcatcttgct ctggatctgc ctgaatcatt ggggctgtat gcagcctggg  11160
cttaaagtga agaatgggat gtcccagaaa tattttgggt gagaagaatc ctggagtaga  11220
tggtgacctg actatccctg tcctatgggc acaatctatc atcagatatt gcattcaaag  11280
ggctatcatg ggatcaagtc ctaagtcaac tgttgtttac ctggcagaca ttcatctagg  11340
agttctcttt tatgccaccc cacagtgatc cgccttttgc agtttatcca ctagggacag  11400
gattgccacc ccacagtggg gcctctatgc ccgggacaag tgtaaaatat agagtatagg  11460
ggttatcatc acagagaagc tattgctgga gggcctctgt tatttcctct ccatgccact  11520
cccattttta acctaccaac tgaaatccca agggagactc caccctgtaa ctagagtcct  11580
cagaggtgag ccatcccata ttaacaaatg ggcattaggg ctaggatgcc aagggatacc  11640
tgaaatggga agttgtgggg ctgagtcctc ctgggaatca gagataatat gtaaacagtt  11700
tgttgagaga ttgatgagag ctgactttga gaggtggcca tgctccctgg tcctcaatag  11760
ggaaggcact acacaagaaa cctgggtttg atcaactgca ctgtgtccta ctcacacatt  11820
```

```
gtgtgcctgg aaaaatgtta cttagtattt ggagggcctc cagaaccccc ctgggtgcaa  11880

gactgggtgc tagtgactgg gtgaatgagt cttggacaca gtggccttgt ctaggttgtg  11940

tgaggtggct aggcatcatg gcaatacctc ataattgatg agtgaggaaa caagactaag  12000

tccttgactc ctcttattac atgacctggt ggatattatg tttaaactct gcaagctgga  12060

atgagtactg ggtgcagatc ccctgggatt ctggctacaa aggtgaatga tagctagtct  12120

gtttattagt agccaaaaaa gtcagtgagg ggtgagtgcc ctgggatgtt gttaagttca  12180

cattgcacac ttggagaccc tctccatcca gtaacatacc agagaaaact gaccaagccc  12240

tcatgggtgt atgggaacaa caaacctcct ggctacttca agggcacata acaccagcaa  12300

ggagcctgtc ataaccacca tctcaaacaa tagaacttcc taagtgaagc aatgacttca  12360

aatctacttg aaggcatgga gtataagcca tgttcctttc agaggggact gtacttctgt  12420

agattacttt ccctcattaa ccagatctgg ccggccgcat gccttgctgg tcgatcgtgt  12480

tggccactct tgtttatcta tcattcctcg ttggtccagt cacagttcta aaagtctatg  12540

gtgttcctta cattgtaagt ttcatatatt tctttattat atcattgcta atataatttg  12600

tttttgacat aaaagttttg gaaaaatttc agatctttgt aatgtggttg gacgctgtca  12660

cgtacttgca tcatcatggt cacgatgata agctgccttg gtacagaggc aaggtaagta  12720

gatcaacatt atttataaga agcaataatg attagtagtt gaataatctg aatttttgat  12780

gtttttgtac aataatagga atggagttat ttacgtggag gattaacaac tgttgataga  12840

gattacggga tcttcaacaa cattcatcac gatattggaa ctcacgtgat ccatcatctt  12900

ttcccacaaa tccctcacta tcacttggtc gatgccgtga gtgatctcgc tctctctcta  12960

gtttcatttg attatattaa agggtgatta attactaaat tagtgatctt aattaatgac  13020

atgcgacaga cgaaagcagc taaacatgtg ttgggaagat actacagaga accaaagacg  13080

tcaggagcaa taccgatcca cttagtggaa agtttggtgg caagtattaa gaaagatcat  13140

tacgtcagtg acactggtga tattgtcttc tacgagacag atccagatct ctacgtttat  13200

gcttctgaca aatccaaaat caattaatct ttcttcctag ctctatttag gaataaaaca  13260

ctcctttggt tttacttatt tctggttgtt tttaagttaa aaatgtactc gtgaaacttt  13320

tttttattaa atgtatttac attacaaatc gtaaaagttt ttgttcgttt tctctatgtt  13380

tttagttaca aacttacaat caaaaaggtc ttaaaaactt tttgatggtg ggacggacaa  13440

aagaaaaagt tcgactgaga gt                                            13462
```

<210> SEQ ID NO 82
<211> LENGTH: 13462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
aatatttata tatatttgtt ttaatggctt attttattgt taaatggata catcagcttg     60

aaatatctac gaacatgcat cattttccta gatacatttg tttgttgctc aaaaaatgaa    120

taacgtagtt aaacgagtga gattcttagc atctgcctcg aaaacgatat gttattgaca    180

attccaattt catttttatg aaaataaaat aatagtttat tttataattg gggtggttg     240

caggagaata agccatcgga cacaccacca gaaccatggc catgttgaaa acgacgagtc    300

ttgggttccg gtaatccccc tctcattatt tttttttctt tttttgaaac tctttcattt    360
```

```
taattttctt agaattctat gtatttattt taatcaatcc tttttccagt gtgaggcttg    420
gacgaccact tgtcagattt gtcgtttagc tgtagtaaac aactgattta aattgtttat    480
ggtactgtag ttaactttaa caacgggcca cttatattcg agccattggc ataaaatgat    540
tcttctcgaa attcgtttac ttttcttagt atttttcagt tttgtagttt acgtagaact    600
aataaaaaga aaaaaactta taaacacacc acatgcaatg aataaattcg aatatataac    660
catactgtta aatattaatt aacattttaa tcttaatttt gcattccagt tgccagaaaa    720
attatacaag aatttgtccc acagtacacg gatgctcaga tacactgtcc ctctccccat    780
gctcgcttac cctctctatc tggtaaatcc taattcctca tttttcttcc tgattataat    840
tacaattttg aatttttaga ttttgagtat taactaaata taaattaaat ttgtttgggg    900
atgactacag tggtacagaa gtcctggtaa agaagggtca cattataacc catacagtag    960
tttatttgcc ccaagcgaga gaaagcttat tgcaacttca ggtaccgcct tttgcagttt   1020
atctctatgc ccgggacaag tggagtccat gctcaacacc gtgcaggatg aggatgacca   1080
ccgcggtagc gacttcgtgg gcgaggaaag cctttcgtcc aaggtggtcc ctcctcgcaa   1140
tcttgttgga tggtgaatat tataaaagcc tgcccttctc gcgggtgttt aaacgtcgac   1200
ctgcaggtca acggatcagg atattcttgt ttaagatgtt gaactctatg gaggtttgta   1260
tgaactgatg atctaggacc ggataagttc ccttcttcat agcgaactta ttcaaagaat   1320
gttttgtgta tcattcttgt tacattgtta ttaatgaaaa aatattattg gtcattggac   1380
tgaacacgag tgttaaatat ggaccaggcc ccaaataaga tccattgata tatgaattaa   1440
ataacaagaa taaatcgagt caccaaacca cttgcctttt ttaacgagac ttgttcacca   1500
acttgataca aaagtcatta tcctatgcaa atcaataatc atacaaaaat atccaataac   1560
actaaaaaat taaaagaaat ggataatttc acaatatgtt atacgataaa gaagttactt   1620
ttccaagaaa ttcactgatt ttataagccc acttgcatta gataaatggc aaaaaaaaac   1680
aaaaaggaaa agaaataaag cacgaagaat tctagaaaat acgaaatacg cttcaatgca   1740
gtgggaccca cggttcaatt attgccaatt ttcagctcca ccgtatattt aaaaaataaa   1800
acgataatgc taaaaaaata taaatcgtaa cgatcgttaa atctcaacgg ctggatctta   1860
tgacgaccgt tagaaattgt ggttgtcgac gagtcagtaa taaacggcgt caaagtggtt   1920
gcagccggca cacacgagtc gtgtttatca actcaaagca caaatacttt tcctcaacct   1980
aaaaataagg caattagcca aaaacaactt tgcgtgtaaa caacgctcaa tacacgtgtc   2040
attttattat tagctattgc ttcaccgcct tagctttctc gtgacctagt cgtcctcgtc   2100
ttttcttctt cttcttctat aaaacaatac ccaaagagct cttcttcttc acaattcaga   2160
tttcaatttc tcaaaatctt aaaaactttc tctcaattct ctctaccgtg atcaaggtaa   2220
atttctgtgt tccttattct ctcaaaatct tcgattttgt tttcgttcga tcccaatttc   2280
gtatatgttc tttggtttag attctgttaa tcttagatcg aagacgattt tctgggtttg   2340
atcgttagat atcatcttaa ttctcgatta gggtttcata gatatcatcc gatttgttca   2400
aataatttga gttttgtcga ataattactc ttcgatttgt gatttctatc tagatctggt   2460
gttagtttct agtttgtgcg atcgaatttg tcgattaatc tgagtttttc tgattaacag   2520
atggcttcat ctgagaacgt tatcactgag ttcatgaggt tcaaggtgag gatggaaggt   2580
actgttaacg gacatgagtt cgagatcgag ggtgagggtg aaggtagacc ttacgaggga   2640
cataacaccg ttaagcttaa ggttacaaag ggtggacctc ttcctttcgc ttgggatatc   2700
```

ctttctcctc aattccaata cggaagcaag gtaagtttgt ggattcttcg tccatgtgat 2760
ctttgagttt ctttagagct tgtgagggat tagtaagtaa caatgcttga gtttttttgct 2820 gctgggcttc gaaaagtttg tcacttgttg gtttgatcca caaggtcttc ttctccatag 2880
ctactagaca tgttttagct taagattcaa gtttatatat gccttgtgga ttaatcattg 2940
cctgattctt ccgtgtcatc tctgagttta tttagagctt ggaagtggtg tagtaataac 3000
taacaatact cttgataagt tgtagcaatg ctcttgatta gtggatgtaa tatgatgttg 3060
ataagatata tgaggcacag aaccaaaagt ggtgcttcca ctagacccgt ttttagccta 3120
aggttcaagt ttataccttg tagatgtttc tgtattgtct gattcttccc tgtgatattt 3180
gaatttctta gagctttgga agtgatatag gaacaatgct cttgtgtgtt tgtctctatg 3240
aagattatcg ctgtcgtgtt tcatccgagt gtgcgggatt ttttgctgct gggtttagcc 3300
tttcttcaaa aagttattac ttgttagttt tattgttttg gtcttgataa gagatgttag 3360
gacagacatg gtgcttcttg tctatagcca ctagacctat tttagcataa ggttaacgaa 3420
attctctcta cataccttgt ggatttgttt acattgcctg atctttcctg tgatcgctgt 3480
catgtttctt tggaatgatt gatgtttata aatggaaaaa tctttgtgca gaagactccc 3540
gcccatctct ctatgcccgg gacaagtgcc accccacagt ggggcaggat gaggatgacc 3600
accatggggt cgcagcgtgt gcgtgtccgt cgtacgttct ggccggccgg gccttgggcg 3660
cgcgatcaga agcgttgcgt tggcgtgtgt gtgcttctgg tttgctttaa ttttaccaag 3720
tttgtttcaa ggtggatcgc gtggtcaagg cccgtgtgct ttaaagaccc accggcactg 3780
gcagtgagtg ttgctgcttg tgtaggcttt ggtacgtatg ggctttattt gcttctggat 3840
gttgtgtact acttgggttt gttgaattat tatgagcagt tgcgtattgt aattcagctg 3900
ggctacctgg acattgttat gtattaataa atgctttgct ttcttctaaa gatctttaag 3960
tgctgtttaa acaaccgaca accactttgc ggacttcctt tcaagagaat tcaataaggt 4020
taattcctaa ttgaaatccg aagataagat tcccacacac ttgtggctga tatcaaaagg 4080
ctactgccta tttaaacaca tctctggaga ctgagaaaat cagacctcca agcatgaaga 4140
agcctgagct tactgctact tctgttgaga agttcctcat cgagaagttc gattctgtgt 4200
ctgatcttat gcagctctct gagggtgagg aatcaagagc tttctctttc gatgttggtg 4260
gaagaggata cgttctcaga gttaactctt gcgctgacgg attctacaag gatagatacg 4320
tgtacagaca cttcgcttca gctgctctcc ctatccctga agttcttgat atcggagagt 4380
tctctgagtc tcttacctac tgtatctcaa gaagggctca gggtgttact cttcaagatc 4440
ttcctgagac tgagcttcct gctgttcttc aacctgttgc tgaggctatg gatgctatcg 4500
ctgctgctga tctttctcaa acttctggat tcggaccttt cggtcctcag ggaatcggac 4560
agtacactac ttggagagat ttcatctgcg ctatcgctga tcctcatgtt taccattggc 4620
agaccgttat ggatgatacc gtttctgctt ctgttgctca agctcttgat gagcttatgc 4680
tttgggctga ggattgtcct gaggttagac atcttgttca cgctgatttc ggatctaaca 4740
acgttctcac cgataacgga agaatcaccg ctgttatcga ttggtctgag gctatgttcg 4800
gagattctca atacgaggtg gccaacatat tcttttggag gccttggctt gcttgtatgg 4860
aacaacagac tagatacttc gagagaaggc atcctgagct tgctggatct cctagactta 4920
gagcttacat gcttaggatc ggacttgatc agctttacca gtctctcgtt gatggaaact 4980
tcgatgatgc tgcttgggct cagggaagat gtgatgctat cgttagatct ggtgctggaa 5040
ctgttggaag aactcaaatc gctagaagat ctgctgctgt ttggactgat ggatgtgttg 5100

-continued

```
aagttctcgc tgattctgga aacagaaggc cttctactag acctagagcc aagaagtgaa   5160
gatcggcggc aatagcttct tagcgccatc ccgggttgat cctatctgtg ttgaaatagt   5220
tgcggtgggc aaggctctct ttcagaaaga caggcggcca aaggaaccca aggtgaggtg   5280
ggctatggct ctcagttcct tgtggaagcg cttggtctaa ggtgcagagg tgttagcggg   5340
atgaagcaaa agtgtccgat tgtaacaaga tatgttgatc ctacgtaagg atattaaagt   5400
atgtattcat cactaatata atcagtgtat tccaatatgt actacgattt ccaatgtctt   5460
tattgtcgcc gtatgtaatc ggcgtcacaa aataatcccc ggtgactttc ttttaatcca   5520
ggatgaaata atatgttatt ataatttttg cgatttggtc cgttatagga attgaagtgt   5580
gcttgcggtc gccaccactc ccatttcata attttacatg tatttgaaaa ataaaaattt   5640
atggtattca atttaaacac gtatacttgt aaagaatgat atcttgaaag aaatatagtt   5700
taaatattta ttgataaaat aacaagtcag gtattatagt ccaagcaaaa acataaattt   5760
attgatgcaa gtttaaattc agaaatattt caataactga ttatatcagc tggtacattg   5820
ccgtagatga aagactgagt gcgatattat ggtgtaatac atagtttaaa cgggcccaag   5880
actcccgccc atctctctat gcccgggaca agtgccaccc cacagtgggg caggatgagg   5940
atgaccagtc agttttactt cccttaattt tctatgtact ttcataatta cttatgttat   6000
tttcttcatg agttttaatg caaattacta tatggactct agtgaaaacg ttcagaatcc   6060
tataaacatg actactgaga cgaacttgag agtagttttg atcatacaca cgtttcatgt   6120
ggtacttgag agttactaat ttttgtcatc ttcgtataag tagtaaaaga tactacaaga   6180
atagtttagt agaaaatact agcggtaggt gaagatttgt cgctatgtac tattattgtc   6240
tagtaacttg agtaacaatt tcgtggtcta aatatcaaat aaaaatggat gagtggttca   6300
ccaaatctag gcatcaaaac tattaatgtc attgtctaga tcttaggtga caccacattt   6360
cgaatattta ttggtaattg agatgttaaa gtaccaatat ttgacttaat aaactaaaag   6420
attttggctt tatcaaatgt agacattgat gacatatcgt tgtcattatc ttgagtatat   6480
acaagtcgat caattaggtg aaagtttagt gtctcgtggt tggtaaacga ttaatacagt   6540
agtatatttt atccaaagac aaaatccaaa tcatttcacc agtatgaata gtattatttt   6600
atcttaaaag ctaaaatctt aaaaaccaag gtagcaccca cgttgagcta gacgatcaaa   6660
tcgatttctg ctttgtccaa tttaccaagc tatttaaagc caaataattg aaatataggt   6720
aggtcgttat attaggctaa gatttatctc aaatgcttaa ctaaaggaat aacaagggat   6780
tctagttgtg tggttttata agattggtcc aatttcactt aagtttgttt attgtagaat   6840
tttatatgtg aataatttga attccaattg aaaagatatt atagtaaaag aaaaaatagt   6900
gcgaacaaaa aactttaatc ccataaaaag aaaaagaaaa atgaaaagtt cttctaacat   6960
ccatattttg catcatatca taaagataag aaagatacat atcatagacg tacagataaa   7020
caaacatatc atcatttgtg aaatacatag tacaataatt tgcttttaaa tagagtttaa   7080
gtcacacaca ctgacacaca cgataaaacg ataatgtctg caaaaacact ttaatcccat   7140
tgcctagagg acagcttctc cactttgtct ttaaggttgg ttttgccgtg ttgtttttat   7200
ctttatataa tgatctattt tttggattat gaaatgaatt cacacatttt aattatttaa   7260
gaagatccat atacaggttt ataacagtac taagtgatga ttatttttttg tttttgcata   7320
gtttagttta ttgggtaaac attcattacg tgtctcttta tacgaatcac ccatccaaaa   7380
tttcaagtag tcttttagtt catttattat ttcataacta tttgacttat tgatttgaca   7440
```

agaaacaaca aaagtgttga cttattgata gattgtggga tcataaaagt aattaagcgt 7500
caaccacgac ccacaacaac aaagcacatg ttatacatta atatctcgtt tacttaatta 7560
cagttttcag aatgccgttt catgtcttgt cactggcgat gttattatca tgttggacaa 7620
tattcgactg ttgtcgtttt tacattttcg tattgactaa aactaaaaaa acaaaactct 7680
gtttcaggtt gggcctagga tccacattgt acacacattt gcttaagtct atggaggcgc 7740
aaggttttaa gtctgtggtt gctgttatag gccttccaaa cgatccatct gttaggttgc 7800
atgaggcttt gggatacaca gcccggggta cattgcgcgc agctggatac aagcatggtg 7860
gatggcatga tgttggtttt tggcaaaggg attttgagtt gccagctcct ccaaggccag 7920
ttaggccagt tacccagatc taatatcaaa atctatttag aaatacacaa tattttgttg 7980
caggcttgct ggagaatcga tctgctatca taaaaattac aaaaaaattt tatttgcctc 8040
aattatttta ggattggtat taaggacgct taaattattt gtcgggtcac tacgcatcat 8100
tgtgattgag aagatcagcg atacgaaata ttcgtagtac tatcgataat ttatttgaaa 8160
attcataaga aaagcaaacg ttacatgaat tgatgaaaca atacaaagac agataaagcc 8220
acgcacattt aggatattgg ccgagattac tgaatattga gtaagatcac ggaatttctg 8280
acaggagcat gtcttcaatt cagcccaaat ggcagttgaa atactcaaac cgccccatat 8340
gcaggagcgg atcattcatt gtttgtttgg ttgcctttgc caacatggga gtccaaggtt 8400
gtttaaacat ttaaataccc tgccaagctt gaggtagcct ccaatttgac ggtgccgcca 8460
gcgacgccgt ctggaactgt cctttttgag gaccactccg tttgtggaga tcatgagagt 8520
ccatgctcaa caccgtgcac tagggacagg attgaagact cccgcccatc tcactaggga 8580
caggattgcc accccacagt ggggcctaga aagactggag ttgcagagtt tgtgtcttct 8640
agattaatcc tccaaacttt tgattaacca aaaaaattat caaactaaca tgttctcctt 8700
ttttctttag aaattctaac gaatttatct ttatactgat ttgaatatac ttaatttggt 8760
catttggatg ccctttacaa cctccttacc aaactattga tcacagtttc tattgctaaa 8820
atcaccaaca aaacgcatgt cgccattcat aattatggtt tcacacctac aactaggcta 8880
ataagtaaat aagtagacaa ctagactcag gtttgaaaaa accataaaag ccatatagcg 8940
ttttctcatt gaaactgcga acacgatcgt gtgaatgttg cagtttctag ttttgataca 9000
aacaaacaaa aacacaattt aatcttagat taaaaagaaa aaagagaacg gagcccacta 9060
gccactcctt caaacgtgtc ttaccaactc tcttctagaa acaaattagg cttcaccttc 9120
ctcttccaac ctctctctct ctctctctct ctttttctca aaccatctct ccataaagcc 9180
ctaatttctt catcacaaga atcagaagaa gaaagatgga cctgcatcta attttcggtc 9240
caacttgcac aggaaagacg acgaccgcga tagctcttgc ccagcagaca gggcttccag 9300
tcctttcgct tgatcgggtc caatgctgtc ctcaactatc aaccggaagc ggacgaccaa 9360
cagtggaaga actgaaagga acgacgcgtc tctaccttga tgatcggcct ctggtggagg 9420
gtatcatcgc agccaagcaa gctcatcata ggctgatcga ggaggtgtat aatcatgagg 9480
ccaacggcgg gcttattctt gagggaggat ccacctcgtt gctcaactgc atggcgcgaa 9540
acagctattg gagtgcagat tttcgttggc atattattcg ccacaagtta cccgaccaag 9600
agaccttcat gaaagcggcc aaggccagag ttaagcagat gttgcacccc gctgcaggcc 9660
attctattat tcaagagttg gtttatcttt ggaatgaacc tcggctgagg cccattctga 9720
aagagatcga tggatatcga tatgccatgt tgtttgctag ccagaaccag atcacggcag 9780
atatgctatt gcagcttgac gcaaatatgg aaggtaagtt gattaatggg atcgctcagg 9840
agtatttcat ccatgcgcgc caacaggaac agaaattccc ccaagttaac gcagccgctt 9900
tcgacggatt cgaaggtcat ccgttcggaa tgtattagaa atcaccagtc tctctctaca 9960
aatctatctc tctctatttt tctccagaat aatgtgtgag tagttcccag ataagggaat 10020
tagggttctt atagggtttc gctcatgtgt tgagcatata agaaaccctt agtatgtatt 10080
tgtatttgta aaatacttct atcaataaaa tttctaattc ctaaaaccaa aatccagtgt 10140
ttaaacgagt ccatgctcaa caccgtgcac tagggacagg attgaagact cccgcccatc 10200
tcactaggga caggattgcc accccacagt ggggcctaga aagactggag ttgcagacat 10260
taaggatgac cagttcgtaa aggtcctgcg gtgtctattg cttttcatag gttaataagt 10320
gtttgctaga ctgtggtgaa aggcctatcc gaagtaaggc cggccggatc cttcatcttt 10380
ggacaaggga ataaagactc cccacttgct actaagaaca atacctaagt tgcccagaca 10440
tgactgtacc cattcagaga cctaccaccc attagggcta tgacactaac actagcccct 10500
ggaggttgac catgctaggc agtgggggtc tcacctatga cccactcaga taggggttta 10560
aaccagtggg tgggatctca gcctcatata ggtgtttgtg gtgagctttc tcctagacaa 10620
gagaaccctg aagaacagca agaaccagct aatatgatat gtagacatag tgggttgctc 10680
aaattttgtg tttagtcata ttagaattga cctcagtgac cactcagaaa gtgcccaagc 10740
ccatctatag gggccaaagt gctattgact ggtgtgtctg tgaattgttc ctccctacag 10800
agttggtgct gatatatcct agcattcttt ggaaaaccta gctagggact gtcaagtgta 10860
agatacctcc tgaattggag ggaacactag ctgccctgta ccttctggct agtaccttac 10920
accctgaatg ggttaggggg tctattattt gctggaaata taccagtttc agtagggctg 10980
ctgccttagg tcccacaagg tgtaacatgt gctcaatagt tgcactacca catgcacgtg 11040
aacttaatga tgttatagcc acaacaccaa ccttggtttg cagtttgaca tccctctgga 11100
atgggtgtag tcatcttgct ctggatctgc ctgaatcatt ggggctgtat gcagcctggg 11160
cttaaagtga agaatgggat gtcccagaaa tattttgggt gagaagaatc ctggagtaga 11220
tggtgacctg actatccctg tcctatgggc acaatctatc atcagatatt gcattcaaag 11280
ggctatcatg ggatcaagtc ctaagtcaac tgttgtttac ctggcagaca ttcatctagg 11340
agttctcttt tatgccaccc cacagtgatc cgccttttgc agtttatcca ctagggacag 11400
gattgccacc ccacagtggg gcctctatgc ccgggacaag tgtaaaatat agagtatagg 11460
ggttatcatc acagagaagc tattgctgga gggcctctgt tatttcctct ccatgccact 11520
cccattttta acctaccaac tgaaatccca agggagactc caccctgtaa ctagagtcct 11580
cagaggtgag ccatcccata ttaacaaatg ggcattaggg ctaggatgcc aagggatacc 11640
tgaaatggga agttgtgggg ctgagtcctc ctgggaatca gagataatat gtaaacagtt 11700
tgttgagaga ttgatgagag ctgactttga gaggtggcca tgctccctgg tcctcaatag 11760
ggaaggcact acacaagaaa cctgggtttg atcaactgca ctgtgtccta ctcacacatt 11820
gtgtgcctgg aaaaatgtta cttagtattt ggagggcctc cagaaccccc ctgggtgcaa 11880
gactgggtgc tagtgactgg gtgaatgagt cttggacaca gtggccttgt ctaggttgtg 11940
tgaggtggct aggcatcatg gcaatacctc ataattgatg agtgaggaaa caagactaag 12000
tccttgactc ctcttattac atgacctggt ggatattatg tttaaactct gcaagctgga 12060
atgagtactg ggtgcagatc ccctgggatt ctggctacaa aggtgaatga tagctagtct 12120
gtttattagt agccaaaaaa gtcagtgagg ggtgagtgcc ctgggatgtt gttaagttca 12180

```
cattgcacac ttggagaccc tctccatcca gtaacatacc agagaaaact gaccaagccc  12240
tcatgggtgt atgggaacaa caaacctcct ggctacttca agggcacata acaccagcaa  12300
ggagcctgtc ataaccacca tctcaaacaa tagaacttcc taagtgaagc aatgacttca  12360
aatctacttg aaggcatgga gtataagcca tgttcctttc agaggggact gtacttctgt  12420
agattacttt ccctcattaa ccagatctgg ccggccgcat gccttgctgg tcgatcatgt  12480
tggccactct tgtttatcta tcattcctcg ttggtccagt cacagttcta aaagtctatg  12540
gtgttcctta cattgtaagt ttcatatatt tcattattat atcattgcta atataatttg  12600
tttttgacat aaagttttgg aaaaatttca gatctttgta atgtggttgg acgctgtcac  12660
gtacttgcat catcatggtc acgatgataa gttgccttgg tacagaggca aggtaagtag  12720
atcaacatta atttataaga agcaacaatg attagtattt gattaatcta aattattgat  12780
gttttgtgta caataatagg aatggagtta tttacgtgga ggattaacaa ctattgatag  12840
agattacggg atcttcaaca acattcatca cgatattgga actcacgtga tccatcatct  12900
tttcccacaa atccctcact atcacttggt tgatgccgtg agtgatctcg ctctctctct  12960
agtttcattt gattaaaatt aaagggtgat taattactaa attagtgatc ttaattaatg  13020
atatgcgaca gacgaaatca gctaaacatg tgttgggaag atactacaga gaaccaaaga  13080
cgtcaggagc aataccgatc cacttggtgg aaagtttggt ggcaagtatt aagaaagatc  13140
attacgtcag tgacactggt gatattgtct tctacgagac agatccagat ctctacgttt  13200
atgcttctga caaatccaaa atcaactaac ctttcttcct agctctattt aggaataaaa  13260
cagtcctttg gtttttactt atttctggtt gtttttaagt taaatgtact cgtgaaactt  13320
tttttaatta aatgtattta cattacaaat caagttttg ttcgttttct ttatgttttt  13380
agttacaata aataaaggtc ttaaaaactt tttgttggtg gggacaaaag aaaaagttcg  13440
actgagagag tcgacaaaat gc                                          13462
```

<210> SEQ ID NO 83
<211> LENGTH: 13462
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
tttttaatt taatttattt ttttaatcgg agaaaaaaat taagaaacca aaaaacagtt     60
ttaatcatgg cctcatgttg gggttgagtt ttatattctg ataagaatcc catcttaaaa    120
accccgttaa acatgctctt accatctgct tcgaaaatga tatgttattg acaattccaa    180
tttcattttt atgaaaataa aataatagtt tattttataa ctgagggtgg ttgcaggaga    240
ataagccatc ggacacacca ccagaaccat ggccatgttg aaaacgacga gtcttgggtt    300
ccggtaatct ttccctctct catatttttt ttcttttttt tgaaattctt tcattttaat    360
tttcttagga ttctatgtat ttattttaat caatcctttt tccagtttga ggctaggacg    420
accacttgtc agatttgtcg tttagctgta gtaaacaact gatttaaatt gtttatagta    480
ctgtagttaa ctttaacaac ggaccactta tattcgagcc attggcataa aatgattctt    540
ctcgaaattc gtttactttt cttagtattt ttcaattttg gagtttacgt agaactaata    600
aaaagaaaaa cttataaaca caccacatgc aatgaataaa ttcgaatata taaccatact    660
gttaaatatt aatttacatt ttaatcttaa ttttgcattc cagttgccag aaaaattata    720
```

-continued

```
caagaatttg tcccacagta cacggatgct cagatacact gtccctctcc ccatgctcgc    780
ttaccctctc tatctggtaa atcctaattc ctaatttttc ttcctgatta taattacaat    840
tttgaatttt tagattttga gtattaacta aatataaatt aaatttgttt ggggatgact    900
acagtggtac agaagtcctg gtaaagaagg gtcacattat aacccataca gtagtttatt    960
tgccccaagc gagagaaagc ttattgcaac ttcaactact ggtaccgcct tttgcagttt   1020
atctctatgc ccgggacaag tggagtccat gctcaacacc gtgcaggatg aggatgacca   1080
ccgcggtagc gacttcgtgg gcgaggaaag cctttcgtcc aaggtggtcc ctcctcgcaa   1140
tcttgttgga tggtgaatat tataaaagcc tgcccttctc gcgggtgttt aaacgtcgac   1200
ctgcaggtca acggatcagg atattcttgt ttaagatgtt gaactctatg gaggtttgta   1260
tgaactgatg atctaggacc ggataagttc ccttcttcat agcgaactta ttcaaagaat   1320
gttttgtgta tcattcttgt tacattgtta ttaatgaaaa aatattattg gtcattggac   1380
tgaacacgag tgttaaatat ggaccaggcc ccaaataaga tccattgata tatgaattaa   1440
ataacaagaa taaatcgagt caccaaacca cttgcctttt ttaacgagac ttgttcacca   1500
acttgataca aaagtcatta tcctatgcaa atcaataatc atacaaaaat atccaataac   1560
actaaaaaat taaaagaaat ggataatttc acaatatgtt atacgataaa gaagttactt   1620
ttccaagaaa ttcactgatt ttataagccc acttgcatta gataaatggc aaaaaaaaac   1680
aaaaaggaaa agaaataaag cacgaagaat tctagaaaat acgaaatacg cttcaatgca   1740
gtgggaccca cggttcaatt attgccaatt ttcagctcca ccgtatattt aaaaaataaa   1800
acgataatgc taaaaaaata taaatcgtaa cgatcgttaa atctcaacgg ctggatctta   1860
tgacgaccgt tagaaattgt ggttgtcgac gagtcagtaa taaacggcgt caaagtggtt   1920
gcagccggca cacacgagtc gtgtttatca actcaaagca caaatacttt tcctcaacct   1980
aaaaataagg caattagcca aaaacaactt tgcgtgtaaa caacgctcaa tacacgtgtc   2040
attttattat tagctattgc ttcaccgcct tagctttctc gtgacctagt cgtcctcgtc   2100
ttttcttctt cttcttctat aaaacaatac ccaaagagct cttcttcttc acaattcaga   2160
tttcaatttc tcaaaatctt aaaaactttc tctcaattct ctctaccgtg atcaaggtaa   2220
atttctgtgt tccttattct ctcaaaatct tcgattttgt tttcgttcga tcccaatttc   2280
gtatatgttc tttggtttag attctgttaa tcttagatcg aagacgattt tctgggtttg   2340
atcgttagat atcatcttaa ttctcgatta gggtttcata gatatcatcc gatttgttca   2400
aataatttga gttttgtcga ataattactc ttcgatttgt gatttctatc tagatctggt   2460
gttagtttct agtttgtgcg atcgaatttg tcgattaatc tgagtttttc tgattaacag   2520
atggcttcat ctgagaacgt tatcactgag ttcatgaggt tcaaggtgag gatggaaggt   2580
actgttaacg gacatgagtt cgagatcgag ggtgagggtg aaggtagacc ttacgaggga   2640
cataacaccg ttaagcttaa ggttacaaag ggtggacctc ttcctttcgc ttgggatatc   2700
ctttctcctc aattccaata cggaagcaag gtaagtttgt ggattcttcg tccatgtgat   2760
ctttgagttt ctttagagct tgtgagggat tagtaagtaa caatgcttga gttttttgct   2820
gctgggcttc gaaaagtttg tcacttgttg gtttgatcca caaggtcttc ttctccatag   2880
ctactagaca tgttttagct taagattcaa gtttatatat gccttgtgga ttaatcattg   2940
cctgattctt ccgtgtcatc tctgagttta tttagagctt ggaagtggtg tagtaataac   3000
taacaatact cttgataagt tgtagcaatg ctcttgatta gtggatgtaa tatgatgttg   3060
ataagatata tgaggcacag aaccaaaagt ggtgcttcca ctagacccgt tttagccta    3120
```

```
aggttcaagt ttataccttg tagatgtttc tgtattgtct gattcttccc tgtgatattt   3180
gaatttctta gagctttgga agtgatatag gaacaatgct cttgtgtgtt tgtctctatg   3240
aagattatcg ctgtcgtgtt tcatccgagt gtgcgggatt ttttgctgct gggtttagcc   3300
tttcttcaaa aagttattac ttgttagttt tattgttttg gtcttgataa gagatgttag   3360
gacagacatg gtgcttcttg tctatagcca ctagacctat tttagcataa ggttaacgaa   3420
attctctcta catacttgt ggatttgttt acattgcctg atctttcctg tgatcgctgt   3480
catgtttctt tggaatgatt gatgtttata aatggaaaaa tctttgtgca gaagactccc   3540
gcccatctct ctatgcccgg gacaagtgcc accccacagt ggggcaggat gaggatgacc   3600
accatggggt cgcagcgtgt gcgtgtccgt cgtacgttct ggccggccgg gccttgggcg   3660
cgcgatcaga agcgttgcgt tggcgtgtgt gtgcttctgg tttgctttaa ttttaccaag   3720
tttgtttcaa ggtggatcgc gtggtcaagg cccgtgtgct ttaaagaccc accggcactg   3780
gcagtgagtg ttgctgcttg tgtaggcttt ggtacgtatg ggctttattt gcttctggat   3840
gttgtgtact acttgggttt gttgaattat tatgagcagt tgcgtattgt aattcagctg   3900
ggctacctgg acattgttat gtattaataa atgctttgct ttcttctaaa gatctttaag   3960
tgctgtttaa acaaccgaca accactttgc ggacttcctt tcaagagaat tcaataaggt   4020
taattcctaa ttgaaatccg aagataagat tcccacacac ttgtggctga tatcaaaagg   4080
ctactgccta tttaaacaca tctctggaga ctgagaaaat cagacctcca agcatgaaga   4140
agcctgagct tactgctact tctgttgaga agttcctcat cgagaagttc gattctgtgt   4200
ctgatcttat gcagctctct gagggtgagg aatcaagagc tttctctttc gatgttggtg   4260
gaagaggata cgttctcaga gttaactctt gcgctgacgg attctacaag gatagatacg   4320
tgtacagaca cttcgcttca gctgctctcc ctatccctga agttcttgat atcggagagt   4380
tctctgagtc tcttacctac tgtatctcaa gaagggctca gggtgttact cttcaagatc   4440
ttcctgagac tgagcttcct gctgttcttc aacctgttgc tgaggctatg gatgctatcg   4500
ctgctgctga tctttctcaa acttctggat tcggaccttt cggtcctcag ggaatcggac   4560
agtacactac ttggagagat ttcatctgcg ctatcgctga tcctcatgtt taccattggc   4620
agaccgttat ggatgatacc gtttctgctt ctgttgctca agctcttgat gagcttatgc   4680
tttgggctga ggattgtcct gaggttagac atcttgttca cgctgatttc ggatctaaca   4740
acgttctcac cgataacgga agaatcaccg ctgttatcga ttggtctgag gctatgttcg   4800
gagattctca atacgaggtg gccaacatat tcttttggag gccttggctt gcttgtatgg   4860
aacaacagac tagatacttc gagagaaggc atcctgagct tgctggatct cctagactta   4920
gagcttacat gcttaggatc ggacttgatc agctttacca gtctctcgtt gatggaaact   4980
tcgatgatgc tgcttgggct cagggaagat gtgatgctat cgttagatct ggtgctggaa   5040
ctgttggaag aactcaaatc gctagaagat ctgctgctgt ttggactgat ggatgtgttg   5100
aagttctcgc tgattctgga aacagaaggc cttctactag acctagagcc aagaagtgaa   5160
gatcggcggc aatagcttct tagcgccatc ccgggttgat cctatctgtg ttgaaatagt   5220
tgcggtgggc aaggctctct ttcagaaaga caggcggcca aaggaaccca aggtgaggtg   5280
ggctatggct ctcagttcct tgtggaagcg cttggtctaa ggtgcagagg tgttagcggg   5340
atgaagcaaa agtgtccgat tgtaacaaga tatgttgatc ctacgtaagg atattaaagt   5400
atgtattcat cactaatata atcagtgtat tccaatatgt actacgattt ccaatgtctt   5460
```

-continued

```
tattgtcgcc gtatgtaatc ggcgtcacaa aataatcccc ggtgactttc ttttaatcca   5520
ggatgaaata atatgttatt ataatttttg cgatttggtc cgttatagga attgaagtgt   5580
gcttgcggtc gccaccactc ccatttcata attttacatg tatttgaaaa ataaaaattt   5640
atggtattca atttaaacac gtatacttgt aaagaatgat atcttgaaag aaatatagtt   5700
taaatattta ttgataaaat aacaagtcag gtattatagt ccaagcaaaa acataaattt   5760
attgatgcaa gtttaaattc agaaatattt caataactga ttatatcagc tggtacattg   5820
ccgtagatga aagactgagt gcgatattat ggtgtaatac atagtttaaa cgggcccaag   5880
actcccgccc atctctctat gcccgggaca agtgccaccc cacagtgggg caggatgagg   5940
atgaccagtc agttttactt cccttaattt tctatgtact ttcataatta cttatgttat   6000
tttcttcatg agttttaatg caaattacta tatggactct agtgaaaacg ttcagaatcc   6060
tataaacatg actactgaga cgaacttgag agtagttttg atcatacaca cgtttcatgt   6120
ggtacttgag agttactaat ttttgtcatc ttcgtataag tagtaaaaga tactacaaga   6180
atagtttagt agaaaatact agcggtaggt gaagatttgt cgctatgtac tattattgtc   6240
tagtaacttg agtaacaatt tcgtggtcta aatatcaaat aaaaatggat gagtggttca   6300
ccaaatctag gcatcaaaac tattaatgtc attgtctaga tcttaggtga caccacattt   6360
cgaatattta ttggtaattg agatgttaaa gtaccaatat ttgacttaat aaactaaaag   6420
attttggctt tatcaaatgt agacattgat gacatatcgt tgtcattatc ttgagtatat   6480
acaagtcgat caattaggtg aaagtttagt gtctcgtggt tggtaaacga ttaatacagt   6540
agtatatttt atccaaagac aaaatccaaa tcatttcacc agtatgaata gtattatttt   6600
atcttaaaag ctaaaatctt aaaaaccaag gtagcaccca cgttgagcta gacgatcaaa   6660
tcgatttctg ctttgtccaa tttaccaagc tatttaaagc caaataattg aaatataggt   6720
aggtcgttat attaggctaa gatttatctc aaatgcttaa ctaaaggaat aacaagggat   6780
tctagttgtg tggttttata agattggtcc aatttcactt aagtttgttt attgtagaat   6840
tttatatgtg aataatttga attccaattg aaaagatatt atagtaaaag aaaaaatagt   6900
gcgaacaaaa aactttaatc ccataaaaag aaaaagaaaa atgaaaagtt cttctaacat   6960
ccatattttg catcatatca taaagataag aaagatacat atcatagacg tacagataaa   7020
caaacatatc atcatttgtg aaatacatag tacaataatt tgcttttaaa tagagtttaa   7080
gtcacacaca ctgacacaca cgataaaacg ataatgtctg caaaaacact ttaatcccat   7140
tgcctagagg acagcttctc cactttgtct ttaaggttgg ttttgccgtg ttgtttttat   7200
ctttatataa tgatctattt tttggattat gaaatgaatt cacacatttt aattatttaa   7260
gaagatccat atacaggttt ataacagtac taagtgatga ttatttttg tttttgcata   7320
gtttagttta ttgggtaaac attcattacg tgtctcttta tacgaatcac ccatccaaaa   7380
tttcaagtag tcttttagtt catttattat ttcataacta tttgacttat tgatttgaca   7440
agaaacaaca aaagtgttga cttattgata gattgtggga tcataaaagt aattaagcgt   7500
caaccacgac ccacaacaac aaagcacatg ttatacatta atatctcgtt tacttaatta   7560
cagttttcag aatgccgttt catgtcttgt cactggcgat gttattatca tgttggacaa   7620
tattcgactg ttgtcgtttt tacattttcg tattgactaa aactaaaaaa acaaaactct   7680
gtttcaggtt gggcctagga tccacattgt acacacattt gcttaagtct atggaggcgc   7740
aaggttttaa gtctgtggtt gctgttatag gccttccaaa cgatccatct gttaggttgc   7800
atgaggcttt gggatacaca gcccggggta cattgcgcgc agctggatac aagcatggtg   7860
```

gatggcatga tgttggtttt tggcaaaggg atttgagtt gccagctcct ccaaggccag 7920
ttaggccagt tacccagatc taatatcaaa atctatttag aaatacacaa tattttgttg 7980
caggcttgct ggagaatcga tctgctatca taaaaattac aaaaaaattt tatttgcctc 8040
aattatttta ggattggtat taaggacgct taaattattt gtcgggtcac tacgcatcat 8100
tgtgattgag aagatcagcg atacgaaata ttcgtagtac tatcgataat ttatttgaaa 8160
attcataaga aaagcaaacg ttacatgaat tgatgaaaca atacaaagac agataaagcc 8220
acgcacattt aggatattgg ccgagattac tgaatattga gtaagatcac ggaatttctg 8280
acaggagcat gtcttcaatt cagcccaaat ggcagttgaa atactcaaac cgccccatat 8340
gcaggagcgg atcattcatt gtttgtttgg ttgcctttgc caacatggga gtccaaggtt 8400
gtttaaacat ttaaataccc tgccaagctt gaggtagcct ccaatttgac ggtgccgcca 8460
gcgacgccgt ctggaactgt cctttttgag gaccactccg tttgtggaga tcatgagagt 8520
ccatgctcaa caccgtgcac tagggacagg attgaagact cccgcccatc tcactaggga 8580
caggattgcc accccacagt ggggcctaga aagactggag ttgcagagtt tgtgtcttct 8640
agattaatcc tccaaacttt tgattaacca aaaaaattat caaactaaca tgttctcctt 8700
ttttctttag aaattctaac gaatttatct ttatactgat ttgaatatac ttaatttggt 8760
catttggatg ccctttacaa cctccttacc aaactattga tcacagtttc tattgctaaa 8820
atcaccaaca aaacgcatgt cgccattcat aattatggtt tcacacctac aactaggcta 8880
ataagtaaat aagtagacaa ctagactcag gtttgaaaaa accataaaag ccatatagcg 8940
ttttctcatt gaaactgcga acacgatcgt gtgaatgttg cagtttctag ttttgataca 9000
aacaaacaaa aacacaattt aatcttagat taaaaagaaa aaagagaacg gagcccacta 9060
gccactcctt caaacgtgtc ttaccaactc tcttctagaa acaaattagg cttcaccttc 9120
ctcttccaac ctctctctct ctctctctct ctttttctca aaccatctct ccataaagcc 9180
ctaatttctt catcacaaga atcagaagaa gaaagatgga cctgcatcta attttcggtc 9240
caacttgcac aggaaagacg acgaccgcga tagctcttgc ccagcagaca gggcttccag 9300
tcctttcgct tgatcgggtc caatgctgtc ctcaactatc aaccggaagc ggacgaccaa 9360
cagtggaaga actgaaagga acgacgcgtc tctaccttga tgatcggcct ctggtggagg 9420
gtatcatcgc agccaagcaa gctcatcata ggctgatcga ggaggtgtat aatcatgagg 9480
ccaacggcgg gcttattctt gagggaggat ccacctcgtt gctcaactgc atggcgcgaa 9540
acagctattg gagtgcagat tttcgttggc atattattcg ccacaagtta cccgaccaag 9600
agaccttcat gaaagcggcc aaggccagag ttaagcagat gttgcacccc gctgcaggcc 9660
attctattat tcaagagttg gtttatcttt ggaatgaacc tcggctgagg cccattctga 9720
aagagatcga tggatatcga tatgccatgt tgtttgctag ccagaaccag atcacggcag 9780
atatgctatt gcagcttgac gcaaatatgg aaggtaagtt gattaatggg atcgctcagg 9840
agtatttcat ccatgcgcgc caacaggaac agaaattccc ccaagttaac gcagccgctt 9900
tcgacggatt cgaaggtcat ccgttcggaa tgtattagaa atcaccagtc tctctctaca 9960
aatctatctc tctctatttt tctccagaat aatgtgtgag tagttcccag ataagggaat 10020
tagggttctt atagggtttc gctcatgtgt tgagcatata agaaaccctt agtatgtatt 10080
tgtatttgta aaatacttct atcaataaaa tttctaattc ctaaaaccaa aatccagtgt 10140
ttaaacgagt ccatgctcaa caccgtgcac tagggacagg attgaagact cccgcccatc 10200

-continued

```
tcactaggga caggattgcc accccacagt ggggcctaga aagactggag ttgcagacat  10260
taaggatgac cagttcgtaa aggtcctgcg gtgtctattg cttttcatag gttaataagt  10320
gtttgctaga ctgtggtgaa aggcctatcc gaagtaaggc cggccggatc cttcatcttt  10380
ggacaaggga ataaagactc cccacttgct actaagaaca atacctaagt tgcccagaca  10440
tgactgtacc cattcagaga cctaccaccc attagggcta tgacactaac actagcccct  10500
ggaggttgac catgctaggc agtgggggtc tcacctatga cccactcaga taggggttta  10560
aaccagtggg tgggatctca gcctcatata ggtgtttgtg gtgagctttc tcctagacaa  10620
gagaaccctg aagaacagca agaaccagct aatatgatat gtagacatag tgggttgctc  10680
aaattttgtg tttagtcata ttagaattga cctcagtgac cactcagaaa gtgcccaagc  10740
ccatctatag gggccaaagt gctattgact ggtgtgtctg tgaattgttc ctccctacag  10800
agttggtgct gatatatcct agcattcttt ggaaaaccta gctagggact gtcaagtgta  10860
agatacctcc tgaattggag ggaacactag ctgccctgta ccttctggct agtaccttac  10920
accctgaatg ggttaggggg tctattattt gctggaaata taccagtttc agtagggctg  10980
ctgccttagg tcccacaagg tgtaacatgt gctcaatagt tgcactacca catgcacgtg  11040
aacttaatga tgttatagcc acaacaccaa ccttggtttg cagtttgaca tccctctgga  11100
atgggtgtag tcatcttgct ctggatctgc ctgaatcatt ggggctgtat gcagcctggg  11160
cttaaagtga agaatgggat gtcccagaaa tattttgggt gagaagaatc ctggagtaga  11220
tggtgacctg actatccctg tcctatgggc acaatctatc atcagatatt gcattcaaag  11280
ggctatcatg ggatcaagtc ctaagtcaac tgttgtttac ctggcagaca ttcatctagg  11340
agttctcttt tatgccaccc cacagtgatc cgccttttgc agtttatcca ctaggacag  11400
gattgccacc ccacagtggg gcctctatgc ccgggacaag tgtaaaatat agagtatagg  11460
ggttatcatc acagagaagc tattgctgga gggcctctgt tatttcctct ccatgccact  11520
cccattttta acctaccaac tgaaatccca agggagactc caccctgtaa ctagagtcct  11580
cagaggtgag ccatcccata ttaacaaatg ggcattaggg ctaggatgcc aagggatacc  11640
tgaaatggga agttgtgggg ctgagtcctc ctgggaatca gagataatat gtaaacagtt  11700
tgttgagaga ttgatgagag ctgactttga gaggtggcca tgctccctgg tcctcaatag  11760
ggaaggcact acacaagaaa cctgggtttg atcaactgca ctgtgtccta ctcacacatt  11820
gtgtgcctgg aaaaatgtta cttagtattt ggagggcctc cagaaccccc ctgggtgcaa  11880
gactgggtgc tagtgactgg gtgaatgagt cttggacaca gtggccttgt ctaggttgtg  11940
tgaggtggct aggcatcatg gcaatacctc ataattgatg agtgaggaaa caagactaag  12000
tccttgactc ctcttattac atgacctggt ggatattatg tttaaactct gcaagctgga  12060
atgagtactg ggtgcagatc ccctgggatt ctggctacaa aggtgaatga tagctagtct  12120
gtttattagt agccaaaaaa gtcagtgagg ggtgagtgcc ctgggatgtt gttaagttca  12180
cattgcacac ttggagaccc tctccatcca gtaacatacc agagaaaact gaccaagccc  12240
tcatgggtgt atgggaacaa caaacctcct ggctacttca agggcacata acaccagcaa  12300
ggagcctgtc ataaccacca tctcaaacaa tagaacttcc taagtgaagc aatgacttca  12360
aatctacttg aaggcatgga gtataagcca tgttcctttc agaggggact gtacttctgt  12420
agattacttt ccctcattaa ccagatctgg ccggccgcat gcggtcgatc gtgttggcca  12480
ctcttgttta tctatcattc ctcgttggtc cagtcacagt tctaaaagtc tatggtgttc  12540
cttacattgt aagtttcata tatttcttta ttatatcatt gctaatataa tttgtttttg  12600
```

acataaaagt tttggaaaaa tttcagatct ttgtaatgtg gttggacgct gtcacgtact 12660
tgcatcatca tggtcacgat gataagctgc cttggtacag aggcaaggta agtagatcaa 12720
cattatttat aagaagcaat aatgattagt agttgaataa tctgaatttt tgatgttttt 12780
gtacaataat aggaatggag ttatttacgt ggaggattaa caactgttga tagagattac 12840
gggatcttca acaacattca tcacgatatt ggaactcacg tgatccatca tcttttccca 12900
caaatccctc actatcactt ggtcgatgcc gtgagtgatc tcgctctctc tctagtttca 12960
tttgattata ttaaagggtg attaattact aaattagtga tcttaattaa tgacatgcga 13020
cagacgaaag cagctaaaca tgtgttggga agatactaca gagaaccaaa gacgtcagga 13080
gcaataccga tccacttagt ggaaagtttg gtggcaagta ttaagaaaga tcattacgtc 13140
agtgacactg gtgatattgt cttctacgag acagatccag atctctacgt ttatgcttct 13200
gacaaatcca aaatcaatta atctttcttc ctagctctat ttaggaataa aacactcctt 13260
tggttttact tatttctggt tgtttttaag ttaaaaatgt actcgtgaaa cttttttttta 13320 ttaaatgtat ttacattaca aatcgtaaaa gtttttgttc gttttctcta tgtttttagt 13380
tacaaactta caatcaaaaa ggtcttaaaa actttttgat ggtgggacgg acaaaagaaa 13440
aagttcgact gagagtcgac aa 13462

<210> SEQ ID NO 84
<211> LENGTH: 13462
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 84
tatatatatt tgttttaatg gcttatttta ttgttaaatg gatacatcag cttgaaatat 60
ctacgaacat gcatcatttt cctagataca tttgtttgtt gctcaaaaaa tgaataacgt 120
agttaaacga gtgagattct tagcatctgc ctcgaaaacg atatgttatt gacaattcca 180
atttcatttt tatgaaaata aaataatagt ttattttata attgggggtg gttgcaggag 240
aataagccat cggacacacc accagaacca tggccatgtt gaaaacgacg agtcttgggt 300
tccggtaatc cccctctcat tatttttttt tcttttttttg aaactctttc attttaattt 360
tcttagaatt ctatgtattt attttaatca atccttttttc cagtgtgagg cttggacgac 420
cacttgtcag atttgtcgtt tagctgtagt aaacaactga tttaaattgt ttatggtact 480
gtagttaact ttaacaacgg gccacttata ttcgagccat tggcataaaa tgattcttct 540
cgaaattcgt ttacttttct tagtattttt cagttttgta gtttacgtag aactaataaa 600
aagaaaaaaa cttataaaca caccacatgc aatgaataaa ttcgaatata taaccatact 660
gttaaatatt aattaacatt ttaatcttaa ttttgcattc cagttgccag aaaaattata 720
caagaatttg tcccacagta cacggatgct cagatacact gtccctctcc ccatgctcgc 780
ttaccctctc tatctggtaa atcctaattc ctcatttttc ttcctgatta taattacaat 840
tttgaatttt tagattttga gtattaacta aatataaatt aaatttgttt ggggatgact 900
acagtggtac agaagtcctg gtaaagaagg gtcacattat aacccataca gtagtttatt 960
tgccccaagc gagagaaagc ttattgcaac ttcaactact ggtaccgcct tttgcagttt 1020
atctctatgc ccgggacaag tggagtccat gctcaacacc gtgcaggatg aggatgacca 1080
ccgcggtagc gacttcgtgg gcgaggaaag cctttcgtcc aaggtggtcc ctcctcgcaa 1140

-continued

```
tcttgttgga tggtgaatat tataaaagcc tgcccttctc gcgggtgttt aaacgtcgac   1200
ctgcaggtca acggatcagg atattcttgt ttaagatgtt gaactctatg gaggtttgta   1260
tgaactgatg atctaggacc ggataagttc ccttcttcat agcgaactta ttcaaagaat   1320
gttttgtgta tcattcttgt tacattgtta ttaatgaaaa aatattattg gtcattggac   1380
tgaacacgag tgttaaatat ggaccaggcc ccaaataaga tccattgata tatgaattaa   1440
ataacaagaa taaatcgagt caccaaacca cttgcctttt ttaacgagac ttgttcacca   1500
acttgataca aaagtcatta tcctatgcaa atcaataatc atacaaaaat atccaataac   1560
actaaaaaat taaaagaaat ggataatttc acaatatgtt atacgataaa gaagttactt   1620
ttccaagaaa ttcactgatt ttataagccc acttgcatta gataaatggc aaaaaaaaac   1680
aaaaaggaaa agaaataaag cacgaagaat tctagaaaat acgaaatacg cttcaatgca   1740
gtgggaccca cggttcaatt attgccaatt ttcagctcca ccgtatattt aaaaaataaa   1800
acgataatgc taaaaaaata taaatcgtaa cgatcgttaa atctcaacgg ctggatctta   1860
tgacgaccgt tagaaattgt ggttgtcgac gagtcagtaa taaacggcgt caaagtggtt   1920
gcagccggca cacacgagtc gtgtttatca actcaaagca caaatacttt tcctcaacct   1980
aaaaataagg caattagcca aaaacaactt tgcgtgtaaa caacgctcaa tacacgtgtc   2040
attttattat tagctattgc ttcaccgcct tagctttctc gtgacctagt cgtcctcgtc   2100
ttttcttctt cttcttctat aaaacaatac ccaaagagct cttcttcttc acaattcaga   2160
tttcaatttc tcaaaatctt aaaaactttc tctcaattct ctctaccgtg atcaaggtaa   2220
atttctgtgt tccttattct ctcaaaatct tcgattttgt tttcgttcga tcccaatttc   2280
gtatatgttc tttggtttag attctgttaa tcttagatcg aagacgattt tctgggtttg   2340
atcgttagat atcatcttaa ttctcgatta gggtttcata gatatcatcc gatttgttca   2400
aataatttga gttttgtcga ataattactc ttcgatttgt gatttctatc tagatctggt   2460
gttagtttct agtttgtgcg atcgaatttg tcgattaatc tgagtttttc tgattaacag   2520
atggcttcat ctgagaacgt tatcactgag ttcatgaggt tcaaggtgag gatggaaggt   2580
actgttaacg gacatgagtt cgagatcgag ggtgagggtg aaggtagacc ttacgaggga   2640
cataacaccg ttaagcttaa ggttacaaag ggtggacctc ttcctttcgc ttgggatatc   2700
ctttctcctc aattccaata cggaagcaag gtaagtttgt ggattcttcg tccatgtgat   2760
ctttgagttt ctttagagct tgtgagggat tagtaagtaa caatgcttga gtttttttgct   2820
gctgggcttc gaaaagtttg tcacttgttg gtttgatcca caaggtcttc ttctccatag   2880
ctactagaca tgttttagct taagattcaa gtttatatat gccttgtgga ttaatcattg   2940
cctgattctt ccgtgtcatc tctgagttta tttagagctt ggaagtggtg tagtaataac   3000
taacaatact cttgataagt tgtagcaatg ctcttgatta gtggatgtaa tatgatgttg   3060
ataagatata tgaggcacag aaccaaaagt ggtgcttcca ctagacccgt tttagcccta   3120
aggttcaagt ttataccttg tagatgtttc tgtattgtct gattcttccc tgtgatattt   3180
gaatttctta gagctttgga agtgatatag gaacaatgct cttgtgtgtt tgtctctatg   3240
aagattatcg ctgtcgtgtt tcatccgagt gtgcgggatt ttttgctgct gggtttagcc   3300
tttcttcaaa aagttattac ttgttagttt tattgttttg gtcttgataa gagatgttag   3360
gacagacatg gtgcttcttg tctatagcca ctagacctat tttagcataa ggttaacgaa   3420
attctctcta catacottgt ggatttgttt acattgcctg atctttcctg tgatcgctgt   3480
```

-continued

```
catgtttctt tggaatgatt gatgtttata aatggaaaaa tctttgtgca gaagactccc   3540
gcccatctct ctatgcccgg gacaagtgcc accccacagt ggggcaggat gaggatgacc   3600
accatggggt cgcagcgtgt gcgtgtccgt cgtacgttct ggccggccgg gccttgggcg   3660
cgcgatcaga agcgttgcgt tggcgtgtgt gtgcttctgg tttgctttaa ttttaccaag   3720
tttgtttcaa ggtggatcgc gtggtcaagg cccgtgtgct ttaaagaccc accggcactg   3780
gcagtgagtg ttgctgcttg tgtaggcttt ggtacgtatg ggctttattt gcttctggat   3840
gttgtgtact acttgggttt gttgaattat tatgagcagt tgcgtattgt aattcagctg   3900
ggctacctgg acattgttat gtattaataa atgctttgct ttcttctaaa gatctttaag   3960
tgctgtttaa acaaccgaca accactttgc ggacttcctt tcaagagaat tcaataaggt   4020
taattcctaa ttgaaatccg aagataagat tcccacacac ttgtggctga tatcaaaagg   4080
ctactgccta tttaaacaca tctctggaga ctgagaaaat cagacctcca agcatgaaga   4140
agcctgagct tactgctact tctgttgaga agttcctcat cgagaagttc gattctgtgt   4200
ctgatcttat gcagctctct gagggtgagg aatcaagagc tttctctttc gatgttggtg   4260
gaagaggata cgttctcaga gttaactctt gcgctgacgg attctacaag gatagatacg   4320
tgtacagaca cttcgcttca gctgctctcc ctatccctga agttcttgat atcggagagt   4380
tctctgagtc tcttacctac tgtatctcaa gaagggctca gggtgttact cttcaagatc   4440
ttcctgagac tgagcttcct gctgttcttc aacctgttgc tgaggctatg gatgctatcg   4500
ctgctgctga tctttctcaa acttctggat tcggaccttt cggtcctcag ggaatcggac   4560
agtacactac ttggagagat ttcatctgcg ctatcgctga tcctcatgtt taccattggc   4620
agaccgttat ggatgatacc gtttctgctt ctgttgctca agctcttgat gagcttatgc   4680
tttgggctga ggattgtcct gaggttagac atcttgttca cgctgatttc ggatctaaca   4740
acgttctcac cgataacgga agaatcaccg ctgttatcga ttggtctgag gctatgttcg   4800
gagattctca atacgaggtg gccaacatat tcttttggag gccttggctt gcttgtatgg   4860
aacaacagac tagatacttc gagagaaggc atcctgagct tgctggatct cctagactta   4920
gagcttacat gcttaggatc ggacttgatc agctttacca gtctctcgtt gatggaaact   4980
tcgatgatgc tgcttgggct cagggaagat gtgatgctat cgttagatct ggtgctggaa   5040
ctgttggaag aactcaaatc gctagaagat ctgctgctgt ttggactgat ggatgtgttg   5100
aagttctcgc tgattctgga aacagaaggc cttctactag acctagagcc aagaagtgaa   5160
gatcggcggc aatagcttct tagcgccatc ccgggttgat cctatctgtg ttgaaatagt   5220
tgcggtgggc aaggctctct ttcagaaaga caggcggcca aaggaaccca aggtgaggtg   5280
ggctatggct ctcagttcct tgtggaagcg cttggtctaa ggtgcagagg tgttagcggg   5340
atgaagcaaa agtgtccgat tgtaacaaga tatgttgatc ctacgtaagg atattaaagt   5400
atgtattcat cactaatata atcagtgtat tccaatatgt actacgattt ccaatgtctt   5460
tattgtcgcc gtatgtaatc ggcgtcacaa aataatcccc ggtgactttc ttttaatcca   5520
ggatgaaata atatgttatt ataattttg cgatttggtc cgttatagga attgaagtgt   5580
gcttgcggtc gccaccactc ccatttcata attttacatg tatttgaaaa ataaaaattt   5640
atggtattca atttaaacac gtatacttgt aaagaatgat atcttgaaag aaatatagtt   5700
taaatattta ttgataaaat aacaagtcag gtattatagt ccaagcaaaa acataaattt   5760
attgatgcaa gtttaaattc agaaatattt caataactga ttatatcagc tggtacattg   5820
ccgtagatga aagactgagt gcgatattat ggtgtaatac atagtttaaa cgggcccaag   5880
```

actcccgccc atctctctat gcccgggaca agtgccaccc cacagtgggg caggatgagg 5940
atgaccagtc agttttactt cccttaattt tctatgtact ttcataatta cttatgttat 6000
tttcttcatg agttttaatg caaattacta tatggactct agtgaaaacg ttcagaatcc 6060
tataaacatg actactgaga cgaacttgag agtagttttg atcatacaca cgtttcatgt 6120
ggtacttgag agttactaat ttttgtcatc ttcgtataag tagtaaaaga tactacaaga 6180
atagtttagt agaaaatact agcggtaggt gaagatttgt cgctatgtac tattattgtc 6240
tagtaacttg agtaacaatt tcgtggtcta aatatcaaat aaaaatggat gagtggttca 6300
ccaaatctag gcatcaaaac tattaatgtc attgtctaga tcttaggtga caccacattt 6360
cgaatattta ttggtaattg agatgttaaa gtaccaatat ttgacttaat aaactaaaag 6420
attttggctt tatcaaatgt agacattgat gacatatcgt tgtcattatc ttgagtatat 6480
acaagtcgat caattaggtg aaagtttagt gtctcgtggt tggtaaacga ttaatacagt 6540
agtatatttt atccaaagac aaaatccaaa tcatttcacc agtatgaata gtattatttt 6600
atcttaaaag ctaaaatctt aaaaaccaag gtagcaccca cgttgagcta gacgatcaaa 6660
tcgatttctg ctttgtccaa tttaccaagc tatttaaagc caaataattg aaatataggt 6720
aggtcgttat attaggctaa gatttatctc aaatgcttaa ctaaaggaat aacaagggat 6780
tctagttgtg tggttttata agattggtcc aatttcactt aagtttgttt attgtagaat 6840
tttatatgtg aataatttga attccaattg aaaagatatt atagtaaaag aaaaaatagt 6900
gcgaacaaaa aactttaatc ccataaaaag aaaaagaaaa atgaaaagtt cttctaacat 6960
ccatattttg catcatatca taaagataag aaagatacat atcatagacg tacagataaa 7020
caaacatatc atcatttgtg aaatacatag tacaataatt tgcttttaaa tagagtttaa 7080
gtcacacaca ctgacacaca cgataaaacg ataatgtctg caaaaacact ttaatcccat 7140
tgcctagagg acagcttctc cactttgtct ttaaggttgg ttttgccgtg ttgtttttat 7200
ctttatataa tgatctattt tttggattat gaaatgaatt cacacatttt aattatttaa 7260
gaagatccat atacaggttt ataacagtac taagtgatga ttattttttg tttttgcata 7320
gtttagttta ttgggtaaac attcattacg tgtctcttta tacgaatcac ccatccaaaa 7380
tttcaagtag tcttttagtt catttattat ttcataacta tttgacttat tgatttgaca 7440
agaaacaaca aaagtgttga cttattgata gattgtggga tcataaaagt aattaagcgt 7500
caaccacgac ccacaacaac aaagcacatg ttatacatta atatctcgtt tacttaatta 7560
cagttttcag aatgccgttt catgtcttgt cactggcgat gttattatca tgttggacaa 7620
tattcgactg ttgtcgtttt tacattttcg tattgactaa aactaaaaaa acaaaactct 7680
gtttcaggtt gggcctagga tccacattgt acacacattt gcttaagtct atggaggcgc 7740
aaggttttaa gtctgtggtt gctgttatag gccttccaaa cgatccatct gttaggttgc 7800
atgaggcttt gggatacaca gcccggggta cattgcgcgc agctggatac aagcatggtg 7860
gatggcatga tgttggtttt tggcaaaggg attttgagtt gccagctcct ccaaggccag 7920
ttaggccagt tacccagatc taatatcaaa atctatttag aaatacacaa tattttgttg 7980
caggcttgct ggagaatcga tctgctatca taaaaattac aaaaaaattt tatttgcctc 8040
aattatttta ggattggtat taaggacgct taaattattt gtcgggtcac tacgcatcat 8100
tgtgattgag aagatcagcg atacgaaata ttcgtagtac tatcgataat ttatttgaaa 8160
attcataaga aaagcaaacg ttacatgaat tgatgaaaca atacaaagac agataaagcc 8220

-continued

```
acgcacattt aggatattgg ccgagattac tgaatattga gtaagatcac ggaatttctg   8280
acaggagcat gtcttcaatt cagcccaaat ggcagttgaa atactcaaac cgccccatat   8340
gcaggagcgg atcattcatt gtttgtttgg ttgcctttgc caacatggga gtccaaggtt   8400
gtttaaacat ttaaataccc tgccaagctt gaggtagcct ccaatttgac ggtgccgcca   8460
gcgacgccgt ctggaactgt cctttttgag gaccactccg tttgtggaga tcatgagagt   8520
ccatgctcaa caccgtgcac tagggacagg attgaagact cccgcccatc tcactaggga   8580
caggattgcc accccacagt ggggcctaga aagactggag ttgcagagtt tgtgtcttct   8640
agattaatcc tccaaacttt tgattaacca aaaaaattat caaactaaca tgttctcctt   8700
ttttctttag aaattctaac gaatttatct ttatactgat ttgaatatac ttaatttggt   8760
catttggatg ccctttacaa cctccttacc aaactattga tcacagtttc tattgctaaa   8820
atcaccaaca aaacgcatgt cgccattcat aattatggtt tcacacctac aactaggcta   8880
ataagtaaat aagtagacaa ctagactcag gtttgaaaaa accataaaag ccatatagcg   8940
ttttctcatt gaaactgcga acacgatcgt gtgaatgttg cagtttctag ttttgataca   9000
aacaaacaaa aacacaattt aatcttagat taaaaagaaa aaagagaacg gagcccacta   9060
gccactcctt caaacgtgtc ttaccaactc tcttctagaa acaaattagg cttcaccttc   9120
ctcttccaac ctctctctct ctctctctct ctttttctca aaccatctct ccataaagcc   9180
ctaatttctt catcacaaga atcagaagaa gaaagatgga cctgcatcta attttcggtc   9240
caacttgcac aggaaagacg acgaccgcga tagctcttgc ccagcagaca gggcttccag   9300
tcctttcgct tgatcgggtc caatgctgtc ctcaactatc aaccggaagc ggacgaccaa   9360
cagtggaaga actgaaagga acgacgcgtc tctaccttga tgatcggcct ctggtggagg   9420
gtatcatcgc agccaagcaa gctcatcata ggctgatcga ggaggtgtat aatcatgagg   9480
ccaacggcgg gcttattctt gagggaggat ccacctcgtt gctcaactgc atggcgcgaa   9540
acagctattg gagtgcagat tttcgttggc atattattcg ccacaagtta cccgaccaag   9600
agaccttcat gaaagcggcc aaggccagag ttaagcagat gttgcacccc gctgcaggcc   9660
attctattat tcaagagttg gtttatcttt ggaatgaacc tcggctgagg cccattctga   9720
aagagatcga tggatatcga tatgccatgt tgtttgctag ccagaaccag atcacggcag   9780
atatgctatt gcagcttgac gcaaatatgg aaggtaagtt gattaatggg atcgctcagg   9840
agtatttcat ccatgcgcgc caacaggaac agaaattccc ccaagttaac gcagccgctt   9900
tcgacggatt cgaaggtcat ccgttcggaa tgtattagaa atcaccagtc tctctctaca   9960
aatctatctc tctctatttt tctccagaat aatgtgtgag tagttcccag ataagggaat  10020
tagggttctt atagggtttc gctcatgtgt tgagcatata agaaaccctt agtatgtatt  10080
tgtatttgta aaatacttct atcaataaaa tttctaattc ctaaaaccaa aatccagtgt  10140
ttaaacgagt ccatgctcaa caccgtgcac tagggacagg attgaagact cccgcccatc  10200
tcactaggga caggattgcc accccacagt ggggcctaga aagactggag ttgcagacat  10260
taaggatgac cagttcgtaa aggtcctgcg gtgtctattg cttttcatag gttaataagt  10320
gtttgctaga ctgtggtgaa aggcctatcc gaagtaaggc cggccggatc cttcatcttt  10380
ggacaaggga ataaagactc cccacttgct actaagaaca atacctaagt tgcccagaca  10440
tgactgtacc cattcagaga cctaccaccc attagggcta tgacactaac actagcccct  10500
ggaggttgac catgctaggc agtgggggtc tcacctatga cccactcaga taggggttta  10560
aaccagtggg tgggatctca gcctcatata ggtgtttgtg gtgagctttc tcctagacaa  10620
```

-continued

```
gagaaccctg aagaacagca agaaccagct aatatgatat gtagacatag tgggttgctc  10680
aaattttgtg tttagtcata ttagaattga cctcagtgac cactcagaaa gtgcccaagc  10740
ccatctatag gggccaaagt gctattgact ggtgtgtctg tgaattgttc ctccctacag  10800
agttggtgct gatatatcct agcattcttt ggaaaaccta gctagggact gtcaagtgta  10860
agatacctcc tgaattggag ggaacactag ctgccctgta ccttctggct agtaccttac  10920
accctgaatg ggttaggggg tctattattt gctggaaata taccagtttc agtagggctg  10980
ctgccttagg tcccacaagg tgtaacatgt gctcaatagt tgcactacca catgcacgtg  11040
aacttaatga tgttatagcc acaacaccaa ccttggtttg cagtttgaca tccctctgga  11100
atgggtgtag tcatcttgct ctggatctgc ctgaatcatt ggggctgtat gcagcctggg  11160
cttaaagtga agaatgggat gtcccagaaa tattttgggt gagaagaatc ctggagtaga  11220
tggtgacctg actatccctg tcctatgggc acaatctatc atcagatatt gcattcaaag  11280
ggctatcatg ggatcaagtc ctaagtcaac tgttgtttac ctggcagaca ttcatctagg  11340
agttctcttt tatgccaccc cacagtgatc cgccttttgc agtttatcca ctagggacag  11400
gattgccacc ccacagtggg gcctctatgc ccgggacaag tgtaaaatat agagtatagg  11460
ggttatcatc acagagaagc tattgctgga gggcctctgt tatttcctct ccatgccact  11520
cccattttta acctaccaac tgaaatccca agggagactc caccctgtaa ctagagtcct  11580
cagaggtgag ccatcccata ttaacaaatg ggcattaggg ctaggatgcc aagggatacc  11640
tgaaatggga agttgtgggg ctgagtcctc ctgggaatca gagataatat gtaaacagtt  11700
tgttgagaga ttgatgagag ctgactttga gaggtggcca tgctccctgg tcctcaatag  11760
ggaaggcact acacaagaaa cctgggtttg atcaactgca ctgtgtccta ctcacacatt  11820
gtgtgcctgg aaaaatgtta cttagtattt ggagggcctc cagaaccccc ctgggtgcaa  11880
gactgggtgc tagtgactgg gtgaatgagt cttggacaca gtggccttgt ctaggttgtg  11940
tgaggtggct aggcatcatg gcaatacctc ataattgatg agtgaggaaa caagactaag  12000
tccttgactc ctcttattac atgacctggt ggatattatg tttaaactct gcaagctgga  12060
atgagtactg ggtgcagatc ccctgggatt ctggctacaa aggtgaatga tagctagtct  12120
gtttattagt agccaaaaaa gtcagtgagg ggtgagtgcc ctgggatgtt gttaagttca  12180
cattgcacac ttggagaccc tctccatcca gtaacatacc agagaaaact gaccaagccc  12240
tcatgggtgt atgggaacaa caaacctcct ggctacttca agggcacata acaccagcaa  12300
ggagcctgtc ataaccacca tctcaaacaa tagaacttcc taagtgaagc aatgacttca  12360
aatctacttg aaggcatgga gtataagcca tgttcctttc agaggggact gtacttctgt  12420
agattacttt ccctcattaa ccagatctgg ccggccgcat gcggtcgatc atgttggcca  12480
ctcttgttta tctatcattc ctcgttggtc cagtcacagt tctaaaagtc tatggtgttc  12540
cttacattgt aagtttcata tatttcatta ttatatcatt gctaatataa tttgtttttg  12600
acataaagtt ttggaaaaat ttcagatctt tgtaatgtgg ttggacgctg tcacgtactt  12660
gcatcatcat ggtcacgatg ataagttgcc ttggtacaga ggcaaggtaa gtagatcaac  12720
attaatttat aagaagcaac aatgattagt atttgattaa tctaaattat tgatgttttg  12780
tgtacaataa taggaatgga gttatttacg tggaggatta acaactattg atagagatta  12840
cgggatcttc aacaacattc atcacgatat tggaactcac gtgatccatc atcttttccc  12900
acaaatccct cactatcact tggttgatgc cgtgagtgat ctcgctctct ctctagtttc  12960
```

```
atttgattaa aattaaaggg tgattaatta ctaaattagt gatcttaatt aatgatatgc  13020

gacagacgaa atcagctaaa catgtgttgg gaagatacta cagagaacca aagacgtcag  13080

gagcaatacc gatccacttg gtggaaagtt tggtggcaag tattaagaaa gatcattacg  13140

tcagtgacac tggtgatatt gtcttctacg agacagatcc agatctctac gtttatgctt  13200

ctgacaaatc caaaatcaac taacctttct tcctagctct atttaggaat aaaacagtcc  13260

tttggttttt acttatttct ggttgttttt aagttaaatg tactcgtgaa acttttttta  13320

attaaatgta tttacattac aaatcaagtt tttgttcgtt ttctttatgt ttttagttac  13380

aataaataaa ggtcttaaaa actttttgtt ggtggggaca aaagaaaaag ttcgactgag  13440

agagtcgaca aaatgcacgc cg                                          13462
```

```
<210> SEQ ID NO 85
<211> LENGTH: 5521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
```

```
tggcaggata tattgtggtg taaacaaatt gacgcttaga caacttaata acacattgcg     60

gacgttttta atgtactgaa ttaacgccga attgaattcg agctcggtac cggggacaac    120

tttgtataga aaagttgggt ggtttaaact atgtattaca ccataatatc gcactcagtc    180

tttcatctac ggcaatgtac cagctgatat aatcagttat tgaaatattt ctgaatttaa    240

acttgcatca ataaatttat gtttttgctt ggactataat acctgacttg ttattttatc    300

aataaatatt taaactatat ttctttcaag atatcattct ttacaagtat acgtgtttaa    360

attgaatacc ataaattttt atttttcaaa tacatgtaaa attatgaaat gggagtggtg    420

gcgaccgcaa gcacacttca attcctataa cggaccaaat cgcaaaaatt ataataacat    480

attatttcat cctggattaa aagaaagtca ccggggatta ttttgtgacg ccgattacat    540

acggcgacaa taaagacatt ggaaatcgta gtacatattg gaatacactg attatattag    600

tgatgaatac atactttaat atccttacgt aggatcaaca tatcttgtta caatcggaca    660

cttttgcttc atcccgctaa cacctctgca ccttagacca agcgcttcca caaggaactg    720

agagccatag cccacctcac cttgggttcc tttggccgcc tgtctttctg aaagagagcc    780

ttgcccaccg caactatttc aacacagata ggatcaaccc gggatggcgc taagaagcta    840

ttgccgccga tcttcacttc ttggctctag gtctagtaga aggccttctg tttccagaat    900

cagcgagaac ttcaacacat ccatcagtcc aaacagcagc agatcttcta gcgatttgag    960

ttcttccaac agttccagca ccagatctaa cgatagcatc acatcttccc tgagcccaag   1020

cagcatcatc gaagtttcca tcaacgagag actggtaaag ctgatcaagt ccgatcctaa   1080

gcatgtaagc tctaagtcta ggagatccag caagctcagg atgccttctc tcgaagtatc   1140

tagtctgttg ttccatacaa gcaagccaag gcctccaaaa gaatatgttg gccacctcgt   1200

attgagaatc tccgaacata gcctcagacc aatcgataac agcggtgatt cttccgttat   1260

cggtgagaac gttgttagat ccgaaatcag cgtgaacaag atgtctaacc tcaggacaat   1320

cctcagccca aagcataagc tcatcaagag cttgagcaac agaagcagaa acggtatcat   1380

ccataacggt ctgccaatgg taaacatgag gatcagcgat agcgcagatg aaatctctcc   1440

aagtagtgta ctgtccgatt ccctgaggac cgaaaggtcc gaatccagaa gtttgagaaa   1500
```

-continued

```
gatcagcagc agcgatagca tccatagcct cagcaacagg ttgaagaaca gcaggaagct   1560
cagtctcagg aagatcttga agagtaacac cctgagccct tcttgagata cagtaggtaa   1620
gagactcaga gaactctccg atatcaagaa cttcagggat agggagagca gctgaagcga   1680
agtgtctgta cacgtatcta tccttgtaga atccgtcagc gcaagagtta actctgagaa   1740
cgtatcctct tccaccaaca tcgaaagaga aagctcttga ttcctcaccc tcagagagct   1800
gcataagatc agacacagaa tcgaacttct cgatgaggaa cttctcaaca gaagtagcag   1860
taagctcagg cttcttcatg cttggaggtc tgattttctc agtctccaga gatgtgttta   1920
aataggcagt agcctttga tatcagccac aagtgtgtgg gaatcttatc ttcggatttc   1980
aattaggaat taaccttatt gaattctctt gaaaggaagt ccgcaaagtg gttgtcggtt   2040
gtttaaacca acttttgtat acaaagttgt cccctctaga gtcgacctgc aggcatgcaa   2100
gcttagcttg agcttggatc agattgtcgt ttcccgcctt cagtttatca caagtttgta   2160
caaaaaagca ggctgtcgac ctgcaggtca acggatcagg atattcttgt ttaagatgtt   2220
gaactctatg gaggtttgta tgaactgatg atctaggacc ggataagttc ccttcttcat   2280
agcgaactta ttcaaagaat gttttgtgta tcattcttgt tacattgtta ttaatgaaaa   2340
aatattattg gtcattggac tgaacacgag tgttaaatat ggaccaggcc ccaaataaga   2400
tccattgata tatgaattaa ataacaagaa taaatcgagt caccaaacca cttgcctttt   2460
ttaacgagac ttgttcacca acttgataca aaagtcatta tcctatgcaa atcaataatc   2520
atacaaaaat atccaataac actaaaaaat taaaagaaat ggataatttc acaatatgtt   2580
atacgataaa gaagttactt ttccaagaaa ttcactgatt ttataagccc acttgcatta   2640
gataaatggc aaaaaaaaac aaaaaggaaa agaaataaag cacgaagaat tctagaaaat   2700
acgaaatacg cttcaatgca gtgggaccca cggttcaatt attgccaatt ttcagctcca   2760
ccgtatattt aaaaaataaa acgataatgc taaaaaaata taaatcgtaa cgatcgttaa   2820
atctcaacgg ctggatctta tgacgaccgt tagaaattgt ggttgtcgac gagtcagtaa   2880
taaacggcgt caaagtggtt gcagccggca cacacgagtc gtgtttatca actcaaagca   2940
caaatacttt tcctcaacct aaaaataagg caattagcca aaaacaactt tgcgtgtaaa   3000
caacgctcaa tacacgtgtc attttattat tagctattgc ttcaccgcct tagctttctc   3060
gtgacctagt cgtcctcgtc ttttcttctt cttcttctat aaaacaatac ccaaagagct   3120
cttcttcttc acaattcaga tttcaatttc tcaaaatctt aaaaactttc tctcaattct   3180
ctctaccgtg atcaaggtaa atttctgtgt tccttattct ctcaaaatct tcgattttgt   3240
tttcgttcga tcccaatttc gtatatgttc tttggtttag attctgttaa tcttagatcg   3300
aagacgattt tctgggtttg atcgttagat atcatcttaa ttctcgatta gggtttcata   3360
gatatcatcc gatttgttca aataatttga gttttgtcga ataattactc ttcgatttgt   3420
gatttctatc tagatctggt gttagtttct agtttgtgcg atcgaatttg tcgattaatc   3480
tgagtttttc tgattaacag atggcttcat ctgagaacgt tatcactgag ttcatgaggt   3540
tcaaggtgag gatggaaggt actgttaacg gacatgagtt cgagatcgag ggtgagggtg   3600
aaggtagacc ttacgaggga cataacaccg ttaagcttaa ggttacaaag ggtggacctc   3660
ttcctttcgc ttgggatatc ctttctcctc aattccaata cggaagcaag gtaagtttgt   3720
ggattcttcg tccatgtgat ctttgagttt ctttagagct tgtgagggat tagtaagtaa   3780
caatgcttga gttttttgct gctgggcttc gaaaagtttg tcacttgttg gtttgatcca   3840
caaggtcttc ttctccatag ctactagaca tgttttagct taagattcaa gtttatatat   3900
```

gccttgtgga ttaatcattg cctgattctt ccgtgtcatc tctgagttta tttagagctt 3960
ggaagtggtg tagtaataac taacaatact cttgataagt tgtagcaatg ctcttgatta 4020
gtggatgtaa tatgatgttg ataagatata tgaggcacag aaccaaaagt ggtgcttcca 4080
ctagacccgt ttttagccta aggttcaagt ttataccttg tagatgtttc tgtattgtct 4140
gattcttccc tgtgatattt gaatttctta gagctttgga agtgatatag gaacaatgct 4200
cttgtgtgtt tgtctctatg aagattatcg ctgtcgtgtt tcatccgagt gtgcgggatt 4260
ttttgctgct gggtttagcc tttcttcaaa aagttattac ttgttagttt tattgttttg 4320
gtcttgataa gagatgttag gacagacatg gtgcttcttg tctatagcca ctagacctat 4380
tttagcataa ggttaacgaa attctctcta catatcttgt ggatttgttt acattgcctg 4440
atctttcctg tgatcgctgt catgtttctt tggaatgatt gatgtttata aatggaaaaa 4500
tctttgtgca ggtttacgtt aagcaccctg ctgatatccc tgattacaag aagctttcat 4560
tccctgaggg attcaagtgg gagagagtta tgaacttcga ggatggtggt gttgctactg 4620
ttactcagga ttcttcactt caggacggat gcttcatcta caaggttaag ttcatcggag 4680
tgaacttccc ttctgatgga cctgttatgc agaaaaagac tatgggatgg gaggcttcta 4740
ccgagagact ttaccctaga gatggtgttc ttaagggtga gactcacaag gctcttaagc 4800
ttaaagatgg tggacactac ctcgtcgagt tcaagtctat ctacatggct aagaagcctg 4860
ttcagcttcc tggttactac tacgttgacg ctaagcttga tatcacctct cacaacgagg 4920
actacactat cgttgagcaa tacgagagaa ctgagggtag acatcacttg ttcctctgat 4980
atcaaaatct atttagaaat acacaatatt ttgttgcagg cttgctggag aatcgatctg 5040
ctatcataaa aattacaaaa aaattttatt tgcctcaatt attttaggat tggtattaag 5100
gacgcttaaa ttatttgtcg ggtcactacg catcattgtg attgagaaga tcagcgatac 5160
gaaatattcg tagtactatc gataatttat ttgaaaattc ataagaaaag caaacgttac 5220
atgaattgat gaaacaatac aaagacagat aaagccacgc acatttagga tattggccga 5280
gattactgaa tattgagtaa gatcacggaa tttctgacag gagcatgtct tcaattcagc 5340
ccaaatggca gttgaaatac tcaaaccgcc ccatatgcag gagcggatca ttcattgttt 5400
gtttggttgc ctttgccaac atgggagtcc aaggtttacc cagctttctt gtacaaagtg 5460
gtgataaact atcagtgttt gacaggatat attggcgggt aaacctaaga gaaaagagcg 5520
t 5521

<210> SEQ ID NO 86
<211> LENGTH: 11708
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86
tggcaggata tattgtggtg taaacaaatt gacgcttaga caacttaata acacattgcg 60
gacgttttta atgtactgaa ttaacgccga attgaattcg agctcggtac ccggggatcc 120
tctagagtcg acctgcaggc atgcaagctt agcttgagct tggatcagat tgtcgtttcc 180
cgccttcagt ttatcacaag tttgtacaaa aaagcaggcg ccttttgcag tttatctcta 240
tgcccgggac aagtggagtc catgctcaac accgtgcagg atgaggatga ccatagcgac 300
ttcgtgggcg aggaaagcct ttcgtccaag gtggtccctc ctcgcaatct tgttggatgg 360

-continued

```
tgaatattat aaaagcctgc ccttctcgcg ggtgtttaaa cgtcgacctg caggtcaacg    420
gatcaggata ttcttgttta agatgttgaa ctctatggag gtttgtatga actgatgatc    480
taggaccgga taagttccct tcttcatagc gaacttattc aaagaatgtt ttgtgtatca    540
ttcttgttac attgttatta atgaaaaaat attattggtc attggactga acacgagtgt    600
taaatatgga ccaggcccca aataagatcc attgatatat gaattaaata acaagaataa    660
atcgagtcac caaaccactt gccttttttta acgagacttg ttcaccaact tgatacaaaa    720
gtcattatcc tatgcaaatc aataatcata caaaaatatc caataacact aaaaaattaa    780
aagaaatgga taatttcaca atatgttata cgataaagaa gttacttttc caagaaattc    840
actgatttta taagcccact tgcattagat aaatggcaaa aaaaaacaaa aaggaaaaga    900
aataaagcac gaagaattct agaaaatacg aaatacgctt caatgcagtg ggacccacgg    960
ttcaattatt gccaattttc agctccaccg tatatttaaa aaataaaacg ataatgctaa   1020
aaaaatataa atcgtaacga tcgttaaatc tcaacggctg gatcttatga cgaccgttag   1080
aaattgtggt tgtcgacgag tcagtaataa acggcgtcaa agtggttgca gccggcacac   1140
acgagtcgtg tttatcaact caaagcacaa atacttttcc tcaacctaaa aataaggcaa   1200
ttagccaaaa acaactttgc gtgtaaacaa cgctcaatac acgtgtcatt ttattattag   1260
ctattgcttc accgccttag ctttctcgtg acctagtcgt cctcgtcttt tcttcttctt   1320
cttctataaa acaataccca aagagctctt cttcttcaca attcagattt caatttctca   1380
aaatcttaaa aactttctct caattctctc taccgtgatc aaggtaaatt tctgtgttcc   1440
ttattctctc aaaatcttcg attttgtttt cgttcgatcc caatttcgta tatgttcttt   1500
ggtttagatt ctgttaatct tagatcgaag acgattttct gggtttgatc gttagatatc   1560
atcttaattc tcgattaggg tttcatagat atcatccgat ttgttcaaat aatttgagtt   1620
ttgtcgaata attactcttc gatttgtgat ttctatctag atctggtgtt agtttctagt   1680
ttgtgcgatc gaatttgtcg attaatctga gtttttctga ttaacagatg gcttcatctg   1740
agaacgttat cactgagttc atgaggttca aggtgaggat ggaaggtact gttaacggac   1800
atgagttcga gatcgagggt gagggtgaag gtagacctta cgagggacat aacaccgtta   1860
agcttaaggt tacaaagggt ggacctcttc ctttcgcttg ggatatcctt tctcctcaat   1920
tccaatacgg aagcaaggta agtttgtgga ttcttcgtcc atgtgatctt tgagtttctt   1980
tagagcttgt gagggattag taagtaacaa tgcttgagtt ttttgctgct gggcttcgaa   2040
aagtttgtca cttgttggtt tgatccacaa ggtcttcttc tccatagcta ctagacatgt   2100
tttagcttaa gattcaagtt tatatatgcc ttgtggatta atcattgcct gattcttccg   2160
tgtcatctct gagtttattt agagcttgga agtggtgtag taataactaa caatactctt   2220
gataagttgt agcaatgctc ttgattagtg gatgtaatat gatgttgata agatatatga   2280
ggcacagaac caaaagtggt gcttccacta gacccgtttt tagcctaagg ttcaagttta   2340
taccttgtag atgtttctgt attgtctgat tcttccctgt gatatttgaa tttcttagag   2400
ctttggaagt gatataggaa caatgctctt gtgtgtttgt ctctatgaag attatcgctg   2460
tcgtgtttca tccgagtgtg cgggattttt tgctgctggg tttagccttt cttcaaaaag   2520
ttattacttg ttagttttat tgttttggtc ttgataagag atgttaggac agacatggtg   2580
cttcttgtct atagccacta gacctatttt agcataaggt taacgaaatt ctctctacat   2640
accttgtgga tttgtttaca ttgcctgatc tttcctgtga tcgctgtcat gtttctttgg   2700
```

-continued aatgattgat gtttataaat ggaaaaatct ttgtgcagaa gactcccgcc catccaggat 2760
gaggatgacc accaccccac agtggggcag gatgaggatg accaggtcgc agcgtgtgcg 2820
tgtccgtcgt acgttctggc cggccgggcc ttgggcgcgc gatcagaagc gttgcgttgg 2880
cgtgtgtgtg cttctggttt gctttaattt taccaagttt gtttcaaggt ggatcgcgtg 2940
gtcaaggccc gtgtgcttta aagacccacc ggcactggca gtgagtgttg ctgcttgtgt 3000
aggctttggt acgtatgggc tttatttgct tctggatgtt gtgtactact tgggtttgtt 3060
gaattattat gagcagttgc gtattgtaat tcagctgggc tacctggaca ttgttatgta 3120
ttaataaatg ctttgctttc ttctaaagat ctttaagtgc tacaactttg tatacaaaag 3180
ttggtttaaa caaccgacaa ccactttgcg gacttccttt caagagaatt caataaggtt 3240
aattcctaat tgaaatccga agataagatt cccacacact tgtggctgat atcaaaaggc 3300
tactgcctat ttaaacacat ctctggagac tgagaaaatc agacctccaa gcatgaagaa 3360
gcctgagctt actgctactt ctgttgagaa gttcctcatc gagaagttcg attctgtgtc 3420
tgatcttatg cagctctctg agggtgagga atcaagagct ttctctttcg atgttggtgg 3480
aagaggatac gttctcagag ttaactcttg cgctgacgga ttctacaagg atagatacgt 3540
gtacagacac ttcgcttcag ctgctctccc tatccctgaa gttcttgata tcggagagtt 3600
ctctgagtct cttacctact gtatctcaag aagggctcag ggtgttactc ttcaagatct 3660
tcctgagact gagcttcctg ctgttcttca acctgttgct gaggctatgg atgctatcgc 3720
tgctgctgat ctttctcaaa cttctggatt cggacctttc ggtcctcagg gaatcggaca 3780
gtacactact tggagagatt tcatctgcgc tatcgctgat cctcatgttt accattggca 3840
gaccgttatg gatgataccg tttctgcttc tgttgctcaa gctcttgatg agcttatgct 3900
ttgggctgag gattgtcctg aggttagaca tcttgttcac gctgatttcg gatctaacaa 3960
cgttctcacc gataacggaa gaatcaccgc tgttatcgat tggtctgagg ctatgttcgg 4020
agattctcaa tacgaggtgg ccaacatatt cttttggagg ccttggcttg cttgtatgga 4080
acaacagact agatacttcg agagaaggca tcctgagctt gctggatctc ctagacttag 4140
agcttacatg cttaggatcg gacttgatca gctttaccag tctctcgttg atggaaactt 4200
cgatgatgct gcttgggctc agggaagatg tgatgctatc gttagatctg gtgctggaac 4260
tgttggaaga actcaaatcg ctagaagatc tgctgctgtt tggactgatg gatgtgttga 4320
agttctcgct gattctggaa acagaaggcc ttctactaga cctagagcca agaagtgaag 4380
atcggcggca atagcttctt agcgccatcc cgggttgatc ctatctgtgt tgaaatagtt 4440
gcggtgggca aggctctctt tcagaaagac aggcggccaa aggaacccaa ggtgaggtgg 4500
gctatggctc tcagttcctt gtggaagcgc ttggtctaag gtgcagaggt gttagcggga 4560
tgaagcaaaa gtgtccgatt gtaacaagat atgttgatcc tacgtaagga tattaaagta 4620
tgtattcatc actaatataa tcagtgtatt ccaatatgta ctacgatttc caatgtcttt 4680
attgtcgccg tatgtaatcg gcgtcacaaa ataatccccg gtgactttct tttaatccag 4740
gatgaaataa tatgttatta taatttttgc gatttggtcc gttataggaa ttgaagtgtg 4800
cttgcggtcg ccaccactcc catttcataa ttttacatgt atttgaaaaa taaaaattta 4860
tggtattcaa tttaaacacg tatacttgta aagaatgata tcttgaaaga aatatagttt 4920
aaatatttat tgataaaata acaagtcagg tattatagtc caagcaaaaa cataaattta 4980
ttgatgcaag tttaaattca gaaatatttc aataactgat tatatcagct ggtacattgc 5040
cgtagatgaa agactgagtg cgatattatg gtgtaataca tagtttaaac cacccaactt 5100
ttctatacaa agttgaagac tcccgcccat ccaggatgag gatgaccacc accccacagt 5160
ggggcaggat gaggatgacc agtcagtttt acttccctta attttctatg tactttcata 5220
attacttatg ttattttctt catgagtttt aatgcaaatt actatatgga ctctagtgaa 5280
aacgttcaga atcctataaa catgactact gagacgaact tgagagtagt tttgatcata 5340
cacacgtttc atgtggtact tgagagttac taatttttgt catcttcgta taagtagtaa 5400
aagatactac aagaatagtt tagtagaaaa tactagcggt aggtgaagat ttgtcgctat 5460
gtactattat tgtctagtaa cttgagtaac aatttcgtgg tctaaatatc aaataaaaat 5520
ggatgagtgg ttcaccaaat ctaggcatca aaactattaa tgtcattgtc tagatcttag 5580
gtgacaccac atttcgaata tttattggta attgagatgt taaagtacca atatttgact 5640
taataaacta aaagattttg gctttatcaa atgtagacat tgatgacata tcgttgtcat 5700
tatcttgagt atatacaagt cgatcaatta ggtgaaagtt tagtgtctcg tggttggtaa 5760
acgattaata cagtagtata ttttatccaa agacaaaatc caaatcattt caccagtatg 5820
aatagtatta ttttatctta aaagctaaaa tcttaaaaac caaggtagca cccacgttga 5880
gctagacgat caaatcgatt tctgctttgt ccaatttacc aagctattta aagccaaata 5940
attgaaatat aggtaggtcg ttatattagg ctaagattta tctcaaatgc ttaactaaag 6000
gaataacaag ggattctagt tgtgtggttt tataagattg gtccaatttc acttaagttt 6060
gtttattgta gaattttata tgtgaataat ttgaattcca attgaaaaga tattatagta 6120
aaagaaaaaa tagtgcgaac aaaaaacttt aatcccataa aaagaaaaag aaaaatgaaa 6180
agttcttcta acatccatat tttgcatcat atcataaaga taagaaagat acatatcata 6240
gacgtacaga taaacaaaca tatcatcatt tgtgaaatac atagtacaat aatttgcttt 6300
taaatagagt ttaagtcaca cacactgaca cacacgataa aacgataatg tctgcaaaaa 6360
cactttaatc ccattgccta gaggacagct tctccacttt gtctttaagg ttggttttgc 6420
cgtgttgttt ttatctttat ataatgatct attttttgga ttatgaaatg aattcacaca 6480
ttttaattat ttaagaagat ccatatacag gtttataaca gtactaagtg atgattattt 6540
tttgtttttg catagtttag tttattgggt aaacattcat tacgtgtctc tttatacgaa 6600
tcacccatcc aaaatttcaa gtagtctttt agttcattta ttatttcata actatttgac 6660
ttattgattt gacaagaaac aacaaaagtg ttgacttatt gatagattgt gggatcataa 6720
aagtaattaa gcgtcaacca cgacccacaa caacaaagca catgttatac attaatatct 6780
cgtttactta attacagttt tcagaatgcc gtttcatgtc ttgtcactgg cgatgttatt 6840
atcatgttgg acaatattcg actgttgtcg tttttacatt ttcgtattga ctaaaactaa 6900
aaaaacaaaa ctctgtttca ggttgggcct aggatccaca ttgtacacac atttgcttaa 6960
gtctatggag gcgcaaggtt ttaagtctgt ggttgctgtt ataggccttc caaacgatcc 7020
atctgttagg ttgcatgagg ctttgggata cacagcccgg ggtacattgc gcgcagctgg 7080
atacaagcat ggtggatggc atgatgttgg tttttggcaa agggattttg agttgccagc 7140
tcctccaagg ccagttaggc cagttaccca gatctaatat caaaatctat ttagaaatac 7200
acaatatttt gttgcaggct tgctggagaa tcgatctgct atcataaaaa ttacaaaaaa 7260
attttatttg cctcaattat tttaggattg gtattaagga cgcttaaatt atttgtcggg 7320
tcactacgca tcattgtgat tgagaagatc agcgatacga aatattcgta gtactatcga 7380
taatttattt gaaaattcat aagaaaagca aacgttacat gaattgatga aacaatacaa 7440
agacagataa agccacgcac atttaggata ttggccgaga ttactgaata ttgagtaaga 7500
tcacggaatt tctgacagga gcatgtcttc aattcagccc aaatggcagt tgaaatactc 7560
aaaccgcccc atatgcagga gcggatcatt cattgtttgt ttggttgcct ttgccaacat 7620
gggagtccaa ggttatttaa ataccctgcc aagcttgagg tagcctccaa tttgacggtg 7680
ccgccagcga cgccgtctgg aactgtcctt tttgaggacc actccgtttg tggagatcat 7740
gaacaacttt gtataataaa gttgaagact cccgcccatc tctctatgcc cgggacaagt 7800
ggagtccatg ctcaacaccg tgcactaggg acaggattgg tttaaacgtt tgtgtcttct 7860
agattaatcc tccaaacttt tgattaacca aaaaaattat caaactaaca tgttctcctt 7920
ttttctttag aaattctaac gaatttatct ttatactgat ttgaatatac ttaatttggt 7980
catttggatg ccctttacaa cctccttacc aaactattga tcacagtttc tattgctaaa 8040
atcaccaaca aaacgcatgt cgccattcat aattatggtt tcacacctac aactaggcta 8100
ataagtaaat aagtagacaa ctagactcag gtttgaaaaa accataaaag ccatatagcg 8160
ttttctcatt gaaactgcga acacgatcgt gtgaatgttg cagtttctag ttttgataca 8220
aacaaacaaa aacacaattt aatcttagat taaaaagaaa aaagagaacg gagcccacta 8280
gccactcctt caaacgtgtc ttaccaactc tcttctagaa acaaattagg cttcaccttc 8340
ctcttccaac ctctctctct ctctctctct ctttttctca aaccatctct ccataaagcc 8400
ctaatttctt catcacaaga atcagaagaa gaaagatgga cctgcatcta attttcggtc 8460
caacttgcac aggaaagacg acgaccgcga tagctcttgc ccagcagaca gggcttccag 8520
tcctttcgct tgatcgggtc caatgctgtc ctcaactatc aaccggaagc ggacgaccaa 8580
cagtggaaga actgaaagga acgacgcgtc tctaccttga tgatcggcct ctggtggagg 8640
gtatcatcgc agccaagcaa gctcatcata ggctgatcga ggaggtgtat aatcatgagg 8700
ccaacggcgg gcttattctt gagggaggat ccacctcgtt gctcaactgc atggcgcgaa 8760
acagctattg gagtgcagat tttcgttggc atattattcg ccacaagtta cccgaccaag 8820
agaccttcat gaaagcggcc aaggccagag ttaagcagat gttgcacccc gctgcaggcc 8880
attctattat tcaagagttg gtttatcttt ggaatgaacc tcggctgagg cccattctga 8940
aagagatcga tggatatcga tatgccatgt tgtttgctag ccagaaccag atcacggcag 9000
atatgctatt gcagcttgac gcaaatatgg aaggtaagtt gattaatggg atcgctcagg 9060
agtatttcat ccatgcgcgc caacaggaac agaaattccc ccaagttaac gcagccgctt 9120
tcgacggatt cgaaggtcat ccgttcggaa tgtattagaa atcaccagtc tctctctaca 9180
aatctatctc tctctatttt tctccagaat aatgtgtgag tagttcccag ataagggaat 9240
tagggttctt atagggtttc gctcatgtgt tgagcatata agaaaccctt agtatgtatt 9300
tgtatttgta aaatacttct atcaataaaa tttctaattc ctaaaaccaa aatccagtgt 9360
ttaaacaaga ctcccgccca tctctctatg cccgggacaa gtggagtcca tgctcaacac 9420
cgtgcactag ggacaggatt gcattaagga tgaccagttc gtaaaggtcc tgcggtgtct 9480
attgcttttc ataggttaat aagtgtttgc tagactgtgg tgaaaggcct atccgaagta 9540
aggccggccg gatccttcat ctttggacaa gggaataaag actccccact tgctactaag 9600
aacaatacct aagttgccca gacatgactg tacccattca gagacctacc acccattagg 9660
gctatgacac taacactagc ccctggaggt tgaccatgct aggcagtggg ggtctcacct 9720
atgacccact cagatagggg tttaaaccag tgggtgggat ctcagcctca tataggtgtt 9780
tgtggtgagc tttctcctag acaagagaac cctgaagaac agcaagaacc agctaatatg 9840

```
atatgtagac atagtgggtt gctcaaattt tgtgtttagt catattagaa ttgacctcag   9900

tgaccactca gaaagtgccc aagcccatct ataggggcca aagtgctatt gactggtgtg   9960

tctgtgaatt gttcctccct acagagttgg tgctgatata tcctagcatt ctttggaaaa  10020

cctagctagg gactgtcaag tgtaagatac ctcctgaatt ggagggaaca ctagctgccc  10080

tgtaccttct ggctagtacc ttacaccctg aatgggttag gggtctatt atttgctgga  10140

aatataccag tttcagtagg gctgctgcct taggtcccac aaggtgtaac atgtgctcaa  10200

tagttgcact accacatgca cgtgaactta atgatgttat agccacaaca ccaaccttgg  10260

tttgcagttt gacatccctc tggaatgggt gtagtcatct tgctctggat ctgcctgaat  10320

cattggggct gtatgcagcc tgggcttaaa gtgaagaatg ggatgtccca gaaatatttt  10380

gggtgagaag aatcctggag tagatggtga cctgactatc cctgtcctat gggcacaatc  10440

tatcatcaga tattgcattc aaagggctat catgggatca agtcctaagt caactgttgt  10500

ttacctggca gacattcatc taggagttct cttttatgcc accccacagt gatccgcctt  10560

ttgcagttta tccactaggg acaggattgc caccccacag tggggcctct atgcccggga  10620

caagtgtaaa atatagagta taggggttat catcacagag aagctattgc tggagggcct  10680

ctgttatttc ctctccatgc cactcccatt tttaacctac caactgaaat cccaagggag  10740

actccaccct gtaactagag tcctcagagg tgagccatcc catattaaca aatgggcatt  10800

agggctagga tgccaaggga tacctgaaat gggaagttgt ggggctgagt cctcctggga  10860

atcagagata atatgtaaac agtttgttga gagattgatg agagctgact ttgagaggtg  10920

gccatgctcc ctggtcctca atagggaagg cactacacaa gaaacctggg tttgatcaac  10980

tgcactgtgt cctactcaca cattgtgtgc ctggaaaaat gttacttagt atttggaggg  11040

cctccagaac ccccctgggt gcaagactgg gtgctagtga ctgggtgaat gagtcttgga  11100

cacagtggcc ttgtctaggt tgtgtgaggt ggctaggcat catggcaata cctcataatt  11160

gatgagtgag gaaacaagac taagtccttg actcctctta ttacatgacc tggtggatat  11220

tatgtttaaa ctctgcaagc tggaatgagt actgggtgca gatcccctgg gattctggct  11280

acaaaggtga atgatagcta gtctgtttat tagtagccaa aaaagtcagt gaggggtgag  11340

tgccctggga tgttgttaag ttcacattgc acacttggag accctctcca tccagtaaca  11400

taccagagaa aactgaccaa gccctcatgg gtgtatggga acaacaaacc tcctggctac  11460

ttcaagggca cataacacca gcaaggagcc tgtcataacc accatctcaa acaatagaac  11520

ttcctaagtg aagcaatgac ttcaaatcta cttgaaggca tggagtataa gccatgttcc  11580

tttcagaggg gactgtactt ctgtagatta ctttccctca ttaaccagat ctggccggcc  11640

tacccagctt tcttgtacaa agtggtgata aactatcagt gtttgacagg atatattggc  11700

gggtaaac                                                           11708
```

<210> SEQ ID NO 87
<211> LENGTH: 11707
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87

```
tggcaggata tattgtggtg taaacaaatt gacgcttaga caacttaata acacattgcg     60

gacgttttta atgtactgaa ttaacgccga attgaattcg agctcggtac ccggggatcc    120
```

```
tctagagtcg acctgcaggc atgcaagctt agcttgagct tggatcagat tgtcgtttcc    180
cgccttcagt ttatcacaag tttgtacaaa aaagcaggct aagactcccg cccatctcac    240
tagggacagg attggagtcc atgctcaaca ccgtgcagga tgaggatgac catagcgact    300
tcgtgggcga ggaaagcctt tcgtccaagg tggtccctcc tcgcaatctt gttggatggt    360
gaatattata aaagcctgcc cttctcgcgg gtgtttaaac gtcgacctgc aggtcaacgg    420
atcaggatat tcttgtttaa gatgttgaac tctatggagg tttgtatgaa ctgatgatct    480
aggaccggat aagttccctt cttcatagcg aacttattca aagaatgttt tgtgtatcat    540
tcttgttaca ttgttattaa tgaaaaaata ttattggtca ttggactgaa cacgagtgtt    600
aaatatggac caggccccaa ataagatcca ttgatatatg aattaaataa caagaataaa    660
tcgagtcacc aaaccacttg cctttttttaa cgagacttgt tcaccaactt gatacaaaag    720
tcattatcct atgcaaatca ataatcatac aaaaatatcc aataacacta aaaaattaaa    780
agaaatggat aatttcacaa tatgttatac gataaagaag ttacttttcc aagaaattca    840
ctgattttat aagcccactt gcattagata aatggcaaaa aaaaacaaaa aggaaaagaa    900
ataaagcacg aagaattcta gaaaatacga aatacgcttc aatgcagtgg gacccacggt    960
tcaattattg ccaatttttca gctccaccgt atatttaaaa aataaaacga taatgctaaa   1020
aaaatataaa tcgtaacgat cgttaaatct caacggctgg atcttatgac gaccgttaga   1080
aattgtggtt gtcgacgagt cagtaataaa cggcgtcaaa gtggttgcag ccggcacaca   1140
cgagtcgtgt ttatcaactc aaagcacaaa tacttttcct caacctaaaa ataaggcaat   1200
tagccaaaaa caactttgcg tgtaaacaac gctcaataca cgtgtcattt tattattagc   1260
tattgcttca ccgccttagc tttctcgtga cctagtcgtc ctcgtctttt cttcttcttc   1320
ttctataaaa caatacccaa agagctcttc ttcttcacaa ttcagatttc aatttctcaa   1380
aatcttaaaa actttctctc aattctctct accgtgatca aggtaaattt ctgtgttcct   1440
tattctctca aaatcttcga ttttgttttc gttcgatccc aatttcgtat atgttctttg   1500
gtttagattc tgttaatctt agatcgaaga cgattttctg ggtttgatcg ttagatatca   1560
tcttaattct cgattagggt ttcatagata tcatccgatt tgttcaaata atttgagttt   1620
tgtcgaataa ttactcttcg atttgtgatt tctatctaga tctggtgtta gtttctagtt   1680
tgtgcgatcg aatttgtcga ttaatctgag tttttctgat taacagatgg cttcatctga   1740
gaacgttatc actgagttca tgaggttcaa ggtgaggatg gaaggtactg ttaacggaca   1800
tgagttcgag atcgagggtg agggtgaagg tagaccttac gagggacata acaccgttaa   1860
gcttaaggtt acaaagggtg gacctcttcc tttcgcttgg gatatccttt ctcctcaatt   1920
ccaatacgga agcaaggtaa gtttgtggat tcttcgtcca tgtgatcttt gagtttcttt   1980
agagcttgtg agggattagt aagtaacaat gcttgagttt tttgctgctg ggcttcgaaa   2040
agtttgtcac ttgttggttt gatccacaag gtcttcttct ccatagctac tagacatgtt   2100
ttagcttaag attcaagttt atatatgcct tgtggattaa tcattgcctg attcttccgt   2160
gtcatctctg agtttattta gagcttggaa gtggtgtagt aataactaac aatactcttg   2220
ataagttgta gcaatgctct tgattagtgg atgtaatatg atgttgataa gatatatgag   2280
gcacagaacc aaaagtggtg cttccactag acccgttttt agcctaaggt tcaagtttat   2340
accttgtaga tgtttctgta ttgtctgatt cttccctgtg atatttgaat ttcttagagc   2400
tttggaagtg atataggaac aatgctcttg tgtgtttgtc tctatgaaga ttatcgctgt   2460
```

```
cgtgtttcat ccgagtgtgc gggatttttt gctgctgggt ttagcctttc ttcaaaaagt   2520
tattacttgt tagttttatt gttttggtct tgataagaga tgttaggaca gacatggtgc   2580
ttcttgtcta tagccactag acctatttta gcataaggtt aacgaaattc tctctacata   2640
ccttgtggat ttgtttacat tgcctgatct ttcctgtgat cgctgtcatg tttctttgga   2700
atgattgatg tttataaatg gaaaaatctt tgtgcagaag actcccgccc atccaggatg   2760
aggatgacca ccaccccaca gtggggcagg atgaggatga ccaggtcgca gcgtgtgcgt   2820
gtccgtcgta cgttctggcc ggccgggcct tgggcgcgcg atcagaagcg ttgcgttggc   2880
gtgtgtgtgc ttctggtttg ctttaatttt accaagtttg tttcaaggtg gatcgcgtgg   2940
tcaaggcccg tgtgctttaa agacccaccg gcactggcag tgagtgttgc tgcttgtgta   3000
ggctttggta cgtatgggct ttatttgctt ctggatgttg tgtactactt gggtttgttg   3060
aattattatg agcagttgcg tattgtaatt cagctgggct acctggacat tgttatgtat   3120
taataaatgc tttgctttct tctaaagatc tttaagtgct acaactttgt atacaaaagt   3180
tggtttaaac aaccgacaac cactttgcgg acttcctttc aagagaattc aataaggtta   3240
attcctaatt gaaatccgaa gataagattc ccacacactt gtggctgata tcaaaaggct   3300
actgcctatt taaacacatc tctggagact gagaaaatca gacctccaag catgaagaag   3360
cctgagctta ctgctacttc tgttgagaag ttcctcatcg agaagttcga ttctgtgtct   3420
gatcttatgc agctctctga gggtgaggaa tcaagagctt tctctttcga tgttggtgga   3480
agaggatacg ttctcagagt taactcttgc gctgacggat tctacaagga tagatacgtg   3540
tacagacact tcgcttcagc tgctctccct atccctgaag ttcttgatat cggagagttc   3600
tctgagtctc ttacctactg tatctcaaga agggctcagg gtgttactct tcaagatctt   3660
cctgagactg agcttcctgc tgttcttcaa cctgttgctg aggctatgga tgctatcgct   3720
gctgctgatc tttctcaaac ttctggattc ggacctttcg gtcctcaggg aatcggacag   3780
tacactactt ggagagattt catctgcgct atcgctgatc ctcatgttta ccattggcag   3840
accgttatgg atgataccgt ttctgcttct gttgctcaag ctcttgatga gcttatgctt   3900
tgggctgagg attgtcctga ggttagacat cttgttcacg ctgatttcgg atctaacaac   3960
gttctcaccg ataacggaag aatcaccgct gttatcgatt ggtctgaggc tatgttcgga   4020
gattctcaat acgaggtggc caacatattc ttttggaggc cttggcttgc ttgtatggaa   4080
caacagacta gatacttcga gagaaggcat cctgagcttg ctggatctcc tagacttaga   4140
gcttacatgc ttaggatcgg acttgatcag ctttaccagt ctctcgttga tggaaacttc   4200
gatgatgctg cttgggctca gggaagatgt gatgctatcg ttagatctgg tgctggaact   4260
gttggaagaa ctcaaatcgc tagaagatct gctgctgttt ggactgatgg atgtgttgaa   4320
gttctcgctg attctggaaa cagaaggcct tctactagac ctagagccaa gaagtgaaga   4380
tcggcggcaa tagcttctta gcgccatccc gggttgatcc tatctgtgtt gaaatagttg   4440
cggtgggcaa ggctctcttt cagaaagaca ggcggccaaa ggaacccaag gtgaggtggg   4500
ctatggctct cagttccttg tggaagcgct tggtctaagg tgcagaggtg ttagcgggat   4560
gaagcaaaag tgtccgattg taacaagata tgttgatcct acgtaaggat attaaagtat   4620
gtattcatca ctaatataat cagtgtattc caatatgtac tacgatttcc aatgtcttta   4680
ttgtcgccgt atgtaatcgg cgtcacaaaa taatccccgg tgactttctt ttaatccagg   4740
atgaaataat atgttattat aatttttgcg atttggtccg ttataggaat tgaagtgtgc   4800
ttgcggtcgc caccactccc atttcataat tttacatgta tttgaaaaat aaaaatttat   4860
```

```
ggtattcaat ttaaacacgt atacttgtaa agaatgatat cttgaaagaa atatagttta   4920
aatatttatt gataaaataa caagtcaggt attatagtcc aagcaaaaac ataaatttat   4980
tgatgcaagt ttaaattcag aaatatttca ataactgatt atatcagctg gtacattgcc   5040
gtagatgaaa gactgagtgc gatattatgg tgtaatacat agtttaaacc acccaacttt   5100
tctatacaaa gttgaagact cccgcccatc caggatgagg atgaccacca ccccacagtg   5160
gggcaggatg aggatgacca gtcagtttta cttcccttaa ttttctatgt actttcataa   5220
ttacttatgt tattttcttc atgagtttta atgcaaatta ctatatggac tctagtgaaa   5280
acgttcagaa tcctataaac atgactactg agacgaactt gagagtagtt ttgatcatac   5340
acacgtttca tgtggtactt gagagttact aatttttgtc atcttcgtat aagtagtaaa   5400
agatactaca agaatagttt agtagaaaat actagcggta ggtgaagatt tgtcgctatg   5460
tactattatt gtctagtaac ttgagtaaca atttcgtggt ctaaatatca aataaaaatg   5520
gatgagtggt tcaccaaatc taggcatcaa aactattaat gtcattgtct agatcttagg   5580
tgacaccaca tttcgaatat ttattggtaa ttgagatgtt aaagtaccaa tatttgactt   5640
aataaactaa aagattttgg ctttatcaaa tgtagacatt gatgacatat cgttgtcatt   5700
atcttgagta tatacaagtc gatcaattag gtgaaagttt agtgtctcgt ggttggtaaa   5760
cgattaatac agtagtatat tttatccaaa gacaaaatcc aaatcatttc accagtatga   5820
atagtattat tttatcttaa aagctaaaat cttaaaaacc aaggtagcac ccacgttgag   5880
ctagacgatc aaatcgattt ctgctttgtc caatttacca agctatttaa agccaaataa   5940
ttgaaatata ggtaggtcgt tatattaggc taagatttat ctcaaatgct taactaaagg   6000
aataacaagg gattctagtt gtgtggtttt ataagattgg tccaatttca cttaagtttg   6060
tttattgtag aattttatat gtgaataatt tgaattccaa ttgaaaagat attatagtaa   6120
aagaaaaaat agtgcgaaca aaaaacttta atcccataaa aagaaaaaga aaaatgaaaa   6180
gttcttctaa catccatatt ttgcatcata tcataaagat aagaaagata catatcatag   6240
acgtacagat aaacaaacat atcatcattt gtgaaataca tagtacaata atttgctttt   6300
aaatagagtt taagtcacac acactgacac acacgataaa acgataatgt ctgcaaaaac   6360
actttaatcc cattgcctag aggacagctt ctccactttg tctttaaggt tggttttgcc   6420
gtgttgtttt tatctttata taatgatcta tttttggat tatgaaatga attcacacat   6480
tttaattatt taagaagatc catatacagg tttataacag tactaagtga tgattatttt   6540
ttgtttttgc atagtttagt ttattgggta aacattcatt acgtgtctct ttatacgaat   6600
cacccatcca aaatttcaag tagtctttta gttcatttat tatttcataa ctatttgact   6660
tattgatttg acaagaaaca acaaaagtgt tgacttattg atagattgtg ggatcataaa   6720
agtaattaag cgtcaaccac gacccacaac aacaaagcac atgttataca ttaatatctc   6780
gtttacttaa ttacagtttt cagaatgccg tttcatgtct tgtcactggc gatgttatta   6840
tcatgttgga caatattcga ctgttgtcgt ttttacattt tcgtattgac taaaactaaa   6900
aaaacaaaac tctgtttcag gttgggccta ggatccacat tgtacacaca tttgcttaag   6960
tctatggagg cgcaaggttt taagtctgtg gttgctgtta taggccttcc aaacgatcca   7020
tctgttaggt tgcatgaggc tttgggatac acagcccggg gtacattgcg cgcagctgga   7080
tacaagcatg gtggatggca tgatgttggt ttttggcaaa gggattttga gttgccagct   7140
cctccaaggc cagttaggcc agttacccag atctaatatc aaaatctatt tagaaataca   7200
```

caatattttg ttgcaggctt gctggagaat cgatctgcta tcataaaaat tacaaaaaaa 7260
ttttatttgc ctcaattatt ttaggattgg tattaaggac gcttaaatta tttgtcgggt 7320
cactacgcat cattgtgatt gagaagatca gcgatacgaa atattcgtag tactatcgat 7380
aatttatttg aaaattcata agaaaagcaa acgttacatg aattgatgaa acaatacaaa 7440
gacagataaa gccacgcaca tttaggatat tggccgagat tactgaatat tgagtaagat 7500
cacggaattt ctgacaggag catgtcttca attcagccca aatggcagtt gaaatactca 7560
aaccgcccca tatgcaggag cggatcattc attgtttgtt tggttgcctt tgccaacatg 7620
ggagtccaag gttatttaaa taccctgcca agcttgaggt agcctccaat ttgacggtgc 7680
cgccagcgac gccgtctgga actgtccttt ttgaggacca ctccgtttgt ggagatcatg 7740
aacaactttg tataataaag ttgaagactc ccgcccatct ctctatgccc gggacaagtg 7800
gagtccatgc tcaacaccgt gcactaggga caggattggt ttaaacgttt gtgtcttcta 7860
gattaatcct ccaaactttt gattaaccaa aaaaattatc aaactaacat gttctccttt 7920
tttctttaga aattctaacg aatttatctt tatactgatt tgaatatact taatttggtc 7980
atttggatgc cctttacaac ctccttacca aactattgat cacagtttct attgctaaaa 8040
tcaccaacaa aacgcatgtc gccattcata attatggttt cacacctaca actaggctaa 8100
taagtaaata agtagacaac tagactcagg tttgaaaaaa ccataaaagc catatagcgt 8160
tttctcattg aaactgcgaa cacgatcgtg tgaatgttgc agtttctagt tttgatacaa 8220
acaaacaaaa acacaattta atcttagatt aaaaagaaaa aagagaacgg agcccactag 8280
ccactccttc aaacgtgtct taccaactct cttctagaaa caaattaggc ttcaccttcc 8340
tcttccaacc tctctctctc tctctctctc tttttctcaa accatctctc cataaagccc 8400
taatttcttc atcacaagaa tcagaagaag aaagatggac ctgcatctaa ttttcggtcc 8460
aacttgcaca ggaaagacga cgaccgcgat agctcttgcc cagcagacag ggcttccagt 8520
cctttcgctt gatcgggtcc aatgctgtcc tcaactatca accggaagcg gacgaccaac 8580
agtggaagaa ctgaaaggaa cgacgcgtct ctaccttgat gatcggcctc tggtggaggg 8640
tatcatcgca gccaagcaag ctcatcatag gctgatcgag gaggtgtata atcatgaggc 8700
caacggcggg cttattcttg agggaggatc cacctcgttg ctcaactgca tggcgcgaaa 8760
cagctattgg agtgcagatt ttcgttggca tattattcgc cacaagttac ccgaccaaga 8820
gaccttcatg aaagcggcca aggccagagt taagcagatg ttgcaccccg ctgcaggcca 8880
ttctattatt caagagttgg tttatctttg gaatgaacct cggctgaggc ccattctgaa 8940
agagatcgat ggatatcgat atgccatgtt gtttgctagc cagaaccaga tcacggcaga 9000
tatgctattg cagcttgacg caaatatgga aggtaagttg attaatggga tcgctcagga 9060
gtatttcatc catgcgcgcc aacaggaaca gaaattcccc caagttaacg cagccgcttt 9120
cgacggattc gaaggtcatc cgttcggaat gtattagaaa tcaccagtct ctctctacaa 9180
atctatctct ctctattttt ctccagaata atgtgtgagt agttcccaga taagggaatt 9240
agggttctta tagggtttcg ctcatgtgtt gagcatataa gaaaccctta gtatgtattt 9300
gtatttgtaa aatacttcta tcaataaaat ttctaattcc taaaaccaaa atccagtgtt 9360
taaacaagac tcccgcccat ctctctatgc ccgggacaag tggagtccat gctcaacacc 9420
gtgcactagg gacaggattg cattaaggat gaccagttcg taaaggtcct gcggtgtcta 9480
ttgcttttca taggttaata agtgtttgct agactgtggt gaaaggccta tccgaagtaa 9540
ggccggccgg atccttcatc tttggacaag ggaataaaga ctccccactt gctactaaga 9600

```
acaataccta agttgcccag acatgactgt acccattcag agacctacca cccattaggg   9660
ctatgacact aacactagcc cctggaggtt gaccatgcta ggcagtgggg gtctcaccta   9720
tgacccactc agataggggt ttaaaccagt gggtgggatc tcagcctcat ataggtgttt   9780
gtggtgagct ttctcctaga caagagaacc ctgaagaaca gcaagaacca gctaatatga   9840
tatgtagaca tagtgggttg ctcaaatttt gtgtttagtc atattagaat tgacctcagt   9900
gaccactcag aaagtgccca agcccatcta taggggccaa agtgctattg actggtgtgt   9960
ctgtgaattg ttcctcccta cagagttggt gctgatatat cctagcattc tttggaaaac  10020
ctagctaggg actgtcaagt gtaagatacc tcctgaattg gagggaacac tagctgccct  10080
gtaccttctg gctagtacct tacaccctga atgggttagg gggtctatta tttgctggaa  10140
atataccagt ttcagtaggg ctgctgcctt aggtcccaca aggtgtaaca tgtgctcaat  10200
agttgcacta ccacatgcac gtgaacttaa tgatgttata gccacaacac caaccttggt  10260
ttgcagtttg acatccctct ggaatgggtg tagtcatctt gctctggatc tgcctgaatc  10320
attggggctg tatgcagcct gggcttaaag tgaagaatgg gatgtcccag aaatattttg  10380
ggtgagaaga atcctggagt agatggtgac ctgactatcc ctgtcctatg ggcacaatct  10440
atcatcagat attgcattca aagggctatc atgggatcaa gtcctaagtc aactgttgtt  10500
tacctggcag acattcatct aggagttctc ttttatgcca ccccacagtg atccgccttt  10560
tgcagtttat ccactaggga caggattgcc accccacagt ggggcctcta tgcccgggac  10620
aagtgtaaaa tatagagtat aggggttatc atcacagaga agctattgct ggagggcctc  10680
tgttatttcc tctccatgcc actcccattt ttaacctacc aactgaaatc ccaagggaga  10740
ctccaccctg taactagagt cctcagaggt gagccatccc atattaacaa atgggcatta  10800
gggctaggat gccaagggat acctgaaatg ggaagttgtg gggctgagtc ctcctgggaa  10860
tcagagataa tatgtaaaca gtttgttgag agattgatga gagctgactt tgagaggtgg  10920
ccatgctccc tggtcctcaa tagggaaggc actacacaag aaacctgggt ttgatcaact  10980
gcactgtgtc ctactcacac attgtgtgcc tggaaaaatg ttacttagta tttggagggc  11040
ctccagaacc cccctgggtg caagactggg tgctagtgac tgggtgaatg agtcttggac  11100
acagtggcct tgtctaggtt gtgtgaggtg gctaggcatc atggcaatac ctcataattg  11160
atgagtgagg aaacaagact aagtccttga ctcctcttat tacatgacct ggtggatatt  11220
atgtttaaac tctgcaagct ggaatgagta ctgggtgcag atcccctggg attctggcta  11280
caaaggtgaa tgatagctag tctgtttatt agtagccaaa aaagtcagtg aggggtgagt  11340
gccctgggat gttgttaagt tcacattgca cacttggaga ccctctccat ccagtaacat  11400
accagagaaa actgaccaag ccctcatggg tgtatgggaa caacaaacct cctggctact  11460
tcaagggcac ataacaccag caaggagcct gtcataacca ccatctcaaa caatagaact  11520
tcctaagtga agcaatgact tcaaatctac ttgaaggcat ggagtataag ccatgttcct  11580
ttcagagggg actgtacttc tgtagattac tttccctcat taaccagatc tggccggcct  11640
acccagcttt cttgtacaaa gtggtgataa actatcagtg tttgacagga tatattggcg  11700
ggtaaac                                                            11707
```

<210> SEQ ID NO 88
<211> LENGTH: 18
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 88
cgagaacttg gcaattcc 18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tggcgattct gagattcc 18

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gactcatcgt actctccctt cg 22

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gactcatcgt actctccctt cg 22

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgttggtgga agaggatacg 20

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
atcagcagca gcgatagc 18

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
atgtccactg ggttcgtgcc 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
gaagggaact tatccggtcc 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 96
tgcgctgcca ttctccaaat 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 97
accgagctcg aattcaattc 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 98
cctgcattcg gttaaacacc 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 99
ccatctggct tctgccttgc 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 100
attccgatcc ccagggcagt 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
gccaacgttg cagccttgct 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
gccctgggat gttgttaagt 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gtaacttagg acttgtgcga 20

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
tctctacctt gatgatcgg 19

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
aacatctgct taactctggc 20

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
atggcttcat ctgagaacg 19

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
ttccgtattg gaattgagg 19

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
ttgcttaagt ctatggaggc g 21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
tgggtaactg gcctaactgg 20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
atgatatgta gacatagtgg g 21

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
agggtgtaag gtactagcc 19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
tgttggtgga agaggatacg 20

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 113
atcagcagca gcgatagc 18

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 114
gtggagaaga actacgagct accc 24

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 115
gactcatcgt actctccctt cg 22

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Arg Ser Asp Asn Leu Ala Arg
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Gln Lys Lys Asp Arg Ser Tyr
1               5

<210> SEQ ID NO 118

<400> SEQUENCE: 118

000

<210> SEQ ID NO 119

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Gln Arg Gly Asn Arg Asn Thr
1 5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Arg Ser Asp His Leu Ser Arg
1 5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Arg Asn Gln Asp Arg Thr Asn
1 5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Asp Arg Ser Asn Leu Ser Arg
1 5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Arg Gln Asp Ser Arg Ser Gln
1 5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Gln Ser Ser Asp Leu Ser Arg
1 5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Asp Arg Ser Ala Leu Ala Arg
1 5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Thr Ser Gly Ser Leu Thr Arg
1 5

<210> SEQ ID NO 127

<400> SEQUENCE: 127

000

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Ala Ala Ser Asn Arg Ser Lys
1 5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Thr Ser Gly Ser Leu Ser Arg
1 5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Arg Ser Asp Ala Leu Ala Arg
1 5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Arg Ser Asp Val Leu Ser Thr
1 5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Trp Gly Arg Leu Arg Lys Leu
1 5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Glu Arg Gly Thr Leu Ala Arg
1 5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Arg Ser Asp Asp Leu Thr Arg
1 5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Arg Ser Asp His Leu Ser Ala
1 5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Gln His Gly Ala Leu Gln Thr
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Ser Gly Asn Leu Thr Arg
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Ser Gly His Leu Ser Arg
1               5

<210> SEQ ID NO 139

<400> SEQUENCE: 139

000

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Ser Asp His Leu Ser Gln
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Thr Arg Asn Arg Trp Arg
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Ser Asp Asn Leu Ser Glu
1 5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Ala Ser Lys Thr Arg Lys Asn
1 5

<210> SEQ ID NO 144

<400> SEQUENCE: 144

000

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Thr Ser Ser Asn Arg Ala Val
1 5

<210> SEQ ID NO 146

<400> SEQUENCE: 146

000

<210> SEQ ID NO 147

<400> SEQUENCE: 147

000

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Arg Ser Asp Val Leu Ser Glu
1 5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Arg Asn Phe Ser Leu Thr Met 1 5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Gln Ser Gly Asp Leu Thr Arg
1 5

<210> SEQ ID NO 151

<400> SEQUENCE: 151

000

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Gln Ser Gly Asn Leu Ala Arg
1 5

<210> SEQ ID NO 153

<400> SEQUENCE: 153

000

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Gln Ser Gly Ser Leu Thr Arg
1 5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Asp Arg Ser His Leu Ala Arg
1 5

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

His Leu Gly Asn Leu Lys Thr
1 5

<210> SEQ ID NO 162

<400> SEQUENCE: 162

000

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Thr Ala Arg Leu Leu Lys Leu
1 5

<210> SEQ ID NO 164

<400> SEQUENCE: 164

000

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Gln Thr Ser His Leu Pro Gln
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Ser Asp Asn Leu Ser Val
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Thr Ser Gly His Leu Ser Arg
1               5

<210> SEQ ID NO 168

<400> SEQUENCE: 168

000

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Ser Asp Ala Leu Ser Thr
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Arg Ser Thr Arg Thr Lys
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Asn Ala His Arg Lys Thr
1 5

<210> SEQ ID NO 172

<400> SEQUENCE: 172

000

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Leu Lys Gln Met Leu Ala Val
1 5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Arg Ser Asp Asn Leu Ser Arg
1 5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Asp Asn Ser Asn Arg Lys Thr
1 5

<210> SEQ ID NO 176

<400> SEQUENCE: 176

000

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

Gln Asn Ala Asn Arg Ile Thr
1 5

<210> SEQ ID NO 178

<400> SEQUENCE: 178

000

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Gln Ser Ser Val Arg Asn Ser
1 5

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Asp Arg Ser Asn Leu Thr Arg
1 5

<210> SEQ ID NO 184

<400> SEQUENCE: 184

000

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Thr Arg Asn Gly Leu Lys Tyr
1 5

<210> SEQ ID NO 186

<400> SEQUENCE: 186

000

<210> SEQ ID NO 187

<400> SEQUENCE: 187

000

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 188

Arg Ser Ser Asp Arg Thr Lys
1               5

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Gln Ser Thr His Arg Asn Ala
1               5

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Arg Ser Asp Thr Leu Ser Gln

-continued 1 5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 207

Gln Arg Asp His Arg Ile Lys
1 5

<210> SEQ ID NO 208

<400> SEQUENCE: 208

000

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 209

Gln Ser Ser Asp Leu Arg Arg
1 5

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Asp Arg Gly Asp Leu Arg Lys
1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Asp Ser Ser Asp Arg Lys Lys
1               5

<210> SEQ ID NO 221

<400> SEQUENCE: 221

000

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Asp Asn Tyr Asn Arg Ala Lys
1               5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Asp Arg Ser His Leu Thr Arg
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Arg Ser Asp Asn Leu Thr Thr
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Arg Ser Asp Asn Leu Ser Asn
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Thr Ser Ser Ser Arg Ile Asn
1               5

<210> SEQ ID NO 227

<400> SEQUENCE: 227

000

<210> SEQ ID NO 228

<400> SEQUENCE: 228

000

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Arg Ser Asp Ala Leu Thr Gln
1               5

<210> SEQ ID NO 230
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 230

Arg Ser Asp Thr Leu Ser Thr
1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Arg Ser Ser Arg Ile Lys
1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Arg Ser Asp Asp Leu Ser Lys
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Asp Asn Ser Asn Arg Ile Lys
1               5

<210> SEQ ID NO 234

<400> SEQUENCE: 234

000

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Ala Gly Asn Leu Ser Lys
1               5

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Leu Arg Gln Thr Leu Arg Asp
1 5

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255
<211> LENGTH: 57
<212> TYPE: DNA
<213> ORGANISM: Brassica napus

<400> SEQUENCE: 255
gcccaaggaa cccttttctg ggccatcttc gtactcggcc acgactggta atttaat 57

<210> SEQ ID NO 256
<211> LENGTH: 58
<212> TYPE: DNA
<213> ORGANISM: Brassica napus

<400> SEQUENCE: 256
agcgagagaa agcttattgc aacttcaact acttgctggt cgatcgtgtt ggccactc 58

<210> SEQ ID NO 257
<211> LENGTH: 28
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 257

gcccaaggaa cccttttctg ggccatct                                          28


<210> SEQ ID NO 258
<211> LENGTH: 28
<212> TYPE: DNA
<213> ORGANISM: Brassica napus

<400> SEQUENCE: 258

cgtactcggc cacgactggt aatttaat                                          28


<210> SEQ ID NO 259
<211> LENGTH: 57
<212> TYPE: DNA
<213> ORGANISM: Brassica napus

<400> SEQUENCE: 259

gcccaaggaa cccttttctg ggccatcttc gtactcggcc acgactggta atttaat          57


<210> SEQ ID NO 260
<211> LENGTH: 57
<212> TYPE: DNA
<213> ORGANISM: Brassica napus

<400> SEQUENCE: 260

gcccaaggaa ccctgttctg ggctatcttc gtactcggcc acgactggta atttaat          57


<210> SEQ ID NO 261
<211> LENGTH: 57
<212> TYPE: DNA
<213> ORGANISM: Brassica napus

<400> SEQUENCE: 261

gcccaaggaa cccttttctg ggccatcttc gtcctcggcc acgactggta aagtttc          57


<210> SEQ ID NO 262
<211> LENGTH: 57
<212> TYPE: DNA
<213> ORGANISM: Brassica napus

<400> SEQUENCE: 262

gcccaaggaa cccttttctg ggccatcttc gtcctcggcc acgactggta aagtttc          57


<210> SEQ ID NO 263
<211> LENGTH: 57
<212> TYPE: DNA
<213> ORGANISM: Brassica napus

<400> SEQUENCE: 263

gcccaaggaa cccttttctg ggccatcttc gttcttggcc acgactggta aattaaa          57


<210> SEQ ID NO 264
<211> LENGTH: 57
<212> TYPE: DNA
<213> ORGANISM: Brassica napus

<400> SEQUENCE: 264

gcccaaggaa cccttttctg ggccatcttc gttcttggcc acgactggta aattaaa          57
```

<210> SEQ ID NO 265
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 265
agcgagagaa agcttattgc aacttcaa 28

<210> SEQ ID NO 266
<211> LENGTH: 28
<212> TYPE: DNA
<213> ORGANISM: Brassica napus

<400> SEQUENCE: 266
acttgctggt cgatcgtgtt ggccactc 28

<210> SEQ ID NO 267
<211> LENGTH: 58
<212> TYPE: DNA
<213> ORGANISM: Brassica napus

<400> SEQUENCE: 267
agcgagagaa agcttattgc aacttcaact acttgctggt cgatcgtgtt ggccactc 58

<210> SEQ ID NO 268
<211> LENGTH: 58
<212> TYPE: DNA
<213> ORGANISM: Brassica napus

<400> SEQUENCE: 268
agcgagagaa agcttattgc aacttcaact acttgctggt cgatcatgtt ggccactc 58

<210> SEQ ID NO 269
<211> LENGTH: 58
<212> TYPE: DNA
<213> ORGANISM: Brassica napus

<400> SEQUENCE: 269
agcgagagaa agcttattgc aacttcaact acttgctggt ccataatgtt ggccattc 58

<210> SEQ ID NO 270
<211> LENGTH: 58
<212> TYPE: DNA
<213> ORGANISM: Brassica napus

<400> SEQUENCE: 270
agcgagagaa agcttattgc aacttcgact acttgctggt ccataatgtt ggcaattc 58

<210> SEQ ID NO 271
<211> LENGTH: 58
<212> TYPE: DNA
<213> ORGANISM: Brassica napus

<400> SEQUENCE: 271
agcgagagga agcttattgc aacttcaaca acttgctggt ccataatgtt ggccactc 58

<210> SEQ ID NO 272
<211> LENGTH: 58
<212> TYPE: DNA
<213> ORGANISM: Brassica napus

<400> SEQUENCE: 272
agcgagagga agcttattgc aacttcaact acttgctggt ccataatgtt ggccactc 58

<210> SEQ ID NO 273
<211> LENGTH: 3292
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 273
ccagaaggta attatccaag atgtagcatc aagaatccaa tgtttacggg aaaaactatg 60
gaagtattat gtaagctcag caagaagcag atcaatatgc ggcacatatg caacctatgt 120
tcaaaaatga agaatgtaca gatacaagat cctatactgc cagaatacga agaagaatac 180
gtagaaattg aaaaagaaga accaggcgaa gaaaagaatc ttgaagacgt aagcactgac 240
gacaacaatg aaaagaagaa gataaggtcg gtgattgtga aagagacata gaggacacat 300
gtaaggtgga aaatgtaagg gcggaaagta accttatcac aaaggaatct tatcccccac 360
tacttatcct tttatatttt tccgtgtcat ttttgccctt gagttttcct atataaggaa 420
ccaagttcgg catttgtgaa aacaagaaaa aatttggtgt aagctatttt ctttgaagta 480
ctgaggatac aacttcagag aaatttgtaa gtttgtagat ctccatggct ccaaggaaga 540
ggaaggagtc taacagggag tcagctagga ggtcaaggta caggaaggtg ggtatccacg 600
gggtacccgc cgctatggct gagaggccct tccagtgtcg aatctgcatg cgtaacttca 660
gtcgtagtga caacctgagc aaccacatcc gcacccacac aggcgagaag ccttttgcct 720
gtgacatttg tgggaggaaa tttgccacca gcagcagccg cataaaccat accaagatac 780
acacgggcag ccaaaagccc ttccagtgtc gaatctgcat gcgtaacttc agtcgtagtg 840
acaacctgag cgaacacatc cgcacccaca caggcgagaa gccttttgcc tgtgacattt 900
gtgggaggaa atttgccgcc agcaagaccc gcaaaaacca taccaagata cacacgggcg 960
agaagccctt ccagtgtcga atctgcatgc gtaagtttgc ccgctccgac gccctgaccc 1020
agcatgccca gagatgcgga ctgcggggat cccaacttgt gaaatcagaa ttggaagaga 1080
aaaagtctga gcttagacac aaattgaagt acgttccaca tgaatatatc gaacttatcg 1140
agattgctag gaactcaaca caggacagaa ttttggagat gaaggttatg gagttcttta 1200
tgaaagtgta cggatatagg ggaaagcacc ttggtggttc taggaaacct gatggtgcaa 1260
tctacactgt gggatcacct attgactatg gtgttatcgt ggatacaaag gcatactctg 1320
gtggatacaa tttgccaatc ggacaagctg acgaaatgca gagatatgtt gaagagaacc 1380
aaactagaaa caaacatatt aatccaaatg aatggtggaa ggtgtatcct tcatctgtta 1440
cagagttcaa attccttttt gtgtctggac actttaaggg taactacaaa gcacagctta 1500
ctaggttgaa ccatattaca aattgcaatg gtgctgtgtt gtcagttgaa gagcttttga 1560
tcggaggtga aatgattaag gcaggaacac ttactttgga ggaagttaga agaaaattca 1620
acaacggtga aatcaatttt agatctggcg gcggagaggg cagaggaagt cttctaacat 1680
gcggtgacgt ggaggagaat cccggcccta ggatggctcc aaggaagagg aaggagtcta 1740
acagggagtc agctaggagg tcaaggtaca ggaaggtggg tatccacggg gtacccgccg 1800
ctatggctga gaggcccttc cagtgtcgaa tctgcatgcg taacttcagt cgtagtgaca 1860
ccctgagcac gcacatccgc acccacacag gcgagaagcc ttttgcctgt gacatttgtg 1920
ggaggaaatt tgccgacagg agcagccgca taaagcatac caagatacac acgggatctc 1980
agaagccctt ccagtgtcga atctgcatgc gtaacttcag tcgctccgac gacctgtcca 2040
agcacatccg cacccacaca ggcgagaagc cttttgcctg tgacatttgt gggaggaagt 2100
ttgccgacaa ctccaaccgc atcaagcatg cccagagatg cggactgcgg ggatcccaac 2160
ttgtgaaatc agaattggaa gagaaaaagt ctgagcttag acacaaattg aagtacgttc 2220
cacatgaata tatcgaactt atcgagattg ctaggaactc aacacaggac agaattttgg 2280
agatgaaggt tatggagttc tttatgaaag tgtacggata taggggaaag caccttggtg 2340
gttctaggaa acctgatggt gcaatctaca ctgtgggatc acctattgac tatggtgtta 2400
tcgtggatac aaaggcatac tctggtggat acaatttgcc aatcggacaa gctgacgaaa 2460
tgcagagata tgttgaagag aaccaaacta gaaacaaaca tattaatcca aatgaatggt 2520
ggaaggtgta tccttcatct gttacagagt tcaaattcct ttttgtgtct ggacacttta 2580
agggtaacta caaagcacag cttactaggt tgaaccatat tacaaattgc aatggtgctg 2640
tgttgtcagt tgaagagctt ttgatcggag gtgaaatgat taaggcagga acacttactt 2700
tggaggaagt tagaagaaaa ttcaacaacg gtgaaatcaa tttttgataa ctcgagctcg 2760
gtcaccagca taatttttat taatgtacta aattactgtt ttgttaaatg caattttgct 2820
ttctcgggat tttaatatca aaatctattt agaaatacac aatattttgt tgcaggcttg 2880
ctggagaatc gatctgctat cataaaaatt acaaaaaaat tttatttgcc tcaattattt 2940
taggattggt attaaggacg cttaaattat ttgtcgggtc actacgcatc attgtgattg 3000
agaagatcag cgatacgaaa tattcgtagt actatcgata atttatttga aaattcataa 3060
gaaaagcaaa cgttacatga attgatgaaa caatacaaag acagataaag ccacgcacat 3120
ttaggatatt ggccgagatt actgaatatt gagtaagatc acggaatttc tgacaggagc 3180
atgtcttcaa ttcagcccaa atggcagttg aaatactcaa accgccccat atgcaggagc 3240
ggatcattca ttgtttgttt ggttgccttt gccaacatgg gagtccaagg tt 3292

<210> SEQ ID NO 274
<211> LENGTH: 3475
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 274
ccagaaggta attatccaag atgtagcatc aagaatccaa tgtttacggg aaaaactatg 60
gaagtattat gtaagctcag caagaagcag atcaatatgc ggcacatatg caacctatgt 120
tcaaaaatga agaatgtaca gatacaagat cctatactgc cagaatacga agaagaatac 180
gtagaaattg aaaaagaaga accaggcgaa gaaaagaatc ttgaagacgt aagcactgac 240
gacaacaatg aaaagaagaa gataaggtcg gtgattgtga aagagacata gaggacacat 300
gtaaggtgga aaatgtaagg gcggaaagta accttatcac aaaggaatct tatcccccac 360
tacttatcct tttatatttt tccgtgtcat ttttgccctt gagttttcct atataaggaa 420
ccaagttcgg catttgtgaa aacaagaaaa aatttggtgt aagctatttt ctttgaagta 480
ctgaggatac aacttcagag aaatttgtaa gtttgtagat ctccatggct ccaaggaaga 540
ggaaggagtc taacagggag tcagctagga ggtcaaggta caggaaggtg ggtatccacg 600
gggtacccgc cgctatggct gagaggccct tccagtgtcg aatctgcatg cgtaacttca 660

```
gtcagtcctc cgacctgtcc cgccacatcc gcacccacac cggcgagaag ccttttgcct    720
gtgacatttg tgggaggaaa tttgcccagg ccggcaacct gtccaagcat accaagatac    780
acacgcatcc cagggcacct attcccaagc ccttccagtg tcgaatctgc atgcgtaagt    840
ttgcccagtc cggcgacctg acccgccata ccaagataca cacgggcgag aagcccttcc    900
agtgtcgaat ctgcatgcgt aacttcagta cctccggctc cctgtcccgc cacatccgca    960
cccacaccgg cgagaagcct tttgcctgtg acatttgtgg gaggaaattt gcccagtccg   1020
gcaacctggc ccgccatgcc cagagatgcg gactgcgggg atcccaactt gtgaaatcag   1080
aattggaaga gaaaaagtct gagcttagac acaaattgaa gtacgttcca catgaatata   1140
tcgaacttat cgagattgct aggaactcaa cacaggacag aattttggag atgaaggtta   1200
tggagttctt tatgaaagtg tacggatata ggggaaagca ccttggtggt tctaggaaac   1260
ctgatggtgc aatctacact gtgggatcac ctattgacta tggtgttatc gtggatacaa   1320
aggcatactc tggtggatac aatttgccaa tcggacaagc tgacgaaatg cagagatatg   1380
ttgaagagaa ccaaactaga aacaaacata ttaatccaaa tgaatggtgg aaggtgtatc   1440
cttcatctgt tacagagttc aaattccttt ttgtgtctgg acactttaag ggtaactaca   1500
aagcacagct tactaggttg aaccatatta caaattgcaa tggtgctgtg ttgtcagttg   1560
aagagctttt gatcggaggt gaaatgatta aggcaggaac acttactttg gaggaagtta   1620
gaagaaaatt caacaacggt gaaatcaatt ttagatctgg cggcggagag ggcagaggaa   1680
gtcttctaac atgcggtgac gtggaggaga atcccggccc taggatggct ccaaggaaga   1740
ggaaggagtc taacagggag tcagctagga ggtcaaggta caggaaggtg ggtatccacg   1800
gggtacccgc cgctatggct gagaggccct tccagtgtcg aatctgcatg cgtaacttca   1860
gtacctccgg ctccctgtcc cgccacatcc gcacccacac cggcgagaag ccttttgcct   1920
gtgacatttg tgggaggaaa tttgccctgc gccagaccct gcgcgaccat accaagatac   1980
acacgggcag ccaaaagccc ttccagtgtc gaatctgcat gcgtaacttc agtacctccg   2040
gcaacctgac ccgccacatc cgcacccaca ccggcgagaa gccttttgcc tgtgacattt   2100
gtgggaggaa atttgccgac cgctccgccc tggcccgcca taccaagata cacacgggat   2160
ctcagaagcc cttccagtgt cgaatctgca tgcgtaactt cagtcgctcc gacgtgctgt   2220
ccgagcacat ccgcacccac accggcgaga agccttttgc ctgtgacatt tgtgggagga   2280
aatttgcccg caacttctcc ctgaccatgc atgcccagag atgcggactg cggggatccc   2340
aacttgtgaa atcagaattg gaagagaaaa agtctgagct tagacacaaa ttgaagtacg   2400
ttccacatga atatatcgaa cttatcgaga ttgctaggaa ctcaacacag gacagaattt   2460
tggagatgaa ggttatggag ttctttatga aagtgtacgg atatagggga aagcaccttg   2520
gtggttctag gaaacctgat ggtgcaatct acactgtggg atcacctatt gactatggtg   2580
ttatcgtgga tacaaaggca tactctggtg gatacaattt gccaatcgga caagctgacg   2640
aaatgcagag atatgttgaa gagaaccaaa ctagaaacaa acatattaat ccaaatgaat   2700
ggtggaaggt gtatccttca tctgttacag agttcaaatt cctttttgtg tctggacact   2760
ttaagggtaa ctacaaagca cagcttacta ggttgaacca tattacaaat tgcaatggtg   2820
ctgtgttgtc agttgaagag cttttgatcg gaggtgaaat gattaaggca ggaacactta   2880
ctttggagga agttagaaga aaattcaaca acggtgaaat caatttttga taactcgagc   2940
tcggtcacca gcataatttt tattaatgta ctaaattact gttttgttaa atgcaatttt   3000
gctttctcgg gattttaata tcaaaatcta tttagaaata cacaatattt tgttgcaggc   3060
```

ttgctggaga atcgatctgc tatcataaaa attacaaaaa aattttattt gcctcaatta 3120
ttttaggatt ggtattaagg acgcttaaat tatttgtcgg gtcactacgc atcattgtga 3180
ttgagaagat cagcgatacg aaatattcgt agtactatcg ataatttatt tgaaaattca 3240
taagaaaagc aaacgttaca tgaattgatg aaacaataca aagacagata aagccacgca 3300
catttaggat attggccgag attactgaat attgagtaag atcacggaat ttctgacagg 3360
agcatgtctt caattcagcc caaatggcag ttgaaatact caaaccgccc catatgcagg 3420
agcggatcat tcattgtttg tttggttgcc tttgccaaca tgggagtcca aggtt 3475

<210> SEQ ID NO 275
<211> LENGTH: 2019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 275
gcccaaggaa cccttttctg ggccatcttc gtactcggcc acgactggta atttaatgga 60
tccaaccgac aaccactttg cggacttcct ttcaagagaa ttcaataagg ttaattccta 120
attgaaatcc gaagataaga ttcccacaca cttgtggctg atatcaaaag gctactgcct 180
atttaaacac atctctggag actgagaaaa tcagacctcc aagcatgaag aagcctgagc 240
ttactgctac ttctgttgag aagttcctca tcgagaagtt cgattctgtg tctgatctta 300
tgcagctctc tgagggtgag gaatcaagag ctttctcttt cgatgttggt ggaagaggat 360
acgttctcag agttaactct tgcgctgacg gattctacaa ggatagatac gtgtacagac 420
acttcgcttc agctgctctc cctatccctg aagttcttga tatcggagag ttctctgagt 480
ctcttaccta ctgtatctca agaagggctc agggtgttac tcttcaagat cttcctgaga 540
ctgagcttcc tgctgttctt caacctgttg ctgaggctat ggatgctatc gctgctgctg 600
atctttctca aacttctgga ttcggacctt tcggtcctca gggaatcgga cagtacacta 660
cttggagaga tttcatctgc gctatcgctg atcctcatgt ttaccattgg cagaccgtta 720
tggatgatac cgtttctgct tctgttgctc aagctcttga tgagcttatg ctttgggctg 780
aggattgtcc tgaggttaga catcttgttc acgctgattt cggatctaac aacgttctca 840
ccgataacgg aagaatcacc gctgttatcg attggtctga ggctatgttc ggagattctc 900
aatacgaggt ggccaacata ttcttttgga ggccttggct tgcttgtatg gaacaacaga 960
ctagatactt cgagagaagg catcctgagc ttgctggatc tcctagactt agagcttaca 1020
tgcttaggat cggacttgat cagctttacc agtctctcgt tgatggaaac ttcgatgatg 1080
ctgcttgggc tcagggaaga tgtgatgcta tcgttagatc tggtgctgga actgttggaa 1140
gaactcaaat cgctagaaga tctgctgctg tttggactga tggatgtgtt gaagttctcg 1200
ctgattctgg aaacagaagg ccttctacta gacctagagc caagaagtga agatcggcgg 1260
caatagcttc ttagcgccat cccgggttga tcctatctgt gttgaaatag ttgcggtggg 1320
caaggctctc tttcagaaag acaggcggcc aaaggaaccc aaggtgaggt gggctatggc 1380
tctcagttcc ttgtggaagc gcttggtcta aggtgcagag gtgttagcgg gatgaagcaa 1440
aagtgtccga ttgtaacaag atatgttgat cctacgtaag gatattaaag tatgtattca 1500
tcactaatat aatcagtgta ttccaatatg tactacgatt tccaatgtct ttattgtcgc 1560
cgtatgtaat cggcgtcaca aaataatccc cggtgacttt cttttaatcc aggatgaaat 1620

```
aatatgttat tataattttt gcgatttggt ccgttatagg aattgaagtg tgcttgcggt   1680

cgccaccact cccatttcat aattttacat gtatttgaaa aataaaaatt tatggtattc   1740

aatttaaaca cgtatacttg taaagaatga tatcttgaaa gaaatatagt ttaaatattt   1800

attgataaaa taacaagtca ggtattatag tccaagcaaa aacataaatt tattgatgca   1860

agtttaaatt cagaaatatt tcaataactg attatatcag ctggtacatt gccgtagatg   1920

aaagactgag tgcgatatta tggtgtaata catagcggcc gcgcccaagg aaccettttc   1980

tgggccatct tcgtactcgg ccacgactgg taatttaat                          2019
```

```
<210> SEQ ID NO 276
<211> LENGTH: 2666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
```

```
gcccaaggaa cccttttctg ggccatcttc gtactcggcc acgactggta atttaatgga     60

tccactagta acggccgcca gtgtgctgga attcgccctt cgtcgacctg caggtcaacg    120

gatcaggata ttcttgttta agatgttgaa ctctatggag gtttgtatga actgatgatc    180

taggaccgga taagttccct tcttcatagc gaacttattc aaagaatgtt ttgtgtatca    240

ttcttgttac attgttatta atgaaaaaat attattggtc attggactga acacgagtgt    300

taaatatgga ccaggcccca aataagatcc attgatatat gaattaaata acaagaataa    360

atcgagtcac caaaccactt gccttttttta acgagacttg ttcaccaact tgatacaaaa    420

gtcattatcc tatgcaaatc aataatcata caaaaaatatc caataacact aaaaaattaa    480

aagaaatgga taatttcaca atatgttata cgataaagaa gttacttttc caagaaattc    540

actgatttta taagcccact tgcattagat aaatggcaaa aaaaaacaaa aaggaaaaga    600

aataaagcac gaagaattct agaaaatacg aaatacgctt caatgcagtg ggacccacgg    660

ttcaattatt gccaattttc agctccaccg tatatttaaa aaataaaacg ataatgctaa    720

aaaaatataa atcgtaacga tcgttaaatc tcaacggctg gatcttatga cgaccgttag    780

aaattgtggt tgtcgacgag tcagtaataa acggcgtcaa agtggttgca gccggcacac    840

acgagtcgtg tttatcaact caaagcacaa atacttttcc tcaacctaaa aataaggcaa    900

ttagccaaaa acaactttgc gtgtaaacaa cgctcaatac acgtgtcatt ttattattag    960

ctattgcttc accgccttag ctttctcgtg acctagtcgt cctcgtcttt tcttcttctt   1020

cttctataaa acaataccca aagagctctt cttcttcaca attcagattt caatttctca   1080

aaatcttaaa aactttctct caattctctc taccgtgatc aaggtaaatt tctgtgttcc   1140

ttattctctc aaaatcttcg attttgtttt cgttcgatcc caatttcgta tatgttcttt   1200

ggtttagatt ctgttaatct tagatcgaag acgattttct gggtttgatc gttagatatc   1260

atcttaattc tcgattaggg tttcatagat atcatccgat ttgttcaaat aatttgagtt   1320

ttgtcgaata attactcttc gatttgtgat ttctatctag atctggtgtt agtttctagt   1380

ttgtgcgatc gaatttgtcg attaatctga gtttttctga ttaacagatg agaggatctg   1440

gatctgagtc tgatgagtct ggacttcctg ctatggaaat cgagtgtaga atcactggaa   1500

cccttaacgg tgttgagttc gagcttgttg gaggtggtga gggaactcct gagcagggaa   1560

gaatgactaa caagatgaag tctaccaagg gtgctcttac cttctctcca taccttcttt   1620
```

ctcacgttat gggatacgga ttctaccact tcggaactta cccatctgga tacgagaacc 1680
ctttccttca tgctatcaac aacggtggat acaccaacac taggatcgag aagtacgagg 1740
atggtggtgt tcttcacgtt agcttctctt acagatacga ggctggaaga gtgatcggag 1800
atttcaaggt tatgggaact ggattccctg aggattctgt tatcttcacc gacaagatca 1860
tcaggtctaa cgctactgtt gagcatcttc atcctatggg agataacgat ctcgatggat 1920
ctttcaccag aaccttctca cttagagatg gtggttacta ctcttctgtg gtggattctc 1980
acatgcactt caagtctgct atccaccctt ctatccttca aaacggtgga cctatgttcg 2040
ctttcagaag agttgaggaa gatcactcta acaccgagct tggaatcgtt gagtaccaac 2100
atgctttcaa gacccctgat gctgatgctg gtgaggaatg ataatatcaa aatctattta 2160
gaaatacaca atattttgtt gcaggcttgc tggagaatcg atctgctatc ataaaaatta 2220
caaaaaaatt ttatttgcct caattatttt aggattggta ttaaggacgc ttaaattatt 2280
tgtcgggtca ctacgcatca ttgtgattga gaagatcagc gatacgaaat attcgtagta 2340
ctatcgataa tttatttgaa aattcataag aaaagcaaac gttacatgaa ttgatgaaac 2400
aatacaaaga cagataaagc cacgcacatt taggatattg gccgagatta ctgaatattg 2460
agtaagatca cggaatttct gacaggagca tgtcttcaat tcagcccaaa tggcagttga 2520
aatactcaaa ccgccccata tgcaggagcg gatcattcat tgtttgtttg gttgcctttg 2580
ccaacatggg agtccaaggt tgcggccgcg cccaaggaac ccttttctgg gccatcttcg 2640
tactcggcca cgactggtaa tttaat 2666

<210> SEQ ID NO 277
<211> LENGTH: 2020
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277
gcccaaggaa cccttttctg ggccatcttc gtactcggcc acgactggta atttaatgga 60
tccaaccgac aaccactttg cggacttcct ttcaagagaa ttcaataagg ttaattccta 120
attgaaatcc gaagataaga ttcccacaca cttgtggctg atatcaaaag gctactgcct 180
atttaaacac atctctggag actgagaaaa tcagacctcc aagcatgaag aagcctgagc 240
ttactgctac ttctgttgag aagttcctca tcgagaagtt cgattctgtg tctgatctta 300
tgcagctctc tgagggtgag gaatcaagag ctttctcttt cgatgttggt ggaagaggat 360
acgttctcag agttaactct tgcgctgacg gattctacaa ggatagatac gtgtacagac 420
acttcgcttc agctgctctc cctatccctg aagttcttga tatcggagag ttctctgagt 480
ctcttaccta ctgtatctca agaagggctc agggtgttac tcttcaagat cttcctgaga 540
ctgagcttcc tgctgttctt caacctgttg ctgaggctat ggatgctatc gctgctgctg 600
atctttctca aacttctgga ttcggacctt tcggtcctca gggaatcgga cagtacacta 660
cttggagaga tttcatctgc gctatcgctg atcctcatgt ttaccattgg cagaccgtta 720
tggatgatac cgtttctgct tctgttgctc aagctcttga tgagcttatg ctttgggctg 780
aggattgtcc tgaggttaga catcttgttc acgctgattt cggatctaac aacgttctca 840
ccgataacgg aagaatcacc gctgttatcg attggtctga ggctatgttc ggagattctc 900
aatacgaggt ggccaacata ttcttttgga ggccttggct tgcttgtatg gaacaacaga 960

```
ctagatactt cgagagaagg catcctgagc ttgctggatc tcctagactt agagcttaca   1020

tgcttaggat cggacttgat cagctttacc agtctctcgt tgatggaaac ttcgatgatg   1080

ctgcttgggc tcagggaaga tgtgatgcta tcgttagatc tggtgctgga actgttggaa   1140

gaactcaaat cgctagaaga tctgctgctg tttggactga tggatgtgtt gaagttctcg   1200

ctgattctgg aaacagaagg ccttctacta gacctagagc caagaagtga agatcggcgg   1260

caatagcttc ttagcgccat cccgggttga tcctatctgt gttgaaatag ttgcggtggg   1320

caaggctctc tttcagaaag acaggcggcc aaaggaaccc aaggtgaggt gggctatggc   1380

tctcagttcc ttgtggaagc gcttggtcta aggtgcagag gtgttagcgg gatgaagcaa   1440

aagtgtccga ttgtaacaag atatgttgat cctacgtaag gatattaaag tatgtattca   1500

tcactaatat aatcagtgta ttccaatatg tactacgatt tccaatgtct ttattgtcgc   1560

cgtatgtaat cggcgtcaca aaataatccc cggtgacttt cttttaatcc aggatgaaat   1620

aatatgttat tataattttt gcgatttggt ccgttatagg aattgaagtg tgcttgcggt   1680

cgccaccact cccatttcat aattttacat gtatttgaaa aataaaaatt tatggtattc   1740

aatttaaaca cgtatacttg taaagaatga tatcttgaaa gaaatatagt ttaaatattt   1800

attgataaaa taacaagtca ggtattatag tccaagcaaa aacataaatt tattgatgca   1860

agtttaaatt cagaaatatt tcaataactg attatatcag ctggtacatt gccgtagatg   1920

aaagactgag tgcgatatta tggtgtaata catagcggcc gcagcgagag aaagcttatt   1980

gcaacttcaa ctacttgctg gtcgatcgtg ttggccactc                         2020


<210> SEQ ID NO 278
<211> LENGTH: 2667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278

gcccaaggaa ccccttttctg ggccatcttc gtactcggcc acgactggta atttaatgga     60

tccactagta acggccgcca gtgtgctgga attcgccctt cgtcgacctg caggtcaacg    120

gatcaggata ttcttgttta agatgttgaa ctctatggag gtttgtatga actgatgatc    180

taggaccgga taagttccct tcttcatagc gaacttattc aaagaatgtt ttgtgtatca    240

ttcttgttac attgttatta atgaaaaaat attattggtc attggactga acacgagtgt    300

taaatatgga ccaggcccca aataagatcc attgatatat gaattaaata acaagaataa    360

atcgagtcac caaaccactt gcctttttta acgagacttg ttcaccaact tgatacaaaa    420

gtcattatcc tatgcaaatc aataatcata caaaaatatc caataacact aaaaaattaa    480

aagaaatgga taatttcaca atatgttata cgataaagaa gttacttttc caagaaattc    540

actgatttta taagcccact tgcattagat aaatggcaaa aaaaaacaaa aaggaaaaga    600

aataaagcac gaagaattct agaaaatacg aaatacgctt caatgcagtg ggacccacgg    660

ttcaattatt gccaattttc agctccaccg tatatttaaa aaataaaacg ataatgctaa    720

aaaaatataa atcgtaacga tcgttaaatc tcaacggctg gatcttatga cgaccgttag    780

aaattgtggt tgtcgacgag tcagtaataa acggcgtcaa agtggttgca gccggcacac    840

acgagtcgtg tttatcaact caaagcacaa atacttttcc tcaacctaaa aataaggcaa    900

ttagccaaaa acaactttgc gtgtaaacaa cgctcaatac acgtgtcatt ttattattag    960
```

ctattgcttc accgccttag ctttctcgtg acctagtcgt cctcgtcttt tcttcttctt 1020
cttctataaa acaataccca aagagctctt cttcttcaca attcagattt caatttctca 1080
aaatcttaaa aactttctct caattctctc taccgtgatc aaggtaaatt tctgtgttcc 1140
ttattctctc aaaatcttcg attttgtttt cgttcgatcc caatttcgta tatgttcttt 1200
ggtttagatt ctgttaatct tagatcgaag acgattttct gggtttgatc gttagatatc 1260
atcttaattc tcgattaggg tttcatagat atcatccgat ttgttcaaat aatttgagtt 1320
ttgtcgaata attactcttc gatttgtgat ttctatctag atctggtgtt agtttctagt 1380
ttgtgcgatc gaatttgtcg attaatctga gtttttctga ttaacagatg agaggatctg 1440
gatctgagtc tgatgagtct ggacttcctg ctatggaaat cgagtgtaga atcactggaa 1500
cccttaacgg tgttgagttc gagcttgttg gaggtggtga gggaactcct gagcagggaa 1560
gaatgactaa caagatgaag tctaccaagg gtgctcttac cttctctcca taccttcttt 1620
ctcacgttat gggatacgga ttctaccact tcggaactta cccatctgga tacgagaacc 1680
ctttccttca tgctatcaac aacggtggat acaccaacac taggatcgag aagtacgagg 1740
atggtggtgt tcttcacgtt agcttctctt acagatacga ggctggaaga gtgatcggag 1800
atttcaaggt tatgggaact ggattccctg aggattctgt tatcttcacc gacaagatca 1860
tcaggtctaa cgctactgtt gagcatcttc atcctatggg agataacgat ctcgatggat 1920
ctttcaccag aaccttctca cttagagatg gtggttacta ctcttctgtg gtggattctc 1980
acatgcactt caagtctgct atccaccctt ctatccttca aaacggtgga cctatgttcg 2040
ctttcagaag agttgaggaa gatcactcta acaccgagct tggaatcgtt gagtaccaac 2100
atgctttcaa gacccctgat gctgatgctg gtgaggaatg ataatatcaa aatctattta 2160
gaaatacaca atattttgtt gcaggcttgc tggagaatcg atctgctatc ataaaaatta 2220
caaaaaaatt ttatttgcct caattatttt aggattggta ttaaggacgc ttaaattatt 2280
tgtcgggtca ctacgcatca ttgtgattga gaagatcagc gatacgaaat attcgtagta 2340
ctatcgataa tttatttgaa aattcataag aaaagcaaac gttacatgaa ttgatgaaac 2400
aatacaaaga cagataaagc cacgcacatt taggatattg gccgagatta ctgaatattg 2460
agtaagatca cggaatttct gacaggagca tgtcttcaat tcagcccaaa tggcagttga 2520
aatactcaaa ccgccccata tgcaggagcg gatcattcat tgtttgtttg gttgcctttg 2580
ccaacatggg agtccaaggt tgcggccgca gcgagagaaa gcttattgca acttcaacta 2640
cttgctggtc gatcgtgttg gccactc 2667

<210> SEQ ID NO 279
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 279
gattcctaag cattgttggg tc 22

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 280
gaaaatctca tatcgaacgt gcgt 24

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 281
cgcttaccct ctctatctgg taa 23

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 282
ccttgcctct gtaccaaggc ag 22

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
gtgtgtggga atcttatctt cgg 23

<210> SEQ ID NO 284
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 284
caagtcaggt attatagtcc aagca 25

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
caagaatatc ctgatccgtt gac 23

<210> SEQ ID NO 286
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 286
tggcagttga aatactcaaa cc 22

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
gtcctttgag atccatgagc tat 23

<210> SEQ ID NO 288
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
gattcctaag cattgttggg ta 22

<210> SEQ ID NO 289
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
tgcgttcaag aaatcaaaga ca 22

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
gaaaatctca tatcgaacgt gcgg 24

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
tctggtaaat cctaattcct c 21

<210> SEQ ID NO 292
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
ccttgcctct gtaccaaggc aa 22

<210> SEQ ID NO 293
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
cttgcctctg taccaaggca acttc 25

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
cttacatgct taggatcgga cttg 24

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
agttccagca ccagatctaa cg 22

<210> SEQ ID NO 296
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 296
ccctgagccc aagcagcatc atcg 24

<210> SEQ ID NO 297
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
cggagagggc gtggaagg 18

<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 298
ttcgatttgc tacagcgtca ac                                            22

<210> SEQ ID NO 299
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 299
aggcaccatc gcaggcttcg ct                                            22

<210> SEQ ID NO 300
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ttctggcctc tttattgggc cgcccaagga acccttttct gggccatctt cgtactcggc   60
cacgactggt aatttaatgg atccactagt aa                                 92

<210> SEQ ID NO 301
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ttctggcctc tttattgggc cgcccaagga acccttttct gggccatctt cgtactcggc   60
cacgactggt aatttaatgg atccactagt aa                                 92

<210> SEQ ID NO 302
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302
ttctggcctc tttattgggc cgcccaagga acccttttct gggccatcca gtcgtggccg   60
agtacgaaga tggcccagat actcggccac gactggtaat ttaatggatc cactagtaa   119

<210> SEQ ID NO 303
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
ttctggcctc tttattgggc cgcccaagga acccttttct gggccatcgt actcggccac   60
gactggtaat ttaatggatc cactagtaa                                     89

<210> SEQ ID NO 304
<211> LENGTH: 137

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304

ttctggcctc tttattgggc cgcccaagga acccttttct aggtatctca gttcggtgta      60

ggtcgttcgc tccaagctgg gctgcgtgca cgaaccgtac tcggccacga ctggtaattt    120

aatggatcca ctagtaa                                                    137

<210> SEQ ID NO 305
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305

ttctggcctc tttattgggc cgcccaagga acccttttct gggccagact ggtaatttaa     60

tggatccact agtaa                                                      75

<210> SEQ ID NO 306
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306

tccaaggttg cggccgcgcc caaggaaccc ttttctgggc catcttcgta ctcggccacg     60

actggtaatt taattttcaa tttattt                                         87

<210> SEQ ID NO 307
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307

tccaaggttg cggccgcgcc caaggaaccc ttttctgggc cattactcgg ccacgactgg     60

taatttaatt ttcaatttat tt                                              82

<210> SEQ ID NO 308
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308

tccaaggttg cggccgcgcc caaggaaccc ttttctgggc catttactcg gccacgactg     60

gtaatttaat tttcaattta ttt                                             83

<210> SEQ ID NO 309
<211> LENGTH: 41
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 309
cgtactcggc cacgactggt aatttaattt tcaatttatt t 41

<210> SEQ ID NO 310
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
tccaaggttg cggccgcgcc caaggaaccc ttttctgggc catcttcgta ctcggccacg 60
actggtaatt taattttcaa tttattt 87

<210> SEQ ID NO 311
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
tccaaggttg cggccgcgcc caaggaaccc ttttctgggc catcttctgg taatttaatt 60
ttcaatttat tttt 74

<210> SEQ ID NO 312
<211> LENGTH: 132
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 312
tccaaggttg cggccgcgcc caaggaaccc ttttctggta gcggtggttt ttttgtttgc 60
aagcagcaga ttacgcgcag aaaaaaagga tcgtactcgg ccacgactgg taatttaatt 120
ttcaatttat tt 132

<210> SEQ ID NO 313
<211> LENGTH: 138
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 313
tccaaggttg cggccgcgcc caaggaaccc ttttctgggc catcttacga gcgtaatggc 60
tggcctgttg aacaagtctg gaaagaaatg cataaacata tcccagccac gactggtaat 120
ttaattttca atttattt 138

<210> SEQ ID NO 314
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 314
tagtttattt gccccaagcg agagaaagct tattgcaact tcaactcgta ctcggccacg 60
actggtaatt taatggatcc actagtaa 88

<210> SEQ ID NO 315
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 315
tagtttattt gccccaagcg agagaaagct tattgcaact tcaact 46

<210> SEQ ID NO 316
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 316
tagtttattt gccccaagcg agagaaagct tattgcaact tcaacg 46

<210> SEQ ID NO 317
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 317
tagtttattt gccccaagcg agagaaagct tattgcaact tcaacttcgt actcggccac 60
gactggtaat ttaatggatc cactagtaa 89

<210> SEQ ID NO 318
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 318
tagtttattt gccccaagcg agagaaagct tattgcaact tcaactatgt actcggccac 60
gactggtaat ttaatggatc cactagtaa 89

<210> SEQ ID NO 319
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 319
tagtttattt gccccaagcg agagaaagct tattgcaact tcatactcgg ccacgactgg 60
taatttaatg gatccactag taa 83

<210> SEQ ID NO 320
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 320
aggtaattta atggatccac tagtaa 26

<210> SEQ ID NO 321
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 321
tccaaggttg cggccgcagc gagagaaagc ttattgcaac ttcaactact tgctggtcga 60
tcgtgttggc cactcttgtt tatctatca 89

<210> SEQ ID NO 322
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 322
tccaaggttg cggccgcagc gagagaaagc ttattgcaac ttcaacttgc tggtcgatcg 60
tgttggccac tcttgtttat ctatca 86

<210> SEQ ID NO 323
<211> LENGTH: 149
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 323
tccaaggttg cggccgcgcg ccgacccagc tttcttgtac aaagttggca ttataagaaa 60
gcattgctta tcaatttgtt gcaacgaaca ggtcactatc agtcaaaact tgctggtcga 120
tcgtgttggc cactcttgtt tatctatca 149

<210> SEQ ID NO 324
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 324
tccaaggttt gcggccgcag cgagagaaag cttattgcaa cttcacttgc tggtcgatcg 60
tgttggccac tcttgtttat ctatca 86

<210> SEQ ID NO 325
<211> LENGTH: 121
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 325
tccaaggttg cggccgcagc gagagaaagc ttattgcaac ttcagataaa agttgctcgc 60
ctgtgtgggt gtggatgcta cttgctggtc gatcgtgttg gccactcttg tttatctatc 120
a 121

<210> SEQ ID NO 326
<211> LENGTH: 94
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 326
tccaaggttg cggccgcagc gagagaaagc ttattgcaac ttcaactaca ctacttgctg 60
gtcgatcgtg ttggccactc ttgtttatct atca 94

<210> SEQ ID NO 327
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 327
tccaaggttg cggccgcagc gagagaaagc ttattgcaac ttcaactact tgctggtcga 60
tcgtgttggc cactcttgtt tatctatca 89

<210> SEQ ID NO 328
<211> LENGTH: 99
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 328
ttctggcctc tttattgggc cgcccaagga accctttttct gggccatctt cgtactcggc 60
cacgactggt aatttaatgg atccaaccga caaccactt 99

<210> SEQ ID NO 329
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (38)..(40)
<223> OTHER INFORMATION: a, c, t, g, unknown or other

<400> SEQUENCE: 329
ttctggcctc tttattgggc cgcccaagga accctttnnn tactcggcca cgactggtaa 60
tttaatggat ccaaccgaca accactt 87

<210> SEQ ID NO 330

```
<211> LENGTH: 245
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(195)
<223> OTHER INFORMATION: a, c, t, g, unknown or other

<400> SEQUENCE: 330

ttctggcctc tttattgggc cgcccaagga acccttttct ggnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnntcgta ctcggccacg actggtaatt taatggatcc aaccgacaac     240

cactt                                                                 245

<210> SEQ ID NO 331
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331

ttctggcctc tttattgggc cgcccaagga acccttttct gg                         42

<210> SEQ ID NO 332
<211> LENGTH: 462
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (50)..(419)
<223> OTHER INFORMATION: a, c, t, g, unknown or other

<400> SEQUENCE: 332

ttctggcctc tttattgggc cgcccaagga acccttttct gggccatctn nnnnnnnnn       60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnnnnnnn     360

nnnnnnnnnn nnnnnnnnnn nnnnnnnnnn nnnnnnnnnn nnnnnnnnnn nnnnnnnnnc     420

ggccacgact ggtaatttaa tggatccaac cgacaaccac tt                        462

<210> SEQ ID NO 333
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(83)
<223> OTHER INFORMATION: a, c, t, g, unknown or other
```

<400> SEQUENCE: 333
ttctggcctc tttattgggc cgcccaagga accctttttct gggccatnnn nnnnnnnnnn 60
nnnnnnnnnn nnnnnnnnnn nnntcgtact cggccacgac tggtaattta atggatccaa 120
ccgacaacca ctt 133

<210> SEQ ID NO 334
<211> LENGTH: 127
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (50)..(127)
<223> OTHER INFORMATION: a, c, t, g, unknown or other

<400> SEQUENCE: 334
ttctggcctc tttattgggc cgcccaagga acccttttct gggccatctn nnnnnnnnnn 60
nnnnnnnnnn nnnnnnnnnn nnnnnnnnnn nnnnnnnnnn nnnnnnnnnn nnnnnnnnnn 120 nnnnnnn 127

<210> SEQ ID NO 335
<211> LENGTH: 104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 335
gtaatacata gcggccgcgc ccaaggaacc cttttctggg ccatcttcgt actcggccac 60
gactggtaat ttaattttca atttattttt tcttcaactt ctta 104

<210> SEQ ID NO 336
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (45)..(48)
<223> OTHER INFORMATION: a, c, t, g, unknown or other

<400> SEQUENCE: 336
gtaatacata gcggccgcgc ccaaggaacc cttttctggg ccatnnnngc cacgactggt 60
aatttaattt tcaatttatt ttttcttcaa cttctta 97

<210> SEQ ID NO 337
<211> LENGTH: 202
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (47)..(158)
<223> OTHER INFORMATION: a, c, t, g, unknown or other

<400> SEQUENCE: 337

-continued

```
gtaatacata gcggccgcgc ccaaggaacc cttttctggg ccatctnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnga ctggtaattt aattttcaat    180

ttattttttc ttcaacttct ta                                              202
```

<210> SEQ ID NO 338
<211> LENGTH: 202
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (47)..(158)
<223> OTHER INFORMATION: a, c, t, g, unknown or other

<400> SEQUENCE: 338

```
gtaatacata gcggccgcgc ccaaggaacc cttttctggg ccatctnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnga ctggtaattt aattttcaat    180

ttattttttc ttcaacttct ta                                              202
```

<210> SEQ ID NO 339
<211> LENGTH: 334
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (45)..(278)
<223> OTHER INFORMATION: a, c, t, g, unknown or other

<400> SEQUENCE: 339

```
gtaatacata gcggccgcgc ccaaggaacc cttttctggg ccatnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnngt actcggccac gactggtaat    300

ttaattttca atttattttt tcttcaactt ctta                                 334
```

<210> SEQ ID NO 340
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 340

```
gtactcggcc acgactggta atttaatttt tctttcaact tctta                     45
```

<210> SEQ ID NO 341
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (25)..(33)
<223> OTHER INFORMATION: a, c, t, g, unknown or other

<400> SEQUENCE: 341
gtaatacata gcggccgcgc ccaannnnnn nnntactcgg ccacgactgg taatttaatt 60
ttcaatttat tttttcttca acttctta 88

<210> SEQ ID NO 342
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (45)..(51)
<223> OTHER INFORMATION: a, c, t, g, unknown or other

<400> SEQUENCE: 342
tgtaatacat agcggccgcg cccaaggaac cctttactcg gccannnnnn ntaatttaat 60
tttcaattta ttttttcttc aacttctta 89

<210> SEQ ID NO 343
<211> LENGTH: 99
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
ttctggcctc tttattgggc cgcccaagga accctttct gggccatctt cgtactcggc 60
cacgactggt aatttaatgg atccaaccga caaccactt 99

<210> SEQ ID NO 344
<211> LENGTH: 305
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (50)..(255)
<223> OTHER INFORMATION: a, c, t, g, unknown or other

<400> SEQUENCE: 344
ttctggcctc tttattgggc cgcccaagga accctttct gggccatctn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnntcgta ctcggccacg actggtaatt taatggatcc aaccgacaac 300
cactt 305

<210> SEQ ID NO 345
<211> LENGTH: 465
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (50)..(422)
<223> OTHER INFORMATION: a, c, t, g, unknown or other

<400> SEQUENCE: 345
ttctggcctc tttattgggc cgcccaagga accctttct gggccatctn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nncggccacg actggtaatt taatggatcc aaccgacaac cactt 465

<210> SEQ ID NO 346
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (45)..(49)
<223> OTHER INFORMATION: a, c, t, g, unknown or other

<400> SEQUENCE: 346
ttctggcctc tttattgggc cgcccaagga accctttct gggcnnnnnt cggccacgac 60
tggtaattta atggatccaa ccgacaacca ctt 93

<210> SEQ ID NO 347
<211> LENGTH: 103
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 347
gtaatacata gcggccgcag cgagagaaag cttattgcaa cttcaactac ttgctggtcg 60
atcgtgttgg ccactcttgt ttatctatca ttcctcgttg gtc 103

<210> SEQ ID NO 348
<211> LENGTH: 330
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (48)..(276)
<223> OTHER INFORMATION: a, c, t, g, unknown or other

<400> SEQUENCE: 348
gtaatacata gcggccgcag cgagagaaag cttattgcaa cttcaacnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180

```
nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnncttg ctggtcgatc gtgttggcca    300

ctcttgttta tctatcattc ctcgttggtc                                     330


<210> SEQ ID NO 349
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(73)
<223> OTHER INFORMATION: a, c, t, g, unknown or other

<400> SEQUENCE: 349

gtaatacata gcggccgcag cgagagaaag cttattgcaa cttcaacnnn nnnnnnnnnn     60

nnnnnnnnnn nnntacttgc tggtcgatcg tgttggccac tcttgtttat ctatcattcc    120

tcgttggtc                                                            129


<210> SEQ ID NO 350
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(80)
<223> OTHER INFORMATION: a, c, t, g, unknown or other

<400> SEQUENCE: 350

gtaatacata gcggccgcag cgagagaaag cttattgcaa cttcaacnnn nnnnnnnnnn     60

nnnnnnnnnn nnnnnnnnnn acttgctggt cgatcgtgtt ggccactctt gtttatctat    120

cattcctcgt tggtc                                                     135


<210> SEQ ID NO 351
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(64)
<223> OTHER INFORMATION: a, c, t, g, unknown or other

<400> SEQUENCE: 351

gtaatacata gcggccgcag cgagagaaag cttattgcaa cttcaacnnn nnnnnnnnnn     60

nnnncttgct ggtcgatcgt gttggccact cttgtttatc tatcattcct cgttggtc      118


<210> SEQ ID NO 352
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 352

cgcccaagga accctttct gggccatggg tttcgccacc tctgacttga gcgtcgattt     60
```

ttaaccaata ggccgaaatc ggcaaaatcc cttataaatc aaaagaatag accgagatag 120
ggttgagtgg ccgctacagg gcgctcccat tcgccattca ggctgcgcaa ctgttgggaa 180
gggcgtttcg gtgcgggcct cttcgctatt acgccagctg gcgaaagggg gatgtgctgc 240
aaggcgatta agttgggtaa cgccagggtt ttcccagtca cgacgttgta aaacgacggc 300
cagtgagcgc gacgtaatac gactcactat agggcgaatt ggcggaaggc cgtcaaggcc 360
gcatcaacga gctcgtgcac gcccaaggaa ccccttttctg ggccatcccg cgcaattggc 420
gagtttggcg cggtgtcggt ggtttccggc tcgattcgcg gcgaaaccat actcggccac 480
gactggtaat ttaatggatc caaccgacaa ccactttgcg gacttccttt caagagaatt 540
caataaggtt aattcctaat tgaaatccga agataagatt cccacacact tg 592

<210> SEQ ID NO 353
<211> LENGTH: 307
<212> TYPE: DNA
<213> ORGANISM: Brassica napus

<400> SEQUENCE: 353
tccatgagct acgtcgcgag agacattttc tccgtcgtgg ctctggccgt cgccgccgtg 60
tattttgata gctggttctt ctggcctctt tattgggccg cccaaggaac cctttttctgg 120 gccattactc ggccacgact ggtaatttaa tggatccaac cgacaaccac tttgcggact 180
tcctttcaag agaattcaat aaggttaatt cctaattgaa atccgaagat aagattccca 240
cacacttgtg gctgatatca aaaggctact gcctatttaa acacatctct ggagaatgag 300
aaaatca 307

<210> SEQ ID NO 354
<211> LENGTH: 687
<212> TYPE: DNA
<213> ORGANISM: Brassica napus

<400> SEQUENCE: 354
ccatgagcta cgtcgcgaga gacattttct ccgtcgtggc tctggccgtc gccgccgtgt 60
attttgatag ctggttcttc tggcctcttt attgggccgc ccaaggaacc cttttctggg 120
ccatgggttt cgccacctct gacttgagcg tcgattttta accaataggc cgaaatcggc 180
aaaatccctt ataaatcaaa agaatagacc gagatagggt tgagtggccg ctacagggcg 240
ctcccattcg ccattcaggc tgcgcaactg ttgggaaggg cgtttcggtg cgggcctctt 300
cgctattacg ccagctggcg aaagggggat gtgctgcaag gcgattaagt tgggtaacgc 360
cagggttttc ccagtcacga cgttgtaaaa cgacggccag tgagcgcgac gtaatacgac 420
tcactatagg gcgaattggc ggaaggccgt caaggccgca tcaacgagct cgtgcacgcc 480
caaggaaccc ttttctgggc catcccgcgc aattggcgag tttggcgcgg tgtcggtggt 540
ttccggctcg attcgcggcg aaaccatact cggccacgac tggtaattta atggatccaa 600
ccgacaacca ctttgcggac ttcctttcaa gagaattcaa taaggttaat tcctaattga 660
aatccgaaga taagattccc acacact 687

<210> SEQ ID NO 355
<211> LENGTH: 618
<212> TYPE: DNA
<213> ORGANISM: Brassica napus

<400> SEQUENCE: 355
tgtcgcgaga gacattttct ccgtcgtggc tctggccgtc gccgccgtgt attttgatag 60
ctggttcttc tggcctcttt attgggccgc ccaaggaacc cttttctggg ccaaaaggcc 120
gcgttgctgg cgtttttcca taggctccgc ccccctgacg agcatcacaa aaatcgacgc 180
tcaagtcaga ggtggcgaaa cccgacagga ctataaagat accaggcgtt tccccctgga 240
agctccctcg tgcgctctcc tgttccgacc ctgccgctta ccggatacct gtccgccttt 300
ctcccttcgg gaagcgtggc gctttctcat agctcacgct gtaggtatct cagttcggtg 360
taggtcgttc gctccaagct gggctgtgtg cacgaacccc ccgttcagcc cgaccgctgc 420
gccttatccg gtaactatcg tcttgagtcc aacccggtaa gacacgactt atcgccactg 480
gcagcagcca ctggtagtac tcggccacga ctggtaattt aatggatcca accgacaacc 540
actttgcgga cttcctttca agagaattca ataaggttaa ttcctaattg aaatccgaag 600
ataagattcc cacacact 618

<210> SEQ ID NO 356
<211> LENGTH: 332
<212> TYPE: DNA
<213> ORGANISM: Brassica napus

<400> SEQUENCE: 356
tttgtccttt gagatccatg agctacgtcg cgagagacat tttctccgtc gtggctctgg 60
ccgtcgccgc cgtgtatttt gatagctggt tcttctggcc tctttattgg gccgcccaag 120
gaaccctttt ctgggccatc ttactcggcc acgactggta atttaatgga tccaaccgac 180
aaccactttg cggacttcct ttcaagagaa ttcaataagg ttaattccta attgaaatcc 240
gaagataaga ttcccacaca cttgtggctg atatcaaaag gctactgcct atttaaacac 300
atctctggag actgagaaaa tcagacctcc aa 332

<210> SEQ ID NO 357
<211> LENGTH: 370
<212> TYPE: DNA
<213> ORGANISM: Brassica napus

<400> SEQUENCE: 357
catgagctac gtcgcgagag acattttctc cgtcgtggct ctggccgtcg ccgccgtgta 60
ttttgatagc tggttcttct ggcctcttta ttgggccgcc caaggaaccc ttttctgggc 120
tacttacgcc agagaaataa ctggctggct gctacaccat gttgccgggc aacgagggag 180
accgtcagta ctcggccacg actggtaatt taatggatcc aaccgacaac cactttgcgg 240
acttcctttc aagagaattc aataaggtta attcctaatt gaaatccgaa gataagattc 300
ccacacactt gtggctgata tcaaaaggct actgcctatt taaacacatc tctggagact 360
gagaaaatca 370

<210> SEQ ID NO 358
<211> LENGTH: 625
<212> TYPE: DNA
<213> ORGANISM: Brassica napus

<400> SEQUENCE: 358
tgagctacgt cgcgagagac attttctccg tcgtggctct ggccgtcgcc gccgtgtatt 60
ttgatagctg gttcttctgg cctctttatt gggccgccca aggaaccctt ttctgggcca 120
aaaggccgcg ttgctggcgt ttttccatag gctccgcccc cctgacgagc atcacaaaaa 180
tcgacgctca agtcagaggt ggcgaaaccc gacaggacta taaagatacc aggcgtttcc 240
ccctggaagc tccctcgtgc gctctcctgt tccgaccctg ccgcttaccg gatacctgtc 300
cgcctttctc ccttcgggaa gcgtggcgct ttctcatagc tcacgctgta ggtatctcag 360
ttcggtgtag gtcgttcgct ccaagctggg ctgtgtgcac gaaccccccg ttcagcccga 420
ccgctgcgcc ttatccggta actatcgtct tgagtccaac ccggtaagac acgacttatc 480
gccactggca gcagccactg gtagtactcg gccacgactg gtaatttaat ggatccaacc 540
gacaaccact ttgcggactt cctttcaaga gaattcaata aggttaattc ctaattgaaa 600
tccgaagata agattcccac acact 625

<210> SEQ ID NO 359
<211> LENGTH: 597
<212> TYPE: DNA
<213> ORGANISM: Brassica napus

<400> SEQUENCE: 359
cgtcgccgcc gtgtattttg atagctggtt cttctggcct ctttattggg ccgcccaagg 60
aacccttttc tgggccatcg cgttaatatt ttgttaaaat tcgcgttaaa tttttgttaa 120
atcagctcat tttttaacca ataggccgaa atcggcaaaa tcccttataa atcaaaagaa 180
tagaccgaga tagggttgag tggccgctac agggcgctcc cattcgccat tcaggctgcg 240
caactgttgg gaagggcgtt tcggtgcggg cctcttcgct attacgccag ctggcgaaag 300
ggggatgtgc tgcaaggcga ttaagttggg taacgccagg gttttcccag tcacgacgtt 360
gtaaaacgac ggccagtgag cgcgacgtaa tacgactcac tatagggcga attggcggaa 420
ggccgtcaag gccacgtgtc ttgtccagag ctcgtgcacg cccaaggaac ccttttctgg 480
gccatcttcg tactcggcca cgactggtaa tttaatggat ccaaccgaca accactttgc 540
ggacttcctt tcaagagaat tcaataaggt taattcctaa ttgaaatccg aagataa 597

<210> SEQ ID NO 360
<211> LENGTH: 590
<212> TYPE: DNA
<213> ORGANISM: Brassica napus

<400> SEQUENCE: 360
ccgtcgccgc cgtgtatttt gatagctggt tcttctggcc tctttattgg gccgcccaag 60
gaaccctttt ctgggccatc gcgttaatat tttgttaaaa ttcgcgttaa atttttgtta 120
aatcagctca ttttttaacc aataggccga aatcggcaaa atcccttata aatcaaaaga 180
atagaccgag atagggttga gtggccgcta cagggcgctc ccattcgcca ttcaggctgc 240
gcaactgttg ggaagggcgt ttcggtgcgg gcctcttcgc tattacgcca gctggcgaaa 300
gggggatgtg ctgcaaggcg attaagttgg gtaacgccag ggttttccca gtcacgacgt 360
tgtaaaacga cggccagtga gcgcgacgta atacgactca ctatagggcg aattggcgga 420
aggccgtcaa ggccacgtgt cttgtccaga gctcgtgcac gcccaaggaa cccttttctg 480
ggccatcttc gtactcggcc acgactggta atttaatgga tccaaccgac aaccactttg 540
cggacttcct ttcaagagaa ttcaataagg ttaattccta attgaaatcc 590

<210> SEQ ID NO 361
<211> LENGTH: 726
<212> TYPE: DNA
<213> ORGANISM: Brassica napus

<400> SEQUENCE: 361

```
gtgcacccaa ctgatcttca gcatcttttt actttcacca gcgtttctgg gtgagcaaaa      60

acaggaaggc aaaatgccgc aaaaaaggga ataagggcga cacggaaatg ttgaatactc     120

atactcttcc tttttcaata ttattgaagc atttatcagg gttattgtct catgagcgga     180

tacatatttg aatgtattta gaaaaataaa caaatagggg ttccgcgcac atttccccga     240

aaagtgccac ctaaattgta agcgttaata ttttgttaaa attcgcgtta aatttttgtt     300

aaatcagctc attttttaac caataggccg aaatcggcaa aatcccttat aaatcaaaag     360

aatagaccca gatagggttg agtggccgct acagggcgct cccattcgcc attcaggctg     420

cgcaactgtt gggaagggcg tttcggtgcg ggcctcttcg ctattacgcc agctggcgaa     480

atgggtcaag tcaggtatta tagtccaagc aaaaacataa atttattgat gcaagtttaa     540

attcagaaat atttcaataa ctgattatat cagctggtac attgccgtag atgaaagact     600

gagtgcgata ttatggtgta atacatagcg gccgcgccca aggaaccctt ttctgggcca     660

tcttcgtact cggccacgac tggtaattta attttcaatt tatttttct tcaacttctt     720

aatttt                                                                726
```

<210> SEQ ID NO 362
<211> LENGTH: 296
<212> TYPE: DNA
<213> ORGANISM: Brassica napus

<400> SEQUENCE: 362

```
tctcaagtca ggtattatag tccaagcaaa aacataaatt tattgatgca agtttaaatt      60

cagaaatatt tcaataactg attatatcag ctggtacatt gccgtagatg aaagactgag     120

tgcgatatta tggtgtaata catagcggcc gcgcccaagg aacccttttc tgggccatct     180

gccacgactg gtaatttaat tttcaattta tttttcttc aacttcttaa ttttgatatg     240

tttatatgtt tttttcgttt tttgcatcgt ctttgatttc ttgaacgcac gttcga         296
```

<210> SEQ ID NO 363
<211> LENGTH: 558
<212> TYPE: DNA
<213> ORGANISM: Brassica napus

<400> SEQUENCE: 363

```
ctctccaagt caggattata gtccaagcaa aaacataaat ttattgatgc aagtttaaat      60

tcagaaatat ttcaataact gattatatca gctggtacat tgccgtagat gaaagactga     120

gtgcgatatt atggtgtaat acatagcggc cgcagcgaga gaaagcttat tgcaacttca     180

attgaagtgt gcttgcggtc gccaccactc ccatttcata attttacatg tatttgaaaa     240

ataaaaattt atggtattca atttaaacac gtatacttgt aaagaatgat atcttgaaag     300

aaatatagtt taaatattct tgctggtcga tcatgttggc cactattgtt tatctatcaa     360

tcctcgttgg tccagtcaca gttacacaag tctatggtgt tccttacctt gcacgcgcca     420

catatttcat tattatatca ttgctaatat aactcgttct tgacataacg ttttggaaaa     480

ctttcagatc tttgtaatgt ggttggacgc tgtcacgtac ttgcatcatc atggtcacga     540

tgataagttg ccttggta                                                   558
```

<210> SEQ ID NO 364
<211> LENGTH: 615
<212> TYPE: DNA
<213> ORGANISM: Brassica napus

<400> SEQUENCE: 364

```
ggtattatag tccaagcaaa aacataaatt tattgatgca agtttaaatt cagaaatatt     60

tcaataactg attatatcag ctggtacatt gccgtagatg aaagactgag tgcgatatta    120

tggtgtaata catagcggcc gcagcgagag aaagcttatt gcaacttcaa ctacttgctg    180

gtcgatcgtg ttggccactc ggtacctgga gcacaagact ggcctcatgg gccttccgct    240

cactgcccgc tttccagtcg ggaaacctgt cgtgccagct gcattaacgc tcaccggctc    300

cagatttatc agcaataaac cagccagccg gaagggccga gcgcagaagt ggtcctgcaa    360

ctttatccgc ctccatccag tctatcatgt tggccactct tgtttatcta tcattcctcg    420

ttggtccagt cacagttcta aaagtctatg gtgttcctta cattgtaagt ttcatatatt    480

tcattattat atcattgcta atataatttg tttttgacat aaagttttgg aaaaatttca    540

gatctttgta atgtggttgg acgctgtcac gtacttgcat catcatggtc acgatgataa    600

gttgccttgg tacag                                                     615
```

```
<210> SEQ ID NO 365
<211> LENGTH: 364
<212> TYPE: DNA
<213> ORGANISM: Brassica napus

<400> SEQUENCE: 365

tggcttggag gtctgatttt ctcagtctcc agagatgtgt ttaaataggc agtagccttt     60

tgatatcagc cacaagtgtg tgggaatctt atcttcggat ttcaattagg aattaacctt    120

attgaattct cttgaaagga agtccgcaaa gtggttgtcg gttggatcca ttaaattacc    180

agtcgtggcc gagtagtctg ttgttccata caagcaagcc aaggccgtac tcggccacga    240

ctggtaattt aattttcaat ttattttttc ttcaacttct taattttgat acgtttatat    300

gtttttttcg ttttttgcat cgtctttgat ttcttgaacg cacgttcgat tgtagatttt    360

cgca                                                                 364
```

```
<210> SEQ ID NO 366
<211> LENGTH: 500
<212> TYPE: DNA
<213> ORGANISM: Brassica napus

<400> SEQUENCE: 366

tatctggtaa atcctaattc ctcatttttc ttcctgatta taattacaat tttgaatttt     60

tagattttga gtattaacta aatataaatt aaatttgttt ggggatgact acagtggtac    120

agaagtcctg gtaaagaagg gtcacattat aacccataca gtagtttatt tgccccaagc    180

gagagaaagc ttattgcaac tgaccatgtt aatgcagctg gcacgacagg tttcccgact    240

ggaaagcggg cagtgagcgg aaggcccatg aggccagtct tgtgctccag gtaccgagtg    300

gccaacacga tcgaccagca agtagttgaa gttgcaataa gctttctctc gctgcggccg    360

ctatgtatta caccataata tcgcactcag tctttcatct acggcaatgt accagctgat    420

ataatcagtt attgaaatat ttctgaatta aacttgcatc aataaattta tgtttttgct    480

tggactataa tccctgactt                                                500
```

```
<210> SEQ ID NO 367
<211> LENGTH: 375
<212> TYPE: DNA
<213> ORGANISM: Brassica napus

<400> SEQUENCE: 367
```

```
gcagtagcct tttgatatca gccacaagtg tgtgggaatc ttatcttcgg atttcaatta     60

ggaattaacc ttattgaatt ctcttgaaag gaagtccgca aagtggttgt cggttggatc    120

cattaaatta ccactacttg ctggtcgatc atgttggcca ctcttgttta tctatcattc    180

ctcgttggtc cagtcacagt tctaaaagtc tatggtgttc cttacattgt aagtttcata    240

tatttcatta ttatatcatt gctaatataa tttgtttttg acataaagtt ttggaaaaat    300

ttcagatctt tgtaatgtgg ttggacgctg tcacgtactt gcatcatcat ggtcacgatg    360

ataagttgcc ttgga                                                     375


<210> SEQ ID NO 368
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368

ttctggcctc tttattgggc cgcccaagga accctttttct gggccatctt cgtactcggc     60

cacgactggt aatttaatgg atccaaccga caaccactt                            99


<210> SEQ ID NO 369
<211> LENGTH: 536
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(489)
<223> OTHER INFORMATION: a, c, t, g, unknown or other

<400> SEQUENCE: 369

ttctggcctc tttattgggc cgcccaagga acccttttct gggccatnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnnnnnnnnn nnnnnnnnnn nnnnnnnnnn nnnnnnnnnn nnnnnnnnnn nnnnnnnnnn    480

nnnnnnnnnt actcggccac gactggtaat ttaatggatc caaccgacaa ccactt        536


<210> SEQ ID NO 370
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(454)
<223> OTHER INFORMATION: a, c, t, g, unknown or other

<400> SEQUENCE: 370

ttctggcctc tttattgggc cgcccaagga acccttttct gggccatcnn nnnnnnnnnn     60
```

| | |
|---|---|
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnntcgtac tcggccacga ctggtaattt | 480 |
| aatggatcca accgacaacc actt | 504 |

<210> SEQ ID NO 371
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(454)
<223> OTHER INFORMATION: a, c, t, g, unknown or other

<400> SEQUENCE: 371

| | |
|---|---|
| ttctggcctc tttattgggc cgcccaagga acccttttct gggccatcnn nnnnnnnnnn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnntcgtac tcggccacga ctggtaattt | 480 |
| aatggatcca accgacaacc actt | 504 |

<210> SEQ ID NO 372
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372

| | |
|---|---|
| ttctggcctc tttattgggc cgcccaagga acccttttct gggccattac tcggccacga | 60 |
| ctggtaattt aatggatcca accgacaacc actt | 94 |

<210> SEQ ID NO 373
<211> LENGTH: 530
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(483)
<223> OTHER INFORMATION: a, c, t, g, unknown or other

<400> SEQUENCE: 373

```
ttctggcctc tttattgggc cgcccaagga accctttct gggccatcnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnnnnnnnnn nnnnnnnnnn nnnnnnnnnn nnnnnnnnnn nnnnnnnnnn nnnnnnnnnn    480

nnntactcgg ccacgactgg taatttaatg gatccaaccg acaaccactt                530
```

<210> SEQ ID NO 374
<211> LENGTH: 470
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (46)..(423)
<223> OTHER INFORMATION: a, c, t, g, unknown or other

<400> SEQUENCE: 374

```
ttctggcctc tttattgggc cgcccaagga accctttct gggccnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnntactcgg ccacgactgg taatttaatg gatccaaccg acaaccactt                470
```

<210> SEQ ID NO 375
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375

```
ttctggcctc tttattgggc cgcccaagga accctttct gggccatctt actcggccac     60

gactggtaat ttaatggatc caaccgacaa ccactt                               96
```

<210> SEQ ID NO 376
<211> LENGTH: 104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 376

```
gtaatacata gcggccgcgc ccaaggaacc cttttctggg ccatcttcgt actcggccac     60

gactggtaat ttaattttca atttattttt tcttcaactt ctta                     104
```

<210> SEQ ID NO 377
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gtaatacata gcggccgcgc ccaaggaacc cttttctggg ccatctgcca cgactggtaa     60
tttaattttc aatttatttt ttcttcaact tctta                               95

<210> SEQ ID NO 378
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 378
gtaatacata gcggccgcag cgagagaaag cttattgcaa cttcaactac ttgctggtcg     60
atcgtgttgg ccactcttgt ttatctatca ttcctcgttg gtc                     103

<210> SEQ ID NO 379
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (47)..(183)
<223> OTHER INFORMATION: a, c, t, g, unknown or other

<400> SEQUENCE: 379
gtaatacata gcggccgcag cgagagaaag cttattgcaa cttcaannnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnncttgctg gtcgatcatg ttggccactc ttgtttatct atcattcctc gttggtc       237

<210> SEQ ID NO 380
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(109)
<223> OTHER INFORMATION: a, c, t, g, unknown or other

<400> SEQUENCE: 380
ttctggcctc tttattgggc cgcccaagga acccttttct gggccatnnn nnnnnnnnnn     60
nnnnnnnnnn nnnnnnnnnn nnnnnnnnnn nnnnnnnnnn nnnnnnnnnt actcggccac    120
gactggtaat ttaatggatc caaccgacaa ccactt                              156

<210> SEQ ID NO 381
<211> LENGTH: 471
<212> TYPE: DNA
<213> ORGANISM: Artificial Sequence -continued

```
<220> FEATURE:
<223> OTHER INFORMATION: Description of Artificial Sequence: Synthetic
      polynucleotide
<220> FEATURE:
<221> NAME/KEY: modified_base
<222> LOCATION: (47)..(424)
<223> OTHER INFORMATION: a, c, t, g, unknown or other

<400> SEQUENCE: 381

ttctggcctc tttattgggc cgcccaagga accctttttct gggccannnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnnntactcg gccacgactg gtaatttaat ggatccaacc gacaaccact t              471


<210> SEQ ID NO 382
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 382

gtaatacata gcggccgcgc ccaaggaacc cttttctggg ccatcttcgt actcggccac     60

gactggtaat ttaattttca atttattttt tcttcaactt ctta                      104


<210> SEQ ID NO 383
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 383

gtaatacata gcggccgcag cgagagaaag cttattgcaa cttcaactac ttgctggtcg     60

atcgtgttgg ccactcggta cctggagcac aagactggcc tca                       103
```